(12) United States Patent
Micheli et al.

(10) Patent No.: US 10,273,244 B2
(45) Date of Patent: Apr. 30, 2019

(54) SUBSTITUTED HEXAHYDROPYRROLO[3,4-B]PYRROLES AND HEXAHYDROCYCLOPENTA[C]PYRROLES AS DOPAMINE RECEPTOR MODULATORS

(71) Applicant: INDIVIOR UK LIMITED, Slough Berkshire (GB)

(72) Inventors: Fabrizio Micheli, Verona (IT); Susanna Cremonesi, Verona (IT); Teresa Semeraro, Verona (IT); Luca Tarsi, Verona (IT)

(73) Assignee: INDIVIOR UK LIMITED, Slough Berkshire (GB)

( * ) Notice: Subject to any disclaimer, the term of this patent is extended or adjusted under 35 U.S.C. 154(b) by 0 days.

(21) Appl. No.: 15/750,128

(22) PCT Filed: Aug. 4, 2016

(86) PCT No.: PCT/IB2016/054708
§ 371 (c)(1),
(2) Date: Feb. 2, 2018

(87) PCT Pub. No.: WO2017/021920
PCT Pub. Date: Feb. 9, 2017

(65) Prior Publication Data
US 2018/0222918 A1 Aug. 9, 2018

(30) Foreign Application Priority Data

Aug. 5, 2015 (GB) .................................. 1513871.2
Oct. 13, 2015 (GB) .................................. 1518125.8

(51) Int. Cl.
| | | |
|---|---|---|
| *A61K 31/403* | (2006.01) | |
| *A61K 31/407* | (2006.01) | |
| *C07D 209/02* | (2006.01) | |
| *C07D 487/04* | (2006.01) | |
| *C07D 498/04* | (2006.01) | |
| *A61P 25/36* | (2006.01) | |
| *A61P 25/32* | (2006.01) | |
| *A61P 25/18* | (2006.01) | |
| *C07D 209/52* | (2006.01) | |

(52) U.S. Cl.
CPC ............ *C07D 498/04* (2013.01); *A61P 25/18* (2018.01); *A61P 25/32* (2018.01); *A61P 25/36* (2018.01); *C07D 209/52* (2013.01); *C07D 487/04* (2013.01)

(58) Field of Classification Search
CPC .. A61K 31/403; A61K 31/407; C07D 209/02; C07D 487/04
USPC .................................. 514/412; 548/452, 453
See application file for complete search history.

(56) References Cited

FOREIGN PATENT DOCUMENTS

| WO | WO-95/15327 A1 | 6/1995 |
|----|----|----|
| WO | WO-2005/080382 A1 | 9/2005 |
| WO | WO-2006/136223 A1 | 12/2006 |
| WO | WO-2015/048507 A1 | 4/2015 |
| WO | WO-2015/095701 A1 | 6/2015 |

OTHER PUBLICATIONS

Database Accession No. 2005:903182 "Preparation of N-substituted 3-azabicycloalkanes as neuroleptics," 6 pages.
Micheli, H. et al. (Aug. 1, 2008). "Selective dopamine D3 receptor antagonists. A decade of progress:1997-2007," *Expert Opin Ther Patents* 18(8):821-840.
Micheli, F. et al. (Apr. 15, 2016). "1,2,4-Triazolyl octahydropyrrolo[2,3-b]pyrroles: A new series of potent and selective dopamine D3 receptor antagonists," *Bioorganic & Medicinal Chemistry* 24(8):1619-1636.
International Search Report dated Oct. 10, 2016, for PCT Application No. PCT/IB2016/054708, filed Aug. 4, 2016, 7 pages.
Written Opinion dated Oct. 10, 2016, for PCT Application No. PCT/IB2016/054708, filed Aug. 4, 2016, 9 pages.

*Primary Examiner* — Douglas M Willis
(74) *Attorney, Agent, or Firm* — Edward D. Grieff; Mintz, Levin, Cohn, Ferris, Glovsky and Popeo, P.C.

(57) ABSTRACT

The disclosure provides compounds having formula (I), wherein the substituents are as defined herein. The compounds are useful for modulating the dopamine $D_3$ receptor and for treating conditions associated therewith, such as addictions, drug dependency, and psychiatric conditions.

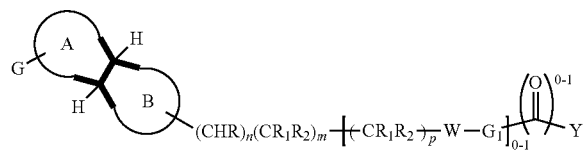

22 Claims, No Drawings

SUBSTITUTED HEXAHYDROPYRROLO[3,4-B]PYRROLES AND HEXAHYDROCYCLOPENTA[C]PYRROLES AS DOPAMINE RECEPTOR MODULATORS

CROSS-REFERENCES TO RELATED APPLICATIONS

This application is a Section 371 US national phase of International Application No. PCT/IB2016/054708 filed Aug. 4, 2016, which claims the benefit of United Kingdom Priority Application No. 1513871.2 filed Aug. 5, 2015 and United Kingdom Priority Application No. 1518125.8, filed Oct. 13, 2015, which are incorporated herein by reference in its entirety and for all purposes.

BACKGROUND

Dopamine receptors are prominent in regulating several aspects of basic brain function. In particular, they are necessary for the normal tasks of the regions they innervate, including motor behavior, motivation, and working memory. Dopamine receptors are also a central element in the brain reward system that controls the learning of many behaviors. There are two main classes of dopamine receptors, D1 and D2, which respectively stimulate and inhibit adenylyl cyclase. Further research revealed the existence of two D1-like receptors, D1 and D5, and three D2-like receptors, D2, D3, and D4.

The selective distribution of the dopamine D3 receptors onto key neurocircuits that underlie the processing of motivationally relevant events has made this target a main focus of significant drug discovery efforts over the last decade. However, identifying selective pharmacological agents for D3 receptors is an ongoing challenge.

Disclosed herein, inter alia, are solutions to these and other problems in the art.

BRIEF SUMMARY OF THE INVENTION

In an aspect, is provided a compound, or a pharmaceutically acceptable salt thereof, having formula (I):

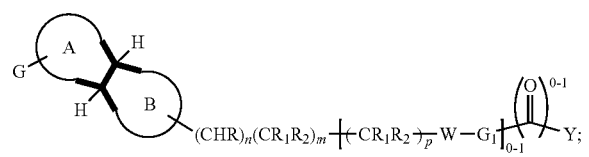

(I)

wherein:

A is a saturated 4-6 carbocyclic ring, optionally in which one or two carbon atoms is heteroatoms selected among nitrogen and oxygen; and in which the group G is linked to a carbon or nitrogen; such ring may optionally be substituted at the carbon atoms or nitrogen atom by one or more $C_{1-4}$alkyl groups;

B is a saturated 4-6 heterocyclic ring in which one or two carbon atoms is heteroatoms selected among Nitrogen or Oxygen and the linking atom is always a Nitrogen atom; such ring may be also substituted at the carbon atoms or, possibly, at the different Nitrogen atom, by one or more $C_{1-4}$alkyl group;

G is phenyl, or a 5-6 membered heteroaromatic group, which is optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, halo$C_{1-4}$alkoxy, $SF_5$, —C(=O)$NH_2$, —C(=O)$OR_3$;

W is S, $SO_2$, O, $CHR_2$, $NR_3$;
n is 0 or 1;
m is 1 or 2;
p is 1 or 2;
z is 0 or 1;
R is hydrogen, $C_{1-4}$alkyl; $C_{1-4}$alkoxy;
$R_1$ is hydrogen, F, $C_{1-4}$alkyl; hydroxyl, $C_{1-4}$alkoxy;
$R_2$ is hydrogen, F, $C_{1-4}$alkyl; hydroxyl, $C_{1-4}$alkoxy;
$R_3$ is hydrogen, $C_{1-4}$alkyl;
$R_4$ is hydrogen or $C_{1-4}$alkyl; or —C(=O)$C_{1-4}$alkyl; —C(=O)$C_{1-4}$alkoxy$C_{1-4}$alkyl; —C(=O)cyclopropyl;
$R_5$ is hydrogen, $C_{1-4}$alkyl;
$R_6$ is hydrogen, $C_{1-4}$alkyl;
$R_7$ is halogen, $C_{1-4}$alkyl; hydroxyl, $C_{1-4}$alkoxy;

$G_1$ is phenyl or a 5-6-membered heteroaromatic group or a 8-11 membered heteroaromatic group; any of which groups is optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy, $SF_5$, —C(=O)$NH_2$, —C(=O)(O)$_zR_3$;

Y is phenyl or a moiety selected from the group consisting of: 5-6 membered heteroaromatic group, a 8-11 membered heteroaromatic group; a saturated mono 3-7 membered carbocyclic group or a 8-11 membered bicyclic carbocyclic group in which one or more atom carbons may be replaced by N($R_4$)$_z$, O, S; any of such groups may be optionally substituted by 1, 2 or 3 substituents selected from: halogen, cyano, hydroxyl, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, —C(=O), —$NHR_4$, —$NR_5R_6$, $SF_5$, —C(=O)(O)$_zR_3$ or =O;

when $G_1$ is a phenyl group, then $G_1$ and Y may optionally be fused together to form a benzofused aromatic or heteroaromatic system which might be optionally substituted by one or two substituents selected from: halogen, cyano, hydroxy, amino $C_{1-4}$alkyl, halo$C_{1-4}$alkyl, $C_{1-4}$alkoxy, halo$C_{1-4}$alkoxy, $C_{1-4}$alkanoyl, —C(=O)$NH_2$, —C(=O)$OR_3$, $SF_5$.

In another aspect, is provided a compound as described herein or a pharmaceutical acceptable salt thereof for use as a medicament.

In an aspect is provided a compound as described herein for the use in the treatment of a condition for which modulation of dopamine D3 receptors is beneficial.

DETAILED DESCRIPTION

The present invention relates to novel compounds, processes for their preparation, intermediates used in these processes, pharmaceutical compositions containing them and their use in therapy, as modulators of dopamine $D_3$ receptors. A new class of compounds which have affinity for dopamine receptors, in particular the dopamine $D_3$ receptor has been found. These compounds have potential in the treatment of conditions wherein modulation, especially antagonism/inhibition, of the D3 receptor is beneficial, e.g. to treat drug dependency or as antipsychotic agents.

Definitions

The term "aryl" refers to an aromatic carbocyclic moiety such as phenyl, biphenyl or naphthyl.

The term "5-6-membered heteroaromatic group" refers to a monocyclic 5- or 6-membered aromatic heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "8-11-membered heteroaromatic group" refers to a bicyclic aromatic ring system containing a total of 8, 9, 10 or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl. Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "saturated mono 3-7 membered carbocyclic group" and the term "8-11 membered bicyclic carbocyclic group" refers to 3 or 4, 5, 6, or 7-membered saturated monocyclic group or 8, 9, 10, 11 membered saturated bicyclic wherein 1, 2, 3, 4 or 5 of the carbon atoms are replaced by a heteroatom independently selected from O, S and $NR_3$ and which is partially or fully saturated. Examples of 3-7 membered carbocyclic group containing heteroatoms which are fully saturated include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl.

Examples of "3-7 membered carbocyclic group containing heteroatoms" which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl.

Examples of "8-11 membered bicyclic carbocyclic group" include decahydroquinolinyl, octahydro-2H-1,4-benzoxazinyl and octahydro-1H-cyclopenta[b]pyridinyl.

Examples of partially saturated "8-11 membered bicyclic rings" include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of these groups may be attached to the rest of the molecule at any suitable position.

Compounds

The disclosure provides compounds of formula (I) or a pharmaceutical acceptable salt thereof:

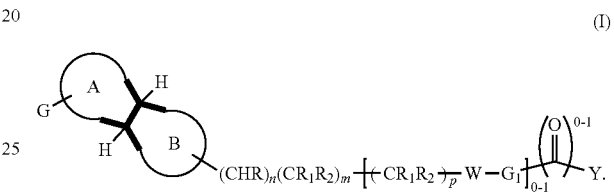

(I)

Ring A is a saturated 4-6 carbocyclic ring, optionally wherein one or two carbon atoms are heteroatoms selected from N and O; wherein the substituent G is linked to a carbon or nitrogen, and ring may optionally be substituted at the carbon atoms or nitrogen atom by one or more $C_{1-4}$alkyl group. Ring B is a saturated 4-6 heterocyclic ring in which one or two carbon atoms is heteroatoms selected among Nitrogen or Oxygen and the linking atom is always a Nitrogen atom; such ring may be also substituted at the carbon atoms or, possibly, at the different Nitrogen atom, by one or more $C_{1-4}$alkyl group. G is phenyl, or a 5-6 membered heteroaromatic group, which may be optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, halo$C_{1-4}$alkoxy, $SF_5$, —C(=O)$NH_2$, —C(=O)$OR_3$. W is —S—, —$SO_2$—, —O—, —$CHR_2$—, —$NR_3$—. The symbol n is 0 or 1. The symbol m is 1 or 2. The symbol p is 1 or 2. The symbol z is 0 or 1. R is hydrogen, $C_{1-4}$alkyl; $C_{1-4}$alkoxy. $R_1$ is hydrogen, F, $C_{1-4}$alkyl; hydroxyl, $C_{1-4}$alkoxy. $R_2$ is hydrogen, F, $C_{1-4}$alkyl; hydroxyl, $C_{1-4}$alkoxy. $R_3$ is hydrogen, $C_{1-4}$alkyl. $R_4$ is hydrogen or $C_{1-4}$alkyl; or —C(=O)$C_{1-4}$alkyl; —C(=O)$C_{1-4}$alkoxy$C_{1-4}$alkyl; —C(=O)cyclopropyl. $R_5$ is hydrogen or $C_{1-4}$alkyl. $R_6$ is hydrogen, or $C_{1-4}$alkyl. $R_7$ is halogen, or $C_{1-4}$alkyl, hydroxyl, or $C_{1-4}$alkoxy. $G_1$ is phenyl or a 5-6-membered heteroaromatic group or a 8-11 membered heteroaromatic group; any of which groups may be optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$ alkyl, $C_{1-4}$alkoxy, halo$C_{1-4}$alkoxy, $SF_5$, —C(=O) $NH_2$, —C(=O)(O)$_zR_3$. Y is phenyl or a moiety selected from the group consisting of: 5-6 membered heteroaromatic group, a 8-11 membered heteroaromatic group; a saturated mono 3-7 membered carbocyclic group or a 8-11 membered bicyclic carbocyclic group in which one or more carbon atoms may be replaced by $N(R_4)_z$, O, S; any of such groups may be optionally substituted by 1, 2 or 3 substituents selected from: halogen, cyano, hydroxyl, $C_{1-4}$alkylamino, C$_{1-4}$alkyl, haloC$_{1-4}$alkyl, C$_{1-4}$alkoxy, haloC$_{1-4}$alkoxy, C$_{1-4}$alkanoyl, —C(=O), —NHR$_4$, —NR$_5$R$_6$, SF$_5$, —C(=O)(O)$_z$R$_3$ or =O. In embodiments, when G$_1$ is a phenyl group, G$_1$ and Y are optionally fused together to form a benzofused aromatic or heteroaromatic system which might be optionally substituted by one or two substituents selected from: halogen, cyano, hydroxy, amino C$_{1-4}$alkyl, haloC$_{1-4}$alkyl, C$_{1-4}$alkoxy, haloC$_{1-4}$alkoxy, C$_{1-4}$alkanoyl, —C(=O)NH$_2$, —C(=O)OR$_3$, SF$_5$.

In embodiments, Ring A and Ring B together have the formula:

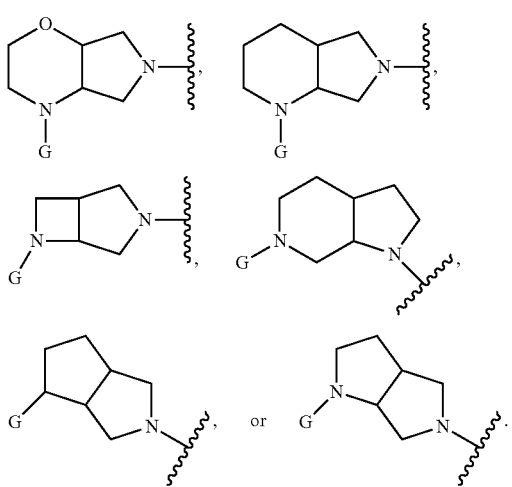

In embodiments, Ring A and Ring B together have the formula:

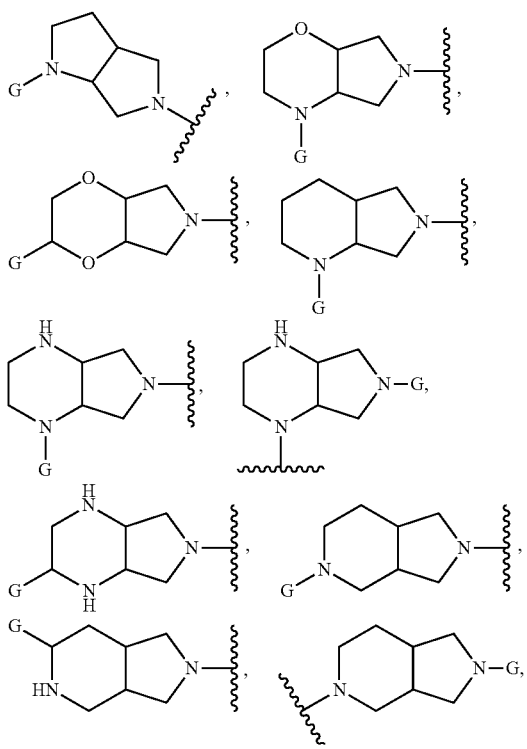

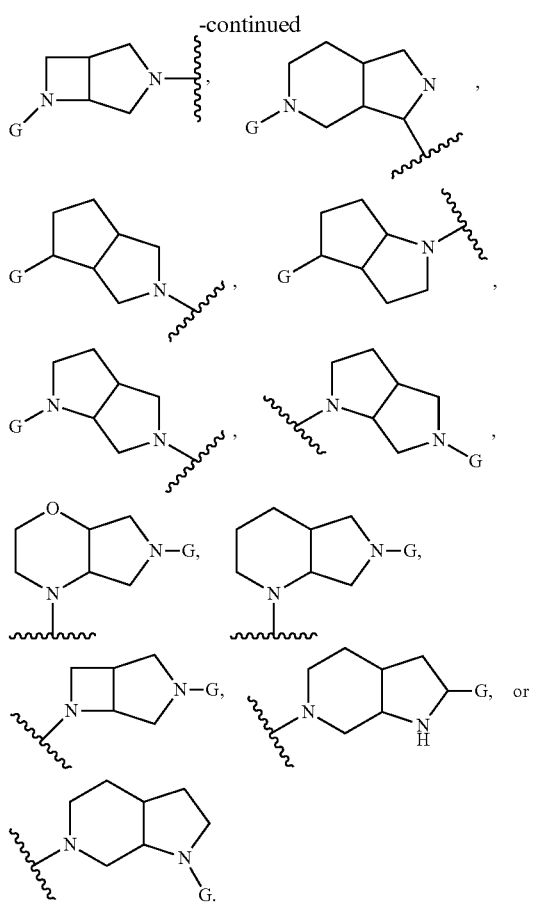

In embodiments, Ring A and Ring B together form a substituted or unsubstituted octahydropyrrolo[2,3-c]pyrrolyl. In embodiments, W is CHR$_2$, O or S and R, R$_1$ and R$_2$ are hydrogen. In embodiments, W is S. In embodiments, G is substituted 6 member heteroaromatic ring (e.g. pyridine, pyrazine) or a phenyl optionally substituted by 1, 2 or 3 substituents selected from: halogen, cyano, C$_{1-4}$alkyl, haloC$_{1-4}$alkyl, C$_{1-4}$alkoxy, haloC$_{1-4}$alkoxy. In embodiments, G may be a phenyl optionally substituted by 1, 2 or 3 substituents selected from: halogen, cyano, C$_{1-4}$alkyl, haloC$_{1-4}$alkyl, C$_{1-4}$alkoxy, haloC$_{1-4}$alkoxy. In embodiments, G$_1$ is substituted 5-6 membered heteroaromatic group. In embodiments, G$_1$ is 4-methyl-4H-1,2,4-triazole.

In embodiments, Y is a saturated mono 3-7 membered carbocyclic group in which 0 or 1 or 2 carbon atoms are replaced by a heteroatom independently selected from O or NR$_3$ (e.g. cyclopentyl, cyclohexyl, morpholinyl, piperidinyl, tetrahedropyranyl, dioxanyl, cyclohexanole); In embodiments, R$_3$ is C(=O)C$_{1-4}$alkyl. In embodiments, Y is a a 5-6 membered heteroaromatic group (e.g. oxazolyl, thiazolyl, 1-methyl-1H-pyrazol-4-yl, furanyl, thiophenyl, 1-methyl-1H-pyrrolyl, thiadiazolyl, piridinyl, 1,2-dihydropyridin-2-one, pirimidinyl, pirazyl, piridazinyl) optionally substituted by one or two substituents selected from: hydroxyl, C$_{1-4}$alkyl, (CH$_2$)$_z$C(=O)N(R$_4$R$_5$). In embodiments, C$_{1-4}$alkyl is methyl. In embodiments, G$_1$ and Y are fused together to form a benzofused heteroaromatic system (e.g. 1H-1,3-benzodiazole).

In embodiments, W is CHR$_2$. In embodiments, W is O. In embodiments, W is S. In embodiments, W is SO$_2$.

In embodiments, Ring A is azetidinyl, oxetanyl, dioxetanyl, pyrrolidinyl, tetrahydrofuranyl, imidazolidinyl, pyrazolidinyl, oxazolidinyl, isoxalolidinyl, dioxolanyl, piperidinyl, oxanyl, piperazinyl, morpholinyl, or dioxanyl. In embodiments, Ring A is dioxetanyl, pyrrolidinyl, tetrahydrofuranyl, imidazolidinyl, pyrazolidinyl, oxazolidinyl, isoxalolidinyl, dioxolanyl, piperidinyl, oxanyl, piperazinyl, morpholinyl, or dioxanyl. In embodiments, Ring A is piperidinyl, oxanyl, piperazinyl, morpholinyl, or dioxanyl. In embodiments, Ring A is piperidinyl.

In embodiments, Ring B is azetidinyl, oxetanyl, dioxetanyl, pyrrolidinyl, tetrahydrofuranyl, imidazolidinyl, pyrazolidinyl, oxazolidinyl, isoxalolidinyl, dioxolanyl, piperidinyl, oxanyl, piperazinyl, morpholinyl, or dioxanyl. In embodiments, Ring B is dioxetanyl, pyrrolidinyl, tetrahydrofuranyl, imidazolidinyl, pyrazolidinyl, oxazolidinyl, isoxalolidinyl, dioxolanyl, piperidinyl, oxanyl, piperazinyl, morpholinyl, or dioxanyl. In embodiments, Ring B is piperidinyl, oxanyl, piperazinyl, morpholinyl, or dioxanyl. In embodiments, Ring B is pyrrolidinyl.

In embodiments, G is an unsubstituted phenyl. In embodiments, G is an unsubstituted a 5 membered heteroaryl. In embodiments, G is an unsubstituted 6 membered heteroaryl. In embodiments, G is an unsubstituted phenyl. In embodiments, G is an unsubstituted pyridyl. In embodiments, G is an unsubstituted pyrazolyl. In embodiments, G is an unsubstituted imidazolyl. In embodiments, G is an unsubstituted oxazolyl. In embodiments, G is an unsubstituted isoxazolyl. In embodiments, G is an unsubstituted thiazolyl. In embodiments, G is an unsubstituted furanyl. In embodiments, G is an unsubstituted pyrrolyl. In embodiments, G is an unsubstituted thienyl.

In embodiments, G is a substituted phenyl. In embodiments, G is a substituted a 5 membered heteroaryl. In embodiments, G is a substituted 6 membered heteroaryl. In embodiments, G is a substituted phenyl. In embodiments, G is a substituted pyridyl. In embodiments, G is a substituted pyrazolyl. In embodiments, G is a substituted imidazolyl. In embodiments, G is a substituted oxazolyl. In embodiments, G is a substituted isoxazolyl. In embodiments, G is a substituted thiazolyl. In embodiments, G is a substituted furanyl. In embodiments, G is a substituted pyrrolyl. In embodiments, G is a substituted thienyl. In embodiments, G is substituted with halogen, —CN, —OH, —NH$_2$, $C_{1-4}$alkylamino, $C_{1-4}$alkyl, halo$C_{1-4}$alkyl, $C_{1-4}$alkoxy, $C_{1-4}$alkanoyl, halo$C_{1-4}$alkoxy, SF$_5$, —C(=O)NH$_2$, —C(=O)OR$_3$. In embodiments, G is substituted with halogen. In embodiments, G is substituted with cyano. In embodiments, G is substituted with hydroxyl. In embodiments, G is substituted with amino. In embodiments, G is substituted with $C_{1-4}$alkylamino. In embodiments, G is substituted with $C_{1-4}$alkyl. In embodiments, G is substituted with halo$C_{1-4}$alkyl. In embodiments, G is substituted with $C_{1-4}$alkoxy. In embodiments, G is substituted with halo$C_{1-4}$alkoxy. In embodiments, G is substituted with SF$_5$. In embodiments, G is substituted with —C(=O)NH$_2$. In embodiments, G is substituted with or —C(=O)(O)$_z$R$_3$.

In embodiments, R$_3$ is hydrogen. In embodiments, R$_3$ is —CH$_3$. In embodiments, R$_3$ is —CH$_2$CH$_3$. In embodiments, R$_2$ is hydrogen. In embodiments, R$_2$ is —CH$_3$. In embodiments, R$_2$ is —F. In embodiments, R$_2$ is —OH. In embodiments, R$_2$ is —CH$_2$CH$_3$. In embodiments, R$_2$ is —OCH$_2$CH$_3$. In embodiments, R$_2$ is —OCH$_3$. In embodiments, R$_1$ is hydrogen. In embodiments, R$_1$ is —CH$_3$. In embodiments, R$_1$ is —F. In embodiments, R$_1$ is —OH. In embodiments, R$_1$ is —CH$_2$CH$_3$. In embodiments, R$_1$ is —OCH$_2$CH$_3$. In embodiments, R$_1$ is —OCH$_3$.

In embodiments, R$_4$ is hydrogen. In embodiments, R$_4$ is $C_{1-4}$alkyl. In embodiments, R$_4$ is —C(=O)C$_{1-4}$alkyl. In embodiments, R$_4$ is —C(=O)C$_{1-4}$alkoxyC$_{1-4}$alkyl. In embodiments, R$_4$ is —C(=O)cyclopropyl. In embodiments, R$_4$ is —C(=O)CH$_3$. In embodiments, R$_4$ is —C(=O)OCH$_3$. In embodiments, R$_4$ is —C(=O)OCH$_2$CH$_3$.

In embodiments, R$_5$ is hydrogen. In embodiments, R$_5$ is —CH$_3$. In embodiments, R$_5$ is —CH$_2$CH$_3$. In embodiments, R$_6$ is hydrogen. In embodiments, R$_6$ is —CH$_3$. In embodiments, R$_6$ is —CH$_2$CH$_3$. In embodiments, R$_7$ is halogen. In embodiments, R$_7$ is —CH$_3$. In embodiments, R$_7$ is —F. In embodiments, R$_7$ is —Cl. In embodiments, R$_7$ is —OH. In embodiments, R$_7$ is —CH$_2$CH$_3$. In embodiments, R$_7$ is —OCH$_2$CH$_3$. In embodiments, R$_7$ is —OCH$_3$.

In embodiments, G$_1$ is phenyl. In embodiments, G$_1$ is an unsubstituted indenyl, naphthyl or azulenyl. In embodiments, G$_1$ is an unsubstituted 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl, benzoxazolyl, benzisoxazolyl, benzothiazolyl, benzisothiazolyl, benzothienyl, benzofuranyl, naphthridinyl, quinolyl, quinoxalinyl, quinazolinyl, cinnolinyl, or isoquinolyl.

In embodiments, G$_1$ is a substituted indenyl, naphthyl or azulenyl. In embodiments, G$_1$ is a substituted 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl, benzoxazolyl, benzisoxazolyl, benzothiazolyl, benzisothiazolyl, benzothienyl, benzofuranyl, naphthridinyl, quinolyl, quinoxalinyl, quinazolinyl, cinnolinyl, or isoquinolyl. In embodiments, G$_1$ is substituted with halogen. In embodiments, G$_1$ is substituted with cyano. In embodiments, G$_1$ is substituted with hydroxyl. In embodiments, G$_1$ is substituted with amino. In embodiments, G$_1$ is substituted with $C_{1-4}$alkylamino. In embodiments, G$_1$ is substituted with $C_{1-4}$alkyl. In embodiments, G$_1$ is substituted with halo$C_{1-4}$alkyl. In embodiments, G$_1$ is substituted with $C_{1-4}$alkoxy. In embodiments, G$_1$ is substituted with halo$C_{1-4}$alkoxy. In embodiments, G$_1$ is substituted with SF$_5$. In embodiments, G$_1$ is substituted with —C(=O)NH$_2$. In embodiments, G$_1$ is substituted with or —C(=O)(O)$_z$R$_3$.

In embodiments, Y is phenyl. In embodiments, Y is an unsubstituted indenyl, naphthyl or azulenyl. In embodiments, Y is an unsubstituted 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl, benzoxazolyl, benzisoxazolyl, benzothiazolyl, benzisothiazolyl, benzothienyl, benzofuranyl, naphthridinyl, quinolyl, quinoxalinyl, quinazolinyl, cinnolinyl, or isoquinolyl.

In embodiments, Y is a substituted indenyl, naphthyl or azulenyl. In embodiments, Y is a substituted 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl, benzoxazolyl, benzisoxazolyl, benzothiazolyl, benzisothiazolyl, benzothienyl, benzofuranyl, naphthridinyl, quinolyl, quinoxalinyl, quinazolinyl, cinnolinyl, or isoquinolyl. In embodiments, Y is substituted with halogen. In embodiments, Y is substituted with cyano. In embodiments, Y is substituted with hydroxyl. In embodiments, Y is substituted with amino. In embodiments, Y is substituted with $C_{1-4}$alkylamino. In embodiments, Y is substituted with $C_{1-4}$alkyl. In embodiments, Y is substituted with halo$C_{1-4}$alkyl. In embodiments, Y is substituted with $C_{1-4}$alkoxy. In embodiments, Y is substituted with halo$C_{1-4}$alkoxy. In embodiments, Y is substituted with SF$_5$. In embodiments, Y is substituted with —C(=O)NH$_2$.

In embodiments, Y is substituted with or —C(═O)(O)$_z$R$_3$.
In embodiments, Y is substituted with ═O.

In embodiments, G$_1$ and Y together form indolyl, isoindolyl, indazolyl, benzimidazolyl, benzoxazolyl, benzisoxazolyl, benzothiazolyl, benzisothiazolyl, benzothienyl, benzofuranyl, naphthridinyl, quinolyl, quinoxalinyl, quinazolinyl, cinnolinyl, or isoquinolyl.

In embodiments, n is 0. In embodiments, n is 1. In embodiments, m is 1. In embodiments, m is 2. In embodiments, p is 1. In embodiments, p is 2. In embodiments, z is 0. In embodiments, z is 1.

In embodiments, the compound has the formula:

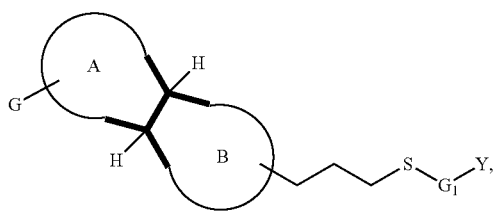

(IA)

wherein A, B, G, G$_1$, and Y, are defined are defined herein.
In embodiments, the compound has the formula:

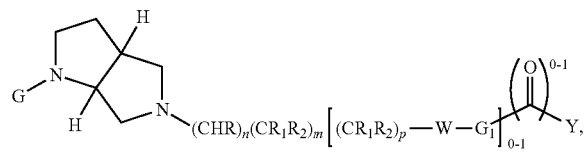

(II)

wherein G, G$_1$, W, Y, n, m, p, R$_1$, R$_2$, and R$_3$ are defined herein.
In embodiments, the compound has the formula:

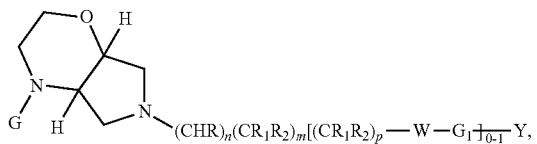

(III)

wherein G, G$_1$, W, Y, n, m, p, z, R, R$_1$, R$_2$, R$_3$, R$_4$, R$_5$, R$_6$ and R$_7$ are defined herein. In embodiments, Ring A and Ring B together form a substituted or unsubstituted octahydropyrrolo[3,4-b]morpholinyl.
In embodiments, the compound has the formula:

(IV)

wherein G, G$_1$, W, Y, n, m, p, z, R, R$_1$, R$_2$, R$_3$, R$_4$, R$_5$, R$_6$ and R$_7$ are defined herein.

In embodiments, the compound has the formula:

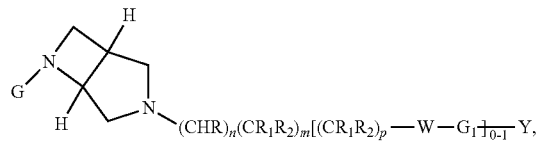

(V)

wherein G, G$_1$, W, Y, n, m, p, z, R$_1$, R$_2$, R$_3$, R$_4$, R$_5$, R$_6$ and R$_7$ are defined herein. In embodiments, Ring A and Ring B together form 3,6-diazabicyclo[3.2.0]heptanyl. In embodiments, W is CHR$_2$, O or S and R, R$_1$ and R$_2$ are hydrogen. In embodiments, W is S.

In embodiments, the compound has the formula:

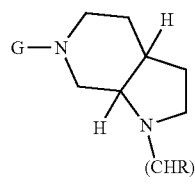

(VI)

wherein G, G$_1$, W, Y, n, m, p, z, R, R$_1$, R$_2$, R$_3$, R$_4$, R$_5$, R$_6$ and R$_7$ are defined herein. In embodiments, Ring A and Ring B together form a substituted or unsubstituted octahydro-1H-pyrrolo[2,3-c]pyridinyl.

In embodiments, the compound has the formula:

(VII)

wherein G, G$_1$, W, Y, n, m, p, z, R, R$_1$, R$_2$, R$_3$, R$_4$, R$_5$, R$_6$ and R$_7$ are defined herein. In embodiments, Ring A and Ring B together form a substituted or unsubstituted octahydro-1H-pyrrolo[2,3-c]pyridinyl.

In another embodiment, the compound has the formula:

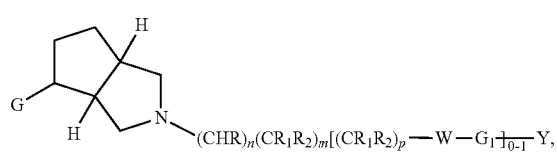

(VIII)

wherein G, $G_1$, W, Y, n, m, p, z, R, $R_1$, $R_2$, $R_3$, $R_4$, $R_5$, $R_6$ and $R_7$ are defined herein. In embodiments, Ring A and Ring B together form a substituted or unsubstituted octahydrocyclopenta[c]pyrrolyl.

In embodiments, the compound has the formula:

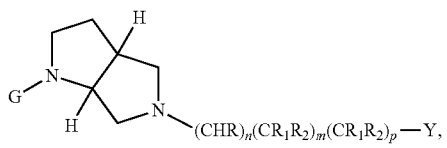

(IX)

wherein G, $G_1$, W, Y, n, m, p, z, R, $R_1$, $R_2$, $R_3$, $R_4$, $R_5$, $R_6$ and $R_7$ are defined herein. In embodiments, Ring A and Ring B together form a substituted or unsubstituted octahydropyrrolo[2,3-c]pyrrolyl.

In embodiments, the compound has the formula (X):

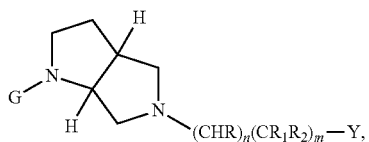

(X)

wherein G, $G_1$, W, Y, n, m, p, z, R, $R_1$, $R_2$, $R_3$, $R_4$, $R_5$, $R_6$ and $R_7$ are defined herein. In embodiments, Ring A and Ring B together form a substituted or unsubstituted octahydropyrrolo[2,3-c]pyrrolyl.

In embodiments, the hydrogens at the junction of Rings A and B may be in a "cis" or "trans" disposition. Relative stereochemistry "cis" is represented by using the bold highlight of the bonds, while the "trans" relative stereochemistry is represented by using bold and dotted highlight of the bonds.

In embodiments, Ring A and Ring B together have the formula:

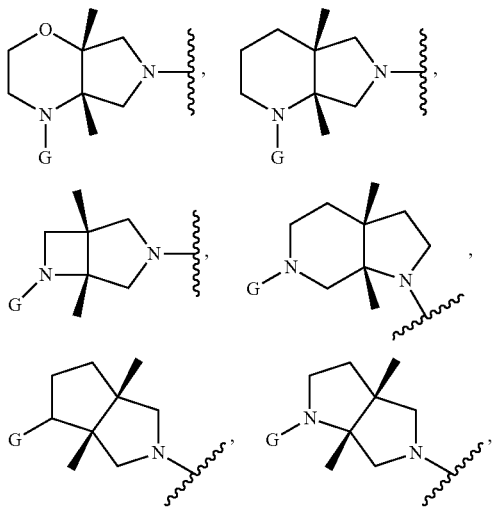

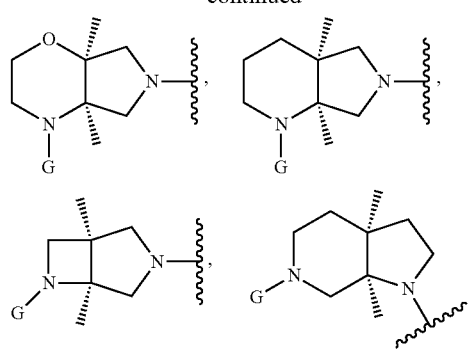

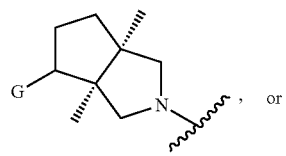, or

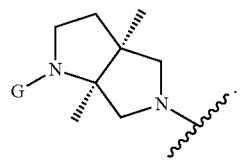

In embodiments, Ring A and Ring B together have the formula:

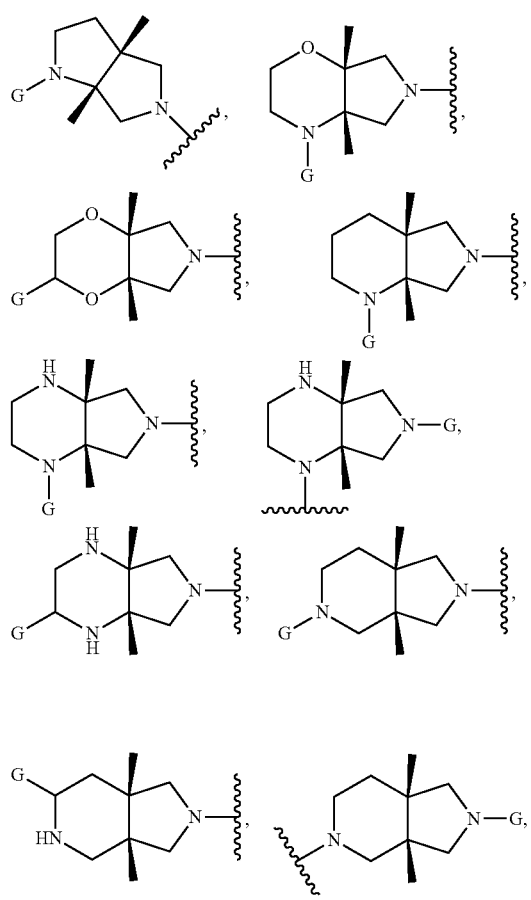

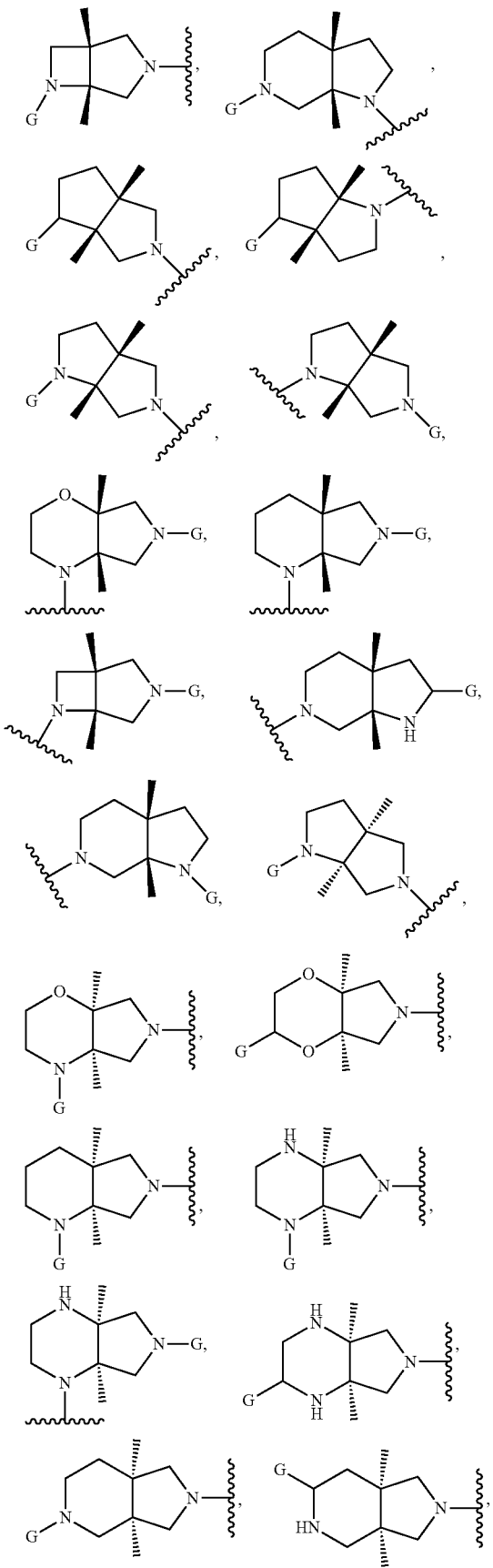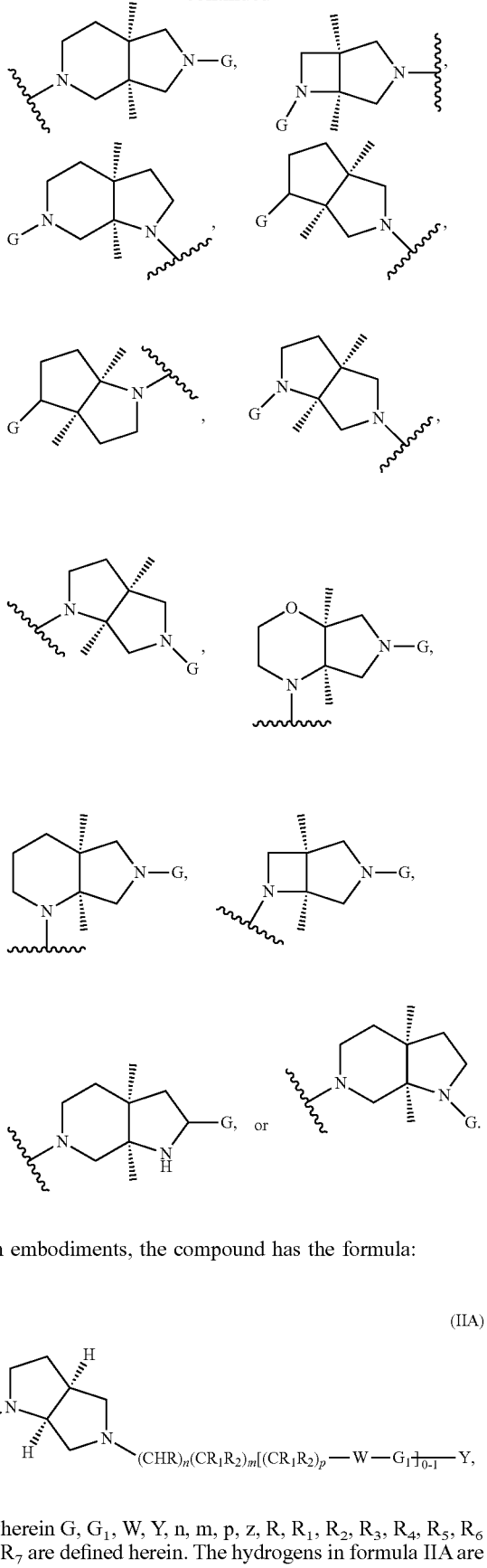
In embodiments, the compound has the formula:
(IIA)
$$G-N-(CHR)_n(CR_1R_2)_m[(CR_1R_2)_p-W-G_1]_{0-1}-Y,$$
wherein G, $G_1$, W, Y, n, m, p, z, R, $R_1$, $R_2$, $R_3$, $R_4$, $R_5$, $R_6$ and $R_7$ are defined herein. The hydrogens in formula IIA are herein referred to as being in the "cis" disposition.

In embodiments, the compound has the formula:

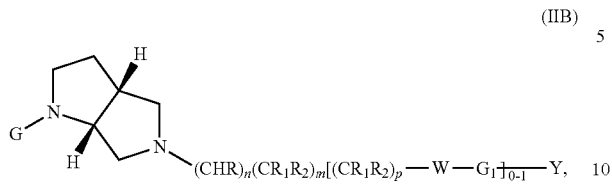
(IIB)

wherein G, $G_1$, W, Y, n, m, p, z, R, $R_1$, $R_2$, $R_3$, $R_4$, $R_5$, $R_6$ and $R_7$ are defined herein. The hydrogens in formula IIB are herein referred to as being in the "cis" disposition.

In embodiments, the compound has the formula:

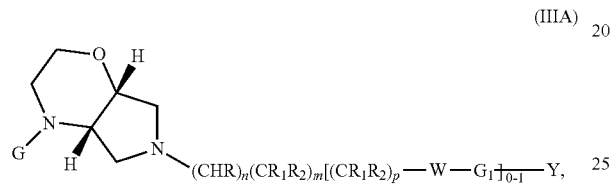
(IIIA)

Wherein G, $G_1$, W, Y, n, m, p, z, R, $R_1$, $R_2$, $R_3$, $R_4$, $R_5$, $R_6$ and $R_7$ are defined herein. The hydrogens in formula IIIA are herein referred to as being in the "cis" disposition.

In embodiments, the compound has the formula:

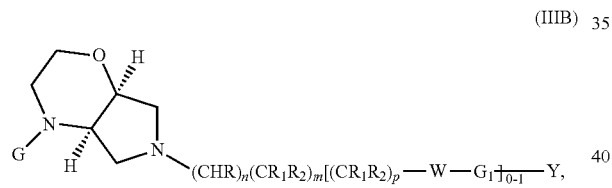
(IIIB)

wherein G, $G_1$, W, Y, n, m, p, z, R, $R_1$, $R_2$, $R_3$, $R_4$, $R_5$, $R_6$ and $R_7$ are defined herein. The hydrogens in formula IIIB are herein referred to as being in the "cis" disposition.

In embodiments, the compound has the formula:

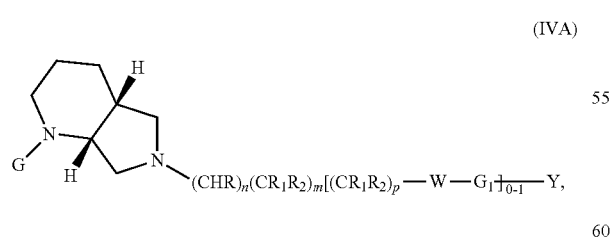
(IVA)

wherein G, $G_1$, W, Y, n, m, p, z, R, $R_1$, $R_2$, $R_3$, $R_4$, $R_5$, $R_6$ and $R_7$ are defined herein. The hydrogens in formula IVA are herein referred to as being in the "cis" disposition.

In embodiments, the compound has the formula:

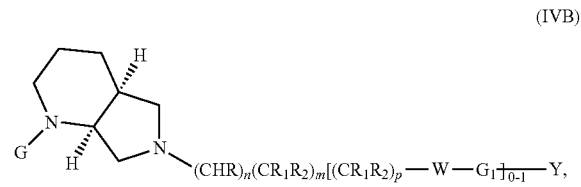
(IVB)

wherein G, $G_1$, W, Y, n, m, p, z, R, $R_1$, $R_2$, $R_3$, $R_4$, $R_5$, $R_6$ and $R_7$ are defined herein. The hydrogens in formula IVB are herein referred to as being in the "cis" disposition.

In embodiments, the compound has the formula:

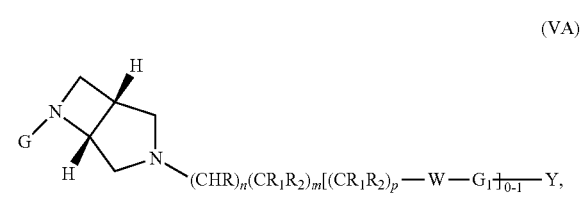
(VA)

wherein G, $G_1$, W, Y, n, m, p, z, R, $R_1$, $R_2$, $R_3$, $R_4$, $R_5$, $R_6$ and $R_7$ are defined herein. The hydrogens in formula VA are herein referred to as being in the "cis" disposition.

In embodiments, the compound has the formula:

(VB)

wherein G, $G_1$, W, Y, n, m, p, z, R, $R_1$, $R_2$, $R_3$, $R_4$, $R_5$, $R_6$ and $R_7$ are defined herein. The hydrogens in formula VB are herein referred to as being in the "cis" disposition.

In embodiments, the compound has the formula:

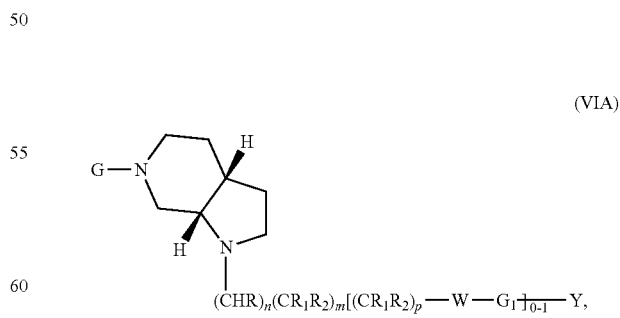
(VIA)

wherein G, $G_1$, W, Y, n, m, p, z, R, $R_1$, $R_2$, $R_3$, $R_4$, $R_5$, $R_6$ and $R_7$ are defined herein. The hydrogens in formula VIA are herein referred to as being in the "cis" disposition.

In embodiments, the compound has the formula:

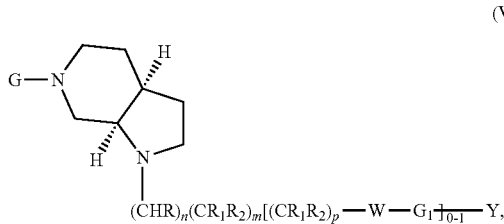
(VIB)

wherein G, $G_1$, W, Y, n, m, p, z, R, $R_1$, $R_2$, $R_3$, $R_4$, $R_5$, $R_6$ and $R_7$ are defined herein. The hydrogens in formula VIB are herein referred to as being in the "cis" disposition.

In embodiments, the compound has the formula:

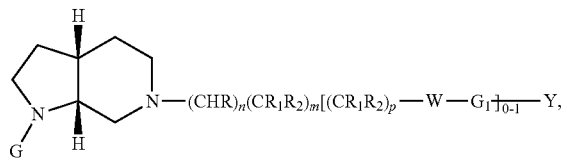
(VIIA)

wherein G, $G_1$, W, Y, n, m, p, z, R, $R_1$, $R_2$, $R_3$, $R_4$, $R_5$, $R_6$ and $R_7$ are defined herein. The hydrogens in formula VIIA are herein referred to as being in the "cis" disposition.

In embodiments, the compound has the formula:

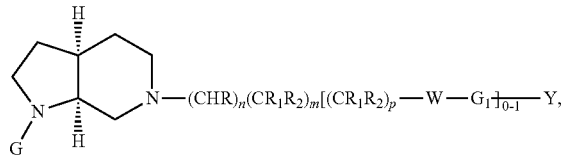
(VIIB)

wherein G, $G_1$, W, Y, n, m, p, z, R, $R_1$, $R_2$, $R_3$, $R_4$, $R_5$, $R_6$ and $R_7$ are defined herein. The hydrogens in formula VIIB are herein referred to as being in the "cis" disposition.

In embodiments, the compound has the formula:

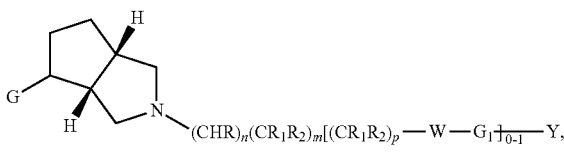
(VIIIA)

wherein G, $G_1$, W, Y, n, m, p, z, R, $R_1$, $R_2$, $R_3$, $R_4$, $R_5$, $R_6$ and $R_7$ are defined herein. The hydrogens in formula VIIIA are herein referred to as being in the "cis" disposition.

In embodiments, the compound has the formula:

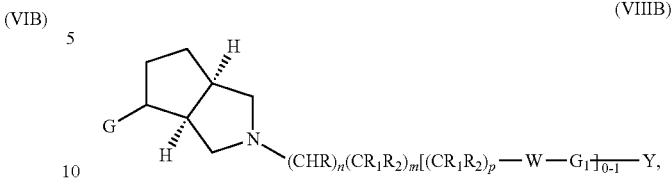
(VIIIB)

wherein G, $G_1$, W, Y, n, m, p, z, R, $R_1$, $R_2$, $R_3$, $R_4$, $R_5$, $R_6$ and $R_7$ are defined herein. The hydrogens in formula VIIIB are herein referred to as being in the "cis" disposition.

In embodiments, the compound has the formula:

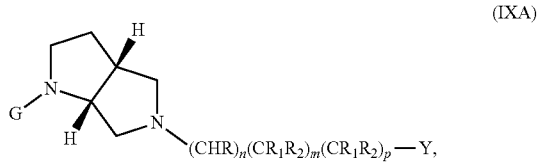
(IXA)

wherein G, $G_1$, W, Y, n, m, p, z, R, $R_1$, $R_2$, $R_3$, $R_4$, $R_5$, $R_6$ and $R_7$ are defined herein. The hydrogens in formula IXA are herein referred to as being in the "cis" disposition.

In embodiments, the compound has the formula:

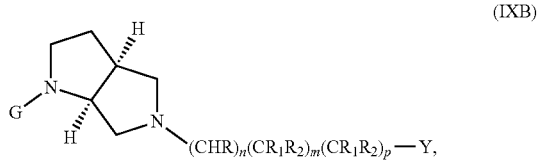
(IXB)

wherein G, $G_1$, W, Y, n, m, p, z, R, $R_1$, $R_2$, $R_3$, $R_4$, $R_5$, $R_6$ and $R_7$ are defined herein. The hydrogens in formula IXB are herein referred to as being in the "cis" disposition.

In embodiments, the compound has the formula (XA):

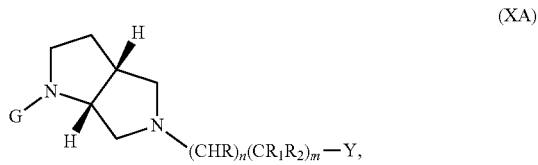
(XA)

wherein G, $G_1$, W, Y, n, m, p, z, R, $R_1$, $R_2$, $R_3$, $R_4$, $R_5$, $R_6$ and $R_7$ are defined herein. The hydrogens in formula IXA are herein referred to as being in the "cis" disposition.

In embodiments, the compound has the formula (XB):

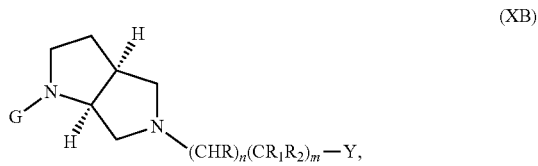
(XB)

wherein G, G$_1$, W, Y, n, m, p, z, R, R$_1$, R$_2$, R$_3$, R$_4$, R$_5$, R$_6$ and R$_7$ are defined herein. The hydrogens in formula IXB are herein referred to as being in the "cis" disposition.

The following embodiments in this paragraph refer to embodiments of formula (I), (II), (III), (IV), (V), (VI), (VII), (VIII), (IX), (X), (IA), (IIA), (IIIA), (IVA), (VA), (VIA), (VIIA), (VIIIA), (IXA), (IIB), (IIIB), (IVB), (VB), (VIB), (VIIB), (VIIIB), (IXB), (XA), and (XB). In embodiments, W is CHR$_2$, O or S and R, R$_1$ and R$_2$ are hydrogen. In embodiments, W is S. In embodiments, G is optionally substituted 6 member heteroaromatic ring (e.g. pyridine, pyrazine) or a phenyl optionally substituted by 1, 2 or 3 substituents selected from: halogen, cyano, C$_{1-4}$alkyl, haloC$_{1-4}$alkyl, C$_{1-4}$alkoxy, haloC$_{1-4}$alkoxy; In embodiments, G may be a phenyl optionally substituted by 1, 2 or 3 substituents selected from: halogen, cyano, C$_{1-4}$alkyl, haloC$_{1-4}$alkyl, C$_{1-4}$alkoxy, haloC$_{1-4}$alkoxy. In embodiments, G$_1$ is optionally substituted 5-6 membered heteroaromatic group. In embodiments, G$_1$ is 4-methyl-4H-1,2,4-triazole. In embodiments, Y is a saturated mono 3-7 membered carbocyclic group in which 0 or 1 or 2 carbon atoms are replaced by a heteroatom independently selected from O or NR$_3$ (e.g. cyclopentyl, cyclohexyl, morpholinyl, piperidinyl, tetrahedropyranyl, dioxanyl, cyclohexanole). In embodiments, R$_3$ is C(=O)C$_{1-4}$alkyl. In embodiments, Y is a 5-6 membered heteroaromatic group (e.g. oxazolyl, thiazolyl, 1-methyl-1H-pyrazol-4-yl, furanyl, thiophenyl, 1-methyl-1H-pyrrolyl, thiadiazolyl, piridinyl, 1,2-dihydropyridin-2-one, pirimidinyl, pirazyl, piridazinyl) optionally substituted by one or two substituents selected from: hydroxyl, C$_{1-4}$alkyl, (CH$_2$)$_z$C(=O)N(R$_4$R$_5$). In embodiments, C$_{1-4}$alkyl is methyl. In embodiments, G$_1$ and Y are fused together to form a benzofused heteroaromatic system (e.g. 1H-1,3-benzodiazole).

Enantiomer 1 refers to the first stereochemical entity (e.g., 3aR,6aR) in the list (e.g., 3aR,6aR or 3aS,6aS). Enantiomer 2 refers to the second stereochemical entity (e.g., 3aS,6aS) in the list (e.g., 3aR,6aR or 3aS,6aS).

In embodiments, the compound is 4-methyl-3-(4-methyl-1,3-oxazol-5-yl)-5-[(3-{1-[4(trifluoromethyl)phenyl]octahydropyrrolo[3,4-b]pyrrol-5-yl}propyl)sulfanyl]-4H-1,2,4-triazole; 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-[5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile; 3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile; 3-[(3aR,6aR or 3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile; 4-methyl-3-(4-methyl-1,3-oxazol-5-yl)-5-[(3-{1-phenyl-octahydropyrrolo[2,3-c]pyrrol-5-yl}propyl)-sulfanyl]-4H-1,2,4-triazole; 3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole; 3-[(3-{1-[2-fluoro-4-(trifluoromethyl)phenyl]-octahydropyrrolo[2,3-c]pyrrol-5-yl}propyl)sulfanyl]-4-methyl-5-(4-methyl-1,3-oxazol-5-yl)-4H-1,2,4-triazole; 3-({3-[(3aS,6aS or 3aR,6aR)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aR,6aR or 3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aS,6aS or 3aR,6aR)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aR,6aR or 3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole; 4-methyl-3-(4-methyl-1,3-oxazol-5-yl)-5-[(3-{1-[2-(trifluoromethoxy)phenyl]-octahydropyrrolo[3,4-b]pyrrol-5-yl}propyl)sulfanyl]-4H-1,2,4-triazole; 3-({3-[1-(2,6-difluorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(3,5-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(2,4-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(3-fluorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole; 3-({3-[(3aR,6aR or 3aS,6aS)-1-[4-(trifluoromethyl)phenyl]-octahydropyrrolo[2,3-c]pyrrol-5-yl]-propyl}sulfanyl)-4-methyl-5-(oxan-4-yl)-4H-1,2,4-triazole; 3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole; 3-({3-[1-(4-fluorophenyl)-octahydropyrrolo[3,4-b]pyrrol-5-yl]propyl}sulfanyl)-4-methyl-5-(oxan-4-yl)-4H-1,2,4-triazole; 3-({3-[(3aS,6aS or 3aR,6aR)-1-(4-fluorophenyl)-octahydropyrrolo[3,4-b]pyrrol-5-yl]propyl}sulfanyl)-4-methyl-5-(oxan-4-yl)-4H-1,2,4-triazole; 3-({3-[(3aR,6aR or 3aS,6aS)-1-(4-fluorophenyl)-octahydropyrrolo[3,4-b]pyrrol-5-yl]propyl}-sulfanyl)-4-methyl-5-(oxan-4-yl)-4H-1,2,4-triazole; 3-cyclopentyl-4-methyl-5-[(3-{1-[4-(trifluoromethyl)phenyl]-octahydropyrrolo[3,4-b]pyrrol-5-yl}propyl)sulfanyl]-4H-1,2,4-triazole; 3-({3-[(3aS,6aS or 3aR,6aR)-1-[4-(trifluoromethyl)phenyl]-octahydropyrrolo[3,4-b]pyrrol-5-yl]-propyl}sulfanyl)-5-cyclopentyl-4-methyl-4H-1,2,4-triazole; 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole; 3-cyclohexyl-4-methyl-5-[(3-{1-[4-(trifluoromethyl)phenyl]-octahydropyrrolo[3,4-b]pyrrol-5-yl}propyl)sulfanyl]-4H-1,2,4-triazol; 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole; 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole; 3-cyclohexyl-5-({3-[1-(4-fluorophenyl)-octahydropyrrolo[3,4-b]pyrrol-5-yl]propyl}sulfanyl)-4-methyl-4H-1,2,4-triazole; 3-({3-[(3aS,6aS or 3aR,6aR)-1-(4-fluorophenyl)-octahydropyrrolo[3,4-b]pyrrol-5-yl]propyl}sulfanyl)-5-cyclohexyl-4-methyl-4H-1,2,4-triazole; 3-({3-[(3aR,6aR or 3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole; 1-methyl-2-[(3-{1-[4-(trifluoromethyl)phenyl]-octahydropyrrolo[3,4-b]pyrrol-5-yl}propyl)sulfanyl]-1H-1,3-benzodiazole; 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}morpholine; 4-[5-({3-[(3aS,6aS or 3aR,6aR)-1-[4-(trifluoromethyl)phenyl]- octahydropyrrolo[3,4-b]pyrrol-5-yl]propyl}sulfanyl)-4-methyl-4H-1,2,4-triazol-3-yl]morpholine; 4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine; 2-{4-methyl-5-[(3-{1-[4-(trifluoromethyl)phenyl]-octahydropyrrolo[2,3-c]pyrrol-5-yl}propyl)-sulfanyl]-4H-1,2,4-triazol-3-yl}pyrazine; 2-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine; 2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine; 3-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile; 2-[5-({3-[1-(4-fluorophenyl)-octahydropyrrolo[3,4-b]pyrrol-5-yl]propyl}sulfanyl)-4-methyl-4H-1,2,4-triazol-3-yl]pyrazine; 2-{4-methyl-5-[(3-{1-[2-(trifluoromethoxy)phenyl]-octahydropyrrolo[3,4-b]pyrrol-5-yl}propyl)-sulfanyl]-4H-1,2,4-triazol-3-yl}pyrazine; 2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine; 2-[5-({3-[1-(3-fluorophenyl)-octahydropyrrolo[3,4-b]pyrrol-5-yl]propyl}sulfanyl)-4-methyl-4H-1,2,4-triazol-3-yl]pyrazine; 2-[5-({3-[1-(2,4-difluorophenyl)-octahydropyrrolo[2,3-c]pyrrol-5-yl]propyl}sulfanyl)-4-methyl-4H-1,2,4-triazol-3-yl]pyrazine; 2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine; 2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine; 2-[4-methyl-5-({3-[1-(4-methylphenyl)-octahydropyrrolo[3,4-b]pyrrol-5-yl]propyl}sulfanyl)-4H-1,2,4-triazol-3-yl]pyrazine; 2-[5-({3-[1-(3-methoxyphenyl)-octahydropyrrolo[3,4-b]pyrrol-5-yl]propyl}sulfanyl)-4-methyl-4H-1,2,4-triazol-3-yl]pyrazine; 2-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile; 2-[4-methyl-5-({3-[1-(3-methylphenyl)-octahydropyrrolo[3,4-b]pyrrol-5-yl]propyl}sulfanyl)-4H-1,2,4-triazol-3-yl]pyrazine; 2-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}pyrazine; 2-{4-methyl-5-[(3-{1-[3-(trifluoromethoxy)phenyl]-octahydropyrrolo[3,4-b]pyrrol-5-yl}propyl)-sulfanyl]-4H-1,2,4-triazol-3-yl}pyrazine; 2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine; 2-{4-methyl-5-[(3-{1-[2-(trifluoromethyl)phenyl]-octahydropyrrolo[3,4-b]pyrrol-5-yl]propyl)sulfanyl]-4H-1,2,4-triazol-3-yl})pyrazine; 2-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine; 2-[5-({3-[1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine; 2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine; 2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine; 2-{5-[(3-{1-[2-fluoro-6-(trifluoromethyl)phenyl]-octahydropyrrolo[3,4-b]pyrrol-5-yl}propyl)sulfanyl]-4-methyl-4H-1,2,4-triazol-3-yl}pyrazine; 2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine; 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrimidine; 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine; 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine; 4-[5-({3-[1-(4-fluorophenyl)-octahydropyrrolo[3,4-b]pyrrol-5-yl]propyl}sulfanyl)-4-methyl-4H-1,2,4-triazol-3-yl]pyrimidine; 3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine; 3-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride; 3-[5-({3-[(3aR,6aR or 3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]pyridine; 3-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine; 3-{4-methyl-5-[(3-{1-[2-(trifluoromethyl)phenyl]-octahydropyrrolo[3,4-b]pyrrol-5-yl}propyl)-sulfanyl]-4H-1,2,4-triazol-3 yl}pyridine; 3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 4-methyl-3-(1-methyl-1H-pyrazol-4-yl)-5-[(3-{1-[4-(trifluoromethyl)phenyl]-octahydropyrrolo[3,4-b]pyrrol-5-yl}propyl)sulfanyl]-4H-1,2,4-triazole; 4-{4-methyl-5-[(3-{1-[4-(trifluoromethyl)phenyl]-octahydropyrrolo[3,4-b]pyrrol-5-yl}propyl)-sulfanyl]-4H-1,2,4-triazol-3-yl}pyridine; 4-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine; 4-{4-methyl-5-[(3-{1-[2-(trifluoromethyl)phenyl]-octahydropyrrolo[3,4-b]pyrrol-5-yl}propyl)-sulfanyl]-4H-1,2,4-triazol-3-yl}pyridine; 4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 2-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine; 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine; 4-methyl-3-(1,3-thiazol-2-yl)-5-[(3-{1-[4-(trifluoromethyl)phenyl]-octahydropyrrolo[3,4-b]pyrrol-5-yl}propyl)sulfanyl]-4H-1,2,4-triazole; 4-methyl-3-(3-methyl-1,2-oxazol-5-yl)-5-[(3-{1-[4-(trifluoromethyl)phenyl]-octahydropyrrolo[3,4-b]pyrrol-5-yl}propyl)sulfanyl]-4H-1,2,4-triazole; 4-methyl-3-(4-methyl-1,3-thiazol-5-yl)-5-[(3-{1-[4-(trifluoromethyl)phenyl]-octahydropyrrolo[3,4-b]pyrrol-5-yl}propyl)sulfanyl]-4H-1,2,4-triazole; 4-{4-methyl-5-[(3-{1-[4-(trifluoromethyl)phenyl]-octahydropyrrolo[2,3-c]pyrrol-5-yl}propyl)sulfanyl]-4H-1,2,4-thiazol-3-yl}-1,2-dihydropyridin-2-one; 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one; 4-[5-({3-[1-(4-fluorophenyl)-octahydropyrrolo[2,3-c]pyrrol-5-yl]propyl}sulfanyl)-4-methyl-4H-1,2,4-thiazol-3-yl]-1,2-dihydropyridin-2-one; 4-[5-({3-[(3aS,6aS or 3aR,6aR)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one; 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[1-(4-fluorophenyl)- octahydropyrrolo[2,3-c]pyrrol-5-yl]propyl}sulfanyl)-4-methyl-4H-1,2,4-triazol-3-yl]-1,2-dihydropyridin-2-one; 5-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl},1,2-dihydropyridin-2-one; 5-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one; 3-({3-[1-(2,6-difluorophenyl)-octahydropyrrolo[3,4-b]pyrrol-5-yl]propyl}sulfanyl)-4-methyl-5-(1-methyl-1H-pyrazol-5-yl)-4H-1,2,4-triazole; 4-methyl-3-(1-methyl-1H-pyrazol-5-yl)-5-[(3-{1-[2-(trifluoromethyl)phenyl]-octahydropyrrolo[3,4-b]pyrrol-5-yl}propyl)sulfanyl]-4H-1,2,4-triazole; 3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole; 1-methyl-5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one; 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one; 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine-2-carboxamide; 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide; 5-[5-({3-[1-(4-fluorophenyl)-octahydropyrrolo[3,4-b]pyrrol-5-yl]propyl})sulfanyl)-4-methyl-4H-1,2,4-triazol-3-yl]pyridine-2-carboxamide; 5-[5-({3-[(3aS,6aS or 3aR,6aR)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aR,6aR or 3aS,6aS)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[1-(2,6-difluorophenyl)-octahydropyrrolo[3,4-b]pyrrol-5-yl]propyl})sulfanyl)-4-methyl-4H-1,2,4-triazol-3-yl]pyridine-2-carboxamide; 5-[5-({3-[(3aS,6aS or 3aR,6aR)-1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aR,6aR or 3aS,6aS)-1-(2,6-difluorophenyl)-octahydropyrrolo[3,4-b]pyrrol-5 yl]propyl}sulfanyl)-4-methyl-4H-1,2,4-triazol-3-yl]pyridine-2-carboxamide; 5-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyridine-2-carboxamide; 5-[5-({3-[(3aS,6aS or 3aR,6aR)-1-(2,4,6-trifluorophenyl)-octahydropyrrolo[2,3-c]pyrrol-5-yl]propyl})sulfanyl)-4-methyl-4H-1,2,4-triazol-3-yl]pyridine-2-carboxamide; 5-[5-({3-[(3aR,6aR or 3aS,6aS)-1-(2,4,6-trifluorophenyl)-octahydropyrrolo[2,3-c]pyrrol-5-yl]-propyl}sulfanyl)-4-methyl-4H-1,2,4-triazol-3-yl]pyridine-2-carboxamide; 4-[5-({3-[1-(4-fluorophenyl)-octahydropyrrolo[3,4-b]pyrrol-5-yl]propyl}sulfanyl)-4-methyl-4H-1,2,4-triazol-3-yl]-1-methyl-1,2-dihydropyridin-2-one; 1-methyl-4-{4-methyl-5-({3-[1-(2,4,6-trifluorophenyl)-octahydropyrrolo[2,3-c]pyrrol-5-yl]propyl}sulfanyl)-4H-1,2,4-triazol-3-yl]-1,2-dihydropyridin-2-one; 4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one; 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol; 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol; 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol; 4-methyl-3-(4-methyl-1,3-oxazol-5-yl)-5-({3-[(4S or 4R)-4-[4-(trifluoromethyl)phenyl]-octahydrocyclopenta[c]pyrrol-2-yl]propyl}sulfanyl)-4H-1,2,4-triazole, Diastereoisomer 1; 3-({3-[(4aR,7aR or 4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole; or pharmaceutical acceptable salt thereof.

In embodiments, the compound is 4-methyl-3-(4-methyl-1,3-oxazol-5-yl)-5-[(3-{1-[4(trifluoromethyl)phenyl]octahydropyrrolo[3,4-b]pyrrol-5-yl}propyl)sulfanyl]-4H-1,2,4-triazole; 3-({3-[(3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-[5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile; 3-[(3aS,6aS)-5-(3-{[4-methyl-5-(4-methyl-1,3-oxazol-5-yl)-4H-1,2,4-triazol-3-yl]-sulfanyl}propyl)-octahydropyrrolo[2,3-c]pyrrol-1-yl]benzonitrile; 3-[(3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile; 4-methyl-3-(4-methyl-1,3-oxazol-5-yl)-5-[(3-{1-phenyl-octahydropyrrolo[2,3-c]pyrrol-5-yl}propyl)sulfanyl]-4H-1,2,4-triazole; 3-({3-[(3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole; 3-[(3-{1-[2-fluoro-4-(trifluoromethyl)phenyl]-octahydropyrrolo[2,3-c]pyrrol-5-yl}propyl)sulfanyl]-4-methyl-5-(4-methyl-1,3-oxazol-5-yl)-4H-1,2,4-triazole; 3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole; 4-methyl-3-(4-methyl-1,3-oxazol-5-yl)-5-[(3-{1-[2-(trifluoromethoxy)phenyl]-octahydropyrrolo[3,4-b]pyrrol-5-yl}propyl)sulfanyl]-4H-1,2,4-triazole; 3-({3-[1-(2,6-difluorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(3,5-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(2,4-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(3-fluorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[(3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole; 3-({3-[(3aS,6aS)-1-[4-(trifluoromethyl)phenyl]-octahydropyrrolo[2,3-c]pyrrol-5-yl]-propyl}sulfanyl)-4-methyl-5-(oxan-4-yl)-4H-1,2,4-triazole; 3-({3-[(3aS,6aS)-1-phenyl-octahydropyrrolo[2,3-c]pyrrol-5-yl]propyl}sulfanyl)-4-methyl-5-(oxan-4-yl)-4H-1,2,4-triazole; 3-({3-[1-(4-fluorophenyl)-octahydropyrrolo[3,4-b]pyrrol-5-yl]propyl}sulfanyl)-4-methyl-5-(oxan-4-yl)-4H-1,2,4-triazole; 3-({3-[(3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole; 3-({3-[(3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole; 3-cyclopentyl-4-methyl-5-[(3-{1-[4-(trifluoromethyl)phenyl]-octahydropyrrolo[3,4-b]pyrrol-5-yl}propyl)sulfanyl]-4H-1,2,4-triazole; 3-({3-[(3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole; 3-({3-[(3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole; 3-cyclohexyl-4-methyl-5-[(3-{1-[4-(trifluoromethyl)phenyl]-octahydropyrrolo[3,4-b]pyrrol-5-yl]-propyl)sulfanyl]-4H-1,2,4-triazol; 3-({3-[(3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole; 3-({3-[(3aS,6aS)-1-[4-(trifluoromethyl)phenyl]-octahydropyrrolo[3,4-b]pyrrol-5-yl]-propyl}sulfanyl)-5-cyclohexyl-4-methyl-AH-1,2,4-triazole; 3-cyclohexyl-5-({3-[1-(4-fluorophenyl)-octahydropyrrolo[3,4-b]pyrrol-5-yl]propyl}sulfanyl)-4-methyl-4H-1,2,4-triazole; 3-({3-[(3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole; 3-({3-[(3aS,6aS)-1-(4-fluorophenyl)-octahydropyrrolo-[3,4-b]pyrrol-5-yl]propyl}sulfanyl)-5-cyclohexyl-4-methyl-4H-1,2,4-triazole; 1-methyl-2-[(3-{1-[4-(trifluoromethyl)phenyl]-octahydropyrrolo[3,4-b]pyrrol-5-yl}propyl)sulfanyl]-1H-1,3-benzodiazole; 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}morpholine; 4-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine; 4-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine; 2-{4-methyl-5-[(3-{1-[4-(trifluoromethyl)phenyl]-octahydropyrrolo[2,3-c]pyrrol-5-yl}propyl)-sulfanyl]-4H-1,2,4-triazol-3-yl}pyrazine; 2-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine; 2-[5-({3-[(3aS,6aS)-1-[4-(trifluoromethyl)phenyl]-octahydropyrrolo[2,3-c]pyrrol-5-yl]-propyl}sulfanyl)-4-methyl-4H-1,2,4-triazol-3-yl]pyrazine; 3-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile; 2-[4-({3-[1-(4-fluorophenyl)-octahydropyrrolo[3,4-b]pyrrol-5-yl]propyl}sulfanyl)-4-methyl-4H-1,2,4-triazol-3-yl]pyrazine; 2-{4-methyl-5-[(3-{1-[2-(trifluoromethoxy)phenyl]-octahydropyrrolo[3,4-b]pyrrol-5-yl}propyl)sulfanyl]-4H-1,2,4-triazol-3-yl}pyrazine; 2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine; 2-[5-({3-[1-(3-fluorophenyl)-octahydropyrrolo[3,4-b]pyrrol-5-yl]propyl})sulfanyl)-4-methyl-4H-1,2,4-triazol-3-yl]pyrazine; 2-[5-({3-[1-(2,4-difluorophenyl)-octahydropyrrolo[2,3-c]pyrrol-5-yl]propyl}sulfanyl)-4-methyl-4H-1,2,4-triazol-3-yl]pyrazine; 2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine; 2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine; 2-[4-methyl-5-({3-[1-(4-methylphenyl)-octahydropyrrolo[3,4-b]pyrrol-5-yl]propyl}sulfanyl)-4H-1,2,4-triazol-3-yl]pyrazine; 2-[5-({3-[1-(3-methoxyphenyl)-octahydropyrrolo[3,4-b]pyrrol-5-yl]propyl}sulfanyl)-4-methyl-4H-1,2,4-triazol-3-yl]pyrazine; 2-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile; 2-[4-methyl-5-({3-[1-(3-methylphenyl)-octahydropyrrolo[3,4-b]pyrrol-5-yl]propyl}sulfanyl)-4H-1,2,4-triazol-3-yl]pyrazine; 2-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}pyrazine; 2-{4-methyl-5-[(3-{1-[3-(trifluoromethoxy)phenyl]-octahydropyrrolo[3,4-b]pyrrol-5-yl}propyl)-sulfanyl]-4H-1,2,4-triazol-3-yl}pyrazine; 2-[5-({3-[(3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine; 2-{4-methyl-5-[(3-{1-[2-(trifluoromethyl)phenyl]-octahydropyrrolo[3,4-b]pyrrol-5-yl}propyl)-sulfanyl]-4H-1,2,4-triazol-3-yl}pyrazine; 2-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine; 2-[5-({3-[1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine; 2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine; 2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine; 2-{5-[(3-{1-[2-fluoro-6-(trifluoromethyl)phenyl]-octahydropyrrolo[3,4-b]pyrrol-5-yl}propyl)sulfanyl]-4-methyl-4H-1,2,4-triazol-3-yl}pyrazine; 2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine; 4-{4-methyl-5-[(3-{1-[4-(trifluoromethyl)phenyl]-octahydropyrrolo[2,3-c]pyrrol-5-yl]propyl)sulfanyl]-4H-1,2,4-triazol-3-yl}pyrimidine; 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine; 4-[5-({3-[(3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine; 4-[5-({3-[(3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine; 4-[5-({3-[(3aS,6aS)-1-[4-(trifluoromethyl)phenyl]-octahydropyrrolo[2,3-c]pyrrol-5-yl]-propyl}sulfanyl)-4-methyl-4H-1,2,4-triazol-3-yl]pyrimidine; 4-[5-({3-[1-(4-fluorophenyl)-octahydropyrrolo[3,4-b]pyrrol-5-yl]propyl}sulfanyl)-4-methyl-4H-1,2,4-triazol-3-yl]pyrimidine; 3-{4-methyl-5-[(3-{1-[4-(trifluoromethyl)phenyl]-octahydropyrrolo[3,4-b]pyrrol-5-yl}propyl)-sulfanyl]-4H-1,2,4-triazol-3-yl}pyridine; 3-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride; 3-[5-({3-[(3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride; 3-[5-({3-[(3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]pyridine; 3-[5-({3-[(3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine; 3-[5-({3-[1-(2,6-difluorophenyl)-octahydropyrrolo[3,4-b]pyrrol-5-yl]propyl})sulfanyl)-4-methyl-4H-1,2,4-triazol-3-yl]pyridine; 3-{4-methyl-5-[(3-{1-[2-(trifluoromethyl)phenyl]-octahydropyrrolo[3,4-b]pyrrol-5-yl}propyl)sulfanyl]-4H-1,2,4-triazol-3yl}pyridine; 3-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 3-[5-({3-[(3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 4-methyl-3-(1-methyl-1H-pyrazol-4-yl)-5-[(3-{1-[4-(trifluoromethyl)phenyl]-octahydropyrrolo[3,4-b]pyrrol-5-yl}propyl)sulfanyl]-4H-1,2,4-triazole; 4-{4-methyl-5-[(3-{1-[4-(trifluoromethyl)phenyl]-octahydropyrrolo[3,4-b]pyrrol-5-yl}propyl)-sulfanyl]-4H-1,2,4-triazol-3-yl}pyridine; 4-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine; 4-{4-methyl-5-[(3-{1-[2-(trifluoromethyl)phenyl]-octahydropyrrolo[3,4-b]pyrrol-5-yl}propyl)-sulfanyl]-4H-1,2,4-triazol-3-yl}pyridine; 4-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 4-[5-({3-[(3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 2-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine; 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine; 4-methyl-3-(1,3-thiazol-2-yl)-5-[(3-{1-[4-(trifluoromethyl)phenyl]-octahydropyrrolo[3,4-b]pyrrol-5-yl}propyl)sulfanyl]-4H-1,2,4-triazole; 4-methyl-3-(3-methyl-1,2-oxazol-5-yl)-5-[(3-{1-[4-(trifluoromethyl)phenyl]-octahydropyrrolo[3,4-b]pyrrol-5-yl}propyl)sulfanyl]-4H-1,2,4-triazole; 4-methyl-3-(4-methyl-1,3-thiazol-5-yl)-5-[(3-{1-[4-(trifluoromethyl)phenyl]-octahydropyrrolo[3,4-b]pyrrol-5-yl}propyl)sulfanyl]-4H-1,2,4-triazole; 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}-1,2-dihydropyridin-2-one; 4-[5-({3-[(3aS,6aS)-1-[4-(trifluoromethyl)phenyl]-octahydropyrrolo[2,3-c]pyrrol-5-yl]-propyl}sulfanyl)-4-methyl-4H-1,2,4-triazol-3-yl]-1,2-dihydropyridin-2-one; 4-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one; 4-[5-({3-[(3aS,6aS)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one; 5-{4-methyl-5-[(3-{1-[4-(trifluoromethyl)phenyl]-octahydropyrrolo[3,4-b]pyrrol-5-yl}propyl)-sulfanyl]-4H-1,2,4-triazol-3-yl}-1,2-dihydropyridin-2-one; 5-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one; 5-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one; 5-[5-({3-[(3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one; 3-({3-[1-(2,6-difluorophenyl)-octahydropyrrolo[3,4-b]pyrrol-5-yl]propyl}sulfanyl)-4-methyl-5-(i-methyl-1H-pyrazol-5-yl)-4H-1,2,4-triazole; 4-methyl-3-(1-methyl-1H-pyrazol-5-yl)-5-[(3-{1-[2-(trifluoromethyl)phenyl]-octahydropyrrolo[3,4-b]pyrrol-5-yl}propyl)sulfanyl]-4H-1,2,4-triazole; 3-({3-[(3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole; 3-({3-[(3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole; 1-methyl-5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[(3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]-1-methyl-1,2-dihydropyridin-2-one; 5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one; 5-{4-methyl-5-[(3-1{1-[4-(trifluoromethyl)phenyl]-octahydropyrrolo[3,4-b]pyrrol-5-yl}propyl)sulfanyl]-4H-1,2,4-triazol-3-yl}pyridine-2-carboxamide; 5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide; 5-[5-({3-[1-(4-fluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aS,6aS)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aS,6aS)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aS,6aS)-1-(2,6-difluorophenyl)-octahydropyrrolo[3,4-b]pyrrol-5-yl]propyl})sulfanyl)-4-methyl-4H-1,2,4-triazol-3-yl]pyridine-2-carboxamide; 5-[5-({3-[(3aS,6aS)-1-(2,6-difluorophenyl)-octahydropyrrolo[3,4-b]pyrrol-5yl]propyl}sulfanyl)-4-methyl-4H-1,2,4-triazol-3-yl]pyridine-2-carboxamide; 5-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyridine-2-carboxamide; 5-[5-({3-[(3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide; 5-[5-({3-[(3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide; 4-[5-({3-[1-(4-fluorophenyl)-octahydropyrrolo[3,4-b]pyrrol-5-yl]propyl}sulfanyl)-4-methyl-4H-1,2,4-triazol-3-yl]-1-methyl-1,2-dihydropyridin-2-one; 1-methyl-4-{4-methyl-5-({3-[1-(2,4,6-trifluorophenyl)-octahydropyrrolo[2,3-c]pyrrol-5-yl]propyl}sulfanyl)-4H-1,2,4-triazol-3-yl]-1,2-dihydropyridin-2-one; 4-[5-({3-[(3aS,6aS)-1-(2,4,6-trifluorophenyl)- octahydropyrrolo[2,3-c]pyrrol-5-yl]-propyl}sulfanyl)-4-methyl-4H-1,2,4-triazol-3-yl]-1-methyl-1,2-dihydropyridin-2-one; 4-[5-({3-[(3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one; 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol; 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol; 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol; 4-methyl-3-(4-methyl-1,3-oxazol-5-yl)-5-({3-[(4S)-4-[4-(trifluoromethyl)phenyl]-octahydrocyclopenta[c]pyrrol-2-yl]propyl}sulfanyl)-4H-1,2,4-triazole; 3-({3-[(4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole; or pharmaceutical acceptable salt thereof.

In embodiments, the compound is as described in Ex. 1: 4-methyl-3-(4-methyl-1,3-oxazol-5-yl)-5-[(3-{1-[4-(trifluoromethyl)phenyl]octahydropyrrolo[3,4-b]pyrrol-5-yl}propyl)sulfanyl]-4H-1,2,4-triazole.

In embodiments, the compound is as described in Ex. 2: 4-methyl-3-(4-methyl-1,3-oxazol-5-yl)-5-[(3-{1-[4-(trifluoromethyl)phenyl]octahydropyrrolo[3,4-b]pyrrol-5-yl}propyl)sulfanyl]-4H-1,2,4-triazole.

In embodiments, the compound is as described in Ex. 3: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 4: 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 4: 3-({3-[(3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 5: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 5: 3-({3-[(3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 6: 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 6: 3-({3-[(3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 7: 3-[5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile.

In embodiments, the compound is as described in Ex. 8: 3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile. In embodiments, the compound is as described in Ex. 8: 3-[(3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile.

In embodiments, the compound is as described in Ex. 9: 3-[(3aR,6aR or 3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile, Enantiomer 2. In embodiments, the compound is as described in Ex. 9: 3-[(3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile.

In embodiments, the compound is as described in Ex. 10: 3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile. In embodiments, the compound is as described in Ex. 10: 3-[(3aS,6aS)-5-(3-{[4-methyl-5-(4-methyl-1,3-oxazol-5-yl)-4H-1,2,4-triazol-3-yl]-sulfanyl}propyl)-octahydropyrrolo[2,3-c]pyrrol-1-yl]benzonitrile.

In embodiments, the compound is as described in Ex. 11: 3-[(3aR,6aR or 3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile. In embodiments, the compound is as described in Ex. 11: 3-[(3aS,6aS)-5-(3-{[4-methyl-5-(4-methyl-1,3-oxazol-5-yl)-4H-1,2,4-triazol-3-yl]-sulfanyl}propyl)-octahydropyrrolo[2,3-c]pyrrol-1-yl]benzonitrile.

In embodiments, the compound is as described in Ex. 12: 4-methyl-3-(4-methyl-1,3-oxazol-5-yl)-5-[(3-{1-phenyl-octahydropyrrolo[2,3-c]pyrrol-5-yl}propyl)sulfanyl]-4H-1,2,4-triazole.

In embodiments, the compound is as described in Ex. 13: 3-({3-[(3aS,6aS or 3aR,6aR)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 13: 3-({3-[(3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 14: 3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 14: 3-({3-[(3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 15: 3-({3-[(3aS,6aS or 3aR,6aR)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 15: 3-({3-[(3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 16: 3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 16: 3-({3-[(3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 17: 3-[(3-{1-[2-fluoro-4-(trifluoromethyl)phenyl]-octahydropyrrolo[2,3-c]pyrrol-5-yl}propyl)sulfanyl]-4-methyl-5-(4-methyl-1,3-oxazol-5-yl)-4H-1,2,4-triazole.

In embodiments, the compound is as described in Ex. 18: 3-({3-[(3aS,6aS or 3aR,6aR)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-

4H-1,2,4-triazole. In embodiments, the compound is as described in Ex. 18: 3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 19: 3-({3-[(3aR,6aR or 3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole. In embodiments, the compound is as described in Ex. 19: 3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 20: 3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 21: 3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 22: 3-({3-[1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 23: 3-({3-[(3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole, Enantiomer 1.

In embodiments, the compound is as described in Ex. 24: 3-({3-[(3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole.

In embodiments, the compound is as described in Ex. 25: 4-methyl-3-(4-methyl-1,3-oxazol-5-yl)-5-[(3-{1-[2-(trifluoromethoxy)phenyl]-octahydropyrrolo[3,4-b]pyrrol-5-yl}propyl)sulfanyl]-4H-1,2,4-triazole.

In embodiments, the compound is as described in Ex. 26: 4-methyl-3-(4-methyl-1,3-oxazol-5-yl)-5-[(3-{1-[4-(trifluoromethoxy)phenyl]-octahydropyrrolo[3,4-b]pyrrol-5-yl}propyl)sulfanyl]-4H-1,2,4-triazole.

In embodiments, the compound is as described in Ex. 27: 3-({3-[1-(2,6-difluorophenyl)-octahydropyrrolo[3,4-b]pyrrol-5-yl]propyl}sulfanyl)-4-methyl-5-(4-methyl-1,3-oxazol-5-yl)-4H-1,2,4-triazole.

In embodiments, the compound is as described in Ex. 28: 3-({3-[1-(3,5-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole.

In embodiments, the compound is as described in Ex. 29: 3-({3-[1-(2,4-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole.

In embodiments, the compound is as described in Ex. 30: 3-({3-[1-(3-fluorophenyl)-octahydropyrrolo[3,4-b]pyrrol-5-yl]propyl}sulfanyl)-4-methyl-5-(4-methyl-1,3-oxazol-5-yl)-4H-1,2,4-triazole.

In embodiments, the compound is as described in Ex. 31: 4-methyl-3-(oxan-4-yl)-5-[(3-{(1-[4-(trifluoromethyl)phenyl]-octahydropyrrolo[2,3-c]pyrrol-5-yl}propyl)sulfanyl]-4H-1,2,4-triazole.

In embodiments, the compound is as described in Ex. 32: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 32: 3-({3-[(3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 33: 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 33: 3-({3-[(3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 34: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 34: 3-({3-[(3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 35: 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 35: 3-({3-[(3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 36: 4-methyl-3-(oxan-4-yl)-5-[(3-{(1-phenyl-octahydropyrrolo[2,3-c]pyrrol-5-yl}propyl)sulfanyl]-4H-1,2,4-triazole.

In embodiments, the compound is as described in Ex. 37: 3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 37: 3-({3-[(3aS,6aS)1-phenyl-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 38: 3-({3-[(3aR,6aR or 3aS,6aS)-1-phenyl-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 38: 3-({3-[(3aS,6aS)-1-phenyl-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 39: 3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 39: 3-({3-[(3aS,6aS)-1-phenyl-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 40: 3-({3-[(3aR,6aR or 3aS,6aS)-1-phenyl-octahydropyrrolo[2,3-c]pyrrol-5-yl]propyl}sulfanyl)-4-methyl-5-(oxan-4-yl)-4H-1,2,4-triazole. In embodiments, the compound is as described in Ex. 40: 3-({3-[(3aS,6aS)-1-phenyl-octahydropyrrolo[2,3-c]pyrrol-5-yl]propyl}sulfanyl)-4-methyl-5-(oxan-4-yl)-4H-1,2,4-triazole.

In embodiments, the compound is as described in Ex. 41: 3-({3-[1-(4-fluorophenyl)-octahydropyrrolo[3,4-b]pyrrol-5-yl]propyl}sulfanyl)-4-methyl-5-(oxan-4-yl)-4H-1,2,4-triazole.

In embodiments, the compound is as described in Ex. 42: 3-({3-[(3aS,6aS or 3aR,6aR)-1-(4-fluorophenyl)-octahydropyrrolo[3,4-b]pyrrol-5-yl]propyl}sulfanyl)-4-methyl-5-(oxan-4-yl)-4H-1,2,4-triazole. In embodiments, the compound is as described in Ex. 42: 3-({3-[(3aS,6aS)-1-(4- fluorophenyl)-octahydropyrrolo[3,4-b]pyrrol-5-yl]propyl}sulfanyl)-4-methyl-5-(oxan-4-yl)-4H-1,2,4-triazole.

In embodiments, the compound is as described in Ex. 43: 3-({3-[(3aR,6aR or 3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole. In embodiments, the compound is as described in Ex. 43: 3-({3-[(3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole.

In embodiments, the compound is as described in Ex. 44: 3-({3-[(3aS,6aS or 3aR,6aR)-1-(4-fluorophenyl)-octahydropyrrolo[3,4-b]pyrrol-5-yl]propyl}sulfanyl)-4-methyl-5-(oxan-4-yl)-4H-1,2,4-triazole. In embodiments, the compound is as described in Ex. 44: 3-({3-[(3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole.

In embodiments, the compound is as described in Ex. 45: 3-({3-[(3aR,6aR or 3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole. In embodiments, the compound is as described in Ex. 45: 3-({3-[(3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole.

In embodiments, the compound is as described in Ex. 46: 3-[5-(3-{[4-methyl-5-(oxan-4-yl)-4H-1,2,4-triazol-3-yl]sulfanyl}propyl)-octahydropyrrolo[2,3-c]pyrrol-1-yl]pyridine.

In embodiments, the compound is as described in Ex. 47: 3-[(3aS,6aS or 3aR,6aR)-5-(3-{[4-methyl-5-(oxan-4-yl)-4H-1,2,4-triazol-3-yl]sulfanyl}propyl)-octahydropyrrolo[2,3-c]pyrrol-1-yl]pyridine. In embodiments, the compound is as described in Ex. 47: 3-[(3aS,6aS)-5-(3-{[4-methyl-5-(oxan-4-yl)-4H-1,2,4-triazol-3-yl]sulfanyl}propyl)-octahydropyrrolo[2,3-c]pyrrol-1-yl]pyridine.

In embodiments, the compound is as described in Ex. 48: 3-[(3aR,6aR or 3aS,6aS)-5-(3-{[4-methyl-5-(oxan-4-yl)-4H-1,2,4-triazol-3-yl]sulfanyl}propyl)-octahydropyrrolo[2,3-c]-pyrrol-1-yl]pyridine. In embodiments, the compound is as described in Ex. 48: 3-[(3aS,6aS)-5-(3-{[4-methyl-5-(oxan-4-yl)-4H-1,2,4-triazol-3-yl]sulfanyl}propyl)-octahydropyrrolo[2,3-c]pyrrol-1-yl]pyridine.

In embodiments, the compound is as described in Ex. 49: 2-[5-(3-{[4-methyl-5-(oxan-4-yl)-4H-1,2,4-triazol-3-yl]sulfanyl}propyl)-octahydropyrrolo[2,3-c]pyrrol-1-yl]-5-(trifluoromethyl)pyrazine.

In embodiments, the compound is as described in Ex. 50: 5-[5-(3-{[4-methyl-5-(oxan-4-yl)-4H-1,2,4-triazol-3-yl]sulfanyl}propyl)-octahydropyrrolo[3,4-b]pyrrol-1-yl]-2-(trifluoromethyl)pyridine.

In embodiments, the compound is as described in Ex. 51: 3-cyclopentyl-4-methyl-5-[(3-{1-[4-(trifluoromethyl)phenyl]-octahydropyrrolo[3,4-b]pyrrol-5-yl}propyl)sulfanyl]-4H-1,2,4-triazole.

In embodiments, the compound is as described in Ex. 52: 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole. In embodiments, the compound is as described in Ex. 52: 3-({3-[(3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole.

In embodiments, the compound is as described in Ex. 53: 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole. In embodiments, the compound is as described in Ex. 53: 3-({3-[(3aS,6aS)-1-[4-(trifluoromethyl)phenyl]-octahydropyrrolo[3,4-b]pyrrol-5-yl]-propyl}sulfanyl)-5-cyclopentyl-4-methyl-4H-1,2,4-triazole.

In embodiments, the compound is as described in Ex. 54: 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole. In embodiments, the compound is as described in Ex. 54: 3-({3-[(3aS,6aS)-1-[4-(trifluoromethyl)phenyl]-octahydropyrrolo[3,4-b]pyrrol-5-yl]-propyl}sulfanyl)-5-cyclopentyl-4-methyl-4H-1,2,4-triazole.

In embodiments, the compound is as described in Ex. 55: 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole. In embodiments, the compound is as described in Ex. 55: 3-({3-[(3aS,6aS)-1-[4-(trifluoromethyl)phenyl]-octahydropyrrolo[3,4-b]pyrrol-5-yl]propyl}-sulfanyl)-5-cyclopentyl-4-methyl-4H-1,2,4-triazole.

In embodiments, the compound is as described in Ex. 56: 3-cyclohexyl-4-methyl-5-[(3-{1-[4-(trifluoromethyl)phenyl]-octahydropyrrolo[3,4-b]pyrrol-5-yl}propyl)sulfanyl]-4H-1,2,4-triazol.

In embodiments, the compound is as described in Ex. 57: 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole. In embodiments, the compound is as described in Ex. 57: 3-({3-[(3aS,6aS)-1-[4-(trifluoromethyl)phenyl]-octahydropyrrolo[3,4-b]-5-yl]-propyl}sulfanyl)-5-cyclohexyl-4-methyl-4H-1,2,4-triazole.

In embodiments, the compound is as described in Ex. 58: 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole. In embodiments, the compound is as described in Ex. 58: 3-({3-[(3aS,6aS)-1-[4-(trifluoromethyl)phenyl]-octahydropyrrolo[3,4-b]pyrrol-5-yl]-propyl}sulfanyl)-5-cyclohexyl-4-methyl-4H-1,2,4-triazole.

In embodiments, the compound is as described in Ex. 59: 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole. In embodiments, the compound is as described in Ex. 59: 3-({3-[(3aS,6aS)-1-[4-(trifluoromethyl)phenyl]-octahydropyrrolo[3,4-b]pyrrol-5-yl]-propyl}sulfanyl)-5-cyclohexyl-4-methyl-4H-1,2,4-triazole.

In embodiments, the compound is as described in Ex. 60: 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole. In embodiments, the compound is as described in Ex. 60: 3-({3-[(3aS,6aS)-1-[4-(trifluoromethyl)phenyl]-octahydropyrrolo[3,4-b]pyrrol-5-yl]-propyl}sulfanyl)-5-cyclohexyl-4-methyl-4H-1,2,4-triazole.

In embodiments, the compound is as described in Ex. 61: 3-cyclohexyl-5-({3-[1-(4-fluorophenyl)-octahydropyrrolo[3,4-b]pyrrol-5-yl]propyl}sulfanyl)-4-methyl-4H-1,2,4-triazole.

In embodiments, the compound is as described in Ex. 62: 3-({3-[(3aS,6aS or 3aR,6aR)-1-(4-fluorophenyl)-octahydropyrrolo[3,4-b]pyrrol-5-yl]propyl}sulfanyl)-5-cyclohexyl-4-methyl-4H-1,2,4-triazole. In embodiments, the compound is as described in Ex. 62: 3-({3-[(3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole.

In embodiments, the compound is as described in Ex. 63: 3-({3-[(3aR,6aR or 3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole. In embodiments, the compound is as described in Ex. 63: 3-({3-[(3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole.

In embodiments, the compound is as described in Ex. 64: 3-({3-[(3aS,6aS or 3aR,6aR)-1-(4-fluorophenyl)-octahydropyrrolo[3,4-b]pyrrol-5-yl]propyl}sulfanyl)-5-cyclohexyl-4-methyl-4H-1,2,4-triazole. In embodiments, the compound is as described in Ex. 64: 3-({3-[(3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole.

In embodiments, the compound is as described in Ex. 65: 3-({3-[(3aR,6aR or 3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole. In embodiments, the compound is as described in Ex. 65: 3-({3-[(3aR,6aR)-1-(4-fluorophenyl)-octahydropyrrolo[3,4-b]pyrrol-5-yl]propyl}sulfanyl)-5-cyclohexyl-4-methyl-4H-1,2,4-triazole.

In embodiments, the compound is as described in Ex. 66: 3-(5-{3-[(5-cyclohexyl-4-methyl-4H-1,2,4-triazol-3-yl)sulfanyl]propyl}-octahydropyrrolo[2,3-c]pyrrol-1-yl)pyridine.

In embodiments, the compound is as described in Ex. 67: 3-[(3aS,6aS or 3aR,6aR)-5-{3-[(5-cyclohexyl-4-methyl-4H-1,2,4-triazol-3-yl)sulfanyl]propyl}-octahydropyrrolo[2,3-c]pyrrol-1-yl]pyridine. In embodiments, the compound is as described in Ex. 67: 3-[(3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine.

In embodiments, the compound is as described in Ex. 68: 3-[(3aR,6aR or 3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine. In embodiments, the compound is as described in Ex. 68: 3-[(3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine.

In embodiments, the compound is as described in Ex. 69: 3-[(3aS,6aS or 3aR,6aR)-5-{3-[(5-cyclohexyl-4-methyl-4H-1,2,4-triazol-3-yl)sulfanyl]propyl}-octahydropyrrolo[2,3-c]pyrrol-1-yl]pyridine. In embodiments, the compound is as described in Ex. 69: 3-[(3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine.

In embodiments, the compound is as described in Ex. 70: 3-[(3aR,6aR or 3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine. In embodiments, the compound is as described in Ex. 70: 3-[(3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine.

In embodiments, the compound is as described in Ex. 71: 3-(1,4-dioxan-2-yl)-4-methyl-5-[(3-{1-[4-(trifluoromethyl)phenyl]-octahydropyrrolo[3,4-b]pyrrol-5-yl}propyl)sulfanyl]-4H-1,2,4-triazol.

In embodiments, the compound is as described in Ex. 72: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole. In embodiments, the compound is as described in Ex. 72: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R)-1,4-dioxan-2-yl]-4-methyl-4H-1,2,4-triazole.

In embodiments, the compound is as described in Ex. 73: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole. In embodiments, the compound is as described in Ex. 73: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2S)-1,4-dioxan-2-yl]-4-methyl-4H-1,2,4-triazole.

In embodiments, the compound is as described in Ex. 74: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole, Isomer 3.

In embodiments, the compound is as described in Ex. 75: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole, Isomer 4.

In embodiments, the compound is as described in Ex. 76: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole, Isomer 1.

In embodiments, the compound is as described in Ex. 77: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole, Isomer 2.

In embodiments, the compound is as described in Ex. 78: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole, Isomer 3.

In embodiments, the compound is as described in Ex. 79: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole, Isomer 4.

In embodiments, the compound is as described in Ex. 80: 1-methyl-2-[(3-{1-[4-(trifluoromethyl)phenyl]-octahydropyrrolo[3,4-b]pyrrol-5-yl}propyl)sulfanyl]-1H-1,3-benzodiazole.

In embodiments, the compound is as described in Ex. 81: 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}morpholine.

In embodiments, the compound is as described in Ex. 82: 4-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine, Enantiomer 1.

In embodiments, the compound is as described in Ex. 83: 4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine. In embodiments, the compound is as described in Ex. 83: 4-[5-({3-[(3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]morpholine.

In embodiments, the compound is as described in Ex. 84: 4-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine. In embodiments, the compound is as described in Ex. 84: 4-[5-({3-[(3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]morpholine.

In embodiments, the compound is as described in Ex. 85: 4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine. In embodiments, the compound is as described in Ex. 85: 4-[5-({3-

[(3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]morpholine.

In embodiments, the compound is as described in Ex. 86: 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridazine.

In embodiments, the compound is as described in Ex. 87: 3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridazine.

In embodiments, the compound is as described in Ex. 88: 35-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrimidine.

In embodiments, the compound is as described in Ex. 89: 2-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrazine.

In embodiments, the compound is as described in Ex. 90: 2-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine, Enantiomer 1. In embodiments, the compound is as described in Ex. 90: 2-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine.

In embodiments, the compound is as described in Ex. 91: 2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine. In embodiments, the compound is as described in Ex. 91: 2-[5-({3-[(3aS,6aS)-1-[4-(trifluoromethyl)phenyl]-octahydropyrrolo[2,3-c]pyrrol-5-yl]-propyl}sulfanyl)-4-methyl-4H-1,2,4-triazol-3-yl]pyrazine.

In embodiments, the compound is as described in Ex. 92: 2-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine. In embodiments, the compound is as described in Ex. 92: 2-[5-({3-[(3aS,6aS)-1-[4-(trifluoromethyl)phenyl]-octahydropyrrolo[2,3-c]pyrrol-5-yl]-propyl}sulfanyl)-4-methyl-4H-1,2,4-triazol-3-yl]pyrazine.

In embodiments, the compound is as described in Ex. 93: 2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine. In embodiments, the compound is as described in Ex. 93: 2-[5-({3-[(3aS,6aS)-1-[4-(trifluoromethyl)phenyl]-octahydropyrrolo[2,3-c]pyrrol-5-yl]-propyl}sulfanyl)-4-methyl-4H-1,2,4-triazol-3-yl]pyrazine.

In embodiments, the compound is as described in Ex. 94: 3-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile.

In embodiments, the compound is as described in Ex. 95: 2-[5-({3-[1-(4-fluorophenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 96: 2-{4-methyl-5-[(3-{1-[2-(trifluoromethoxy)phenyl]-octahydropyrrolo[3,4-b]pyrrol-5-yl}propyl)sulfanyl]-4H-1,2,4-triazol-3-yl}pyrazine.

In embodiments, the compound is as described in Ex. 97: 2-{4-methyl-5-[(3-{1-[4-(trifluoromethoxy)phenyl]-octahydropyrrolo[3,4-b]pyrrol-5-yl}propyl)sulfanyl]-4H-1,2,4-triazol-3-yl}pyrazine.

In embodiments, the compound is as described in Ex. 98: 2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 99: 2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 100: 2-[5-({3-[1-(3-fluorophenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 101: 2-[5-({3-[1-(2-fluorophenyl)-octahydropyrrolo[2,3-c]pyrrol-5-yl]propyl}sulfanyl)-4-methyl-4H-1,2,4-triazol-3-yl]pyrazine.

In embodiments, the compound is as described in Ex. 102: 2-[5-({3-[1-(2,4-difluorophenyl)-octahydropyrrolo[2,3-c]pyrrol-5-yl]propyl}sulfanyl)-4-methyl-4H-1,2,4-triazol-3-yl]pyrazine.

In embodiments, the compound is as described in Ex. 103: 2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine. In embodiments, the compound is as described in Ex. 103: 2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine.

In embodiments, the compound is as described in Ex. 104: 2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine. In embodiments, the compound is as described in Ex. 104: 2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine.

In embodiments, the compound is as described in Ex. 105: 2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine. In embodiments, the compound is as described in Ex. 105: 2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine.

In embodiments, the compound is as described in Ex. 106: 2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine. In embodiments, the compound is as described in Ex. 106: 2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine.

In embodiments, the compound is as described in Ex. 107: 2-[5-({3-[1-(4-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 108: 2-[4-methyl-5-({3-[1-(4-methylphenyl)-octahydropyrrolo[3,4-b]pyrrol-5-yl]propyl}sulfanyl)-4H-1,2,4-triazol-3-yl]pyrazine.

In embodiments, the compound is as described in Ex. 109: 2-[5-({3-[1-(3-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 110: 2-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile.

In embodiments, the compound is as described in Ex. 111: 2-[4-methyl-5-({3-[1-(3-methylphenyl)-octahydropyrrolo[3,4-b]pyrrol-5-yl]propyl}sulfanyl)-4H-1,2,4-triazol-3-yl]pyrazine.

In embodiments, the compound is as described in Ex. 112: 2-[5-({3-[1-(2-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 113: 2-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}pyrazine.

In embodiments, the compound is as described in Ex. 114: 2-{4-methyl-5-[(3-{1-[3-(trifluoromethoxy)phenyl]-octahydropyrrolo[3,4-b]pyrrol-5-yl}propyl)sulfanyl]-4H-1,2,4-triazol-3-yl}pyrazine.

In embodiments, the compound is as described in Ex. 115: 2-{4-methyl-5-[(3-{1-[2-(propan-2-yloxy)phenyl]-octahydropyrrolo[3,4-b]pyrrol-5-yl}propyl)sulfanyl]-4H-1,2,4-triazol-3-yl}pyrazine.

In embodiments, the compound is as described in Ex. 116: 2-[5-({3-[(3aS,6aS or 3aR,6aR)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine. In embodiments, the compound is as described in Ex. 116: 2-[5-({3-[(3aS,6aS)-1-[2-(propan-2-yloxy)phenyl]-octahydropyrrolo[3,4-b]pyrrol-5-yl]-propyl}sulfanyl)-4-methyl-4H-1,2,4-triazol-3-yl]pyrazine.

In embodiments, the compound is as described in Ex. 117: 2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine. In embodiments, the compound is as described in Ex. 117: 2-[5-({3-[(3aS,6aS)-1-[2-(propan-2-yloxy)phenyl]-octahydropyrrolo[3,4-b]pyrrol-5-yl]-propyl}sulfanyl)-4-methyl-4H-1,2,4-triazol-3-yl]pyrazine.

In embodiments, the compound is as described in Ex. 118: 2-[5-({3-[(3aS,6aS or 3aR,6aR)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine, Enantiomer 1. In embodiments, the compound is as described in Ex. 118: 2-[5-({3-[(3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine.

In embodiments, the compound is as described in Ex. 119: 2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine, Enantiomer 2. In embodiments, the compound is as described in Ex. 119: 2-[5-({3-[(3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine.

In embodiments, the compound is as described in Ex. 120: 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyrazine.

In embodiments, the compound is as described in Ex. 121: 2-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine. In embodiments, the compound is as described in Ex. 121: 2-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine.

In embodiments, the compound is as described in Ex. 122: 2-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine. In embodiments, the compound is as described in Ex. 122: 2-[5-({3-[(3aS,6aS)-1-[2-(trifluoromethyl)phenyl]-octahydropyrrolo[3,4-b]pyrrol-5-yl]-propyl}sulfanyl)-4-methyl-4H-1,2,4-triazol-3-yl]pyrazine.

In embodiments, the compound is as described in Ex. 123: 2-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine. In embodiments, the compound is as described in Ex. 123: 2-[5-({3-[(3aS,6aS)-1-[2-(trifluoromethyl)phenyl]-octahydropyrrolo[3,4-b]pyrrol-5-yl]-propyl}sulfanyl)-4-methyl-4H-1,2,4-triazol-3-yl]pyrazine.

In embodiments, the compound is as described in Ex. 124: 2-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine. In embodiments, the compound is as described in Ex. 124: 2-[5-({3-[(3aS,6aS)-1-[2-(trifluoromethyl)phenyl]-octahydropyrrolo[3,4-b]pyrrol-5-yl]-propyl}sulfanyl)-4-methyl-4H-1,2,4-triazol-3-yl]pyrazine.

In embodiments, the compound is as described in Ex. 125: 2-[5-({3-[1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 126: 2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine. In embodiments, the compound is as described in Ex. 126: 2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 127: 2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine. In embodiments, the compound is as described in Ex. 127: 2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 128: 2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine. In embodiments, the compound is as described in Ex. 128: 2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 129: 2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine. In embodiments, the compound is as described in Ex. 129: 2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine.

In embodiments, the compound is as described in Ex. 130: 2-{5-[(3-{1-[4-fluoro-2-(trifluoromethyl)phenyl]-octahydropyrrolo[3,4-b]pyrrol-5-yl}propyl)sulfanyl]-4-methyl-4H-1,2,4-triazol-3-yl}pyrazine.

In embodiments, the compound is as described in Ex. 131: 2-{5-[(3-{1-[2-fluoro-6-(trifluoromethyl)phenyl]-octahydropyrrolo[3,4-b]pyrrol-5-yl}propyl)sulfanyl]-4-methyl-4H-1,2,4-triazol-3-yl}pyrazine.

In embodiments, the compound is as described in Ex. 132: 2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine.

In embodiments, the compound is as described in Ex. 133: 2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine.

In embodiments, the compound is as described in Ex. 134: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrimidine.

In embodiments, the compound is as described in Ex. 135: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine. In embodiments, the compound is as described in Ex. 135: 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine.

In embodiments, the compound is as described in Ex. 136: 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine. In embodiments, the compound is as described in Ex. 136: 4-[5-({3-[(3aS,6aS)-1-[4-(trifluoromethyl)phenyl]-octahydropyrrolo[2,3-c]pyrrol-5-yl]-propyl}sulfanyl)-4-methyl-4H-1,2,4-triazol-3-yl]pyrimidine.

In embodiments, the compound is as described in Ex. 137: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine.

In embodiments, the compound is as described in Ex. 138: 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine.

In embodiments, the compound is as described in Ex. 139: 4-[5-({3-[1-(4-fluorophenyl)-octahydropyrrolo[3,4-b]pyrrol-5-yl]propyl}sulfanyl)-4-methyl-4H-1,2,4-triazol-3-yl]pyrimidine.

In embodiments, the compound is as described in Ex. 140: 1-(4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}piperidin-1-yl)ethan-1-one.

In embodiments, the compound is as described in Ex. 141: 3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine.

In embodiments, the compound is as described in Ex. 142: 3-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine. In embodiments, the compound is as described in Ex. 142: 3-[5-({3-[(3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]pyridine.

In embodiments, the compound is as described in Ex. 143: 3-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine. In embodiments, the compound is as described in Ex. 143: 3-[5-({3-[(3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]pyridine.

In embodiments, the compound is as described in Ex. 144: 3-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride.

In embodiments, the compound is as described in Ex. 145: 3-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 146: 3-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine.

In embodiments, the compound is as described in Ex. 147: 3-{4-methyl-5-[(3-{1-[2-(trifluoromethyl)phenyl]-octahydropyrrolo[3,4-b]pyrrol-5-yl}propyl)sulfanyl]-4H-1,2,4-triazol-3 yl}pyridine.

In embodiments, the compound is as described in Ex. 148: 3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine. In embodiments, the compound is as described in Ex. 148: 3-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 149: 3-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine. In embodiments, the compound is as described in Ex. 149: 3-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 150: 3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 151: 3-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 152: 4-methyl-3-(1-methyl-1H-pyrazol-4-yl)-5-[(3-{1-[4-(trifluoromethyl)phenyl]-octahydropyrrolo[3,4-b]pyrrol-5-yl}propyl)sulfanyl]-4H-1,2,4-triazole.

In embodiments, the compound is as described in Ex. 153: 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine.

In embodiments, the compound is as described in Ex. 154: 4-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine.

In embodiments, the compound is as described in Ex. 155: 4-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine.

In embodiments, the compound is as described in Ex. 156: 4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine. In embodiments, the compound is as described in Ex. 156: 4-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 157: 4-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine. In embodiments, the compound is as described in Ex. 157: 4-[5-({3-[(3aS, 6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 158: 4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 159: 4-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine.

In embodiments, the compound is as described in Ex. 160: 2-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine.

In embodiments, the compound is as described in Ex. 161: 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine.

In embodiments, the compound is as described in Ex. 162: 4-methyl-3-(1,3-thiazol-2-yl)-5-[(3-{1-[4-(trifluoromethyl)phenyl]-octahydropyrrolo[3,4-b]pyrrol-5-yl}propyl)sulfanyl]-4H-1,2,4-triazole.

In embodiments, the compound is as described in Ex. 163: 4-methyl-3-(3-methyl-1,2-oxazol-5-yl)-5-[(3-{1-[4-(trifluoromethyl)phenyl]-octahydropyrrolo[3,4-b]pyrrol-5-yl}propyl)sulfanyl]-4H-1,2,4-triazole.

In embodiments, the compound is as described in Ex. 164: 4-methyl-3-(4-methyl-1,3-thiazol-5-yl)-5-[(3-{1-[4-(trifluoromethyl)phenyl]-octahydropyrrolo[3,4-b]pyrrol-5-yl}propyl)sulfanyl]-4H-1,2,4-triazole.

In embodiments, the compound is as described in Ex. 165: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}-1,2-dihydropyridin-2-one.

In embodiments, the compound is as described in Ex. 166: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one. In embodiments, the compound is as described in Ex. 166: 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one.

In embodiments, the compound is as described in Ex. 167: 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one. In embodiments, the compound is as described in Ex. 167: 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one.

In embodiments, the compound is as described in Ex. 168: 4-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one.

In embodiments, the compound is as described in Ex. 169: 4-[5-({3-[(3aS,6aS or 3aR,6aR)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one. In embodiments, the compound is as described in Ex. 169: 4-[5-({3-[(3aS,6aS)-1-(4-fluorophenyl)-octahydropyrrolo[2,3-c]pyrrol-5-yl]propyl}-sulfanyl)-4-methyl-4H-1,2,4-triazol-3-yl]-1,2-dihydropyridin-2-one.

In embodiments, the compound is as described in Ex. 170: 4-[5-({3-[(3aR,6aR or 3aS,6aS)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one. In embodiments, the compound is as described in Ex. 170: 4-[5-({3-[(3aS,6aS)-1-(4-fluorophenyl)-octahydropyrrolo[2,3-c]pyrrol-5-yl]propyl}-sulfanyl)-4-methyl-4H-1,2,4-triazol-3-yl]-1,2-dihydropyridin-2-one.

In embodiments, the compound is as described in Ex. 171: 4-[5-({3-[(3aS,6aS or 3aR,6aR)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one. In embodiments, the compound is as described in Ex. 171: 4-[5-({3-[(3aS,6aS)-1-(4-fluorophenyl)-octahydropyrrolo[2,3-c]pyrrol-5-yl]propyl}-sulfanyl)-4-methyl-4H-1,2,4-triazol-3-yl]-1,2-dihydropyridin-2-one.

In embodiments, the compound is as described in Ex. 172: 4-[5-({3-[(3aR,6aR or 3aS,6aS)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one. In embodiments, the compound is as described in Ex. 172: 4-[5-({3-[(3aS,6aS)-1-(4-fluorophenyl)-octahydropyrrolo[2,3-c]pyrrol-5-yl]propyl}-sulfanyl)-4-methyl-4H-1,2,4-triazol-3-yl]-1,2-dihydropyridin-2-one.

In embodiments, the compound is as described in Ex. 173: 4-[5-({3-[1-(2,6-difluorophenyl)-octahydropyrrolo[3,4-b]pyrrol-5-yl]propyl}sulfanyl)-4-methyl-4H-1,2,4-triazol-3-yl]-1,2-dihydropyridin-2-one.

In embodiments, the compound is as described in Ex. 174: 4-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one.

In embodiments, the compound is as described in Ex. 175: 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one.

In embodiments, the compound is as described in Ex. 176: 5-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one.

In embodiments, the compound is as described in Ex. 177: 5-[5-({3-[1-(2,6-difluorophenyl)-octahydropyrrolo[3,4-b]pyrrol-5-yl]propyl}sulfanyl)-4-methyl-4H-1,2,4-triazol-3-yl]-1,2-dihydropyridin-2-one.

In embodiments, the compound is as described in Ex. 178: 5-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one.

In embodiments, the compound is as described in Ex. 179: 5-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one.

In embodiments, the compound is as described in Ex. 180: 5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one. In embodiments, the compound is as described in Ex. 180: 5-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one.

In embodiments, the compound is as described in Ex. 181: 5-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one. In embodiments, the compound is as described in Ex. 181: 5-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one.

In embodiments, the compound is as described in Ex. 182: 5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one.

In embodiments, the compound is as described in Ex. 183: 5-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one.

In embodiments, the compound is as described in Ex. 184: 3-({3-[1-(2,6-difluorophenyl)-octahydropyrrolo[3,4-b]pyrrol-5-yl]propyl}sulfanyl)-4-methyl-5-(1-methyl-1H-pyrazol-5-yl)-4H-1,2,4-triazole.

In embodiments, the compound is as described in Ex. 185: 4-methyl-3-(1-methyl-1H-pyrazol-5-yl)-5-[(3-{1-[2-(trifluoromethyl)phenyl]-octahydropyrrolo[3,4-b]pyrrol-5-yl}propyl)sulfanyl]-4H-1,2,4-triazole.

In embodiments, the compound is as described in Ex. 186: 3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole. In embodiments, the compound is as described in Ex. 186: 3-({3-[(3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole.

In embodiments, the compound is as described in Ex. 187: 3-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole. In embodiments, the compound is as described in Ex. 187: 3-({3-[(3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole.

In embodiments, the compound is as described in Ex. 188: 3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole.

In embodiments, the compound is as described in Ex. 189: 3-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole.

In embodiments, the compound is as described in Ex. 190: 3-[5-({3-[1-(2,6-difluorophenyl)-octahydropyrrolo[3,4-b]pyrrol-5-yl]propyl}sulfanyl)-4-methyl-4H-1,2,4-triazol-3-yl]-2-methylpyridine.

In embodiments, the compound is as described in Ex. 191: 4-methyl-3-(pyrrolidine-1-carbonyl)-5-[(3-{1-[4-(trifluoromethyl)phenyl]-octahydropyrrolo[3,4-b]pyrrol-5-yl}propyl)sulfanyl]-4H-1,2,4-triazole.

In embodiments, the compound is as described in Ex. 192: 1-methyl-5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one.

In embodiments, the compound is as described in Ex. 193: 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one. In embodiments, the compound is as described in Ex. 193: 5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one.

In embodiments, the compound is as described in Ex. 194: 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one. In embodiments, the compound is as described in Ex. 194: 5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one.

In embodiments, the compound is as described in Ex. 195: 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine-2-carboxamide.

In embodiments, the compound is as described in Ex. 196: 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide. In embodiments, the compound is as described in Ex. 196: 5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide.

In embodiments, the compound is as described in Ex. 197: 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide. In embodiments, the compound is as described in Ex. 197: 5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide.

In embodiments, the compound is as described in Ex. 198: 5-[5-({3-[1-(4-fluorophenyl)-octahydropyrrolo[3,4-b]pyrrol-5-yl]propyl}sulfanyl)-4-methyl-4H-1,2,4-triazol-3-yl]pyridine-2-carboxamide.

In embodiments, the compound is as described in Ex. 199: 5-[5-({3-[(3aS,6aS or 3aR,6aR)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide. In embodiments, the compound is as described in Ex. 199: 5-[5-({3-[(3aS,6aS)-1-(4-fluorophenyl)-octahydropyrrolo[3,4-b]pyrrol-5-yl]propyl}-sulfanyl)-4-methyl-4H-1,2,4-triazol-3-yl]pyridine-2-carboxamide.

In embodiments, the compound is as described in Ex. 200: 5-[5-({3-[(3aR,6aR or 3aS,6aS)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide. In embodiments, the compound is as described in Ex. 200: 5-[5-({3-[(3aS,6aS)-1-(4-fluorophenyl)-octahydropyrrolo[3,4-b]pyrrol-5-yl]propyl}-sulfanyl)-4-methyl-4H-1,2,4-triazol-3-yl]pyridine-2-carboxamide.

In embodiments, the compound is as described in Ex. 201: 5-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide.

In embodiments, the compound is as described in Ex. 202: 5-[5-({3-[(3aS,6aS or 3aR,6aR)-1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide. In embodiments, the compound is as described in Ex. 202: 5-[5-({3-[(3aS,6aS)-1-(2,6-difluorophenyl)-octahydropyrrolo[3,4-b]pyrrol-5-yl]propyl}-sulfanyl)-4-methyl-4H-1,2,4-triazol-3-yl]pyridine-2-carboxamide.

In embodiments, the compound is as described in Ex. 203: 5-[5-({3-[(3aR,6aR or 3aS,6aS)-1-(2,6-difluorophenyl)-octahydropyrrolo[3,4-b]pyrrol-5 yl]propyl}sulfanyl)-4-methyl-4H-1,2,4-triazol-3-yl]pyridine-2-carboxamide. In embodiments, the compound is as described in Ex. 203: 5-[5-({3-[(3aS,6aS)-1-(2,6-difluorophenyl)-octahydropyrrolo[3,4-b]pyrrol-5 yl]propyl}-sulfanyl)-4-methyl-4H-1,2,4-triazol-3-yl]pyridine-2-carboxamide.

In embodiments, the compound is as described in Ex. 204: 5-{4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyridine-2-carboxamide.

In embodiments, the compound is as described in Ex. 205: 5-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide. In embodiments, the compound is as described in Ex. 205: 5-[5-({3-[(3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide.

In embodiments, the compound is as described in Ex. 206: 5-[5-({3-[(3aR,6aR or 3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide. In embodiments, the compound is as described in Ex. 206: 5-[5-({3-[(3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide.

In embodiments, the compound is as described in Ex. 207: 4-[5-({3-[1-(4-fluorophenyl)-octahydropyrrolo[3,4-b]pyrrol-5-yl]propyl}sulfanyl)-4-methyl-4H-1,2,4-triazol-3-yl]-1-methyl-1,2-dihydropyridin-2-one.

In embodiments, the compound is as described in Ex. 208: 1-methyl-4-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]-1,2-dihydropyridin-2-one.

In embodiments, the compound is as described in Ex. 209: 4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one. In embodiments, the compound is as described in Ex. 209: 4-[5-({3-[(3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one.

In embodiments, the compound is as described in Ex. 210: 4-[5-({3-[(3aR,6aR or 3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one. In embodiments, the compound is as described in Ex. 210: 4-[5-({3-[(3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one.

In embodiments, the compound is as described in Ex. 211: 4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one.

In embodiments, the compound is as described in Ex. 212: 4-methyl-3-(oxan-4-yl)-5-(3-{1-[4-(trifluoromethyl)phenyl]-octahydro-pyrrolo[3,4-b]pyrrol-5-yl}propoxy)-4H-1,2,4-triazole.

In embodiments, the compound is as described in Ex. 213: 4-methyl-3-(oxan-4-yl)-5-(4-{(1-[4-(trifluoromethyl)phenyl]-octahydropyrrolo[2,3-c]pyrrol-5-yl}butyl)-4H-1,2,4-triazole.

In embodiments, the compound is as described in Ex. 214: 3-{4-[(3aS,6As or 3aR,6aR)-1-[4-(trifluoromethyl)phenyl]-octahydropyrrolo[3,4-b]pyrrol-5-yl]butyl}-4-methyl-5-(oxan-4-yl)-4H-1,2,4-triazole. In embodiments, the compound is as described in Ex. 214: 3-{4-[(3aS,6aS)-1-[4-(trifluoromethyl)phenyl]-octahydropyrrolo[3,4-b]pyrrol-5-yl]butyl}-4-methyl-5-(oxan-4-yl)-4H-1,2,4-triazole.

In embodiments, the compound is as described in Ex. 215: 3-{4-[(3aR,6aR or 3aS,6aS)-1-[4-(trifluoromethyl)phenyl]-octahydropyrrolo[3,4-b]pyrrol-5-yl]butyl}-4-methyl-5-(oxan-4-yl)-4H-1,2,4-triazole. In embodiments, the compound is as described in Ex. 215: 3-{4-[(3aS,6aS)-1-[4-(trifluoromethyl)phenyl]-octahydropyrrolo[3,4-b]pyrrol-5-yl]butyl}-4-methyl-5-(oxan-4-yl)-4H-1,2,4-triazole.

In embodiments, the compound is as described in Ex. 216: 3-{4-[(3aS,6aS or 3aR,6aR)-1-[4-(trifluoromethyl)phenyl]-octahydropyrrolo[3,4-b]pyrrol-5-yl]butyl}-4-methyl-5-(oxan-4-yl)-4H-1,2,4-triazole.

In embodiments, the compound is as described in Ex. 217: 3-{4-[1-(4-fluorophenyl)-octahydropyrrolo[2,3-c]pyrrol-5-yl]butyl}-4-methyl-5-(4-methyl-1,3-oxazol-5-yl)-4H-1,2,4-triazole dihydrochloride.

In embodiments, the compound is as described in Ex. 218: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol.

In embodiments, the compound is as described in Ex. 219: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol. In embodiments, the compound is as described in Ex. 219: 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol.

In embodiments, the compound is as described in Ex. 220: 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol. In embodiments, the compound is as described in Ex. 220: 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol.

In embodiments, the compound is as described in Ex. 221: 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol. In embodiments, the compound is as described in Ex. 221: 4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol.

In embodiments, the compound is as described in Ex. 222: N-(4-{2[(3aS,6aS or 3aR,6aR) 1-[4-(trifluoromethyl)phenyl]-octahydropyrrolo[3,4-b]pyrrol-5-yl]ethyl}cyclohexyl)-3 methoxypropanamide. In embodiments, the compound is as described in Ex. 222: N-(4-{2 [(3aS,6aS) 1-[4-(trifluoromethyl)phenyl]-octahydropyrrolo[3,4-b]pyrrol-5-yl]ethyl}cyclohexyl)-3 methoxypropanamide.

In embodiments, the compound is as described in Ex. 223: N-(4-{2-[(3aR,6aR or 3aS,6aS)-1-[4-(trifluoromethyl)phenyl]-octahydropyrrolo[3,4-b]pyrrol-5-yl]ethyl}cyclohexyl)-3-methoxypropanamide. In embodiments, the compound is as described in Ex. 223: N-(4-{2-[(3aS,6aS)-1-[4-(trifluoromethyl)phenyl]-octahydropyrrolo[3,4-b]pyrrol-5-yl]ethyl}cyclohexyl)-3-methoxypropanamide.

In embodiments, the compound is as described in Ex. 224: 4-methyl-3-(4-methyl-1,3-oxazol-5-yl)-5-({3-[(4S or 4R)-4-[4-(trifluoromethyl)phenyl]-octahydrocyclopenta[c]pyrrol-2-yl]propyl}sulfanyl)-4H-1,2,4-triazole. In embodiments, the compound is as described in Ex. 224: 4-methyl-3-(4-methyl-1,3-oxazol-5-yl)-5-({3-[(4S)-4-[4-(trifluoromethyl)phenyl]-octahydrocyclopenta[c]pyrrol-2-yl]propyl}sulfanyl)-4H-1,2,4-triazole.

In embodiments, the compound is as described in Ex. 225: 4-methyl-3-(4-methyl-1,3-oxazol-5-yl)-5-({3-[(4R or 4S)-4-[4-(trifluoromethyl)phenyl]-octahydrocyclopenta[c]pyrrol-2-yl]propyl}sulfanyl)-4H-1,2,4-triazole. In embodiments, the compound is as described in Ex. 225: 4-methyl-3-(4-methyl-1,3-oxazol-5-yl)-5-({3-[(4S)-4-[4-(trifluoromethyl)phenyl]-octahydrocyclopenta[c]pyrrol-2-yl]propyl}sulfanyl)-4H-1,2,4-triazole.

In embodiments, the compound is as described in Ex. 226: 4-methyl-3-(4-methyl-1,3-oxazol-5-yl)-5-({3-[(4S or 4R)-4-[4-(trifluoromethyl)phenyl]-octahydrocyclopenta[c]pyrrol-2-yl]propyl}sulfanyl)-4H-1,2,4-triazole. In embodiments, the compound is as described in Ex. 226: 4-methyl-3-(4-methyl-1,3-oxazol-5-yl)-5-({3-[(4S)-4-[4-(trifluoromethyl)phenyl]-octahydrocyclopenta[c]pyrrol-2-yl]propyl}sulfanyl)-4H-1,2,4-triazole.

In embodiments, the compound is as described in Ex. 227: 4-methyl-3-(4-methyl-1,3-oxazol-5-yl)-5-({3-[(4R or 4S)-4-[4-(trifluoromethyl)phenyl]-octahydrocyclopenta[c]pyrrol-2-yl]propyl}sulfanyl)-4H-1,2,4-triazole. In embodiments, the compound is as described in Ex. 227: 4-methyl-3-(4-methyl-1,3-oxazol-5-yl)-5-({3-[(4S)-4-[4-(trifluoromethyl)phenyl]-octahydrocyclopenta[c]pyrrol-2-yl]propyl}sulfanyl)-4H-1,2,4-triazole.

In embodiments, the compound is as described in Ex. 228: 3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane.

In embodiments, the compound is as described in Ex. 229: (1R,5S or 1S,5R)-3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane. In embodiments, the compound is as described in Ex. 229: (1R,5S)-3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane.

In embodiments, the compound is as described in Ex. 230: (1S,5R or 1R,5S)-3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane. In embodiments, the compound is as described in Ex. 230: (1R,5S)-3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane.

In embodiments, the compound is as described in Ex. 231: 4-methyl-3-(4-methyl-1,3-oxazol-5-yl)-5-[(3-{1-[4-(trifluoromethyl)phenyl]-octahydro-1H-pyrrolo[3,4-b]pyridin-6-yl}propyl)sulfanyl]-4H-1,2,4-triazole.

In embodiments, the compound is as described in Ex. 232: 3-({3-[(4aS,7aS or 4aR,7aR)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole. In embodiments, the compound is as described in Ex. 232: 3-({3-[(4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole.

In embodiments, the compound is as described in Ex. 233: 3-({3-[(4aR,7aR or 4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole. In embodiments, the compound is as described in Ex. 233: 3-({3-[(4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole.

In embodiments, the compound is as described in Ex. 234: 3-[6-(3-{[4-methyl-5-(4-methyl-1,3-oxazol-5-yl)-4H-1,2,4-triazol-3-yl]sulfanyl}propyl)-octahydro-1H-pyrrolo[3,4-b]pyridin-1-yl]benzonitrile.

In embodiments, the compound is as described in Ex. 235: 3-[6-(3-{[4-methyl-5-(4-methyl-1,3-oxazol-5-yl)-4H-1,2,4-triazol-3-yl]sulfanyl}propyl)-octahydro-1H-pyrrolo[3,4-b]pyridin-1-yl]benzonitrile.

In embodiments, the compound is as described in Ex. 236: 4-methyl-3-(4-methyl-1,3-oxazol-5-yl)-5-[(3-{4-[4-(trifluoromethyl)phenyl]-octahydropyrrolo[3,4-b]morpholin-6-yl}propyl)sulfanyl]-4H-1,2,4-triazole.

In embodiments, the compound is as described in Ex. 237: 3-({3-[(4aR,7aS or 4aS,7aR)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole. In embodiments, the compound is as described in Ex. 237: 3-({3-[(4aR,7aS)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole.

In embodiments, the compound is as described in Ex. 238: 3-({3-[(4aS,7aR or 4aR,7aS)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole. In embodiments, the compound is as described in Ex. 238: 3-({3-[(4aR,7aS)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole.

In embodiments, the compound is as described in Ex. 239: 3-({3-[(4aS,7aR or 4aR,7aS)-4-[4-(trifluoromethyl)phenyl]-octahydropyrrolo[3,4-b]morpholin-6-yl]-propyl}sulfanyl)-4-methyl-5-(4-methyl-1,3-oxazol-5-yl)-4H-1,2,4-triazole. In embodiments, the compound is as described in Ex. 239: 3-({3-[(4aR,7aS)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole.

In embodiments, the compound is as described in Ex. 240: 4-methyl-3-(4-methyl-1,3-oxazol-5-yl)-5-[(4-{1-[4-(trifluoromethyl)phenyl]-octahydro-1H-pyrrolo[2,3-c]pyridin-6-yl}butyl)sulfanyl]-4H-1,2,4-triazole.

In embodiments, the compound is as described in Ex. 241: 4-methyl-3-(4-methyl-1,3-oxazol-5-yl)-5-[(3-{1-[4-(trifluoromethyl)phenyl]-octahydro-1H-pyrrolo[2,3-c]pyridin-6-yl}propyl)sulfanyl]-4H-1,2,4-triazole.

In embodiments, the compound is as described in Ex. 242: 3-({3-[(3aR,7aS or 3aS,7aR)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole. In embodiments, the compound is as described in Ex. 242: 3-({3-[(3aR,7aS)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole.

In embodiments, the compound is as described in Ex. 243: 3-({3-[(3aS,7aR or 3aR,7aS)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole. In embodiments, the compound is as described in Ex. 243: 3-({3-[(3aR,7aS)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole.

In embodiments, the compound is as described in Ex. 244: 4-methyl-3-(4-methyl-1,3-oxazol-5-yl)-5-[(3-{6-[4-(trifluoromethyl)phenyl]-octahydro-1H-pyrrolo[2,3-c]pyridin-1-yl}propyl)sulfanyl]-4H-1,2,4-triazole; or a pharmaceutical acceptable salt thereof.

Pharmaceutical Compositions

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

Certain of the compounds of the invention may form acid addition salts with one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, *arachis* oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule. Each dosage unit for oral administration contains for example from 1 to 250 mg (and for parenteral administration contains for example from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Methods of Making

The present invention also provides a process for preparing a compound of formula (I) or a salt thereof as defined above.

The process of the present invention for preparing compounds of formula (I) comprises the steps of: (a) reacting a compound of formula (X):

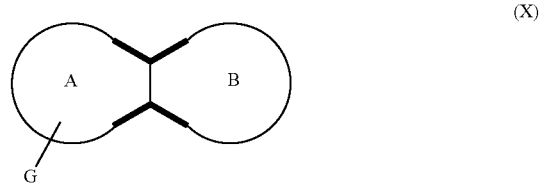

wherein G, A and B are as defined for formula (I), with a compound of formula (XI):

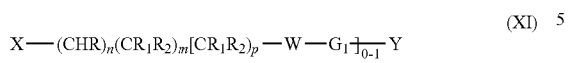

wherein R, R$_1$, R$_2$, n, m, p, W, G$_1$ and Y are as defined for formula (I) and X is a leaving group or an aldehyde, and thereafter optionally for process (a): (i) removing any protecting group(s); and/or (ii) forming a salt; and/or (iii) converting a compound of formula (I) or a salt thereof to another compound of formula (I) or a salt thereof.

Process (a) may be performed using conventional methods for the formation of a tertiary amine. When X is a leaving group, it can be halogen such as chlorine. Alternatively X can be a sulfonyloxy group such C1-4alkylsulfonyloxy (e.g. methanesulfonyloxy), C1-4alkylsulfonyloxy or haloC1-4alkylsulfonyloxy (e.g. trifluoromethanesulfonyloxy); or arylsulf176onyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more C1-2alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

When X is an aldehyde the reaction may be carried out using a reducing agent such as sodium triacetoxyborohydride in a suitable solvent such as dichloromethane or acetonitrile optionally in the presence of acetic acid or a Lewis acid in a catalytic amount and at a suitable temperature such as room temperature.

In one aspect of the present invention there are provided synthetic processes for the preparation of compounds of formula (II).

Compounds of formula (X) where A and B form an octahydropyrrolo[2,3-c]pyrrole system of formula (Xa):

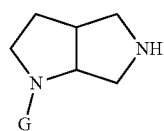

(Xa)

may be prepared in analogy to what reported in U.S. Pat. No. 4,990,517 wherein G is defined as for formula (I).

The synthetic process is provided and comprises the following steps of Scheme 1:

Scheme 1

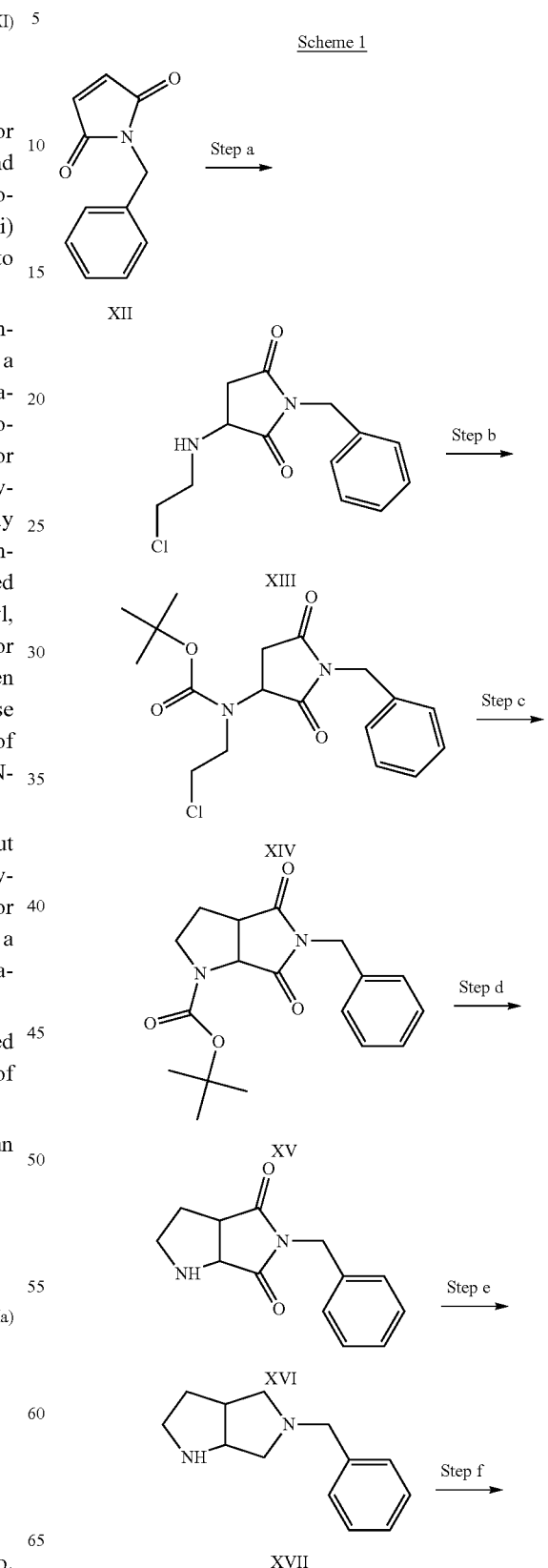

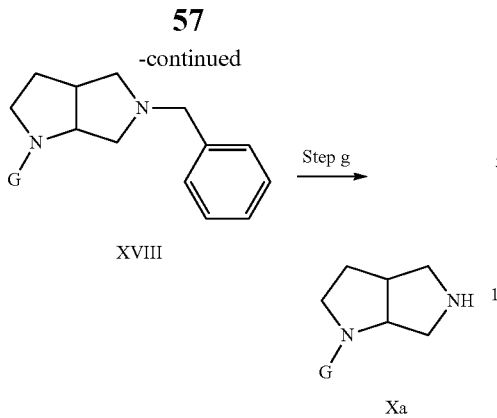

wherein: step a means nitrogen addition to the double bond of the maleimide (XII) to provide substituted imide (XIII); step b means protection of secondary amine (XIII) to give the N-Boc protected derivative (XIV); step c means ring closure of derivative (XIV) to give the bicyclic compound (XV); step d means deprotection ofN-Boc bycicle (XV) to give the corresponding secondary amine (XVI); step e means reduction of the imide (XVI) to give the diamine bicycle (XVII); step f means arylation of secondary amine (XVII) to give the corresponding substituted bicycle (XVIII); step g means deprotection of benzylamine (XVIII) to give the compound of formula (Xa).

Step a may be effected refluxing benzylmaleimide with chloroethyl amine in the presence of a suitable base such as a tertiary amine, for example triethylamine, in a suitable solvent such as dioxane. This is followed by allowing time to react as appropriate and a suitable workup.

Step b can be performed using standard reaction conditions for a Boc protection such as treating the amine with Boc-anhydride in a suitable solvent such as dichloromethane at a temperature such as room temperature. This is followed by allowing time to react as appropriate and a suitable workup.

Step c consists of treating the N-Boc protected derivative (XIV) with a strong base such as sodium hydride at an appropriate temperature ranging from 0° C. to room temperature in a suitable solvent such as dimethylformamide. This is followed by allowing time to react as appropriate and a suitable workup.

Step d can be performed using standard reaction conditions for a Boc deprotection such as treating the Boc-protected amine with an acid such as trifluoroacetic acid in a suitable solvent such as dichloromethane at a temperature such as room temperature. This is followed by allowing time to react as appropriate and a suitable workup.

Step e can be performed using a suitable reducing agent in a compatible solvent, such as Lithium aluminium hydride solution in THF at a temperature ranging from room temperature to reflux. This is followed by a suitable workup.

Step f consists of arylating the amine via Buchwald reaction or SNAr reaction. Step f may be performed using conventional methods for the Buchwald reactions reacting the amine with the appropriate aryl/heteroaryl halide such as chloride or bromide in the presence of a base such as sodium terbutoxide, a palladium source such as $Pd_2(dba)_3$ and a ligand such as (±)BINAP in a suitable solvent such as toluene at a temperature of 100° C. This is followed by allowing time to react as appropriate and a suitable workup.

Alternatively, step f may be performed using standard conditions fo SNAr reactions reacting the amine with the appropriate aryl/heteroaryl halide such as fluoride or chloride in the presence of a base such as potassium carbonate, in a suitable solvent such as DMSO at a temperature ranging from room temperature to 100° C. This is followed by allowing time to react as appropriate and a suitable workup.

Step g consists of deprotection of benzylamine using well known procedures for example via hydrogenation reaction refluxing a solution of benzylamine in a suitable solvent such as methanol in the presence of a hydrogen source such as ammonium formate and a hydrogenation catalyst such as palladium on carbon. This is followed by allowing time to react as appropriate and a suitable workup.

Compounds of formula (X) where A and B form an octahydropyrrolo[2,3-c]pyrrole system of formula (Xa) may be alternatively prepared in analogy to what reported in EP 0 393 424 A2, wherein G is defined as for formula (I). The synthetic process is provided and comprises the following steps in Scheme 2:

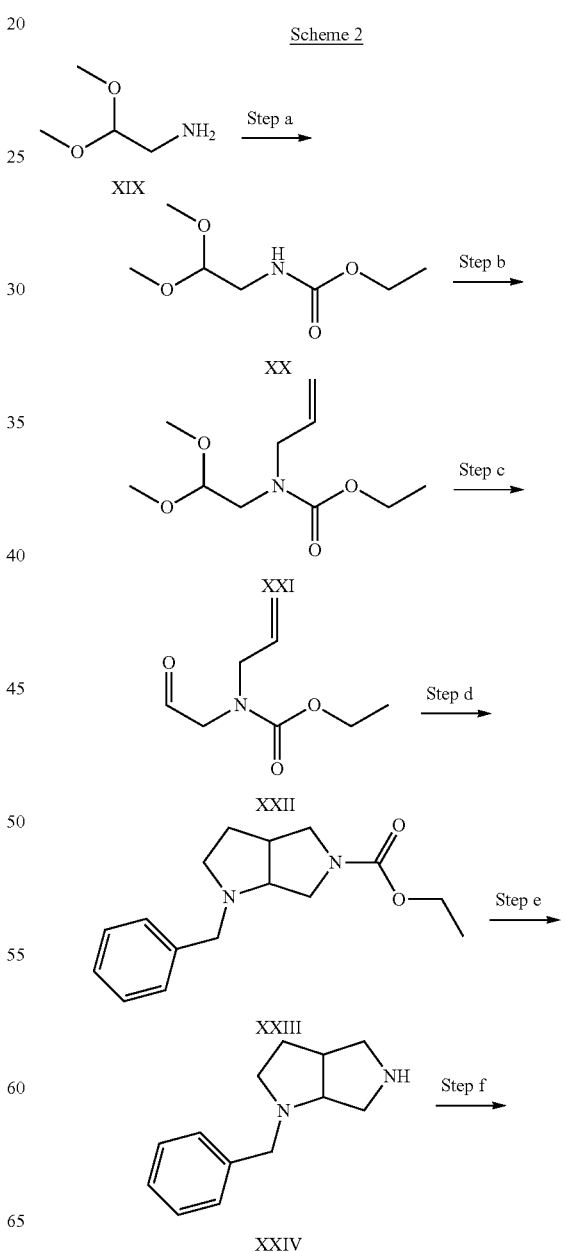

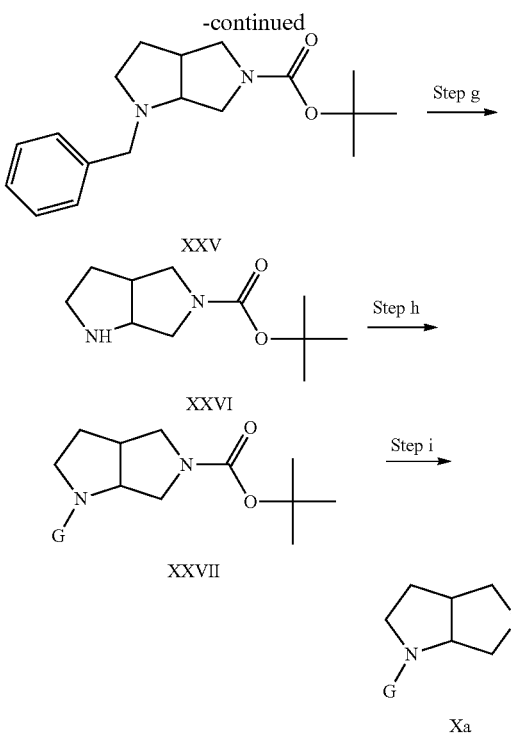

wherein: step a means protection of primary amine (XIX) as ethyl carbamate (XX); step b means allylation of carbamate (XX) to give the corresponding allyl derivative (XXI); step c means deprotection of the dimethylacetal (XXI) to give the corresponding aldehyde (XXII); step d means ring closure of derivative (XXII) to give the orthogonally protected bicycle (XXIII); step e means deprotection of ethylcarbamate (XXIII) to give the mono-protected bicycle (XXIV); step f means Boc-protection of the secondary amine (XXIV) to give the corresponding Boc-protected bicycle (XXV); step g means deprotection of benzylamine (XXV) to give the mono-protected derivative (XXVI); step h means arylation of secondary amine (XXVI) to give the substituted bicycle (XXVII); step i means Boc-deprotection (XXVII) to give the compound of formula (Xa).

Step a may be effected reacting aminoacetaldehyde dimethyl acetale with ethyl chloroformate in the presence of a base such as sodium hydroxide and in a suitable solvent such as a mixture dichloromethane/water at a temperature ranging from 0° C. to room temperature. This is followed by allowing time to react as appropriate and a suitable workup.

Step b can be performed treating the carbamate (XX) with a base such as potassium hydroxide and adding an allylhalide such as allylbromide in a suitable solvent such as toluene and in the presence of a phase transfer catalyst such as triethylbenzylammonium chloride at an appropriate temperature such as room temperature. This is followed by allowing time to react as appropriate and a suitable workup.

Step c may be performed treating the dimethylacetale (XXI) with acidic conditions such as refluxing in formic acid. This is followed by allowing time to react as appropriate and a suitable workup.

Step d may be effected reacting the intermediate (XXII) with benzylglycine in a suitable solvent such as toluene at reflux temperature. This is followed by allowing time to react as appropriate and a suitable workup.

Step e may be performed treating the ethylcarbamate (XXIII) with strong acidic conditions such as refluxing in hydrogen chloride 37%. This is followed by allowing time to react as appropriate and a suitable workup.

Step f may be performed using standard reaction conditions for a Boc protection such as treating the amine with Boc-anhydride in a suitable solvent such as dichloromethane at a temperature such as room temperature. This is followed by allowing time to react as appropriate and a suitable workup.

Step g consists of deprotection of benzylamine using well known procedures for example via hydrogenation reaction refluxing a solution of benzylamine in a suitable solvent such as methanol in the presence of a hydrogen source such as ammonium formate and a hydrogenation catalyst such as palladium on carbon. This is followed by allowing time to react as appropriate and a suitable workup.

Step h consists of arylating the amine via Buchwald reaction or SNAr reaction. Step f may be performed using conventional methods for the Buchwald reactions reacting the amine with the appropriate aryl/heteroaryl halide such as chloride or bromide in the presence of a base such as sodium terbutoxide, a palladium source such as $Pd_2(dba)_3$ and a ligand such as (+)BINAP in a suitable solvent such as toluene at a temperature of 100° C. This is followed by allowing time to react as appropriate and a suitable workup. Alternatively step f may be performed using standard conditions fo SNAr reactions reacting the amine with the appropriate aryl/heteroaryl halide such as fluoride or chloride in the presence of a base such as potassium carbonate, in a suitable solvent such as DMSO at a temperature ranging from room temperature to 100° C. This is followed by allowing time to react as appropriate and a suitable workup.

Step i can be performed using standard reaction conditions for a Boc deprotection such as treating the Boc-protected amine with an acid such as trifluoroacetic acid in a suitable solvent such as dichloromethane at a temperature such as room temperature. This is followed by allowing time to react as appropriate and a suitable workup.

Compounds of formula (X) where A and B form an octahydropyrrolo[2,3-c]pyrrole system of formula (Xa) wherein G is defined as for formula (I) may be alternatively synthesised with a process comprising the following steps of Scheme 3:

Scheme 3:

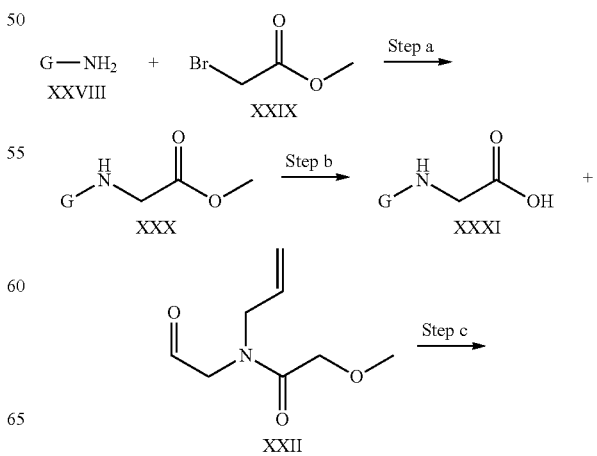

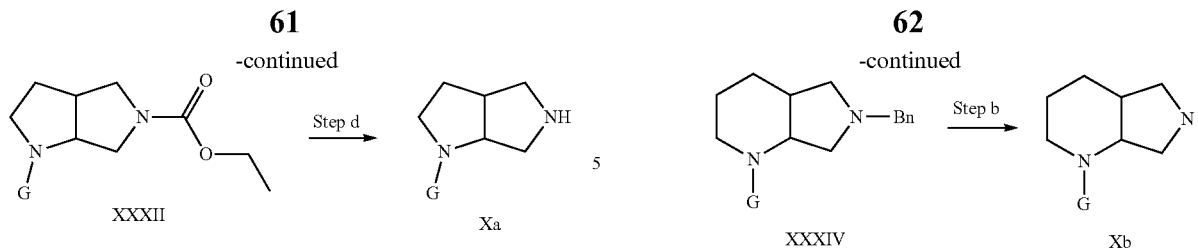

wherein: step a means alkylation of primary aryl amine (XXVIII) as alkyl derivative (XXIX); step b means hydrolysis of ester (XXX) to give the corresponding acid derivative (XXXI); step c means ring closure between derivatives (XXII) and (XXXI) to give the protected bicycle (XXXII); step d means deprotection of ethylcarbamate (XXXII) to give the the compound of formula (Xa).

Step a may be effected reacting aryl amine with methyl 2-bromoacetate in the presence of a base such as N,N-Diisopropylethylamine and in a suitable solvent such as DMF at a temperature ranging from room temperature to 60° C. This is followed by allowing time to react as appropriate and a suitable workup.

Step b can be performed treating the alkyl derivative (XXX) with a base such as lithium hydroxide in a suitable solvent such as a mixture of tetrahydrofuran/methanol/water at an appropriate temperature such as room temperature. This is followed by allowing time to react as appropriate and a suitable workup.

Step c may be effected reacting the intermediate (XXII) with the intermediate (XXXI) in a suitable solvent such as toluene in presence of a suitable base such as N,N-Diisopropylethylamine at reflux temperature. This is followed by allowing time to react as appropriate and a suitable workup.

Step d may be performed treating the protected bicycle (XXXII) with strong acidic conditions such as refluxing in hydrogen chloride 37%. This is followed by allowing time to react as appropriate and a suitable workup.

Compounds of formula (X) where A and B form an octahydro-1H-pyrrolo[3,4-b]pyridine system of formula (Xb) wherein G is defined as for formula (I)

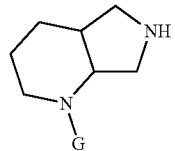

(Xb)

may be prepared from commercially available material; the synthetic process is provided and comprises the following steps of Scheme 4:

Scheme 4:

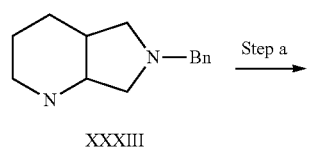

XXXIII wherein: step a means arylation of secondary amine (XXXIII) to give the substituted bicycle (XXXIV); step b means deprotection of benzylamine (XXXIV) to give the compound of formula (Xb).

Step a consists of arylating the commercially available amine via Buchwald reaction or SNAr reaction. Step a may be performed using conventional methods for the Buchwald reactions reacting the amine with the appropriate aryl/heteroaryl halide such as chloride or bromide in the presence of a base such as sodium terbutoxide, a palladium source such as Pd$_2$(dba)$_3$ and a ligand such as (±)BINAP in a suitable solvent such as toluene at a temperature of 100° C. This is followed by allowing time to react as appropriate and a suitable workup. Alternatively step a may be performed using standard conditions for SNAr reactions reacting the amine with the appropriate aryl/heteroaryl halide such as fluoride or chloride in the presence of a base such as potassium carbonate, in a suitable solvent such as DMSO at a temperature ranging from room temperature to 100° C. This is followed by allowing time to react as appropriate and a suitable workup.

Step b consists of deprotection of benzylamine using well known procedures for example via hydrogenation reaction refluxing a solution of benzylamine in a suitable solvent such as methanol in the presence of a hydrogen source such as ammonium formate and a hydrogenation catalyst such as palladium on carbon. This is followed by allowing time to react as appropriate and a suitable workup.

Compounds of formula (X) where A and B form a 3,6-diazabicyclo[3.2.0]heptane system of formula (Xc) wherein G is defined as for formula (I):

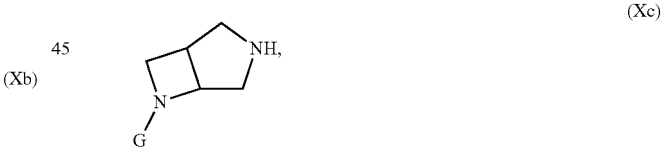

may be prepared in analogy to what reported in WO 02/070523, wherein G is defined as for formula (I). The synthetic process is provided and comprises the following steps of Scheme 5:

Scheme 5:

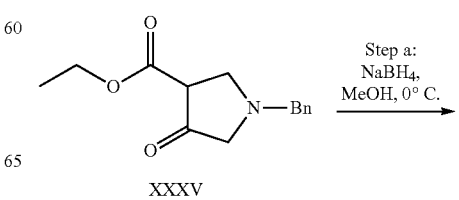

XXXV

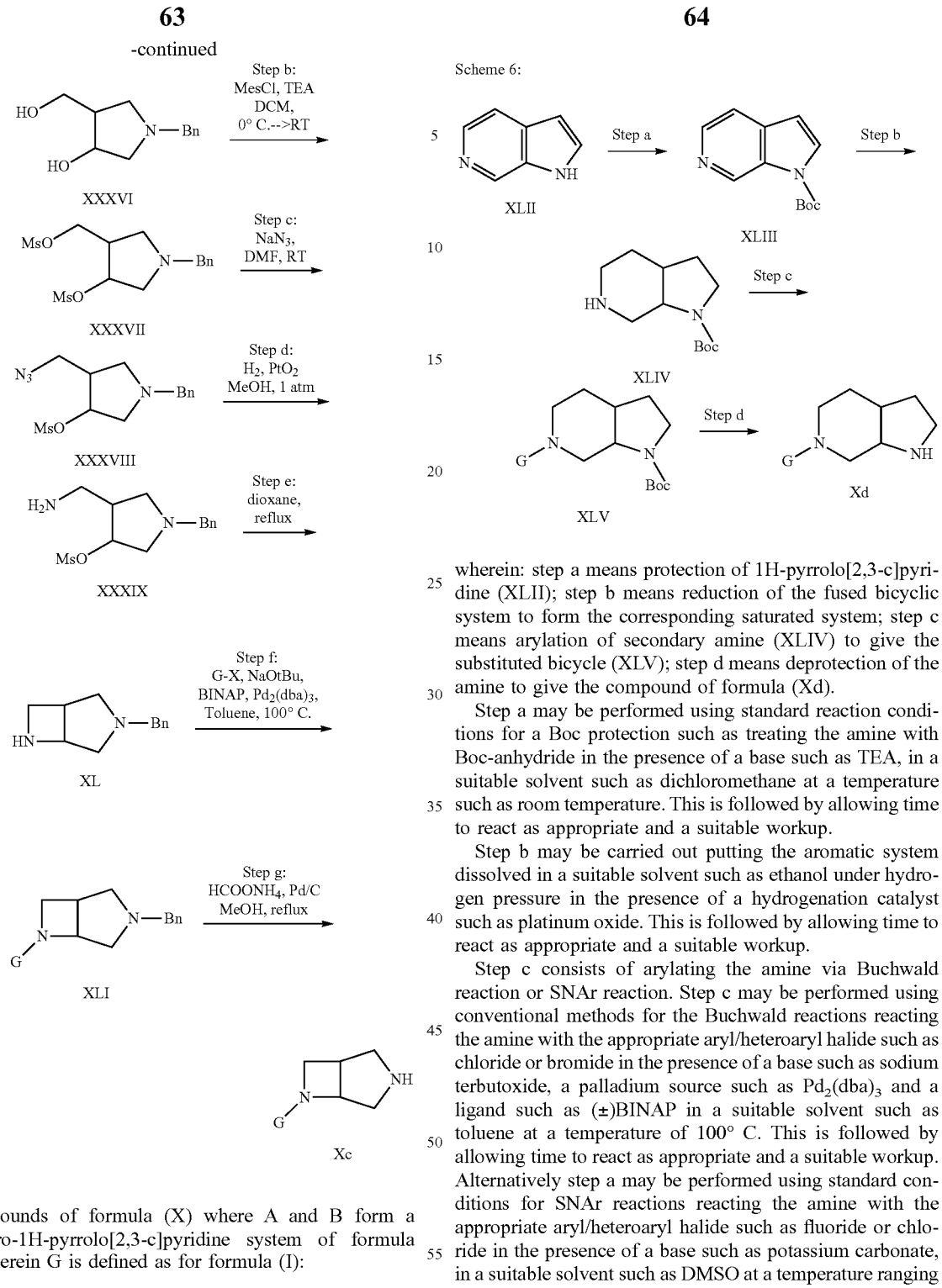

wherein: step a means protection of 1H-pyrrolo[2,3-c]pyridine (XLII); step b means reduction of the fused bicyclic system to form the corresponding saturated system; step c means arylation of secondary amine (XLIV) to give the substituted bicycle (XLV); step d means deprotection of the amine to give the compound of formula (Xd).

Step a may be performed using standard reaction conditions for a Boc protection such as treating the amine with Boc-anhydride in the presence of a base such as TEA, in a suitable solvent such as dichloromethane at a temperature such as room temperature. This is followed by allowing time to react as appropriate and a suitable workup.

Step b may be carried out putting the aromatic system dissolved in a suitable solvent such as ethanol under hydrogen pressure in the presence of a hydrogenation catalyst such as platinum oxide. This is followed by allowing time to react as appropriate and a suitable workup.

Step c consists of arylating the amine via Buchwald reaction or SNAr reaction. Step c may be performed using conventional methods for the Buchwald reactions reacting the amine with the appropriate aryl/heteroaryl halide such as chloride or bromide in the presence of a base such as sodium terbutoxide, a palladium source such as Pd$_2$(dba)$_3$ and a ligand such as (±)BINAP in a suitable solvent such as toluene at a temperature of 100° C. This is followed by allowing time to react as appropriate and a suitable workup. Alternatively step a may be performed using standard conditions for SNAr reactions reacting the amine with the appropriate aryl/heteroaryl halide such as fluoride or chloride in the presence of a base such as potassium carbonate, in a suitable solvent such as DMSO at a temperature ranging from room temperature to 100° C. This is followed by allowing time to react as appropriate and a suitable workup.

Step d can be performed using standard reaction conditions for a Boc deprotection such as treating the Boc-protected amine with an acid such as trifluoroacetic acid in a suitable solvent such as dichloromethane at a temperature such as room temperature. This is followed by allowing time to react as appropriate and a suitable workup.

Compounds of formula (X) where A and B form a octahydro-1H-pyrrolo[2,3-c]pyridine system of formula (Xd) wherein G is defined as for formula (I):

may be synthesised with a process comprising the following steps of Scheme 6:

Alternatively, compounds of formula (X), where A and B form a octahydro-1H-pyrrolo[2,3-c]pyridine system of formula (Xe), wherein G is defined as for formula (I):

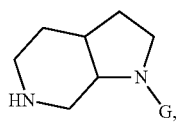

(Xe)

can be prepared using procedure well known to those skilled in the art starting from saturated bicyclic system (XLIV) (see Step b Scheme 6) orthogonally protecting and deprotecting the system in order to introduce the G group as defined for formula (I) in the appropriate position. Example of orthogonal protection may involve using Boc and Cbz-protecting group.

Compounds of formula (X) where A and B form a octahydropyrrolo[3,4-b]morpholine system of formula (Xf) wherein G is defined as for formula (I):

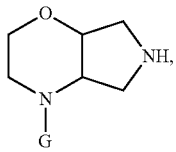

(Xf)

may be prepared in analogy to what reported in WO2012019426, wherein G is defined as for formula (I). The synthetic process is provided and comprises the following steps of Scheme 7.

Scheme 7:

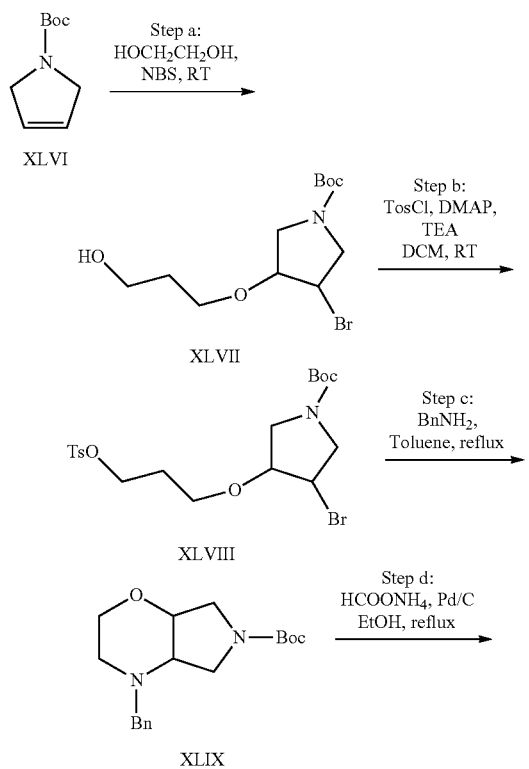

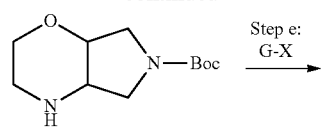

Step e: G-X →

L

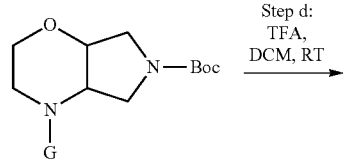

Step d: TFA, DCM, RT →

LI

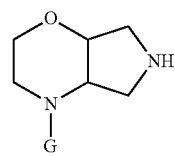

Xf

Compounds of formula (X) where A and B form a octahydrocyclopenta[c]pyrrole system of formula (Xg) wherein G is defined as for formula (I):

(Xg)

may be prepared in analogy to what reported in U.S. Pat. No. 5,541,217, wherein G is defined as for formula (I). The synthetic process is provided and comprises the following steps of Scheme 8.

Scheme 8:

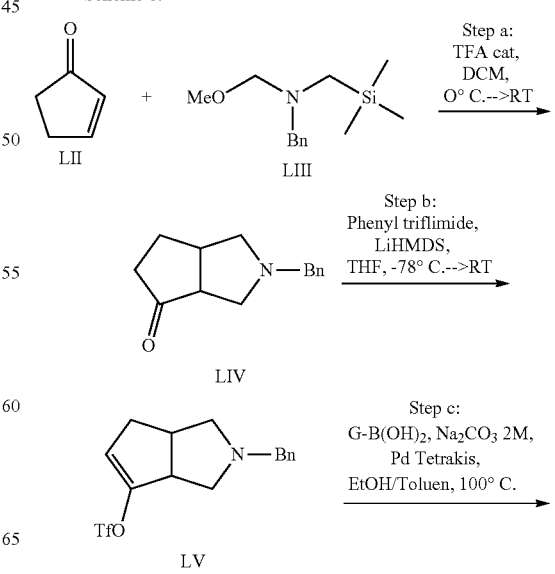

-continued
Step d:
HCOONH₄,
Pd/C, MeOH,
reflux

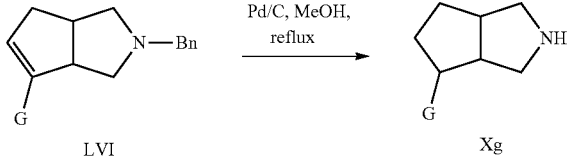

LVI                          Xg

A compound of formula (XI) may itself be prepared by reacting a compound of formula (LVII):

 (LVII), wherein G₁ and Y are as hereinbefore defined with a compound of formula (LVIII):

 (LVIII), wherein X is defined as for formula (XI) and L is a leaving group, e.g., a bromine atom. For typical reaction conditions, see Preparation 3 hereinafter.

A compound of formula (XI) wherein W is SO or SO₂ may itself be prepared by
a) reacting a compound of formula (LIX):

S-G₁-Y                          (LIX)

wherein G₁ and Y are as hereinbefore defined and S is a sulfur atom with a compound of formula (LVIII):

 (LVIII), wherein X is defined as for formula (XI) and L is a leaving group, e.g., a bromine atom. For typical reaction conditions, see Preparation 3 hereinafter; oxydizing the sulphur with an appropriate oxydizing agent such as oxone or m-chloroperbenzoic acid in a suitable solvent such as dichloromethane.

Compounds of formula (I) wherein W is oxygen and G, R, R₁, R₂, n, m, p, G₁ and Y are as defined as above, may be prepared by reacting a compound of formula (LX):

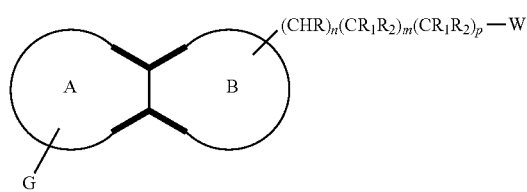
(LX)

wherein G, R, R₁, R₂, n, m and p are as defined for formula (I), with a compound of formula (LXI):

X-G₁-Y                          (LXI)

wherein G₁ and Y are as hereinbefore defined and X is a leaving group such as methyl sulphone. For typical reaction conditions see Example 213.

Methods of Use

The compounds described herein exhibit affinity for dopamine receptors, in particular the D₃ receptor, and are expected to be useful in the treatment of disease states which require modulation of such receptors.

Such affinity is typically calculated from the IC₅₀ as the concentration of a compound necessary to displace 50% of the radiolabeled ligand from the receptor, and is reported as a "K_i" value calculated by the following equation:

$$K_i = \frac{IC_{50}}{1 + L/K_D}$$

where L=radioligand and K_D=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 7. In one aspect the compounds described herein having a pKi between 7 and 8. In another aspect the compounds described herein have a pKi between 8 and 9. In a further aspect the compounds described herein a pKi greater than 9.

Many of the compounds described herein also been found to have greater affinity for dopamine D₃ than for D₂ receptors. The therapeutic effect of currently available antipsychotic agents (neuroleptics) is generally believed to be exerted via blockade of D₂ receptors; however this mechanism is also thought to be responsible for undesirable extrapyramidal side effects (eps) associated with many neuroleptic agents. It has been suggested that blockade of the recently characterised dopamine D₃ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. ≥10× or ≥100× higher) affinity for dopamine D₃ than dopamine D₂ receptors (such affinity can be measured using standard methodology for example using cloned dopamine receptors—see herein). Said compounds may suitably be used as selective modulators of D₃ receptors.

From the localisation of D₃ receptors, it could also be envisaged that the compounds could also have utility for the treatment of substance abuse where it has been suggested that D3 receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

The compounds described herein may be used for treatment of drug dependency, including withdrawal symptoms from drugs of abuse, such as alcohol, cocaine, opiates, nicotine, benzodiazepines and inhibition of tolerance induced by opioids. In addition, compounds described herein may be used to reduce cravings and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence. In embodiments, methods for reducing drug cravings refers to methods for reducing the incidents of relapse, methods of treating relapse, or methods of preventing relapse, where the relapse refers to any drug relapse, such as alcohol, opioids, and the like.

The compounds described herein are can be used as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and dopaminergic agonists, to reduce the side effects experienced with these treatments on long term use (e.g. see Schwartz et al., Brain Res. Reviews, 1998, 26, 236-242).

Within the context of the present invention, the terms describing the indications used herein are classified in the Diagnostic and Statistical Manual of Mental Disorders, 4th Edition, published by the American Psychiatric Association (DSM-V). The various subtypes of the disorders mentioned herein are contemplated as part of the present invention.

Within the context of the present invention, the term "schizophrenia spectrum and other psychotic disorder" includes: Schizotypal (personality disorder; Delusional Disorder; Brief Psychotic Disorder; Schizopreniform Disorder; Schizophrenia; Schizoaffective Disorder; Substance/Medication-Induced Psychotic Disorder; Psychotic Disorder due to another Medical Condition.

Within the context of the present invention, the term "catatonia" includes: Catatonia Associated With Another Mental Disorder (Catatonia Specifier); Catatonic Disorder Due to another Medical Condition; Unspecified Catatonia; Other Specified Schizophrenia Spectrum and other Psychotic Disorder; Unspecified Schizophrenia Spectrum and other Psychotic Disorder.

Within the context of the present invention, the term "obsessive-compulsive disorder" includes: Obsessive Compulsive Disorder; Body Dismorphic Disorder; Hoarding Disorder; Trichotillomania (Hair-Pulling Disorder); Excoriation (Skin-Picking) Disorder; Substance/Medication-Induced Obsessive-Compulsive and Related Disorder; Obsessive-Compulsive and Related Duisorder due to Another Medical Condition; Other Specified Obsessive-Compulsive and Related Disorders; Unspecified Obsessive-Compulsive and Related Disorders.

Within the context of the present invention, the term "feeding and eating disorders" includes: Pica; Ruminant Disorder; Avoidant/Restrictive Food Intake Disorder; Anorexia Nervosa; Bulimia Nervosa; Binge-Eating Disorder; Other Specified Feeding or eating Disorder; Unspecified Feeding or Eating Disorder.

Within the context of the present invention, the term "sexual disfunctions" includes: Delayed ejaculation; Erectile Disorder; Female Orgasmic Disorder; Female Sexual Interest/Arousal Disorder; Genito-Pelvic Pain/Penetration Disorder; Male Hypoactive Sexual Desire Disorder; Premature (early) Ejaculation; Substance/Medication-Induced Sexual Dysfunction; Unspecified Sexual Dysfunction.

Within the context of the present invention, the term "substance-related disorders and addictive disorders" includes: Substance-Related Disorders such as Substance Use Disorders; Substance-Induced Disorders; Substance Intoxication and Withdrawal; Substance/Medication-Induced Mental Disorders; Alcohol-Related Disorders such as Alcohol Use Disorder; Alcohol Intoxication; Alcohol Withdrawal; Other Alcohol-Induced Disorders; Unspecified Alcohol-Related Disorders; Caffeine-Related Disorders such as Caffeine Intoxication; Caffeine Withdrawal; Other Caffeine-Induced Disorders; Unspecified Caffeine-Related Disorders; *Cannabis*-Related Disorders such as *Cannabis* Use Disorder; *Cannabis* Intoxication; *Cannabis* Withdrawal; Other *Cannabis*-Induced Disorders; Unspecified *Cannabis*-Related Disorders; Hallucinogen-Related Disorders such as Phencyclidine Use Disorder; Other Hallucinogen Use Disorder; Phencyclidine Intoxication; Other Hallucinogen Intoxication; Hallucinogen Persisting Perception Disorder; Other Phencyclidine-Induced Disorders; Other Hallucinogen-Induced Disorders Unspecified Phencyclidine-Related Disorders; Unspecified Hallucinogen-Related Disorders; Inhalant-Related Disorders such as Inhalant Use Disorder; Inhalant Intoxication; Other Inhalant-Induced Disorders; Unspecified Inhalant-Related Disorders; Opioid-Related Disorders such as Opioid Use Disorder; Opioid Intoxication; Opioid Withdrawal; Other Opioid-Induced Disorders; Unspecified Opioid-Related Disorders; Sedative-, Hypnotic-, or Anxiolytic-Related Disorders such as Sedative-, Hypnotic-, or Anxiolytic Use Disorder; Sedative-, Hypnotic-, or Anxiolytic Intoxication; Sedative-, Hypnotic-, or Anxiolytic Withdrawal; Other Sedative-, Hypnotic-, or Anxiolytic-Induced Disorders; Unspecified Sedative-, Hypnotic-, or Anxiolytic-Related Disorders; Stimulant-Related Disorders such as Stimulant Use Disorder; Stimulant Intoxication; Stimulant Withdrawal; Other Stimulant-Induced Disorders; Unspecified Stimulant-Related Disorders; Tobacco-Related Disorders such as Tobacco Use Disorder; Tobacco Intoxication; Tobacco Withdrawal; Other Tobacco-Induced Disorders; Unspecified Tobacco-Related Disorders; Other (or Unknown) Substance-Related Disorders such as Other (or Unknown) Substance Use Disorder; Other (or Unknown) Substance Intoxication; Other (or Unknown) Substance Withdrawal; Other (or Unknown) Substance-Induced Disorders; Unspecified Other (or Unknown) Substance-Related Disorders.

Within the context of the present invention, the term "non-substance-related disorders and addictive disorders" includes: gambling and gambling disorders.

In a further aspect therefore the present invention provides a method of treating a condition for which modulation (especially antagonism/inhibition) of dopamine receptors (especially dopamine $D_3$ receptors) is beneficial, which comprises administering to a mammal (e.g. human) in need thereof an effective amount of a compound described herein or a pharmaceutically (i.e physiologically) acceptable salt thereof. Such conditions in particular include psychoses/psychotic conditions such as schizophrenia, and substance abuse.

The invention also provides the use of the compounds described herein or a pharmaceutically acceptable salt thereof in the manufacture of a medicament for the treatment of a condition in a mammal for which modulation (especially antagonism/inhibition) of dopamine receptors (especially dopamine $D_3$ receptors) is beneficial.

The invention also provides a compound described herein or a pharmaceutically acceptable salt thereof for use in the treatment of a condition in a mammal for which modulation (especially antagonism/inhibition) of dopamine receptors (especially dopamine $D_3$ receptors) is beneficial.

In one embodiment, $D_3$ antagonists according to the present invention are used in the treatment of psychoses such as schizophrenia or in the treatment of substance abuse.

Thus, a still further aspect the invention provides a method of treating a psychotic condition (e.g. schizophrenia)

or substance abuse which comprises administering to a mammal (e.g. human) in need thereof an effective amount of a compound described herein defined or a pharmaceutically acceptable salt thereof.

Also provided is the use of a compound described herein or a pharmaceutically acceptable salt thereof in the manufacture of a medicament for the treatment of a psychotic condition (e.g. schizophrenia) or substance abuse in a mammal.

Also provided is a compound described herein or a pharmaceutically acceptable salt thereof for use in the treatment of a psychotic condition (e.g. schizophrenia) or substance abuse in a mammal.

Also provided is a compound described herein or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The invention is further illustrated by the following non-limiting examples.

In the procedures that follow, after each starting material, reference to a preparation or Example by number is typically provided. This is provided merely for assistance to the skilled chemist. The starting material may not necessarily have been prepared from the batch referred to.

Where reference is made to the use of a "similar or analogous or as" procedure, as will be appreciated by those skilled in the art, such procedure may involve minor variation, for example reaction temperature, reagent/solvent amount, reaction time, work-up conditions or chromatographic purification conditions. All temperatures refer to ° C. Reagents and solvents were purchased from commercial suppliers (e.g. Aldrich, Fluorochem, Enamine, ABCR, Apollo) and used as received unless otherwise indicated. Proton Magnetic Resonance (NMR) spectra may be typically recorded either on Varian instruments at 400 or 500 MHz, or on a Bruker instrument at 400 MHz. Chemical shifts are expressed in parts of million (ppm, $\delta$ units). Chemical shifts are reported in ppm downfield ($\delta$) from $Me_4Si$, used as internal standard, and are typically assigned as singlets (s), broad singlets (br.s.), doublets (d), doublets of doublets (dd), doublets of doublets of doublets (ddd), doublets of triplets (dt), triplets (t), triplets of doublets (td), quartets (q), or multiplets (m).

LCMS may be recorded under the following conditions: DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative ES ionisation mode. The QC methods used were two, one operated under low pH conditions and another one operated under high pH. Details of the method operated under low pH conditions were: column, Acquity BEH $C_{18}$, 1.7 μm, 2.1×50 mm or Acquity CSH $C_{18}$, 1.7 μm, 2.1×50 mm, the temperature column was 40° C.; mobile phase solvent A was milliQ water+0.1% HCOOH, mobile phase solvent B MeCN+0.1% HCOOH. The flow rate was 1 mL/min. The gradient table was t=0 min 97% A—3% B, t=1.5 min 0.1% A—99.9% B, t=1.9 min 0.1% A—99.9% B and t=2 min 97% A—3% B. The UV detection range was 210-350 nm and the $ES^+/ES^-$ range was 100-1000 amu.

Details of the method operated under high pH conditions were the same of those listed above for the low pH method apart from: column Acquity BEH $C_{18}$, 1.7 μm, 2.1×50 mm; mobile phase solvent A was 10 mM acqueous solution of $NH_4HCO_3$ adjusted to pH=10 with ammonia, mobile phase solvent B MeCN.

Semipreparative mass directed autopurifications (MDAP) were carried out using Waters Fractionlynx™ systems operated under low or high pH chromatographic conditions. The stationary phases used were, XTerra C18, XBridge C18, Sunfire C18, XSelect C18, Gemini AXIA C18. The length of the columns was 5, 10 or 15 cm, while the internal diameter was 19, 21 or 30 mm. The particle size of the stationary phases was 5 or 10 μm. The purifications were carried out using low pH or high pH chromatographic conditions. The mobile phase solvent composition was the same used for QC analysis. The combinations stationary/mobile phases used were: XTerra, XBridge, Sunfire, XSelect—low pH mobile phases and XTerra, XBridge, Gemini AXIA—high pH mobile phases. All the purifications were carried out with the column kept at room T. The flow rate used was 17 or 20 mL/min for columns of internal diameter 19 or 21 mm and 40 or 43 mL/min for columns of internal diameter 30 mm. The trigger for the collection of the target species was the presence of the target m/z ratio value in the TIC MS signal. The gradient timetable was customised on the Rt behaviour of the target species.

Purification may also be performed using Biotage® Isolera or Biotage® SPI flash chromatography systems, these instruments work with Biotage® KP-SIL cartridges, Biotage® KP-NH cartidges or Biotage® KP-C18 cartridges. Unless otherwise stated, all reactions are typically performed under inert atmosphere (for example under Nitrogen).

The following abbreviations are used in the text: EtOAc, AcOEt, EA=ethyl acetate, $Et_2O$=diethyl ether, MeOH=methanol, EtOH=ethanol, THF=tetrahydrofuran, FC refers to flash chromatography, Tlc refers to thin layer chromatography on silica plates, and dried refers to a solution dried over anhydrous sodium sulphate, r.t. (RT) refers to room temperature, DMSO=dimethyl sulfoxide; ON=overnight, DMF=N,N'-dimethylformamide, DCM=dichloromethane, DCE=dichloroethane, DME=1,2-Dimethoxyethane, Cy, cHex=cyclohexane, TEA=triethylamine, DIPEA=N,N-Diisopropylethylamine, $Boc_2O$=Di-tert-butyl dicarbonate, TFA=trifluoroacetic acid, $Pd_2(dba)_3$=Tris(dibenzylideneacetone)dipalladium(0), TPP=triphenylphosphine, AcOH=acetic acid, LAH=Lithium aluminum hydride, LiHMDS=Lithium bis(trimethylsilyl)amide, BINAP=(R/S)-(±)-2,2'-Bis(diphenylphosphino)-1,1'-binaphthalene, TPP=triphenylphosphine, $Pd_2(dba)_3$=Tris(dibenzylideneacetone) dipalladium(0), T3P=Propylphosphonic anhydride, SCX Cartridge=Strong Cation Exchange Cartridge, ipa=isopropylamine, FA=formic acid, Py=pyridine, TBAF=Tetrabutylammonium fluoride, TBDMSCl=tert-Butyldimethylsilyl chloride, HOBt*$H_2O$=1-Hydroxybenzotriazole hydrate, EDC*HCl=N-(3-Dimethylaminopropyl)-N'-ethylcarbodiimide hydrochloride.

73

Preparation 1: 4-methyl-1,3-oxazole-5-carboxylic acid

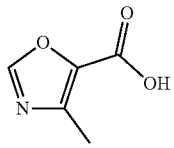

A stirred mixture of ethyl 2-chloro-3-oxobutanoate (16.8 mL, 121.51 mmol) and formamide (13.5 mL, 340.23 mmol) was heated to 120° C. After 6 hrs the mixture was allowed to cool to RT and stirred under nitrogen ON. The mixture was treated with 3 M NaOH (120 mL, reaction moderately exothermic) and stirred at RT for 4 hrs. EtOAc (120 mL) was added and the phases allowed separating. The organic layer was discarded while the aqueous was acidified with 37% aqueous HCl to pH 2 (~40 mL). A precipitate started to form. The suspension was treated with EtOAc (160 mL) and, vigorously shaken. Phases were separated and the aqueous one was further extracted with EtOAc twice (120 mL). The combined organic layers were concentrated to low volume. Fresh EtOAc (160 mL) was added and the mixture evaporated to dryness under vacuum. The collected solid was placed in the oven at 45° C. ON under reduced pressure to give 8.52 g of title compound (p1, y=44%), rusty brown solid. MS (m/z): 128.0 [MH]$^+$.

Preparation 2: 4-methyl-5-(4-methyl-1,3-oxazol-5-yl)-4H-1,2,4-triazole-3-thiol

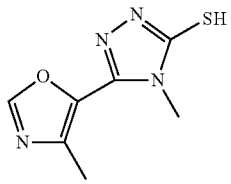

To a solution of 4-methyl-1,3-oxazole-5-carboxylic acid (p1, 2 g, 15.7 mmol) in DMF (9 mL), 4-Methyl-3-thiosemicarbazide (1.82 g; 17.27 mmol) was added. DIPEA (4.8 mL, 28.26 mmol) was added drop wise at RT, then the mixture was cooled in an ice bath before adding T3P (50% w/w in EtOAc) (14 mL, 23.55 mmol). The reaction was stirred at RT ON. NaOH 4 M solution (15 mL) was added (resulting pH=8). The reaction was diluted with EtOAc and the two resulting phases were separated (the upper organic layer eliminated). The pH was increased to 11 NaOH 4 M and the mixture heated to 70° C. for 30-40 min. The clear rusty red solution was then cooled to RT for 3 hrs, then 37% HCl was slowly added till pH 5. The clear solution was extracted 3 times with DCM; combined organics were dried over a phase separator and concentrated to obtain a brown solid. It was purified by C18 cartridge (eluting from H$_2$O+0.1% HCOOH to 20% CH$_3$CN+0.1% HCOOH). Fractions containing the product were concentrated to reduce the volume, then extracted twice with DCM to obtain 605 mg of title compound (p2, y=17%) as yellow solid. MS (m/z): 197.1 [MH]$^+$.

74

Preparation 3: 3-[(3-chloropropyl)sulfanyl]-4-methyl-5-(4-methyl-1,3-oxazol-5-yl)-4H-1,2,4-triazole

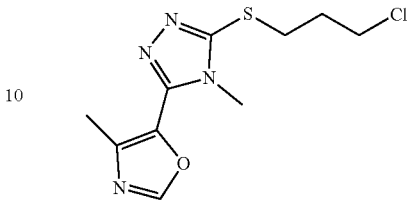

To a suspension of 4-methyl-5-(4-methyl-1,3-oxazol-5-yl)-4H-1,2,4-triazole-3-thiol (p2, 400 mg, 2.03 mmol) in a mixture MeOH/Acetone (1.3 mL/3.2 mL) at RT, 1-Bromo-3-chloropropane (260 µL, 2.64 mmol) was added, followed by K$_2$CO$_3$ (392 mg, 2.84 mmol) and the mixture was stirred at RT for 4.5 hrs. It was partitioned between water and EtOAc and phases were separated. Organic one was washed with brine then dried and concentrated under reduced pressure to obtain 509 mg of yellow solid. It was purified by FC on SiO$_2$ cartridge (eluting from cHex to EtOAc) affording 400 mg of title compound (p3, y=65%), as pale yellow solid. MS (m/z): 273.1 [MH]$^+$.

Preparation 4: 4-methyl-5-(oxan-4-yl)-4H-1,2,4-triazole-3-thiol

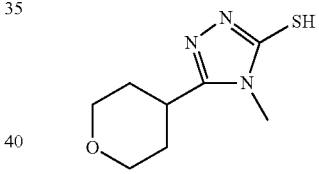

To a solution of oxane-4-carboxylic acid (5 g, 38.42 mmol) in DMF (23 mL), 4-methyl-3-thiosemicarbazide (4.45 mg; 42.26 mmol) was added. DIPEA (11.8 mL, 69.15 mmol) was added dropwise at RT, then the mixture was cooled in an ice bath before adding T3P (50% w/w in EtOAc) (35 mL, 57.63 mmol). The reaction was stirred at RT ON. NaOH 4 M solution was added (resulting pH=8). The reaction was diluted with EtOAc and the two resulting phases were separated (the upper organic layer eliminated). The pH was increased to 11 NaOH 4 M and the mixture heated to 70° C. for 40 min. The solution was then cooled down to 0° C. HCl 6 N was slowly added till pH~5. The white precipitate was filtered and washed with cHex, then dried ON at 50° C. to afford 3.47 g of title compound as white solid. The mother liquor was extracted with DCM (2×), the organic layer was dried and evaporated to obtain an oil which was triturated with Et$_2$O to afford a white off precipitate which was filtered and dried ON at 50° C. to afford further 1.8 g of title compound as pale yellow solid (p4, total y=69%). MS (m/z): 200.2 [MH]$^+$.

Preparation 5: 3-[(3-chloropropyl)sulfanyl]-4-methyl-5-(oxan-4-yl)-4H-1,2,4-triazole

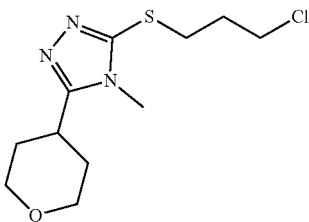 [SMILES: Cn1c(SCCCCl)nnc1C1CCOCC1]

To a suspension of 4-methyl-5-(oxan-4-yl)-4H-1,2,4-triazole-3-thiol (p4, 1.8 g, 9.03 mmol) in a mixture MeOH/Acetone (6 mL/15 mL) at RT 1-Bromo-3-chloropropane (1.16 mL, 11.74 mmol) was added followed by $K_2CO_3$ (1.75 g, 12.64 mmol) and the mixture was stirred at RT for 4 hrs. Then it was partitioned between water and DCM and phases were separated. Organic one was dried and concentrated under reduced pressure. Crude material was purified by FC on NH cartridge (eluting from cHex to 70% EtOAc) affording 1.57 g of title compound (p5, y=63%). MS (m/z): 276.1 $[MH]^+$.

Preparation 6: 5-cyclopentyl-4-methyl-4H-1,2,4-triazole-3-thiol

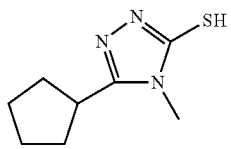

To a solution of Cyclopentanecarboxylic acid (0.95 mL, 8.76 mmol) in DMF (5 mL), 4-Methyl-3-thiosemicarbazide (1 g; 9.64 mmol) was added. DIPEA (2.7 mL, 15.76 mmol) was added drop wise at RT, then the mixture was cooled in an ice bath before adding T3P (50% w/w in EtOAc) (8 mL, 13.14 mmol). The reaction was stirred at RT ON.

NaOH 4 M solution was added (resulting pH=8). The reaction was diluted with EtOAc and the two resulting phases were separated (the upper organic layer eliminated). The pH was increased to 11 and the mixture heated to 70° C. for 40 min. The solution was then cooled down to 0° C. HCl 6 N was slowly added till pH~5. The white precipitate was filtered and washed with pentane, then dried to afford 266 mg of title compound (p6, y=16%) as white solid. MS (m/z): 184.0 $[MH]^+$.

Preparation 7: 3-[(3-chloropropyl)sulfanyl]-5-cyclopentyl-4-methyl-4H-1,2,4-triazole

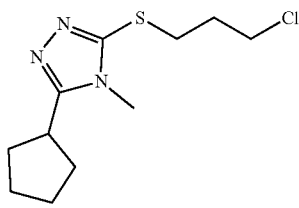 [SMILES: Cn1c(SCCCCl)nnc1C1CCCC1]

To a suspension of 5-cyclopentyl-4-methyl-4H-1,2,4-triazole-3-thiol (p6, 266 mg, 1.45 mmol) in a mixture MeOH/Acetone (0.9 mL/2.2 mL) at RT 1-Bromo-3-chloropropane (190 µL, 1.88 mmol) was added followed by $K_2CO_3$ (280 mg, 2.03 mmol) and the mixture was stirred at RT for 4 hrs. Then it was partitioned between water and DCM, phases were separated. Organic one was washed with brine then dried and concentrated under reduced pressure. Crude material was purified by FC on $SiO_2$ cartridge (eluting from cHex to AcOEt) affording 200 mg of title compound (p7, y=53%) as pale yellow oil. MS (m/z): 260.0 $[MH]^+$.

Preparation 8: 5-cyclohexyl-4-methyl-4H-1,2,4-triazole-3-thiol

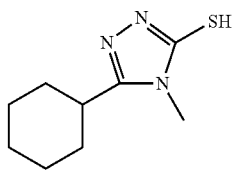

To a solution of cyclohexanecarboxylic acid (3 g, 2.91 mL, 23.4 mmol) in DMF (13.8 mL), 4-Methyl-3-thiosemicarbazide (2.7 g; 26.55 mmol) was added. DIPEA (7.20 mL, 42.12 mmol) was added dropwise at RT, then the mixture was cooled in an icebath before adding T3P (50% w/w in EtOAc) (23.83 mL, 35.1 mmol). The reaction was stirred at RT ON. NaOH 4 M solution was added (resulting pH=8). The reaction was diluted with EtOAc and the two resulting phases were separated. Presence of white solid was observed at the interface; therefore phases were separated collecting the white solid together with the organic phase. The aqueous layer was treated with NaOH 2N until pH=11 and heated to 70° C. for 40 min, then cooled down to 0° C. and treated with HCl 6 N (slow addition) till pH~5. A white solid precipitated that was filtered, dissolved in DMC, dried and evaporated under vacuum affording a first batch of 5-cyclohexyl-4-methyl-4H-1,2,4-triazole-3-thiol (0.67 g). The white solid collected with the organic phase, was filtered and identified as the desired intermediate. Therefore it was dissolved with NaOH 2N (10 mL) and the solution heated to 70° C. for 1 hr. The solution was then cooled down to 0° C. and HCl 6 N was slowly added till pH~5. A white solid precipitated that was filtered, dissolved in DMC, dried and evaporated under vacuum affording a second batch of 5-cyclohexyl-4-methyl-4H-1,2,4-triazole-3-thiol (2.57 g). Batches were combined affording 3.24 g of title compound (p8, y=70%). MS (m/z): 198.0 $[MH]^+$.

Preparation 9: 3-[(3-chloropropyl)sulfanyl]-5-cyclohexyl-4-methyl-4H-1,2,4-triazole

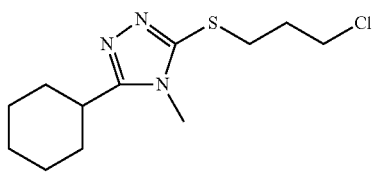 [SMILES: Cn1c(SCCCCl)nnc1C1CCCCC1]

To a suspension of 5-cyclohexyl-4-methyl-4H-1,2,4-triazole-3-thiol (p8, 1.57 g, 7.96 mmol) in a mixture MeOH/

Acetone (5.25 mL/13.21 mL) at RT 1-Bromo-3-chloropropane (1.02 mL, 10.34 mmol) was added followed by K₂CO₃ (1.54 g, 11.14 mmol) and the mixture was stirred at RT for 4 hrs. Then it was partitioned between water and DCM and phases were separated. Organic one was dried and concentrated under reduced pressure. Crude material was purified by FC on SiO₂ (eluting from cHex to EtOAc) affording 1.92 g of title compound (p9, y=88%) as a white solid. MS (m/z): 274.0 [MH]⁺.

Preparation 10: 5-(1,4-dioxan-2-yl)-4-methyl-4H-1,2,4-triazole-3-thiol

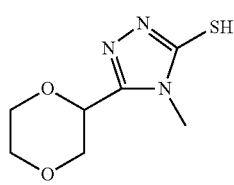

To a solution of 1,4-dioxane-2-carboxylic acid (0.5 g, 3.78 mmol) in DMF (2.23 mL), 4-Methyl-3-thiosemicarbazide (0.44 g, 26.55 mmol) was added. DIPEA (1.16 mL, 6.8 mmol) was added dropwise at RT, then the mixture was cooled in an icebath before adding T3P (50% w/w in EtOAc) (3.37 mL, 5.67 mmol). The reaction was stirred at RT ON. NaOH 4 M solution was added (resulting pH=8). The reaction was diluted with EtOAc and the two resulting phases were separated. The pH of the aqueous layer was increased to 11 NaOH 4 M and the mixture heated to 70° C. for 40 min. The solution was cooled to RT, then cooled down to 0° C. and HCl 6 N was slowly added till pH~5. The aqueous layer was extracted three times with DCM and combined organics were dried and concentrate under vacuum. The crude was purified by FC on SiO₂ (eluent: from cyclohexane to 50% of ethyl acetate) to give 0.489 g of title compound as white solid (p10, yield 64.21%). MS (m/z): 202.0 [MH]⁺.

Preparation 11: 3-[(3-chloropropyl)sulfanyl]-5-(1,4-dioxan-2-yl)-4-methyl-4H-1,2,4-triazole

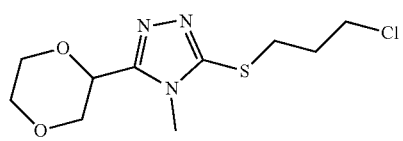 [SMILES: Cn1c(SCCCCl)nnc1C1COCCO1]

To a suspension of 5-(1,4-dioxan-2-yl)-4-methyl-4H-1,2,4-triazole-3-thiol (p10, 0.2 g, 0.99 mmol) in a mixture MeOH/Acetone (1 mL/2.5 mL) at RT, 1-Bromo-3-chloropropane (0.127 mL, 1.287 mmol) was added followed by K₂CO₃ (127 mg, 1.386 mmol) and the mixture was stirred at rt for 4 hrs. Then it was partitioned between water and DCM and phases were separated. Organic one was dried and concentrated under reduced pressure. Crude material was purified by FC on SiO₂ gel (eluent: from Cy to AcOEt 100%) affording the title compound (p11, 0.21 g) as a white solid. MS (m/z): 278.0 [MH]⁺.

Preparation 12: 2-[(3-chloropropyl)sulfanyl]-1-methyl-1H-1,3-benzodiazole

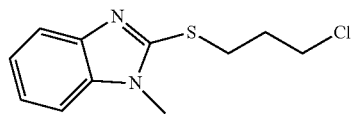

To a suspension of 1-methyl-1H-1,3-benzodiazole-2-thiol (200 mg, 1.22 mmol) in a mixture MeOH/Acetone (1.8 mL/4.4 mL) at RT, 1-Bromo-3-chloropropane (156 µL, 1.58 mmol) was added followed by K₂CO₃ (236 mg, 1.7 mmol) and the mixture was stirred at RT for 18 hrs. Then it was partitioned between water and EtOAc and phases were separated. Organic one was dried and concentrated under reduced pressure. Crude material was purified by FC on NH cartridge (eluting from cHex to 50% EtOAc) affording 282 mg of title compound (p12, y=96%). MS (m/z): 241.1 [MH]⁺.

Preparation 13: 4-{5-[(3-chloropropyl)sulfanyl]-4-methyl-4H-1,2,4-triazol-3-yl}morpholine

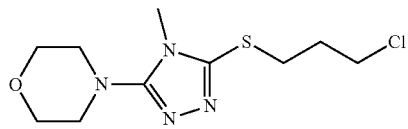 [SMILES: Cn1c(SCCCCl)nnc1N1CCOCC1]

To a suspension of 4-methyl-5-(morpholin-4-yl)-4H-1,2,4-triazole-3-thiol (commercially available, 0.2 g, 1 mmol) in a mixture MeOH/Acetone (0.6 mL/1.5 mL) at RT, 1-Bromo-3-chloropropane (0.128 mL, 1.3 mmol) was added followed by K₂CO₃ (0.193 g, 1.4 mmol) and the mixture was stirred at RT ON. Then it was partitioned between water and DCM and phases were separated. Organic one was dried and concentrated under reduced pressure. Crude material was purified by FC on SiO₂ column (eluent: from Cy to AcOEt 100%) affording 0.219 g of title compound (p13, y=79%). MS (m/z): 277.2 [MH]⁺.

Preparation 14: 4-methyl-5-(pyridazin-4-yl)-4H-1,2,4-triazole-3-thiol

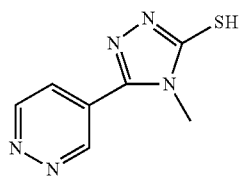

To a solution of pyridazine-4-carboxylic acid (1 g, 8.06 mmol) in DMF (4.6 mL), 4-Methyl-3-thiosemicarbazide (932 mg, 8.86 mmol) was added. DIPEA (2.48 mL, 14.5 mmol) was added dropwise at RT, then the mixture was cooled in an icebath before adding T3P (50% w/w in EtOAc) (7.2 mL, 12.09 mmol). The reaction was stirred at RT ON. NaOH 4 M solution was added (resulting pH=8). The reaction was diluted with EtOAc and the two resulting phases were separated (the upper organic layer eliminated). The pH was increased to 11 NaOH 4 M and the mixture heated to 70° C. for 3.5 hrs. The solution was cooled down to 0° C. HCl 6 N was slowly added till pH~5. A solid formation was observed. The mixture was left stirring at 0° C. for further 1 h then the solid was filtered washing with water and Cy. The solid was collected and dried under vacuum affording 1.29 g of title compound (p14, y=83%). MS (m/z): 194.1 [MH]⁺.

Preparation 15: 4-{5-[(3-chloropropyl)sulfanyl]-4-methyl-4H-1,2,4-triazol-3-yl}pyridazine

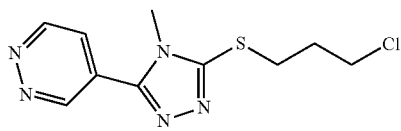 [SMILES: Cn1c(SCCCCl)nnc1-c1ccnnc1]

To a suspension of 4-methyl-5-(pyridazin-4-yl)-4H-1,2,4-triazole-3-thiol (p14, 1.29 g, 6.67 mmol) in a mixture MeOH/Acetone (3.3 mL/8.3 mL) at RT, 1-Bromo-3-chloropropane (0.858 mL, 8.68 mmol) was added followed by K₂CO₃ (1.29 g, 9.34 mmol) and the mixture was stirred at RT ON. Then it was partitioned between water and DCM and phases were separated. Organic one was dried and concentrated under reduced pressure. Crude material was purified by FC on NH column (eluent: from Cy to AcOEt 100%) affording 1.3 g of title compound (p15, y=72%). MS (m/z): 270.2 [MH]⁺.

Preparation 16: 4-methyl-5-(pyridazin-3-yl)-4H-1,2,4-triazole-3-thiol

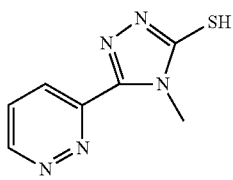

To a solution of pyridazine-4-carboxylic acid (1 g, 8.06 mmol) in DMF (4.6 mL), 4-Methyl-3-thiosemicarbazide (932 mg; 8.86 mmol) was added. DIPEA (2.48 mL, 14.5 mmol) was added dropwise at RT, then the mixture was cooled in an icebath before adding T3P (50% w/w in EtOAc) (7.2 mL, 12.09 mmol). The reaction was stirred at RT ON. NaOH 4 M solution was added (resulting pH=8). The reaction was diluted with EtOAc and the two resulting phases were separated (the upper organic layer eliminated). The pH was increased to 11 NaOH 4 M and the mixture heated to 70° C. for 40 min. The solution was then cooled down to 0° C. HCl 6 N was slowly added till pH~5. A solid formation was observed. The mixture was left stirring at 0° C. for further 1 h then the solid was filtered washing with water and Cy. The solid was collected and dried under vacuum affording 1.23 g of title compound (p16, y=79%). MS (m/z): 194.1 [MH]⁺.

Preparation 17: 3-{5-[(3-chloropropyl)sulfanyl]-4-methyl-4H-1,2,4-triazol-3-yl}pyridazine

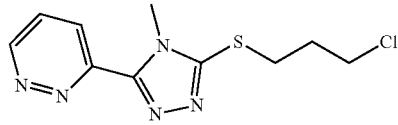 [SMILES: Cn1c(SCCCCl)nnc1-c1cccnn1]

To a suspension of 4-methyl-5-(pyridazin-3-yl)-4H-1,2,4-triazole-3-thiol (p16, 1.23 g, 6.36 mmol) in a mixture MeOH/Acetone (3.3 mL/8.3 mL) at RT 1-Bromo-3-chloropropane (0.818 mL, 8.27 mmol) was added followed by K₂CO₃ (1.23 g, 8.9 mmol) and the mixture was stirred at RT on. Then it was partitioned between water and DCM and phases were separated. Organic one was dried and concentrated under reduced pressure. Crude material was purified by FC on NH column (eluent: from Cy to EtOAc 100%) affording 1.3 g of title compound (p17, y=76%). MS (m/z): 270.2 [MH]⁺.

Preparation 18: 4-methyl-5-(pyrimidin-5-yl)-4H-1,2,4-triazole-3-thiol

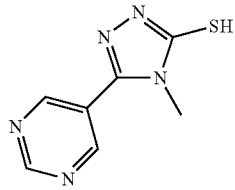

To a solution of pyrimidine-5-carboxylic acid (1 g, 8.05 mmol) in DMF (4.5 mL), 4-methyl-3-thiosemicarbazide (930 mg; 8.86 mmol) was added. DIPEA (2.5 mL, 14.5 mmol) was added drop-wise at RT, then the mixture was cooled in an ice bath before adding T3P (50% w/w in EtOAc) (7.36 mL, 12.09 mmol). The reaction was stirred at RT ON. NaOH 4 M solution was added (resulting pH=8). The reaction was diluted with EtOAc. The solid present at the interface was filtered. The two resulting phases were separated (the upper organic layer eliminated). The solid was added to the aqueous phase, pH was increased to 11 NaOH 4 M and the mixture heated to 70° C. for 1 h. The solution was then then cooled down to 0° C. HCl 6 N was slowly added till pH~5. The white precipitate was filtered and washed with cHex, then dried to afford 4-methyl-5-(pyrimidin-5-yl)-4H-1,2,4-triazole-3-thiol (p18, 320 mg y=20%). MS (m/z): 194.2 [MH]⁺.

Preparation 19: 5-{5-[(3-chloropropyl)sulfanyl]-4-methyl-4H-1,2,4-triazol-3-yl}pyrimidine

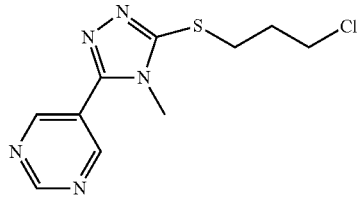 [SMILES: Cn1c(SCCCCl)nnc1-c1cncnc1]

To a suspension of 4-methyl-5-(pyrimidin-5-yl)-4H-1,2,4-triazole-3-thiol (p18, 0.32 g, 1.65 mmol) in a mixture MeOH/Acetone (0.6 mL/1.8 mL) at RT 1-Bromo-3-chloropropane (0.213 mL, 2.15 mmol) was added followed by $K_2CO_3$ (0.32 g, 2.31 mmol) and the mixture was stirred at RT for 4 hrs. Then it was partitioned between water and DCM and phases were separated. Organic one was dried and concentrated under reduced pressure. Crude material was purified by FC on NH column (eluent: from Cy to AcOEt 70%) affording 40 mg of title compound (p19, y=9%). MS (m/z): 270.0 $[MH]^+$.

Preparation 20: 4-methyl-5-(pyrazin-2-yl)-4H-1,2,4-triazole-3-thiol

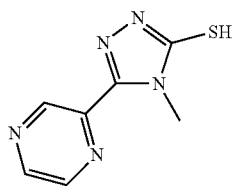

To a solution of pyrazine-2-carboxylic acid (1 g, 8.06 mmol) in DMF (5 mL), 4-methyl-3-thiosemicarbazide (933 mg, 8.87 mmol) was added. DIPEA (2.5 mL, 14.5 mmol) was added drop-wise at RT, then the mixture was cooled in an ice-bath before adding T3P (50% w/w in EtOAc) (7.1 mL, 12.09 mmol). The reaction was stirred at RT on. NaOH 4 M solution (7.5 mL) was added (resulting pH=8). The reaction was diluted with EtOAc and the two resulting phases were separated (the upper organic layer eliminated). The pH was increased to 11 NaOH 4 M and the mixture heated to 70° C. for 2 h. The yellow solution was then cooled in an ice bath and 37% HCl was slowly added till pH 5. A precipitate formed. It was filtered under vacuum, washed with water and Cy and dried to obtain 1.44 g of title compound (p20, y=%92). MS (m/z): 194.1 $[MH]^+$.

Preparation 21: 2-{5-[(3-chloropropyl)sulfanyl]-4-methyl-4H-1,2,4-triazol-3-yl}pyrazine

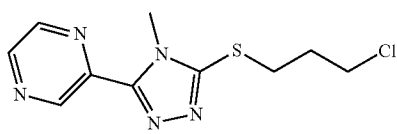 [SMILES: Cn1c(SCCCCl)nnc1-c1cnccn1]

To a suspension of 4-methyl-5-(pyrazin-2-yl)-4H-1,2,4-triazole-3-thiol (p20, 1.44 g, 7.45 mmol) in a mixture MeOH/Acetone (4.5 mL/11.5 mL) at RT, 1-Bromo-3-chloropropane (810 µL, 8.2 mmol) was added, followed by $K_2CO_3$ (1.44 g, 10.4 mmol) and the mixture was stirred at RT on. It was partitioned between water and AcOEt and phases were separated. Organic one was washed with brine, then dried and concentrated under reduced pressure. Crude material was purified by FC on $SiO_2$ column (eluent: from Cy to AcOEt) affording 1.7 g of title compound (p21, y=84%). MS (m/z): 270.1 $[MH]^+$.

Preparation 22: 4-methyl-5-(pyrimidin-4-yl)-4H-1,2,4-triazole-3-thiol

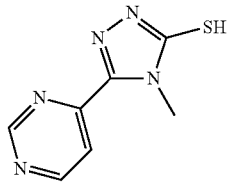

To a solution of pyrimidine-4-carboxylic acid (1 g, 8.06 mmol) in DMF (5 mL), 4-methyl-3-thiosemicarbazide (933 mg; 8.87 mmol) was added. DIPEA (2.5 mL, 14.5 mmol) was added drop-wise at RT, then the mixture was cooled in an ice-bath before adding T3P (50% w/w in EtOAc) (7.1 mL, 12.09 mmol). The reaction was stirred at RT ON. NaOH 4 M solution (7.5 mL) was added (resulting pH=8). The reaction was diluted with EtOAc and the two resulting phases were separated (the upper organic layer eliminated). The pH was increased to 11 NaOH 4 M and the mixture heated to 70° C. for 2.5 hrs. The brown solution was then cooled with an ice bath and 37% HCl was slowly added till pH 5. A precipitate formed. It was filtered under vacuum, washed with water and Cy and dried to obtain 1.46 g of title compound (p22, y=93%). MS (m/z): 194.1 $[MH]^+$.

Preparation 23: 4-{5-[(3-chloropropyl)sulfanyl]-4-methyl-4H-1,2,4-triazol-3-yl}pyrimidine

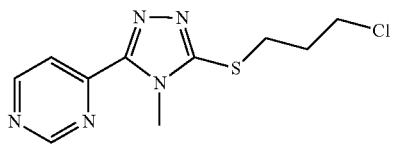 [SMILES: Cn1c(SCCCCl)nnc1-c1ccncn1]

To a suspension of 4-methyl-5-(pyrimidin-4-yl)-4H-1,2,4-triazole-3-thiol (p22, 1.46 g, 7.55 mmol) in a mixture MeOH/Acetone (4.5 mL/11.5 mL) at RT, 1-Bromo-3-chloropropane (816 µL, 8.3 mmol) was added, followed by $K_2CO_3$ (1.46 g, 10.57 mmol) and the mixture was stirred at RT on. It was partitioned between water and AcOEt and phases were separated. Organic one was washed with brine, then dried and concentrated under reduced pressure. Crude material was purified by FC on $SiO_2$ cartridge (eluent: from Cy to AcOEt) affording 1.45 g of title compound (p23, y=71%). MS (m/z): 269.9 $[MH]^+$.

Preparation 24: tert-butyl 4-(4-methyl-5-sulfanyl-4H-1,2,4-triazol-3-yl)piperidine-1-carboxylate

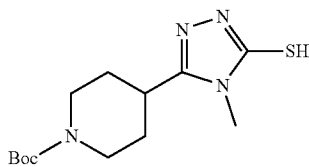 [SMILES: Cn1c(S)nnc1C1CCN(C(=O)OC(C)(C)C)CC1]

To a stirred solution of 1-Boc-piperidine-4-carboxylic acid (1.0 g, 4.36 mmol) in DMF (3 mL), 4-methyl-3-thiosemicarbazide (0.504 g, 4.8 mmol) and DIPEA (1.37 mL, 7.85 mmol) were subsequently added. The mixture was cooled to 0° C. then T3P (50% wt/EA) (3.9 mL, 6.54 mmol) was added dropwise. The ice-bath was removed and the resulting reaction mixture was stirred at RT for 3 hrs.

Aqueous 3 M NaOH solution was added (resulting pH~8) followed by AcOEt and the two resulting phases were separated (the upper organic layer was eliminated). Additional 4 M NaOH was added up to pH 11 then the mixture was heated to 70° C. and stirred for 40 min. The solution was cooled to RT and 6 N HCl was slowly added until pH 5. The product was extracted with DCM several times. The organic phase was washed with brine, filtered and evaporated to afford 1.08 g of title compound (p24, y=83%) as white solid. MS (m/z): 299.2 [MH]+.

Preparation 25: tert-butyl 4-{5-[(3-chloropropyl)sulfanyl]-4-methyl-4H-1,2,4-triazol-3-yl}piperidine-1-carboxylate

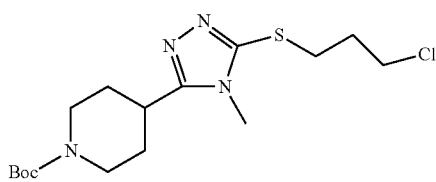 [SMILES: Cn1c(SCCCCl)nnc1C1CCN(C(=O)OC(C)(C)C)CC1]

To a suspension of tert-butyl 4-(4-methyl-5-sulfanyl-4H-1,2,4-triazol-3-yl)piperidine-1-carboxylate (p24, 1.08 g, 3.62 mmol) in a mixture MeOH/Acetone (4 mL/9 mL) at RT 1-Bromo-3-chloropropane (465 µL, 4.7 mmol) was added followed by K₂CO3 (700 mg, 5.07 mmol) and the mixture was stirred at RT ON. Then it was partitioned between water and DCM and phases were separated. Organic one was washed with brine then dried and concentrated under reduced pressure. Crude material was purified by FC on NH column (eluent:Cy to Cy/AcOEt 1:1) affording 1.08 g of title compound (p25, y=79%). MS (m/z): 375.3 [MH]+.

Preparation 26: 4-methyl-5-(pyridin-3-yl)-4H-1,2,4-triazole-3-thiol

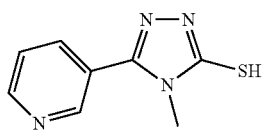

To a solution of pyridine-3-carboxylic acid (1.0 g, 8.12 mmol) and 4-methyl-3-thiosemicarbazide (0.94 g, 8.93 mmol) in DMF (4 mL), DIPEA (2.6 mL, 14.62 mmol) was added. The stirred mixture was cooled to 0° C. then T3P (50% wt/EA) (7.3 mL, 12.18 mmol) was added portionwise. The ice-bath was removed and the resulting reaction mixture was shaken at RT in a PLS apparatus on. Aqueous 4 M NaOH solution was added (resulting in pH~8) and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH~5 and a precipitate started to form. The mixture was stirred for 10 min then filtered. The solid was washed with water and dried under vacuum at 45° C. ON affording 0.96 g of title compound (p26, y=61%). MS (m/z): 193.1 [MH]+.

Preparation 27: 3-{5-[(3-chloropropyl)sulfanyl]-4-methyl-4H-1,2,4-triazol-3-yl}pyridine

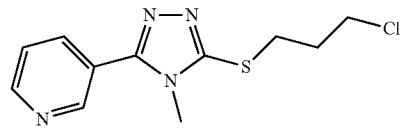 [SMILES: Cn1c(SCCCCl)nnc1-c1cccnc1]

To a mixture of 4-methyl-5-(pyridin-3-yl)-4H-1,2,4-triazole-3-thiol (p26, 100 mg, 0.52 mmol) and K₂CO₃ (93 mg, 0.68 mmol) in MeOH/Acetone (0.3/0.8 mL), 1-bromo-3-chloropropane (0.057 mL, 0.57 mmol) was added and the resulting reaction mixture was shaken at RT in a PLS apparatus ON. The mixture was filtered, the solid was washed with DCM and the filtrate was concentrated under reduced pressure to give 123 mg 3 of title compound (p27, y=88%). MS (m/z): 269.2 [MH]+.

Preparation 28: 4-methyl-5-(1-methyl-1H-pyrazol-4-yl)-4H-1,2,4-triazole-3-thiol

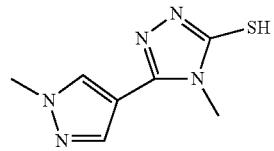

To a solution of 1-methyl-1H-pyrazole-4-carboxylic acid (1 g, 7.93 mmol) in DMF (5 mL), 4-methyl-3-thiosemicarbazide (0.917 g, 8.723 mmol) was added. DIPEA (2.4 mL, 14.3 mmol) was added dropwise at RT, then the mixture was cooled in an ice bath before adding T3P (50% w/w in EtOAc) (7.1 mL, 11.9 mmol). The reaction was stirred at RT ON. NaOH 4 M solution was added (resulting pH=8). The reaction was diluted with EtOAc and the two resulting phases were separated (the upper organic layer eliminated). The pH was adjusted to 11 with NaOH 4 M and the mixture heated to 70° C. for 1.5 h. The solution was then cooled to RT for 2 hrs, then 37% HCl was slowly added till pH 5. A precipitate formed. It was filtered under vacuum to obtain 649 mg of title compound (p28, y=45%). MS (m/z): 196.0 [MH]+.

Preparation 29: 3-[(3-chloropropyl)sulfanyl]-4-methyl-5-(1-methyl-1H-pyrazol-4-yl)-4H-1,2,4-triazole

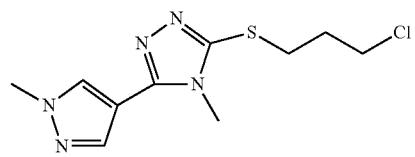 [SMILES: Cn1cc(-c2nnc(SCCCCl)n2C)cn1]

To a suspension of 4-methyl-5-(1-methyl-1H-pyrazol-4-yl)-4H-1,2,4-triazole-3-thiol (p28, 694 mg, 3.55 mmol) in a mixture MeOH/Acetone (1.9 mL/5 mL) at RT, 1-Bromo-3-chloropropane (386 μL, 3.905 mmol) was added, followed by $K_2CO_3$ (687 mg, 4.97 mmol) and the mixture was stirred at RT for 5 hrs. The mixture was filtered with DCM and the filtrate was concentrated in vacuum. Crude material was purified by FC on $SiO_2$ cartridge (eluent: from Cy to EtOAc) to obtain 830 mg of title compound (p29, y=86%). MS (m/z): 272.0 [MH]$^+$.

Preparation 30: 4-methyl-5-(pyridin-4-yl)-4H-1,2,4-triazole-3-thiol

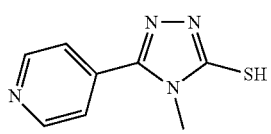

To a solution of pyridine-4-carboxylic acid (1.0 g, 8.12 mmol) and 4-methyl-3-thiosemicarbazide (0.94 g, 8.93 mmol) in DMF (4 mL), DIPEA (2.6 mL, 14.62 mmol) was added. The stirred mixture was cooled to 0° C. then T3P (50% wt/EA) (7.3 mL, 12.18 mmol) was added portionwise. The ice-bath was removed and the resulting reaction mixture was shaken at RT in a PLS apparatus on. Aqueous 4 M NaOH solution was added (resulting in pH~8) and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH~5 and a precipitate started to form. The mixture was stirred for 10 min then filtered. The solid was washed with water and dried under vacuum at 45° C. ON affording 1.31 g of title compound (p30, y=84%). MS (m/z): 193.1[MH]$^+$.

Preparation 31: 4-{5-[(3-chloropropyl)sulfanyl]-4-methyl-4H-1,2,4-triazol-3-yl}pyridine

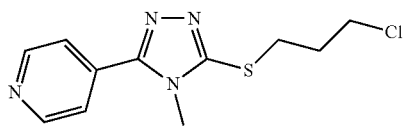 [SMILES: Cn1c(SCCCCl)nnc1-c1ccncc1]

To a mixture of 4-methyl-5-(pyridin-4-yl)-4H-1,2,4-triazole-3-thiol (p30, 100 mg, 0.52 mmol) and $K_2CO_3$ (93 mg, 0.68 mmol) in MeOH/Acetone (0.3/0.8 mL), 1-bromo-3-chloropropane (0.057 mL, 0.57 mmol) was added and the resulting reaction mixture was shaken at RT in a PLS apparatus ON. The mixture was filtered, the solid was washed with DCM and the filtrate was concentrated under reduced pressure to give 116 mg of title compound (p31, y=83%). MS (m/z): 269.2 [MH]$^+$.

Preparation 32: 4-methyl-5-(pyridin-2-yl)-4H-1,2,4-triazole-3-thiol

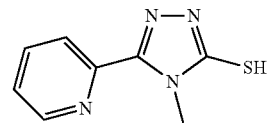

To a solution of pyridine-2-carboxylic acid (1.0 g, 8.12 mmol) and 4-methyl-3-thiosemicarbazide (0.94 g, 8.93 mmol) in DMF (4 mL), DIPEA (2.6 mL, 14.62 mmol) was added. The stirred mixture was cooled to 0° C. then T3P (50% wt/EA) (7.3 mL, 12.18 mmol) was added portionwise. The ice-bath was removed and the resulting reaction mixture was shaken at RT in a PLS apparatus on. Aqueous 4 M NaOH solution was added (resulting in pH~8) and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH~5 and a precipitate started to form. The mixture was stirred for 10 min then filtered. The solid was washed with water and dried under vacuum at 45° C. ON affording 1.3 g of title compound thiol (p32, y=83%). MS (m/z): 193.1[MH]$^+$.

Preparation 33: 2-{5-[(3-chloropropyl)sulfanyl]-4-methyl-4H-1,2,4-triazol-3-yl}pyridine

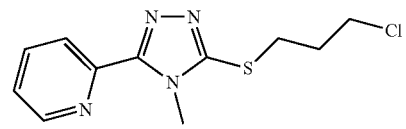 [SMILES: Cn1c(SCCCCl)nnc1-c1ccccn1]

To a mixture of 4-methyl-5-(pyridin-2-yl)-4H-1,2,4-triazole-3-thiol (p32, 100 mg, 0.52 mmol) and $K_2CO_3$ (93 mg, 0.68 mmol) in MeOH/Acetone (0.3/0.8 mL), 1-bromo-3-chloropropane (0.057 mL, 0.57 mmol) was added and the resulting reaction mixture was shaken at RT in a PLS apparatus ON. The mixture was filtered, the solid was washed with DCM and the filtrate was concentrated under reduced pressure to give 112 mg of title compound (p33, y=80%). MS (m/z): 269.2 [MH]$^+$.

Preparation 34: 4-methyl-5-(1,3-thiazol-2-yl)-4H-1,2,4-triazole-3-thiol

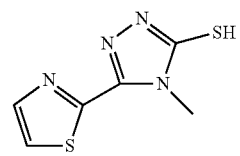

To a solution of 1,3-thiazole-2-carboxylic acid (1 g, 7.74 mmol) in DMF (5 mL), 4-methyl-3-thiosemicarbazide (0.895 g, 8.514 mmol) was added. DIPEA (2.4 mL, 14 mmol) was added drop wise at RT, then the mixture was cooled in an ice bath before adding T3P (50% w/w in EtOAc) (6.9 mL, 11.6 mmol). The reaction was stirred at RT ON. NaOH 4 M solution was added (resulting pH=8). The reaction was diluted with EtOAc and the two resulting phases were separated (the upper organic layer eliminated). The pH was adjusted to 11 with NaOH 4 M and the mixture heated to 70° C. for 2.5 h. The solution was then cooled to RT for 2 hrs, then 37% HCl was slowly added till pH 5. A precipitate formed. It was filtered under vacuum to obtain a brown solid. Mother liquor was left standing and a precipitate formed again. It was filtered under vacuum to obtain a brown solid. The two solids were combined to obtain 914 mg of title compound (p34, y=59%). MS (m/z): 198.9 [MH]⁺.

Preparation 35: 3-[(3-chloropropyl)sulfanyl]-4-methyl-5-(1,3-thiazol-2-yl)-4H-1,2,4-triazole

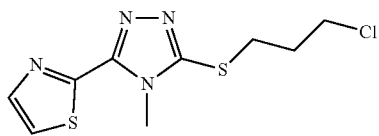 [SMILES: Cn1c(SCCCCl)nnc1-c1nccs1]

To a suspension of 4-methyl-5-(1,3-thiazol-2-yl)-4H-1,2,4-triazole-3-thiol (p34, 914 mg, 4.6 mmol) in a mixture MeOH/Acetone (2.6 mL/7 mL) at RT, 1-Bromo-3-chloropropane (500 µL, 5.06 mmol) was added, followed by K₂CO₃ (890 g, 6.44 mmol) and the mixture was stirred at RT on. The mixture was filtered and the solid washed with DCM. The filtrate was concentrated under vacuum to obtain 1.23 g 3 of title compound (p35, y=84%). MS (m/z): 274.9[MH].

Preparation 36: 4-methyl-5-(3-methyl-1,2-oxazol-5-yl)-4H-1,2,4-triazole-3-thiol

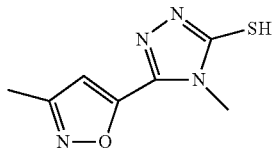

To a solution of 3-methyl-1,2-oxazole-5-carboxylic acid (337 mg, 2.65 mmol) in DMF (1.6 mL), 4-methyl-3-thiosemicarbazide (306 mg, 2.915 mmol) was added. DIPEA (0.814 mL, 4.77 mmol) was added drop wise at RT, then the mixture was cooled in an ice bath before adding T3P (50% w/w in EtOAc) (2.36 mL, 3.975 mmol). The reaction was stirred at RT ON. NaOH 4 M solution (2.5 mL) was added (resulting pH=8). The reaction was diluted with EtOAc and the two resulting phases were separated (the upper organic layer eliminated). The pH was adjusted to 11 with NaOH 4 M and the mixture heated to 70° C. for 1 h. The clear rusty red solution was then cooled to RT for 2 hrs, then 37% HCl was slowly added till pH 5. A precipitate formed. It was filtered under vacuum to obtain 389 mg of title compound (p36, y=74%). MS (m/z): 197.0 [MH]⁺.

Preparation 37: 3-[(3-chloropropyl)sulfanyl]-4-methyl-5-(3-methyl-1,2-oxazol-5-yl)-4H-1,2,4-triazole

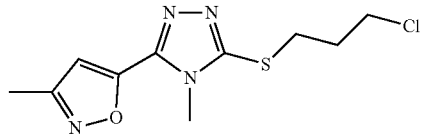 [SMILES: Cc1cc(-c2nnc(SCCCCl)n2C)on1]

To a suspension of 4-methyl-5-(3-methyl-1,2-oxazol-5-yl)-4H-1,2,4-triazole-3-thiol (p36, 389 mg, 1.98 mmol) in a mixture MeOH/Acetone (1.2 mL/3.3 mL) at RT, 1-bromo-3-chloropropane (196 µL, 2.838 mmol) was added, followed by K₂CO₃ (383 g, 2.77 mmol) and the mixture was stirred at RT on. It was partitioned between water and AcOEt and phases were separated. Organic one was washed with brine, then dried and concentrated under reduced pressure. Water was extracted again with DCM, organic phase was separated, dried and concentrated and added to the previous residue. Crude material was purified by FC on SiO₂ cartridge (eluent: from Cy to AcOEt) affording 431 mg of title compound (p37, y=80%). MS (m/z): 273.0 [MH]⁺.

Preparation 38: 4-methyl-5-(4-methyl-1,3-thiazol-5-yl)-4H-1,2,4-triazole-3-thiol

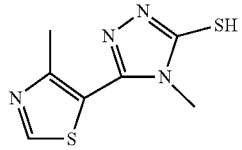

To a solution of 4-methyl-1,3-thiazole-5-carboxylic acid (1.09 g, 7.6 mmol) in DMF (5 mL), 4-methyl-3-thiosemicarbazide (0.879 g, 8.36 mmol) was added. DIPEA (2.34 mL, 13.7 mmol) was added drop wise at RT, then the mixture was cooled in an ice bath before adding T3P (50% w/w in EtOAc) (6.7 mL, 11.4 mmol). The reaction was stirred at RT ON. NaOH 4 M solution was added (resulting pH=8). The reaction was diluted with EtOAc and the two resulting phases were separated (the upper organic layer eliminated). The pH was adjusted to 11 with NaOH 4 M and the mixture heated to 70° C. for 1.5 h. The solution was then cooled to RT for 2 hrs, then 37% HCl was slowly added till pH 5. A precipitate formed. It was filtered under vacuum to obtain 1.033 g of title compound (p38, y=64%). MS (m/z): 212.9 [MH]⁺.

Preparation 39: 3-[(3-chloropropyl)sulfanyl]-4-methyl-5-(4-methyl-1,3-thiazol-5-yl)-4H-1,2,4-triazole

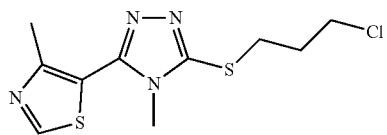 [SMILES: Cc1ncsc1-c1nnc(SCCCCl)n1C]

To a suspension of 4-methyl-5-(4-methyl-1,3-thiazole-5-yl)-4H-1,2,4-triazole-3-thiol (p38, 1.033 g, 4.86 mmol) in a mixture MeOH/Acetone (2.6 mL/7 mL) at RT, 1-Bromo-3-chloropropane (529 μL, 5.35 mmol) was added, followed by K$_2$CO$_3$ (940 g, 6.8 mmol) and the mixture was stirred at RT on. The mixture was filtered and the filtrate was concentrated in vacuum. Crude material was purified by FC on SiO$_2$ cartridge (eluent: from Cy to EtOAc) to obtain 989 mg of title compound (p39, y=70%). MS (m/z): 289.0 [MH]$^+$.

Preparation 40: 4-(4-methyl-5-sulfanyl-4H-1,2,4-triazol-3-yl)-1,2-dihydropyridin-2-one

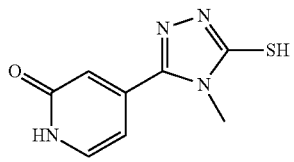

To a stirred solution of 2-oxo-1,2-dihydropyridine-4-carboxylic acid (1.0 g, 7.19 mmol) in DMF (4.5 mL), 4-methyl-3-thiosemicarbazide (0.83 g, 7.91 mmol) and DIPEA (2.3 mL) were subsequently added. The mixture was cooled to 0° C. then T3P (50% wt/EA) (6.4 mL, 10.79 mmol) was added portion-wise. The ice-bath was removed and the resulting reaction mixture was stirred ON at RT. Aqueous 4 M NaOH solution was added (resulting pH~8) and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH~5. A precipitate started to form, the mixture was filtered, the solid was washed with water and dried under vacuum at 40° C. ON to give 0.68 g of title compound (p40, y=45%). MS (m/z): 209.1 [MH]$^+$.

Preparation 41: 4-{5-[(3-chloropropyl)sulfanyl]-4-methyl-4H-1,2,4-triazol-3-yl}-1,2-dihydropyridin-2-one

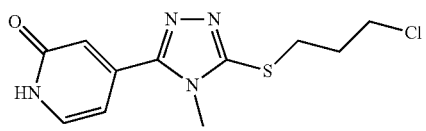 [SMILES: Cn1c(SCCCCl)nnc1-c1cc[nH]c(=O)c1]

To a mixture of 4-(4-methyl-5-sulfanyl-4H-1,2,4-triazol-3-yl)-1,2-dihydropyridin-2-one (p40, 0.68 g, 3.27 mmol) K$_2$CO$_3$ (0.59 g, 4.25 mmol) in MeOH/Acetone (2/5 mL), 1-bromo-3-chloropropane (0.36 mL, 3.60 mmol) was added and the resulting reaction mixture was shaken at RT in a PLS apparatus ON. The mixture was filtered, the solid was washed with DCM and the filtrate was concentrated under reduced pressure to give 340 mg of title compound (p41, y=36%). MS (m/z): 285.2 [MH]$^+$.

Preparation 42: 5-(4-methyl-5-sulfanyl-4H-1,2,4-triazol-3-yl)-2,3-dihydropyridin-2-one

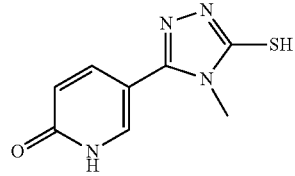

To a solution of 6-oxo-1,6-dihydropyridine-3-carboxylic acid (1.0 g, 7.19 mmol) and 4-methyl-3-thiosemicarbazide (0.83 g, 7.91 mmol) in DMF (4.5 mL), DIPEA (2.3 mL, 12.94 mmol) was added. The stirred mixture was cooled to 0° C. then T3P (50% wt/EA) (6.4 mL, 10.79 mmol) was added portion-wise. The ice-bath was removed and the resulting reaction mixture was shaken at RT in a PLS apparatus on. Aqueous 4 M NaOH solution was added (resulting in pH~8) and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH~5 and a precipitate started to form. The mixture was stirred for 10 min then filtered. The solid was washed with water and dried under vacuum at 45° C. ON affording 0.89 g of title compound (p42, y=60%). MS (m/z): 209.1 [MH]$^+$.

Preparation 43: 5-{5-[(3-chloropropyl)sulfanyl]-4-methyl-4H-1,2,4-triazol-3-yl}-1,2-dihydropyridin-2-one

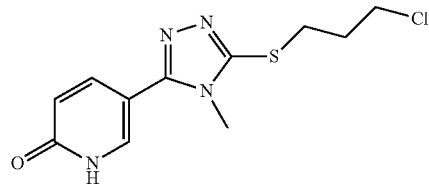 [SMILES: Cn1c(SCCCCl)nnc1-c1ccc(=O)[nH]c1]

To a mixture of 5-(4-methyl-5-sulfanyl-4H-1,2,4-triazol-3-yl)-2,3-dihydropyridin-2-one (p42, 100 mg, 0.48 mmol) and K$_2$CO$_3$ (86 mg, 0.62 mmol) in MeOH/Acetone (0.3/0.8 mL), 1-bromo-3-chloropropane (0.052 mL, 0.53 mmol) was added and the resulting reaction mixture was shaken at RT in a PLS apparatus ON. The mixture was filtered and the solid washed with DCM, the filtrate was concentrated under reduced pressure. Crude material was purified by FC on SiO$_2$ (eluent: DCM to 45% MeOH) affording 53 mg of title compound (p43, y=39%). MS (m/z): 285.2 [MH]$^+$.

Preparation 44: 4-methyl-5-(1-methyl-1H-pyrazol-5-yl)-4H-1,2,4-triazole-3-thiol

To a stirred solution of 1-methyl-1H-pyrazole-5-carboxylic acid (0.5 g, 3.96 mmol) in DMF (2 mL), 4-methyl-3-thiosemicarbazide (0.46 g, 4.36 mmol) and DIPEA (1.24 mL, 7.13 mmol) were subsequently added. The mixture was cooled to 0° C. then T3P (50% wt/EA) (3.56 mL, 5.94 mmol) was added portion-wise. The ice-bath was removed and the resulting reaction mixture was stirred ON at RT. Aqueous 4 M NaOH solution was added up to pH~8 and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH~5 and a precipitate formed. The mixture was filtered; the solid was washed with water and dried under vacuum at 45° C. ON affording 0.49 g of title compound (p44, y=64%). MS (m/z): 196.1 [MH]$^+$.

Preparation 45: 3-[(3-chloropropyl)sulfanyl]-4-methyl-5-(1-methyl-1H-pyrazol-5-yl)-4H-1,2,4-triazole

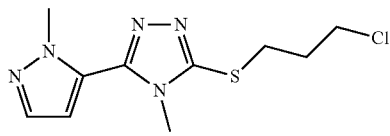 [SMILES: Cn1nccc1-c1nnc(SCCCCl)n1C]

To a mixture of 4-methyl-5-(1-methyl-1H-pyrazol-5-yl)-4H-1,2,4-triazole-3-thiol (p44, 100 mg, 0.51 mmol) and K$_2$CO$_3$ (92 mg, 0.66 mmol) in MeOH/Acetone (0.3 mL/0.8 mL), 1-bromo-3-chloropropane (0.056 mL, 0.56 mmol) was added and the resulting reaction mixture was shaken at RT in a PLS apparatus ON. The mixture was diluted with EtOAc and filtered, the solid was washed with EtOAc and the filtrate was concentrated under reduced pressure to give 112 mg of title compound (p45, y=87%). MS (m/z): 272.3 [MH]$^+$.

Preparation 46: 4-methyl-5-(2-methylpyridin-3-yl)-4H-1,2,4-triazole-3-thiol

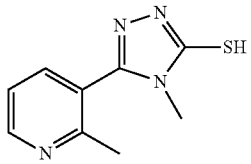

To a mixture of 2-methylpyridine-3-carboxylic acid (1.0 g, 7.29 mmol) in DMF (4 mL), 4-methyl-3-thiosemicarbazide (0.84 g, 8.02 mmol) and DIPEA (2.3 mL, 13.12 mmol) were subsequently added. The mixture was cooled to 0° C. then T3P (50% wt/EA) (6.5 mL, 10.94 mmol) was added portion-wise. The ice-bath was removed and the resulting reaction mixture was stirred ON at RT. Aqueous 4 M NaOH solution was added drop-wise up to pH~8, EtOAc was added and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH~5. A precipitate started to form, after 15 min the mixture was filtered, the solid was washed with water and dried under vacuum at 45° C. ON to give 0.44 g of the title product (p46, y=29%) as white solid. MS (m/z): 207.2 [MH]$^+$.

Preparation 47: 3-{5-[(3-chloropropyl)sulfanyl]-4-methyl-4H-1,2,4-triazol-3-yl}-2-methylpyridine

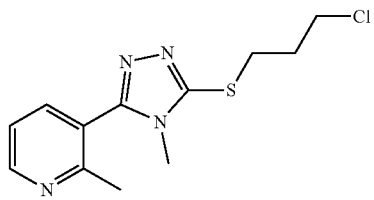 [SMILES: Cc1ncccc1-c1nnc(SCCCCl)n1C]

To a mixture of 4-methyl-5-(2-methylpyridin-3-yl)-4H-1,2,4-triazole-3-thiol (p46, 0.44 g, 2.13 mmol), K$_2$CO$_3$ (0.38 g, 2.77 mmol) in MeOH/Acetone (1.3 mL/3.5 mL), 1-bromo-3-chloropropane (0.23 mL, 2.35 mmol) was added and the resulting reaction mixture was shaken at RT in a PLS apparatus ON. The mixture was filtered, the solid was washed with DCM and the filtrate was concentrated under reduced pressure. The crude material was purified by FC on NH cartridge (eluent: from Cy to 55% EtOAc) to give 0.38 g of title compound (p47, y=63%). MS (m/z): 283.2 [MH]$^+$.

Preparation 48: methyl 2-oxo-2-(pyrrolidin-1-yl)acetate

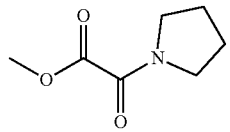

Pyrrolidine (2.1 mL, 25.4 mmol) and TEA (3.6 mL, 25.4 mmol) were dissolved in Et$_2$O (50 mL) at 0° C. and Methyl chlorooxoacetate (2.1 mL, 22.85 mmol) was added slowly. The mixture was slowly warmed to RT over 2 hrs. The mixture was filtered and the filtrate is concentrated under vacuum to afford 3.5 g of title compound (p48, y=97%) as yellow oil. MS (m/z): 157.9 [M]$^+$.

Preparation 49: 2-oxo-2-(pyrrolidin-1-yl)acetic acid

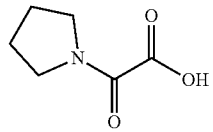

Methyl 2-oxo-2-(pyrrolidin-1-yl)acetate (p48, 3.5 g, 22.27 mmol) was dissolved in THF (25 mL) and 3 M NaOH (14 mL) was added. The mixture was stirred at RT for 2 hrs. It was acidified to pH 3 using 6M HCl and extracted with EtOAc. The aqueous phase was acidified to pH 1 using 6M HCl and extracted with DCM. The organics were combined and evaporated to afford 2.9 g of title compound (p49, y=90%). MS (m/z): 144.0 [MH]$^+$.

Preparation 50: 4-methyl-5-(pyrrolidine-1-carbonyl)-4H-1,2,4-triazole-3-thiol

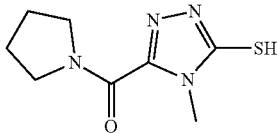

To a stirred solution of 2-oxo-2-(pyrrolidin-1-yl) acetic acid (p49, 1.0 g, 6.98 mmol) in DMF (4.2 mL), 4-methyl-3-thiosemicarbazide (0.81 g, 7.68) and DIPEA (2.19 mL, 12.56 mmol) were subsequently added. The mixture was cooled to 0° C. then T3P (50% wt/EA) (6.2 mL, 10.47 mmol) was added portion-wise. The ice-bath was removed and the resulting reaction mixture was stirred 2 hrs at RT. Aqueous 4 M NaOH solution was added (resulting pH~8) and the two resulting phases were separated (the upper organic layer was eliminated). Additional 4 M NaOH was added up to pH~11 then the mixture was heated to 70° C. and stirred for 90 min. The solution was cooled to RT and 6 N HCl was slowly added until pH 4 and extracted several times with DCM. The organic solution was dried and evaporated to afford 1 g of title compound (p50, y=crude). MS (m/z): 213.1 [MH]$^+$.

Preparation 51: 3-[(3-chloropropyl)sulfanyl]-4-methyl-5-(pyrrolidine-1-carbonyl)-4H-1,2,4-triazole

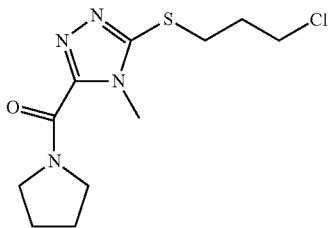 [SMILES: Cn1c(SCCCCl)nnc1C(=O)N1CCCC1]

To a suspension of 4-methyl-5-(pyrrolidine-1-carbonyl)-4H-1,2,4-triazole-3-thiol (p50, 1 g, 4.7 mmol) in a mixture MeOH/Acetone (3 mL/8 mL) at RT, 1-Bromo-3-chloropropane (511 µL, 5.17 mmol) was added, followed by K$_2$CO$_3$ (0.91 g, 6.58 mmol) and the mixture was stirred at RT ON. It was partitioned between water and DCM and phases were separated. Organic one was dried and concentrated under reduced pressure. The crude material was purified by FC on SiO$_2$ cartridge (eluent: from Cy to AcOEt) affording 1.14 g of title compound (p51, y=84%). MS (m/z): 288.9 [M]$^+$.

Preparation 52: 1-methyl-5-(4-methyl-5-sulfanyl-4H-1,2,4-triazol-3-yl)-1,2-dihydropyridin-2-one

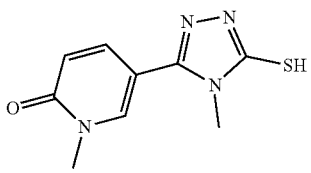

To a stirred solution of 1-Methyl-6-oxo-1,6-dihydropyridine-3-carboxylic acid (1.0 g, 6.53 mmol) in DMF (4 mL), 4-methyl-3-thiosemicarbazide (0755 g, 7.18) and DIPEA (2.05 mL, 11.75 mmol) were subsequently added. The mixture was cooled to 0° C. then T3P (50% wt/EA) (5.8 mL, 9.79 mmol) was added portion-wise. The ice-bath was removed and the resulting reaction mixture was stirred ON at RT. Aqueous 4 M NaOH solution was added (resulting pH8) and the two resulting phases were separated (the upper organic layer was eliminated). Additional 4 M NaOH was added up to pH~11 then the mixture was heated to 70° C. and stirred for 40 min. The solution was cooled to RT and 37% HCl was slowly added until pH 4 and a precipitate was obtained. The precipitate was filtered and dried to afford 0.94 g of title compound (p52, y=65%). MS (m/z): 223.1 [MH]$^+$.

Preparation 53: 5-{5-[(3-chloropropyl)sulfanyl]-4-methyl-4H-1,2,4-triazol-3-yl}-1-methyl-1,2-dihydropyridin-2-one

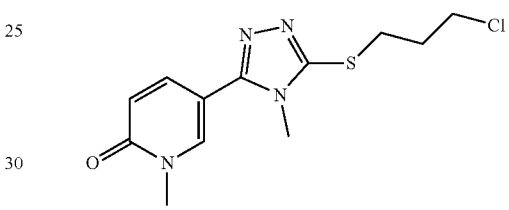

To a suspension of 1-methyl-5-(4-methyl-5-sulfanyl-4H-1,2,4-triazol-3-yl)-1,2-dihydropyridin-2-one (p52, 0.94 g, 4.22 mmol) in a mixture MeOH/Acetone (2.8 mL/7.5 mL) at RT, 1-Bromo-3-chloropropane (460 µL, 4.64 mmol) was added, followed by K$_2$CO$_3$ (0.82 g, 5.9 mmol) and the mixture was stirred at RT ON. It was partitioned between water and DCM and phases were separated. Organic one was dried and concentrated under reduced pressure. The crude material was purified by FC on NH cartridge (eluent: from Cy to AcOEt) affording 1.02 g of title compound (p53, y=80%). MS (m/z): 299.2 [MH]$^+$.

Preparation 54: 5-(4-methyl-5-sulfanyl-4H-1,2,4-triazol-3-yl)pyridine-2-carbonitrile

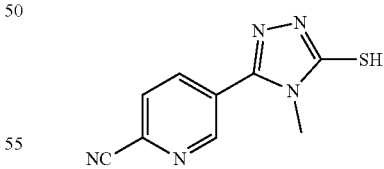

To a stirred solution of 6-cyanopyridine-3-carboxylic acid (1.0 g, 6.75 mmol) in DMF (3.9 mL), 4-methyl-3-thiosemicarbazide (0.78 g, 7.43 mmol) and DIPEA (2.1 mL, 12.15 mmol) were subsequently added. The mixture was cooled to 0° C. then T3P (50% wt/EA) (6.0 mL, 10.13 mmol) was added portion-wise. The ice-bath was removed and the resulting reaction mixture was stirred ON at RT. Aqueous 0.5 M NaOH solution was added (resulting pH~8) and the two resulting phases were separated (the upper organic layer was eliminated) then the mixture was heated to 70° C. and stirred for 1.5 h. The solution was cooled to RT and 37% HCl was slowly added until pH~6. The mixture was stirred for 5 min then it was filtered. The solid was washed with water and dried under vacuum at 45° C. ON affording 1.45 g of title compound (p54, y=95%). MS (m/z): 218.1 [MH]+.

Preparation 55: 5-(4-methyl-5-sulfanyl-4H-1,2,4-triazol-3-yl)pyridine-2-carboxamide

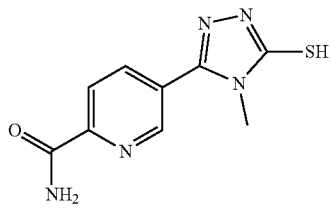 [SMILES: Cn1c(S)nnc1-c1ccc(C(N)=O)nc1]

A mixture of 5-(4-methyl-5-sulfanyl-4H-1,2,4-triazol-3-yl)pyridine-2-carbonitrile (p54, 1.35 g, 6.21 mmol) and crushed KOH (1.05 g, 18.64 mmol) in t-BuOH (80 mL) was heated to 90° C. and stirred for 1.5 h. After allowing the mixture to reach RT it was filtered and the yellow solid washed with t-BuOH then dried under vacuum. The solid was taken up with water, the pH was brought to 4-5 by adding 37% HCl then the mixture was filtered, the solid was washed with water and dried under vacuum at 45° C. ON affording 0.99 g of title compound (p55, y=68%). MS (m/z): 236.2 [MH]+.

Preparation 56: 5-{5-[(3-chloropropyl)sulfanyl]-4-methyl-4H-1,2,4-triazol-3-yl}pyridine-2-carboxamide

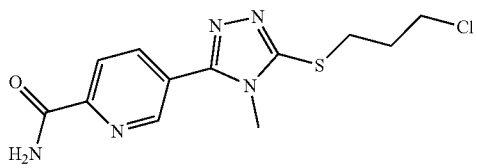 [SMILES: Cn1c(SCCCCl)nnc1-c1ccc(C(N)=O)nc1]

To a mixture of 5-(4-methyl-5-sulfanyl-4H-1,2,4-triazol-3-yl)pyridine-2-carboxamide (p55, 980 mg, 4.17 mmol) and K$_2$CO$_3$ (750 mg, 4.59 mmol) in MeOH/Acetone (2.7 mL/7.1 mL), 1-bromo-3-chloropropane (0.45 mL, 4.59 mmol) was added and the resulting reaction mixture was shaken at RT in a PLS apparatus ON. The mixture was filtered; the solid was washed with DCM and dried under vacuum affording a first batch of title compound. The remaining solution was concentrated under reduced pressure and the crude material was purified by FC on SiO$_2$ (eluent: DCM to 5% MeOH) affording further 0.47 of title compound. The two batches were combined affording 910 mg of title compound (p56, y=70%). MS (m/z): 312.2 [MH]+.

Preparation 57: 1-methyl-4-(4-methyl-5-sulfanyl-4H-1,2,4-triazol-3-yl)-1,2-dihydropyridin-2-one

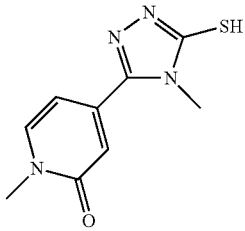

To a stirred solution of 1-methyl-2-oxo-1,2-dihydro-pyridine-4-carboxylic acid (1.0 g, 6.53 mmol) in DMF (4 mL), 4-methyl-3-thiosemicarbazide (0.755 g, 7.18) and DIPEA (2.05 mL, 11.75 mmol) were subsequently added. The mixture was cooled to 0° C. then T3P (50% wt/EA) (5.8 mL, 9.79 mmol) was added portion-wise. The ice-bath was removed and the resulting reaction mixture was stirred ON at RT. Aqueous 4 M NaOH solution was added (resulting pH~8) and the two resulting phases were separated (the upper organic layer was eliminated). Additional 4 M NaOH was added up to pH~11 then the mixture was heated to 70° C. and stirred for 1 h. The solution was cooled to RT and 37% HCl was slowly added until pH 4 and a precipitate was obtained. The precipitate was filtered and dried to afford 0.745 g of title compound (p57, y=51%). MS (m/z): 223.1 [MH]+.

Preparation 58: 4-{5-[(3-chloropropyl)sulfanyl]-4-methyl-4H-1,2,4-triazol-3-yl}-1-methyl-1,2-dihydropyridin-2-one

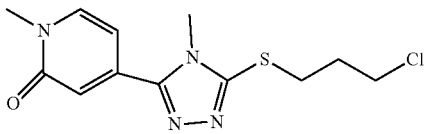 [SMILES: Cn1c(SCCCCl)nnc1-c1ccn(C)c(=O)c1]

To a suspension of 1-methyl-4-(4-methyl-5-sulfanyl-4H-1,2,4-triazol-3-yl)-1,2-dihydropyridin-2-one (p57, 0.745 g, 3.35 mmol) in a mixture MeOH/Acetone (2.2 mL/6 mL) at RT, 1-Bromo-3-chloropropane (365 µL, 3.68 mmol) was added, followed by K$_2$CO$_3$ (0.65 g, 4.69 mmol) and the mixture was stirred at RT ON. It was partitioned between water and DCM and phases were separated. Organic one was dried and concentrated under reduced pressure. The crude material was purified by FC on NH cartridge (eluent: from Cy to AcOEt) affording 0.8 g of title compound (p58, y=80%) as white solid. MS (m/z): 299.2 [MH]+.

Preparation 59: 1-benzyl-3-[(2-chloroethyl)amino]pyrrolidine-2,5-dione

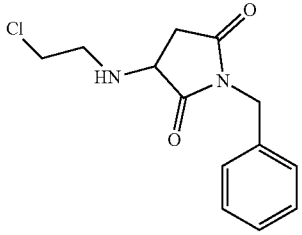 [SMILES: O=C1CC(NCCCl)C(=O)N1Cc1ccccc1]

To a stirred solution of benzylmaleimide (1.62 g, 8.62 mmol) in dioxane (9 mL), chloroethyl amine (1 g, 8.62 mmol) was added followed by drop wise addition of TEA (1.2 mL, 8.62 mmol). The resulting mixture was heated at reflux on. Then, after cooling, it was poured into ice and extracted several times with DCM. The organic phase was separated, dried and evaporated, the residue was purified by FC on SiO$_2$ cartridge (eluting from cHex to 60% EtOAc) to afford 1.84 g of the title compound as orange oil (p59, y=80%). MS (m/z): 267.2 [MH]$^+$.

Preparation 60: tert-butyl N-(1-benzyl-2,5-dioxopyrrolidin-3-yl)-N-(2-chloroethyl)carbamate

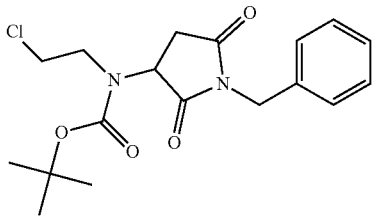 [SMILES: CC(C)(C)OC(=O)N(CCCl)C1CC(=O)N(Cc2ccccc2)C1=O]

To a stirred solution of 1-benzyl-3-[(2-chloroethyl)amino]pyrrolidine-2,5-dione (p59, 1.84 g, 6.9 mmol) in DCM (40 mL), di-tert-butyl carbonate (1.65 g, 7.6 mmol) was added portion-wise and the resulting reaction mixture was left stirring at RT for 48 hrs. The reaction mixture was washed with NH$_4$Cl and extracted with DCM several times. The organic phase was washed with brine, dried and evaporated. The resulting yellow solid was purified by FC on SiO$_2$ cartridge (eluting from cHex to 50% EtOAc) to afford 2 g of the title compound (p60, y=79%) as white solid. MS (m/z): 367.2 [MH]$^+$, 311.2 [M–56]$^+$

Preparation 61: tert-butyl 5-benzyl-4,6-dioxo-octahydropyrrolo[3,4-b]pyrrole-1-carboxylate

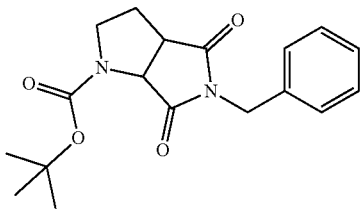 [SMILES: CC(C)(C)OC(=O)N1CCC2C(=O)N(Cc3ccccc3)C(=O)C21]

To a stirred solution of NaH (60% in oil) (150 mg, 3.6 mmol) in DMF (10 mL), at 0° C., tert-butyl N-(1-benzyl-2,5-dioxopyrrolidin-3-yl)-N-(2-chloroethyl)carbamate (p60, 1.1 g, 3 mmol) was added portion-wise and the resulting reaction mixture was left stirring at RT for 1 h. The reaction mixture became purple. Then it was poured into ice and extracted with DCM several times. The organic phase was washed with brine, dried and evaporated. The resulting residue was purified by FC on SiO$_2$ cartridge (eluting from cHex to 50% EtOAc) to afford 0.24 g of the title compound (p61, y=24%). MS (m/z): 331.3 [MH]$^+$.

Preparation 62: 5-benzyl-octahydropyrrolo[3,4-b]pyrrole-4,6-dione

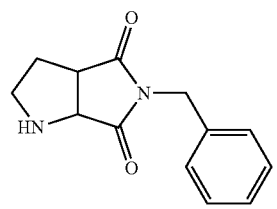 [SMILES: O=C1C2CCNC2C(=O)N1Cc1ccccc1]

To a stirred solution of tert-butyl 5-benzyl-4,6-dioxo-octahydropyrrolo[3,4-b]pyrrole-1-carboxylate (p61, 240 mg, 0.72 mmol) in DCM (8 mL) TFA (1.5 mL) was added and the resulting reaction solution was left stirring at RT for 1 h. Solvent was removed under vacuum and the residue was charged on SCX eluting with 1 M NH$_3$ in MeOH to afford 150 mg the title compound (p62, y=90%) as yellow oil. MS (m/z): 231.2[MH]$^+$.

Preparation 63: 5-benzyl-octahydropyrrolo[2,3-c]pyrrole

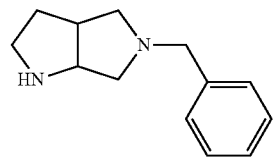 [SMILES: c1ccc(CN2CC3CCNC3C2)cc1]

To a stirred solution of 5-benzyl-octahydropyrrolo[3,4-b]pyrrole-4,6-dione (p62, 150 mg, 0.65 mmol) in THF (8 mL), 1 M LiAlH$_4$ in THF (1.95 mL, 1.95 mmol) was added drop wise, the resulting solution was then heated at reflux for 1 h. It was cooled to 0° C. and quenched with Na$_2$SO$_4$·10H$_2$O until gas evolution ceased. The suspension was filtered; the salts were washed with EtOAc. After solvent evaporation 130 mg of title compound (p63, y=98%) were obtained as pale yellow oil. MS (m/z): 203.2 [MH]$^+$.

Preparation 64: 5-benzyl-1-[4-(trifluoromethyl)phenyl]-octahydropyrrolo[2,3-c]pyrrole

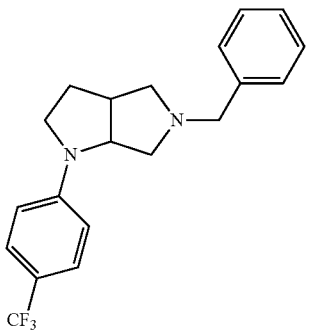 [SMILES: FC(F)(F)c1ccc(N2CCC3CN(Cc4ccccc4)CC32)cc1]

5-benzyl-octahydropyrrolo[2,3-c]pyrrole (p63, 130 mg, 0.65 mmol), 1-bromo-4-(trifluoromethyl)benzene (0.09 mL, 0.65 mmol), BINAP (40 mg, 0.065 mmol) and t-BuONa (125 mg, 1.3 mmol) were dissolved in toluene (2 mL) and degassed for 10 min, then $Pd_2(dba)_3$ (18 mg, 0.02 mmol) was added. The resulting mixture was stirred at 100° C. for 12 hrs. The solution was filtered using EtOAc. The filtrate was evaporated under vacuum and the residue was purified by FC on $SiO_2$ cartridge (eluting from cHex to EtOAc) affording 95 mg of title compound (p64, y=42%) as yellow oil. MS (m/z): 347.3 $[MH]^+$.

Preparation 65: ethyl N-(2,2-dimethoxyethyl)carbamate

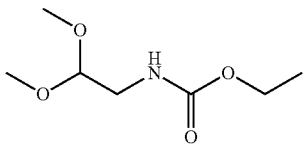

Ethyl chloroformate (4.37 mL, 45.77 mmol) was added drop wise to an ice cooled solution of aminoacetaldehyde dimethyl acetale (5 mL, 45.77 mmol) and NaOH (2.05 g, 51.26 mmol) in a mixture of $DCM/H_2O$ (25/12 mL) keeping the internal temperature below 10° C. After addition ceased the reaction mixture was vigorously stirred at RT ON. The two phases were separated and the organic one was washed with brine, then dried and evaporated to afford 8.1 g of the title compound (p65, y=quant) as colourless oil. MS (m/z): 178.1 $[MH]^+$.

Preparation 66: ethyl N-(2,2-dimethoxyethyl)-N-(prop-2-en-1-yl)carbamate

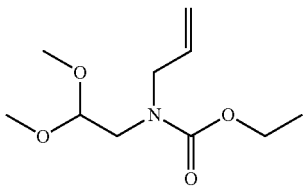

Ethyl N-(2,2-dimethoxyethyl)carbamate (p65, 3 g, 16.93 mmol) was dissolved in toluene (20 mL), KOH (4.1 g, 73 mmol), and Triethylbenzylammonium chloride (0.06 g, cat) were added and the mixture was stirred for 10 min, then allyl bromide (1.465 mL, 16.93 mmol) was added dropwise. The reaction mixture was stirred at RT on. The salts were filtered and washed with EtOAc; the organic solution was washed with brine and evaporated. The residue was purified by FC on $SiO_2$ cartridge (eluting from cHex to 25% EtOAc) to afford 2.5 g of title compound (p66, y=68%) as colourless oil. NMR: $^1$HNMR ($CDCl_3$) δ: 5.69-5.85 (m, 1H), 5.06-5.20 (m, 2H), 4.40-4.58 (m, 1H), 4.10-4.23 (m, 2H), 3.90-4.02 (m, 2H), 3.40 (s, 6H), 3.32 (br. s, 2H), 1.27 (t, 3H).

Preparation 67: ethyl N-(2-oxoethyl)-N-(prop-2-en-1-yl)carbamate

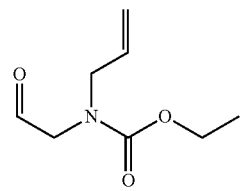

Ethyl N-(2,2-dimethoxyethyl)-N-(prop-2-en-1-yl)carbamate (p66, 2.5 g, 11.5 mmol) was dissolved in formic acid (5.5 mL) and heated at reflux for 30 min. It was poured into ice and extracted several times with DCM. The organic phase was washed with $NaHCO_3$ ss, dried and evaporated to afford 1.78 g of title compound (p67, y=90%) as yellow oil. NMR: $^1$HNMR ($CDCl_3$) δ:9.59 (d, 1H), 5.71-5.85 (m, 1H), 5.10-5.25 (m, 2H), 4.11-4.24 (m, 2H), 3.89-4.06 (m, 4H), 1.18-1.35 (m, 3H).

Preparation 68: ethyl 1-benzyl-octahydropyrrolo[2,3-c]pyrrole-5-carboxylate

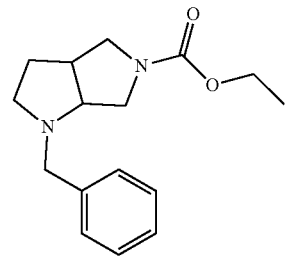 [SMILES: CCOC(=O)N1CC2CCN(Cc3ccccc3)C2C1]

Ethyl N-(2-oxoethyl)-N-(prop-2-en-1-yl)carbamate (p67, 1.78 g, 10.39 mmol) was dissolved in toluene (30 mL), benzyl glycine (1.72 g, 10.39 mmol) was added and the resulting mixture was heated at reflux for 4 hrs. Solvent was removed under vacuum, the residue was purified by FC on NH cartridge (eluting from cHex to 20% EtOAc) to afford 2.6 g of title compound (p68, y=91%) as yellow oil. MS (m/z): 275.2 $[MH]^+$.

Preparation 69: 1-benzyl-octahydropyrrolo[2,3-c]pyrrole

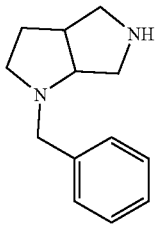 [SMILES: c1ccc(CN2CCC3CNCC32)cc1]

Ethyl 1-benzyl-octahydropyrrolo[2,3-c]pyrrole-5-carboxylate (p68, 2.1 g, 7.65 mmol) was dissolved in HCl 37% (11 mL) and heated at reflux for 24 hrs. pH was adjusted to 8 with $Na_2CO_3$ ss and the product was extracted several times with DCM. The organic phase was dried and evaporated to afford 1.4 g of title compound (p69, y=90%) as brown oil. It was used as such in the next reaction. MS (m/z): 203.2 $[MH]^+$.

Preparation 70: tert-butyl 1-benzyl-octahydropyrrolo[2,3-c]pyrrole-5-carboxylate

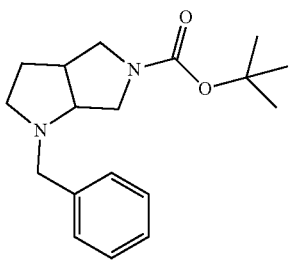 [SMILES: CC(C)(C)OC(=O)N1CC2CCN(Cc3ccccc3)C2C1]

A solution of Di-tert-butyl dicarbonate (1.8 g, 8.28 mmol) in DCM (10 mL) was added to a solution of 1-benzyl-octahydropyrrolo[2,3-c]pyrrole (p69, 1.4 g, 6.9 mmol) in DCM (20 mL). The solution was stirred at RT for 4 hrs. Solvent was removed under vacuum and the residue was purified by FC on $SiO_2$ cartridge (eluting from cHex to 35% EtOAc) to afford 1.68 g of title compound (p70, y=80%) as colourless oil. MS (m/z): 303.3 $[MH]^+$.

Preparation 71: tert-butyl octahydropyrrolo[3,4-b]pyrrole-5-carboxylate

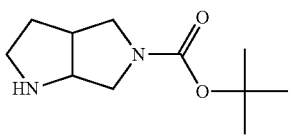

To a solution of tert-butyl 1-benzyl-octahydropyrrolo[2,3-c]pyrrole-5-carboxylate (p70, 1.68 g, 5.5 mmol) in MeOH (40 mL) under $N_2$, ammonium formate (3.5 g, 55.5 mmol) was added followed by Pd/C (600 mg). The mixture was heated at reflux for 2 hrs, then cooled and filtered over a pad of Celite® rinsing with MeOH. After evaporation the residue was dissolved with DCM and washed with $NaHCO_3$ ss, the organic phase was separated, dried and evaporated to afford 1.1 g of title compound (p71, y=93%) as grey oil. MS (m/z): 213.2 $[MH]^+$.

Preparation 72: tert-butyl 1-[4-(trifluoromethyl)phenyl]-octahydropyrrolo[2,3-c]pyrrole-5-carboxylate

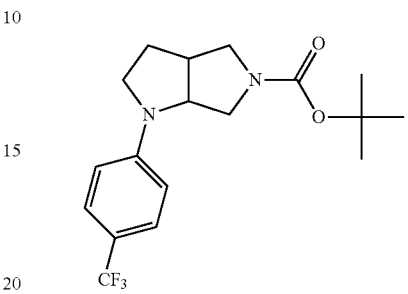

tert-butyl octahydropyrrolo[3,4-b]pyrrole-5-carboxylate (p71, 150 mg, 0.7 mmol), 1-Bromo-4-(trifluoromethyl)benzene (0.099 mL, 0.7 mmol), BINAP (44 mg, 0.07 mmol) and t-BuONa (135 mg, 1.4 mmol) were dissolved in toluene (2.5 mL) and degassed for 10 min, then $Pd_2(dba)_3$ (20 mg, 0.021 mmol) was added. The resulting mixture was stirred at 100° C. for 3 hrs. The solution was filtered using EtOAc. The filtrate was evaporated under vacuum and the residue was purified by FC on $SiO_2$ cartridge (eluting from cHex to 20% EtOAc) affording 240 mg of title compound (p72, y=97%) as yellow oil. MS (m/z): 357.3 $[MH]^+$.

Preparation 73: 1-[4-(trifluoromethyl)phenyl]-octahydropyrrolo[3,4-b]pyrrole

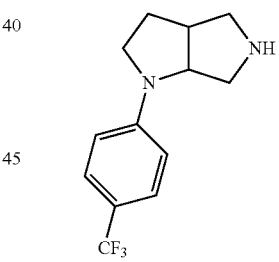

Method 1: To a solution of 5-benzyl-1-[4-(trifluoromethyl)phenyl]-octahydropyrrolo[2,3-c]pyrrole (p64, 95 mg, 0.274) in MeOH (6 mL) under $N_2$, ammonium formate (173 mg, 2.74 mmol) was added followed by Pd/C (40 mg). The mixture was heated at reflux for 90 min, then cooled and filtered over a pad of Celite® rinsing with MeOH. After evaporation the residue was charged on SCX eluting with 1 M $NH_3$ in MeOH to afford 70 mg of the title compound (p73, y=quant) as yellow oil.

Method 2: To a stirred solution of tert-butyl 1-[4-(trifluoromethyl)phenyl]-octahydropyrrolo[2,3-c]pyrrole-5-carboxylate (p72, 240 mg, 0.67 mmol) in DCM (7 mL) TFA (0.9 mL) was added and the resulting reaction solution was left stirring at RT for 2 hrs. Solvent was removed under vacuum and the residue was purified by SCX cartridge eluting with 1 M $NH_3$ in MeOH to afford a crude material which was purified by FC on NH cartridge (eluting from Preparation 74: 3-{octahydropyrrolo[2,3-c]pyrrol-1-yl}benzonitrile

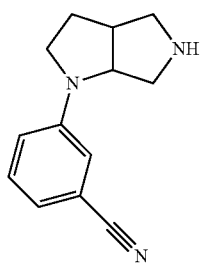 [SMILES: N#Cc1cccc(N2CCC3CNCC32)c1]

Step a: tert-butyl octahydropyrrolo[3,4-b]pyrrole-5-carboxylate (p71, 200 mg, 0.94 mmol), 3-Bromobenzonitrile (171 mg, 0.94 mmol), BINAP (58 mg, 0.094 mmol) and t-BuONa (180 mg, 1.88 mmol) were dissolved in toluene (2.5 mL) and degassed for 10 min, then Pd$_2$(dba)$_3$ (26 mg, 0.0282 mmol) was added. The resulting mixture was stirred at 100° C. for 4 hrs. The solution was filtered using EtOAc. The filtrate was evaporated under vacuum and the residue was purified by FC on SiO$_2$ cartridge (eluting from cHex to 40% EtOAc) affording 200 mg of title compound as yellow oil.

Step b: To a stirred solution of tert-butyl 1-(3-cyanophenyl)-octahydropyrrolo[3,4-b]pyrrole-5-carboxylate (200 mg, 0.64 mmol) in DCM (4 mL) TFA (0.5 mL) was added and the resulting reaction solution was left stirring at RT for 2 hrs. Solvent was removed under vacuum and the residue was purified by SCX cartridge eluting with 1 M NH$_3$ in MeOH to afford after evaporation 135 mg of title compound (p74, y=67%) as yellow oil. MS (m/z): 214.2 [MH]$^+$.

The following intermediates were prepared in analogy with Preparation 74 reacting tert-butyl octahydropyrrolo[3,4-b]pyrrole-5-carboxylate (p71) with the appropriate aryl bromides.

| Prep | structure | name | Yield | MS (m/z) |
|---|---|---|---|---|
| p75 | 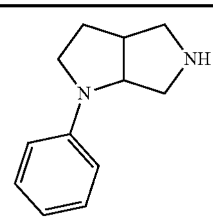 | 1-phenyl-octahydropyrrolo[2,3-c]pyrrole | 84% | 189.1 [MH]$^+$ |
| p76 | 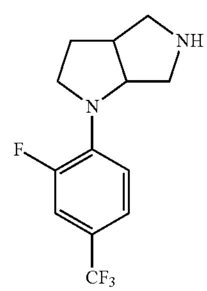 | 1-[2-fluoro-4-(trifluoromethyl)phenyl]-octahydropyrrolo[3,4-b]pyrrole | 36% | 275.2 [MH]$^+$ |
| p77 | 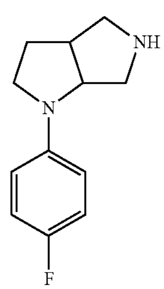 [SMILES: Fc1ccc(N2CCC3CNCC32)cc1] | 1-(4-fluorophenyl)-octahydropyrrolo[3,4-b]pyrrole | 44% | 207.0 [MH]$^+$ |
| p78 | 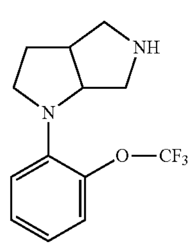 [SMILES: FC(F)(F)Oc1ccccc1N1CCC2CNCC21] | 1-[2-(trifluoromethoxy)phenyl]-octahydropyrrolo[3,4-b]pyrrole | 51% | 273.3 [MH]$^+$ |

-continued

| Prep | structure | name | Yield | MS (m/z) |
|---|---|---|---|---|
| p79 | 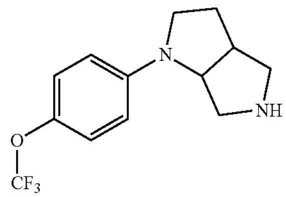 [SMILES: FC(F)(F)Oc1ccc(N2CCC3CNCC32)cc1] | 1-[4-(trifluoromethoxy)phenyl]-octahydropyrrolo[3,4-b]pyrrole | 64% | 273.3 [MH]+ |
| p80 | 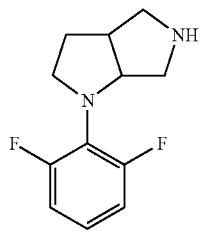 [SMILES: Fc1cccc(F)c1N1CCC2CNCC21] | 1-(2,6-difluorophenyl)-octahydropyrrolo[3,4-b]pyrrole | 24% | 225.2 [MH]+ |
| p81 | 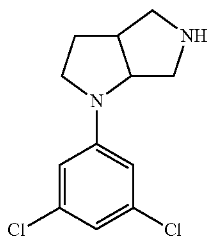 [SMILES: Clc1cc(Cl)cc(N2CCC3CNCC32)c1] | 1-(3,5-dichlorophenyl)-octahydropyrrolo[3,4-b]pyrrole | 64% | 257.1 [M]+ |
| p82 | 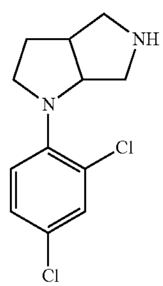 [SMILES: Clc1ccc(N2CCC3CNCC32)c(Cl)c1] | 1-(2,4-dichlorophenyl)-octahydropyrrolo[3,4-b]pyrrole | 88% | 257.1 [M]+ |
| p83 | 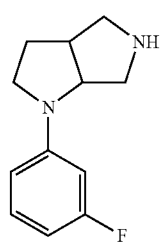 [SMILES: Fc1cccc(N2CCC3CNCC32)c1] | 1-(3-fluorophenyl)-octahydropyrrolo[3,4-b]pyrrole | 67% | 207.2 [MH]+ |
| p84 | 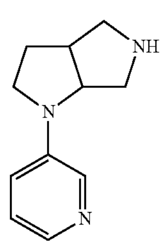 [SMILES: c1cncc(N2CCC3CNCC32)c1] | 3-{octahydropyrrolo[3,4-b]pyrrol-1-yl}pyridine | 60% | 190.3 [MH]+ |

-continued

| Prep | name | Yield | MS (m/z) |
|---|---|---|---|
| p85 | 5-{octahydropyrrolo[3,4-b]pyrrol-1-yl}-2-(trifluoromethyl)pyridine | 65% | 258.3 [MH]+ |
| p86 | 1-(2-fluorophenyl)-octahydropyrrolo[2,3-c]pyrrole | 75% | 207.3 [MH]+ |
| p87 | 1-(2,4-fluorophenyl)-octahydropyrrolo[2,3-c]pyrrole | 47% | 225.3 [MH]+ |
| p88 | 1-(4-methoxyphenyl)-octahydropyrrolo[2,3-c]pyrrole | 31% | 219.2 [MH]+ |
| p89 | 1-(4-methylphenyl)-octahydropyrrolo[2,3-c]pyrrole | 58% | 203.1 [MH]+ |
| p90 | 1-(3-methoxyphenyl)-octahydropyrrolo[2,3-c]pyrrole | 60% | 219.2 [MH]+ |
| p91 | 2-{octahydropyrrolo[2,3-c]pyrrol-1-yl}benzonitrile | 22% | 214.3 [MH]+ |

-continued

| Prep | structure | name | Yield | MS (m/z) |
|---|---|---|---|---|
| p92 | 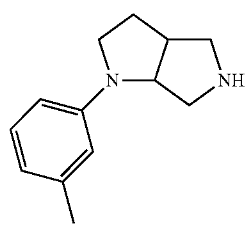 | 1-(3-methylphenyl)-octahydropyrrolo[2,3-c]pyrrole | 57% | 203.1 [MH]+ |
| p93 | 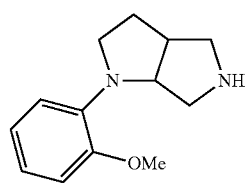 [SMILES: COc1ccccc1N1CCC2CNCC21] | 1-(2-methoxyphenyl)-octahydropyrrolo[2,3-c]pyrrole | 68% | 219.3 [MH]+ |
| p94 | 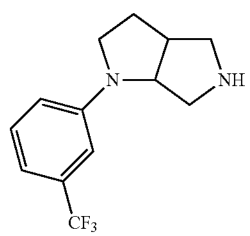 [SMILES: FC(F)(F)c1cccc(N2CCC3CNCC32)c1] | 1-[3-(trifluoromethyl)phenyl]-octahydropyrrolo[2,3-c]pyrrole | 85% | 257.3 [MH]+ |
| p95 | 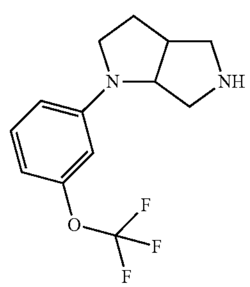 [SMILES: FC(F)(F)Oc1cccc(N2CCC3CNCC32)c1] | 1-[3-(trifluoromethoxy)phenyl]-octahydropyrrolo[2,3-c]pyrrole | 76% | 273.3 [MH]+ |
| p96 | 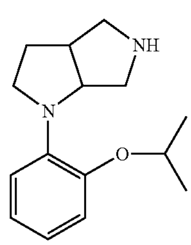 [SMILES: CC(C)Oc1ccccc1N1CCC2CNCC21] | 1-[2-(propan-2-yloxy)phenyl]-octahydropyrrolo[3,4-b]pyrrole | 49% | 247.3 [MH]+ |
| p97 | 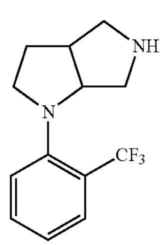 [SMILES: FC(F)(F)c1ccccc1N1CCC2CNCC21] | 1-[2-(trifluoromethyl)phenyl]-octahydropyrrolo[3,4-b]pyrrole | 67% | 257.2 [MH]+ |

-continued

| Prep | structure | name | Yield | MS (m/z) |
|---|---|---|---|---|
| p98 | 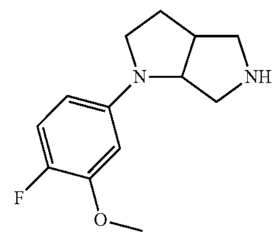 [SMILES: COc1cc(N2CCC3CNCC32)ccc1F] | 1-(4-fluoro-3-methoxyphenyl)-octahydropyrrolo[2,3-c]pyrrole | 74% | 237.2 [MH]+ |
| p99 | 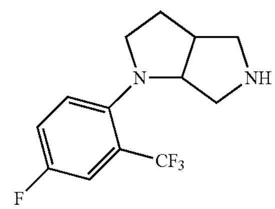 [SMILES: Fc1ccc(N2CCC3CNCC32)c(C(F)(F)F)c1] | 1-[4-fluoro-2-(trifluoromethyl)phenyl]-octahydropyrrolo[2,3-c]pyrrole | 58% | 275.2 [MH]+ |
| p100 | 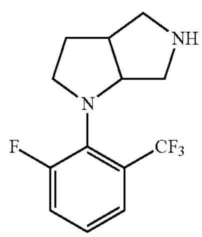 [SMILES: Fc1cccc(C(F)(F)F)c1N1CCC2CNCC21] | 1-[2-fluoro-6-(trifluoromethyl)phenyl]-octahydropyrrolo[3,4-b]pyrrole | 20% | 275.2 [MH]+ |

Preparation 101: tert-butyl 1-(2,4,6-trifluorophenyl)-octahydropyrrolo[2,3-c]pyrrole-5-carboxylate

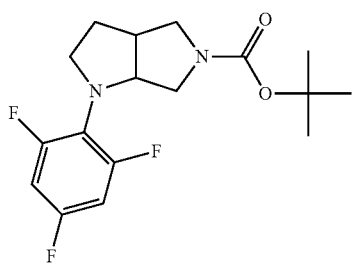 [SMILES: CC(C)(C)OC(=O)N1CC2CCN(c3c(F)cc(F)cc3F)C2C1]

tert-butyl octahydropyrrolo[3,4-b]pyrrole-5-carboxylate (p71, 150 mg, 0.7 mmol), 1-Bromo-2,4,6-trifluorobenzene (0.084 mL, 0.7 mmol), BINAP (43 mg, 0.07 mmol) and t-BuONa (134 mg, 1.4 mmol) were dissolved in toluene (2 mL) and degassed for 10 min, then Pd$_2$(dba)$_3$ (20 mg, 0.021 mmol) was added. The resulting mixture was stirred at 100° C. on. The solution was filtered using EtOAc. The filtrate was evaporated under vacuum and the residue was purified by FC on SiO$_2$ cartridge (eluting from cHex to 20% EtOAc) affording 25 mg of title compound (p101, y=10%) as yellow oil. MS (m/z): 343.3[MH]+.

Preparation 102: methyl 2-[(2,4,6-trifluorophenyl)amino]acetate

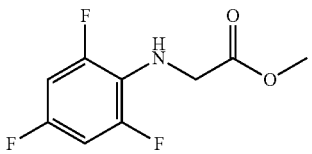

In a sealed vial, a solution of 2,4,6-trifluoroaniline (2.8 g, 19.03 mmol), methyl 2-bromoacetate (2.0 mL, 20.93 mmol) and DIPEA (4.6 mL, 26.64 mmol) in DMF (12 mL) was shaken at 60° C. for 24 hrs. The mixture was diluted with EtOAc and water, the organic phase was washed with water, dried over sodium sulfate and the solvent removed under reduced pressure. The residue was purified by FC on SiO2 (eluent: Cyo 12% EtOAC) affording 3.67 g of title compound (p102, y=88%) as clear yellow oil. MS (m/z): 220.1 [MH]+.

Preparation 103: 2-[(2,4,6-trifluorophenyl)amino]acetic acid

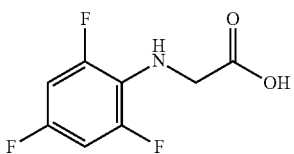 [SMILES: O=C(O)CNc1c(F)cc(F)cc1F]

A mixture of methyl 2-[(2,4,6-trifluorophenyl)amino]acetate (p102, 5.53 g, 25.23 mmol) and lithium hydroxide monohydrate (1.27 g, 30.28 mmol) in THF/MeOH/water (13/13/7 mL) was stirred ON at RT. The mixture was concentrated under reduced pressure and the residue was taken up with water. Aqueous 1 M HCl was added up to pH 6-7 then the mixture was extracted 3 times with DCM. The combined organic phases were dried by using a phase separator cartridge and the solution was concentrated under vacuum to give 3.61 g of title compound (p103, y=92%) as white solid. MS (m/z): 206.1 [MH]$^+$.

Preparation 104: 1-(2,4,6-fluorophenyl)-octahydropyrrolo[2,3-c]pyrrole

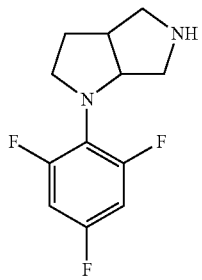

Method 1: To a stirred solution of tert-butyl 1-(2,4,6-trifluorophenyl)-octahydropyrrolo[2,3-c]pyrrole-5-carboxylate (p101, 25 mg, 0.07 mmol) in DCM (3 mL) TFA (0.2 mL) was added and the resulting reaction solution was left stirring at RT for 2 hrs. Solvent was removed under vacuum and the residue was purified by SCX cartridge eluting with 1 M NH$_3$ in MeOH to afford after evaporation 10 mg of title compound (p104, y=59%) as yellow oil.

Method 2: Step A: ethyl N-(2-oxoethyl)-N-(prop-2-en-1-yl)carbamate (p67, 2.89 g, 16.88 mmol) was dissolved in toluene (40 mL), 2-[(2,4,6-trifluorophenyl)amino]acetic acid (p103, 3.46 g, 16.88 mmol) and DIPEA (3.2 mL, 18.57 mmol) were subsequently added and the resulting mixture heated at reflux for 8 hrs. The reaction mixture was concentrated under reduced pressure. The crude material was purified by FC on SiO$_2$ (eluent cHex to 25% EtOAc) affording 0.41 g of ethyl 1-(2,4,6-trifluorophenyl)-octahydropyrrolo[2,3-c]pyrrole-5-carboxylate used as such in the next step.

Step B: ethyl 1-(2,4,6-trifluorophenyl)-octahydropyrrolo[2,3-c]pyrrole-5-carboxylate (0.41 g, from step A) was treated with 37% aq. HCl (10 mL) and the resulting mixture was refluxed for 8 hrs. The mixture was concentrated under reduced pressure, the residue was dissolved in MeOH and the solution charged on SCX cartridge (eluting with MeOH and 2N NH$_3$/MeOH) affording 0.21 g of title compound (p104, y=5%). MS (m/z): 243.2 [MH]$^+$.

Preparation 105: 2-{octahydropyrrolo[3,4-b]pyrrol-1-yl}-5-(trifluoromethyl)pyrazine

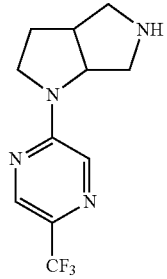 [SMILES: FC(F)(F)c1cnc(N2CCC3CNCC32)cn1]

Step a: tert-butyl octahydropyrrolo[3,4-b]pyrrole-5-carboxylate (p71, 100 mg, 0.47 mmol), 2-Chloro-5-(trifluoromethyl)pyrazine (95 mg, 0.47 mmol) and K$_2$CO$_3$ (110 mg, 0.8 mmol) were mixed in DMSO and heated at 100° C. for 5 min. The reaction mixture was cooled at RT and diluted with brine and EtOAc; the organic phase was separated and washed 2 times with brine, then dried and evaporated. The crude material was purified by FC on SiO$_2$ cartridge (eluent: cHEx to 30% EtOAc) to afford 100 mg of tert-butyl 1-[5-(trifluoromethyl)pyrazin-2-yl]-octahydropyrrolo[2,3-c]pyrrole-5-carboxylate as yellow oil.

Step b: To a stirred solution of tert-butyl 1-[5-(trifluoromethyl)pyrazin-2-yl]-octahydropyrrolo[2,3-c]pyrrole-5-carboxylate (100 mg, 0.279 mmol) in DCM (5 mL) TFA (0.5 mL) was added and the resulting reaction solution was left stirring at RT for 1 h. Solvent was removed under vacuum and the residue was purified by SCX cartridge eluting with 1 M NH$_3$ in MeOH to afford after evaporation 72 mg of title compound (p105, y=60%) as orange oil. MS (m/z): 259.3 [MH]$^+$.

Synthesis and Characterization of Exemplary Compounds

Example 1: 4-methyl-3-(4-methyl-1,3-oxazol-5-yl)-5-[(3-{1-[4-(trifluoromethyl)phenyl] octahydropyrrolo[3,4-b]pyrrol-5-yl}propyl)sulfanyl]-4H-1,2,4-triazole (E1)

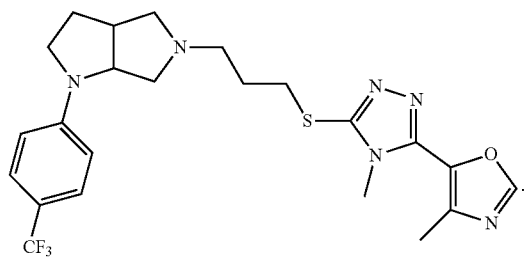 [SMILES: Cc1ncoc1-c1nnc(SCCCN2CC3CCN(c4ccc(C(F)(F)F)cc4)C3C2)n1C]

1-[4-(trifluoromethyl)phenyl]-octahydropyrrolo[3,4-b]pyrrole (prepared as in p73, 50 mg, 0.195 mmol), 3-[(3-chloropropyl)sulfanyl]-4-methyl-5-(4-methyl-1,3-oxazol-5-yl)-4H-1,2,4-triazole (p3, 58 mg, 0.21 mmol), Na$_2$CO$_3$ (22 mg, 0.21 mmol) and NaI (310 mg, 0.21 mmol) were dissolved in DMF (0.2 mL) and heated at 60° C. ON. The mixture was diluted with water and EtOAc and extracted several times with EtOAc. The organic phase was washed with brine, dried and evaporated. The residue was purified by FC on SiO$_2$ cartridge (eluting from DCM to 5% of MeOH) to afford 50 mg of the title compound (E1, y=48%) as pale yellow foam. NMR: $^1$H NMR (CHLOROFORM-d) δ: 7.93 (s, 1H), 7.43 (d, 2H), 6.55 (d, 2H), 4.12-4.20 (m, 1H), 3.66 (s, 3H), 3.43-3.54 (m, 1H), 3.22-3.41 (m, 3H), 2.89-3.01 (m, 1H), 2.72 (dd, 1H), 2.45-2.67 (m, 8H), 2.11-2.23 (m, 1H), 1.89-2.05 (m, 3H). MS (m/z): 493.3 [MH]$^+$.

Example 2: 4-methyl-3-(4-methyl-1,3-oxazol-5-yl)-5-[(3-{1-[4-(trifluoromethyl)phenyl] octahydropyrrolo[3,4-b]pyrrol-5-yl}propyl)sulfanyl]-4H-1,2,4-triazole dihydrochloride (E2)

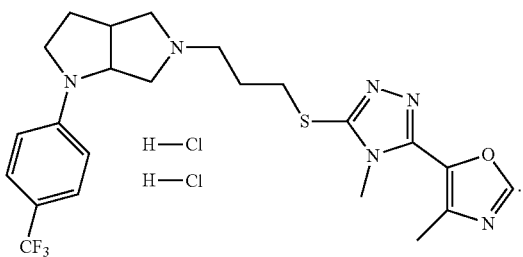

4-methyl-3-(4-methyl-1,3-oxazol-5-yl)-5-[(3-{1-[4-(trifluoromethyl)phenyl]octahydropyrrolo[3,4-b]pyrrol-5-yl}propyl)sulfanyl]-4H-1,2,4-triazole (E1, 50 mg) was dissolved in Et$_2$O and treated with 2.2 eq of 1N HCl in Et$_2$O to afford, after evaporation, 53.7 mg of title compound (E2) as white off solid. MS (m/z): 493.3 [MH]$^+$.

Example 3 and Example 4: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E3, Enantiomer 1) and 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E4, Enantiomer 2)

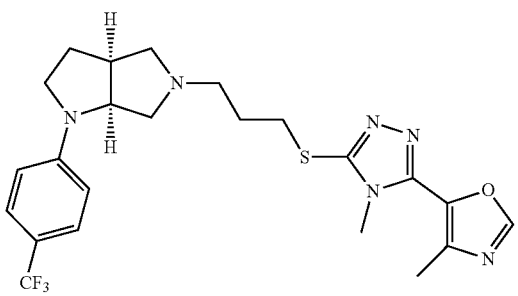

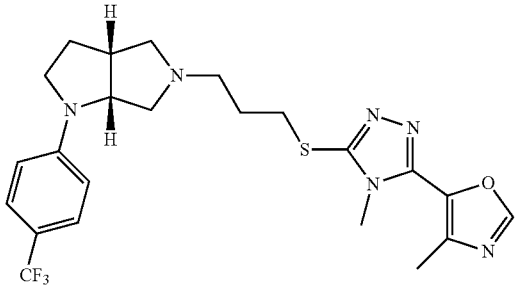

4-methyl-3-(4-methyl-1,3-oxazol-5-yl)-5-[(3-{1-[4-(trifluoromethyl)phenyl]octahydropyrrolo[3,4-b]pyrrol-5-yl}propyl)sulfanyl]-4H-1,2,4-triazole (E1, 48 mg) was separated into the single enantiomers by preparative chiral HPLC, obtaining 17 mg of 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E3, Enantiomer 1) and 16 mg of 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E4, Enantiomer 2).

Preparative Chromatography:

| | |
|---|---|
| Column | Chiralpak AS-H (25 × 2.0 cm), 5 μm |
| Mobile phase | n-Hexane/Ethanol 60/40% v/v |
| Flow rate (mL/min) | 14 mL/min |
| DAD detection | 220 nm |
| Loop | 1000 μL |
| Injection | 12 mg/injection |

Example 3 Enantiomer 1: ret. time 6.6 min, 100% ee MS (m/z): 493.3 [MH]$^+$.

Example 4 Enantiomer 2: ret. time 9.3 min, 100% ee MS (m/z): 493.3 [MH]$^+$.

Example 5: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole dihydrochloride (E5, Enantiomer 1)

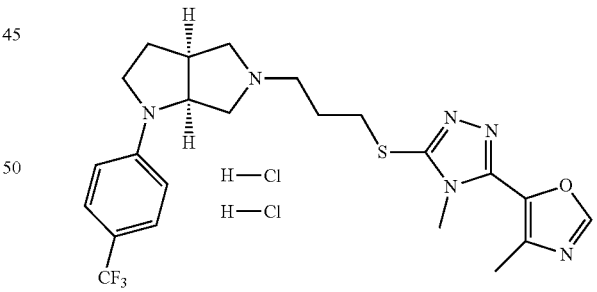

3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E3, 17 mg, Enantiomer 1) was dissolved in Et$_2$O and treated with 2.2. eq of 1N HCl in Et$_2$O to afford, after evaporation, 18.5 mg of title compound (E5, Enantiomer 1). MS (m/z): 493.3 [MH]$^+$.

Example 6: 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole dihydrochloride (E6, Enantiomer 2)

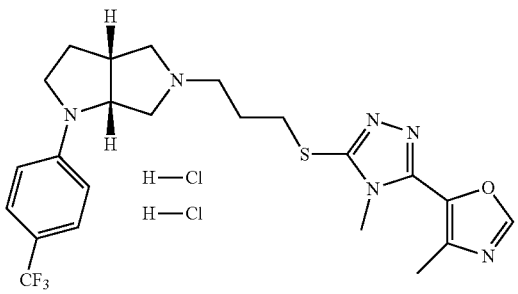

3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E4, 16 mg, Enantiomer 2) was dissolved in Et$_2$O and treated with 2.2. eq of 1N HCl in Et$_2$O to afford, after evaporation, 16.5 mg of title compound (E6, Enantiomer 2). MS (m/z): 493.3 [MH]$^+$.

Example 7: 3-[5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E7)

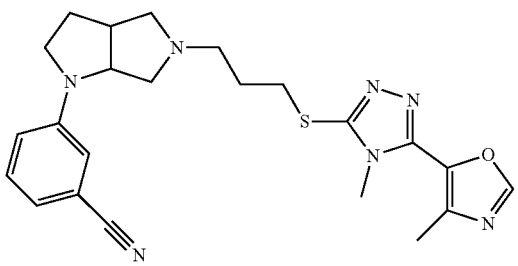 [SMILES: Cc1ncoc1-c1nnc(SCCCN2CC3CCN(c4cccc(C#N)c4)C3C2)n1C]

The title compound was prepared in analogy to the method described in Example 1 in 45 mg yield as a pale yellow foam (E7, y=43%) from 3-{octahydropyrrolo[2,3-c]pyrrol-1-yl}benzonitrile (p74, 50 mg, 0.23 mmol) and 3-[(3-chloropropyl)sulfanyl]-4-methyl-5-(4-methyl-1,3-oxazol-5-yl)-4H-1,2,4-triazole (p3, 63 mg, 0.23 mmol). NMR: $^1$H NMR (Acetone-d$_6$) δ: 8.26 (s, 1H), 7.29-7.36 (m, 1H), 6.85-6.97 (m, 3H), 4.21 (s, 1H), 3.75 (s, 3H), 3.45-3.52 (m, 1H), 3.19-3.37 (m, 3H), 2.93-3.04 (m, 1H), 2.69-2.76 (m, 2H), 2.48-2.61 (m, 3H), 2.40-2.47 (m, 4H), 2.13-2.24 (m, 1H), 1.88-2.04 (m, 3H) MS (m/z): 450.3 [MH]$^+$.

Example 8 and Example 9: 3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E8, Enantiomer 1) and 3-[(3aR,6aR or 3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E9, Enantiomer 2)

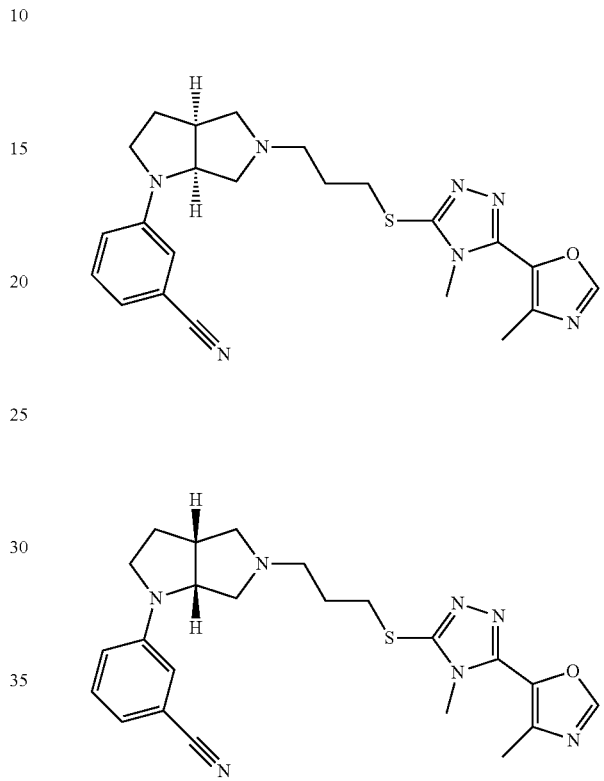

3-[5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E7, 42 mg) was separated into the single enantiomers by preparative chiral HPLC, obtaining 19 mg of 3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E8, Enantiomer 1) and 20 mg of 3-[(3aR,6aR or 3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E9, Enantiomer 2).

Preparative Chromatography:

| Column | Chiralpak AD-H (25 × 2 cm), 5 μm |
|---|---|
| Mobile phase | n-Hexane/(Ethanol + 0.1% ipa) 25/75% v/v |
| Flow rate (mL/min) | 14 |
| DAD detection | 220 nm |
| Loop | 1000 μL |
| injection | 14 mg (each injection) |

Example 8 Enantiomer 1: ret. time 12.8 min, 100% ee MS (m/z): 450.3 [MH]$^+$.

Example 9 Enantiomer 2: ret. time 17.0 min, 96% ee MS (m/z): 450.3 [MH]$^+$.

Example 10: 3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile dihydrochloride (E10, Enantiomer 1)

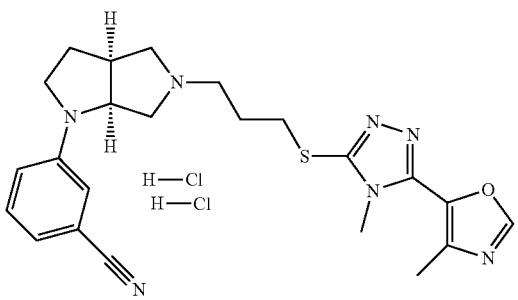

3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E8, Enantiomer 1, 19 mg) was dissolved in Et$_2$O and treated with 2.2. eq of 1N HCl in Et$_2$O to afford, after evaporation, 22 mg of title compound (E10, Enantiomer 1). MS (m/z): 450.3 [MH]$^+$.

Example 11: 3-[(3aR,6aR or 3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile dihydrochloride (E11, Enantiomer 2)

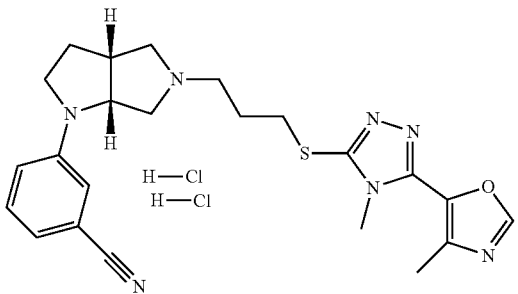

3-[(3aR,6aR or 3aS,6aS)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile (E9, Enantiomer 2, 20 mg) was dissolved in Et$_2$O and treated with 2.2. eq of 1N HCl in Et$_2$O to afford, after evaporation, 22 mg of title compound (E11, Enantiomer 2). MS (m/z): 450.3 [MH]$^+$.

Example 12: 4-methyl-3-(4-methyl-1,3-oxazol-5-yl)-5-[(3-{1-phenyl-octahydropyrrolo-[2,3-c]pyrrol-5-yl}propyl)sulfanyl]-4H-1,2,4-triazole (E12)

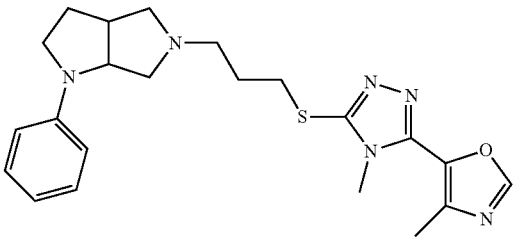 [SMILES: Cc1ncoc1-c1nnc(SCCCN2CC3CCN(c4ccccc4)C3C2)n1C]

The title compound was prepared in analogy to the method described in Example 1 in 45 mg yield as a pale yellow foam (E12, y=46%) from 1-phenyl-octahydropyrrolo[2,3-c]pyrrole (p75, 50 mg, 0.23 mmol) and 3-[(3-chloropropyl)sulfanyl]-methyl-5-(4-methyl-1,3-oxazol-5-yl)-4H-1,2,4-triazole (p3, 63 mg, 0.23 mmol). NMR: $^1$H NMR (Acetone-d$_6$) δ: 8.26 (s, 1H), 7.09-7.22 (m, 2H), 6.53-6.65 (m, 3H), 4.07-4.20 (m, 1H), 3.75 (s, 3H), 3.16-3.52 (m, 4H), 2.94 (br. s., 1H), 2.73 (br. s., 2H), 2.36-2.61 (m, 7H), 2.10-2.21 (m, 1H), 1.87-1.99 (m, 3H) MS (m/z): 425.4 [MH]$^+$.

Example 13 and Example 14: 3-({3-[(3aS,6aS or 3aR,6aR)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole (E13, Enantiomer 1) and 3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole (E14, Enantiomer 2)

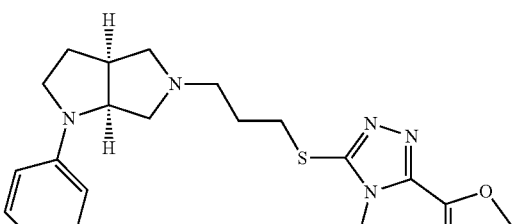

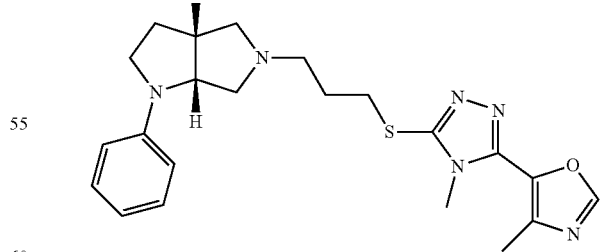

4-methyl-3-(4-methyl-1,3-oxazol-5-yl)-5-[(3-{1-phenyl-octahydropyrrolo[2,3-c]pyrrol-5-yl}propyl)sulfanyl]-4H-1,2,4-triazole (E12, 44 mg) was separated into the single enantiomers by preparative chiral HPLC, obtaining 16 mg of 3-({3-[(3aS,6aS or 3aR,6aR)-1-phenyl-octahydropyrrolo[2,3-c]pyrrol-5-yl]propyl}sulfanyl)-4-methyl-5-(4-methyl-1,3- oxazol-5-yl)-4H-1,2,4-triazole (E13, Enantiomer 1) and 15 mg of 3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole (E14, Enantiomer 2).

Preparative Chromatography:

| | |
|---|---|
| Column | Chiralpak AD-H (25 × 2 cm), 5 μm |
| Mobile phase | n-Hexane/(Ethanol + 0.1% ipa) 25/75% v/v |
| Flow rate (mL/min) | 14 |
| DAD detection | 220 nm |
| Loop injection | 600 μL 9 mg (each injection) |

Example 13 Enantiomer 1: ret. time 9.7 min, 100% ee MS (m/z): 425.4 [MH]$^+$.

Example 14 Enantiomer 2: ret. time 11.5 min, 94% ee MS (m/z): 425.4 [MH]$^+$.

Example 15: 3-({3-[(3aS,6aS or 3aR,6aR)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole dihydrochloride (E15, Enantiomer 1)

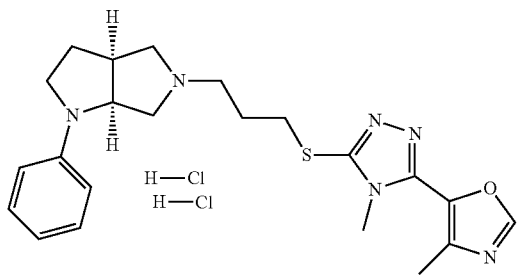

3-({3-[(3aS,6aS or 3aR,6aR)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole (E13, Enantiomer 1, 16 mg) was dissolved in Et$_2$O and treated with 2.2. eq of 1N HCl in Et$_2$O to afford, after evaporation, 19.4 mg of title compound (E15, Enantiomer 1). MS (m/z): 425.4 [MH]$^+$.

Example 16: 3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole dihydrochloride (E16, Enantiomer 2)

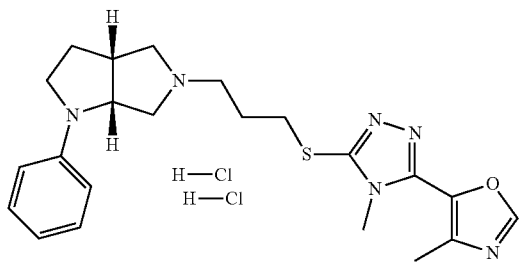

3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole (E14, Enantiomer 2, 15 mg) was dissolved in Et$_2$O and treated with 2.2. eq of 1N HCl in Et$_2$O to afford, after evaporation, 18.5 mg of title compound (E16, Enantiomer 2). MS (m/z): 425.4 [MH]$^+$.

Example 17: 3-[(3-{1-[2-fluoro-4-(trifluoromethyl)phenyl]-octahydropyrrolo[2,3-c]pyrrol-5-yl}propyl)sulfanyl]-4-methyl-5-(4-methyl-1,3-oxazol-5-yl)-4H-1,2,4-triazole (E17)

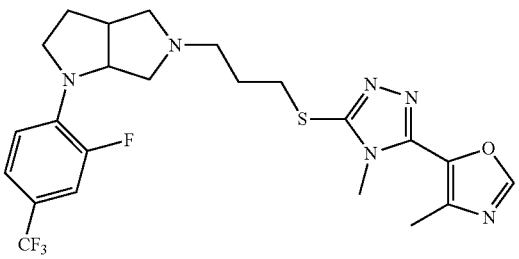 [SMILES: Cc1ncoc1-c1nnc(SCCCN2CC3CCN(c4ccc(C(F)(F)F)cc4F)C3C2)n1C]

The title compound was prepared in analogy to the method described in Example 1 in 55 mg yield as a pale yellow foam (E17, y=55%) from 1-[2-fluoro-4-(trifluoromethyl)phenyl]-octahydropyrrolo[3,4-b]pyrrole (p76, 53 mg, 0.195 mmol) and 3-[(3-chloropropyl)sulfanyl]-4-methyl-5-(4-methyl-1,3-oxazol-5-yl)-4H-1,2,4-triazole (p3, 53 mg, 0.195 mmol). NMR: $^1$H NMR (Acetone-d$_6$) δ: 8.26 (s, 1H), 7.26-7.39 (m, 2H), 6.84-6.96 (m, 1H), 4.55 (q, 1H), 3.74 (s, 3H), 3.49-3.63 (m, 1H), 3.43 (td, 1H), 3.14-3.35 (m, 2H), 2.92-3.03 (m, 1H), 2.72 (d, 2H), 2.38-2.54 (m, 6H), 2.07-2.15 (m, 2H), 1.88 (dd, 3H) MS (m/z): 511.3 [MH]$^+$.

Example 18 and Example 19: 3-({3-[(3aS,6aS or 3aR,6aR)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E18, Enantiomer 1) and 3-({3-[(3aR,6aR or 3aS,6aS)-1-[2-fluoro-4-(trifluoromethyl)phenyl]-octahydropyrrolo[2,3-c]pyrrol-5-yl]-propyl}sulfanyl)-4-methyl-5-(4-methyl-1,3-oxazol-5-yl)-4H-1,2,4-triazole (E19, Enantiomer 2)

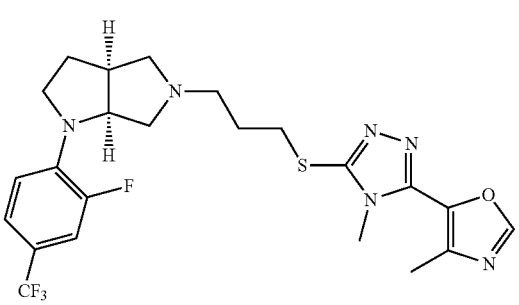

-continued

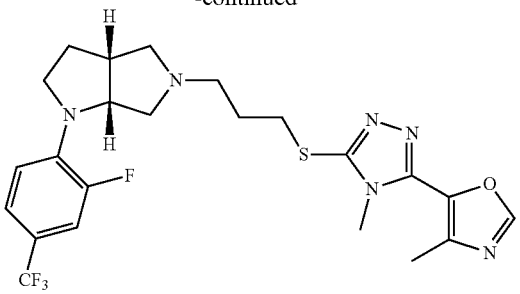

3-[(3-{1-[2-fluoro-4-(trifluoromethyl)phenyl]-octahydropyrrolo[2,3-c]pyrrol-5-yl}propyl)sulfanyl]-4-methyl-5-(4-methyl-1,3-oxazol-5-yl)-4H-1,2,4-triazole (E17, 53 mg) was separated into the single enantiomers by preparative chiral HPLC, obtaining 21 mg of 3-({3-[(3aS,6aS or 3aR,6aR)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E18, Enantiomer 1) and 21 mg of 3-({3-[(3aR,6aR or 3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole (E19, Enantiomer 2).

Preparative Chromatography:

| | |
|---|---|
| Column | Chiralcel OJ-H (25 × 2 cm), 5 μm |
| Mobile phase | n-Hexane/(Ethanol + 0.1% ipa) 55/45% v/v |
| Flow rate (mL/min) | 14 |
| DAD detection | 220 nm |
| Loop | 1500 μL |
| injection | 26 mg (each injection) |

Example 18 Enantiomer 1: ret. time 8.6 min, 100 ee MS (m/z): 511.3 [MH]$^+$.

Example 19 Enantiomer 2: ret. time 11.2 min, 100% ee MS (m/z): 511.3 [MH]$^+$.

Example 20: 3-({3-[(3aS,6aS or 3aR,6aR)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole dihydrochloride (E20, Enantiomer 1)

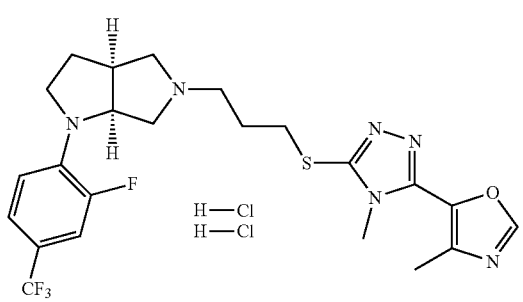

3-({3-[(3aS,6aS or 3aR,6aR)-1-[2-fluoro-4-(trifluoromethyl)phenyl]-octahydropyrrolo-[2,3-c]pyrrol-5-yl]propyl}sulfanyl)-4-methyl-5-(4-methyl-1,3-oxazol-5-yl)-4H-1,2,4-triazole (E18, Enantiomer 1, 21 mg) was dissolved in Et$_2$O and treated with 2.2. eq of 1N HCl in Et$_2$O to afford, after evaporation, 22 mg of title compound (E20, Enantiomer 1). MS (m/z): 511.3 [MH]$^+$.

Example 21: 3-({3-[(3aR,6aR or 3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole dihydrochloride (E21, Enantiomer 2)

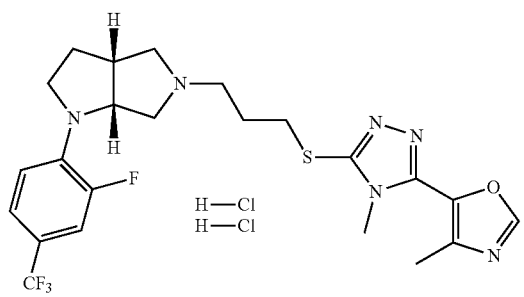

3-({3-[(3aR,6aR or 3aS,6aS)-1-[2-fluoro-4-(trifluoromethyl)phenyl]-octahydropyrrolo-[2,3-c]pyrrol-5-yl]propyl}sulfanyl)-4-methyl-5-(4-methyl-1,3-oxazol-5-yl)-4H-1,2,4-triazole (E19, Enantiomer 2, 21 mg) was dissolved in Et$_2$O and treated with 2.2. eq of 1N HCl in Et$_2$O to afford, after evaporation, 14 mg of title compound (E21, Enantiomer 2). MS (m/z): 511.3 [MH]$^+$.

Example 22: 3-({3-[1-(4-fluorophenyl)-octahydropyrrolo[2,3-c]pyrrol-5-yl]propyl}-sulfanyl)-4-methyl-5-(4-methyl-1,3-oxazol-5-yl)-4H-1,2,4-triazole (E22)

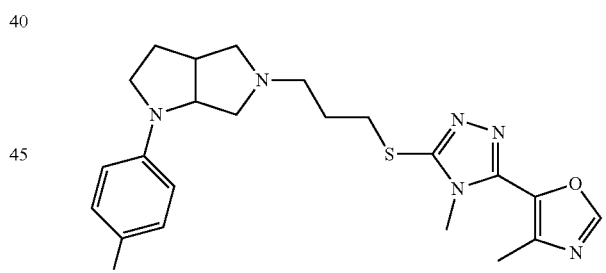

The title compound was prepared in analogy to the method described in Example 1 in 55 mg yield as a white foam (E22, y=57%) from 1-(4-fluorophenyl)-octahydropyrrolo[3,4-b]pyrrole (p77, 45 mg, 0.218 mmol) and 3-[(3-chloropropyl)sulfanyl]-4-methyl-5-(4-methyl-1,3-oxazol-5-yl)-4H-1,2,4-triazole (p3, 60 mg, 0.218 mmol). NMR: $^1$H NMR (Acetone-d$_6$) δ: 8.22-8.30 (m, 1H), 6.89-7.00 (m, 2H), 6.52-6.62 (m, 2H), 4.08 (ddd, 1H), 3.71-3.79 (m, 3H), 3.37-3.46 (m, 1H), 3.13-3.36 (m, 3H), 2.87-2.99 (m, 1H), 2.65-2.75 (m, 2H), 2.44-2.60 (m, 3H), 2.36-2.44 (m, 4H), 2.05-2.21 (m, 2H), 1.83-2.00 (m, 3H). MS (m/z): 443.3 [MH]$^+$.

Example 23 and Example 24: 3-({3-[(3aS,6aS or 3aR,6aR)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole (E23, Enantiomer 1) and 3-({3-[(3aR,6aR or 3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole (E24, Enantiomer 2)

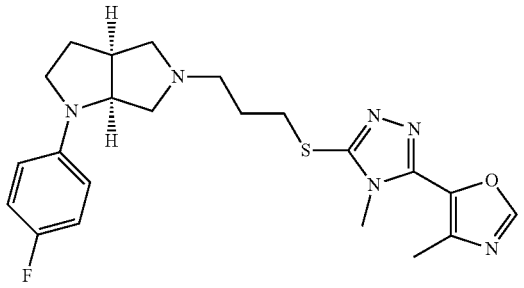

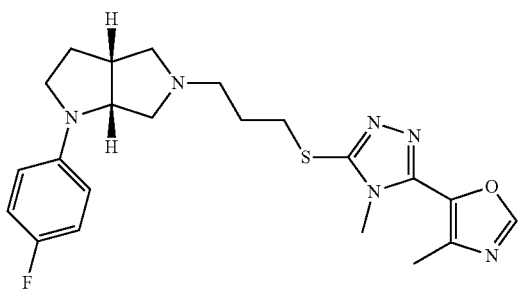

3-({3-[1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole (E22, 55 mg) was separated into the single enantiomers by preparative chiral HPLC, obtaining 22.8 mg of 3-({3-[(3aS,6aS or 3aR,6aR)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole (E23, Enantiomer 1) and 22.7 mg of 3-({3-[(3aR,6aR or 3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole (E24, Enantiomer 2).

Preparative Chromatography:

| | |
|---|---|
| Column | Chiralpak AS-H (25 × 2 cm), 5 μm |
| Mobile phase | n-Hexane/(Ethanol + 0.1% ipa) 50/50% v/v |
| Flow rate (mL/min) | 14 |
| DAD detection | 220 nm |
| Loop | 700 μL |
| injection | 18 mg (each injection) |

Example 23 Enantiomer 1: ret. time 6.3 min, 100% ee MS (m/z): 443.3 [MH]$^+$.

Example 24 Enantiomer 2: ret. time 8.5 min, 100% ee MS (m/z): 443.3 [MH]$^+$.

Example 25: 4-methyl-3-(4-methyl-1,3-oxazol-5-yl)-5-[(3-{1-[2-(trifluoromethoxy)phenyl]-octahydropyrrolo[3,4-b]pyrrol-5-yl}propyl)sulfanyl]-4H-H-1,2,4-triazole (E25)

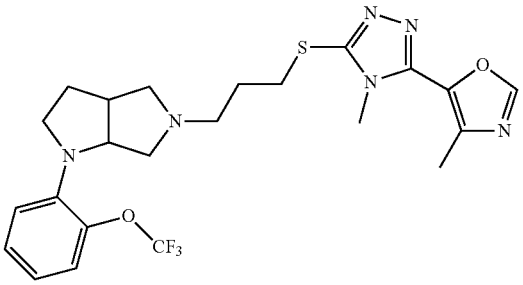 [SMILES: Cc1ncoc1-c1nnc(SCCCN2CC3CCN(c4ccccc4OC(F)(F)F)C3C2)n1C]

The title compound was prepared in analogy to the method described in Example 1 in 33 mg yield (E25, y=51%) from 1-[2-(trifluoromethoxy)phenyl]-octahydropyrrolo[3,4-b]pyrrole (p78, 35 mg, 0.128 mmol) and 3-[(3-chloropropyl)sulfanyl]-4-methyl-5-(4-methyl-1,3-oxazol-5-yl)-4H-1,2,4-triazole (p3, 39 mg, 0.14 mmol). NMR: $^1$H NMR (Acetone-d$_6$) δ: 8.28 (s, 1H), 7.16-7.25 (m, 2H), 6.95 (d, 1H), 6.78-6.87 (m, 1H), 4.56 (m, 1H), 3.75 (s, 3H), 3.46-3.58 (m, 1H), 3.11-3.33 (m, 4H), 2.96 (d, 1H), 2.63 (m, 1H), 2.47-2.57 (m, 2H), 2.36-2.47 (m, 5H), 2.32 (m, 1H), 1.76-1.94 (m, 3H). MS (m/z): 509.5[MH]$^+$.

Example 26: 4-methyl-3-(4-methyl-1,3-oxazol-5-yl)-5-[(3-{1-[4-(trifluoromethoxy)phenyl]-octahydropyrrolo[3,4-b]pyrrol-5-yl}propyl)sulfanyl]-4H-1,2,4-triazole (E26)

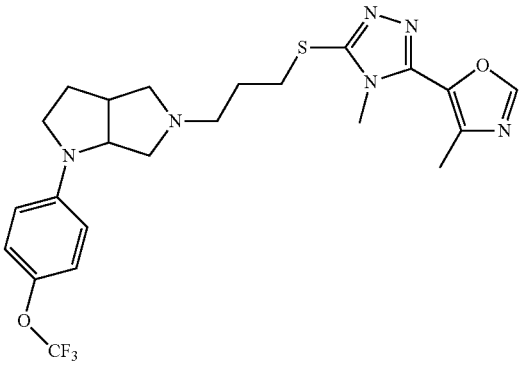 [SMILES: Cc1ncoc1-c1nnc(SCCCN2CC3CCN(c4ccc(OC(F)(F)F)cc4)C3C2)n1C]

The title compound was prepared in analogy to the method described in Example 1 in 49 mg yield (E26, y=65%) from 1-[4-(trifluoromethoxy)phenyl]-octahydropyrrolo[3,4-b]pyrrole (p79, 40 mg, 0.147 mmol) and 3-[(3-chloropropyl)sulfanyl]-4-methyl-5-(4-methyl-1,3-oxazol-5-yl)-4H-1,2,4-triazole (p3, 44 mg, 0.16 mmol). NMR: $^1$H NMR (Acetone-d$_6$) δ: 8.27 (s, 1H), 7.13 (d, 2H), 6.59-6.67 (m, 2H), 4.15 (s, 1H), 3.76 (s, 3H), 3.40-3.50 (m, 1H), 3.19-3.36 (m, 3H), 2.92-3.01 (m, 1H), 2.73 (s, 2H), 2.53 (s, 3H), 2.42 (s, 4H), 2.11-2.20 (m, 1H), 1.89-2.02 (m, 3H). MS (m/z): 509.5[MH]$^+$.

Example 27: 3-({3-[1-(2,6-difluorophenyl)-octahydropyrrolo[3,4-b]pyrrol-5-yl]propyl}sulfanyl)-4-methyl-5-(4-methyl-1,3-oxazol-5-yl)-4H-1,2,4-triazole (E27)

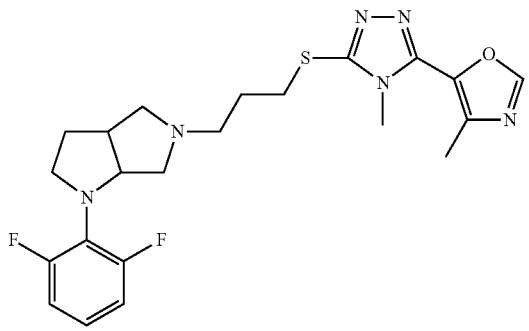 [SMILES: Cc1ncoc1-c1nnc(SCCCN2CC3CCN(c4c(F)cccc4F)C3C2)n1C]

The title compound was prepared in analogy to the method described in Example 1 in 46 mg yield (E27, y=73%) from 1-(2,6-difluorophenyl)-octahydropyrrolo[3,4-b]pyrrole (p80, 30 mg, 0.134 mmol) and 3-[(3-chloropropyl)sulfanyl]-4-methyl-5-(4-methyl-1,3-oxazol-5-yl)-4H-1,2,4-triazole (p3, 37 mg, 0.134 mmol). NMR: $^1$H NMR (Acetone-$d_6$) δ: 8.24-8.33 (m, 1H), 6.81-7.01 (m, 3H), 4.43-4.53 (m, 1H), 3.76-3.89 (m, 4H), 3.21-3.38 (m, 3H), 2.91 (br. s., 1H), 2.37-2.72 (m, 5H), 2.44 (s, 3H), 2.23-2.33 (m, 1H), 1.73-1.99 (m, 4H). MS (m/z): 461.4[MH]$^+$.

Example 28: 3-({3-[1-(3,5-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole (E28)

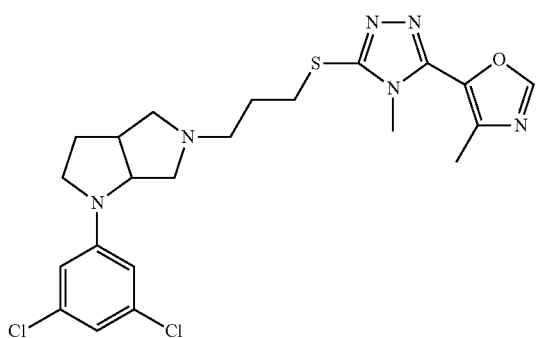 [SMILES: Cc1ncoc1-c1nnc(SCCCN2CC3CCN(c4cc(Cl)cc(Cl)c4)C3C2)n1C]

The title compound was prepared in analogy to the method described in Example 1 in 27.5 mg yield (E28, y=41%) from 1-(3,5-dichlorophenyl)-octahydropyrrolo[3,4-b]pyrrole (p81, 35 mg, 0.134 mmol) and 3-[(3-chloropropyl)sulfanyl]-4-methyl-5-(4-methyl-1,3-oxazol-5-yl)-4H-1,2,4-triazole (p3, 37 mg, 0.134 mmol). NMR: $^1$H NMR (Acetone-$d_6$) δ: 8.27 (s, 1H), 6.64 (s, 1H), 6.53 (d, 2H), 4.16-4.25 (m, 1H), 3.77 (s, 3H), 3.42-3.52 (m, 1H), 3.20-3.39 (m, 3H), 2.95-3.06 (m, 1H), 2.71-2.80 (m, 2H), 2.47-2.61 (m, 3H), 2.39-2.47 (m, 4H), 2.12-2.23 (m, 1H), 1.88-2.04 (m, 3H). MS (m/z): 493.3[M]$^+$.

Example 29: 3-({3-[1-(2,4-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole (E29)

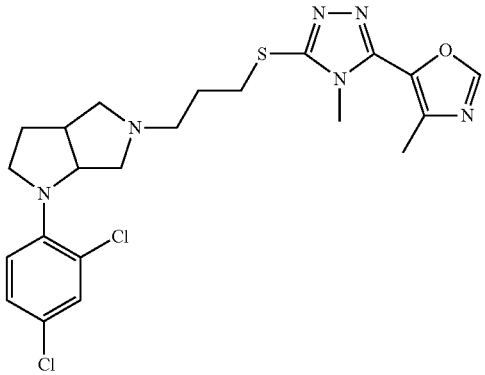 [SMILES: Cc1ncoc1-c1nnc(SCCCN2CC3CCN(c4ccc(Cl)cc4Cl)C3C2)n1C]

The title compound was prepared in analogy to the method described in Example 1 in 21 mg yield (E29, y=31.7%) from 1-(2,4-dichlorophenyl)-octahydropyrrolo[3,4-b]pyrrole (p82, 30 mg, 0.134 mmol) and 33-[(3-chloropropyl)sulfanyl]-4-methyl-5-(4-methyl-1,3-oxazol-5-yl)-4H-1,2,4-triazole (p3, 37 mg, 0.134 mmol). NMR: $^1$H NMR (Acetone-$d_6$) δ: 8.28 (s, 1H), 7.34 (d, 1H), 7.21 (m, 1H), 7.07 (d, 1H), 4.88 (m, 1H), 3.77 (s, 3H), 3.57-3.66 (m, 1H), 3.23 (d, 2H), 3.13 (s, 1H), 2.91-3.01 (m, 1H), 2.66 (m, 1H), 2.35-2.55 (m, 7H), 2.19 (m, 1H), 1.98-2.04 (m, 1H), 1.78-1.90 (m, 3H). MS (m/z): 493.3[M]$^+$.

Example 30: 3-({3-[1-(3-fluorophenyl)-octahydropyrrolo[3,4-b]pyrrol-5-yl]propyl}sulfanyl)-4-methyl-5-(4-methyl-1,3-oxazol-5-yl)-4H-1,2,4-triazole (E30)

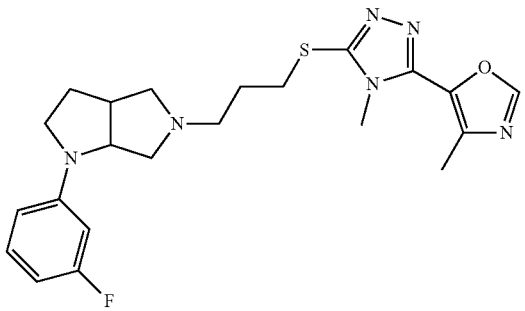 [SMILES: Cc1ncoc1-c1nnc(SCCCN2CC3CCN(c4cccc(F)c4)C3C2)n1C]

The title compound was prepared in analogy to the method described in Example 1 in 36 mg yield (E30, y=48%) from 1-(3-fluorophenyl)-octahydropyrrolo[3,4-b]pyrrole (p83, 35 mg, 0.17 mmol) and 3-[(3-chloropropyl)sulfanyl]-4-methyl-5-(4-methyl-1,3-oxazol-5-yl)-4H-1,2,4-triazole (p3, 51 mg, 0.19 mmol). NMR: $^1$H NMR (Acetone-$d_6$) δ: 8.27 (s, 1H), 7.11-7.19 (m, 1H), 6.26-6.42 (m, 3H), 4.14 (m, 1H), 3.76 (s, 3H), 3.39-3.47 (m, 1H), 3.19-3.37 (m, 3H), 2.92-3.01 (m, 1H), 2.68-2.77 (m, 2H), 2.47-2.59 (m, 3H), 2.42 (s, 4H), 2.11-2.19 (m, 1H), 1.89-2.01 (m, 3H). MS (m/z): 443.5[MH]$^+$.

Example 31: 4-methyl-3-(oxan-4-yl)-5-[(3-{1-[4-(trifluoromethyl)phenyl]-octahydropyrrolo[2,3-c]pyrrol-5-yl}propyl)sulfanyl]-4H-1,2,4-triazole (E31)

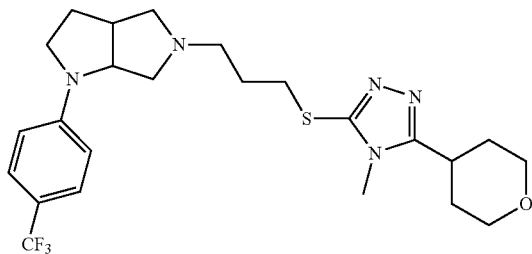 [SMILES: Cn1c(SCCCN2CC3CCN(c4ccc(C(F)(F)F)cc4)C3C2)nnc1C1CCOCC1]

The title compound was prepared in analogy to the method described in Example 1 in 50 mg yield as pale yellow foam (E31, y=46%) from 1-[4-(trifluoromethyl)phenyl]-octahydropyrrolo[3,4-b]pyrrole (prepared as in p73, 56 mg, 0.217 mmol) and 3-[(3-chloropropyl)sulfanyl]-4-methyl-5-(oxan-4-yl)-4H-1,2,4-triazole (p5, 60 mg, 0.217 mmol). NMR: $^1$H NMR (Acetone-$d_6$) δ: 7.48 (d, 2H), 6.72 (d, 2H), 4.25 (br. s., 1H), 3.99 (dt, 2H), 3.46-3.63 (m, 5H), 3.32-3.45 (m, 1H), 2.96-3.29 (m, 4H), 2.73 (br. s., 3H), 2.40-2.64 (m, 4H), 2.14-2.28 (m, 1H), 1.80-2.07 (m, 7H). MS (m/z): 496.3 [MH]$^+$.

Example 32 and Example 33: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole (E32, Enantiomer 1) and 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4 triazole (E33, Enantiomer 2)

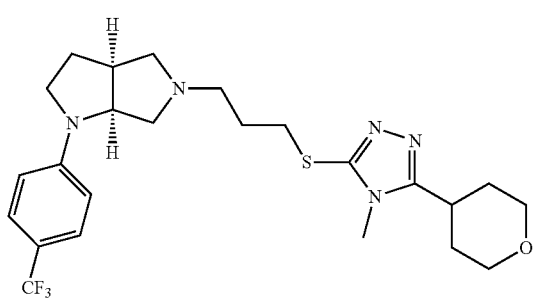

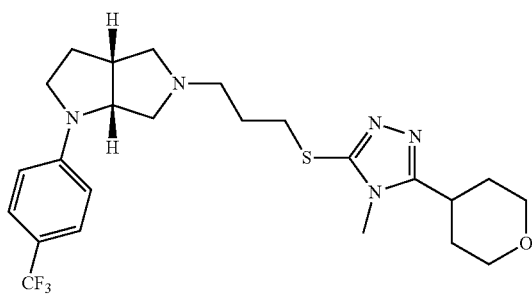

4-methyl-3-(oxan-4-yl)-5-[(3-{1-[4-(trifluoromethyl)phenyl]-octahydropyrrolo[2,3-c]pyrrol-5-yl}propyl)sulfanyl]-4H-1,2,4-triazole (E31, 50 mg) was separated into the single enantiomers by preparative chiral HPLC, obtaining 19.3 mg of 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole (E32, Enantiomer 1) and 18.6 mg of 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4 triazole (E33, Enantiomer 2).

Preparative Chromatography:

| | |
|---|---|
| Column | Chiralpak AS-H (25 × 2 cm), 5 μm |
| Mobile phase | n-Hexane/(Ethanol + 0.1% ipa) 70/30% v/v |
| Flow rate (mL/min) | 14 |
| DAD detection | 220 nm |
| Loop | 750 μL |
| injection | 25 mg (each injection) |

Example 32 Enantiomer 1: ret time 6.9 min, 100% ee MS (m/z): 496.3 [MH]$^+$.

Example 33 Enantiomer 2: ret time 9.3 min, 100% ee MS (m/z): 496.3 [MH]$^+$.

Example 34: 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole dihydrochloride (E34, Enantiomer 1)

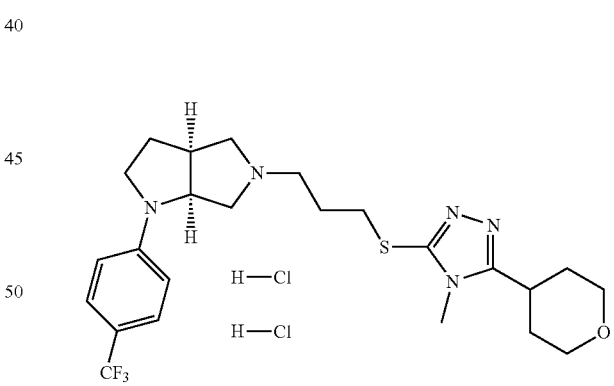

3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole (E34, Enantiomer 1, 19.3 mg) was dissolved in Et$_2$O and treated with 2.2. eq of 1N HCl in Et$_2$O to afford, after evaporation, 21.2 mg of title compound as white solid (E34, Enantiomer 1). MS (m/z): 496.3 [MH]$^+$.

Example 35: 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4 triazole dihydrochloride (E35, Enantiomer 2)

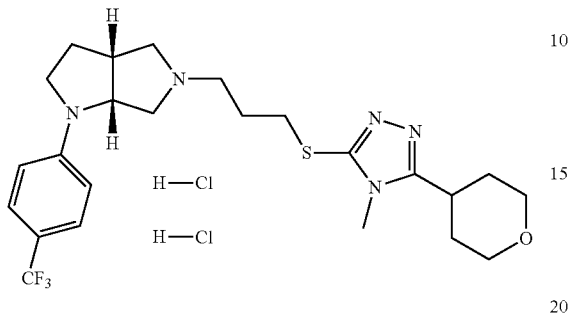

3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4 triazole (E33, Enantiomer 2, 18.6 mg) was dissolved in Et$_2$O and treated with 2.2. eq of 1N HCl in Et$_2$O to afford, after evaporation, 21 mg of title compound as white solid (E35, Enantiomer 2). MS (m/z): 496.3 [MH]$^+$.

Example 36: 4-methyl-3-(oxan-4-yl)-5-[(3-{1-phenyl-octahydropyrrolo[2,3-c]pyrrol-5-yl}propyl)sulfanyl]-4H-1,2,4-triazole (E36)

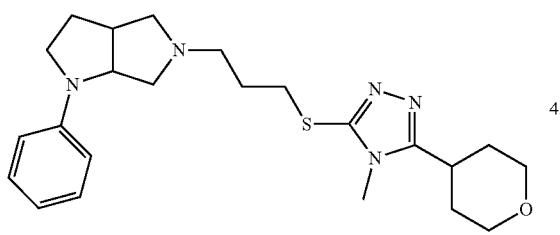

The title compound was prepared in analogy to the method described in Example 1 in 62 mg yield as a colourless oil (E36, y=48%) from 1-phenyl-octahydropyrrolo[2,3-c]pyrrole (p75, 57 mg, 0.3 mmol) and 3-[(3-chloropropyl)sulfanyl]-4-methyl-5-(oxan-4-yl)-4H-1,2,4-triazole (p5, 83 mg, 0.3 mmol). NMR: $^1$H NMR (CDCl$_3$) δ: 7.21-7.29 (m, 2H), 6.77 (t, 1H), 6.58 (d, 2H), 4.24-4.42 (m, 1H), 4.13 (d, 2H), 3.48-3.66 (m, 7H), 3.11-3.43 (m, 5H), 2.70-3.11 (m, 5H), 2.01-2.29 (m, 6H), 1.81-1.97 (m, 2H). MS (m/z): 428.4 [MH]$^+$.

Example 37 and Example 38: 3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole (E37, Enantiomer 1) and 3-({3-[(3aR,6aR or 3aS,6aS)-1-phenyl-octahydropyrrolo[2,3-c]pyrrol-5-yl]propyl}sulfanyl)-4-methyl-5-(oxan-4-yl)-4H-1,2,4-triazole (E38, Enantiomer 2)

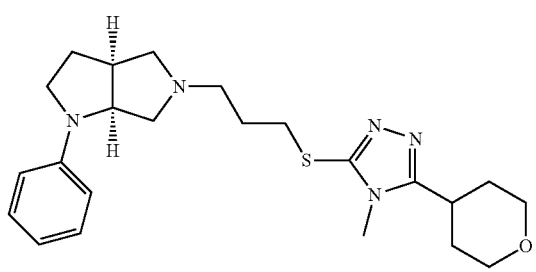

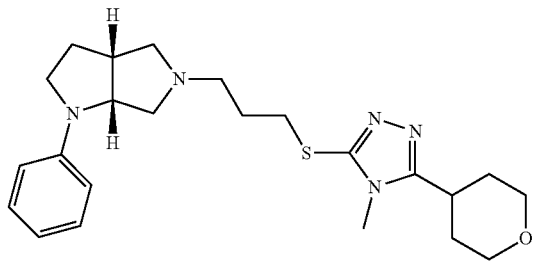

4-methyl-3-(oxan-4-yl)-5-[(3-{1-phenyl-octahydropyrrolo[2,3-c]pyrrol-5-yl}propyl)sulfanyl]-4H-1,2,4-triazole (E36, 60 mg) was separated into the single enantiomers by preparative chiral HPLC, obtaining 20 mg of 3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole (E37, Enantiomer 1) and 20 mg of 3-({3-[(3aR,6aR or 3aS,6aS)-1-phenyl-octahydropyrrolo[2,3-c]pyrrol-5-yl]propyl}sulfanyl)-4-methyl-5-(oxan-4-yl)-4H-1,2,4-triazole (E38, Enantiomer 2).

Preparative Chromatography:

| | |
|---|---|
| Column | Chiralpak AD-H (25 × 2.0 cm), 5 µm |
| Mobile phase | n-Hexane/(Ethanol + 0.1% ipa) 75/25% v/v |
| Flow rate (mL/min) | 14 mL/min |
| DAD detection | 220 nm |
| Loop | 500 µL |
| Injection | 10 mg/injection |

Example 37 Enantiomer 1: ret. time 8.8 min, 100% ee MS (m/z): 428.4 [MH]$^+$.

Example 38 Enantiomer 2: ret. time 11.6 min, 98.4% ee MS (m/z): 428.4 [MH]$^+$.

Example 39: 3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole dihydrochloride (E39, Enantiomer 1)

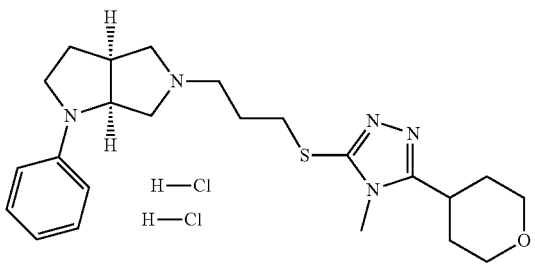

3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole (E37, Enantiomer 1, 20 mg) was dissolved in Et$_2$O and treated with 2.2. eq of 1N HCl in Et$_2$O to afford, after evaporation, 21 mg of title compound as white solid (E39, Enantiomer 1). MS (m/z): 428.4 [MH]$^+$.

Example 40: 3-({3-[(3aR,6aR or 3aS,6aS)-1-phenyl-octahydropyrrolo[2,3-c]pyrrol-5-yl]propyl}sulfanyl)-4-methyl-5-(oxan-4-yl)-4H-1,2,4-triazole dihydrochloride (E40, Enantiomer 2)

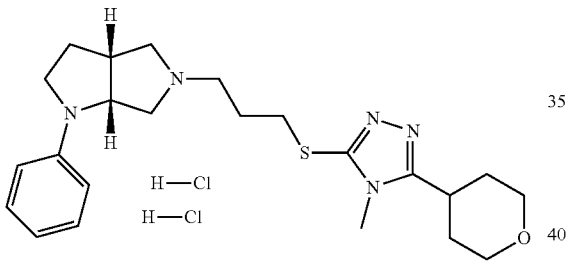

3-({3-[(3aR,6aR or 3aS,6aS)-1-phenyl-octahydropyrrolo[2,3-c]pyrrol-5-yl]propyl}-sulfanyl)-4-methyl-5-(oxan-4-yl)-4H-1,2,4-triazole (E38, Enantiomer 2, 20 mg) was dissolved in Et$_2$O and treated with 2.2. eq of 1N HCl in Et$_2$O to afford, after evaporation, 23 mg of title compound as white solid (E40, Enantiomer 2). MS (m/z): 428.4 [MH]$^+$.

Example 41: 3-({3-[1-(4-fluorophenyl)-octahydropyrrolo[3,4-b]pyrrol-5-yl]propyl}-sulfanyl)-4-methyl-5-(oxan-4-yl)-4H-1,2,4-triazole (E41)

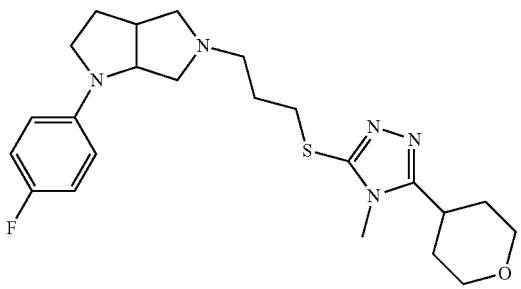 [SMILES: Cn1c(SCCCN2CC3CCN(c4ccc(F)cc4)C3C2)nnc1C1CCOCC1]

The title compound was prepared in analogy to the method described in Example 1 in 57 mg yield (E41, y=53%) from 1-(4-fluorophenyl)-octahydropyrrolo[2,3-c]pyrrole (p77, 50 mg, 0.24 mmol) and 3-[(3-chloropropyl)sulfanyl]-4-methyl-5-(oxan-4-yl)-4H-1,2,4-triazole (p5, 73 mg, 0.266 mmol). NMR: $^1$H NMR (Acetone-d$_6$) δ: 6.92-7.03 (m, 2H), 6.52-6.66 (m, 2H), 4.06-4.13 (m, 1H), 3.99 (dt, 2H), 3.58 (s, 3H), 3.52 (td, 2H), 3.38-3.46 (m, 1H), 3.03-3.27 (m, 4H), 2.88-2.99 (m, 1H), 2.70 (td, 2H), 2.37-2.57 (m, 4H), 2.10-2.21 (m, 1H), 1.80-2.00 (m, 7H). MS (m/z): 446.5 [MH]$^+$.

Example 42 and Example 43: 3-({3-[(3aS,6aS or 3aR,6aR)-1-(4-fluorophenyl)-octahydropyrrolo[3,4-b]pyrrol-5-yl]propyl}sulfanyl)-4-methyl-5-(oxan-4-yl)-4H-1,2,4-triazole (E42, Enantiomer 1) and 3-({3-[(3aR,6aR or 3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole (E43, Enantiomer 2)

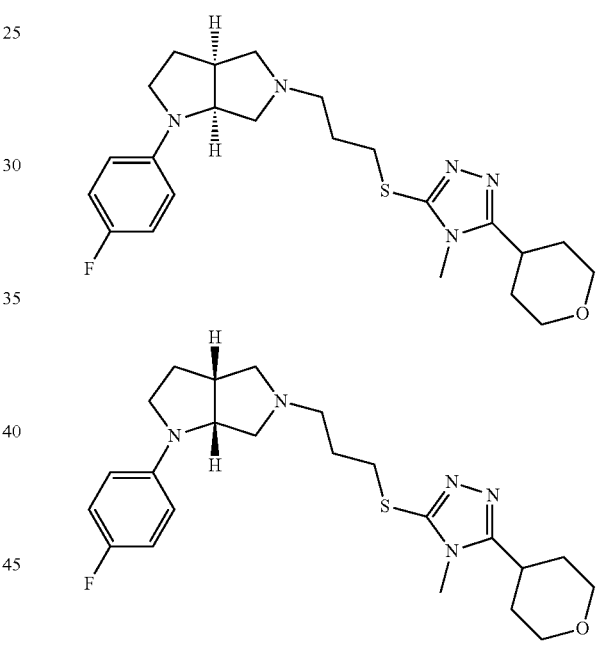

3-({3-[1-(4-fluorophenyl)-octahydropyrrolo[3,4-b]pyrrol-5-yl]propyl}sulfanyl)-4-methyl-5-(oxan-4-yl)-4H-1,2,4-triazole (E41, 57 mg) was separated into the single enantiomers by preparative chiral HPLC, obtaining 22 mg of 3-({3-[(3aS,6aS or 3aR,6aR)-1-(4-fluorophenyl)-octahydropyrrolo[3,4-b]pyrrol-5-yl]propyl}sulfanyl)-4-methyl-5-(oxan-4-yl)-4H-1,2,4-triazole (E42, Enantiomer 1) and 21.7 mg of 3-({3-[(3aR,6aR or 3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole (E43, Enantiomer 2).

Preparative Chromatography:

| Column | Chiralcel OJ-H (25 × 2.0 cm), 5 µm |
|---|---|
| Mobile phase | n-Hexane/(Ethanol/Methanol 1/1 + 0.1% ipa) 50/50% v/v |

| | |
|---|---|
| Flow rate (mL/min) | 19 mL/min |
| DAD detection | 220 nm |
| Loop | 2000 µL |
| Injection | 28.5 mg/injection |

Example 42 Enantiomer 1: ret. time 8.5 min, 100% ee MS (m/z): 446.5 [MH]⁺.

Example 43 Enantiomer 2: ret. time 12.3 min, 100% ee MS (m/z): 446.5 [MH]⁺.

Example 44: 3-({3-[(3aS,6aS or 3aR,6aR)-1-(4-fluorophenyl)-octahydropyrrolo[3,4-b]pyrrol-5-yl]propyl}sulfanyl)-4-methyl-5-(oxan-4-yl)-4H-1,2,4-triazole (E44, Enantiomer 1)

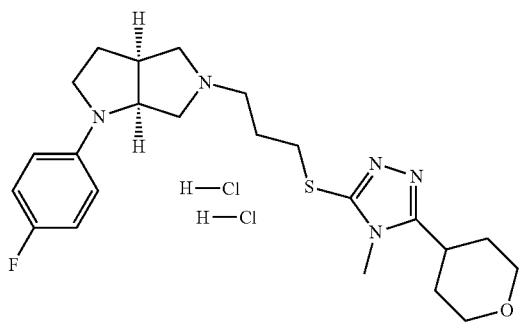

3-({3-[(3aS,6aS or 3aR,6aR)-1-(4-fluorophenyl)-octahydropyrrolo[3,4-b]pyrrol-5-yl]-propyl}sulfanyl)-4-methyl-5-(oxan-4-yl)-4H-1,2,4-triazole (E42, Enantiomer 1, 22 mg) was dissolved with Et₂O and treated with 2.2 eq of 1 M HCl in Et₂O to afford 22.2 mg of title compound as white solid (E44, Enantiomer 1). MS (m/z): 446.5 [MH]⁺.

Example 45: 3-({3-[(3aR,6aR or 3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole (E45, Enantiomer 2)

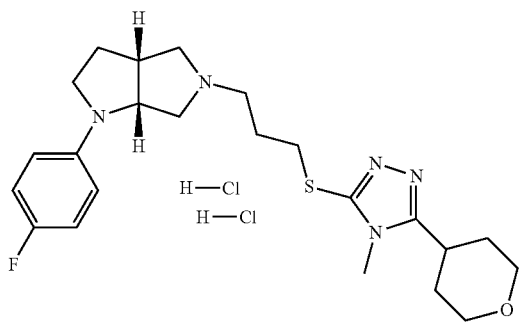

3-({3-[(3aR,6aR or 3aS,6aS)-1-(4-fluorophenyl)-octahydropyrrolo[3,4-b]pyrrol-5-yl]-propyl}sulfanyl)-4-methyl-5-(oxan-4-yl)-4H-1,2,4-triazole (E43, Enantiomer 2, 21.7 mg) was dissolved with Et₂O and treated with 2.2 eq of 1 M HCl in Et₂O to afford 23 mg of title compound as white solid (E45, Enantiomer 2). MS (m/z): 446.5 [MH]⁺.

Example 46: 3-[5-(3-{[4-methyl-5-(oxan-4-yl)-4H-1,2,4-triazol-3-yl]sulfanyl}propyl)-octahydropyrrolo[2,3-c]pyrrol-1-yl]pyridine (E46)

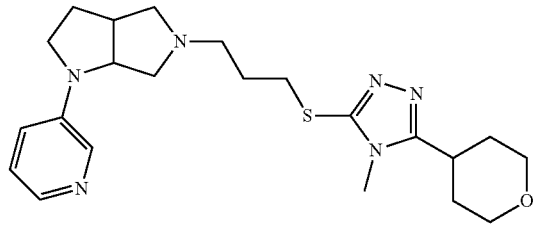 [SMILES: Cn1c(SCCCN2CC3CCN(c4cccnc4)C3C2)nnc1C1CCOCC1]

The title compound was prepared in analogy to the method described in Example 1 in 40 mg yield as a colorless oil (E46, y=33%) from 3-{octahydropyrrolo[3,4-b]pyrrol-1-yl}pyridine (p84, 54 mg, 0.28 mmol) and 3-[(3-chloropropyl)sulfanyl]-4-methyl-5-(oxan-4-yl)-4H-1,2,4-triazole (p5, 82 mg, 0.3 mmol.) NMR: ¹H NMR (Acetone-d₆) δ: 7.97 (d, 1H), 7.86 (dd, 1H), 7.10 (dd, 1H), 6.91 (ddd, 1H), 4.13-4.19 (m, 1H), 3.92-4.00 (m, 2H), 3.55 (s, 3H), 3.42-3.53 (m, 3H), 3.23-3.31 (m, 1H), 3.02-3.23 (m, 3H), 2.90-2.99 (m, 1H), 2.67-2.73 (m, 2H), 2.45-2.54 (m, 3H), 2.41 (dd, 1H), 2.11-2.20 (m, 1H), 1.78-1.99 (m, 7H). MS (m/z): 429.4 [MH]⁺.

Example 47 and Example 48: 3-[(3aS,6aS or 3aR,6aR)-5-(3-{[4-methyl-5-(oxan-4-yl)-4H-1,2,4-triazol-3-yl]sulfanyl}propyl)-octahydropyrrolo[2,3-c]pyrrol-1-yl]pyridine (E47, Enantiomer 1) and 3-[(3aR,6aR or 3aS,6aS)-5-(3-{[4-methyl-5-(oxan-4-yl)-4H-1,2,4-triazol-3-yl]sulfanyl}propyl)-octahydropyrrolo[2,3-c]pyrrol-1-yl]pyridine (E48, Enantiomer 2)

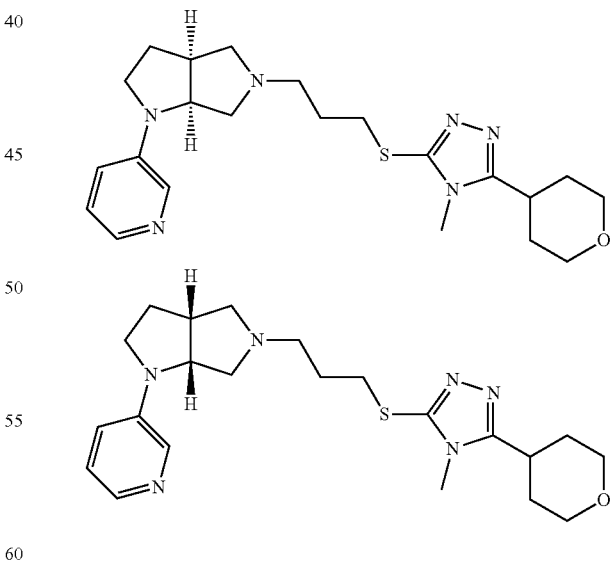

3-[5-(3-{[4-methyl-5-(oxan-4-yl)-4H-1,2,4-triazol-3-yl]sulfanyl}propyl)-octahydropyrrolo[2,3-c]pyrrol-1-yl]pyridine (E46, 38 mg) was separated into the single enantiomers by preparative chiral HPLC, obtaining 13.3 mg of 3-[(3aS, 6aS or 3aR,6aR)-5-(3-{[4-methyl-5-(oxan-4-yl)-4H-1,2,4-triazol-3-yl]sulfanyl}propyl)-octahydropyrrolo[2,3-c]pyrrol-1-yl]pyridine (E47, Enantiomer 1) and 13.6 mg of 3-[(3aR,6aR or 3aS,6aS)-5-(3-{[4-methyl-5-(oxan-4-yl)-4H-1,2,4-triazol-3-yl]sulfanyl}propyl)-octahydropyrrolo[2,3-c]pyrrol-1-yl]pyridine (E48, Enantiomer 2).

Preparative Chromatography:

| Column | Chiralpak AD-H (25 × 2 cm), 5 μm |
|---|---|
| Mobile phase | n-Hexane/(Ethanol/Methanol 1/1 + 0.1% ipa) 20/80 v/v |
| Flow rate (mL/min) | 14 |
| DAD detection | 220 nm |
| Loop | 1500 μL |
| injection | 19 mg (each injection) |

Example 47 Enantiomer 1: ret. time 9.3 min, 100% ee MS (m/z): 429.4 [MH]+.

Example 48 Enantiomer 2: ret. time 11.3 min, 97.4% ee MS (m/z): 429.4 [MH]+.

Example 49: 2-[5-(3-{[4-methyl-5-(oxan-4-yl)-4H-1,2,4-triazol-3-yl]sulfanyl}propyl)-octahydropyrrolo[2,3-c]pyrrol-1-yl]-5-(trifluoromethyl)pyrazine (E49)

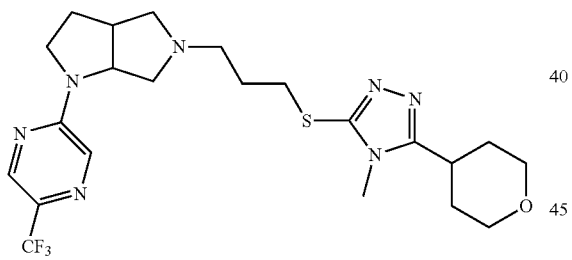

The title compound was prepared in analogy to the method described in Example 1 in 56 mg yield as a colorless oil (E49, y=40%) from 2-{octahydropyrrolo[3,4-b]pyrrol-1-yl}-5-(trifluoromethyl)pyrazine (p105, 72 mg, 0.278 mmol) and 3-[(3-chloropropyl)sulfanyl]-4-methyl-5-(oxan-4-yl)-4H-1,2,4-triazole (p5, 82 mg, 0.3 mmol.) NMR: $^1$H NMR (Acetone-d$_6$) δ: 8.41 (s, 1H), 8.06 (d, 1H), 4.53-4.60 (m, 1H), 3.95-4.02 (m, 2H), 3.81 (br. s., 1H), 3.64-3.74 (m, 1H), 3.48-3.62 (m, 5H), 2.99-3.29 (m, 4H), 2.86 (d, 1H), 2.76-2.80 (m, 1H), 2.45-2.66 (m, 4H), 2.18-2.26 (m, 1H), 1.81-1.93 (m, 5H). MS (m/z): 498.5 [MH]+.

Example 50: 5-[5-(3-{[4-methyl-5-(oxan-4-yl)-4H-1,2,4-triazol-3-yl]sulfanyl}propyl)-octahydropyrrolo[3,4-b]pyrrol-1-yl]-2-(trifluoromethyl)pyridine (E50)

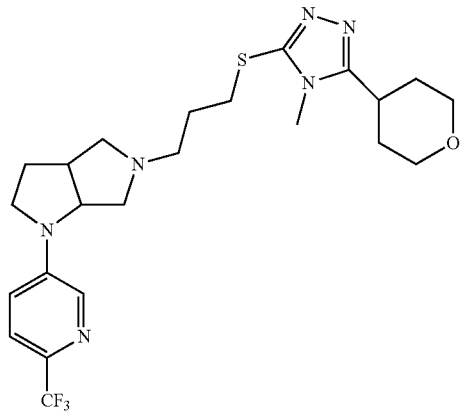 [SMILES: Cn1c(SCCCN2CC3CCN(c4ccc(C(F)(F)F)nc4)C3C2)nnc1C1CCOCC1]

The title compound was prepared in analogy to the method described in Example 1 in 32 mg yield as a colorless oil (E50, y=21%) from 5-{octahydropyrrolo[3,4-b]pyrrol-1-yl}-2-(trifluoromethyl)pyridine (p85, 78 mg, 0.3 mmol) and 3-[(3-chloropropyl)sulfanyl]-4-methyl-5-(oxan-4-yl)-4H-1,2,4-triazole (p5, 100 mg, 0.36 mmol.) NMR: $^1$H NMR (Acetone-d$_6$) δ: 8.07 (d, 1H), 7.57 (d, 1H), 7.07 (m, 1H), 4.29-4.36 (m, 1H), 3.95-4.02 (m, 2H), 3.42-3.63 (m, 7H), 2.97-3.28 (m, 4H), 2.71-2.80 (m, 2H), 2.43-2.62 (m, 4H), 2.16-2.28 (m, 1H), 1.98-2.07 (m, 1H), 1.81-1.96 (m, 6H). MS (m/z): 497.5 [MH]+.

Example 51: 3-cyclopentyl-4-methyl-5-[(3-{1-[4-(trifluoromethyl)phenyl]-octahydropyrrolo[3,4-b]pyrrol-5-yl}propyl)sulfanyl]-4H-1,2,4-triazole (E51)

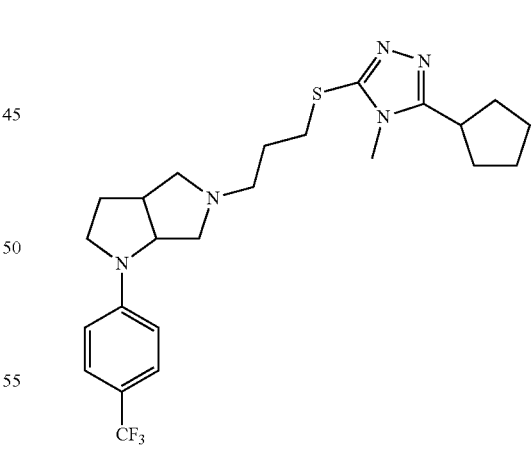

The title compound was prepared in analogy to the method described in Example 1 in 25 mg yield as as yellow oil (E51, y=26%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-5-cyclopentyl-4-methyl-4H-1,2,4-triazole (p7, 50 mg, 0.195 mmol). NMR: $^1$H NMR (CDCl$_3$) δ: 7.46 (d, 2H), 6.52-6.62 (m, 2H), 4.18-4.45 (m, 1H), 3.53-3.71 (m, 1H), 3.47 (s, 3H), 3.33-

3.44 (m, 1H), 3.12-3.26 (m, 3H), 2.54-2.98 (m, 5H), 1.93-2.30 (m, 9H), 1.87 (m, 3H), 1.67-1.77 (m, 2H). MS (m/z): 448.4 [MH]+.

Example 52 and Example 53: 3-({3-[(3aS,6aS or 3aR,6aR)-1-[4-(trifluoromethyl)phenyl]-octahydro-pyrrolo[3,4-b]pyrrol-5-yl]propyl}sulfanyl)-5-cyclopentyl-4-methyl-4H-1,2,4-triazole (E52, Enantiomer 1) and 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2, 4-triazole (E53, Enantiomer 2)

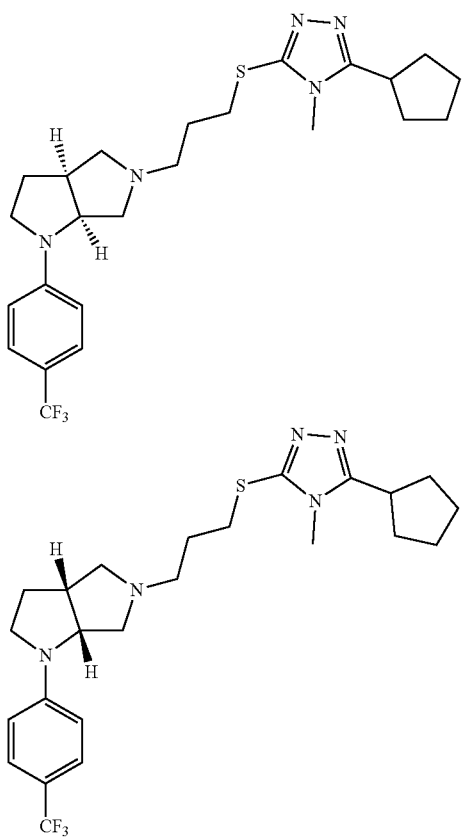

3-cyclopentyl-4-methyl-5-[(3-{1-[4-(trifluoromethyl)phenyl]-octahydropyrrolo[3,4-b]pyrrol-5-yl}propyl)sulfanyl]-4H-1,2,4-triazole (E51, 26 mg) was separated into the single enantiomers by preparative chiral HPLC, obtaining 9 mg of 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole (E52, Enantiomer 1) and 10 mg of 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole (E53, Enantiomer 2).

Preparative Chromatography:

| Column | Chiralcel OJ-H (25 × 2 cm), 5 μm |
|---|---|
| Mobile phase | n-Hexane/(Ethanol/Methanol 1/1 + 0.1% ipa) 50/50 v/v |
| Flow rate (mL/min) | 20 |
| DAD detection | 220 nm |
| Loop injection | 1000 μL 13 mg (each injection) |

Example 52 Enantiomer 1: ret. time 5.5 min, 100% ee MS (m/z): 448.4 [MH]+.

Example 53 Enantiomer 2: ret. time 11.4 min, 100% ee MS (m/z): 448.4 [MH]+.

Example 54: 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole dihydrochloride (E54, Enantiomer 1)

3-({3-[(3aS,6aS or 3aR,6aR)-1-[4-(trifluoromethyl)phenyl]-octahydropyrrolo[3,4-b]-pyrrol-5-yl]propyl}sulfanyl)-5-cyclopentyl-4-methyl-4H-1,2,4-triazole (E52, Enantiomer 1, 9 mg) was dissolved in Et₂O and treated with 2.2. eq of 1N HCl in Et₂O to afford, after evaporation, 9 mg of title compound as white solid (E54, Enantiomer 1). MS (m/z): 448.4 [MH]+.

Example 55: 3-({3-[(3aR,6aR or 3aS,6aS)-1-[4-(trifluoromethyl)phenyl]-octahydro-pyrrolo[3,4-b]pyrrol-5-yl]propyl}sulfanyl)-5-cyclopentyl-4-methyl-4H-1,2,4-triazole dihydrochloride (E55, Enantiomer 2)

3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole (E53, Enantiomer 2, 10 mg) was dissolved in Et₂O and treated with 2.2. eq of 1N HCl in Et₂O to afford, after evaporation, 9 mg of title compound as white solid (E55, Enantiomer 2). MS (m/z): 448.4 [MH]⁺.

Example 56: 3-cyclohexyl-4-methyl-5-[(3-{1-[4-(trifluoromethyl)phenyl]-octahydropyrrolo[3,4-b]pyrrol-5-yl}propyl)sulfanyl]-4H-1,2,4-triazol (E56)

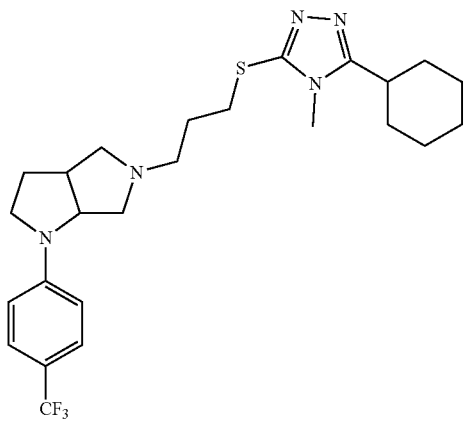 [SMILES: Cn1c(SCCCN2CC3CCN(c4ccc(C(F)(F)F)cc4)C3C2)nnc1C1CCCCC1]

The title compound was prepared in analogy to the method described in Example 1 in 52 mg yield as as pale yellow oil (E56, y=54%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-5-cyclohexyl-4-methyl-4H-1,2,4-triazole (p9, 54 mg, 0.195 mmol). NMR: ¹H NMR (CDCl₃) δ: 7.45 (d, 2H), 6.56 (d, 2H), 4.13-4.33 (m, 1H), 3.49-3.59 (m, 1H), 3.45 (s, 3H), 3.31-3.41 (m, 1H), 3.20 (d, 2H), 2.96-3.10 (m, 1H), 2.54-2.85 (m, 6H), 2.12-2.25 (m, 1H), 1.85-2.07 (m, 6H), 1.69-1.81 (m, 4H), 1.36 (d, 4H). MS (m/z): 494.2 [MH]⁺.

Example 57 and Example 58: 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole (E57, Enantiomer 1) and 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole (E58, Enantiomer 2)

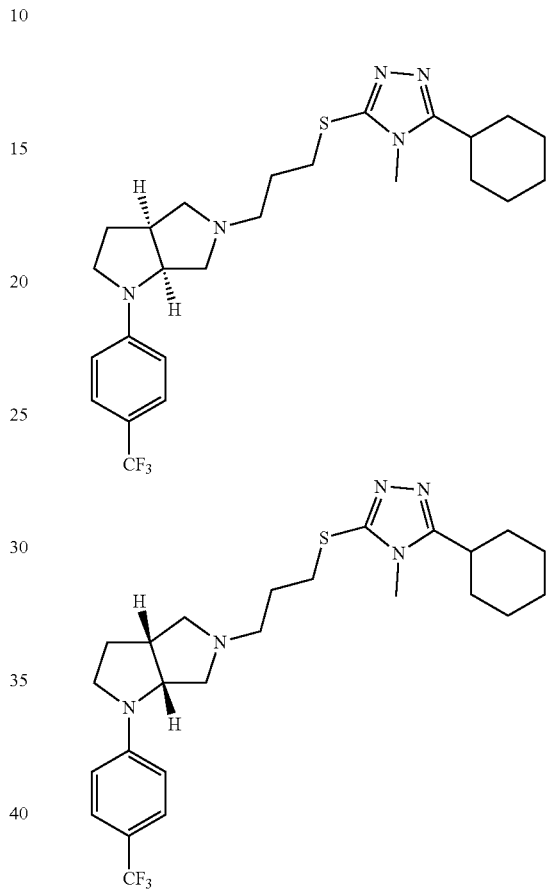

3-cyclohexyl-4-methyl-5-[(3-{1-[4-(trifluoromethyl)phenyl]-octahydropyrrolo[3,4-b]pyrrol-5-yl}propyl)sulfanyl]-4H-1,2,4-triazol (E56, 50 mg) was separated into the single enantiomers by preparative chiral HPLC, obtaining 18 mg of 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole (E57, Enantiomer 1) and 8 mg of 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole (E58, Enantiomer 2).

Preparative Chromatography:

| Column | Chiralcel OJ-H (25 × 2 cm), 5 μm |
|---|---|
| Mobile phase | n-Hexane/(Ethanol/Methanol 1/1 + 0.1% ipa) 50/50 v/v |
| Flow rate (mL/min) | 20 |
| DAD detection | 220 nm |
| Loop | 1000 μL |
| injection | 50 mg (each injection) |

Example 57 Enantiomer 1: ret. time 5.5 min, 100% ee MS (m/z): 494.2 [MH]⁺.

Example 58 Enantiomer 2: ret. time 11.7 min, 91.2% ee MS (m/z): 494.2 [MH]$^+$.

Example 59: 3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole dihydrochloride (E59, Enantiomer 1)

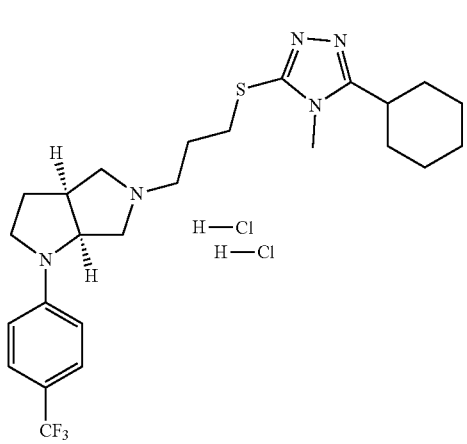

3-({3-[(3aS,6aS or 3aR,6aR)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole (E57, Enantiomer 1, 18 mg) was dissolved in Et$_2$O and treated with 2.2. eq of 1N HCl in Et$_2$O to afford, after evaporation, 18.3 mg of title compound (E59, Enantiomer 1). MS (m/z): 494.2 [MH]$^+$.

Example 60: 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole (E60, Enantiomer 2)

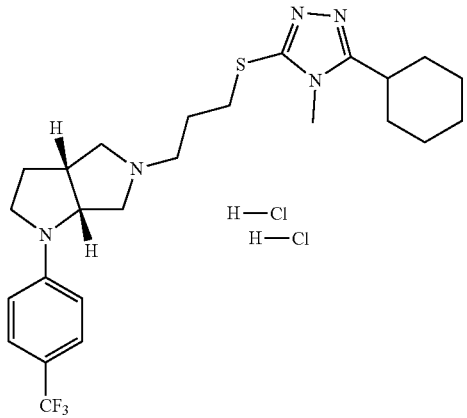

3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole (E58, Enantiomer 2, 8 mg) was dissolved in Et$_2$O and treated with 2.2. eq of 1N HCl in Et$_2$O to afford, after evaporation, 8.1 mg of title compound (E60, Enantiomer 2). MS (m/z): 494.2 [MH]$^+$.

Example 61: 3-cyclohexyl-5-({3-[1-(4-fluorophenyl)-octahydropyrrolo[3,4-b]pyrrol-5-yl]propyl}sulfanyl)-4-methyl-4H-1,2,4-triazole (E61)

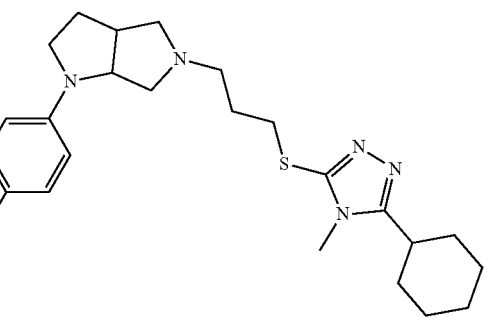

The title compound was prepared in analogy to the method described in Example 1 in 43.5 mg yield (E61, y=41%) from 1-(4-fluorophenyl)-octahydropyrrolo[2,3-c]pyrrole (p77, 50 mg, 0.24 mmol) and 3-[(3-chloropropyl)sulfanyl]-5-cyclohexyl-4-methyl-4H-1,2,4-triazole (p9, 73 mg, 0.266 mmol). NMR: $^1$H NMR (Acetone-d$_6$) δ: 6.96 (t, 2H), 6.58 (dd, 2H), 4.05-4.13 (m, 1H), 3.54 (s, 3H), 3.37-3.46 (m, 1H), 3.20 (s, 3H), 2.86-2.98 (m, 1H), 2.63-2.81 (m, 3H), 2.49 (br. s., 4H), 2.10-2.20 (m, 1H), 1.80-1.98 (m, 7H), 1.68-1.78 (m, 1H), 1.54-1.67 (m, 2H), 1.25-1.50 (m, 3H). MS (m/z): 444.1 [MH]$^+$.

Example 62 and Example 63: 3-({3-[(3aS,6aS or 3aR,6aR)-1-(4-fluorophenyl)-octahydropyrrolo[3,4-b]pyrrol-5-yl]propyl}sulfanyl)-5-cyclohexyl-4-methyl-4H-1,2,4-triazole (E62, Enantiomer 1) and 3-({3-[(3aR,6aR or 3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole (E63, Enantiomer 2)

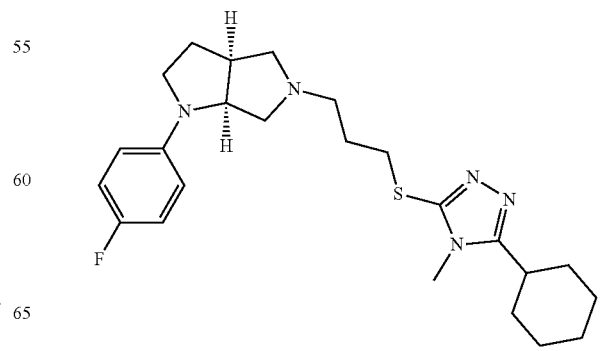

-continued

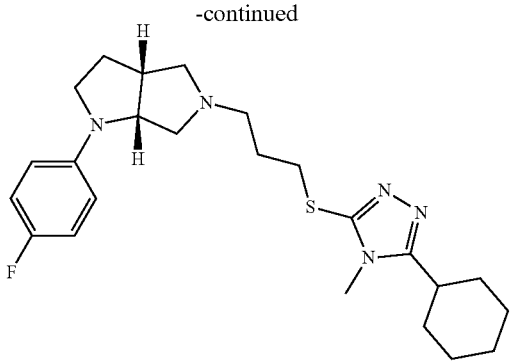

3-cyclohexyl-5-({3-[1-(4-fluorophenyl)-octahydropyr-rolo[3,4-b]pyrrol-5-yl]propyl}sulfanyl)-4-methyl-4H-1,2,4-triazole (E61, 41 mg) was separated into the single enantiomers by preparative chiral HPLC, obtaining 14.5 mg of 3-({3-[(3aS,6aS or 3aR,6aR)-1-(4-fluorophenyl)-octahy-dropyrrolo[3,4-b]pyrrol-5-yl]propyl}sulfanyl)-5-cyclo-hexyl-4-methyl-4H-1,2,4-triazole (E62, Enantiomer 1) and 16.5 mg of 3-({3-[(3aR,6aR or 3aS,6aS)-1-(4-fluorophe-nyl)-octahydropyrrolo[3,4-b]pyrrol-5-yl]propyl}sulfanyl)-5-cyclohexyl-4-methyl-4H-1,2,4-triazole (E63, Enantiomer 2).

Preparative Chromatography:

| | |
|---|---|
| Column | Chiralcel OJ-H (25 × 2.0 cm), 5 μm |
| Mobile phase | n-Hexane/(Ethanol/Methanol 1/1 + 0.1% ipa) 50/50% v/v |
| Flow rate (mL/min) | 18 mL/min |
| DAD detection | 220 nm |
| Loop | 1000 μL |
| Injection | 20.5 mg/injection |

Example 62 Enantiomer 1: ret. time 7.1 min, 100% ee MS (m/z): 444.1 [MH]$^+$.

Example 63 Enantiomer 2: ret. time 9.8 min, 100% ee MS (m/z): 444.1 [MH]$^+$.

Example 64: 3-({3-[(3aS,6aS or 3aR,6aR)-1-(4-fluorophenyl)-octahydropyrrolo[3,4-b]pyrrol-5-yl]propyl}sulfanyl)-5-cyclohexyl-4-methyl-4H-1,2,4-triazole dihydrochloride (E64, Enantiomer 1)

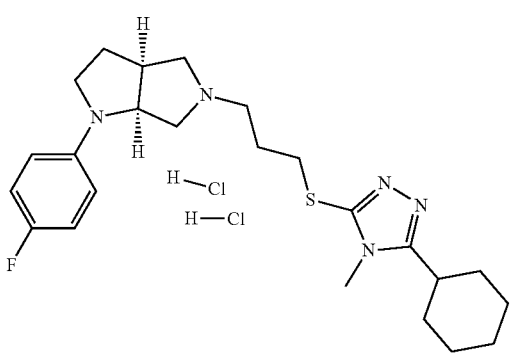

3-({3-[(3aS,6aS or 3aR,6aR)-1-(4-fluorophenyl)-octahy-dropyrrolo[3,4-b]pyrrol-5-yl]-propyl}sulfanyl)-5-cyclo-hexyl-4-methyl-4H-1,2,4-triazole (E62, Enantiomer 1, 14.5 mg) was dissolved with Et$_2$O and treated with 2.2 eq of 1 M HCl in Et$_2$O to afford 16.7 mg of title compound as white solid (E64, Enantiomer 1). MS (m/z): 444.1 [MH]$^+$.

Example 65: 3-({3-[(3aR,6aR or 3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole dihydrochloride (E65, Enantiomer 2)

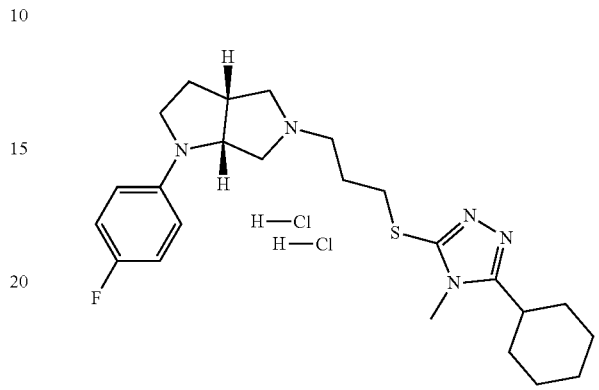

3-({3-[(3aR,6aR or 3aS,6aS)-1-(4-fluorophenyl)-octahy-dropyrrolo[3,4-b]pyrrol-5-yl]-propyl}sulfanyl)-5-cyclo-hexyl-4-methyl-4H-1,2,4-triazole (E63, Enantiomer 2, 16.5 mg) was dissolved with Et$_2$O and treated with 2.2 eq of 1 M HCl in Et$_2$O to afford 18.6 mg of title compound as white solid (E65, Enantiomer 2). MS (m/z): 444.1 [MH]$^+$.

Example 66: 3-(5-{3-[(5-cyclohexyl-4-methyl-4H-1,2,4-triazol-3-yl)sulfanyl]propyl}-octahydropyrrolo[2,3-c]pyrrol-1-yl)pyridine (E66)

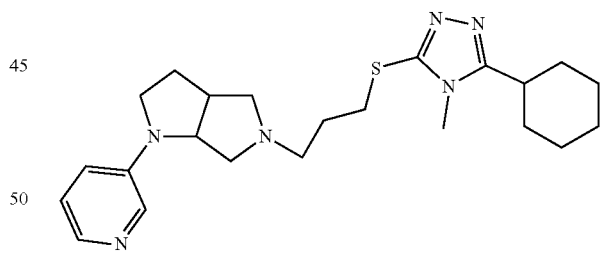

The title compound was prepared in analogy to the method described in Example 1 in 60 mg yield (E66, y=54%) from 3-{octahydropyrrolo[2,3-c]pyrrol-1-yl}pyridine (p84, 50 mg, 0.26 mmol) and 3-[(3-chloropro-pyl)sulfanyl]-5-cyclohexyl-4-methyl-4H-1,2,4-triazole (p9, 79 mg, 0.29 mmol). NMR: $^1$H NMR (Acetone-d$_6$) δ:7.99 (d, 1H), 7.89 (d, 1H), 7.10-7.15 (m, 1H), 6.89-6.97 (m, 1H), 4.16-4.21 (m, 1H), 3.55 (s, 3H), 3.44-3.52 (m, 1H), 3.27-3.34 (m, 1H), 3.07-3.24 (m, 2H), 2.94-3.03 (m, 1H), 2.69-2.79 (m, 3H), 2.47-2.57 (m, 3H), 2.39-2.47 (m, 1H), 2.13-2.22 (m, 1H), 1.80-2.02 (m, 7H), 1.74 (d, 1H), 1.55-1.69 (m, 2H), 1.27-1.51 (m, 3H). MS (m/z): 427.4[MH]$^+$.

Example 67 and Example 68: 3-[(3aS,6aS or 3aR, 6aR)-5-{3-[(5-cyclohexyl-4-methyl-4H-1,2,4-triazol-3-yl)sulfanyl]propyl}-octahydropyrrolo[2,3-c]pyrrol-1-yl]pyridine (E67, Enantiomer 1) and 3-[(3aR,6aR or 3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine (E68, Enantiomer 2)

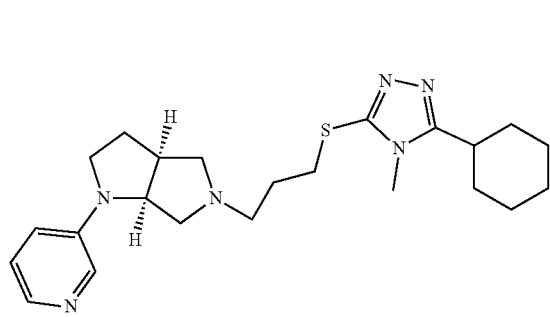 [SMILES: Cn1c(SCCCN2CC3CCN(c4cccnc4)C3C2)nnc1C1CCCCC1]

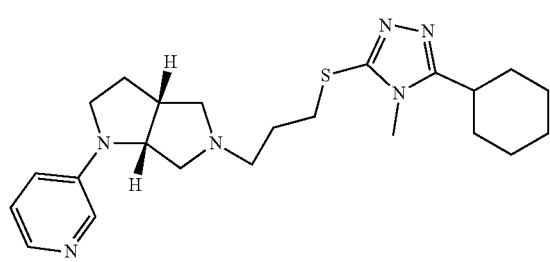

3-(5-{3-[(5-cyclohexyl-4-methyl-4H-1,2,4-triazol-3-yl)sulfanyl]propyl}-octahydropyrrolo[2,3-c]pyrrol-1-yl)pyridine (E66, 57 mg) was separated into the single enantiomers by preparative chiral HPLC, obtaining 14.7 mg of 3-[(3aS, 6aS or 3aR,6aR)-5-{3-[(5-cyclohexyl-4-methyl-4H-1,2,4-triazol-3-yl)sulfanyl]propyl}-octahydropyrrolo[2,3-c]pyrrol-1-yl]pyridine (E67, Enantiomer 1) and 19 mg of 3-[(3aR, 6aR or 3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine (E68, Enantiomer 2).

Preparative Chromatography:

| Column | Chiralpak AS-H (25 × 2 cm), 5 μm |
|---|---|
| Modifier | (Ethanol + 0.1% ipa) 17% |
| Flow rate (mL/min) | 46 |
| Pressure (bar) | 120 |
| Temperature (° C.) | 38 |
| UV detection | 220 nm |
| Loop | 500 μL |
| injection | 18.3 mg (each injection) |

Example 67 Enantiomer 1: ret time 11 min, 100% ee MS (m/z): 427.4 [MH]+.

Example 68 Enantiomer 2: ret time 18.1 min, 100% ee MS (m/z): 427.4 [MH]+.

Example 69: 3-[(3aS,6aS or 3aR,6aR)-5-{3-[(5-cyclohexyl-4-methyl-4H-1,2,4-triazol-3-yl)sulfanyl]propyl}-octahydropyrrolo[2,3-c]pyrrol-1-yl]pyridine trihydrochloride (E69, Enantiomer 1)

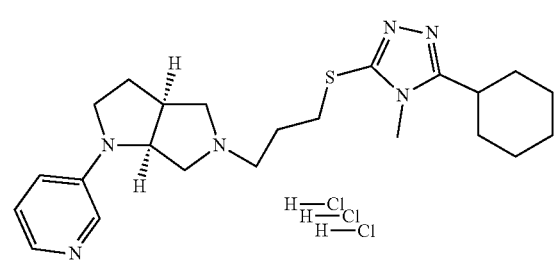

3-[(3aS,6aS or 3aR,6aR)-5-{3-[(5-cyclohexyl-4-methyl-4H-1,2,4-triazol-3-yl)sulfanyl]propyl}-octahydropyrrolo[2,3-c]pyrrol-1-yl]pyridine (E67, Enantiomer 1, 14.7 mg) was dissolved in Et$_2$O and treated with 3.3. eq of 2N HCl in Et$_2$O to afford, after evaporation, 15 mg of title compound (E69, Enantiomer 1). MS (m/z): 427.4 [MH]+.

Example 70: 3-[(3aR,6aR or 3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine trihydrochloride (E70, Enantiomer 2)

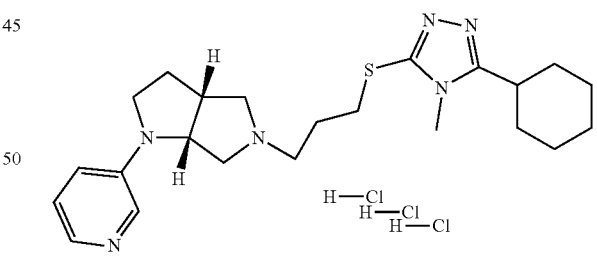

3-[(3aR,6aR or 3aS,6aS)-5-{3-[(5-cyclohexyl-4-methyl-4H-1,2,4-triazol-3-yl)sulfanyl]propyl}-octahydropyrrolo[2,3-c]pyrrol-1-yl]pyridine (E68, Enantiomer 2, 19 mg) was dissolved in Et$_2$O and treated with 3.3. eq of 2N HCl in Et$_2$O to afford, after evaporation, 21 mg of title compound (E70, Enantiomer 2). MS (m/z): 427.4 [MH]+.

Example 71: 3-(1,4-dioxan-2-yl)-4-methyl-5-[(3-{1-[4-(trifluoromethyl)phenyl]-octahydropyrrolo[3,4-b]pyrrol-5-yl}propyl)sulfanyl]-4H-1,2,4-triazol diasteroisomeric mixture (E71)

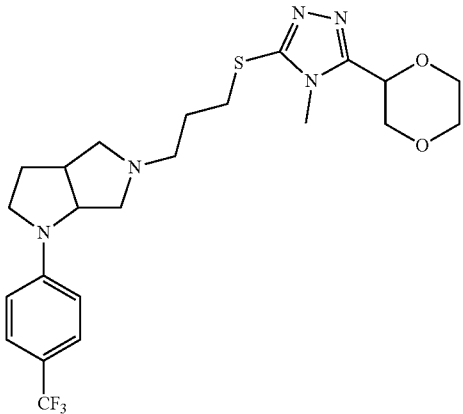 [SMILES: Cn1c(SCCCN2CC3CCN(c4ccc(C(F)(F)F)cc4)C3C2)nnc1C1COCCO1]

The title compound was prepared in analogy to the method described in Example 1 in 40 mg yield as as pale yellow oil (E71, y=41%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-5-(1,4-dioxan-2-yl)-4-methyl-4H-1,2,4-triazole (p11, 142 mg, 0.394 mmol). NMR: $^1$H NMR (CDCl$_3$) δ: 7.44 (d, 2H), 6.52-6.62 (m, 2H), 4.69-4.80 (m, 1H), 4.15-4.24 (m, 2H), 4.05-4.14 (m, 1H), 3.88 (d, 2H), 3.70-3.85 (m, 2H), 3.57 (s, 3H), 3.45-3.54 (m, 1H), 3.16-3.40 (m, 3H), 2.91-3.03 (m, 1H), 2.49-2.78 (m, 6H), 2.11-2.23 (m, 1H), 1.90-2.04 (m, 3H). MS (m/z): 498.1 [MH]$^+$.

Example 72, Example 73, Example 74 and Example 75: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole: Isomer 1 (E72), Isomer 2 (E73), Isomer 3 (E74) and Isomer 4 (E75)

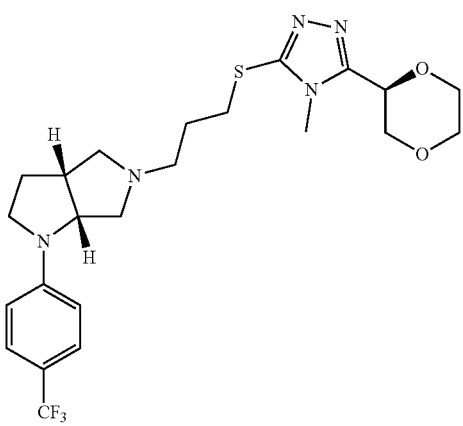

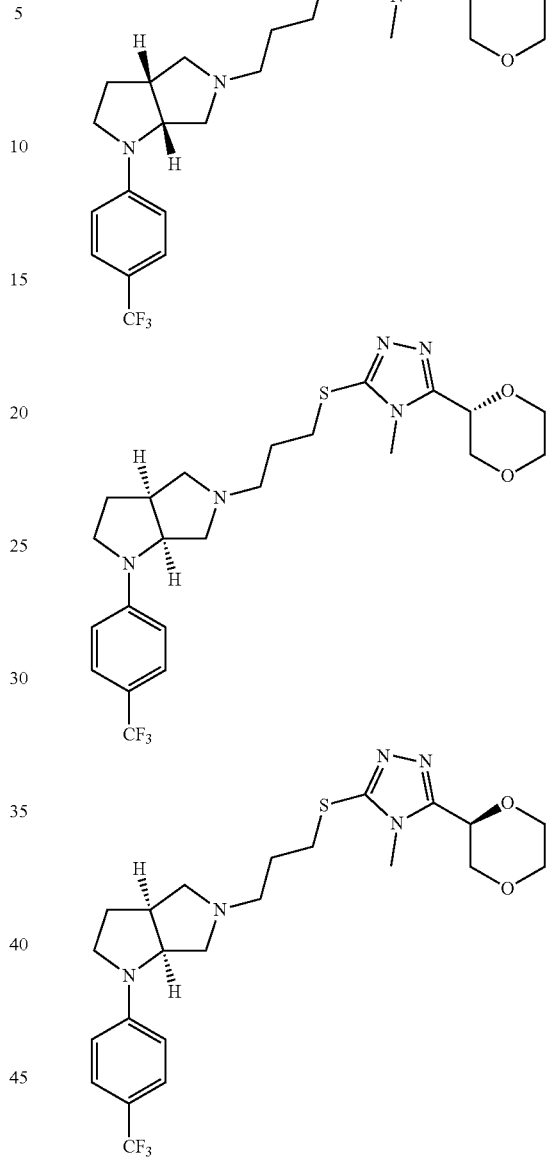

3-(1,4-dioxan-2-yl)-4-methyl-5-[(3-{1-[4-(trifluoromethyl)phenyl]-octahydropyrrolo[3,4-b]pyrrol-5-yl}propyl)sulfanyl]-4H-1,2,4-triazol diasteroisomeric mixture (E71, 38 mg) was separated into the single isomers by preparative chiral HPLC.

Preparative Chromatography:

| | |
|---|---|
| Column | Chiralcel OJ-H (25 × 2 cm), 5 um |
| Mobile phase | n-Hexane/(Ethanol/Methanol 1/1 + 0.1% ipa) 50/50 v/v |
| Flow rate (mL/min) | 18 |
| DAD detection | 220 nm |
| Loop | 1000 µL |
| injection | 19 mg (each injection) | obtaining:
Isomer 1 (E72, 7.2 mg): ret. time 8.2 min, 100% ee MS (m/z): 498.1 [MH]$^+$.

Isomer 2 (E73, 6.8 mg): ret. time 10.1 min, 100% ee MS (m/z): 498.1 [MH]⁺.

Isomer 3 (E74, 5.6 mg): ret. time 18.8 min, 100% ee MS (m/z): 498.1 [MH]⁺.

Isomer 4 (E75, 4.6 mg): ret. time 24.7 min, 100% ee MS (m/z): 498.1 [MH]⁺.

Example 76: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole dihydrochloride (E76, Isomer 1)

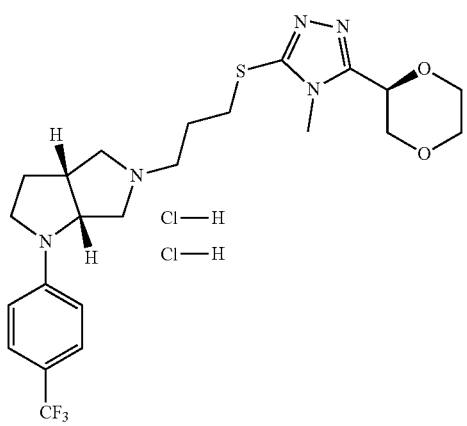

3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole (E72, Isomer 1, 7.2 mg) was dissolved in Et₂O and treated with 2.2. eq of 1N HCl in Et₂O to afford, after evaporation, 7.4 mg of title compound (E76, Isomer 1). MS (m/z): 498.1 [MH]⁺.

Example 77: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole dihydrochloride (E77, Isomer 2)

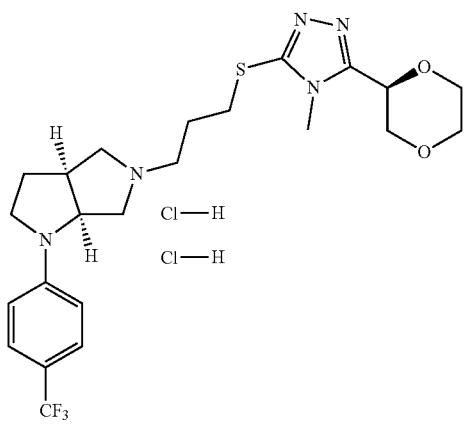

3-({3-[(3aR,6aR or 3aS,6aS)-1-[4-(trifluoromethyl)phenyl]-octahydropyrrolo[3,4-b]-pyrrol-5-yl]propyl}sulfanyl)-5-[(2R or 2S)-1,4-dioxan-2-yl]-4-methyl-4H-1,2,4-triazole (E73, Isomer 2, 6.8 mg) was dissolved in Et₂O and treated with 2.2 eq of 1N HCl in Et₂O to afford, after evaporation, 6.9 mg of title compound (E77, Isomer 2). MS (m/z): 498.1 [MH]⁺.

Example 78: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole dihydrochloride (E78, Isomer 3)

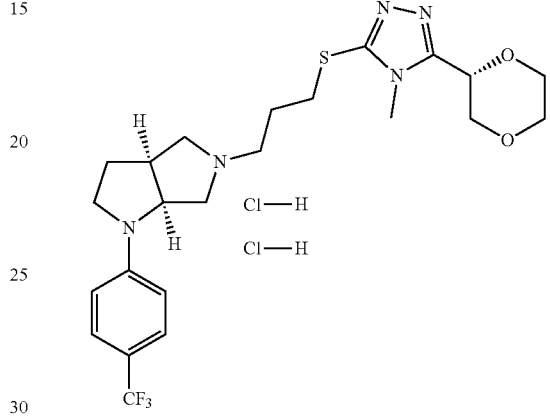

3-({3-[(3aR,6aR or 3aS,6aS)-1-[4-(trifluoromethyl)phenyl]-octahydropyrrolo[3,4-b]-pyrrol-5-yl]propyl}sulfanyl)-5-[(2R or 2S)-1,4-dioxan-2-yl]-4-methyl-4H-1,2,4-triazole (E74, Isomer 3, 5.6 mg) was dissolved in Et₂O and treated with 2.2. eq of 1N HCl in Et₂O to afford, after evaporation, 5.6 mg of title compound (E78, Isomer 3). MS (m/z): 498.1 [MH]⁺.

Example 79: 3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole dihydrochloride (E79, Isomer 4)

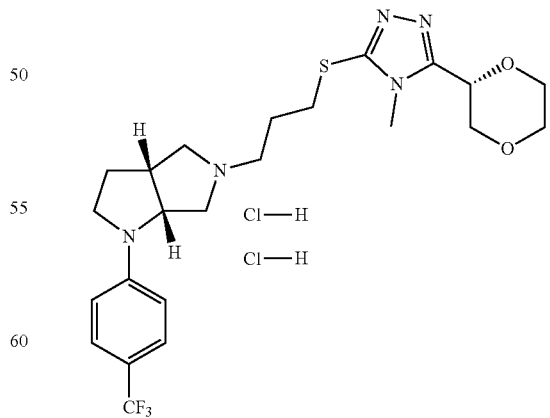

3-({3-[(3aR,6aR or 3aS,6aS)-1-[4-(trifluoromethyl)phenyl]-octahydropyrrolo[3,4-b]pyrrol-5-yl]propyl}sulfanyl)-5-[(2R or 2S)-1,4-dioxan-2-yl]-4-methyl-4H-1,2,4-triazole (E75, Isomer 4, 4.6 mg) was dissolved in Et₂O and treated with 2.2. eq of 1N HCl in Et₂O to afford, after evaporation, 4.6 mg of title compound (E79, Isomer 4). MS (m/z): 498.1 [MH]⁺.

Example 80: 1-methyl-2-[(3-{1-[4-(trifluoromethyl)phenyl]-octahydropyrrolo[3,4-b]pyrrol-5-yl}propyl)sulfanyl]-1H-1,3-benzodiazole (E80)

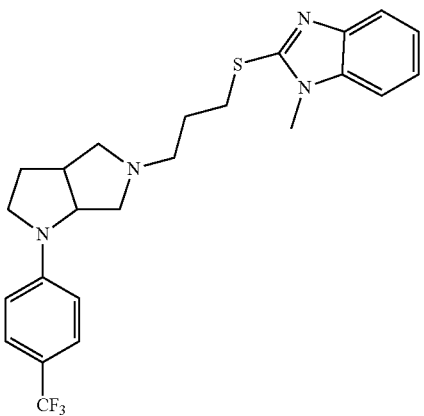 [SMILES: Cn1c(SCCCN2CC3CCN(c4ccc(C(F)(F)F)cc4)C3C2)nc2ccccc21]

The title compound was prepared in analogy to the method described in Example 1 in 33 mg yield (E80, y=37%) from 1-[4-(trifluoromethyl)phenyl]-octahydropyrrolo[3,4-b]pyrrole (prepared as in p73, 50 mg, 0.195 mmol) and 2-[(3-chloropropyl)sulfanyl]-1-methyl-1H-1,3-benzodiazole (p12, 51 mg, 0.21 mmol). NMR: ¹H NMR (CDCl₃) δ: 7.57-7.67 (m, 1H), 7.42-7.51 (m, 2H), 7.16-7.27 (m, 3H), 6.55 (d, 2H), 4.32 (br. s., 1H), 3.68 (s, 3H), 3.53-3.63 (m, 1H), 3.37-3.49 (m, 3H), 3.15 (br. s., 2H), 2.80 (br. s., 4H), 1.97-2.28 (m, 5H). MS (m/z): 461.5 [MH]⁺.

Example 81: 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}morpholine (E81)

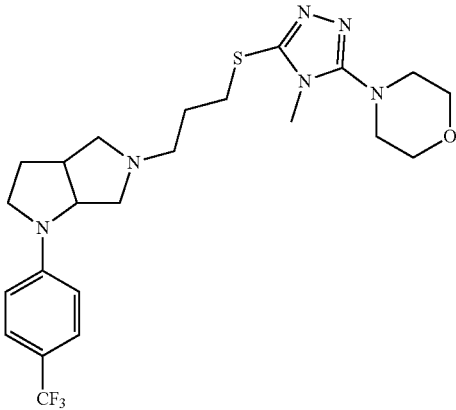 [SMILES: Cn1c(SCCCN2CC3CCN(c4ccc(C(F)(F)F)cc4)C3C2)nnc1N1CCOCC1]

The title compound was prepared in analogy to the method described in Example 1 in 24 mg yield (E81, y=25%) from 1-[4-(trifluoromethyl)phenyl]-octahydropyrrolo[3,4-b]pyrrole (prepared as in p73, 50 mg, 0.195 mmol) and 4-{5-[(3-chloropropyl)sulfanyl]-4-methyl-4H-1,2,4-triazol-3-yl}morpholine (p13, 58 mg, 0.21 mmol). NMR: ¹H NMR (Acetone-d₆) δ: 7.44-7.50 (m, 2H), 6.67-6.75 (m, 2H), 4.20-4.29 (m, 1H), 3.75-3.84 (m, 4H), 3.46-3.56 (m, 1H), 3.45 (s, 3H), 3.36-3.43 (m, 1H), 3.04-3.23 (m, 6H), 3.01 (d, 1H), 2.70-2.77 (m, 2H), 2.38-2.62 (m, 4H), 2.15-2.25 (m, 1H), 1.96-2.04 (m, 1H), 1.81-1.94 (m, 2H). MS (m/z): 497.5 [MH]⁺.

Example 82 and Example 83: 4-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine (E82, Enantiomer 1) and 4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine (E83, Enantiomer 2)

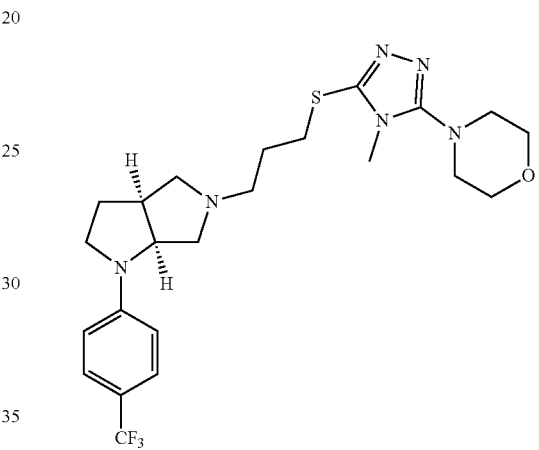

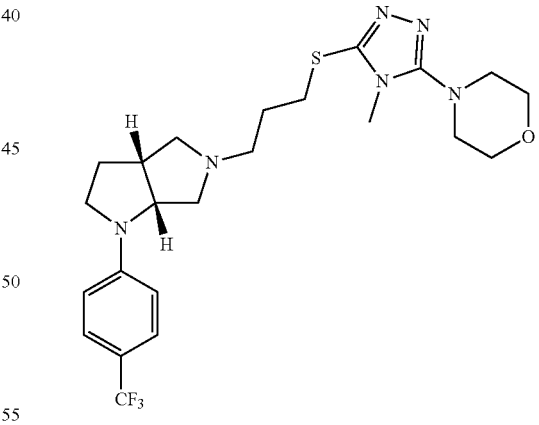

4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}morpholine (E81, 22 mg) was separated into the single enantiomers by preparative chiral HPLC, obtaining 8 mg of 4-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine (E82, Enantiomer 1) and 9 mg of 4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine (E83, Enantiomer 2).

Preparative Chromatography:

| Column | Chiralpak AS-H (25 × 2 cm), 5 µm |
| --- | --- |
| Modifier | (Ethanol + 0.1% ipa) 13% v/v |
| Flow rate (mL/min) | 46 |
| Pressure (bar) | 120 |
| Temperature(° C.) | 38 |
| UV detection | 220 nm |
| Loop | 750 µL |
| injection | 11 mg (each injection) |

Example 82 Enantiomer 1: ret. time 5.9 min, 100% ee MS (m/z): 497.5 [MH]$^+$.

Example 83 Enantiomer 2: ret. time 7.6 min, 97.6% ee MS (m/z): 497.5 [MH]$^+$.

Example 84: 4-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine dihydrochloride (E84, Enantiomer 1)

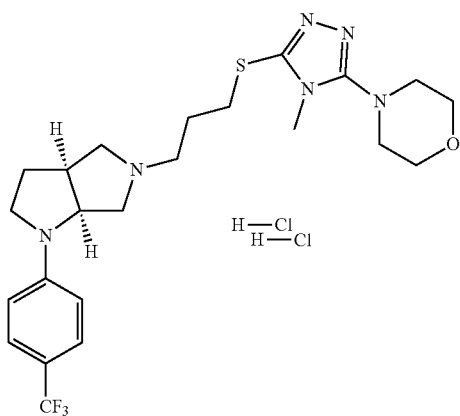

4-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine (E82, Enantiomer 1) (E, Enantiomer 1, 8 mg) was dissolved in Et$_2$O and treated with 2.2. eq of 1N HCl in Et$_2$O to afford, after evaporation, 7 mg of title compound (E84, Enantiomer 1). MS (m/z): 497.5 [MH]$^+$.

Example 85: 4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine dihydrochloride (E85, Enantiomer 2)

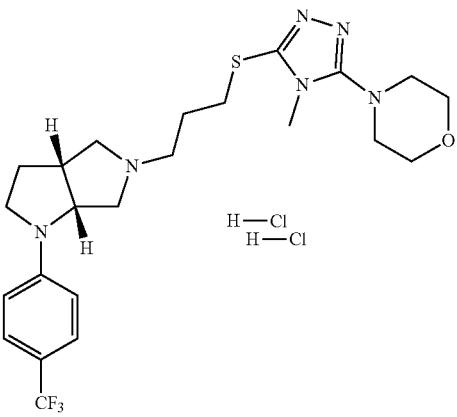

4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine (E83, Enantiomer 2, 9 mg) was dissolved in Et$_2$O and treated with 2.2. eq of 1N HCl in Et$_2$O to afford, after evaporation, 7 mg of title compound (E85, Enantiomer 2). MS (m/z): 497.5 [MH]$^+$.

Example 86: 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridazine (E86)

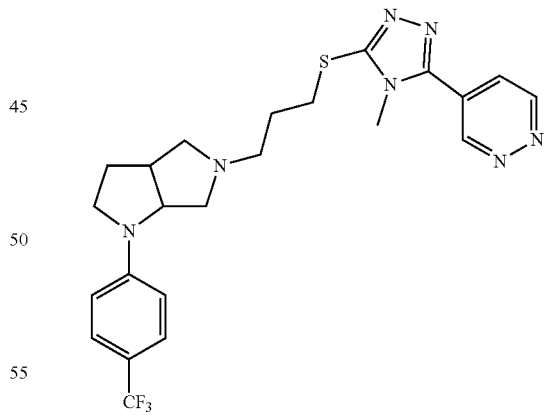

The title compound was prepared in analogy to the method described in Example in 46 mg yield (E86, y=48%) from 1-[4-(trifluoromethyl)phenyl]-octahydropyrrolo[3,4-b]pyrrole (prepared as in p73, 50 mg, 0.195 mmol) and 4-{5-[(3-chloropropyl)sulfanyl]-4-methyl-4H-1,2,4-triazol-3-yl}pyridazine (p15, 57 mg, 0.21 mmol). NMR: $^1$H NMR (Acetone-d$_6$) δ: 9.63 (d, 1H), 9.34-9.44 (m, 1H), 8.03 (m, 1H), 7.46 (d, 2H), 6.71 (d, 2H), 4.20-4.30 (m, 1H), 3.85 (s, 3H), 3.47-3.56 (m, 1H), 3.24-3.44 (m, 4H), 2.95-3.06 (m, 1H), 2.51-2.64 (m, 3H), 2.43-2.50 (m, 1H), 2.14-2.26 (m, 2H), 1.89-2.04 (m, 3H). MS (m/z): 490.4 [MH]⁺.

Example 87: 3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridazine (E87)

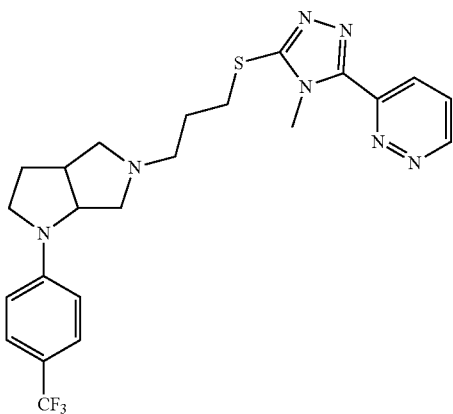 [SMILES: Cn1c(SCCCN2CC3CCN(c4ccc(C(F)(F)F)cc4)C3C2)nnc1-c1cccnn1]

The title compound was prepared in analogy to the method described in Example 1 in 52 mg yield (E87, y=54%) from 1-[4-(trifluoromethyl)phenyl]-octahydropyrrolo[3,4-b]pyrrole (prepared as in p73, 50 mg, 0.195 mmol) and 3-{5-[(3-chloropropyl)sulfanyl]-4-methyl-4H-1,2,4-triazol-3-yl}pyridazine (p17, 57 mg, 0.21 mmol). NMR: ¹H NMR (Acetone-d₆) δ: 9.29 (m, 1H), 8.38 (m, 1H), 7.85 (m, 1H), 7.45 (d, 2H), 6.69 (d, 2H), 4.18-4.28 (m, 1H), 4.07 (s, 3H), 3.46-3.56 (m, 1H), 3.25-3.45 (m, 4H), 2.94-3.05 (m, 1H), 2.50-2.65 (m, 4H), 2.42-2.50 (m, 1H), 2.13-2.24 (m, 2H), 1.92-2.02 (m, 2H). MS (m/z): 490.4 [MH]⁺.

Example 88: 5-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrimidine (E88)

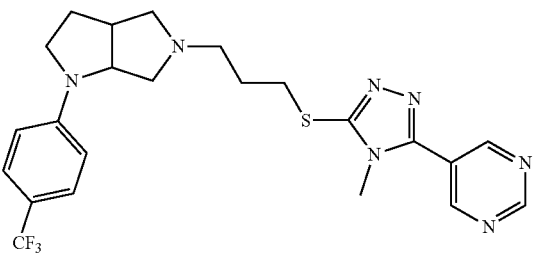 [SMILES: Cn1c(SCCCN2CC3CCN(c4ccc(C(F)(F)F)cc4)C3C2)nnc1-c1cncnc1]

The title compound was prepared in analogy to the method described in Example 1 in 20 mg yield as yellow sticky foam (E88, y=21%) from 1-[4-(trifluoromethyl)phenyl]-octahydropyrrolo[3,4-b]pyrrole (prepared as in p73, 34 mg, 0.134 mmol) and 5-{5-[(3-chloropropyl)sulfanyl]-4-methyl-4H-1,2,4-triazol-3-yl}pyrimidine (p19, 40 mg, 0.148 mmol). NMR: ¹H NMR (Acetone-d₆) δ: 9.26-9.33 (m, 1H), 9.15 (s, 2H), 7.41-7.52 (m, 2H), 6.65-6.76 (m, 2H), 4.22-4.28 (m, 1H), 3.78 (s, 3H), 3.47-3.57 (m, 1H), 3.22-3.44 (m, 4H), 2.96-3.06 (m, 1H), 2.74-2.76 (m, 1H), 2.51-2.64 (m, 3H), 2.43-2.51 (m, 1H), 2.15-2.25 (m, 1H), 1.92-2.04 (m, 3H). MS (m/z): 490.5 [MH]⁺.

Example 89: 2-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrazine (E89)

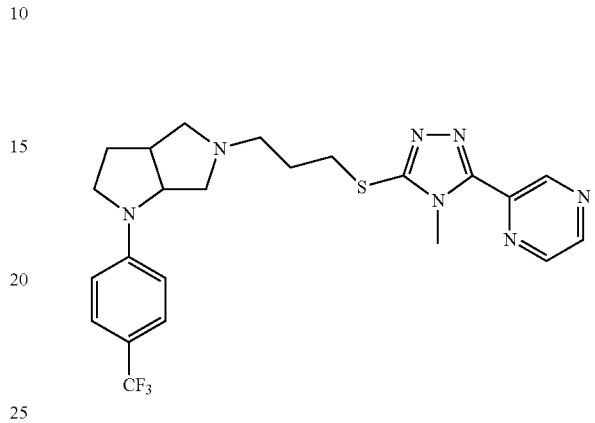

The title compound was prepared in analogy to the method described in Example 1 in 63 mg yield as yellow gum (E89, y=65%) from 1-[4-(trifluoromethyl)phenyl]-octahydropyrrolo[2,3-c]pyrrole (prepared as in p73, 50 mg, 0.2 mmol) and 2-{5-[(3-chloropropyl)sulfanyl]-4-methyl-4H-1,2,4-triazol-3-yl}pyrazine (p21, 59 mg, 0.22 mmol). NMR: ¹H NMR (Acetone-d₆) δ: 9.37 (d, 1H), 8.66-8.77 (m, 2H), 7.45 (d, 2H), 6.69 (d, 2H), 4.20-4.31 (m, 1H), 3.97 (s, 3H), 3.46-3.55 (m, 1H), 3.36 (d, 2H), 3.24-3.33 (m, 1H), 2.94-3.04 (m, 1H), 2.71-2.74 (m, 1H), 2.49-2.63 (m, 4H), 2.42-2.48 (m, 1H), 2.13-2.20 (m, 1H), 1.92-2.03 (m, 3H). MS (m/z): 490.4[MH]⁺.

Example 90 and Example 91: 2-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine (E90, Enantiomer 1) and 2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine (E91, Enantiomer 2)

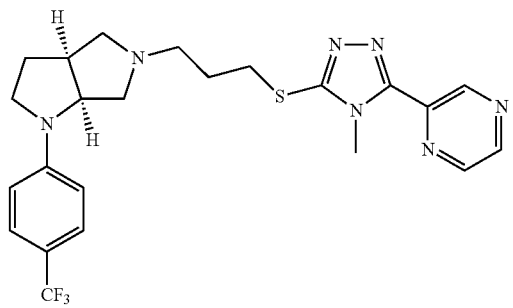

-continued

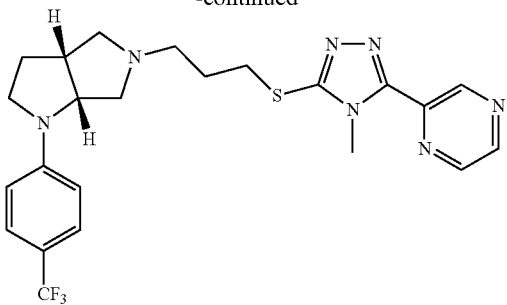

2-{4-methyl-5-[(3-{1-[4-(trifluoromethyl)phenyl]-octahydropyrrolo[2,3-c]pyrrol-5 yl}propyl)sulfanyl]-4H-1,2,4-triazol-3-yl}pyrazine (E89, 60 mg) was separated into the single enantiomers by preparative chiral HPLC, obtaining 18 mg of 2-[5-({3-[(3aS,6aS or 3aR,6aR)-1-[4-(trifluoromethyl)phenyl]-octahydropyrrolo[2,3c]pyrrol-5-yl]propyl}sulfanyl)-4-methyl-4H-1,2,4-triazol-3-yl]pyrazine (E90, Enantiomer 1) and 24 mg of 2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine (E91, Enantiomer 2).

Preparative Chromatography:

| | |
|---|---|
| Column | Chiralpak AS-H (25 × 2 cm), 5 µm |
| Modifier | (Ethanol + 0.1% ipa) 15% v/v |
| Flow rate (mL/min) | 46 |
| Pressure (bar) | 120 |
| Temperature(° C.) | 38 |
| UV detection | 220 nm |
| Loop | 500 µL |
| injection | 14.5 mg (each injection) |

Example 90 Enantiomer 1: ret. time 7.6 min, 100% ee MS (m/z): 490.4 [MH]+.

Example 91 Enantiomer 2: ret. time 10.0 min, 100% ee MS (m/z): 490.4 [MH]+.

Example 92: 2-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine dihydrochloride (E92, Enantiomer 1)

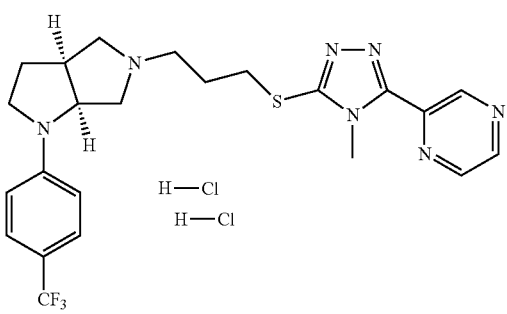

2-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine (E90, Enantiomer 1, 17 mg) was dissolved in Et2O and treated with 2.2. eq of 1N HCl in Et2O to afford, after evaporation, 16.5 mg of title compound (E92, Enantiomer 1). MS (m/z): 490.4 [MH]+.

Example 93: 2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine (E93, Enantiomer 2)

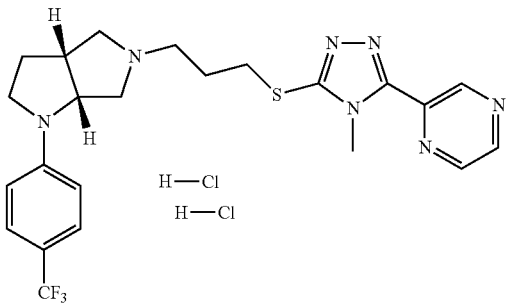

2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine (E91, Enantiomer 2, 22 mg) was dissolved in Et2O and treated with 2.2. eq of 1N HCl in Et2O to afford, after evaporation, 24 mg of title compound (E93, Enantiomer 2). MS (m/z): 490.4 [MH]+.

Example 94: 3-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile (E94)

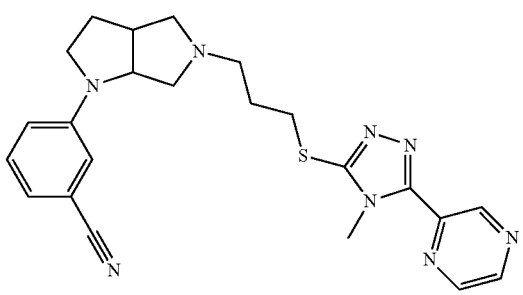 [SMILES: Cn1c(SCCCN2CC3CCN(c4cccc(C#N)c4)C3C2)nnc1-c1cnccn1]

The title compound was prepared in analogy to the method described in Example 1 in 46 mg yield as white foam (E94, y=43%) from 3-{octahydropyrrolo[2,3-c]pyrrol-1-yl}benzonitrile (p74, 51 mg, 0.24 mmol) and 2-{5-[(3-chloropropyl)sulfanyl]-4-methyl-4H-1,2,4-triazol-3-yl}pyrazine (p21, 71 mg, 0.26 mmol). NMR: $^1$H NMR (Acetone-d$_6$) δ: 9.38 (d, 1H), 8.68-8.76 (m, 2H), 7.34 (m, 1H), 6.86-6.99 (m, 3H), 4.23 (m, 1H), 3.99 (s, 3H), 3.46-3.55 (m, 1H), 3.24-3.43 (m, 3H), 2.96-3.06 (m, 1H), 2.74-2.79 (m, 2H), 2.50-2.64 (m, 3H), 2.46 (m, 1H), 2.13-2.22 (m, 1H), 1.88-2.04 (m, 3H). MS (m/z): 447.5 [MH]+.

Example 95: 2-[5-({3-[1-(4-fluorophenyl)-octahydropyrrolo[3,4-b]pyrrol-5-yl]propyl}sulfanyl)-4-methyl-4H-1,2,4-triazol-3-yl]pyrazine (E95)

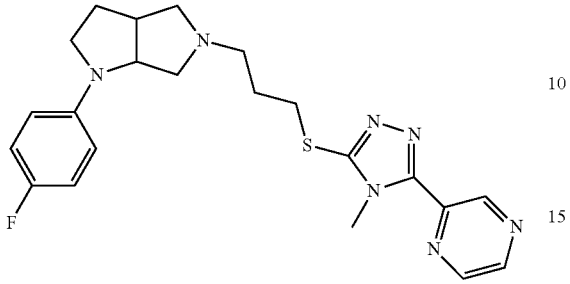

The title compound was prepared in analogy to the method described in Example 1 in 63 mg yield (E95, y=60%) from 1-(4-fluorophenyl)-octahydropyrrolo[2,3-c]pyrrole (p77, 50 mg, 0.24 mmol) and 2-{5-[(3-chloropropyl)sulfanyl]-4-methyl-4H-1,2,4-triazol-3-yl}pyrazine (p21, 72 mg, 0.266 mmol). NMR: $^1$H NMR (Acetone-$d_6$) δ: 9.38 (d, 1H), 8.67-8.77 (m, 2H), 6.91-7.00 (m, 2H), 6.54-6.62 (m, 2H), 4.10 (s, 1H), 4.00 (s, 3H), 3.16-3.48 (m, 4H), 2.95 (br. s., 1H), 2.69-2.76 (m, 2H), 2.39-2.63 (m, 4H), 2.12-2.21 (m, 1H), 2.04-2.09 (m, 1H), 1.92-2.00 (m, 2H). MS (m/z): 440.5 [MH]$^+$.

Example 96: 2-{4-methyl-5-[(3-{1-[2-(trifluoromethoxy)phenyl]-octahydropyrrolo[3,4-b]pyrrol-5-yl}propyl)sulfanyl]-4H-1,2,4-triazol-3-yl}pyrazine (E96)

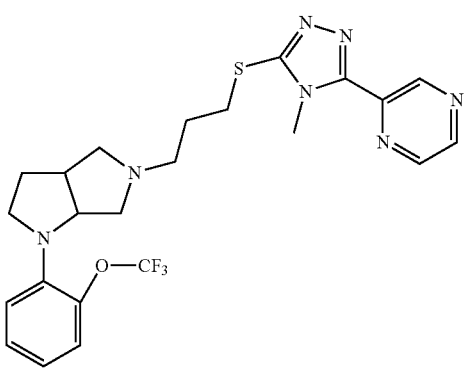 [SMILES: Cn1c(SCCCN2CC3CCN(c4ccccc4OC(F)(F)F)C3C2)nnc1-c1cnccn1]

The title compound was prepared in analogy to the method described in Example 1 in 19 mg yield (E96, y=29%) from 1-[2-(trifluoromethoxy)phenyl]-octahydropyrrolo[3,4-b]pyrrole (p78, 35 mg, 0.128 mmol) and 2-{5-[(3-chloropropyl)sulfanyl]-4-methyl-4H-1,2,4-triazol-3-yl}pyrazine (p21, 38 mg, 0.14 mmol). NMR: $^1$H NMR (Acetone-$d_6$) δ: 9.38 (d, 1H), 8.67-8.78 (m, 2H), 7.15-7.26 (m, 2H), 6.96 (d, 1H), 6.78-6.88 (m, 1H), 4.57 (m, 1H), 3.98 (s, 3H), 3.53 (m, 1H), 3.17-3.35 (m, 3H), 2.97 (d, 1H), 2.65 (m, 1H), 2.49-2.57 (m, 2H), 2.41-2.48 (m, 2H), 2.29-2.35 (m, 1H), 2.02-2.05 (m, 1H), 1.80-1.95 (m, 3H). MS (m/z): 506.4[MH]$^+$.

Example 97: 2-{4-methyl-5-[(3-{1-[4-(trifluoromethoxy)phenyl]-octahydropyrrolo[3,4-b]pyrrol-5-yl}propyl)sulfanyl]-4H-1,2,4-triazol-3-yl}pyrazine (E97)

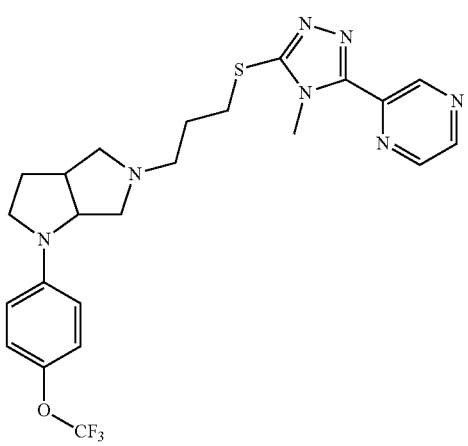 [SMILES: Cn1c(SCCCN2CC3CCN(c4ccc(OC(F)(F)F)cc4)C3C2)nnc1-c1cnccn1]

The title compound was prepared in analogy to the method described in Example 1 in 43 mg yield (E97, y=58%) from 1-[4-(trifluoromethoxy)phenyl]-octahydropyrrolo[3,4-b]pyrrole (p79, 40 mg, 0.147 mmol) and 2-{5-[(3-chloropropyl)sulfanyl]-4-methyl-4H-1,2,4-triazol-3-yl}pyrazine (p21, 44 mg, 0.16 mmol). NMR: $^1$H NMR (Acetone-$d_6$) δ: 9.34-9.41 (m, 1H), 8.66-8.76 (m, 2H), 7.08-7.16 (m, 2H), 6.58-6.66 (m, 2H), 4.10-4.19 (m, 1H), 3.98 (s, 3H), 3.21-3.53 (m, 4H), 2.91-3.03 (m, 1H), 2.68-2.76 (m, 2H), 2.54 (s, 4H), 2.11-2.21 (m, 1H), 1.88-2.02 (m, 3H). MS (m/z): 506.5[MH]$^+$.

Example 98: 2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine (E98)

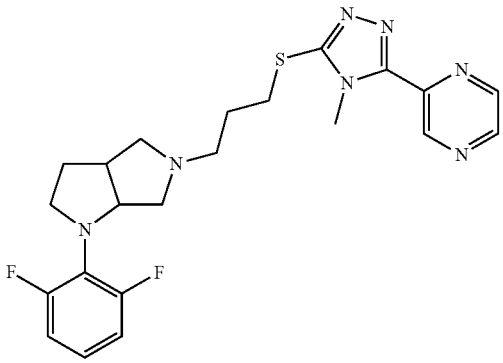 [SMILES: Cn1c(SCCCN2CC3CCN(c4c(F)cccc4F)C3C2)nnc1-c1cnccn1]

The title compound was prepared in analogy to the method described in Example 1 in 19.7 mg yield (E98, y=39%) from 1-(2,6-difluorophenyl)-octahydropyrrolo[3,4-b]pyrrole (p80, 25 mg, 0.11 mmol) and 2-{5-[(3-chloropropyl)sulfanyl]-4-methyl-4H-1,2,4-triazol-3-yl}pyrazine (p21, 30 mg, 0.11 mmol). NMR: $^1$H NMR (Acetone-$d_6$) δ: 9.39 (d, 1H), 8.70-8.78 (m, 2H), 6.83-6.97 (m, 3H), 4.50 (br. s., 1H), 4.02 (s, 3H), 3.83 (m, 1H), 3.25-3.43 (m, 3H), 2.93 (br. s., 1H), 2.39-2.72 (m, 5H), 2.24-2.39 (m, 1H), 1.76-2.03 (m, 4H). MS (m/z): 458.5[MH]$^+$.

Example 99: 2-[5-({3-[1-(2,6-difluorophenyl)-octa-hydropyrrolo[3,4-b]pyrrol-5-yl]propyl}sulfanyl)-4-methyl-4H-1,2,4-triazol-3-yl]pyrazine dihydrochloride (E99)

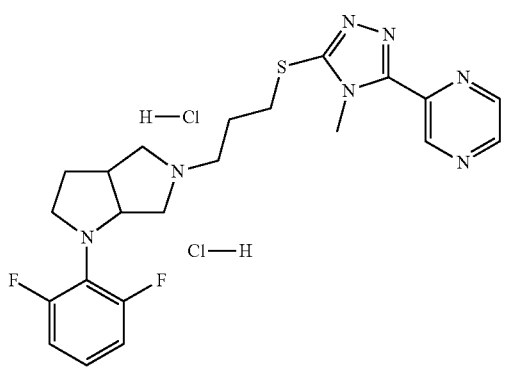

2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine (E98, 19.7 mg) was dissolved in Et$_2$O and treated with 2.2. eq of 2N HCl in Et$_2$O to afford, after evaporation, 13 mg of title compound (E99). MS (m/z): 458.5 [MH]$^+$.

Example 100: 2-[5-({3-[1-(3-fluorophenyl)-octahydropyrrolo[3,4-b]pyrrol-5-yl]propyl}sulfanyl)-4-methyl-4H-1,2,4-triazol-3-yl]pyrazine (E100)

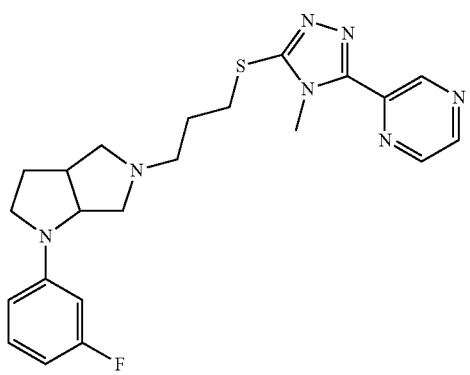 [SMILES: Cn1c(SCCCN2CC3CCN(c4cccc(F)c4)C3C2)nnc1-c1cnccn1]

The title compound was prepared in analogy to the method described in Example 1 in 48 mg yield (E100, y=64%) from 1-(3-fluorophenyl)-octahydropyrrolo[3,4-b]pyrrole (p83, 35 mg, 0.17 mmol) and 2-{5-[(3-chloropropyl)sulfanyl]-4-methyl-4H-1,2,4-triazol-3-yl}pyrazine (p21, 50 mg, 0.19 mmol). NMR: $^1$H NMR (Acetone-d$_6$) δ: 9.37 (d, 1H), 8.66-8.77 (m, 2H), 7.15 (d, 1H), 6.24-6.43 (m, 3H), 4.10-4.18 (m, 1H), 3.99 (s, 3H), 3.22-3.50 (m, 4H), 2.92-3.01 (m, 1H), 2.70-2.79 (m, 3H), 2.47-2.63 (m, 2H), 2.40-2.47 (m, 1H), 2.10-2.19 (m, 1H), 1.87-2.01 (br. s., 3H). MS (m/z): 440.5[MH]$^+$.

Example 101: 2-[5-({3-[1-(2-fluorophenyl)-octahydropyrrolo[2,3-c]pyrrol-5-yl]propyl}sulfanyl)-4-methyl-4H-1,2,4-triazol-3-yl]pyrazine (E101)

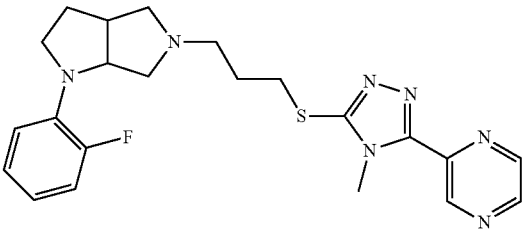 [SMILES: Cn1c(SCCCN2CC3CCN(c4ccccc4F)C3C2)nnc1-c1cnccn1]

The title compound was prepared in analogy to the method described in Example 1 in 72 mg yield as yellow oil (E101, y=46%) from 1-(2-fluorophenyl)-octahydropyrrolo[2,3-c]pyrrole (p86, 74 mg, 0.358 mmol) and 2-{5-[(3-chloropropyl)sulfanyl]-4-methyl-4H-1,2,4-triazol-3-yl}pyrazine (p21, 106 mg, 0.39 mmol). NMR: $^1$H NMR (Acetone-d$_6$) δ: 9.37 (s, 1H), 8.71 (s, 2H), 6.94-7.09 (m, 2H), 6.65-6.87 (m, 3H), 4.40-4.55 (m, 1H), 3.99 (s, 3H), 3.43-3.53 (m, 1H), 3.17-3.36 (m, 4H), 2.86-3.00 (m, 1H), 2.59-2.72 (m, 2H), 2.40-2.54 (m, 3H), 2.26-2.38 (m, 1H), 1.79-1.97 (m, 3H). MS (m/z): 440.6 [MH]$^+$.

Example 102: 2-[5-({3-[1-(2,4-difluorophenyl)-octahydropyrrolo[2,3-c]pyrrol-5-yl]propyl}sulfanyl)-4-methyl-4H-1,2,4-triazol-3-yl]pyrazine (E102)

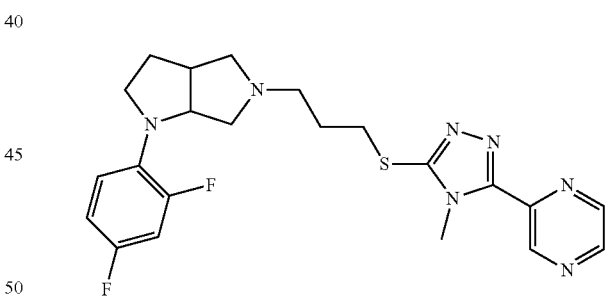

The title compound was prepared in analogy to the method described in Example 1 in 62 mg yield as yellow oil (E102, y=61%) from 1-(2,4-fluorophenyl)-octahydropyrrolo[2,3-c]pyrrole (p87, 50 mg, 0.22 mmol) and 2-{5-[(3-chloropropyl)sulfanyl]-4-methyl-4H-1,2,4-triazol-3-yl}pyrazine (p21, 66 mg, 0.245 mmol). NMR: $^1$H NMR (Acetone-d$_6$) δ: 9.38 (d, 1H), 8.72 (m, 2H), 6.89-6.98 (m, 1H), 6.84 (d, 2H), 4.31-4.51 (m, 1H), 3.99 (s, 3H), 3.13-3.54 (m, 5H), 2.87-3.01 (m, 1H), 2.57-2.72 (m, 2H), 2.40-2.54 (m, 3H), 2.24-2.34 (m, 1H), 1.79-1.96 (m, 3H). MS (m/z): 458.5 [MH]$^+$.

Example 103 and Example 104: 2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine (E103, Enantiomer 1) and 2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine (E104, Enantiomer 2)

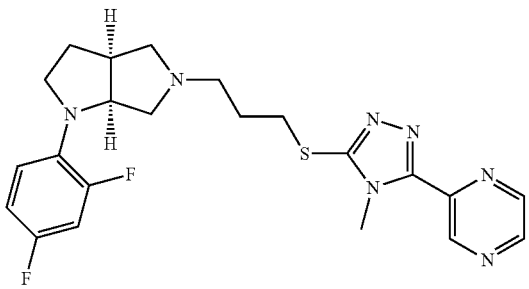

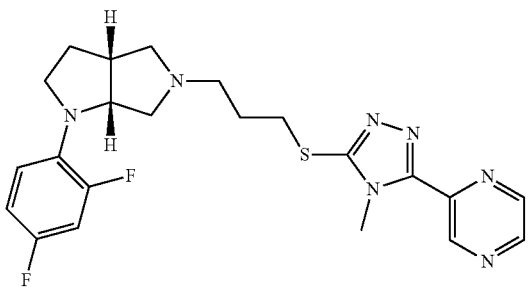

2-[5-({3-[1-(2,4-difluorophenyl)-octahydropyrrolo[2,3-c]pyrrol-5-yl]propyl}sulfanyl)-4-methyl-4H-1,2,4-triazol-3-yl]pyrazine (E102, 60 mg) was separated into the single enantiomers by preparative chiral HPLC, obtaining 22.9 mg of 2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine (E103, Enantiomer 1) and 21.9 mg of 2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine (E104, Enantiomer 2).

Preparative Chromatography:

| | |
|---|---|
| Column | Chiralpak As-H (25 × 2 cm), 5 μm |
| Mobile phase | n-Hexane/(2-Propanol + 0.1% ipa) 70/30% v/v |
| Flow rate (mL/min) | 18 |
| DAD detection | 220 nm |
| Loop | 1000 μL |
| injection | 20 mg (each injection) |

Example 103 Enantiomer 1: ret. time 11.4 min, 100% ee MS (m/z): 458.5 [MH]+.

Example 104 Enantiomer 2: ret. time 15.2 min, 100% ee MS (m/z): 458.5 [MH]+.

Example 105: 2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine dihydrochloride (E105, Enantiomer 1)

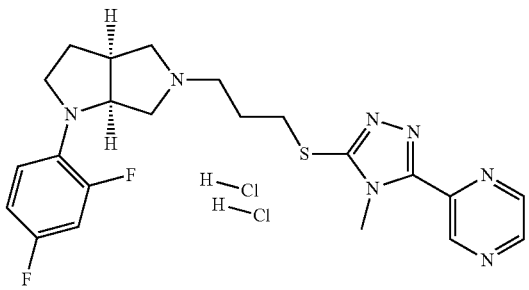

2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine (E103, Enantiomer 1, 22.9 mg) was dissolved in $Et_2O$ and treated with 2.2. eq of 1N HCl in $Et_2O$ to afford, after evaporation, 22.9 mg of title compound (E105, Enantiomer 1). MS (m/z): 458.5 [MH]+.

Example 106: 2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine dihydrochloride (E106, Enantiomer 2)

2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine (E104, Enantiomer 2, 21.9 mg) was dissolved in $Et_2O$ and treated with 2.2. eq of 1N HCl in $Et_2O$ to afford, after evaporation, 22.7 mg of title compound (E106, Enantiomer 2). MS (m/z): 458.5 [MH]+.

Example 107 2-[5-({3-[1-(4-methoxyphenyl)-octahydropyrrolo[3,4-b]pyrrol-5-yl]propyl}sulfanyl)-4-methyl-4H-1,2,4-triazol-3-yl]pyrazine (E107)

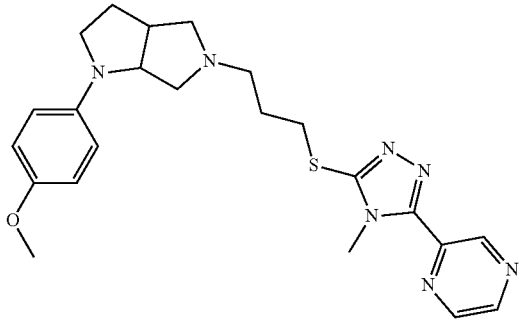 [SMILES: COc1ccc(N2CCC3CN(CCCSc4nnc(-c5cnccn5)n4C)CC32)cc1]

The title compound was prepared in analogy to the method described in Example 1 in 41 mg yield as orange sticky oil (E107, y=62%) from 1-(4-methoxyphenyl)-octahydropyrrolo[2,3-c]pyrrole (p88, 32 mg, 0.146 mmol) and 2-{5-[(3-chloropropyl)sulfanyl]-4-methyl-4H-1,2,4-triazol-3-yl}pyrazine (p21, 44 mg, 0.16 mmol). NMR: $^1$H NMR (Acetone-d$_6$) δ: 9.38 (d, 1H), 8.69-8.75 (m, 2H), 6.78-6.85 (m, 2H), 6.53-6.60 (m, 2H), 4.07 (br. s., 1H), 4.00 (s, 3H), 3.72 (s, 3H), 3.26-3.45 (m, 4H), 3.11-3.19 (m, 1H), 2.92 (br. s., 1H), 2.73 (br. s., 2H), 2.39-2.62 (m, 4H), 2.10-2.19 (m, 1H), 1.89-2.02 (m, 2H). MS (m/z): 452.4 [MH]$^+$.

Example 108: 2-[4-methyl-5-({3-[1-(4-methylphenyl)-octahydropyrrolo[3,4-b]pyrrol-5-yl]propyl}sulfanyl)-4H-1,2,4-triazol-3-yl]pyrazine (E108)

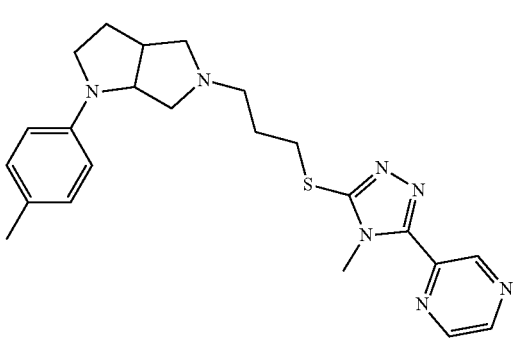 [SMILES: Cc1ccc(N2CCC3CN(CCCSc4nnc(-c5cnccn5)n4C)CC32)cc1]

The title compound was prepared in analogy to the method described in Example 1 in 12 mg yield as sticky oil (E108, y=10%) from 1-(4-methylphenyl)-octahydropyrrolo[2,3-c]pyrrole (p89, 55 mg, 0.27 mmol) and 2-{5-[(3-chloropropyl)sulfanyl]-4-methyl-4H-1,2,4-triazol-3-yl}pyrazine (p21, 80 mg, 0.297 mmol). NMR: $^1$H NMR (Acetone-d$_6$) δ: 9.38 (d, 1H), 8.68-8.76 (m, 2H), 6.99 (d, 2H), 6.51 (d, 2H), 4.05-4.13 (m, 1H), 3.99 (s, 3H), 3.24-3.47 (m, 4H), 3.19 (d, 1H), 2.92 (br. s., 1H), 2.72 (m, 2H), 2.39-2.60 (m, 4H), 2.21 (s, 3H), 2.11-2.19 (m, 1H), 1.88-2.01 (m, 2H). MS (m/z): 436.5 [MH]$^+$.

Example 109: 2-[5-({3-[1-(3-methoxyphenyl)-octahydropyrrolo[3,4-b]pyrrol-5-yl]propyl}sulfanyl)-4-methyl-4H-1,2,4-triazol-3-yl]pyrazine (E109)

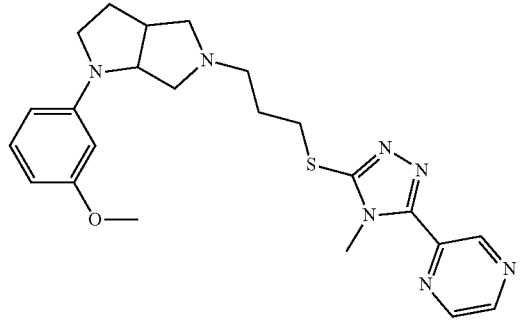 [SMILES: COc1cccc(N2CCC3CN(CCCSc4nnc(-c5cnccn5)n4C)CC32)c1]

The title compound was prepared in analogy to the method described in Example 1 in 35 mg yield as yellow sticky solid (E109, y=27%) from 1-(3-methoxyphenyl)-octahydropyrrolo[2,3-c]pyrrole (p90, 62 mg, 0.28 mmol) and 2-{5-[(3-chloropropyl)sulfanyl]-4-methyl-4H-1,2,4-triazol3-yl}pyrazine (p21, 83 mg, 0.308 mmol). NMR: $^1$H NMR (Acetone-d$_6$) δ: 9.33-9.42 (m, 1H), 8.67-8.78 (m, 2H), 7.02-7.11 (m, 1H), 6.15-6.27 (m, 2H), 6.10-6.15 (m, 1H), 4.09-4.18 (m, 1H), 4.00 (s, 3H), 3.76 (s, 3H), 3.18-3.51 (m, 4H), 2.88-3.02 (m, 1H), 2.65-2.75 (m, 2H), 2.40-2.65 (m, 4H), 2.12-2.20 (m, 1H), 1.89-2.03 (m, 3H). MS (m/z): 452.4 [MH]$^+$.

Example 110: 2-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile (E110)

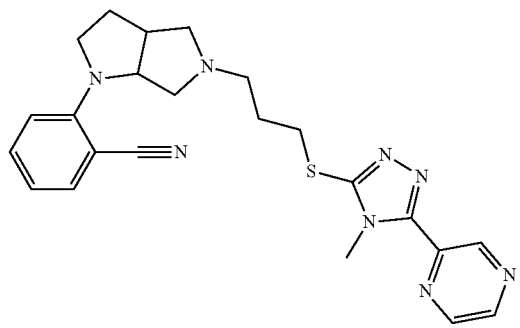 [SMILES: Cn1c(SCCCN2CC3CCN(c4ccccc4C#N)C3C2)nnc1-c1cnccn1]

The title compound was prepared in analogy to the method described in Example 1 in 26 mg yield as pale yellow sticky solid (E110, y=58%) from 2-{octahydropyrrolo[2,3-c]pyrrol-1-yl}benzonitrile (p91, 22 mg, 0.1 mmol) and 2-{5-[(3-chloropropyl)sulfanyl]-4-methyl-4H-1,2,4-triazol-3-yl}pyrazine (p21, 30 mg, 0.11 mmol). NMR: $^1$H NMR (Acetone-d$_6$) δ: 9.38 (d, 1H), 8.68-8.77 (m, 2H), 7.38-7.53 (m, 2H), 6.87 (d, 1H), 6.77 (m, 1H), 4.87 (m, 1H), 3.99 (s, 3H), 3.71 (m, 1H), 3.52-3.62 (m, 1H), 3.20-3.41 (m, 2H), 3.00-3.10 (m, 1H), 2.74-2.80 (m, 2H), 2.45-2.58 (m, 4H), 2.12-2.20 (m, 1H), 1.88-2.03 (m, 3H). MS (m/z): [MH]$^+$.

Example 111: 2-[4-methyl-5-({3-[1-(3-methylphenyl)-octahydropyrrolo[3,4-b]pyrrol-5-yl]propyl}sulfanyl)-4H-1,2,4-triazol-3-yl]pyrazine (E111)

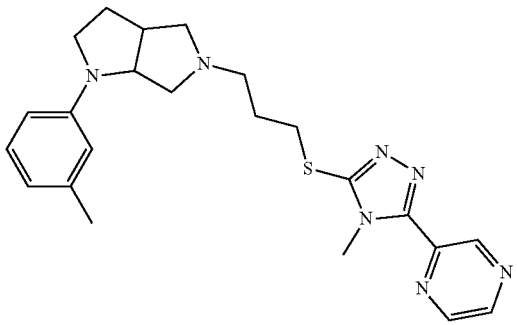 [SMILES: Cc1cccc(N2CCC3CN(CCCSc4nnc(-c5cnccn5)n4C)CC32)c1]

The title compound was prepared in analogy to the method described in Example 1 in 62 mg yield as yellow foam (E111, y=52%) from 1-(3-methylphenyl)-octahydropyrrolo[2,3-c]pyrrole (p92, 55 mg, 0.27 mmol) and 2-{5-[(3-chloropropyl)sulfanyl]-4-methyl-4H-1,2,4-triazol-3-yl}pyrazine (p21, 80 mg, 0.297 mmol). NMR: $^1$H NMR (Acetone-$d_6$) δ: 9.38 (d, 1H), 8.67-8.77 (m, 2H), 7.04 (m, 1H), 6.35-6.48 (m, 3H), 4.12 (m, 1H), 4.00 (s, 3H), 3.18-3.48 (m, 4H), 2.89-2.98 (m, 1H), 2.69-2.77 (m, 2H), 2.40-2.61 (m, 4H), 2.26 (s, 3H), 2.12-2.20 (m, 1H), 1.89-2.02 (m, 3H). MS (m/z): 436.5[MH]$^+$.

Example 112: 2-[5-({3-[1-(2-methoxyphenyl)-octahydropyrrolo[3,4-b]pyrrol-5-yl]propyl}sulfanyl)-4-methyl-4H-1,2,4-triazol-3-yl]pyrazine (E112)

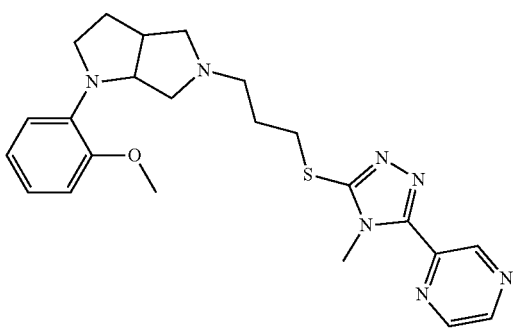 [SMILES: COc1ccccc1N1CCC2CN(CCCSc3nnc(-c4cnccn4)n3C)CC21]

The title compound was prepared in analogy to the method described in Example 1 in 70 mg yield as yellow oil (E112, y=50%) from 1-(2-methoxyphenyl)-octahydropyrrolo[2,3-c]pyrrole (p93, 69 mg, 0.31 mmol) and 2-{5-[(3-chloropropyl)sulfanyl]-4-methyl-4H-1,2,4-triazol-3-yl}pyrazine (p21, 90 mg, 0.34 mmol). NMR: $^1$H NMR (Acetone-$d_6$) δ: 9.33-9.43 (m, 1H), 8.68-8.79 (m, 2H), 6.71-6.92 (m, 4H), 4.70-4.78 (m, 1H), 4.00 (s, 3H), 3.84 (s, 3H), 3.45-3.56 (m, 1H), 3.22-3.39 (m, 2H), 3.06-3.17 (m, 1H), 2.85-2.97 (m, 1H), 2.74-2.84 (m, 1H), 2.38-2.66 (m, 5H), 1.97-2.04 (m, 1H), 1.77-1.97 (m, 3H). MS (m/z): 452.5[MH]$^+$.

Example 113: 2-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}pyrazine (E113)

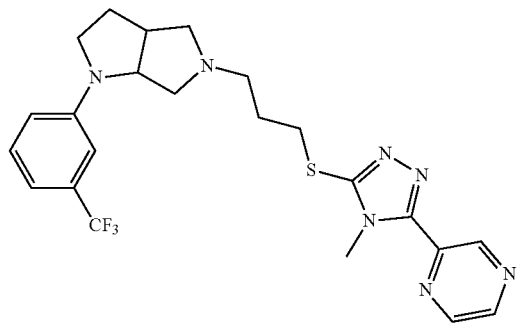 [SMILES: Cn1c(SCCCN2CC3CCN(c4cccc(C(F)(F)F)c4)C3C2)nnc1-c1cnccn1]

The title compound was prepared in analogy to the method described in Example 1 in 43 mg yield (E113, y=45%) from 1-[3-(trifluoromethyl)phenyl]-octahydropyrrolo[2,3-c]pyrrole (p94, 50 mg, 0.195 mmol) and 2-{5-[(3-chloropropyl)sulfanyl]-4-methyl-4H-1,2,4-triazol-3-yl}pyrazine (p21, 58 mg, 0.214 mmol). NMR: $^1$H NMR (Acetone-$d_6$) δ: 9.36 (d, 1H), 8.67-8.76 (m, 2H), 7.30-7.39 (m, 1H), 6.86-6.93 (m, 1H), 6.80 (s, 2H), 4.17-4.26 (m, 1H), 3.98 (s, 3H), 3.45-3.55 (m, 1H), 3.23-3.44 (m, 3H), 2.94-3.05 (m, 1H), 2.72-2.77 (m, 2H), 2.56 (d, 3H), 2.41-2.49 (m, 1H), 2.12-2.20 (m, 1H), 1.96 (s, 3H). MS (m/z): 490.4 [MH]$^+$.

Example 114: 2-{4-methyl-5-[(3-{1-[3-(trifluoromethoxy)phenyl]-octahydropyrrolo[3,4-b]pyrrol-5-yl}propyl)sulfanyl]-4H-1,2,4-triazol-3-yl}pyrazine (E114)

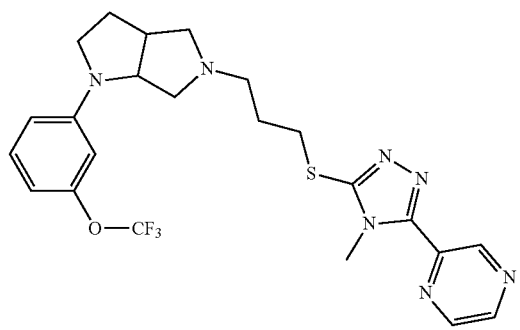 [SMILES: Cn1c(SCCCN2CC3CCN(c4cccc(OC(F)(F)F)c4)C3C2)nnc1-c1cnccn1]

The title compound was prepared in analogy to the method described in Example 1 in 25 mg yield (E114, y=27%) from 1-[3-(trifluoromethoxy)phenyl]-octahydropyrrolo[2,3-c]pyrrole (p95, 50 mg, 0.18 mmol) and 2-{5-[(3-chloropropyl)sulfanyl]-4-methyl-4H-1,2,4-triazol-3-yl}pyrazine (p21, 54 mg, 0.2 mmol). NMR: $^1$H NMR (Acetone-$d_6$) δ: 8.70 (m, 2H), 7.19-7.29 (m, 1H), 6.48-6.62 (m, 1H), 6.41-6.47 (m, 1H), 5.77-5.80 (m, 1H), 4.16 (s, 1H), 3.98 (s, 3H), 3.21-3.51 (m, 4H), 2.93-3.03 (m, 1H), 2.71-2.77 (m, 2H), 2.38-2.64 (m, 4H), 2.11-2.20 (m, 1H), 1.86-2.03 (m, 3H). MS (m/z): 506.4[MH]$^+$.

Example 115: 2-{4-methyl-5-[(3-{1-[2-(propan-2-yloxy)phenyl]-octahydropyrrolo[3,4-b]pyrrol-5-yl}propyl)sulfanyl]-4H-1,2,4-triazol-3-yl}pyrazine (E115)

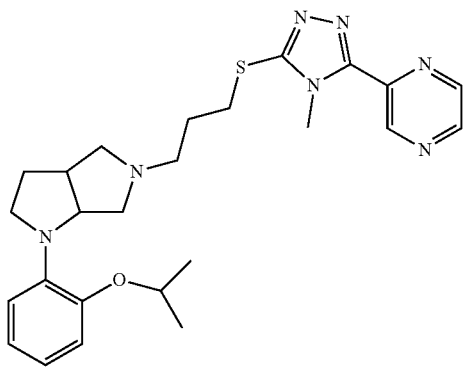 [SMILES: CC(C)Oc1ccccc1N1CCC2CN(CCCSc3nnc(-c4cnccn4)n3C)CC21]

The title compound was prepared in analogy to the method described in Example 1 in 50 mg yield (E115, y=45%) from 1-[2-(propan-2-yloxy)phenyl]-octahydropyrrolo[3,4-b]pyrrole (p96, 57 mg, 0.23 mmol) and 2-{5-[(3-chloropropyl)sulfanyl]-4-methyl-4H-1,2,4-triazol-3-yl}pyrazine (p21, 62 mg, 0.23 mmol). NMR: $^1$H NMR (Acetone-d$_6$) δ: 9.37 (d, 1H), 8.66-8.76 (m, 2H), 6.63-6.91 (m, 5H), 4.82 (br. s., 1H), 4.60 (m, 1H), 3.94-4.01 (m, 3H), 3.46 (d, 1H), 3.27 (m, 2H), 3.09 (m, 1H), 2.88 (br. s., 1H), 2.34-2.69 (m, 5H), 2.12-2.23 (m, 1H), 1.97-2.02 (m, 1H), 1.76-1.93 (m, 3H), 1.30-1.34 (m, 6H). MS (m/z): 480.5 [MH]$^+$.

Example 116 and Example 117: 2-[5-({3-[(3aS,6aS or 3aR,6aR)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine (E116, Enantiomer 1) and 2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine (E117, Enantiomer 2)

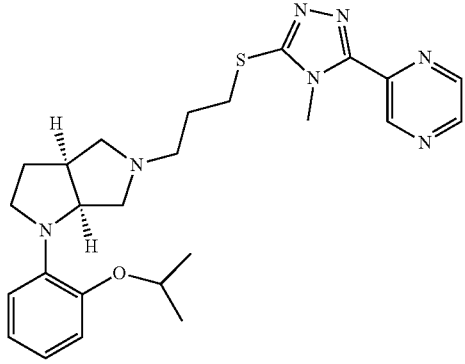

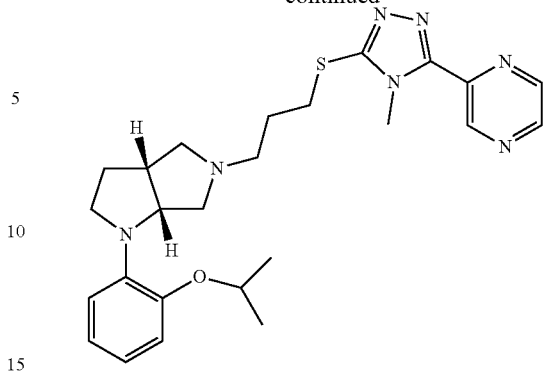

2-{4-methyl-5-[(3-{1-[2-(propan-2-yloxy)phenyl]-octahydropyrrolo[3,4-b]pyrrol-5-yl}propyl)sulfanyl]-4H-1,2,4-triazol-3-yl}pyrazine (E115, 45 mg) was separated into the single enantiomers by preparative chiral HPLC, obtaining 13 mg of 2-[5-({3-[(3aS,6aS or 3aR,6aR)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine (E116, Enantiomer 1) and 15 mg of 2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine (E117, Enantiomer 2).

Preparative Chromatography:

| | |
|---|---|
| Column | Chiralpak AD-H (25 × 2 cm), 5 μm |
| Mobile phase | n-Hexane/(Ethanol + 0.1% ipa) 30/70 v/v |
| Flow rate (mL/min) | 14 |
| DAD detection | 220 nm |
| Loop | 1000 μL |
| injection | 15 mg (each injection) |

Example 116 Enantiomer 1: ret. time 10.3 min, 100% ee MS (m/z): 480.5 [MH]$^+$.
Example 117 Enantiomer 2: ret. time 11.8 min, 100% ee MS (m/z): 480.5 [MH]$^+$.

Example 118: 2-[5-({3-[(3aS,6aS or 3aR,6aR)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine dihydrochloride (E118, Enantiomer 1)

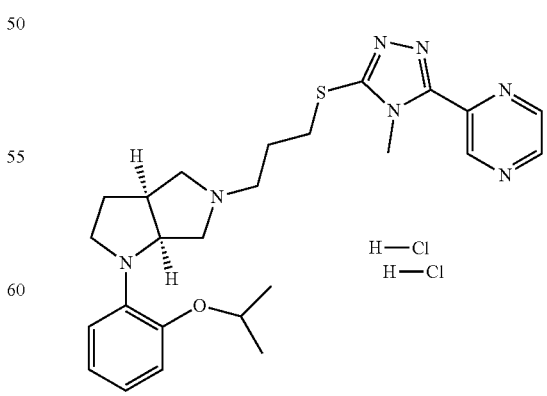

2-[5-({3-[(3aS,6aS or 3aR,6aR)-1-[2-(propan-2-yloxy)phenyl]-octahydropyrrolo[3,4-b]pyrrol-5-yl]

propyl}sulfanyl)-4-methyl-4H-1,2,4-triazol-3-yl]pyrazine (E116, Enantiomer 1, 13 mg) was dissolved in Et₂O and treated with 2.2. eq of 2N HCl in Et₂O to afford, after evaporation, 14.7 mg of title compound (E118, Enantiomer 1). MS (m/z): 480.5 [MH]⁺.

Example 119: 2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine dihydrochloride (E119, Enantiomer 2)

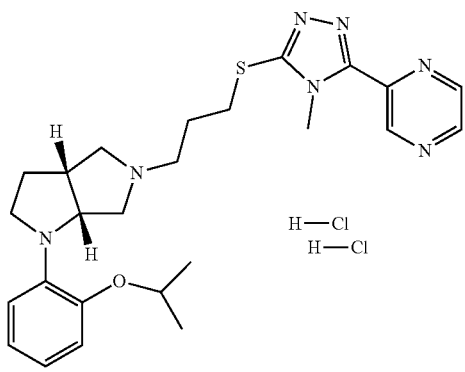

2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine (E117, Enantiomer 2, 15 mg) was dissolved in Et₂O and treated with 2.2. eq of 2N HCl in Et₂O to afford, after evaporation, 17 mg of title compound (E119, Enantiomer 2). MS (m/z): 480.5 [MH]⁺.

Example 120: 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyrazine (E120)

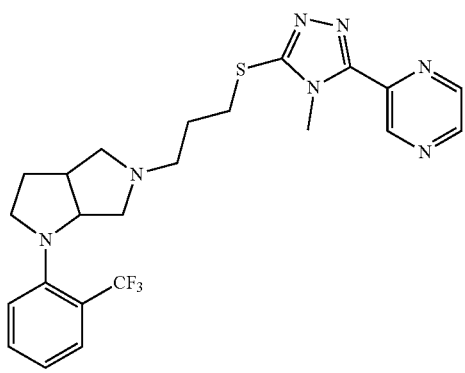 [SMILES: Cn1c(SCCCN2CC3CCN(c4ccccc4C(F)(F)F)C3C2)nnc1-c1cnccn1]

The title compound was prepared in analogy to the method described in Example 1 in 50 mg yield (E120, y=65%) from 1-[2-(propan-2-yloxy)phenyl]-octahydropyrrolo[3,4-b]pyrrole (p97, 38.6 mg, 0.157 mmol) and 2-{5-[(3-chloropropyl)sulfanyl]-4-methyl-4H-1,2,4-triazol-3-yl}pyrazine (p21, 43 mg, 0.157 mmol). NMR: ¹H NMR (Acetone-d₆) δ: 9.38 (d, 1H), 8.68-8.77 (m, 2H), 7.62 (d, 1H), 7.52 (br. s., 1H), 7.33 (br. s., 1H), 7.08 (br. s., 1H), 4.43 (br. s., 1H), 4.01 (s, 3H), 3.59-3.66 (m, 1H), 3.25-3.44 (m, 2H), 3.05-3.13 (m, 1H), 2.97 (br. s., 1H), 2.67-2.87 (m, 4H), 2.41-2.65 (m, 3H), 1.78-1.97 (m, 3H). MS (m/z): 490.4 [MH]⁺.

Example 121 and Example 122: 2-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine (E121, Enantiomer 1) and 2-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine (E122, Enantiomer 2)

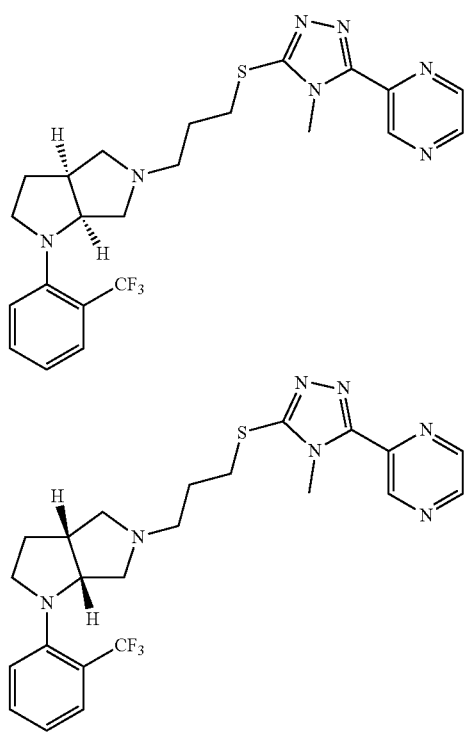

2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyrazine (E120, 45 mg) was separated into the single enantiomers by preparative chiral HPLC, obtaining 15 mg of 2-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine (E121, Enantiomer 1) and 16 mg of 2-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine (E122, Enantiomer 2).

Preparative Chromatography:

| | |
|---|---|
| Column | Chiralpak AD-H (25 × 2 cm), 5 µm |
| Modifier | (2-Propanol + 0.1% ipa) 20% |
| Flow rate (mL/min) | 45 |
| Pressure (bar) | 120 |
| Temperature (° C.) | 38 |
| UV detection | 220 nm |
| Loop | 500 µL |
| injection | 11.3 mg (each injection) |

Example 121 Enantiomer 1: ret. time 15.3 min, 100% ee MS (m/z): 490.4 [MH]⁺.

Example 122 Enantiomer 2: ret. time 17.4 min, 95.6% ee MS (m/z): 490.4 [MH]⁺.

Example 123: 2-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine dihydrochloride (E123, Enantiomer 1)

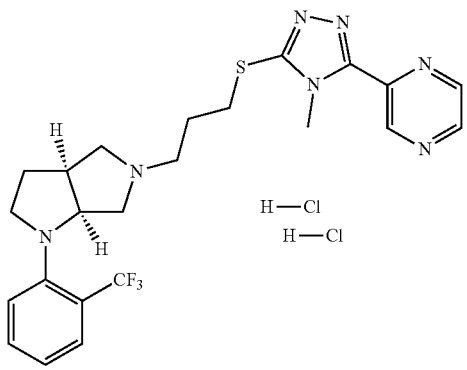

2-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine (E121, Enantiomer 1, 15 mg) was dissolved in Et₂O and treated with 2.2. eq of 2N HCl in Et₂O to afford, after evaporation, 16.8 mg of title compound (E123, Enantiomer 1). MS (m/z): 490.4 [MH]⁺.

Example 124: 2-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine dihydrochloride (E124, Enantiomer 2)

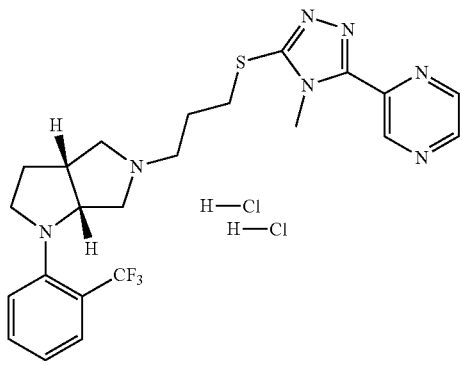

2-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine (E122, Enantiomer 2, 16 mg) was dissolved in Et₂O and treated with 2.2. eq of 2N HCl in Et₂O to afford, after evaporation, 17.9 mg of title compound (E124, Enantiomer 2). MS (m/z): 490.4 [MH]⁺.

Example 125: 2-[5-({3-[1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine (E125)

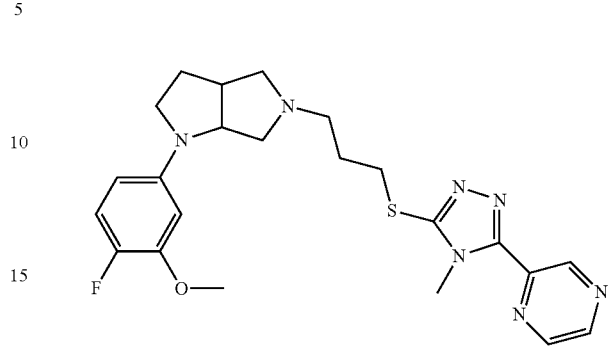

The title compound was prepared in analogy to the method described in Example 1 in 112 mg yield (E125, y=48%) from 1-(4-fluoro-3-methoxyphenyl)-octahydropyrrolo[2,3-c]pyrrole (p98, 42 mg, 0.177 mmol) and 2-{5-[(3-chloropropyl)sulfanyl]-4-methyl-4H-1,2,4-triazol-3-yl}pyrazine (p21, 53 mg, 0.195 mmol). NMR: ¹H NMR (Acetone-d₆) δ: 9.35-9.40 (m, 1H), 8.67-8.74 (m, 2H), 6.88-6.95 (m, 1H), 6.28-6.33 (m, 1H), 6.04-6.10 (m, 1H), 4.07-4.16 (m, 1H), 3.99 (s, 3H), 3.86 (s, 3H), 3.16-3.47 (m, 4H), 2.92 (d, 1H), 2.66-2.77 (m, 2H), 2.40-2.60 (m, 4H), 2.10-2.18 (m, 1H), 1.89-2.01 (m, 3H). MS (m/z): 470.4 [MH]⁺.

Example 126 and Example 127: 2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine (E126, Enantiomer 1) and 2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine (E127, Enantiomer 2)

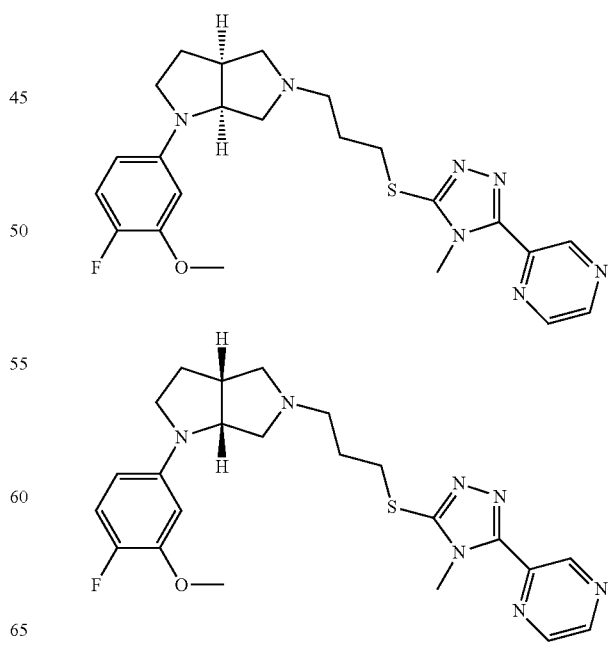

2-[5-({3-[1-(4-fluoro-3-methoxyphenyl)-octahydropyr-rolo[3,4-b]pyrrol-5-yl]propyl}sulfanyl)-4-methyl-4H-1,2,4-triazol-3-yl]pyrazine (E125, 37 mg) was separated into the single enantiomers by preparative chiral HPLC, obtaining 14.5 mg of 2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine (E126, Enantiomer 1) and 16.5 mg of 2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine (E127, Enantiomer 2).

Preparative Chromatography:

| Column | Chiralcel AD-H (25 × 2 cm), 5 μm |
|---|---|
| Mobile phase | n-Hexane/(Ethanol + 0.1% ipa) 20/80 v/v |
| Flow rate (mL/min) | 14 |
| DAD detection | 220 nm |
| Loop | 500 μL |
| injection | 7 mg (each injection) |

Example 126 Enantiomer 1: ret. time 20 min, 100% ee MS (m/z): 470.4 [MH]+.

Example 127 Enantiomer 2: ret. time 24.7 min, 97.4% ee MS (m/z): 470.4 [MH]+.

Example 128: 2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine trihydrochloride (E128, Enantiomer 1)

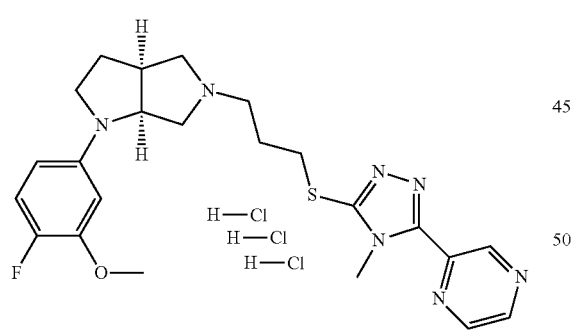

2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine (E126, Enantiomer 1, 14.5 mg) was dissolved in Et$_2$O and treated with 3.3. eq of 1N HCl in Et$_2$O to afford, after evaporation, 5.8 mg of title compound (E128, Enantiomer 1). MS (m/z): 470.4 [MH]+.

Example 129: 2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine trihydrochloride (E129, Enantiomer 2)

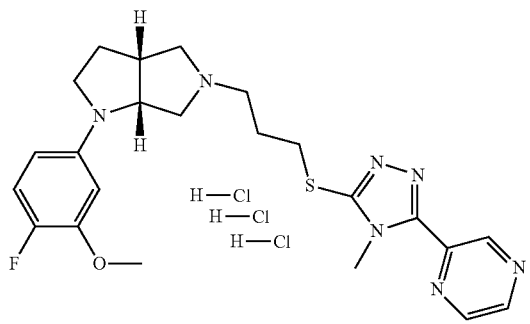

2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine (E127, Enantiomer 2, 16.5 mg) was dissolved in Et$_2$O and treated with 3.3. eq of 1N HCl in Et$_2$O to afford, after evaporation, 6.4 mg of title compound (E129, Enantiomer 2). MS (m/z): 470.4 [MH]+.

Example 130: 2-{5-[(3-{1-[4-fluoro-2-(trifluoromethyl)phenyl]-octahydropyrrolo[3,4-b]pyrrol-5-yl}propyl)sulfanyl]-4-methyl-4H-1,2,4-triazol-3-yl}pyrazine (E130)

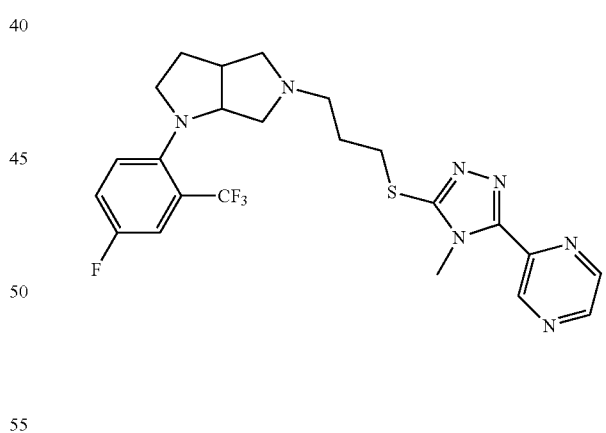

The title compound was prepared in analogy to the method described in Example 1 in 72 mg yield (E130, y=72%) from 1-[4-fluoro-2-(trifluoromethyl)phenyl]-octahydropyrrolo[2,3-c]pyrrole (p99, 25 mg, 0.11 mmol) and 2-(5-[(3-chloropropyl)sulfanyl]-4-methyl-4H-1,2,4-triazol-3-yl}pyrazine (p21, 57 mg, 0.21 mmol). NMR: $^1$H NMR (Acetone-d$_6$) δ: 9.37-9.40 (m, 1H), 8.68-8.76 (m, 2H), 7.33-7.53 (m, 3H), 4.23-4.33 (m, 1H), 4.02 (s, 3H), 3.57 (d, 1H), 3.37 (br. s., 2H), 3.02 (d, 2H), 2.59-2.75 (m, 2H), 2.48 (br. s., 4H), 2.08-2.18 (m, 1H), 1.77-1.98 (m, 3H). MS (m/z): 508.4[MH]+.

Example 131: 2-{5-[(3-{1-[2-fluoro-6-(trifluoromethyl)phenyl]-octahydropyrrolo[3,4-b]pyrrol-5-yl}propyl)sulfanyl]-4-methyl-4H-1,2,4-triazol-3-yl}pyrazine (E131)

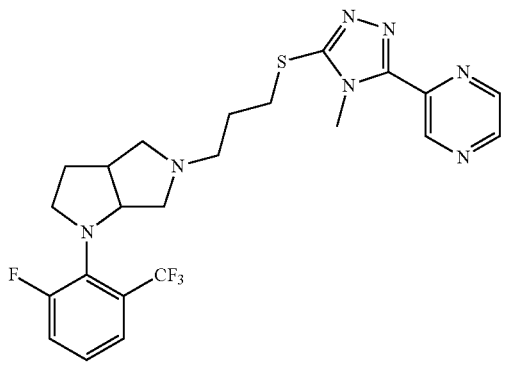

The title compound was prepared in analogy to the method described in Example 1 in 32 mg yield (E131, y=66%) from 1-[2-fluoro-6-(trifluoromethyl)phenyl]-octahydropyrrolo[3,4-b]pyrrole (p100, 26 mg, 0.095 mmol) and 2-{5-[(3-chloropropyl)sulfanyl]-4-methyl-4H-1,2,4-triazol-3-yl}pyrazine (p21, 26 mg, 0.095 mmol). NMR: $^1$H NMR (CDCl$_3$) δ: 9.56 (d, 1H), 8.59-8.66 (m, 2H), 7.42-7.48 (m, 1H), 7.23-7.27 (m, 2H), 4.16 (br. s., 1H), 4.02 (s, 3H), 3.37-3.46 (m, 3H), 2.94-3.18 (m, 2H), 2.74 (br. s., 5H), 1.99-2.21 (m, 3H), 1.85 (br. s., 1H), 1.27-1.39 (m, 1H). MS (m/z): 508.4[MH]$^+$.

Example 132: 2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine (E132)

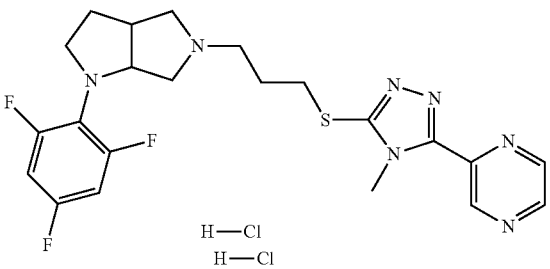

The title compound was prepared in analogy to the method described in Example 1 in 13 mg yield (E132, y=68%) from 1-(2,4,6-fluorophenyl)-octahydropyrrolo[2,3-c]pyrrole (p104, 10 mg, 0.04 mmol) and 2-{5-[(3-chloropropyl)sulfanyl]-4-methyl-4H-1,2,4-triazol-3-yl}pyrazine (p21, 14 mg, 0.05 mmol). NMR: $^1$H NMR (Acetone-d$_6$) δ: 9.37 (d, 1H), 8.66-8.78 (m, 2H), 6.85 (s, 2H), 4.28-4.40 (m, 1H), 4.01 (s, 3H), 3.66-3.79 (m, 1H), 3.17-3.44 (m, 3H), 2.85-2.97 (m, 1H), 2.36-2.72 (m, 5H), 1.74-2.01 (m, 5H). MS (m/z): 476.3[MH]$^+$.

Example 133: 2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine dihydrochloride (E133)

2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine (E132, 13 mg) was dissolved in Et$_2$O and treated with 2.2. eq of 1N HCl in Et$_2$O to afford, after evaporation, 14.3 mg of title compound (E133). MS (m/z): 476.3 [MH]$^+$.

Example 134: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrimidine (E134)

The title compound was prepared in analogy to the method described in Example 1 in 59 mg yield (E134, y=58%) from 1-[4-(trifluoromethyl)phenyl]-octahydropyrrolo[3,4-b]pyrrole (prepared as in p73, 50 mg, 0.195 mmol) and 4-{5-[(3-chloropropyl)sulfanyl]-4-methyl-4H-1,2,4-triazol-3-yl}pyrimidine (p23, 59 mg, 0.22 mmol). NMR: $^1$H NMR (Acetone-d$_6$) δ: 9.28 (d, 1H), 8.95 (d, 1H), 8.23 (m, 1H), 7.63 (d, 2H), 7.31-7.45 (m, 2H), 4.09 (s, 3H), 3.34-3.47 (m, 2H), 2.56-2.75 (m, 4H), 2.26-2.39 (m, 1H), 1.97-2.05 (m, 3H), 1.63-1.80 (m, 1H), 1.40-1.55 (m, 1H), 1.19-1.37 (m, 3H). MS (m/z): 490.4[MH]$^+$.

Example 135 and Example 136: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine (E135, Enantiomer 1) and 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine (E136, Enantiomer 2)

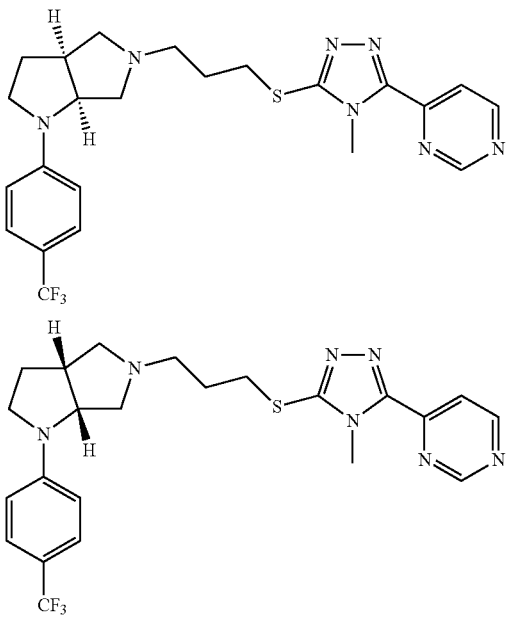

4-{4-methyl-5-[(3-{1-[4-(trifluoromethyl)phenyl]-octahydropyrrolo[2,3-c]pyrrol-5 yl}propyl)sulfanyl]-4H-1,2,4-triazol-3-yl}pyrimidine (E134, 57 mg) was separated into the single enantiomers by preparative chiral HPLC, obtaining 21 mg of 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine (E135, Enantiomer 1) and 20 mg of 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine (E136, Enantiomer 2)

Preparative Chromatography:

| Column | Chiralpak AS-H (25 × 2 cm), 5 μm |
|---|---|
| Modifier | (Ethanol + 0.1% ipa) 15% |
| Flow rate (mL/min) | 46 |
| Pressure (bar) | 120 |
| Temperature (° C.) | 38 |
| UV detection | 220 nm |
| Loop | 500 μL |
| injection | 14 mg (each injection) |

Example 135 Enantiomer 1: ret. time 5.6 min, 100% ee MS (m/z): 490.4 [MH]$^+$.

Example 136 Enantiomer 2: ret. time 7.5 min, 100% ee MS (m/z): 490.4 [MH]$^+$.

Example 137: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine dihydrochloride (E137, Enantiomer 1)

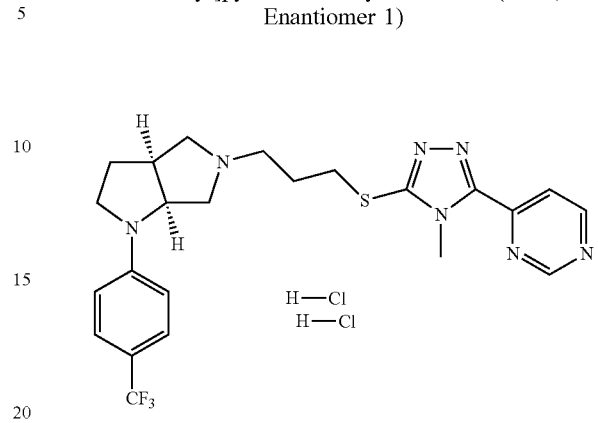

4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine (E135, Enantiomer 1, 21 mg) was dissolved in Et$_2$O/DCM and treated with 2.2. eq of 1N HCl in Et$_2$O to afford, after evaporation, 23 mg of title compound (E137, Enantiomer 1). MS (m/z): 490.4 [MH]$^+$.

Example 138: 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine dihydrochloride (E138, Enantiomer 2)

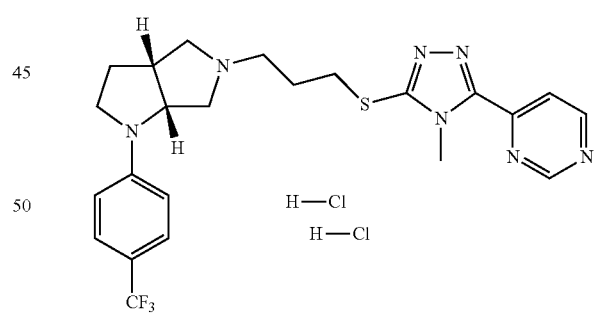

4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine (E136, Enantiomer 2, 20 mg) was dissolved in Et$_2$O/DCM and treated with 2.2. eq of 1N HCl in Et$_2$O to afford, after evaporation, 19 mg of title compound (E138, Enantiomer 2). MS (m/z): 490.4 [MH]$^+$.

Example 139: 4-[5-({3-[1-(4-fluorophenyl)-octahydropyrrolo[3,4-b]pyrrol-5-yl]propyl}sulfanyl)-4-methyl-4H-1,2,4-triazol-3-yl]pyrimidine (E139)

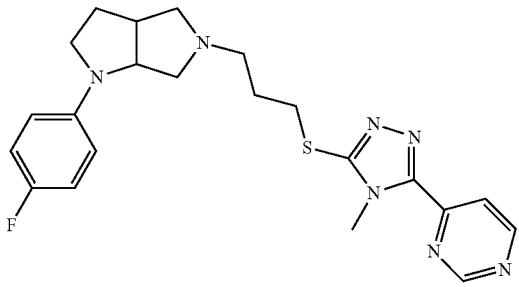 [SMILES: Cn1c(SCCCN2CC3CCN(c4ccc(F)cc4)C3C2)nnc1-c1ccncn1]

The title compound was prepared in analogy to the method described in Example 1 in 72 mg yield as yellow sticky oil (E139, y=68%) from 1-(4-fluorophenyl)-octahydropyrrolo[2,3-c]pyrrole (p77, 50 mg, 0.24 mmol) and 4-{5-[(3-chloropropyl)sulfanyl]-4-methyl-4H-1,2,4-triazol-3-yl}pyrimidine (p23, 72 mg, 0.266 mmol). NMR: $^1$H NMR (Acetone-d$_6$) δ: 9.24-9.33 (m, 1H), 8.89-9.00 (m, 1H), 8.17-8.27 (m, 1H), 6.90-7.02 (m, 2H), 6.52-6.64 (m, 2H), 4.07 (s, 4H), 3.27-3.47 (m, 3H), 3.15-3.24 (m, 1H), 2.89-3.01 (m, 1H), 2.73 (s, 2H), 2.56 (d, 4H), 2.11-2.21 (m, 1H), 1.97 (d, 3H). MS (m/z): 440.5 [MH]$^+$.

Preparation 106: tert-butyl 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}piperidine-1-carboxylate

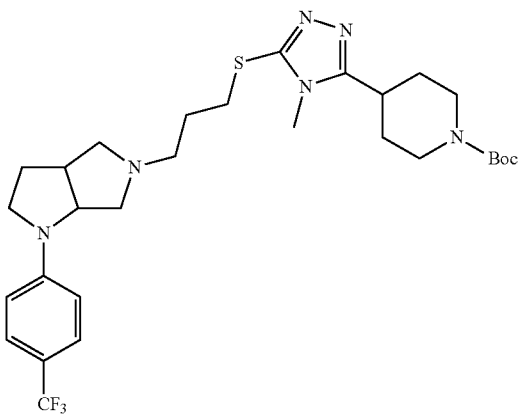 [SMILES: Cn1c(SCCCN2CC3CCN(c4ccc(C(F)(F)F)cc4)C3C2)nnc1C1CCN(C(=O)OC(C)(C)C)CC1]

1-[4-(trifluoromethyl)phenyl]-octahydropyrrolo[2,3-c]pyrrole (prepared as in p73, 50 mg, 0.195 mmol), tert-butyl 4-{5-[(3-chloropropyl)sulfanyl]-4-methyl-4H-1,2,4-triazol-3-yl}piperidine-1-carboxylate (p25, 80 mg, 0.21 mmol), Na$_2$CO$_3$ (25 mg, 0.234 mmol) and NaI (35 mg, 0.234 mmol) were dissolved in DMF (0.2 mL) and heated at 60° C. ON. The mixture was cooled down to RT and partitioned between water and DCM. Phases were separated and the solvent eliminated under reduced pressure. Crude was purified by FC on SiO$_2$ cartridge (eluent: DCM to 10% MeOH) affording tert-butyl 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}piperidine-1-carboxylate (p106, 47 mg, y=40%). MS (m/z): 595.6 [MH]$^+$.

Preparation 107: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}piperidine

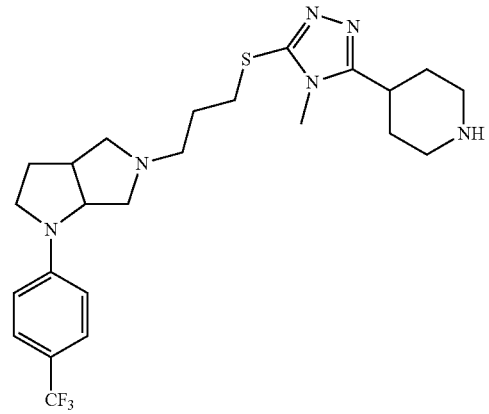 [SMILES: Cn1c(SCCCN2CC3CCN(c4ccc(C(F)(F)F)cc4)C3C2)nnc1C1CCNCC1]

To a solution of tert-butyl 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}piperidine-1-carboxylate (p106, 47 mg, 0.08 mmol) in DCM (5 mL), TFA (0.5 mL) was added and the reaction was stirred at RT for 1 h. The reaction mixture was concentrated under vacuum. The residue was loaded on a SCX cartridge and eluted with MeOH/NH$_3$ 1 M in MeOH to obtain 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}piperidine (p107, 39 mg, y=98%). MS (m/z): 495.5 [MH]$^+$.

Example 140: 1-(4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}piperidin-1-yl)ethan-1-one (E140)

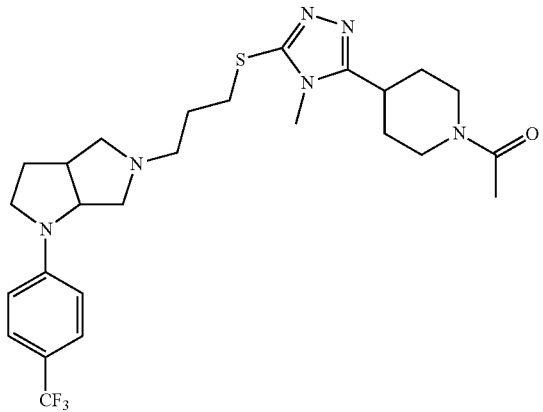 [SMILES: CC(=O)N1CCC(c2nnc(SCCCN3CC4CCN(c5ccc(C(F)(F)F)cc5)C4C3)n2C)CC1]

To a solution of 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}piperidine (p107, 39 mg, 0.079 mmol) in DCM (1 mL), Ac$_2$O (9 uL, 0.095 mmol) and Py (15 uL, 0.18 mmol) were added and the mixture was stirred at RT for 1 h. The reaction mixture was diluted with water and extracted with DCM. Organic phase was dried and concentrated under reduced pressure and crude purified by FC on NH column (eluent: from Cy to 50% AcOEt) affording 1-(4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}piperidin-1-yl)ethan-1-one (E140, 15 mg, y=35%). NMR: 1H NMR (Acetone-d₆) δ: 7.48 (d, 2H), 6.71 (d, 2H), 4.50 (d, 1H), 4.24 (m, 1H), 4.01 (d, 1H), 3.56-3.62 (m, 3H), 3.47-3.55 (m, 1H), 3.35-3.43 (m, 1H), 3.07-3.33 (m, 4H), 3.01 (d, 1H), 2.82-2.86 (m, 1H), 2.69-2.77 (m, 2H), 2.41-2.61 (m, 4H), 2.16-2.27 (m, 1H), 2.09 (s, 3H), 1.82-2.04 (m, 6H), 1.61-1.73 (m, 1H). MS (m/z): 537.5[MH]⁺.

Example 141: 3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine (E141)

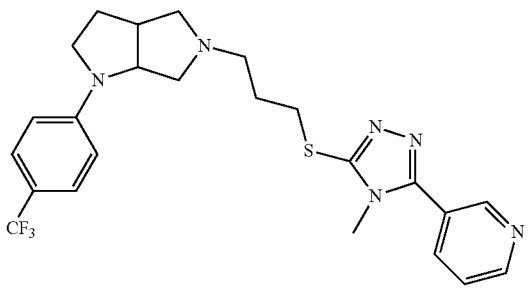 [SMILES: Cn1c(SCCCN2CC3CCN(c4ccc(C(F)(F)F)cc4)C3C2)nnc1-c1cccnc1]

The title compound was prepared in analogy to the method described in Example 1 in 54 mg yield (E141, y=56%) from 1-[4-(trifluoromethyl)phenyl]-octahydropyrrolo[3,4-b]pyrrole (prepared as in p73, 50 mg, 0.195 mmol) and 3-{5-[(3-chloropropyl)sulfanyl]-4-methyl-4H-1,2,4-triazol-3-yl}pyridine (p27, 56 mg, 0.21 mmol). NMR: ¹H NMR (Acetone-d₆) δ: 8.95 (d, 1H), 8.73 (m, 1H), 8.14 (m, 1H), 7.57 (m, 1H), 7.46 (d, 2H), 6.71 (d, 2H), 4.25 (m, 1H), 3.72 (s, 3H), 3.47-3.56 (m, 1H), 3.19-3.44 (m, 3H), 2.94-3.06 (m, 1H), 2.72-2.78 (m, 2H), 2.41-2.63 (m, 4H), 2.13-2.25 (m, 1H), 1.87-2.03 (m, 3H). MS (m/z): 489.4[MH]⁺.

Example 142 and Example 143: 3-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine (E142, Enantiomer 1) and 3-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine (E143, Enantiomer 2)

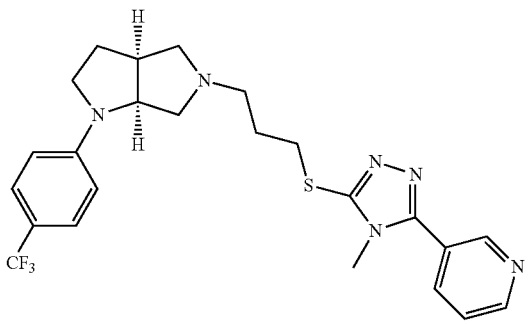

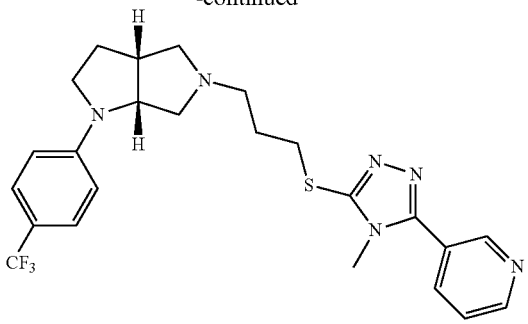

3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine (E141, 52 mg) was separated into the single enantiomers by preparative chiral HPLC, obtaining 21 mg of 3-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine (E142, Enantiomer 1) and 21 mg of 3-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine (E143, Enantiomer 2).

Preparative Chromatography:

| Column | Chiralcel OJ-H (25 × 2 cm), 5 μm |
|---|---|
| Modifier | (Methanol + 0.1% ipa) 20% |
| Flow rate (mLl/min) | 45 |
| Pressure (bar) | 120 |
| Temperature (° C.) | 38 |
| UV detection | 220 nm |
| Loop | 650 μL |
| injection | 16.3 mg (each injection) |

Example 142 Enantiomer 1: ret. time 5.9 min, 100% ee MS (m/z): 489.4 [MH]⁺.

Example 143 Enantiomer 2: ret. time 9.2 min, 100% ee MS (m/z): 489.4 [MH]⁺.

Example 144: 3-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride (E144, Enantiomer 1)

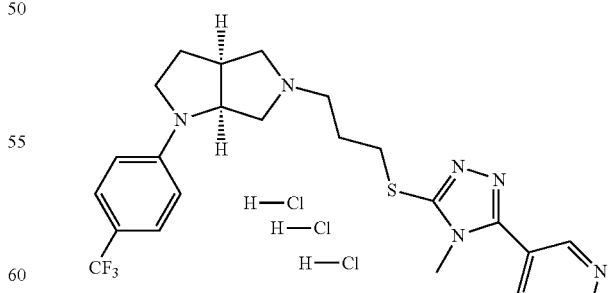

3-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine (E142, Enantiomer 1, 21 mg) was dissolved in Et₂O and treated with 3.3. eq of 1N HCl in Et₂O to afford, after evaporation, 23.5 mg of title compound (E144, Enantiomer 1). MS (m/z): 489.4 [MH]⁺.

Example 145: 3-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride (E145, Enantiomer 2)

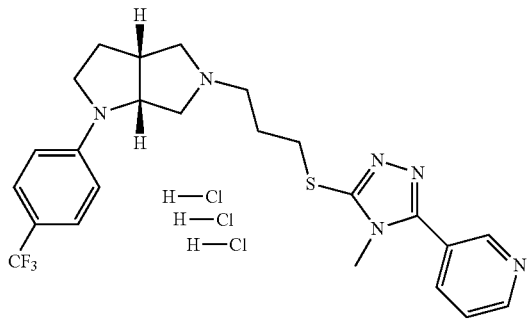

3-[5-({3-[(3aR,6aR or 3aS,6aS)-1-[4-(trifluoromethyl) phenyl]-octahydropyrrolo[3,4-b]pyrrol-5-yl] propyl}sulfanyl)-4-methyl-4H-1,2,4-triazol-3-yl]pyridine (E143, Enantiomer 2, 21 mg) was dissolved in Et₂O and treated with 3.3. eq of 1N HCl in Et₂O to afford, after evaporation, 23.8 mg of title compound (E145, Enantiomer 2). MS (m/z): 489.4 [MH]⁺.

Example 146: 3-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine (E146)

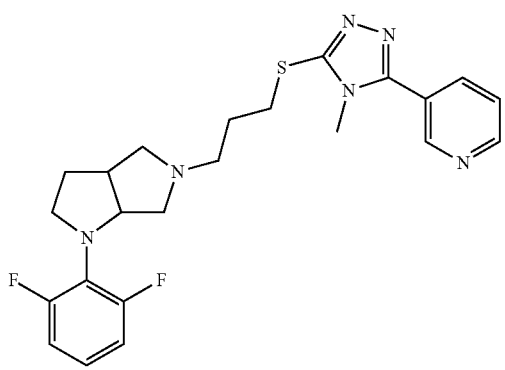 [SMILES: Cn1c(SCCCN2CC3CCN(c4c(F)cccc4F)C3C2)nnc1-c1cccnc1]

The title compound was prepared in analogy to the method described in Example 1 in 35 mg yield (E146, y=57%) from 1-(2,6-difluorophenyl)-octahydropyrrolo[3,4-b]pyrrole (p80, 30 mg, 0.134 mmol) and 3-{5-[(3-chloropropyl)sulfanyl]-4-methyl-4H-1,2,4-triazol-3-yl}pyridine (p27, 36 mg, 0.134 mmol). NMR: ¹H NMR (Acetone-d₆) δ: 8.96 (d, 1H), 8.68-8.81 (m, 1H), 8.10-8.21 (m, 1H), 7.52-7.64 (m, 1H), 6.80-6.99 (m, 3H), 4.41-4.57 (m, 1H), 3.79-3.90 (m, 1H), 3.76 (s, 3H), 3.22-3.39 (m, 3H), 2.88-3.00 (m, 1H), 2.40-2.74 (m, 5H), 2.26-2.40 (m, 1H), 1.88-2.03 (m, 3H), 1.77-1.88 (m, 1H). MS (m/z): 457.4[MH]⁺.

Example 147: 3-{4-methyl-5-[(3-{1-[2-(trifluoromethyl)phenyl]-octahydropyrrolo[3,4-b]pyrrol-5-yl}propyl)sulfanyl]-4H-1,2,4-triazol-3 yl}pyridine (E147)

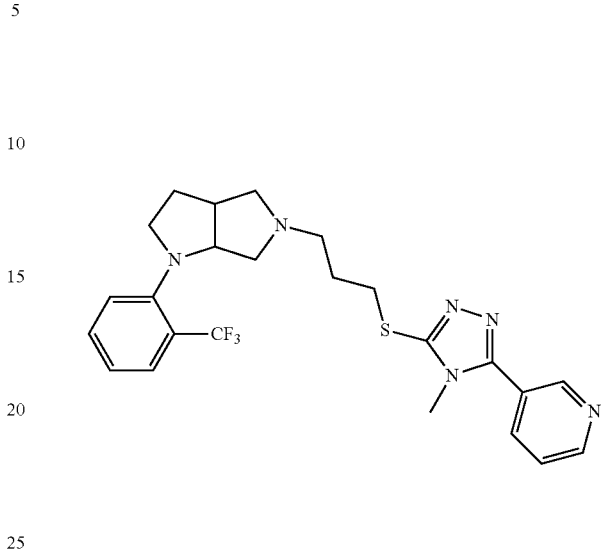

The title compound was prepared in analogy to the method described in Example 1 in 57 mg yield (E147, y=57%) from 1-[2-(trifluoromethyl)phenyl]-octahydropyrrolo[3,4-b]pyrrole (p97, 50 mg, 0.195 mmol) and 3-{5-[(3-chloropropyl)sulfanyl]-4-methyl-4H-1,2,4-triazol-3-yl}pyridine (p27, 56 mg, 0.21 mmol). NMR: ¹H NMR (Acetone-d₆) δ: 8.96 (d, 1H), 8.72-8.75 (m, 1H), 8.13-8.18 (m, 1H), 7.55-7.64 (m, 2H), 7.48-7.55 (m, 1H), 7.31 (d, 1H), 7.06 (t, 1H), 4.41 (m, 1H), 3.74 (s, 3H), 3.62 (m, 1H), 3.20-3.36 (m, 2H), 3.06-3.13 (m, 1H), 2.96 (m, 1H), 2.69 (m, 1H), 2.57 (d, 1H), 2.38-2.53 (m, 3H), 2.20 (m, 1H), 2.00-2.04 (m, 1H), 1.79-1.95 (m, 3H). MS (m/z): 489.4 [MH]⁺.

Example 148 and Example 149: 3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E148, Enantiomer 1) and 3-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E149, Enantiomer 2)

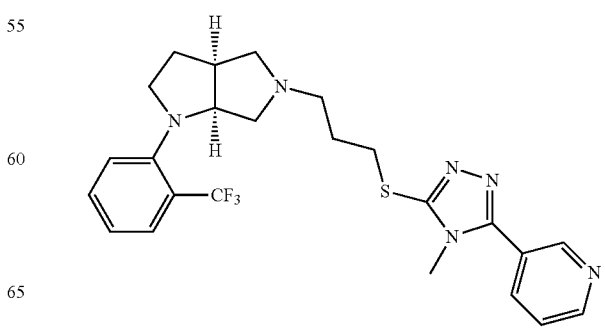

-continued

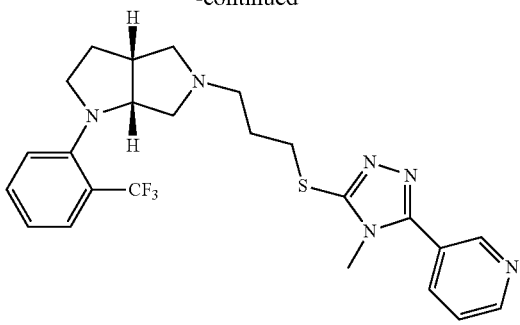

3-{4-methyl-5-[(3-{1-[2-(trifluoromethyl)phenyl]-octahydropyrrolo[3,4-b]pyrrol-5-yl}propyl)sulfanyl]-4H-1,2,4-triazol-3 yl}pyridine (E147, 50 mg) was separated into the single enantiomers by preparative chiral HPLC, obtaining 19 mg of 3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E148, Enantiomer 1) and 19 mg of 3-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E149, Enantiomer 2).

Preparative Chromatography:

| | |
|---|---|
| Column | Chiralcel AD-H (25 × 2 cm), 5 μm |
| Mobile phase | n-Hexane/(Ethanol + 0.1% ipa) 30/70 v/v |
| Flow rate (mL/min) | 14 |
| DAD detection | 220 nm |
| Loop | 1000 μL |
| injection | 22 mg (each injection) |

Example 148 Enantiomer 1: ret. time 5.8 min, 100% ee MS (m/z): 489.4 [MH]$^+$.

Example 149 Enantiomer 2: ret. time 7.1 min, 100% ee MS (m/z): 489.4 [MH]$^+$.

Example 150: 3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride (E150, Enantiomer 1)

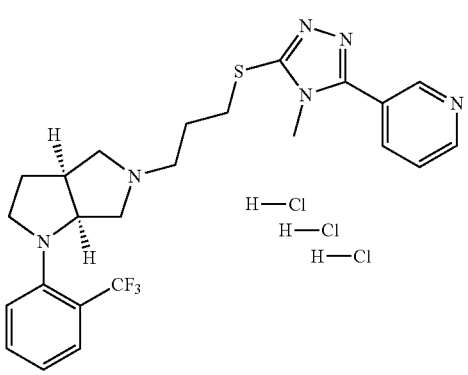

3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E148, Enantiomer 1, 19 mg) was dissolved in Et$_2$O and treated with 3.3. eq of 1N HCl in Et$_2$O to afford, after evaporation, 21.1 mg of title compound (E150, Enantiomer 1). MS (m/z): 489.4 [MH]$^+$.

Example 151: 3-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride (E151, Enantiomer 2)

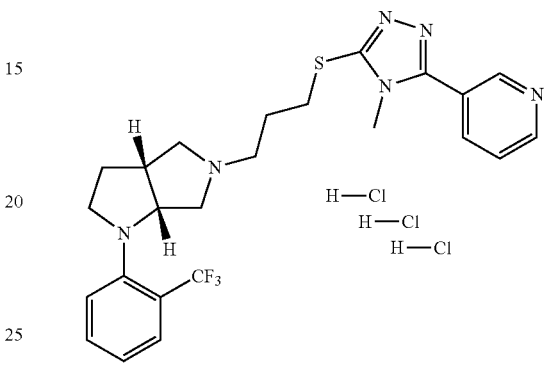

3-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E149, Enantiomer 2, 19 mg) was dissolved in Et$_2$O and treated with 3.3. eq of 1N HCl in Et$_2$O to afford, after evaporation, 21 mg of title compound (E151, Enantiomer 2). MS (m/z): 489.4 [MH]$^+$.

Example 152: 4-methyl-3-(1-methyl-1H-pyrazol-4-yl)-5-[(3-{1-[4-(trifluoromethyl)phenyl]-octahydropyrrolo[3,4-b]pyrrol-5-yl}propyl)sulfanyl]-4H-1,2,4-triazole (E152)

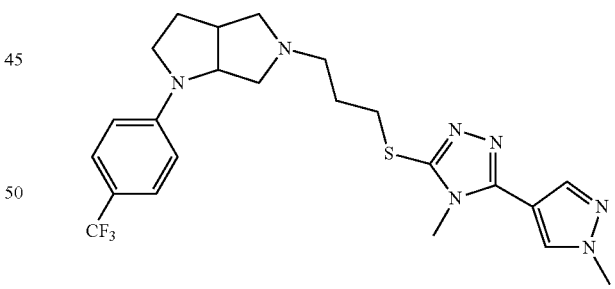

The title compound was prepared in analogy to the method described in Example 1 in 46 mg yield (E152, y=48%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-4-methyl-5-(1-methyl-1H-pyrazol-4-yl)-4H-1,2,4-triazole (p29, 57 mg, 0.21 mmol). NMR: $^1$H NMR (Acetone-d$_6$) δ: 8.13 (s, 1H), 7.87 (s, 1H), 7.47 (d, 2H), 6.71 (d, 2H), 4.25 (m, 1H), 4.00 (s, 3H), 3.70 (s, 3H), 3.46-3.56 (m, 1H), 3.34-3.45 (m, 1H), 3.10-3.30 (m, 2H), 3.00 (br. s., 1H), 2.69-2.76 (m, 2H), 2.42-2.62 (m, 4H), 2.12-2.21 (m, 1H), 1.87-2.04 (m, 3H). MS (m/z): 492.4 [MH]$^+$.

Example 153: 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine (E153)

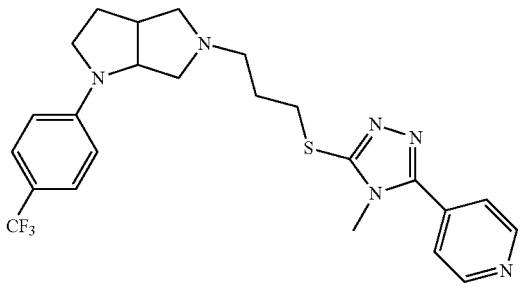 [SMILES: Cn1c(SCCCN2CC3CCN(c4ccc(C(F)(F)F)cc4)C3C2)nnc1-c1ccncc1]

The title compound was prepared in analogy to the method described in Example 1 in 54 mg yield (E153, y=56%) from 1-[4-(trifluoromethyl)phenyl]-octahydropyrrolo[3,4-b]pyrrole (prepared as in p73, 50 mg, 0.195 mmol) and 4-{5-[(3-chloropropyl)sulfanyl]-4-methyl-4H-1,2,4-triazol-3-yl}pyridine (p31, 56 mg, 0.21 mmol). NMR: $^1$H NMR (Acetone-$d_6$) δ: 8.75-8.80 (m, 2H), 7.74-7.78 (m, 2H), 7.47 (d, 2H), 6.71 (d, 2H), 4.26 (m, 1H), 3.78 (s, 3H), 3.47-3.55 (m, 1H), 3.22-3.45 (m, 3H), 2.97-3.05 (m, 1H), 2.73-2.79 (m, 2H), 2.44-2.62 (m, 4H), 2.15-2.23 (m, 1H), 1.90-2.05 (m, 3H). MS (m/z): 489.4[MH]$^+$.

Example 154: 4-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine (E154)

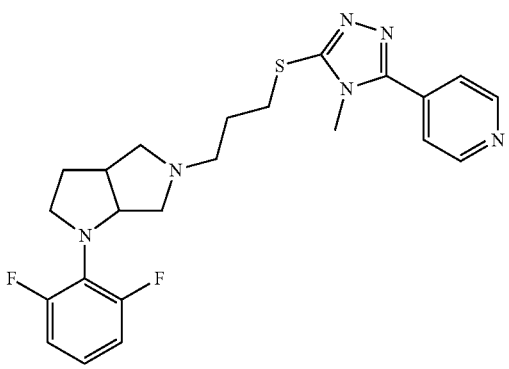 [SMILES: Cn1c(SCCCN2CC3CCN(c4c(F)cccc4F)C3C2)nnc1-c1ccncc1]

The title compound was prepared in analogy to the method described in Example 1 in 36 mg yield (E154, y=59%) from 1-(2,6-difluorophenyl)-octahydropyrrolo[3,4-b]pyrrole (p80, 30 mg, 0.134 mmol) and 4-{5-[(3-chloropropyl)sulfanyl]-4-methyl-4H-1,2,4-triazol-3-yl}pyridine (p31, 36 mg, 0.134 mmol). NMR: $^1$H NMR (Acetone-$d_6$) δ: 8.72-8.87 (m, 2H), 7.72-7.82 (m, 2H), 6.81-7.00 (m, 3H), 4.44-4.56 (m, 1H), 3.77-3.91 (m, 4H), 3.34 (m, 3H), 2.94 (br. s., 1H), 2.38-2.73 (m, 5H), 2.24-2.38 (m, 1H), 1.75-2.02 (m, 4H). MS (m/z): 457.4[MH]$^+$.

Example 155: 4-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine (E155)

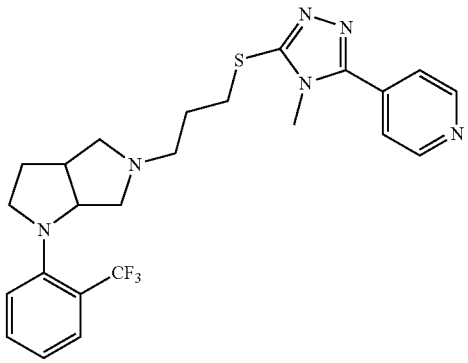 [SMILES: Cn1c(SCCCN2CC3CCN(c4ccccc4C(F)(F)F)C3C2)nnc1-c1ccncc1]

The title compound was prepared in analogy to the method described in Example 1 in 43 mg yield (E155, y=50%) from 1-[2-(trifluoromethyl)phenyl]-octahydropyrrolo[3,4-b]pyrrole (p97, 43 mg, 0.174 mmol) and 4-{5-[(3-chloropropyl)sulfanyl]-4-methyl-4H-1,2,4-triazol-3-yl}pyridine (p31, 47 mg, 0.174 mmol). NMR: $^1$H NMR (Acetone-$d_6$) δ: 8.96 (d, 1H), 8.72-8.75 (m, 1H), 8.13-8.18 (m, 1H), 7.55-7.64 (m, 2H), 7.48-7.55 (m, 1H), 7.31 (d, 1H), 7.06 (t, 1H), 4.41 (m, 1H), 3.74 (s, 3H), 3.62 (m, 1H), 3.20-3.36 (m, 2H), 3.06-3.13 (m, 1H), 2.96 (m, 1H), 2.69 (m, 1H), 2.57 (d, 1H), 2.38-2.53 (m, 3H), 2.20 (m, 1H), 2.00-2.04 (m, 1H), 1.79-1.95 (m, 3H). MS (m/z): 489.4 [MH]$^+$.

Example 156 and Example 157: 4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E156, Enantiomer 1) and 4-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E157, Enantiomer 2)

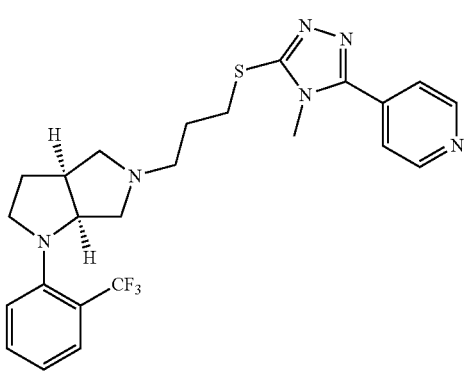

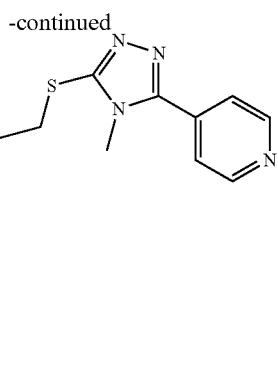

4-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine (E155, 40 mg) was separated into the single enantiomers by preparative chiral HPLC, obtaining 13 mg of 4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E156, Enantiomer 1) and 13 mg of 4-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E157, Enantiomer 2)

Preparative Chromatography:

| | |
|---|---|
| Column | Chiralcel OJ-H (25 × 2 cm), 5 μm |
| Mobile phase | n-Hexane/(Ethanol + 0.1% ipa) 70/30 v/v |
| Flow rate (mL/min) | 17 |
| DAD detection | 220 nm |
| Loop | 1000 μL |
| injection | 20 mg (each injection) |

Example 156 Enantiomer 1: ret. time 8.3 min, 100% ee MS (m/z): 489.4 [MH]⁺.

Example 157 Enantiomer 2: ret. time 11.9 min, 100% ee MS (m/z): 489.4 [MH]⁺.

Example 158: 4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride (E158, Enantiomer 1)

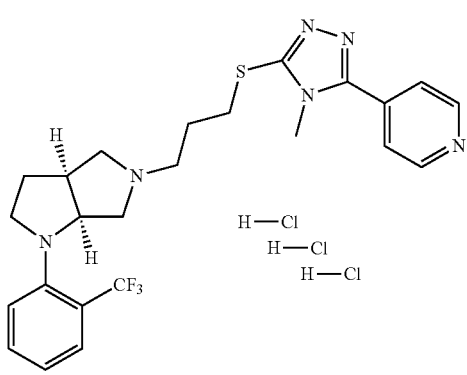

4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E156, Enantiomer 1, 13 mg) was dissolved in Et₂O and treated with 3.3. eq of 2N HCl in Et₂O to afford, after evaporation, 8.7 mg of title compound (E158, Enantiomer 1). MS (m/z): 489.4 [MH]⁺.

Example 159: 4-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride (E159, Enantiomer 2)

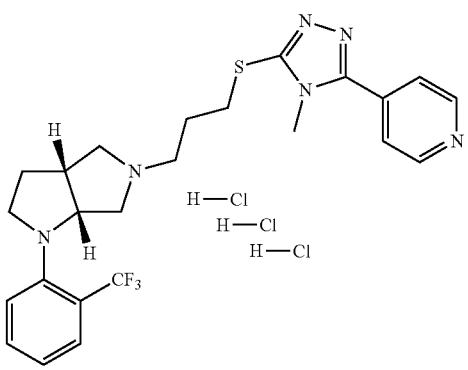

4-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine (E157, Enantiomer 2, 13 mg) was dissolved in Et₂O and treated with 3.3. eq of 2N HCl in Et₂O to afford, after evaporation, 14.5 mg of title compound (E159, Enantiomer 2). MS (m/z): 489.4 [MH]⁺.

Example 160: 2-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine (E160)

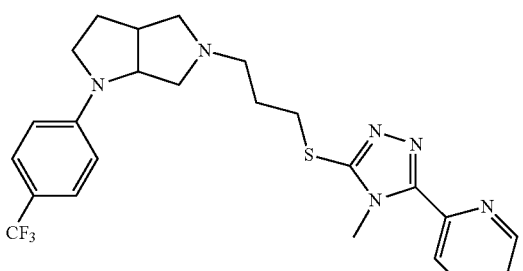

The title compound was prepared in analogy to the method described in Example 1 in 31 mg yield (E160, y=32%) from 1-[4-(trifluoromethyl)phenyl]-octahydropyrrolo[3,4-b]pyrrole (prepared as in p73, 50 mg, 0.195 mmol) and 2-{5-[(3-chloropropyl)sulfanyl]-4-methyl-4H-1,2,4-triazol-3-yl}pyridine (p33, 56 mg, 0.21 mmol). NMR: ¹H NMR (Acetone-d₆) δ: 8.69-8.73 (m, 1H), 8.20 (s, 1H), 7.94-8.00 (m, 1H), 7.46 (d, 3H), 6.70 (d, 2H), 4.24 (s, 1H), 4.01 (s, 3H), 3.49 (s, 1H), 3.21-3.42 (m, 3H), 2.94-3.04 (m, 1H), 2.75 (d, 2H), 2.43-2.62 (m, 4H), 2.12-2.20 (m, 1H), 1.90-2.03 (m, 3H). MS (m/z): 489.4[MH]⁺.

Example 161: 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine (E161)

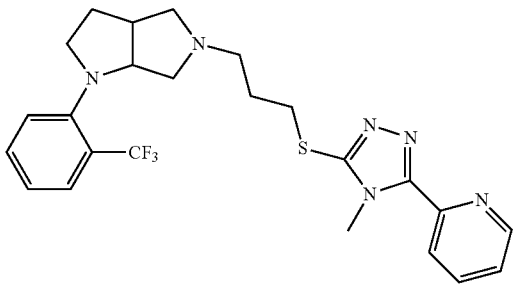 [SMILES: Cn1c(SCCCN2CC3CCN(c4ccccc4C(F)(F)F)C3C2)nnc1-c1ccccn1]

The title compound was prepared in analogy to the method described in Example 1 in 33 mg yield (E161, y=35%) from 1-2-(trifluoromethyl)phenyl]-octahydropyrrolo[3,4-b]pyrrole (p97, 50 mg, 0.195 mmol) and 2-{5-[(3-chloropropyl)sulfanyl]-4-methyl-4H-1,2,4-triazol-3-yl}pyridine (p33, 56 mg, 0.21 mmol). NMR: $^1$H NMR (Acetone-$d_6$) δ: 8.70-8.76 (m, 1H), 8.21-8.26 (m, 1H), 7.95-8.02 (m, 1H), 7.60-7.66 (m, 1H), 7.46-7.56 (m, 2H), 7.27-7.37 (m, 1H), 7.04-7.15 (m, 1H), 4.40-4.47 (m, 1H), 4.04 (s, 3H), 3.59-3.67 (m, 1H), 3.23-3.40 (m, 2H), 3.06-3.14 (m, 1H), 2.93-3.04 (m, 1H), 2.66-2.74 (m, 2H), 2.38-2.64 (m, 4H), 2.16-2.26 (m, 1H), 1.79-1.97 (m, 3H). MS (m/z): 489.4[MH]$^+$.

Example 162: 4-methyl-3-(1,3-thiazol-2-yl)-5-[(3-{1-[4-(trifluoromethyl)phenyl]-octahydropyrrolo[3,4-b]pyrrol-5-yl}propyl)sulfanyl]-4H-1,2,4-triazole (E162)

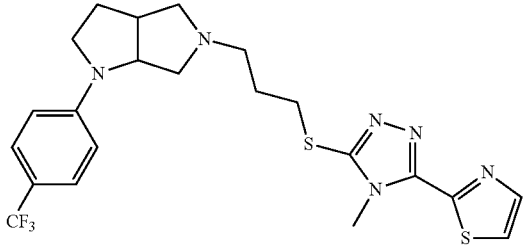 [SMILES: Cn1c(SCCCN2CC3CCN(c4ccc(C(F)(F)F)cc4)C3C2)nnc1-c1nccs1]

The title compound was prepared in analogy to the method described in Example 1 in 56 mg yield (E162, y=58%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-4-methyl-5-(1,3-thiazol-2-yl)-4H-1,2,4-triazole (p35, 57 mg, 0.21 mmol). NMR: $^1$H NMR (Acetone-$d_6$) δ: 8.03 (d, 1H), 7.80 (d, 1H), 7.46 (d, 2H), 6.70 (d, 2H), 4.24 (m, 1H), 4.01 (s, 3H), 3.47-3.56 (m, 1H), 3.32-3.42 (m, 2H), 3.22-3.31 (m, 1H), 2.97-3.05 (m, 1H), 2.74 (s, 2H), 2.42-2.61 (m, 4H), 2.17 (d, 1H), 1.88-2.03 (m, 3H). MS (m/z): 495.3[MH]$^+$.

Example 163: 4-methyl-3-(3-methyl-1,2-oxazol-5-yl)-5-[(3-{1-[4-(trifluoromethyl)phenyl]-octahydropyrrolo[3,4-b]pyrrol-5-yl}propyl)sulfanyl]-4H-1,2,4-triazole (E163)

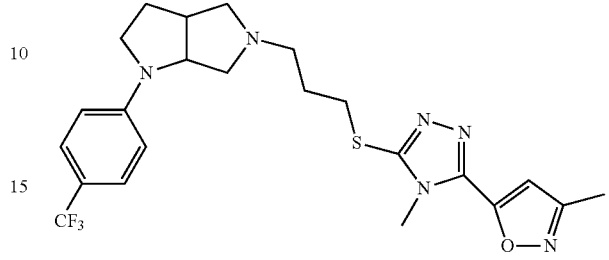

The title compound was prepared in analogy to the method described in Example 1 in 36 mg yield (E163, y=37%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-4-methyl-5-(3-methyl-1,2-oxazol-5-yl)-4H-1,2,4-triazole (p37, 57 mg, 0.21 mmol). NMR: $^1$H NMR (Acetone-$d_6$) δ: 7.46 (d, 2H), 6.88 (s, 1H), 6.70 (d, 2H), 4.19-4.29 (m, 1H), 3.84 (s, 3H), 3.45-3.56 (m, 1H), 3.20-3.43 (m, 3H), 2.93-3.05 (m, 1H), 2.75 (d, 2H), 2.41-2.62 (m, 4H), 2.38 (s, 3H), 2.15-2.25 (m, 1H), 1.94 (d, 3H). MS (m/z): 493.4[MH]$^+$.

Example 164: 4-methyl-3-(4-methyl-1,3-thiazol-5-yl)-5-[(3-{1-[4-(trifluoromethyl)phenyl]-octahydropyrrolo[3,4-b]pyrrol-5-yl}propyl)sulfanyl]-4H-1,2,4-triazole (E164)

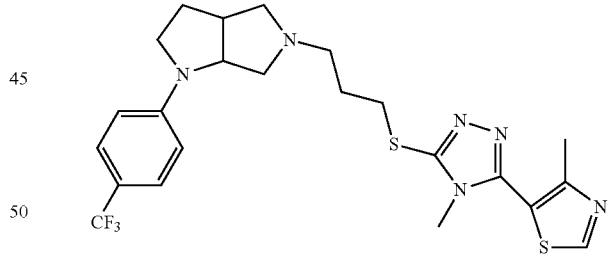

The title compound was prepared in analogy to the method described in Example 1 in 67 mg yield (E164, y=67%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-4-methyl-5-(4-methyl-1,3-thiazol-5-yl)-4H-1,2,4-triazole (p39, 61 mg, 0.21 mmol). NMR: $^1$H NMR (Acetone-$d_6$) δ: 9.15 (s, 1H), 7.47 (d, 2H), 6.72 (d, 2H), 4.26 (m, 1H), 3.57 (s, 3H), 3.48-3.56 (m, 1H), 3.20-3.45 (m, 3H), 2.97-3.07 (m, 1H), 2.73-2.80 (m, 2H), 2.51-2.64 (m, 3H), 2.43-2.51 (m, 4H), 2.15-2.26 (m, 1H), 1.90-2.05 (m, 3H). MS (m/z): 509.4[MH]$^+$.

197

Example 165: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}-1,2-dihydropyridin-2-one (E165)

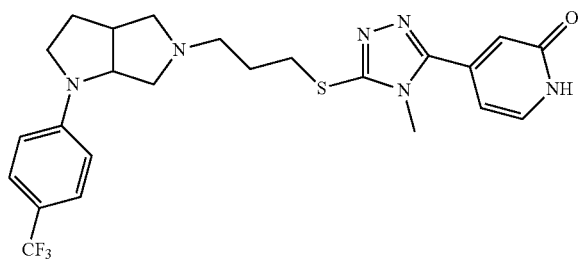 [SMILES: Cn1c(SCCCN2CC3CCN(c4ccc(C(F)(F)F)cc4)C3C2)nnc1-c1cc[nH]c(=O)c1]

The title compound was prepared in analogy to the method described in Example 1 in 93 mg yield (E165, y=59%) from 1-[4-(trifluoromethyl)phenyl]-octahydropyrrolo[2,3-c]pyrrole (prepared as in p73, 80 mg, 0.31 mmol) and 4-{5-[(3-chloropropyl)sulfanyl]-4-methyl-4H-1,2,4-triazol-3-yl}-1,2-dihydropyridin-2-one (p41, 98 mg, 0.34 mmol). NMR: $^1$H NMR (CDCl$_3$) δ:12.20-12.50 (m, 1H), 7.37-7.52 (m, 3H), 6.75-6.85 (m, 2H), 6.56 (d, 2H), 4.18 (br. s., 1H), 3.60-3.70 (m, 3H), 3.45-3.57 (m, 1H), 3.21-3.45 (m, 3H), 2.97 (br. s., 1H), 2.45-2.83 (m, 6H), 2.12-2.28 (m, 1H), 1.89-2.11 (m, 3H). MS (m/z): 505.4[MH]$^+$.

Example 166 and Example 167: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one (E166, Enantiomer 1) and 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one (E167, Enantiomer 2)

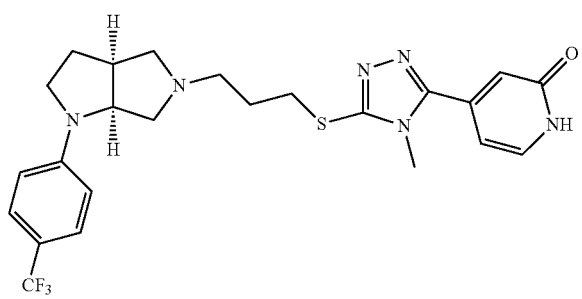

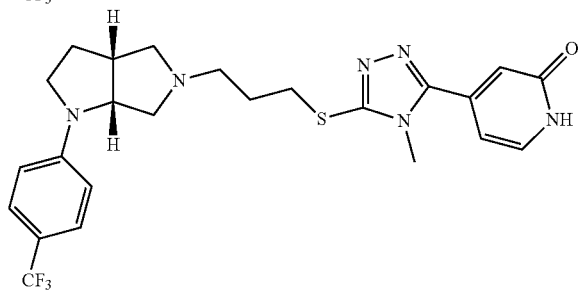

4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}-1,2-dihydropyridin-2-one (E165, 110 mg) was separated into the single enantiomers by preparative chiral HPLC, obtaining 36 mg of 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one (E166, Enantiomer 1) and 37 mg of 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one (E167, Enantiomer 2).

Preparative Chromatography:

| | |
|---|---|
| Column | Chiralcel AD-H (25 × 2 cm), 5 µm |
| Mobile phase | n-Hexane/(Ethanol + 0.1% ipa) 30/70 v/v |
| Flow rate (mL/min) | 14 |
| DAD detection | 220 nm |
| Loop | 1000 µL |
| injection | 22 mg (each injection) |

Example 166 Enantiomer 1: ret. time 7.7 min, 100% ee MS (m/z): 505.4 [MH]$^+$.

Example 167 Enantiomer 2: ret. time 10.3 min, 100% ee MS (m/z): 505.4 [MH]$^+$.

Example 168: 4-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E168)

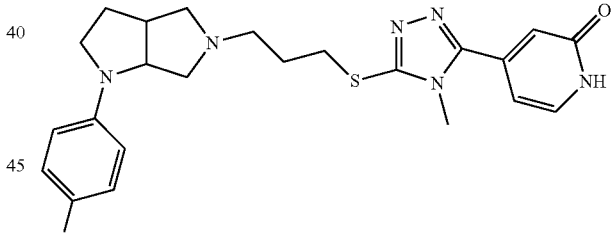

The title compound was prepared in analogy to the method described in Example 1 in 32 mg yield (E168, y=36%) from 1-(4-fluorophenyl)-octahydropyrrolo[2,3-c]pyrrole (p77, 40 mg, 0.194 mmol) and 4-{5-[(3-chloropropyl)sulfanyl]-4-methyl-4H-1,2,4-triazol-3-yl}-1,2-dihydropyridin-2-one (p41, 60 mg, 0.21 mmol). NMR: $^1$H NMR (MeOD-d$_4$) δ: 7.58-7.64 (m, 1H), 6.88-6.97 (m, 2H), 6.83-6.88 (m, 1H), 6.69-6.76 (m, 1H), 6.53-6.61 (m, 2H), 4.04-4.13 (m, 1H), 3.73 (s, 3H), 3.42-3.51 (m, 1H), 3.24-3.27 (m, 2H), 3.11-3.21 (m, 1H), 2.97 (br. s., 1H), 2.54-2.72 (m, 6H), 2.11-2.27 (m, 1H), 1.87-2.01 (m, 3H) MS (m/z): 455.3 [MH]$^+$.

Example 169 and Example 170: 4-[5-({3-[(3aS,6aS or 3aR,6aR)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E169, Enantiomer 1) and 4-[5-({3-[(3aR,6aR or 3aS,6aS)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E170, Enantiomer 2)

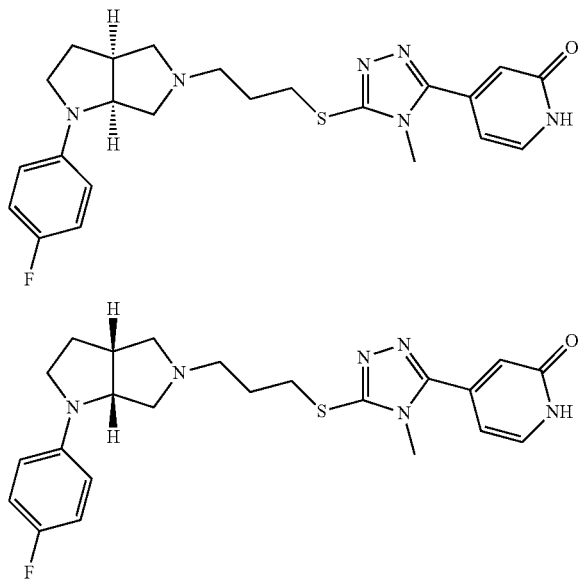

4-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E168, 30 mg) was separated into the single enantiomers by preparative chiral HPLC, obtaining 7 mg of 4-[5-({3-[(3aS,6aS or 3aR,6aR)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E169, Enantiomer 1) and 10 mg of 4-[5-({3-[(3aR,6aR or 3aS,6aS)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E170, Enantiomer 2)

Preparative Chromatography:

| | |
|---|---|
| Column | Chiralcel OJ-H (25 × 2 cm), 5 μm |
| Mobile phase | n-Hexane/(Ethanol/Methanol1/1 + 0.1% ipa) 40/60 v/v |
| Flow rate (mL/min) | 18 |
| DAD detection | 220 nm |
| Loop | 1000 μL |
| injection | 15 mg (each injection) |

Example 169 Enantiomer 1: ret. time 8.7 min, 100% ee MS (m/z): 455.3 [MH]$^+$.

Example 170 Enantiomer 2: ret. time 10.8 min, 100% ee MS (m/z): 455.3 [MH]$^+$.

Example 171: 4-[5-({3-[(3aS,6aS or 3aR,6aR)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one dihydrochloride (E171, Enantiomer 1)

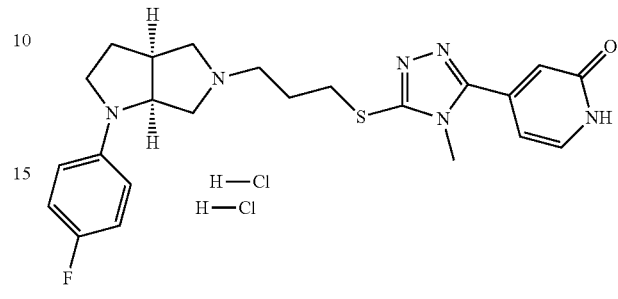

4-[5-({3-[(3aS,6aS or 3aR,6aR)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E169, Enantiomer 1, 7 mg) was dissolved in Et$_2$O and treated with 2.2. eq of 1N HCl in Et$_2$O to afford, after evaporation, 5.3 mg of title compound (E171, Enantiomer 1). MS (m/z): 455.3 [MH]$^+$.

Example 172: 4-[5-({3-[(3aR,6aR or 3aS,6aS)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one dihydrochloride (E172, Enantiomer 2)

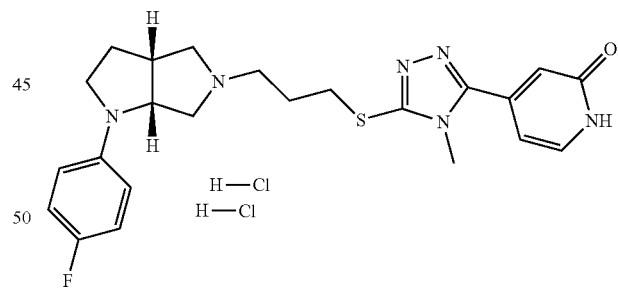

4-[5-({3-[(3aR,6aR or 3aS,6aS)-1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E170, Enantiomer 2, 10 mg) was dissolved in Et$_2$O and treated with 2.2. eq of 1N HCl in Et$_2$O to afford, after evaporation, 10.6 mg of title compound (E172, Enantiomer 2). MS (m/z): 455.3 [MH]$^+$.

Example 173: 4-[5-({3-[1-(2,6-difluorophenyl)-octahydropyrrolo[3,4-b]pyrrol-5-yl]propyl}sulfanyl)-4-methyl-4H-1,2,4-triazol-3-yl]-1,2-dihydropyridin-2-one (E173)

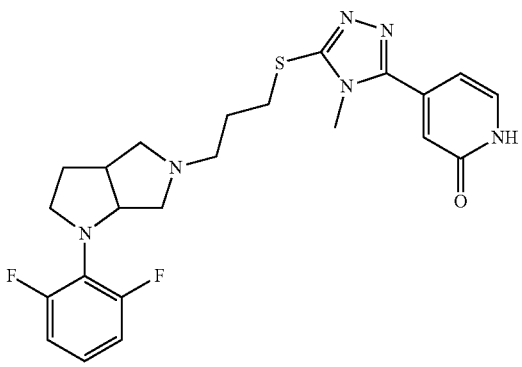 [SMILES: Cn1c(SCCCN2CC3CCN(c4c(F)cccc4F)C3C2)nnc1-c1cc[nH]c(=O)c1]

The title compound was prepared in analogy to the method described in Example 1 in 32.3 mg yield (E173, y=51%) from 1-(2,6-difluorophenyl)-octahydropyrrolo[3,4-b]pyrrole (p80, 30 mg, 0.134 mmol) and 4-{5-[(3-chloropropyl)sulfanyl]-4-methyl-4H-1,2,4-triazol-3-yl}-1,2-dihydropyridin-2-one (p41, 39 mg, 0.134 mmol). NMR: $^1$H NMR (Acetone-d$_6$) δ: 10.64-10.81 (m, 1H), 7.59 (d, 1H), 6.91 (d, 3H), 6.71 (d, 1H), 6.61 (m, 1H), 4.42-4.57 (m, 1H), 3.79 (s, 4H), 3.33 (d, 3H), 2.89-3.04 (m, 1H), 2.40-2.73 (m, 5H), 2.20-2.34 (m, 1H), 1.76-2.04 (m, 4H). MS (m/z): 473.4 [MH]$^+$.

Example 174: 4-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one (E174)

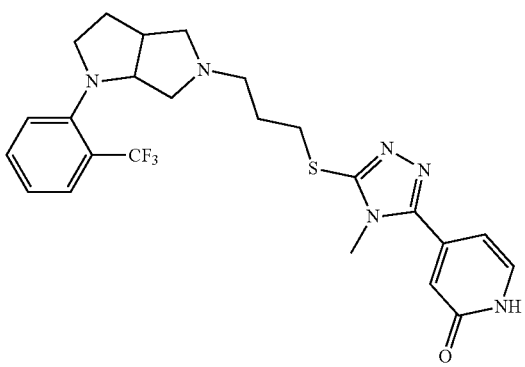 [SMILES: Cn1c(SCCCN2CC3CCN(c4ccccc4C(F)(F)F)C3C2)nnc1-c1cc[nH]c(=O)c1]

The title compound was prepared in analogy to the method described in Example 1 in 35 mg yield (E174, y=35%) from 1-[2-(trifluoromethyl)phenyl]-octahydropyrrolo[3,4-b]pyrrole (p97, 50 mg, 0.195 mmol) and 4-{5-[(3-chloropropyl)sulfanyl]-4-methyl-4H-1,2,4-triazol-3-yl}-1,2-dihydropyridin-2-one (p41, 60 mg, 0.21 mmol). NMR: $^1$H NMR (Acetone-d$_6$) δ: 7.56-7.67 (m, 2H), 7.48-7.56 (m, 1H), 7.28-7.35 (m, 1H), 7.04-7.12 (m, 1H), 6.69-6.73 (m, 1H), 6.57-6.65 (m, 1H), 4.38-4.46 (m, 1H), 3.79 (s, 3H), 3.63 (d, 1H), 3.22-3.40 (m, 2H), 3.06-3.16 (m, 1H), 2.89-3.03 (m, 1H), 2.67-2.72 (m, 1H), 2.57 (d, 1H), 2.39-2.54 (m, 3H), 2.17-2.28 (m, 1H), 2.05 (br. s., 1H), 1.79-1.97 (m, 3H). MS (m/z): 505.4[MH]$^+$.

Example 175: 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one (E175)

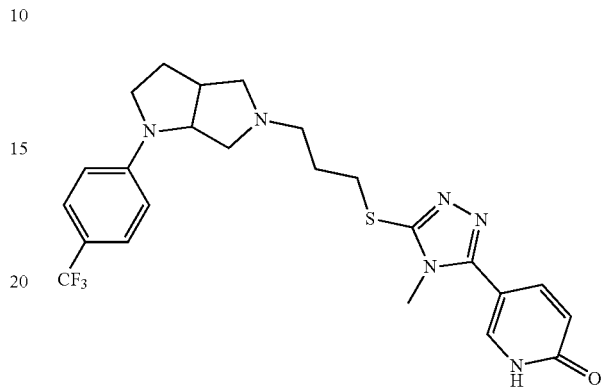

The title compound was prepared in analogy to the method described in Example 1 in 21 mg yield (E175, y=21%) from 1-[4-(trifluoromethyl)phenyl]-octahydropyrrolo[2,3-c]pyrrole (prepared as in p73, 50 mg, 0.195 mmol) and 5-{5-[(3-chloropropyl)sulfanyl]-4-methyl-4H-1,2,4-triazol-3-yl}-1,2-dihydropyridin-2-one (p43, 60 mg, 0.21 mmol). NMR: $^1$H NMR (Acetone-d$_6$) δ: 7.86 (d, 1H), 7.77 (m, 1H), 7.47 (d, 2H), 6.71 (d, 2H), 6.51 (d, 1H), 4.25 (s, 1H), 3.67 (s, 3H), 3.48-3.55 (m, 1H), 3.35-3.44 (m, 1H), 3.15-3.34 (m, 2H), 3.01 (d, 1H), 2.72-2.79 (m, 2H), 2.43-2.62 (m, 4H), 2.15-2.22 (m, 1H), 1.88-2.04 (m, 3H). MS (m/z): 505.4[MH]$^+$.

Example 176: 5-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one (E176)

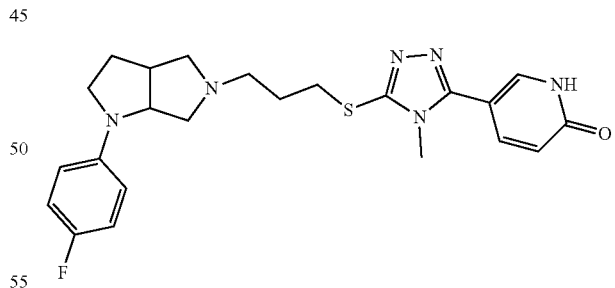

The title compound was prepared in analogy to the method described in Example 1 in 23 mg yield (E176, y=26%) from 1-(4-fluorophenyl)-octahydropyrrolo[2,3-c]pyrrole (p77, 40 mg, 0.194 mmol) and 5-{5-[(3-chloropropyl)sulfanyl]-4-methyl-4H-1,2,4-triazol-3-yl}-1,2-dihydropyridin-2-one (p43, 60 mg, 0.21 mmol). NMR: $^1$H NMR (MeOD-d$_4$) δ: 7.82-7.88 (m, 2H), 6.89-6.96 (m, 2H), 6.68 (d, 1H), 6.55-6.62 (m, 2H), 4.11 (m, 1H), 3.63-3.67 (m, 3H), 3.46-3.54 (m, 1H), 3.14-3.27 (m, 3H), 2.96-3.07 (m, 1H), 2.61-2.79 (m, 6H), 2.14-2.25 (m, 1H), 1.88-2.02 (m, 3H). MS (m/z): 455.3[MH]$^+$.

Example 177: 5-[5-({3-[1-(2,6-difluorophenyl)-octa-hydropyrrolo[3,4-b]pyrrol-5-yl]propyl}sulfanyl)-4-methyl-4H-1,2,4-triazol-3-yl]-1,2-dihydropyridin-2-one (E177)

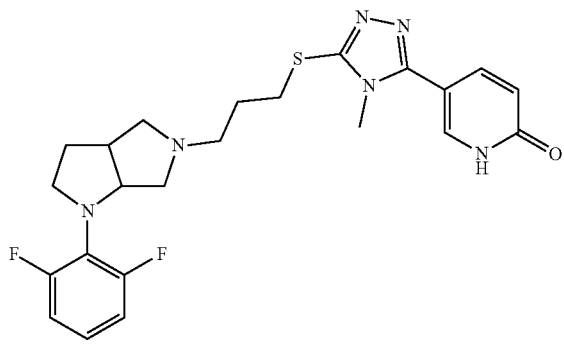 [SMILES: Cn1c(SCCCN2CC3CCN(c4c(F)cccc4F)C3C2)nnc1-c1ccc(=O)[nH]c1]

The title compound was prepared in analogy to the method described in Example 1 in 32 mg yield (E177, y=50%) from 1-(2,6-difluorophenyl)-octahydropyrrolo[3,4-b]pyrrole (p80, 30 mg, 0.134 mmol) and 5-{5-[(3-chloropropyl)sulfanyl]-4-methyl-4H-1,2,4-triazol-3-yl}-1,2-dihydropyridin-2-one (p43, 39 mg, 0.134 mmol). NMR: $^1$H NMR (Acetone-d$_6$) δ: 7.86 (d, 1H), 7.79 (m, 1H), 6.81-6.97 (m, 3H), 6.52 (d, 1H), 4.48 (m, 1H), 3.83 (dmin, 1H), 3.69 (s, 3H), 3.15-3.37 (m, 3H), 2.86-2.96 (m, 1H), 2.56-2.69 (m, 2H), 2.41-2.55 (m, 3H), 2.20-2.32 (m, 1H), 2.09-2.13 (m, 1H), 1.75-2.04 (m, 3H). MS (m/z): 473.4 [MH]$^+$.

Example 178: 5-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one (E178)

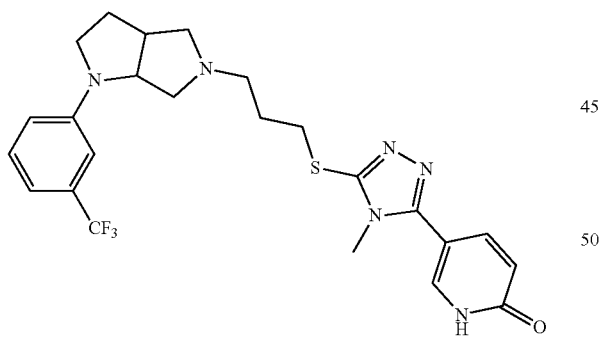

The title compound was prepared in analogy to the method described in Example 1 in 38 mg yield (E178, y=38%) from 1-[3-(trifluoromethyl)phenyl]-octahydropyrrolo[3,4-b]pyrrole (p94, 50 mg, 0.195 mmol) and 5-{5-[(3-chloropropyl)sulfanyl]-4-methyl-4H-1,2,4-triazol-3-yl}-1,2-dihydropyridin-2-one (p43, 60 mg, 0.21 mmol). NMR: $^1$H NMR (Acetone-d$_6$) δ: 7.82-7.89 (m, 1H), 7.73-7.82 (m, 1H), 7.34-7.42 (m, 1H), 6.89-6.95 (m, 1H), 6.78-6.89 (m, 2H), 6.48-6.55 (m, 1H), 4.19-4.27 (m, 1H), 3.67 (s, 2H), 3.47-3.57 (m, 1H), 3.15-3.39 (m, 3H), 2.94-3.07 (m, 1H), 2.72-2.76 (m, 2H), 2.43-2.61 (m, 4H), 2.16-2.23 (m, 1H), 1.87-2.04 (m, 3H). MS (m/z): 505.4[MH]$^+$.

Example 179: 5-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one (E179)

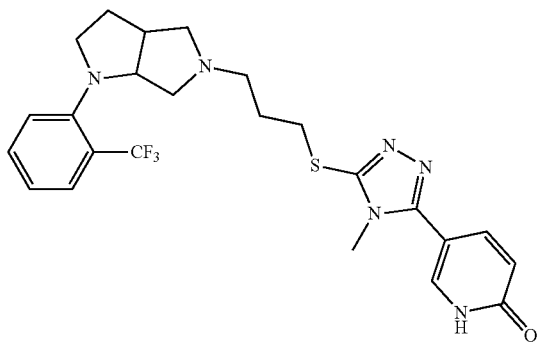 [SMILES: Cn1c(SCCCN2CC3CCN(c4ccccc4C(F)(F)F)C3C2)nnc1-c1ccc(=O)[nH]c1]

The title compound was prepared in analogy to the method described in Example 1 in 107 mg yield (E179, y=54%) from 1-[2-(trifluoromethyl)phenyl]-octahydropyrrolo[3,4-b]pyrrole (p97, 100 mg, 0.31 mmol) and 5-(5-[(3-chloropropyl)sulfanyl]-4-methyl-4H-1,2,4-triazol-3-yl)-1,2-dihydropyridin-2-one (p43, 120 mg, 0.42 mmol). NMR: $^1$H NMR (Acetone-d$_6$) δ: 7.84-7.88 (m, 1H), 7.75-7.81 (m, 1H), 7.59-7.65 (m, 1H), 7.47-7.55 (m, 1H), 7.27-7.34 (m, 1H), 7.03-7.12 (m, 1H), 6.51 (d, 1H), 4.38-4.44 (m, 1H), 3.68 (s, 3H), 3.56-3.65 (m, 1H), 3.14-3.31 (m, 2H), 3.06-3.12 (m, 1H), 2.89-3.01 (m, 1H), 2.63-2.72 (m, 1H), 2.53-2.59 (m, 1H), 2.36-2.53 (m, 4H), 2.15-2.23 (m, 1H), 1.77-1.87 (br. s., 3H). MS (m/z): 505.4[MH]$^+$.

Example 180 and Example 181: 5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one (E180, Enantiomer 1) and 5-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one (E181, Enantiomer 2)

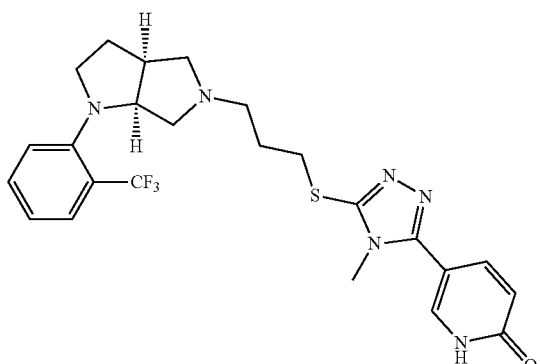

-continued

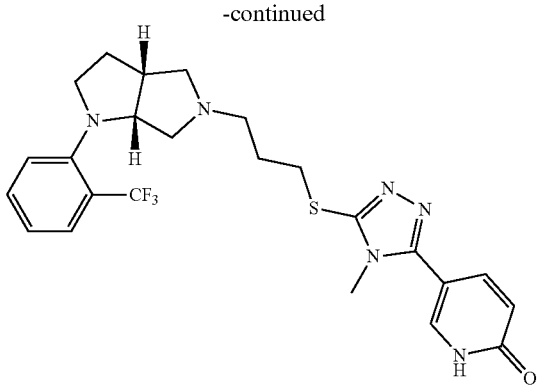

5-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one (E179, 127 mg) was separated into the single enantiomers by preparative chiral HPLC, obtaining 37 mg of 5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one (E180, Enantiomer 1) and 37 mg of 5-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one (E181, Enantiomer 2).

Preparative Chromatography:

| | |
|---|---|
| Column | Chiralcel OJ-H (25 × 2 cm), 5 μm |
| Mobile phase | n-Hexane/(Ethanol + 0.1% ipa) 75/25 v/v |
| Flow rate (mL/min) | 17 |
| DAD detection | 220 nm |
| Loop | 2000 μL |
| injection | 12.6 mg (each injection) |

Example 180 Enantiomer 1: ret. time 7.1 min, 100% ee MS (m/z): 505.4 [MH]$^+$.

Example 181 Enantiomer 2: ret. time 9.6 min, 100% ee MS (m/z): 505.4 [MH]$^+$.

Example 182: 5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one dihydrochloride (E182, Enantiomer 1)

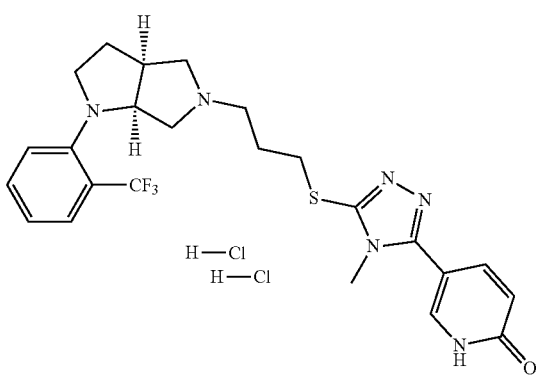

5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one (E180, Enantiomer 1, 37 mg) was dissolved in Et$_2$O and treated with 2.2. eq of 1N HCl in Et$_2$O to afford, after evaporation, 42 mg of title compound (E182, Enantiomer 1). MS (m/z): 505.4 [MH]$^+$.

Example 183: 5-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one dihydrochloride (E183, Enantiomer 2)

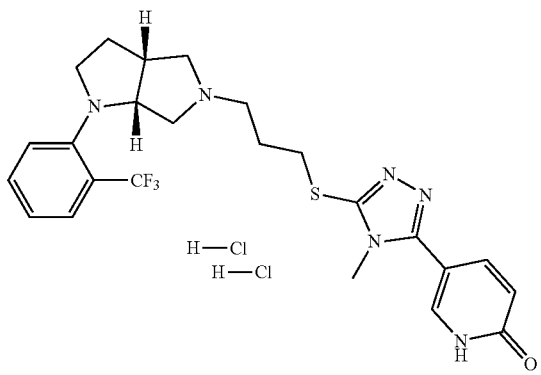

5-[5-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one (E181, Enantiomer 2, 37 mg) was dissolved in Et$_2$O and treated with 2.2. eq of 1N HCl in Et$_2$O to afford, after evaporation, 41 mg of title compound (E183, Enantiomer 2). MS (m/z): 505.4 [MH]$^+$.

Example 184: 3-({3-[1-(2,6-difluorophenyl)-octahydropyrrolo[3,4-b]pyrrol-5-yl]propyl}sulfanyl)-4-methyl-5-(1-methyl-1H-pyrazol-5-yl)-4H-1,2,4-triazole (E184)

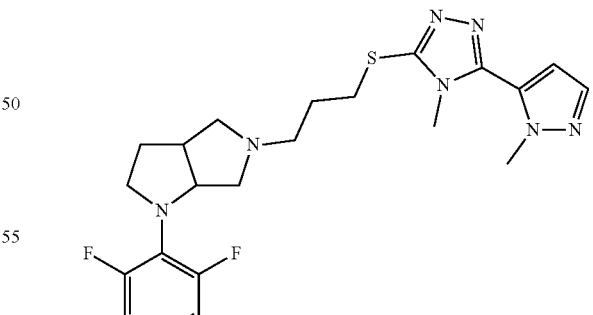

The title compound was prepared in analogy to the method described in Example 1 in 36 mg yield (E184, y=58%) from 1-(2,6-difluorophenyl)-octahydropyrrolo[3,4-b]pyrrole (p80, 30 mg, 0.134 mmol) and 3-[(3-chloropropyl)sulfanyl]-4-methyl-5-(1-methyl-1H-pyrazol-5-yl)-4H-1,2,4-triazole (p45, 37 mg, 0.134 mmol). NMR: $^1$H NMR (Acetone-d$_6$) δ: 7.58 (d, 1H), 6.84-7.01 (m, 3H), 6.73 (d, 1H), 4.50 (br. s., 1H), 4.06 (s, 3H), 3.78-3.91 (m, 1H), 3.69 (s, 3H), 3.33 (m, 3H), 2.94 (br. s., 1H), 2.40-2.73 (m, 5H), 2.24-2.40 (m, 1H), 1.75-2.03 (m, 4H). MS (m/z): 460.5 [MH]+.

Example 185: 4-methyl-3-(1-methyl-1H-pyrazol-5-yl)-5-[(3-{1-[2-(trifluoromethyl)phenyl]-octahydropyrrolo[3,4-b]pyrrol-5-yl}propyl)sulfanyl]-4H-1,2,4-triazole (E185)

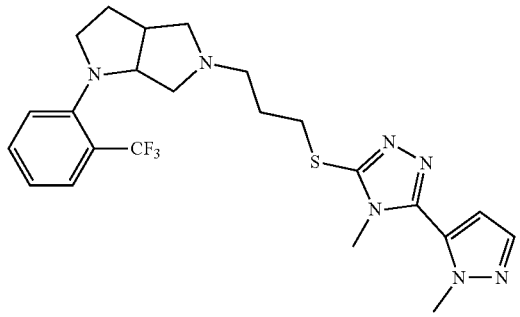 [SMILES: Cn1nccc1-c1nnc(SCCCN2CC3CCN(c4ccccc4C(F)(F)F)C3C2)n1C]

The title compound was prepared in analogy to the method described in Example 1 in 112 mg yield (E185, y=58%) from 1-[2-(trifluoromethyl)phenyl]-octahydropyrrolo[3,4-b]pyrrole (p97, 100 mg, 0.39 mmol) and 3-[(3-chloropropyl)sulfanyl]-4-methyl-5-(1-methyl-1H-pyrazol-5-yl)-4H-1,2,4-triazole (p45, 114 mg, 0.42 mmol). NMR: $^1$H NMR (Acetone-d$_6$) δ: 7.61 (s, 1H), 7.58 (d, 1H), 7.47-7.54 (m, 1H), 7.29-7.34 (m, 1H), 7.04-7.11 (m, 1H), 6.72 (d, 1H), 4.38-4.44 (m, 1H), 4.06 (s, 3H), 3.67 (s, 3H), 3.62 (d, 1H), 3.22-3.35 (m, 2H), 3.06-3.12 (m, 1H), 2.92-2.99 (m, 1H), 2.65-2.73 (m, 1H), 2.56 (d, 1H), 2.39-2.52 (m, 3H), 2.16-2.25 (m, 2H), 1.79-1.93 (m, 3H). MS (m/z): 492.4[MH]+.

Example 186 and Example 187: 3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole (E186, Enantiomer 1) and 3-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole (E187, Enantiomer 2)

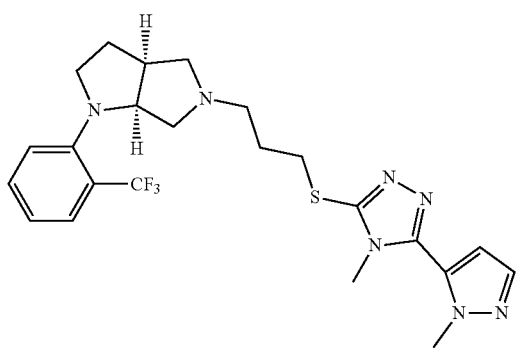

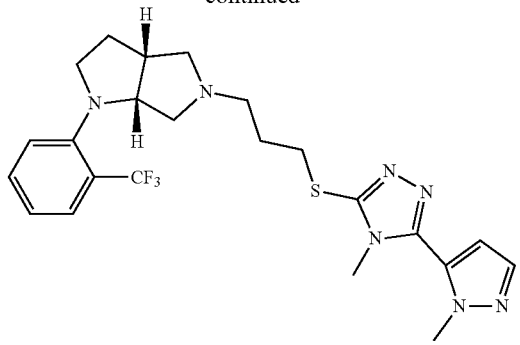

4-methyl-3-(1-methyl-1H-pyrazol-5-yl)-5-[(3-{1-[2-(trifluoromethyl)phenyl]-octahydropyrrolo[3,4-b]pyrrol-5-yl}propyl)sulfanyl]-4H-1,2,4-triazole (E185, 110 mg) was separated into the single enantiomers by preparative chiral HPLC, obtaining 37 mg of 3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole (E186, Enantiomer 1) and 38 mg of 3-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole (E187, Enantiomer 2)

Preparative Chromatography:

| | |
|---|---|
| Column | Chiralcel OJ-H (25 × 2 cm), 5 μm |
| Mobile phase | n-Hexane/(Ethanol + 0.1% ipa) 60/40 v/v |
| Flow rate (mL/min) | 18 |
| DAD detection | 220 nm |
| Loop | 2500 μL |
| injection | 55 mg (each injection) |

Example 186 Enantiomer 1: ret. time 6.9 min, 100% ee MS (m/z): 492.4 [MH]+.
Example 187 Enantiomer 2: ret. time 14.5 min, 100% ee MS (m/z): 492.4 [MH]+.

Example 188: 3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole dihydrochloride (E188, Enantiomer 1)

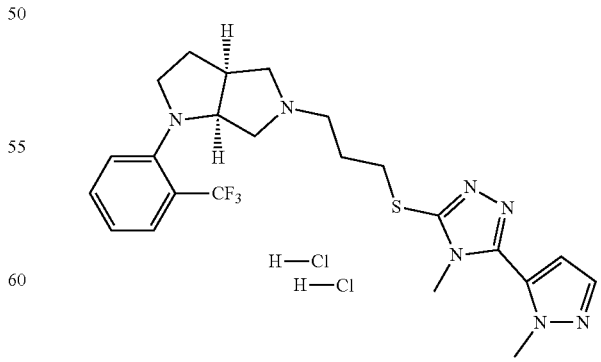

3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole (E186, Enantiomer 1, 37 mg) was dissolved in Et$_2$O and treated with 2.2. eq of 1N HCl in Et$_2$O to afford, after evaporation, 38 mg of title compound (E188, Enantiomer 1). MS (m/z): 492.4 [MH]$^+$.

Example 189: 3-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole dihydrochloride (E189, Enantiomer 2)

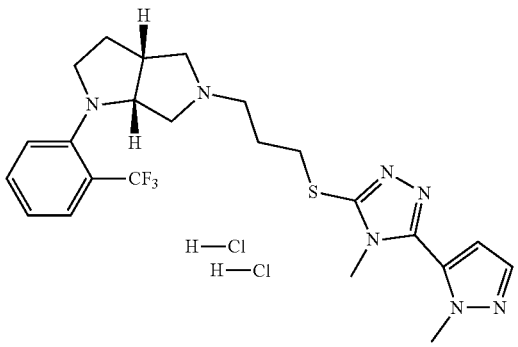

3-({3-[(3aR,6aR or 3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole (E187, Enantiomer 2, 38 mg) was dissolved in Et$_2$O and treated with 2.2. eq of 1N HCl in Et$_2$O to afford, after evaporation, 38 mg of title compound (E189, Enantiomer 2). MS (m/z): 492.4 [MH]$^+$.

Example 190: 3-[5-({3-[1-(2,6-difluorophenyl)-octahydropyrrolo[3,4-b]pyrrol-5-yl]propyl}sulfanyl)-4-methyl-4H-1,2,4-triazol-3-yl]-2-methylpyridine (E190)

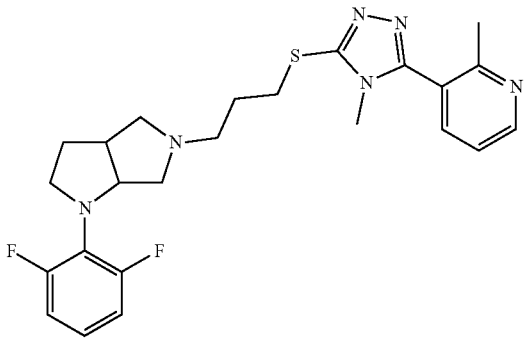 [SMILES: Cc1ncccc1-c1nnc(SCCCN2CC3CCN(c4c(F)cccc4F)C3C2)n1C]

The title compound was prepared in analogy to the method described in Example 1 in 16.8 mg yield (E190, y=27%) from 1-(2,6-difluorophenyl)-octahydropyrrolo[3,4-b]pyrrole (p80, 30 mg, 0.134 mmol) and 3-{5-[(3-chloropropyl)sulfanyl]-4-methyl-4H-1,2,4-triazol-3-yl}-2-methylpyridine (p47, 38 mg, 0.134 mmol). NMR: $^1$H NMR (Acetone-d$_6$) δ: 8.65 (m, 1H), 7.81 (m, 1H), 7.39 (m, 1H), 6.82-7.00 (m, 3H), 4.49 (br. s., 1H), 3.78-3.90 (m, 1H), 3.49 (s, 3H), 3.20-3.38 (m, 3H), 2.87-2.98 (m, 1H), 2.58-2.74 (m, 2H), 2.51 (m, 3H), 2.45 (s, 3H), 2.29 (m, 1H), 1.77-2.05 (m, 4H). MS (m/z): 471.4 [MH]$^+$.

Example 191: 4-methyl-3-(pyrrolidine-1-carbonyl)-5-[(3-{1-[4-(trifluoromethyl)phenyl]-octahydropyrrolo[3,4-b]pyrrol-5-yl}propyl)sulfanyl]-4H-1,2,4-triazole (E191)

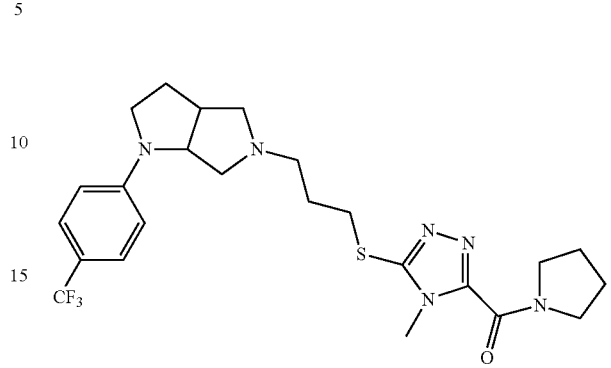

The title compound was prepared in analogy to the method described in Example 1 in 60 mg yield (E191, y=60%) from 1-[4-(trifluoromethyl)phenyl]-octahydropyrrolo[3,4-b]pyrrole (prepared as in p73, 50 mg, 0.195 mmol) and 3-[(3-chloropropyl)sulfanyl]-4-methyl-5-(pyrrolidine-1-carbonyl)-4H-1,2,4-triazole (p51, 62 mg, 0.214 mmol). NMR: $^1$H NMR (Acetone-d$_6$) δ: 7.47 (d, 2H), 6.71 (d, 2H), 4.25 (s, 1H), 3.93 (m, 2H), 3.75 (s, 3H), 3.58 (m, 2H), 3.48-3.56 (m, 1H), 3.32-3.45 (m, 2H), 3.22-3.32 (m, 1H), 2.97-3.05 (m, 1H), 2.71-2.78 (m, 2H), 2.43-2.62 (m, 4H), 2.14-2.25 (m, 1H), 1.88-2.04 (m, 7H). MS (m/z): 509.0 [MH]$^+$.

Example 192: 1-methyl-5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one (E192)

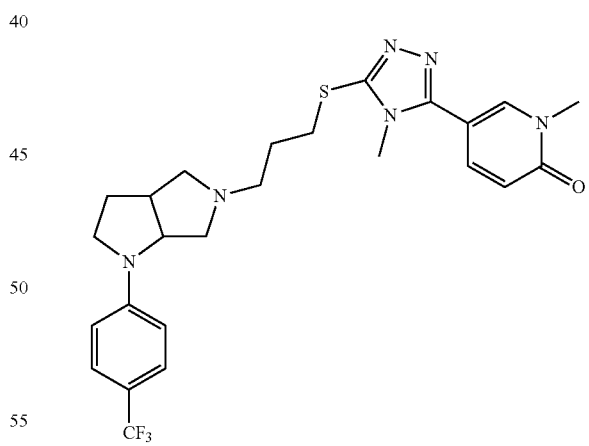

The title compound was prepared in analogy to the method described in Example 1 in 37 mg yield (E192, y=36%) from 1-[4-(trifluoromethyl)phenyl]-octahydropyrrolo[2,3-c]pyrrole (prepared as in p73, 50 mg, 0.195 mmol) and 5-{5-[(3-chloropropyl)sulfanyl]-4-methyl-4H-1,2,4-triazol-3-yl}-1-methyl-1,2-dihydropyridin-2-one (p53, 59 mg, 0.195 mmol). NMR: $^1$H NMR (Acetone-d$_6$) δ: 8.01-8.05 (m, 1H), 7.70-7.76 (m, 1H), 7.44-7.51 (m, 2H), 6.67-6.75 (m, 2H), 6.48-6.54 (m, 1H), 4.25 (m, 1H), 3.67 (s, 3H), 3.57-3.62 (m, 3H), 3.46-3.56 (m, 1H), 3.35-3.45 (m, 1H), 3.14-

3.35 (m, 2H), 3.01 (br. s., 1H), 2.71-2.77 (m, 2H), 2.42-2.64 (m, 4H), 2.15-2.22 (m, 1H), 1.86-2.04 (m, 3H). MS (m/z): 519.4[MH]+.

Example 193 and Example 194: 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one (E193, Enantiomer 1) and 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one (E194, Enantiomer 2)

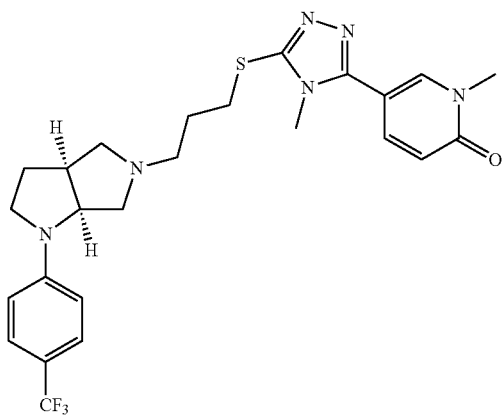 [SMILES: Cn1c(SCCCN2CC3CCN(c4ccc(C(F)(F)F)cc4)C3C2)nnc1-c1ccc(=O)n(C)c1]

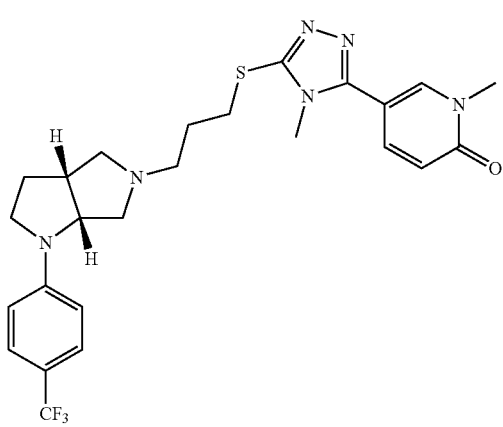

1-methyl-5-(4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl-1,2-dihydropyridin-2-one (E192, 32 mg) was separated into the single enantiomers by preparative chiral HPLC, obtaining 9.8 mg of 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one (E193, Enantiomer 1) and 5.5 mg of 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one (E194, Enantiomer 2)

Preparative Chromatography:

| Column | Chiralcel AD-H (25 × 2 cm), 5 µm |
|---|---|
| Mobile phase | n-Hexane/(Ethanol + 0.1% ipa) 50/50 v/v |
| Flow rate (mL/min) | 20 |
| DAD detection | 220 nm |
| Loop | 1500 µL |
| injection | 21 mg (each injection) |

Example 193 Enantiomer 1: ret. time 11.9 min, 100% ee MS (m/z): 519.4 [MH]+.

Example 194 Enantiomer 2: ret. time 22 min, 100% ee MS (m/z): 519.4 [MH]+.

Example 195: 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine-2-carboxamide (E195)

The title compound was prepared in analogy to the method described in Example 1 in 36 mg yield (E195, y=35%) from 1-[4-(trifluoromethyl)phenyl]-octahydropyrrolo[2,3-c]pyrrole (prepared as in p73, 50 mg, 0.195 mmol) and 5-{5-[(3-chloropropyl)sulfanyl]-4-methyl-4H-1,2,4-triazol-3-yl}pyridine-2-carboxamide (p56, 61 mg, 0.195 mmol). NMR: 1H NMR (DMSO-$d_6$) δ: 8.97-9.00 (m, 1H), 8.31-8.37 (m, 1H), 8.16-8.26 (m, 2H), 7.73-7.81 (m, 1H), 7.42-7.49 (m, 2H), 6.63-6.71 (m, 2H), 4.14-4.23 (m, 1H), 4.04-4.14 (m, 1H), 3.64 (s, 3H), 3.34-3.46 (m, 2H), 3.13-3.27 (m, 3H), 2.93 (br. s., 1H), 2.56-2.65 (m, 2H), 2.38-2.49 (m, 2H), 2.11 (m, 1H), 1.79-1.97 (m, 3H). MS (m/z): 532.4[MH]+.

Example 196 and Example 197: 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide (E196, Enantiomer 1) and 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide (E197, Enantiomer 2)

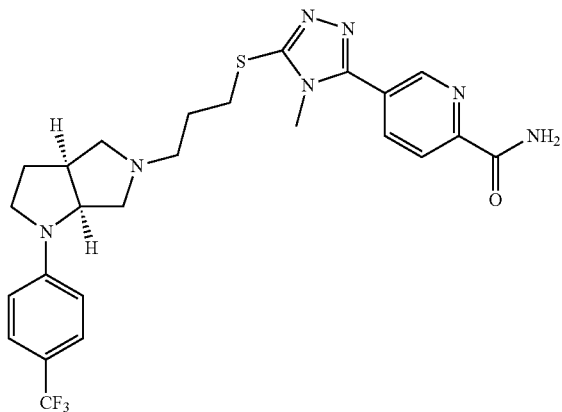 [SMILES: Cn1c(SCCCN2CC3CCN(c4ccc(C(F)(F)F)cc4)C3C2)nnc1-c1ccc(C(N)=O)nc1]

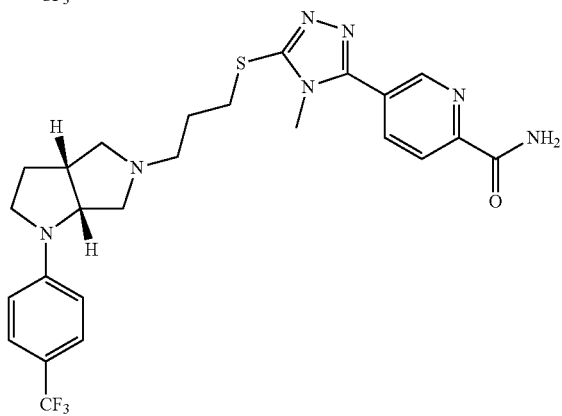

5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine-2-carboxamide (E195, 34 mg) was separated into the single enantiomers by preparative chiral HPLC, obtaining 12.2 mg of 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide (E196, Enantiomer 1) and 11 mg of 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide (E197, Enantiomer 2).
Preparative Chromatography:

| Column | Chiralcel OJ-H (25 × 2 cm), 5 μm |
|---|---|
| Mobile phase | n-Hexane/(Ethanol/Methanol + 0.1% ipa) 30/70 v/v |
| Flow rate (mL/min) | 20 |
| DAD detection | 220 nm |
| Loop | 1000 μL |
| injection | 17 mg (each injection) |

Example 196 Enantiomer 1: ret. time 12.4 min, 100% ee MS (m/z): 532.4 [MH]$^+$.

Example 197 Enantiomer 2: ret. time 16.5 min, 100% ee MS (m/z): 532.4 [MH]$^+$.

Example 198: 5-[5-({3-[1-(4-fluorophenyl)-octahydropyrrolo[3,4-b]pyrrol-5-yl]propyl}sulfanyl)-4-methyl-4H-1,2,4-triazol-3-yl]pyridine-2-carboxamide (E198)

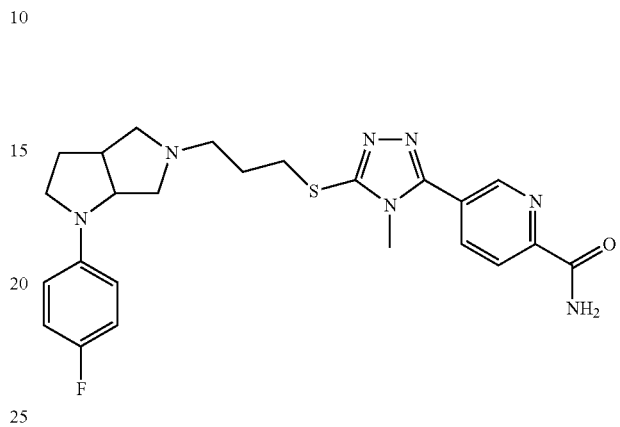

The title compound was prepared in analogy to the method described in Example 1 in 64.2 mg yield (E198, y=53%) from 1-(4-fluorophenyl)-octahydropyrrolo[3,4-b]pyrrole (p77, 50 mg, 0.24 mmol) and 5-{5-[(3-chloropropyl)sulfanyl]-4-methyl-4H-1,2,4-triazol-3-yl}pyridine-2-carboxamide (p56, 82 mg, 0.264 mmol). NMR: $^1$H NMR (Acetone-d$_6$) δ: 9.00 (m, 1H), 8.33-8.42 (m, 1H), 8.24-8.33 (m, 1H), 7.91-8.08 (m, 1H), 6.83-7.05 (m, 3H), 6.53-6.67 (m, 2H), 4.07-4.15 (m, 1H), 3.74-3.81 (m, 3H), 3.40-3.49 (m, 1H), 3.16-3.40 (m, 3H), 2.90-3.01 (m, 1H), 2.69-2.77 (m, 2H), 2.40-2.62 (m, 4H), 2.13-2.21 (m, 1H), 1.96 (m, 3H). MS (m/z): 482.4[MH]$^+$.

Example 199 and Example 200: 5-[5-({3-[(3aS,6aS or 3aR,6aR)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide (E199, Enantiomer 1) and 5-[5-({3-[(3aR,6aR or 3aS,6aS)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide (E200, Enantiomer 2)

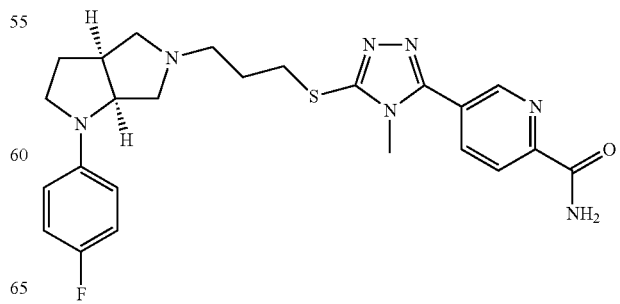

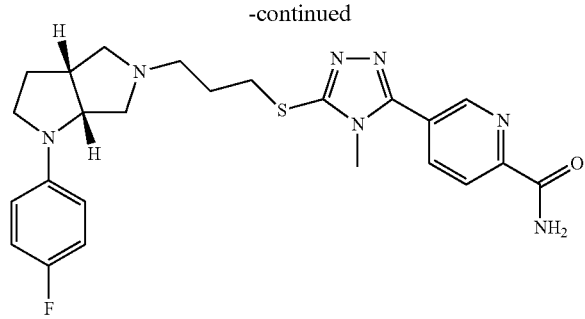

5-[5-({3-[1-(4-fluorophenyl)-octahydropyrrolo[3,4-b]pyrrol-5-yl]propyl}sulfanyl)-4-methyl-4H-1,2,4-triazol-3-yl]pyridine-2-carboxamide (E198, 60 mg) was separated into the single enantiomers by preparative chiral HPLC, obtaining 21 mg of 5-[5-({3-[(3aS,6aS or 3aR,6aR)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide (E199, Enantiomer 1) and 22.4 mg of 5-[5-({3-[(3aR,6aR or 3aS,6aS)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide (E200, Enantiomer 2)

Preparative Chromatography:

| | |
|---|---|
| Column | Chiralcel OJ-H (25 × 2 cm), 5 μm |
| Mobile phase | (Ethanol/Methanol + 0.1% ipa) 30/70 v/v |
| Flow rate (mL/min) | 18 |
| DAD detection | 220 nm |
| Loop | 4500 μL |
| injection | 30 mg (each injection) |

Example 199 Enantiomer 1: ret. time 16 min, 100% ee MS (m/z): 482.4 [MH]$^+$.

Example 200 Enantiomer 2: ret. time 26.1 min, 100% ee MS (m/z): 482.4 [MH]$^+$.

Example 201: 5-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide (E201)

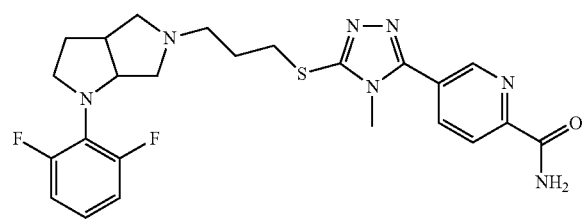 [SMILES: Cn1c(SCCCN2CC3CCN(c4c(F)cccc4F)C3C2)nnc1-c1ccc(C(N)=O)nc1]

The title compound was prepared in analogy to the method described in Example 1 in 36.3 mg yield (E201, y=49%) from 1-(2,6-difluorophenyl)-octahydropyrrolo[3,4-b]pyrrole (p80, 33.7 mg, 0.15 mmol) and 5-{5-[(3-chloropropyl)sulfanyl]-4-methyl-4H-1,2,4-triazol-3-yl}pyridine-2-carboxamide (p56, 51 mg, 0.165 mmol). NMR: $^1$H NMR (Acetone-d$_6$) δ: 8.98-9.02 (m, 1H), 8.35-8.41 (m, 1H), 8.27-8.33 (m, 1H), 7.95-8.08 (m, 1H), 6.83-6.96 (m, 4H), 4.44-4.54 (m, 1H), 3.78-3.90 (m, 4H), 3.24-3.41 (m, 3H), 2.92 (d, 1H), 2.57-2.71 (m, 2H), 2.44-2.57 (m, 3H), 2.28 (m, 1H), 1.88-2.04 (m, 3H), 1.77-1.86 (m, 1H). MS (m/z): 500.3[MH]$^+$.

Example 202 and Example 203: 5-[5-({3-[(3aS,6aS or 3aR,6aR)-1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide (E202, Enantiomer 1) and 5-[5-({3-[(3aR,6aR or 3aS,6aS)-1-(2,6-difluorophenyl)-octahydropyrrolo[3,4-b]pyrrol-5 yl]propyl}sulfanyl)-4-methyl-4H-1,2,4-triazol-3-yl]pyridine-2-carboxamide (E203, Enantiomer 2)

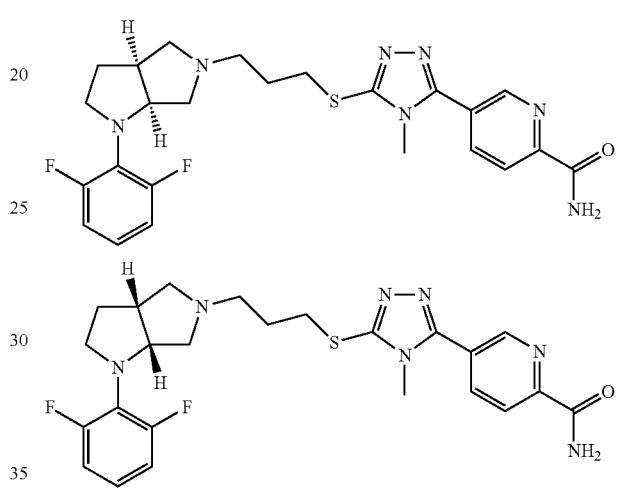

5-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide (E201, 33 mg) was separated into the single enantiomers by preparative chiral HPLC, obtaining 8.3 mg of 5-[5-({3-[(3aS,6aS or 3aR,6aR)-1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide (E202, Enantiomer 1) and 7.5 mg of 5-[5-({3-[(3aR,6aR or 3aS,6aS)-1-(2,6-difluorophenyl)-octahydropyrrolo[3,4-b]pyrrol-5yl]propyl}sulfanyl)-4-methyl-4H-1,2,4-triazol-3-yl]pyridine-2-carboxamide (E203, Enantiomer 2)

Preparative Chromatography:

| | |
|---|---|
| Column | Chiralpak OJ-H (25 × 2 cm), 5 μm |
| Modifier | (2-Propanol + 0.1% ipa) 22% v/v |
| Flow rate (mL/min) | 45 |
| Pressure (bar) | 120 |
| Temperature (° C.) | 38 |
| UV detection | 220 nm |
| Loop | 400 μL |
| injection | 6.6 mg (each injection) |

Example 202 Enantiomer 1: ret. time 12.7 min, 100% ee MS (m/z): 500.3 [MH]$^+$.

Example 203 Enantiomer 2: ret. time 14.6 min, 100% ee MS (m/z): 500.3 [MH]$^+$.

Example 204: 5-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyridine-2-carboxamide (E204)

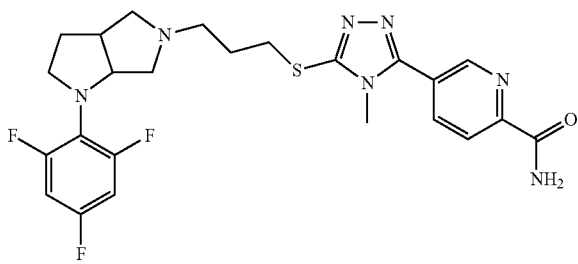 [SMILES: Cn1c(SCCCN2CC3CCN(c4c(F)cc(F)cc4F)C3C2)nnc1-c1ccc(C(N)=O)nc1]

The title compound was prepared in analogy to the method described in Example 1 in 32.3 mg yield (E204, y=50%) from 1-(2,4,6-trifluorophenyl)-octahydropyrrolo[2,3-c]pyrrole (p104, 30 mg, 0.124 mmol) and 5-{5-[(3-chloropropyl)sulfanyl]-4-methyl-4H-1,2,4-triazol-3-yl}pyridine-2-carboxamide (p56, 43 mg, 0.136 mmol). NMR: $^1$H NMR (Acetone-$d_6$) δ: 9.01 (m, 1H), 8.35-8.41 (m, 1H), 8.28-8.33 (m, 1H), 8.02 (br. s., 1H), 6.79-6.99 (m, 3H), 4.35 (br. s., 1H), 3.80-3.85 (m, 3H), 3.76 (m, 1H), 3.20-3.40 (m, 3H), 2.91 (br. s., 1H), 2.61-2.73 (m, 2H), 2.42-2.59 (m, 3H), 2.20-2.25 (m, 1H), 1.89-2.04 (m, 3H), 1.78-1.86 (m, 1H). MS (m/z): 518.3[MH]$^+$.

Example 205 and Example 206: 5-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide (E205, Enantiomer 1) and 5-[5-({3-[(3aR,6aR or 3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide (E206, Enantiomer 2)

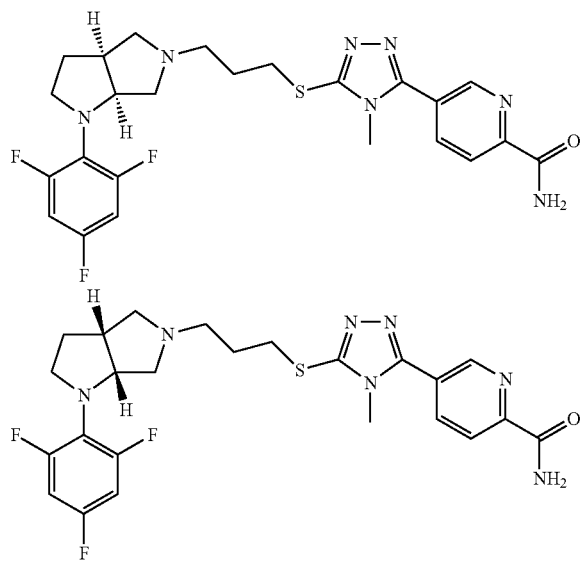

5-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyridine-2-carboxamide (E204, 28 mg) was separated into the single enantiomers by preparative chiral HPLC, obtaining 8.1 mg of 5-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide (E205, Enantiomer 1) and 10.4 mg of 5-[5-({3-[(3aR,6aR or 3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide (E206, Enantiomer 2).

Preparative Chromatography:

| | |
|---|---|
| Column | Chiralcel OJ-H (25 × 2 cm), 5 μm |
| Mobile phase | n-Hexane/(2-Propanol/Methanol + 0.1% ipa) 40/60 v/v |
| Flow rate (mL/min) | 18 |
| DAD detection | 220 nm |
| Loop | 1000 μL |
| injection | 5 mg (each injection) |

Example 205 Enantiomer 1: ret. time 9.7 min, 100% ee MS (m/z): 518.3 [MH]$^+$.

Example 206 Enantiomer 2: ret. time 11.2 min, 100% ee MS (m/z): 518.3 [MH]$^+$.

Example 207: 4-[5-({3-[1-(4-fluorophenyl)-octahydropyrrolo[3,4-b]pyrrol-5-yl]propyl}sulfanyl)-4-methyl-4H-1,2,4-triazol-3-yl]-1-methyl-1,2-dihydropyridin-2-one (E207)

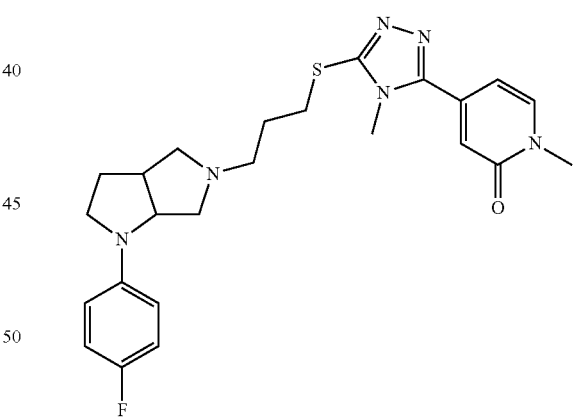

The title compound was prepared in analogy to the method described in Example 1 in 71 mg yield (E207, y=63%) from 1-(4-fluorophenyl)-octahydropyrrolo[3,4-b]pyrrole (p77, 50 mg, 0.24 mmol) and 4-{5-[(3-chloropropyl)sulfanyl]-4-methyl-4H-1,2,4-triazol-3-yl}-1-methyl-1,2-dihydropyridin-2-one (p58, 72 mg, 0.21 mmol). NMR: $^1$H NMR (Acetone-$d_6$) δ: 7.74 (d, 1H), 6.90-7.01 (m, 2H), 6.71 (d, 1H), 6.54-6.63 (m, 3H), 4.01-4.20 (m, 1H), 3.77 (s, 3H), 3.56 (s, 3H), 3.45 (d, 1H), 3.15-3.39 (m, 4H), 2.97 (br. s., 1H), 2.73 (br. s., 2H), 2.38-2.63 (m, 3H), 2.11-2.21 (m, 1H), 1.84-2.02 (m, 3H). MS (m/z): 469.3[MH]$^+$.

Example 208: 1-methyl-4-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]-1,2-dihydropyridin-2-one (E208)

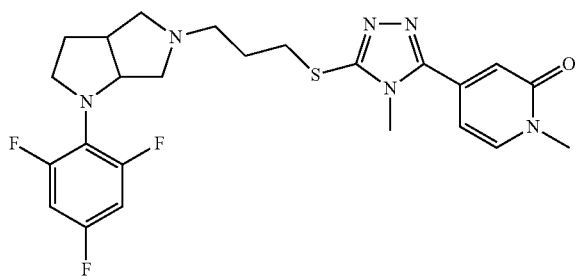 [SMILES: Cn1c(SCCCN2CC3CCN(c4c(F)cc(F)cc4F)C3C2)nnc1-c1ccn(C)c(=O)c1]

The title compound was prepared in analogy to the method described in Example 1 in 32 mg yield (E208, y=51%) from 1-(2,4,6-trifluorophenyl)-octahydropyrrolo[2,3-c]pyrrole (p104, 30 mg, 0.195 mmol) and 4-{5-[(3-chloropropyl)sulfanyl]-4-methyl-4H-1,2,4-triazol-3-yl}-1-methyl-1,2-dihydropyridin-2-one (p58, 41 mg, 0.136 mmol). NMR: $^1$H NMR (Acetone-$d_6$) δ: 7.75 (d, 1H), 6.83-6.91 (m, 2H), 6.72 (d, 1H), 6.60 (m, 1H), 4.30-4.37 (m, 1H), 3.79 (s, 3H), 3.70-3.78 (m, 1H), 3.56 (s, 3H), 3.20-3.36 (m, 3H), 2.86-2.95 (m, 1H), 2.60-2.71 (m, 2H), 2.42-2.58 (m, 3H), 1.86-2.03 (m, 4H), 1.77-1.86 (m, 1H). MS (m/z): 505.3[MH]$^+$.

Example 209 and Example 210: 4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one (E209, Enantiomer 1) and 4-[5-({3-[(3aR,6aR or 3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one (E210, Enantiomer 2)

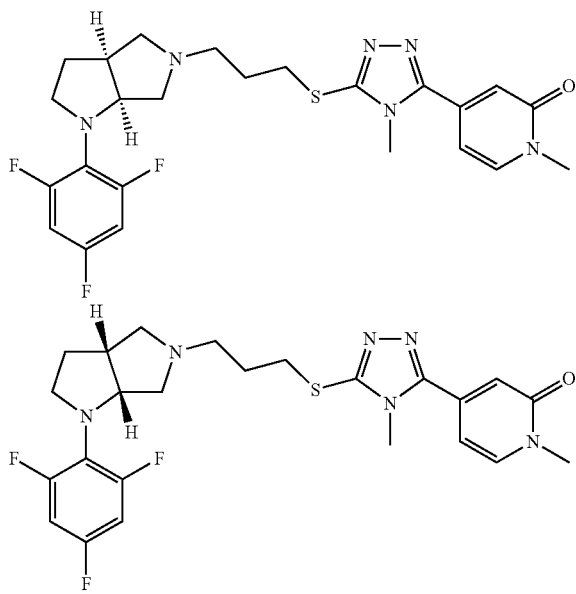

1-methyl-4-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]-1,2-dihydropyridin-2-one (E208, 28 mg) was separated into the single enantiomers by preparative chiral HPLC, obtaining 10.9 mg of 4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one (E209, Enantiomer 1) and 12.7 mg of 4-[5-({3-[(3aR,6aR or 3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one (E210, Enantiomer 2).

Preparative Chromatography:

| | |
|---|---|
| Column | Chiralcel OJ-H (25 × 2 cm), 5 μm |
| Mobile phase | n-Hexane/(Ethanol/Methanol1/1 + 0.1% ipa) 30/70 v/v |
| Flow rate (mL/min) | 17 |
| DAD detection | 220 nm |
| Loop | 1000 μL |
| injection | 7 mg (each injection) |

Example 209 Enantiomer 1: ret. time 5.4 min, 100% ee MS (m/z): 505.3 [MH]$^+$.

Example 210 Enantiomer 2: ret. time 6.2 min, 100% ee MS (m/z): 505.3 [MH]$^+$.

Example 211: 4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one dihydrochloride (E211, Enantiomer 1)

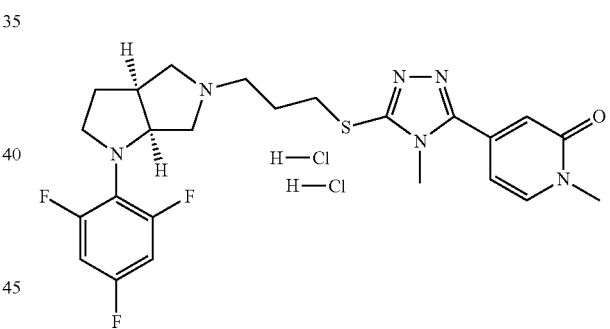

4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one (E209, Enantiomer 1, 10.9 mg) was dissolved in Et$_2$O and treated with 2.2. eq of 2N HCl in Et$_2$O to afford, after evaporation, 11.1 mg of title compound (E211, Enantiomer 1). MS (m/z): 505.3 [MH]$^+$.

Preparation 108: 4-methyl-3-(methylsulfanyl)-5-(oxan-4-yl)-4H-1,2,4-triazole

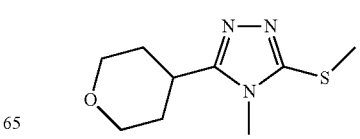

To a solution of 4-methyl-5-(oxan-4-yl)-4H-1,2,4-triazole-3-thiol (p4, 500 mg, 2.5 mmol) in EtOH (3.75 mL) iodomethane (187 µL, 3 mmol) was added drop wise. The resulting mixture was stirred at 80° C. for 30'. Solvent was evaporated under vacuum, the residue was dissolved in NaOH 1 M and extracted three times with DCM. Combined organics were dried over Na$_2$SO$_4$ and concentrated to obtain 482 mg of title compound (p108, y=90%) as white solid. MS (m/z): 214.2 [MH]$^+$.

Preparation 109: 3-methanesulfonyl-4-methyl-5-(oxan-4-yl)-4H-1,2,4-triazole

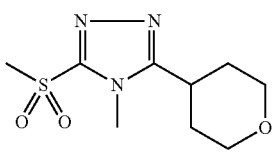 [SMILES: Cn1c(C2CCOCC2)nnc1S(C)(=O)=O]

To a solution of 4-methyl-3-(methylsulfanyl)-5-(oxan-4-yl)-4H-1,2,4-triazole (p108, 482 mg, 2.26 mmol) in DCM (6 mL) 3-chloro perbenzoic acid (1.17 g, 6.78 mmol) was added portionwise. The resulting mixture was stirred at RT for 3 hrs. EtOAc was added to complete dissolution, followed by NaHCO$_3$ ss. Phases were separated and the aqueous one was backextracted before with EtOAc and after with DCM. Combined organics were dried over Na$_2$SO$_4$ and concentrated to obtain 412 mg of title compound (p109, y=71%) as white solid. MS (m/z): 246. I[MH]$^+$.

Preparation 110: 5-{3-[(tert-butyldimethylsilyl)oxy]propyl}-1-[4-(trifluoromethyl)-phenyl]-octahydropyrrolo[3,4-b]pyrrole

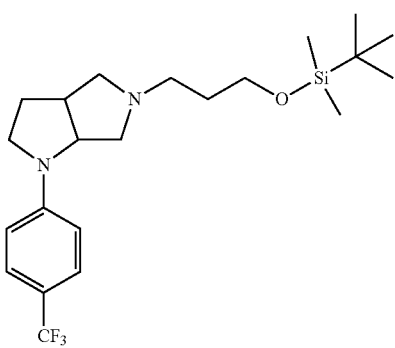 [SMILES: CC(C)(C)[Si](C)(C)OCCCN1CC2CCN(c3ccc(C(F)(F)F)cc3)C2C1]

A mixture of 1-[4-(trifluoromethyl)phenyl]-octahydropyrrolo[3,4-b]pyrrole (prepared as in p73, 121 mg, 0.47 mmol), (3-bromopropoxy) (tert-butyl) dimethylsilane (0.163 mL, 0.705 mmol), TEA (0.197 mL, 1.41 mmol), NaI (14 mg, 0.094 mmol) in THF (2 mL) was stirred at RT on. The reaction was heated to 65° C. and stirred for 5 hrs, then it was left standing at RT over weekend. The mixture was concentrated under reduced pressure and the residue partitioned between water and DCM. Organic phase was separated, dried and concentrated under reduced pressure. Crude material was then purified by FC on SiO$_2$ cartridge (eluting from cHex to 20% EtOAc) affording 175 mg of title compound (p110, y=87%). MS (m/z): 429.5 [MH]$^+$.

Preparation 111: 3-{1-[4-(trifluoromethyl)phenyl]-octahydropyrrolo[3,4-b]pyrrol-5-yl}propan-1-ol

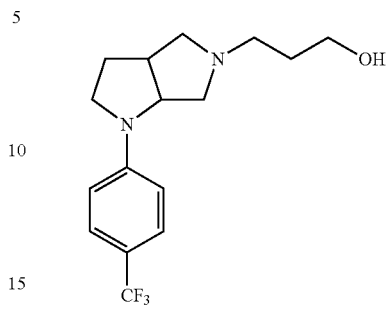

5-{3-[(tert-butyldimethylsilyl)oxy]propyl}-1-[4-(trifluoromethyl)phenyl]-octahydropyrrolo[3,4-b]pyrrole (p110, 175 mg, 0.41 mmol) was dissolved in THF (2 mL) and treated with HCl 1 M (2 mL). The mixture was left stirring at RT for 1 hr, then THF was evaporated and the residue was neutralized with NaHCO$_3$ ss and extracted with DCM. Organic phase was dried and concentrated affording 105 mg of title compound (p111, y=81%) that was used as such in the next step. MS (m/z): 315.3 [MH]$^+$.

Example 212: 4-methyl-3-(oxan-4-yl)-5-(3-{1-[4-(trifluoromethyl)phenyl]-octahydro-pyrrolo[3,4-b]pyrrol-5-yl}propoxy)-4H-1,2,4-triazole (E212)

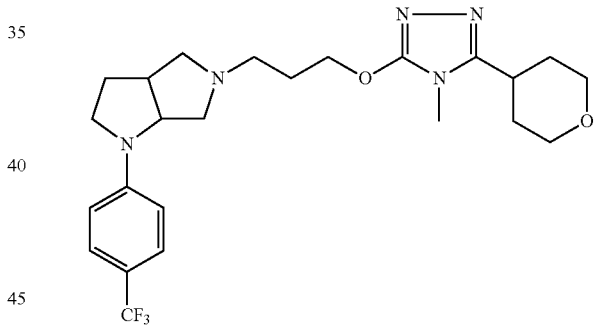

To a solution of 3-{1-[4-(trifluoromethyl)phenyl]-octahydropyrrolo[3,4-b]pyrrol-5-yl}propan-1-ol (p111, 55 mg, 0.17 mmol) in DMF (1.5 mL), 3-methanesulfonyl-4-methyl-5-(oxan-4-yl)-4H-1,2,4-triazole (p109, 43 mg, 0.17 mmol) was added followed by NaH 60% in mineral oil (10 mg, 0.255 mmol) and the mixture was shaken in a PLS apparatus at 60° C. for 4 hrs. Further NaH was added (2×10 mg) and the mixture was shaken for an overall time of 40 hrs at 60° C. The reaction was cooled down to RT, quenched with water and extracted with DCM. Organic phase was dried and concentrated under reduced pressure. Crude material was purified by FC on SiO$_2$ cartridge (eluting from DCM to 10% MeOH) and then further purified by FC on NH cartridge (eluting from cHex to EtOAc) affording 22 mg of title compound (E212, y=27%). NMR: $^1$H NMR (Acetone-d$_6$) δ: 7.45 (d, 2H), 6.68 (d, 2H), 4.39 (dt, 2H), 4.22 (s, 1H), 3.94 (dt, 2H), 3.43-3.55 (m, 3H), 3.30-3.41 (m, 4H), 2.87-3.04 (m, 2H), 2.68-2.77 (m, 2H), 2.40-2.65 (m, 4H), 2.11-2.26 (m, 1H), 1.74-2.02 (m, 7H). MS (m/z): 480.5 [MH]$^+$.

Preparation 112: oxane-4-carbohydrazide

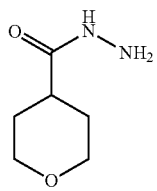

To a stirred solution of methyl tetrahydro-2H-pyran-4-carboxylate (4 g, 27.75 mmol) in MeOH (50 mL) at RT, hydrazine monohydrate (10.8 mL, 222 mmol) was added portion-wise and the resulting reaction mixture was stirred at reflux ON. The mixture was allowed to reach RT and concentrated under vacuum affording 3.9 g of title compound (p112, y=98%) as white solid. MS (m/z): 145.1 [MH]$^+$.

Preparation 113: methyl hex-5-enecarboximidate hydrochloride

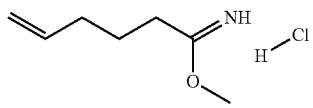

To a stirred solution of 5-hexenenitrile (2 g, 21.02 mmol) and MeOH (0.96 mL) in Et$_2$O (20 mL), at 0° C., HCl gas was bubbled for 10 min. The reaction mixture was concentrated under vacuum and the brown oil was taken up with ether. The solid was filtered, washed with ether and dried under vacuum affording 1.20 g, of title compound (p113, y=42%) as white solid that was used as such in the next step. NMR: (DMSO-d$_6$) δ: 11.34-11.86 (m, 1H), 5.68-5.89 (m, 1H), 4.93-5.11 (m, 2H), 3.98-4.14 (m, 3H), 2.56-2.69 (m, 2H), 2.00-2.13 (m, 2H), 1.62-1.78 (m, 2H)

Preparation 114: N,N'-dimethylhexa-5-enimidamide hydrochloride

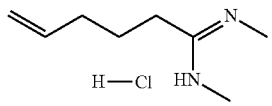

To a stirred solution of methyl hex-5-enecarboximidate hydrochloride (p113, 1.29 g, 7.88 mmol) in MeOH (6 mL), at RT, a 33% wt. solution of MeNH$_2$ in ethanol (5.9 mL, 47.28 mmol) was added and the resulting reaction mixture was stirred at reflux for 6 hrs and ON at RT. The mixture was then concentrated under vacuum affording crude N,N'-dimethylhexa-5-enimidamide hydrochloride (p114, 1.47 g) as pale brown oil that was used as such in the next step. MS (m/z): 141.1 [MH]$^+$.

Preparation 115: 4-methyl-3-(oxan-4-yl)-5-(pent-4-en-1-yl)-4H-1,2,4-triazole

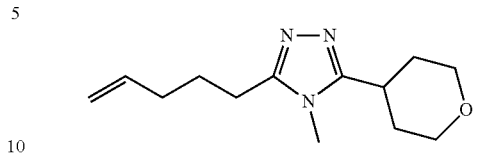

A suspension of N,N'-dimethylhexa-5-enimidamide hydrochloride (p114, 1.47 g, 8.32 mmol), oxane-4-carbohydrazide (p112, 1.20 g, 8.32) and K$_2$CO$_3$ (1.15 g, 8.32 mmol) in MeOH (50 mL) was heated to reflux and stirred for 24 hrs. The mixture was then filtered and the organic solution was concentrated under vacuum. The crude material was purified by FC on SiO$_2$ cartridge (eluting from DCM to 10% MeOH) to give two batches of the title compound 4-methyl-3-(oxan-4-yl)-5-(pent-4-en-1-yl)-4H-1,2,4-triazole (p115, batch 1: 0.20 g, purity >80% by NMR and batch 2: 0.75 g, purity <70% by NMR). NMR: $^1$H NMR (CDCl$_3$) d: 5.74-5.91 (m, 1H), 4.94-5.12 (m, 2H), 3.99-4.17 (m, 2H), 3.53-3.61 (m, 2H), 3.52 (s, 3H), 2.87-2.96 (m, 1H), 2.70-2.77 (m, 2H), 2.05-2.25 (m, 4H), 1.83-2.02 (m, 3H)

Example 213: 4-methyl-3-(oxan-4-yl)-5-(4-{1-[4-(trifluoromethyl)phenyl]-octahydropyrrolo[2,3-c]pyrrol-5-yl}butyl)-4H-1,2,4-triazole (E213)

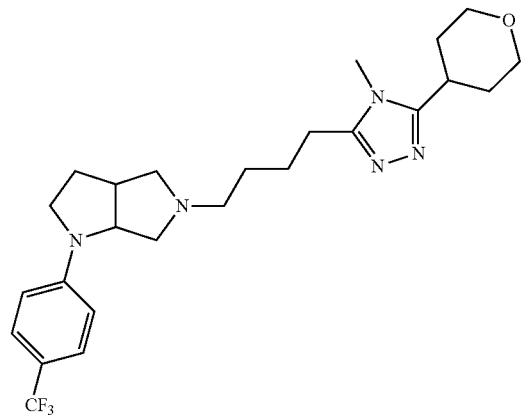 [SMILES: Cn1c(CCCCN2CC3CCN(c4ccc(C(F)(F)F)cc4)C3C2)nnc1C1CCOCC1]

Step A: To a solution of 4-methyl-3-(oxan-4-yl)-5-(pent-4-en-1-yl)-4H-1,2,4-triazole (p115, 190 mg, 0.81 mmol) in THF/H$_2$O (7/1.4 mL) were subsequently added OsO$_4$ (0.28 mL, 0.041 mmol, 4% solution in water) and NaIO$_4$ (520 mg, 2.43 mmol). The reaction mixture was stirred ON at RT. Water was added and the mixture was extracted with DCM. The organic phase was dried and the solvent removed under vacuum affording 84 mg of 4-methyl-3-(oxan-4-yl)-5-(pent-4-en-1-yl)-4H-1,2,4-triazole as colorless oil that was used as such.

Step B: To a solution of 4-methyl-3-(oxan-4-yl)-5-(pent-4-en-1-yl)-4H-1,2,4-triazole (from Step A, 80 mg) and 1-[4-(trifluoromethyl)phenyl]-octahydropyrrolo[2,3-c]pyrrole (prepared as in p73, 86 mg, 0.34 mmol) in DCM (2.5 mL), at RT and under a nitrogen atmosphere, sodium triacetoxyborohydride (108 mg, 0.51 mmol) was added portion-wise and the resulting reaction mixture was stirred ON. A solution of concentrated ammonium chloride was added, the mixture was diluted with DCM, the organic phase was washed with water, dried over sodium sulfate and the solvent removed under vacuum. The crude material was purified by FC on SiO$_2$ cartridge (eluting from DCM to 15% MeOH) affording 81 mg of title compound (E213, y=49%). NMR: $^1$H NMR (CHLOROFORM-d$_6$) δ: 7.39-7.51 (m, 2H), 6.52-6.62 (m, 2H), 4.22 (br. s., 1H), 4.07-4.15 (m, 2H), 3.54 (dd, 3H), 3.45 (s, 3H), 3.31-3.40 (m, 1H), 2.97-3.10 (m, 1H), 2.83-2.93 (m, 1H), 2.59-2.83 (m, 6H), 2.53 (br. s., 2H), 2.06 (s, 4H), 1.93-2.03 (m, 1H), 1.76-1.90 (m, 4H), 1.66 (br. s., 1H). MS (m/z): 478.5[MH]$^+$.

Example 214 and Example 215: 3-{4-[(3aS,6aS or 3aR,6aR)-1-[4-(trifluoromethyl)phenyl]-octahydropyrrolo[3,4-b]pyrrol-5-yl]butyl}-4-methyl-5-(oxan-4-yl)-4H-1,2,4-triazole (E214, Enantiomer 1) and 3-{4-[(3aR,6aR or 3aS,6aS)-1-[4-(trifluoromethyl)phenyl]-octahydropyrrolo[3,4-b]pyrrol-5-yl]butyl}-4-methyl-5-(oxan-4-yl)-4H-1,2,4-triazole (E215, Enantiomer 2)

Preparative Chromatography:

| Column | Chiralpak AD-H (25 × 2 cm), 5 μm |
|---|---|
| Modifier | (Methanol + 0.1% ipa) 25% |
| Flow rate (mL/min) | 46 |
| Pressure (bar) | 120 |
| Temperature (° C.) | 38 |
| UV detection | 220 nm |
| Loop | 500 μL |
| injection | 20.2 mg (each injection) |

Example 214 Enantiomer 1: ret. time 6.9 min MS (m/z): 478.5 [MH]$^+$.

Example 215 Enantiomer 2: ret. time 13.4 min MS (m/z): 478.5 [MH]$^+$.

Example 216: 3-{4-[(3aS,6aS or 3aR,6aR)-1-[4-(trifluoromethyl)phenyl]-octahydropyrrolo[3,4-b]pyrrol-5-yl]butyl}-4-methyl-5-(oxan-4-yl)-4H-1,2,4-triazole dihydrochloride (E216, Enantiomer 1)

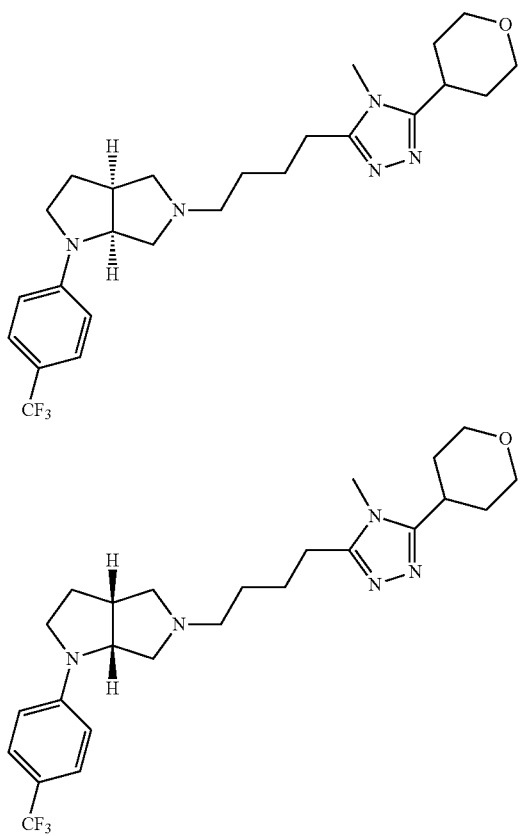

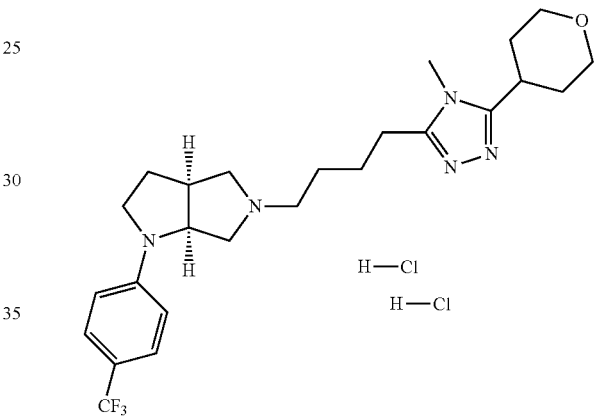

3-{4-[(3aS,6aS or 3aR,6aR)-1-[4-(trifluoromethyl)phenyl]-octahydropyrrolo[3,4-b]pyrrol-5-yl]butyl}-4-methyl-5-(oxan-4-yl)-4H-1,2,4-triazole (E214, Enantiomer 1, 25 mg) was dissolved in DCM and treated with 2.2. eq of 2N HCl in Et$_2$O to afford, after evaporation, 26 mg of title compound (E216, Enantiomer 1). MS (m/z): 478.5 [MH]$^+$.

Preparation 116: ({[(tert-butoxy)carbonyl]amino}amino)(4-methyl-1,3-oxazol-5-yl)methanone

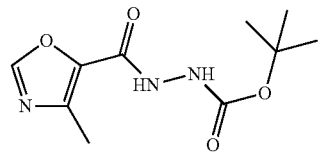 [SMILES: Cc1ncoc1C(=O)NNC(=O)OC(C)(C)C]

4-methyl-3-(oxan-4-yl)-5-(4-{1-[4-(trifluoromethyl)phenyl]-octahydropyrrolo[2,3-c]pyrrol-5-yl}butyl)-4H-1,2,4-triazole (E213, 81 mg) was separated into the single enantiomers by preparative chiral HPLC, obtaining 25 mg of 3-{4-[(3aS,6aS or 3aR,6aR)-1-[4-(trifluoromethyl)phenyl]-octahydropyrrolo[3,4-b]pyrrol-5-yl]butyl}-4-methyl-5-(oxan-4-yl)-4H-1,2,4-triazole (E214, Enantiomer 1) and 26 mg of and 3-{4-[(3aR,6aR or 3aS,6aS)-1-[4-(trifluoromethyl)phenyl]-octahydropyrrolo[3,4-b]pyrrol-5-yl]butyl}-4-methyl-5-(oxan-4-yl)-4H-1,2,4-triazole (E215, Enantiomer 2).

To a stirred suspension of 4-methyl-1,3-oxazole-5-carboxylic acid (1.0 g, 7.87 mmol) in DCM (10 mL), at RT, oxalyl chloride (1.5 mL, 11.81 mmol) was added portionwise followed after 3 min by a catalytic amount of DMF (4 drops) and the resulting reaction mixture was stirred at RT for 2 hrs then the clear mixture was concentrated under reduced pressure. The residue was dissolved in DCM (5 mL) and this solution was added drop-wise to a stirred solution of tert-butyl carbazate (3.64 g, 27.55 mmol) and TEA (4.1 mL, 11.02 mmol) in DCM (10 mL), at 0° C. and under a nitrogen atmosphere. The resulting reaction mixture was stirred at 0° C. for 3 hrs then it was allowed to reach RT and stirred ON. The mixture was concentrated under vacuum and the residue was taken up with EA and water. The organic phase was washed with water, saturated ammonium chloride solution, dried over sodium sulfate and the solvent removed under reduced pressure. The crude material was purified by FC on $SiO_2$ cartridge (eluting from Cy to 60% EA) to give 2.45 g of title compound (p116, y=quant.) as white waxy solid. MS (m/z): 242.2 $[MH]^+$.

Preparation 117:
4-methyl-1,3-oxazole-5-carbohydrazide

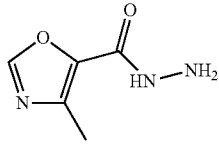

To a stirred solution of ({[(tert-butoxy)carbonyl]amino}amino)(4-methyl-1,3-oxazol-5-yl)methanone (p116, 1.23 g, 5.1 mmol) in dioxane (5 mL), at RT, 4N/dioxane HCl (26 mL) was added portion-wise and the resulting reaction mixture was stirred at RT for 3 hrs. The mixture was filtered and the solid was dried under vacuum ON then it was loaded on a SCX (eluting with MeOH and 2N $NH_3$/MeOH) affording 366 mg of title compound (p117, y=51%) as light yellow solid. NMR: (DMSO-$d_6$) δ: 9.68 (br. s., 1H), 8.38 (s, 1H), 4.47 (br. s., 2H), 2.37 (s, 3H)

Preparation 118: 4-methyl-3-(4-methyl-1,3-oxazol-5-yl)-5-(pent-4-en-1-yl)-4H-1,2,4-triazole

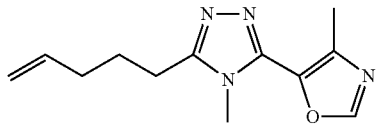 [SMILES: C=CCCCc1nnc(-c2ocnc2C)n1C]

A mixture of N,N'-dimethylhexa-5-enimidamide hydrochloride (p114, 458 mg, 2.59 mmol), 4-methyl-1,3-oxazole-5-carbohydrazide (p117, 366 mg, 2.59 mmol) and $K_2CO_3$ (537 mg, 3.89 mmol) in MeOH (20 mL) was refluxed for 32 hrs. The mixture was then allowed to reach RT, concentrated under reduced pressure and the residue was taken-up with DCM and concentrated aqueous sodium bicarbonate solution. The organic phase was washed with water, dried over sodium sulphate and the solvent removed under vacuum. The crude material was purified by FC on $SiO_2$ cartridge (eluting with DCM/MeOH from 100/0 to 96/4) then further purified by FC on NH column (eluting with Cy/EA from 100/0 to 65/35) affording 107 mg of title compound (p118, y=18%) as pale yellow waxy solid. MS (m/z): 233.2 $[MH]^+$.

Example 217: 3-{4-[1-(4-fluorophenyl)-octahydro-pyrrolo[2,3-c]pyrrol-5-yl]butyl}-4-methyl-5-(4-methyl-1,3-oxazol-5-yl)-4H-1,2,4-triazole dihydrochloride (E217)

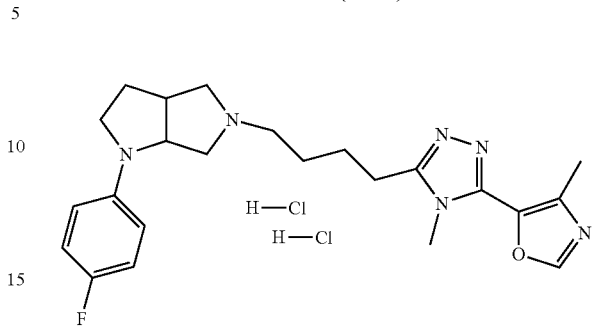

Step A: To a solution of 4-methyl-3-(4-methyl-1,3-oxazol-5-yl)-5-(pent-4-en-1-yl)-4H-1,2,4-triazole (p118, 107 mg, 0.46 mmol) in THF/$H_2O$ (4/00.8 mL) were subsequently added $OsO_4$ (0.15 mL, 4% solution in water, 0.023 mmol) and $NaIO_4$ (295 mg, 1.38 mmol). The reaction mixture was stirred ON at RT. Water was added and the mixture was extracted with DCM. The organic phase was dried over sodium sulfate and the solvent removed under vacuum affording 4-[4-methyl-5-(4-methyl-1,3-oxazol-5-yl)-4H-1,2,4-triazol-3-yl]butanal (107 mg) that was used as crude in the next step.

Step B: In a vial a solution of 4-[4-methyl-5-(4-methyl-1,3-oxazol-5-yl)-4H-1,2,4-triazol-3-yl]butanal (53 mg from step A) and 1-(4-fluorophenyl)-octahydropyrrolo[2,3-c]pyrrole (p77.42 mg, 0.2 mmol) in DCM (0.6 mL) was shaken for 10 min at RT then Na(AcO)$_3$BH (73 mg, 0.35 mmol) was added portion-wise and the resulting reaction mixture was shaken ON at RT in a PLS apparatus. The mixture was diluted with DCM and washed with concentrated sodium bicarbonate solution. The organic phase was dried over sodium sulfate and the solvent removed under vacuum. The residue was purified by FC on SiO2 (eluent: DCM to 5% MeOH), and then purified again by FC on NH (eluent: from Cy to 55% EtOAC) to give 3-{4-[1-(4-fluorophenyl)-octahydropyrrolo[2,3-c]pyrrol-5-yl]butyl}-4-methyl-5-(4-methyl-1,3-oxazol-5-yl)-4H-1,2,4-triazole (16 mg, y=19%).

Step C: 3-{4-[1-(4-fluorophenyl)-octahydropyrrolo[2,3-c]pyrrol-5-yl]butyl}-4-methyl-5-(4-methyl-1,3-oxazol-5-yl)-4H-1,2,4-triazole (19 mg, from step B) was dissolved in DCM (0.2 mL) then 2N HCl/ether (0.041 mL) was added and the reaction mixture was concentrated under vacuum. The solid so obtained was triturated with ether and dried under vacuum at 45° C. ON affording 3-{4-[1-(4-fluorophenyl)-octahydropyrrolo[2,3-c]pyrrol-5-yl]butyl}-4-methyl-5-(4-methyl-1,3-oxazol-5-yl)-4H-1,2,4-triazole dihydrochloride (E217, 17 mg, y=90%) as white solid. NMR: $^1$H NMR (DMSO-$d_6$) δ: 10.55-10.71 (m, 1H), 10.08-10.29 (m, 1H), 8.56 (s, 1H), 7.06 (m, 2H), 6.55-6.67 (m, 2H), 4.34 (br. s., 1H), 3.01-3.83 (m, 11H), 2.65-2.96 (m, 3H), 2.35 (s, 3H), 1.98-2.23 (m, 2H), 1.71-1.97 (m, 4H). MS (m/z): 425.4 $[MH]^+$.

Preparation 119: 3-{4-[(tert-butyldimethylsilyl)oxy]cyclohexyl}-5-[(3-chloropropyl)sulfanyl]-4-methyl-4H-1,2,4-triazole

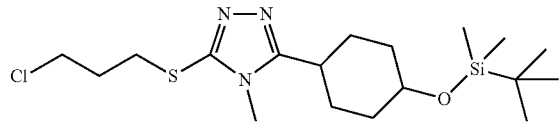 [SMILES: Cn1c(SCCCCl)nnc1C1CCC(O[Si](C)(C)C(C)(C)C)CC1]

Step a: To a stirred solution of 4-oxocyclohexane-1-carboxylic acid (1.0 g, 7.03 mmol) in MeOH (65 mL), at RT, sodium borohydride (0.53 g, 14.07 mmol) was added portion-wise and the resulting reaction mixture was stirred at RT for 1 h. The mixture was then concentrated under vacuum and the residue was taken up with DCM and aqueous 1N HCl. The organic phase was washed with water, dried and concentrated under reduced pressure to give 4-hydroxycyclohexane-1-carboxylic acid (0.62 g) that was used as such in the next step.

Step b: To a stirred solution of 4-hydroxycyclohexane-1-carboxylic acid (0.62 g from step a) and imidazole (0.59 g, 8.60 mmol) in DMF (4 mL), at RT, TBDMSCl (0.71 g, 4.63 mmol) was added portion-wise and the resulting reaction mixture was stirred ON at RT. Ether and aqueous 1 M HCl were added, the organic phase was washed with aqueous 1 M HCl, brine, dried over sodium sulfate and the solvent removed under vacuum affording 4-[(tert-butyldimethylsilyl)oxy]cyclohexane-1-carboxylic acid (0.80 g) that was used as crude in the next step.

Step c: To a stirred solution of 4-[(tert-butyldimethylsilyl)oxy]cyclohexane-1-carboxylic acid (0.80 g from step b) in DMF (4 mL), 4-methyl-3-thiosemicarbazide (0.36 g, 3.41 mmol) and DIPEA (1.0 mL, 5.56 mmol) were subsequently added. The mixture was cooled to 0° C. then T3P (50% wt/EA) (2.8 mL, 4.64 mmol) was added portion-wise. The ice-bath was removed and the resulting reaction mixture was stirred ON at RT. Aqueous 4 M NaOH solution was added (resulting pH~8) and the two resulting phases were separated (the upper organic layer was eliminated). Additional 4 M NaOH was added up to pH~11 then the mixture was heated to 70° C. and stirred for 40 min. After allowing the mixture to reach RT, aqueous 37% HCl was added up to pH~5 and the mixture extracted with EA. The organic phase was washed with water, dried over sodium sulfate and the solvent removed under reduced pressure to give 4-(4-methyl-5-sulfanyl-4H-1,2,4-triazol-3-yl)cyclohexan-1-one (0.17 g) that was used as crude in the next step.

Step d: To a solution of 5-(4-[(tert-butyldimethylsilyl)oxy]cyclohexyl)-4-methyl-4H-1,2,4-triazole-3-thiol (170 mg from step c) in MeOH/Acetone (0.8 mL/1.9 mL) at RT, 1-bromo-3-chloropropane (0.067 mL, 0.67 mmol) was added followed by K₂CO₃ (101 mg, 0.73 mmol) and the resulting reaction mixture was stirred ON at RT. The mixture was diluted with EA, filtered and concentrated under reduced pressure. The crude material was purified by FC on SiO₂ cartridge (eluting from Cy to 50% EA) to give 3-{4-[(tert-butyldimethylsilyl)oxy]cyclohexyl}-5-[(3-chloropropyl)sulfanyl]-4-methyl-4H-1,2,4-triazole (p119, 142 mg as mixture of isomers). MS (m/z): 404.4 [MH]⁺.

Preparation 120: 3-{4-[(tert-butyldimethylsilyl)oxy]cyclohexyl}-4-methyl-5-[(3-{1-[4-(trifluoromethyl)phenyl]-octahydropyrrolo[2,3-c]pyrrol-5-yl}propyl)sulfanyl]-4H-1,2,4-triazole

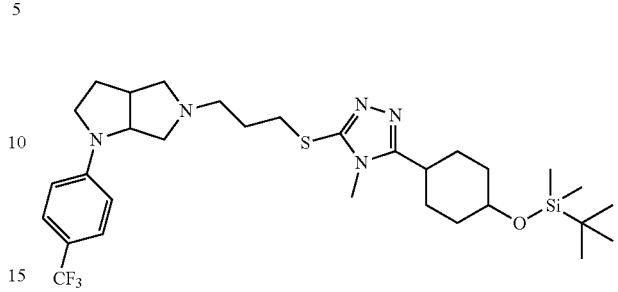

A sealed vial containing a mixture of 1-[4-(trifluoromethyl)phenyl]-octahydropyrrolo[2,3-c]pyrrole (prepared as in p73, 88 mg, 0.34 mmol), 3-{4-[(tert-butyldimethylsilyl)oxy]cyclohexyl}-5-[(3-chloropropyl)sulfanyl]-4-methyl-4H-1,2,4-triazole (p119, 126 mg, 0.31 mmol), Na₂CO₃ (39 mg, 0.37 mmol) and NaI (46 mg, 0.31 mmol) and DMF (0.4 mL) was shaken ON at 60° C. in a PLS apparatus. The mixture was diluted with EtOAc, the organic phase was washed with water, dried over sodium sulfate and the solvent removed under reduced pressure. The crude material was purified by FC on SiO₂ cartridge (eluent: DCM to 3% MeOH) to give 69 mg of the title compound (p120, y=15%). MS (m/z): 624.7[MH]⁺.

Example 218: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol (E218, racemic diastereoisomer as geometric mixture)

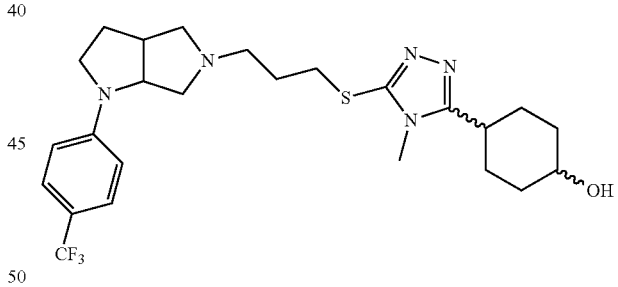

To a solution of 3-{4-[(tert-butyldimethylsilyl)oxy]cyclohexyl}-4-methyl-5-[(3-{1-[4-(trifluoromethyl)phenyl]-octahydropyrrolo[2,3-c]pyrrol-5-yl}propyl)sulfanyl]-4H-1,2,4-triazole (p120, 69 mg, 0.11 mmol) in THF (0.8 mL), at RT, a 1 M/THF solution of TBAF (0.12 mL, 0.12 mmol) was added portion-wise and the resulting reaction mixture was stirred for 2 hrs. The mixture was diluted with EtOAc, the organic phase was washed with water, dried over sodium sulfate and the solvent removed under reduced pressure. The crude material was purified by FC on SiO₂ (eluent: DCM to 25% MeOH) to give 27 mg of the title compound (E218, y=48%). NMR: ¹H NMR (CDCl₃) δ: 7.43 (d, 2H), 6.55 (d, 2H), 4.12-4.19 (m, 1H), 3.69-3.78 (m, 1H), 3.40-3.53 (m, 4H), 3.28-3.36 (m, 1H), 3.11-3.28 (m, 2H), 2.89-3.00 (m, 1H), 2.46-2.75 (m, 7H), 2.08-2.22 (m, 3H), 1.62-2.04 (m, 7H), 1.34-1.47 (m, 2H). MS (m/z): 510.5[MH]⁺.

231

Example 219 and Example 220: 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol (E219, enantiomer 1 single unknown geometric isomer) and 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol (E220, enantiomer 2 single unknown geometric isomer)

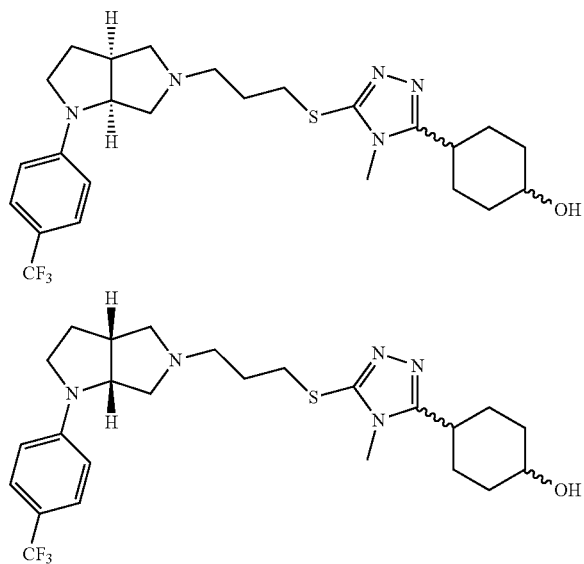

4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol (E218, racemic diastereoisomer (CIS) as geometric mixture, 25 mg) was separated into the single isomers by preparative chiral HPLC, obtaining 7.7 mg of 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol (E219, enantiomer 1 single unknown geometric isomer) and 8.8 mg of 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol (E220, enantiomer 2 single unknown geometric isomer).

Preparative Chromatography:

| Column | Chiralpak AS-H (25 × 2 cm), 5 µm |
|---|---|
| Modifier | (Methanol + 0.1% ipa) 9% |
| Flow rate (mL/min) | 44 |
| Pressure (bar) | 120 |
| Temperature(° C.) | 38 |
| UV detection | 220 nm |
| Loop | 500 µL |
| injection | 12.5 mg (each injection) |

Example 219 Enantiomer 1 single unknown geometric isomer: ret. time 12.7 min, 94.1% as NMR: $^1$H NMR (Acetone-d$_6$) δ: 7.45 (d, 2H), 6.69 (d, 2H), 4.20-4.25 (m, 1H), 3.55-3.66 (m, 2H), 3.53 (s, 3H), 3.45-3.51 (m, 1H), 3.29-3.43 (m, 2H), 3.14-3.23 (m, 1H), 3.04-3.14 (m, 1H), 2.98 (br. s., 1H), 2.66-2.74 (m, 2H), 2.39-2.59 (m, 4H), 2.12-2.18 (m, 1H), 1.91-2.02 (m, 4H), 1.81-1.89 (m, 2H), 1.60-1.73 (m, 2H), 1.32-1.44 (m, 2H). MS (m/z): 510.5 [MH]$^+$.

Example 220 Enantiomer 2 single geometric isomer: ret. time 15.6 min, 100% as NMR: $^1$H NMR (Acetone-d$_6$) δ: 7.45 (d, 2H), 6.69 (d, 2H), 4.20-4.25 (m, 1H), 3.55-3.66 (m, 2H), 3.53 (s, 3H), 3.45-3.51 (m, 1H), 3.29-3.43 (m, 2H), 3.14-3.23 (m, 1H), 3.04-3.14 (m, 1H), 2.98 (br. s., 1H), 2.66-2.74 (m, 2H), 2.39-2.59 (m, 4H), 2.12-2.18 (m, 1H), 1.91-2.02 (m, 4H), 1.81-1.89 (m, 2H), 1.60-1.73 (m, 2H), 1.32-1.44 (m, 2H). MS (m/z): 510.5 [MH]$^+$.

Example 221: 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol dihydrochloride (E221, Enantiomer 2 Single Unknown Geometric Isomer)

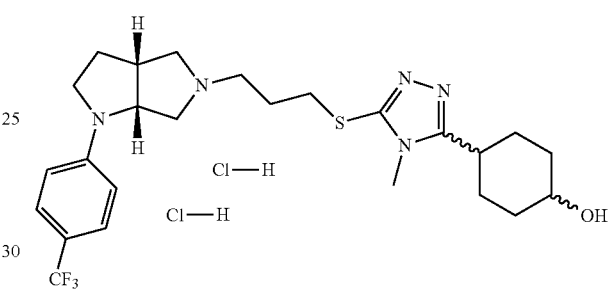

4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol (E220, enantiomer 2 single unknown geometric isomer, 8.8 mg) was dissolved in Et$_2$O and treated with 2.2. eq of 2N HCl in Et$_2$O to afford, after evaporation, 8 mg of title compound (E221, Enantiomer 2). MS (m/z): 510.5 [MH]$^+$.

Preparation 121: ethyl 2-{1,4-dioxaspiro[4.5]decan-8-ylidene}acetate

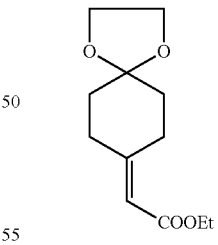

To a suspension of NaH (60% suspension in oil) (1.42 g, 35.45 mmol) in THF (190 mL) at 0° C., under N$_2$, ethyl 2-(diethoxyphosphoryl)acetate (7 mL, 35.45 mmol) was added drop-wise. The mixture was stirred for 30', then 1,4-dioxaspiro[4.5]decan-8-one (5 g, 32 mmol) in THF (20 mL) was added drop-wise. The resulting mixture was stirred at RT for 2 hrs and then concentrated under vacuum. The residue was taken up with Et$_2$O, washed with water and Brine, dried over Na$_2$SO$_4$ and concentrated to obtain 7.58 g of title compound (p121, y=quant) as colourless oil. MS (m/z): 227.2 [MH]$^+$.

Preparation 122: ethyl 2-{1,4-dioxaspiro[4.5]decan-8-yl}acetate

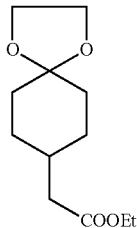 [SMILES: CCOC(=O)CC1CCC2(CC1)OCCO2]

Ethyl 2-{1,4-dioxaspiro[4.5]decan-8-ylidene}acetate (p121, 7.48 g, 33 mmol) was dissolved in MeOH (150 mL) under $N_2$ and Ammonium formate (18.7 mg, 297 mmol) was added followed by Pd/C (1.12 g). The resulting mixture was stirred at reflux for 1.5 h. After cooling, it was filtered over a pad of Celite®, the solvent was evaporated to afford colourless oil. It was dissolved in DCM and was washed with water. The organic phase was separated, dried over a phase separator and concentrated to obtain, 4.24 g of title compound (p122, y=56%), as colourless oil. MS (m/z): 229.2[MH]$^+$.

Preparation 123: 2-{1,4-dioxaspiro[4.5]decan-8-yl}ethan-1-ol

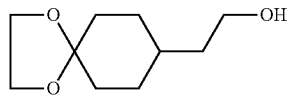

To a solution of ethyl 2-{1,4-dioxaspiro[4.5]decan-8-yl}acetate (p122, 4.24 g, 18.6 mmol) in THF (35 mL), under $N_2$, at −78° C., LiAlH$_4$ 2 M in THF (7.5 mL, 14.88 mmol) was slowly added dropwise. The reaction was partially lifted from the dry-ice bath and left gradually warming and stirred for 2.5 h. Na$_2$SO$_4$*10H$_2$O was added portion wise at −20° C. until gas evolution ceased. It was filtered over a pad of Celite® and concentrated to obtain 4.08 g of title compound (p123, y=crude) as white solid. MS (m/z): 187.2[MH]$^+$.

Preparation 124: 2-{,4-dioxaspiro[4.5]decan-8-yl}acetaldehyde

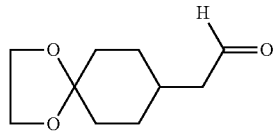 [SMILES: O=CCC1CCC2(CC1)OCCO2]

To a solution of 2-{1,4-dioxaspiro[4.5]decan-8-yl}ethan-1-ol (p123, 1.5 g, 8.05 mmol) in DMSO (57 mL) TEA (11 mL, 78.1 mmol) was added, followed by Sulfur trioxide pyridine complex (4.04 g, 25.4 mmol). The reaction was stirred at RT for 1 h. Then NaHCO$_3$ sat. sol. was added and the mixture was extracted three times with DCM, combined organics were dried over a phase separator and concentrated to obtain a yellow liquid. Brine was added and the mixture was extracted three times with Et$_2$O, combined organics were dried and concentrated to obtain 1.016 g of title compound (p124, y=crude) as yellow oil, that was used as such in the next experiment. MS (m/z): 185. I[MH]$^+$.

Preparation 125: 5-(2-{1,4-dioxaspiro[4.5]decan-8-yl}ethyl)-1-[4-(trifluoromethyl)-phenyl]-octahydro-pyrrolo[3,4-b]pyrrole

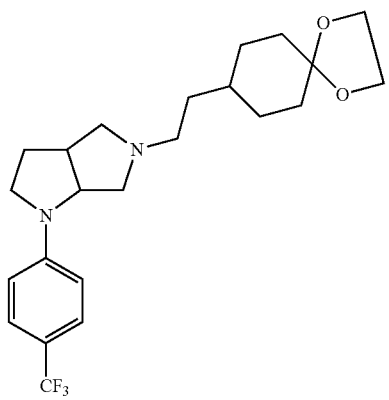 [SMILES: FC(F)(F)c1ccc(N2CCC3CN(CCC4CCC5(CC4)OCCO5)CC32)cc1]

To a suspension of 1-[4-(trifluoromethyl)phenyl]-octahydropyrrolo[3,4-b]pyrrole (prepared as in p73, 60 mg, 0.234 mmol) in DCM (2.5 mL), 2-{1,4-dioxaspiro[4.5]decan-8-yl}acetaldehyde (p124, 43 mg, 0.234 mmol) was added and the mixture was stirred at RT for 15 min, then cooled down to 0° C. Sodium triacetoxyborohydride (74 mg, 0.351 mmol) was added, the mixture was allowed to reach RT and left stirring at that temperature on. The day after it was treated with NaHCO$_3$ ss and phases were separated. Organic one was dried and concentrated under reduced pressure affording 91.5 mg of yellow oil. It was purified by FC on NH cartridge (eluting from cHex 10/0 to 30% EtOAc), affording 79 mg of title compound (p125, y=73%), as colourless oil. MS (m/z): 425.4 [MH]$^+$.

Preparation 126: 4-(2-{1-[4-(trifluoromethyl)phenyl]-octahydropyrrolo[3,4-b]pyrrol-5-yl}ethyl)cyclohexan-1-one

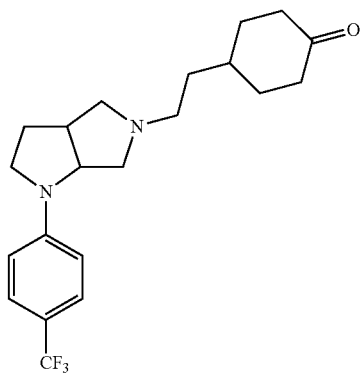 [SMILES: O=C1CCC(CCN2CC3CCN(c4ccc(C(F)(F)F)cc4)C3C2)CC1]

To a solution of 5-(2-{1,4-dioxaspiro[4.5]decan-8-yl}ethyl)-1-[4-(trifluoromethyl)phenyl]-octahydropyrrolo[3,4-b]pyrrole (p125, 79 mg, 0.19 mmol) in a mixture THF/H₂O 0.45/0.45 mL, HCl 6 N (0.048 mL) was added and the mixture was stirred at RT for 22 hrs. The mixture was then cooled to 10° C. and treated with NaHCO₃ ss till pH~8, then diluted with EtOAc. Phases were separated, aqueous one was back extracted with EtOAc and combined organics were dried and concentrated affording 61 mg of title compound (p126, y=77%) as colourless oil that was used as such in next step. MS (m/z): 381.4 [MH]⁺.

Preparation 127: 4-(2-{1-[4-(trifluoromethyl)phenyl]-octahydropyrrolo[3,4-b]pyrrol-5 yl}ethyl)cyclohexan-1-amine

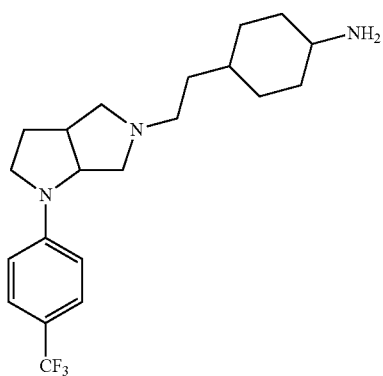 [SMILES: NC1CCC(CCN2CC3CCN(c4ccc(C(F)(F)F)cc4)C3C2)CC1]

A mixture of 4-(2-{1-[4-(trifluoromethyl)phenyl]-octahydropyrrolo[3,4-b]pyrrol-5-yl}ethyl)cyclohexan-1-one (p126, 61 mg, 0.16 mmol), ammonium acetate (123 mg, 1.6 mmol), sodium cyanoborohydride (70 mg, 1.12 mmol) in MeOH (2.5 mL) were heated at 55° C. for 1.5 h. It was cooled to RT and acidified to pH 2 with 6 N HCl. Then it was basified using NaOH 2 M and extracted twice with DCM. Organic phase was dried and concentrated to obtain 63.5 mg of title compound (p127, y=quant) as white sticky solid. MS (m/z): 382.3 [MH]⁺.

Preparation 128: 3-methoxy-N-[4-(2-{1-[4-(trifluoromethyl)phenyl]-octahydropyrrolo[3,4-b]pyrrol-5-yl}ethyl)cyclohexyl]propanamide isomeric mixture

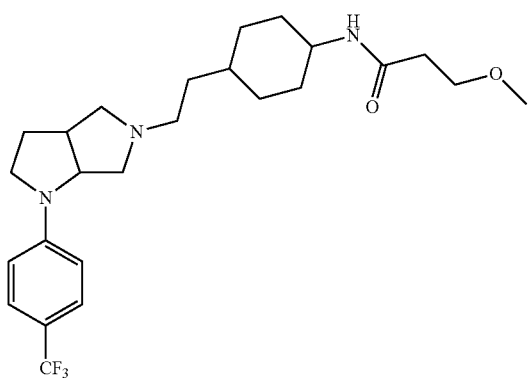 [SMILES: COCCC(=O)NC1CCC(CCN2CC3CCN(c4ccc(C(F)(F)F)cc4)C3C2)CC1]

A mixture of HOBt*H₂O (22 mg, 0.1669 mmol), EDC*HCl (32 mg, 0.166 mmol), 3-Methoxypropionic acid (16 μL, 0.166 mmol) and TEA (70 μL, 0.5 mmol) in DCM (2 mL) was stirred at RT for 10'. After this time, 4-(2-{1-[4-(trifluoromethyl)phenyl]-octahydropyrrolo[3,4-b]pyrrol-5 yl}ethyl)cyclohexan-1-amine (p127, 63.5 mg, 0.166 mmol) in DCM (3 mL) was added and the reaction was stirred at RT ON. Then it was washed with NaHCO₃, NH₄Cl and brine, dried over a Phase Separator filter tube and concentrated. The residue was purified by FC on NH cartridge (eluting from cHex to 40% EtOAc) to afford the title compound (p128, 50 mg) as cis/trans mixture. MS (m/z): 468.5 [MH]⁺.

Example 222 and Example 223: N-(4-{2[(3aS,6aS or 3aR,6aR) 1-[4-(trifluoromethyl)phenyl]-octahydropyrrolo[3,4-b]pyrrol-5-yl]ethyl}cyclohexyl)-3 methoxypropanamide (E222, Enantiomer 1 isomer trans), and N-(4-{2-[(3aR,6aR or 3aS,6aS)-1-[4-(trifluoromethyl)phenyl]-octahydropyrrolo[3,4-b]pyrrol-5-yl]ethyl}cyclohexyl)-3-methoxypropanamide (E223, Enantiomer 2 isomer trans)

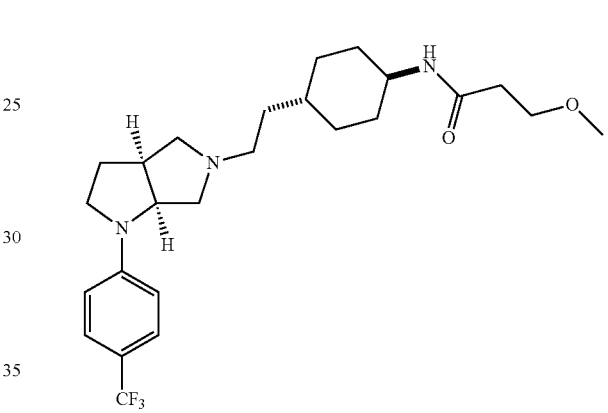

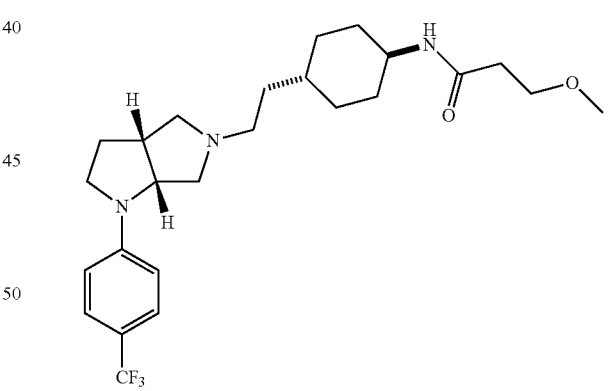

3-methoxy-N-[4-(2-{1-[4-(trifluoromethyl)phenyl]-octahydropyrrolo[3,4-b]pyrrol-5-yl}ethyl)cyclohexyl]propanamide isomeric mixture (p128, 50 mg) was separated into the single enantiomers of geometric isomer trans by preparative chiral HPLC, 12.3 mg of N-(4-({2[(3aS,6aS or 3aR,6aR) 1-[4-(trifluoromethyl)phenyl]-octahydropyrrolo[3,4-b]pyrrol-5-yl]ethyl}cyclohexyl)-3 methoxypropanamide (E222, Enantiomer 1 geometric isomer trans) and 13.3 mg of N-(4-{2-[(3aR,6aR or 3aS,6aS)-1-[4-(trifluoromethyl)phenyl]-octahydropyrrolo[3,4-b]pyrrol-5-yl]ethyl}cyclohexyl)-3-methoxypropanamide (E223, Enantiomer 2 geometric isomer trans).

Preparative Chromatography:

| | |
|---|---|
| Column | Chiralpak AD-H (25 × 2.0 cm), 5μ |
| Mobile phase | n-Hexane/Ethanol 75/25% v/v |
| Flow rate (mL/min) | 14 mL/min |
| DAD detection | 220 nm |
| Loop | 700 μL |
| Injection | 11.7 mg/injection |

Example 222 Enantiomer 1 isomer trans: ret. time 9.2 min, 100% ee NMR: $^1$H NMR (Acetone-d$_6$) δ: 7.45 (d, 2H), 6.79 (d, 1H), 6.68 (d, 2H), 4.21 (t, 1H), 3.57-3.62 (m, 1H), 3.56 (t, 2H), 3.42-3.50 (m, 1H), 3.36 (td, 1H), 3.24 (s, 3H), 2.89-3.05 (m, 1H), 2.72 (dd, 1H), 2.65 (dd, 1H), 2.33-2.43 (m, 3H), 2.30 (t, 2H), 2.11-2.22 (m, 1H), 1.91-2.00 (m, 1H), 1.81-1.90 (m, 2H), 1.68-1.79 (m, 2H), 1.34 (q, 2H), 1.26 (dd, 1H), 1.06-1.19 (m, 2H), 0.91-1.05 (m, 2H). MS (m/z): 468.5 [MH]$^+$.

Example 223 Enantiomer 2 isomer trans: ret. time 10.3 min, 96.2% ee NMR: $^1$H NMR (Acetone-d$_6$) δ: 7.45 (d, 2H), 6.79 (d, 1H), 6.68 (d, 2H), 4.21 (t, 1H), 3.57-3.62 (m, 1H), 3.56 (t, 2H), 3.42-3.50 (m, 1H), 3.36 (td, 1H), 3.24 (s, 3H), 2.89-3.05 (m, 1H), 2.72 (dd, 1H), 2.65 (dd, 1H), 2.33-2.43 (m, 3H), 2.30 (t, 2H), 2.11-2.22 (m, 1H), 1.91-2.00 (m, 1H), 1.81-1.90 (m, 2H), 1.68-1.79 (m, 2H), 1.34 (q, 2H), 1.26 (dd, 1H), 1.06-1.19 (m, 2H), 0.91-1.05 (m, 2H). MS (m/z): 468.5 [MH]$^+$.

Preparation 129: 2-benzyl-octahydrocyclopenta[c]pyrrol-4-one

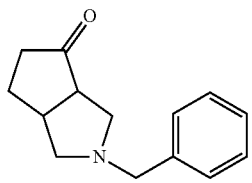 [SMILES: O=C1CCC2CN(Cc3ccccc3)CC12]

To an ice cooled solution of 2-cyclopenten-1-one (0.84 mL, 8 mmol) and benzyl-1-methoxymethyl-1-trimethylsilylmethyl amine (3 mL, 12 mmol) in DCM (40 mL) was added trifluoroacetic acid (0.06 mL). The reaction mixture was allowed to warm to RT and it was stirred for 18 hrs. The mixture was diluted with saturated aqueous sodium bicarbonate, and the organic phase was separated. The aqueous layer was extracted two times with dichloromethane, and the combined organic layers were washed with saturated aqueous sodium bicarbonate, dried and concentrated. The residue was purified by FC on C$_{18}$ cartridge (eluting from H$_2$O+1% FA to 10% CH$_3$CN+1% FA) affording 700 mg of title compound (p129, y=40%) as pink-orange oil. MS (m/z): 216.2[MH]$^+$.

Preparation 130: 2-benzyl-1H,2H,3H,3aH,6H,6aH-cyclopenta[c]pyrrol-4-yl trifluoromethanesulfonate

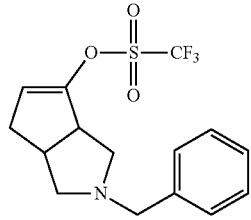 [SMILES: O=S(=O)(OC1=CCC2CN(Cc3ccccc3)CC12)C(F)(F)F]

A solution of 2-benzyl-octahydrocyclopenta[c]pyrrol-4-one (p129, 350 mg, 1.625 mmol) in THF (15 mL) was cooled down to −78° C.; LiHMDS (2.11 mL, 2.11 mmol) was added drop wise. Once the addition was complete, the solution was stirred for 30 min, then a suspension of N-Phenyl-bis(trifluoromethanesulfonimide) (754 mg, 2.11 mmol) in THF (5 mL) was added. The reaction mixture was allowed to reach RT and left under stirring at that temperature on. Water and EtOAc were added, the product was extracted several times and the organic phases reunited were dried and evaporated. The residue was purified by FC on SiO$_2$ cartridge (eluting from cHex to 30% EtOAc) to afford 140 mg of title compound (p130, y=25%). MS (m/z): 348.2[MH]$^+$.

Preparation 131: 2-benzyl-6-[4-(trifluoromethyl)phenyl]-1H,2H,3H,3aH,4H,6aH-cyclopenta[c]pyrrole

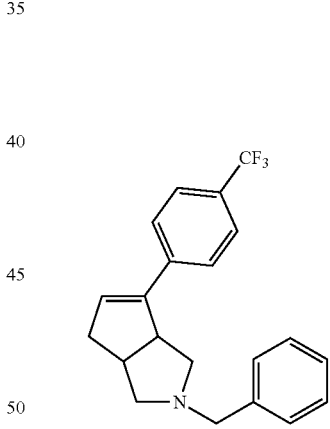

2-benzyl-1H,2H,3H,3aH,6H,6aH-cyclopenta[c]pyrrol-4-yl trifluoromethanesulfonate (p130, 140 mg, 0.4 mmol) and 4-(Trifluoromethyl)phenylboronic acid (152 mg, 0.8 mmol) were dissolved in EtOH/toluene (2+1 mL), 2 M Na$_2$CO$_3$ aq (0.4 mL, 0.8 mmol) was added before bubbling N$_2$ for 5 min, then Pd tetrakis (46 mg, 0.04 mmol) was added. The reaction mixture was heated at 100° C. for 90 min. The mixture was partitioned between EtOAc and water. The organic layer was separated and concentrated, and the residue was purified by FC on SiO$_2$ cartridge (eluting from cHex to 40% EtOAc) to afford 90 mg of title compound (p131, y=65%). MS (m/z): 344.3[MH]$^+$.

Preparation 132: 4-[4-(trifluoromethyl)phenyl]-octahydrocyclopenta[c]pyrrole

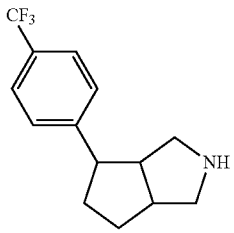 [SMILES: FC(F)(F)c1ccc(C2CCC3CNCC32)cc1]

Ammonium formate (165 mg, 2.62 mmol) was added to a solution of 2-benzyl-6-[4-(trifluoromethyl)phenyl]-1H,2H,3H,3aH,4H,6aH-cyclopenta[c]pyrrole (p131, 90 mg, 0.262 mmol) in MeOH (8 mL) under $N_2$. Pd/C (50 mg) was added and the resulting mixture was refluxed for 1 h. The mixture was filtered over a pad of Celite® using MeOH. The solvent was evaporated and the residue was charged on SCX eluting with 1N $NH_3$ in MeOH to afford, after evaporation, 46 mg of title compound (p132, y=crude) as diastereoisomers mixture that was used as such in the next step. MS (m/z): 256.2[MH]$^+$.

Example 224 and Example 225: 4-methyl-3-(4-methyl-1,3-oxazol-5-yl)-5-({3-[(4S or 4R)-4-[4-(trifluoromethyl)phenyl]-octahydrocyclopenta[c]pyrrol-2-yl]propyl}sulfanyl)-4H-1,2,4-triazole (E224, Diastereoisomer 1) and 4-methyl-3-(4-methyl-1,3-oxazol-5-yl)-5-({3-[(4R or 4S)-4-[4-(trifluoromethyl)phenyl]-octahydrocyclopenta[c]pyrrol-2-yl]propyl}sulfanyl)-4H-1,2,4-triazole (E225, Diastereoisomer 2)

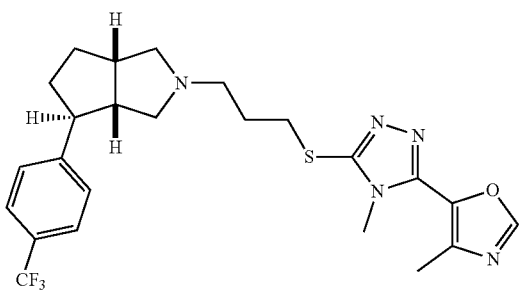

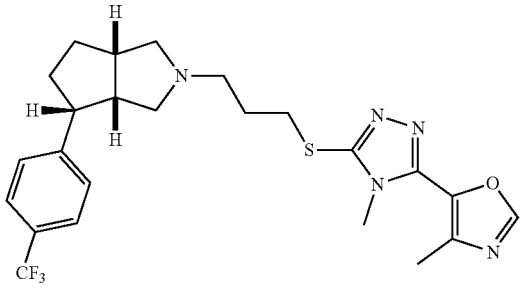

4-[4-(trifluoromethyl)phenyl]-octahydrocyclopenta[c]pyrrole (p132, 46 mg, 0.18 mmol), 3-[(3-chloropropyl)sulfanyl]-4-methyl-5-(4-methyl-1,3-oxazol-5-yl)-4H-1,2,4-triazole (p3, 54 mg, 0.198 mmol), $Na_2CO_3$ (21 mg, 0.198 mmol) and NaI (30 mg, 0.198 mmol) were dissolved in DMF (0.2 mL) and heated at 60° C. for 6 hrs. The mixture was diluted with water and EtOAc and extracted several times with EtOAc. The organic phase was washed with brine, dried and evaporated. The residue was purified by FC on NH cartridge (eluting from cHex to 35% of EtOAc) to afford 5 mg of free base of title compound (E224, y=6%, Diastereoisomer 1) as pale yellow oil and 20 mg of the free base of the title compound isomer 2 (E225, y=22%, Diastereoisomer 2) as pale yellow oil. MS (m/z): 492.3 [MH]$^+$.

Example 226: 4-methyl-3-(4-methyl-1,3-oxazol-5-yl)-5-({3-[(4S or 4R)-4-[4-(trifluoromethyl)phenyl]-octahydrocyclopenta[c]pyrrol-2-yl]propyl}sulfanyl)-4H-1,2,4-triazole hydrochloride (E226, Diastereoisomer 1)

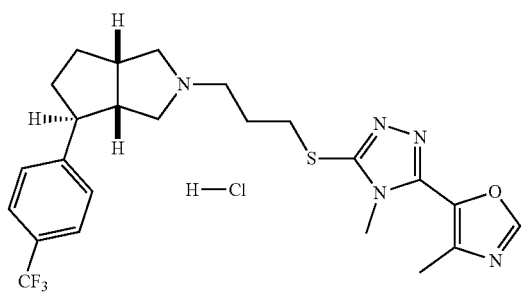 [SMILES: Cc1ncoc1-c1nnc(SCCCN2C[C@H]3CC[C@H](c4ccc(C(F)(F)F)cc4)[C@H]3C2)n1C ; Cl]

4-methyl-3-(4-methyl-1,3-oxazol-5-yl)-5-({3-[(4S or 4R)-4-[4-(trifluoromethyl)-phenyl]-octahydrocyclopenta[c]pyrrol-2-yl]propyl}sulfanyl)-4H-1,2,4-triazole (E224, Diastereoisomer 1, 5 mg) was dissolved in $Et_2O$ and treated with 1.1 eq of 1N HCl in $Et_2O$ to afford, after evaporation, 5 mg of the title compound (E226, Diastereoisomer 1) as white solid. NMR: $^1$H NMR (Acetone-$d_6$) δ: 8.27 (s, 1H), 7.51-7.69 (m, 4H), 3.88-3.96 (m, 1H), 3.81 (s, 3H), 3.52-3.64 (m, 2H), 3.41-3.49 (m, 2H), 3.30-3.36 (m, 2H), 3.23-3.28 (m, 1H), 3.12-3.23 (m, 2H), 2.90-2.97 (m, 1H), 2.41 (s, 3H), 2.23-2.41 (m, 2H), 2.10-2.20 (m, 2H), 2.08 (br. s., 1H), 1.72-1.86 (m, 1H). MS (m/z): 492.3 [MH]$^+$.

Example 227: 4-methyl-3-(4-methyl-1,3-oxazol-5-yl)-5-({3-[(4R or 4S)-4-[4-(trifluoromethyl)phenyl]-octahydrocyclopenta[c]pyrrol-2-yl]propyl}sulfanyl)-4H-1,2,4-triazole hydrochloride (E227, Diastereoisomer 2)

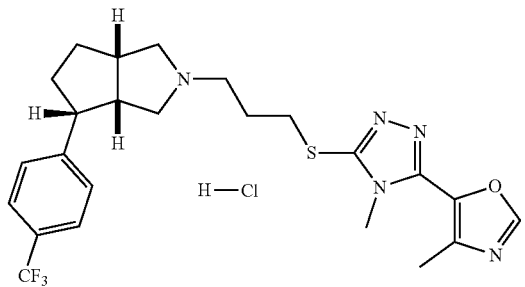 [SMILES: Cc1ncoc1-c1nnc(SCCCN2C[C@H]3CC[C@@H](c4ccc(C(F)(F)F)cc4)[C@H]3C2)n1C ; Cl]

4-methyl-3-(4-methyl-1,3-oxazol-5-yl)-5-({3-[(4R or 4S)-4-[4-(trifluoromethyl)-phenyl]-octahydrocyclopenta[c]pyrrol-2-yl]propyl}sulfanyl)-4H-1,2,4-triazole (E225, Diastereoisomer 2, 20 mg) was dissolved in $Et_2O$ and treated with 1.1 eq of 1N HCl in Et$_2$O to afford, after evaporation, 20 mg of the title compound as white solid (E227, Diastereoisomer 2). NMR: $^1$H NMR (Acetone-d$_6$) δ: 13.08 (br. s., 1H), 8.26 (s, 1H), 7.54-7.73 (m, 5H), 3.82-3.94 (m, 1H), 3.77 (s, 3H), 3.48 (br. s., 2H), 3.39 (t, 2H), 3.23 (t, 3H), 3.13 (t, 1H), 2.64-2.73 (m, 1H), 2.35-2.47 (m, 4H), 2.10-2.28 (m, 4H), 1.75 (dd, 1H). MS (m/z): 492.3 [MH]$^+$.

Preparation 133: 1-benzyl-4-(hydroxymethyl)pyrrolidin-3-ol

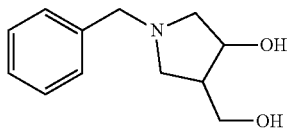 [SMILES: OCC1CN(Cc2ccccc2)CC1O]

To a stirred solution of ethyl 1-benzyl-4-oxopyrrolidine-3-carboxylate (5 g, 20.2 mmol) in MeOH (75 mL) at 0° C., NaBH$_4$ (4.58 g, 121.2 mmol) was added in portion of 250 mg over 30'. Then the solution was warmed to RT and stirred ON. Solvent was removed under vacuum. The residue was dissolved in EtOAc (75 mL) and NaOH 2 M (25 mL), organic phase was separated and the aqueous phase was washed again with EtOAc (60 mL×2). Combined organics were dried over Na$_2$SO$_4$ and concentrated to obtain 5.7 g of a yellow oil that was purified by FC on SiO$_2$ cartridge (eluting from DCM to MeOH 100%) to obtain 1.88 g of title compound as yellow oil (p133). MS (m/z):208.2 [MH]$^+$.

Preparation 134: [1-benzyl-4-(methanesulfonyloxy)pyrrolidin-3-yl]methyl methanesulfonate

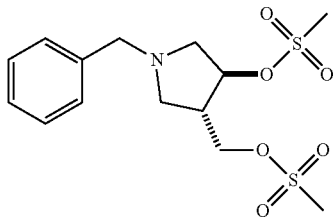 [SMILES: CS(=O)(=O)OC[C@@H]1CN(Cc2ccccc2)C[C@H]1OS(C)(=O)=O]

1-benzyl-4-(hydroxymethyl)pyrrolidin-3-ol (p133, 1.88 g, 9 mmol) was dissolved in DCM (27 mL) and TEA (3.14 mL, 22.5 mmol) was added. The solution was cooled to 0° C. and methanesulfonyl chloride (1.53 mL, 19.8 mmol) was added drop wise over 30'. The mixture was allowed to warm to RT and stirred vigorously for 2 hrs. Further TEA (0.628 mL, 4.5 mmol) and methanesulfonyl chloride (0.347 mL, 4.5 mmol) were added and the reaction was stirred at RT for 1.5 h. Then the reaction mixture was concentrated, the residue was diluted with EtOAc (100 mL) and washed with NaOH 1 M (25 mL×2) and Brine (25 mL). The organic layer was dried and concentrated. Crude material was purified by FC on SiO$_2$ cartridge (eluting from 60% Cy to EtOAc) to obtain 590 mg of title compound (p134, y=18%, diastereoisomer TRANS) as yellow oil. MS (m/z): 364.3 [MH]$^+$.

Preparation 135: 4-(azidomethyl)-1-benzylpyrrolidin-3-ylmethanesulfonate

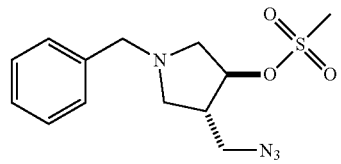

[1-benzyl-4-(methanesulfonyloxy)pyrrolidin-3-yl]methyl methanesulfonate (p134, 590 mg, 1.6 mmol) was dissolved in DMF (9 mL) and Sodium azide (104 mg, 1.6 mmol) was added portion wise. The mixture was stirred at RT for 5 days. The reaction was then diluted with EtOAc (270 mL) and washed with water (9×15 mL). Organic phase was quickly concentrated under vacuum to obtain a yellow oil that was purified by FC on SiO$_2$ cartridge (eluting from cHex to 50% EtOAc) to obtain 303 mg of title compound (p135, y=61%) as colourless oil. MS (m/z): 311.2 [MH]$^+$.

Preparation 136: 4-(aminomethyl)-1-benzylpyrrolidin-3-yl methanesulfonate

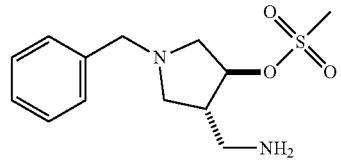 [SMILES: CS(=O)(=O)O[C@@H]1CN(Cc2ccccc2)C[C@H]1CN]

4-(azidomethyl)-1-benzylpyrrolidin-3-ylmethanesulfonate (p135, 303 mg, 0.98 mmol) was dissolved in MeOH (10 mL), PtO$_2$ (30.3 mg, 0.13 mmol) was added and the mixture was stirred under 1 atm of H$_2$ for 1 h. The mixture was filtered through a pad of Celite® and the filtrate was concentrated under vacuum to obtain 277 mg of title compound (p136, y=99%) as colourless gel. MS (m/z): 285.2 [MH]$^+$.

Preparation 137: 3-benzyl-3,6-diazabicyclo[3.2.0]heptane

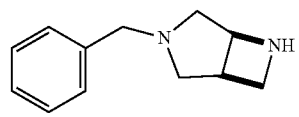

4-(aminomethyl)-1-benzylpyrrolidin-3-yl methanesulfonate (p136, 277 mg, 0.97 mmol) was refluxed in 1,4-dioxane (5 mL) ON. The reaction was cooled down to RT and concentrated to obtain 304 mg of title compound (p137, y=crude), as brown oil that was used as crude in the next experiment. MS (m/z): 189.2 [MH]$^+$.

Preparation 138: 3-benzyl-6-[4-(trifluoromethyl)phenyl]-3,6-diazabicyclo-[3.2.0]heptane

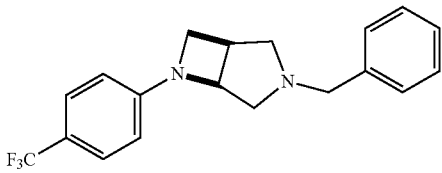

3-benzyl-3,6-diazabicyclo[3.2.0]heptane (p137, 304 mg, 0.97 mmol), 1-bromo-4-(trifluoromethyl)benzene (0.177 mL, 1.26 mmol), BINAP (78 mg, 0.126 mmol) and t-BuONa (244 mg, 2.54 mmol) were dissolved in toluene (4 mL) and degassed for 10', then Pd$_2$(dba)$_3$ (25 mg, 0.0276 mmol) was added. The resulting mixture was stirred at 100° C. for 3 hrs. The solution was filtered through Celite® using EtOAc. The filtrate was evaporated under vacuum to give a brown oil that was purified by FC on SiO$_2$ cartridge (eluting from Cy to 10% EtOAc) to obtain 150.8 mg of title compound (p138, y=46%) as yellow oil. MS (m/z): 333.3 [MH]$^+$.

Preparation 139: 6-[4-(trifluoromethyl)phenyl]-3,6-diazabicyclo[3.2.0]heptane

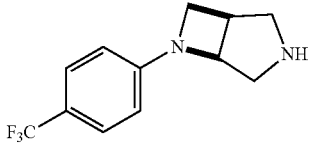

3-benzyl-6-[4-(trifluoromethyl)phenyl]-3,6-diazabicyclo[3.2.0]heptane (p138, 150.8 mg, 0.45 mmol) was dissolved in MeOH (2 mL) under N$_2$ and ammonium formate (255 mg, 4.05 mmol) was added followed by Pd/C (15 mg). The reaction was heated to 78° C. for 1 h. After cooling, it was filtered over a pad of Celite®, the solvent was evaporated to afford a grey solid. It was partitioned between DCM and NaHCO$_3$ (aqueous phase pH~7) and washed three times with DCM. Organic layers were combined, dried and concentrated to obtain 88 mg of title compound (p139, y=64%) as yellow oil. MS (m/z): 243.2 [MH]$^+$.

Example 228: 3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane (E228)

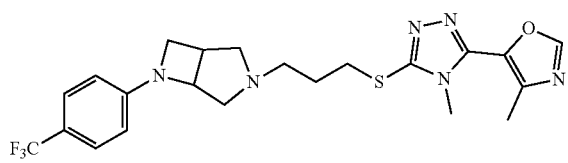 [SMILES: Cc1ncoc1-c1nnc(SCCCN2CC3CN(c4ccc(C(F)(F)F)cc4)C3C2)n1C]

6-[4-(trifluoromethyl)phenyl]-3,6-diazabicyclo[3.2.0]heptane (p139, 54 mg, 0.22 mmol), 3-[(3-chloropropyl)sulfanyl]-4-methyl-5-(4-methyl-1,3-oxazol-5-yl)-4H-1,2,4-triazole (p3, 60 mg, 0.22 mmol), Na$_2$CO$_3$ (28 mg, 0.264 mmol) and NaI (40 mg, 0.264 mmol) were dissolved in DMF (0.180 mL) and heated at 60° C. ON. The mixture was diluted with water and extracted twice with DCM. The organic phase was filtered through a Phase Separator and evaporated to obtain 85 mg of a yellow oil that was purified by FC on SiO$_2$ cartridge (eluting from DCM to 5% of MeOH) to obtain two batches of title compound 27 mg and 25 mg respectively (E228, y=49% over 2 batches) as yellow gum. NMR: $^1$H NMR (Acetone-d$_6$) δ: 8.26 (s, 1H), 7.40 (d, 2H), 6.46 (d, 2H), 4.70 (dd, 1H), 3.97 (t, 1H), 3.67-3.77 (m, 4H), 3.42 (d, 1H), 3.10-3.34 (m, 4H), 2.59-2.73 (m, 2H), 2.41 (s, 3H), 1.92-2.14 (m, 4H). MS (m/z): 479.3 [MH]$^+$.

Example 229 and Example 230: (1R,5S or 1S,5R)-3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane (E229, Enantiomer 1) and (1S,5R or 1R,5S)-3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane (E230, Enantiomer 2)

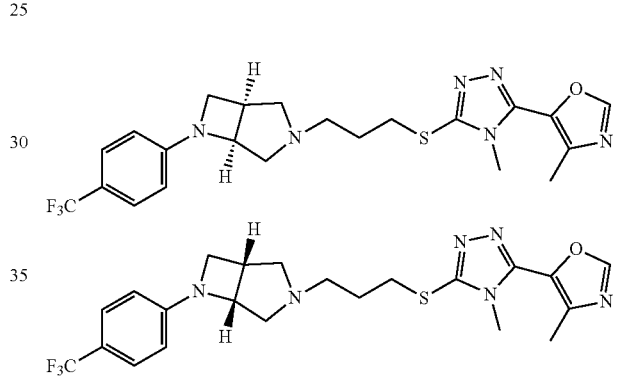

3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane (E228, 25 mg) were separated into the single enantiomers by preparative chiral HPLC, obtaining 8.4 mg of (1R,5S or 1S,5R)-3-(3-{[(4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane (E229, Enantiomer 1) and 9.1 mg of (1S,5R or 1R,5S)-3-(3-{[4-methyl-5-(4-methyl-1,3-oxazol-5-yl)-4H-1,2,4-triazol-3-yl]sulfanyl}propyl)-6-[4-(trifluoromethyl)phenyl]-3,6-diazabicyclo[3.2.0]heptane (E230, Enantiomer 2).

Preparative Chromatography:

| | |
|---|---|
| Column | Chiralcel OJ-H (25 × 2 cm), 5 μm |
| Mobile phase | n-Hexane/(Ethanol + 0.1% ipa) 30/70% v/v |
| Flow rate (mL/min) | 14 |
| DAD detection | 220 nm |
| Loop | 750 μL |
| injection | 12 mg (each injection) |

Example 229 Enantiomer 1: ret. time 11.8 min, 100% ee MS (m/z): 479.3 [MH]$^+$.

Example 230 Enantiomer 2: ret. time 14.7 min, 100% ee MS (m/z): 479.3 [MH]$^+$.

Preparation 140: 6-benzyl-1-[4-(trifluoromethyl)phenyl]-octahydro-1H-pyrrolo[3,4-b]pyridine

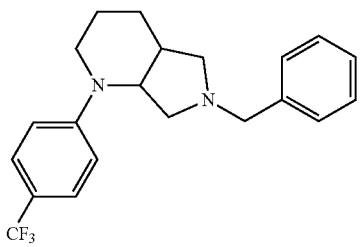 [SMILES: FC(F)(F)c1ccc(N2CCCC3CN(Cc4ccccc4)CC32)cc1]

6-benzyl-octahydro-pyrrolo[3,4-b]pyridine (commercially available from Fluorochem, 150 mg, 0.69 mmol), 1-bromo-4-(trifluoromethyl)benzene (0.097 mL, 0.69 mmol), BINAP (43 mg, 0.069 mmol) and t-BuONa (132 mg, 1.38 mmol) were dissolved in toluene (2 mL) and degassed for 10 min, then $Pd_2(dba)_3$ (19 mg, 0.02 mmol) was added. The resulting mixture was stirred at 100° C. for 12 hrs. The solution was filtered using EtOAc. The filtrate was evaporated under vacuum and the residue was purified by FC on NH cartridge (eluting from cHex to 30% EtOAc) affording 220 mg of title compound (p140, y=88%) as orange oil. MS (m/z): 361.3 [MH]$^+$.

Preparation 141: 1-[4-(trifluoromethyl)phenyl]-octahydro-1H-pyrrolo[3,4-b]pyridine

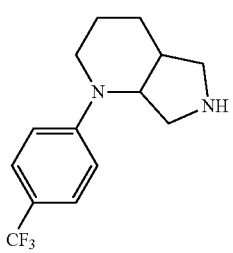 [SMILES: FC(F)(F)c1ccc(N2CCCC3CNCC32)cc1]

To a stirred solution of 6-benzyl-1-[4-(trifluoromethyl)phenyl]-octahydro-1H-pyrrolo[3,4-b]pyridine (p140, 220 mg, 0.6 mmol) in MeOH (8 mL), under $N_2$, ammonium formate (384 mg, 6 mmol) was added followed by Pd/C (60 mg) the resulting solution was refluxed for 1 h. Solvent was removed under vacuum and the residue was charged on SCX cartridge eluting with 1 M $NH_3$ in MeOH to afford 130 mg of title compound (p141, y=81%) as yellow oil. MS (m/z): 271.2 [MH]$^+$.

Example 231: 4-methyl-3-(4-methyl-1,3-oxazol-5-yl)-5-[(3-{1-[4-(trifluoromethyl)phenyl]-octahydro-1H-pyrrolo[3,4-b]pyridin-6-yl}propyl)sulfanyl]-4H-1,2,4-triazole (E231)

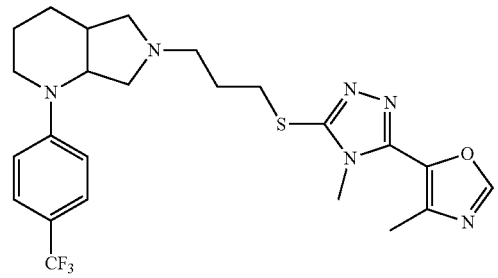 [SMILES: Cc1ncoc1-c1nnc(SCCCN2CC3CCCN(c4ccc(C(F)(F)F)cc4)C3C2)n1C]

1-[4-(trifluoromethyl)phenyl]-octahydro-1H-pyrrolo[3,4-b]pyridine (p141, 53 mg, 0.195 mmol), 3-[(3-chloropropyl)sulfanyl]-4-methyl-5-(4-methyl-1,3-oxazol-5-yl)-4H-1,2,4-triazole (p3, 58 mg, 0.21 mmol), $Na_2CO_3$ (22 mg, 0.21 mmol) and NaI (310 mg, 0.21 mmol) were dissolved in DMF (0.2 mL) and heated at 60° C. ON. The mixture was diluted with water and EtOAc and extracted several times with EtOAc. The organic phase was washed with brine, dried and evaporated. The residue was purified by FC on $SiO_2$ cartridge (eluting from DCM to 10% of MeOH) to afford 40 mg of title compound (E231, y=40%) as yellow oil. NMR: $^1$H NMR (DMSO-$d_6$) δ: 8.56 (s, 1H), 7.47 (d, 2H), 7.00 (d, 2H), 4.40-4.51 (m, 1H), 3.68 (s, 3H), 3.52-3.61 (m, 1H), 3.19 (d, 3H), 2.82-2.94 (m, 2H), 2.66-2.81 (m, 2H), 2.57-2.65 (m, 1H), 2.41-2.48 (m, 1H), 2.38 (s, 3H), 2.26-2.34 (m, 1H), 1.83 (br. s., 3H), 1.67-1.77 (m, 1H), 1.47-1.61 (m, 2H). MS (m/z): 507.3 [MH]$^+$.

Example 232 and Example 233: 3-({3-[(4aS,7aS or 4aR,7aR)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole (E232, Enantiomer 1) and 3-({3-[(4aR,7aR or 4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole (E233, Enantiomer 2)

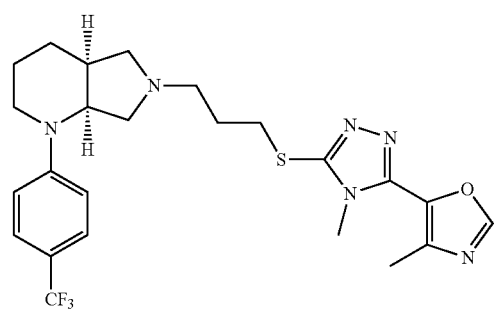

-continued

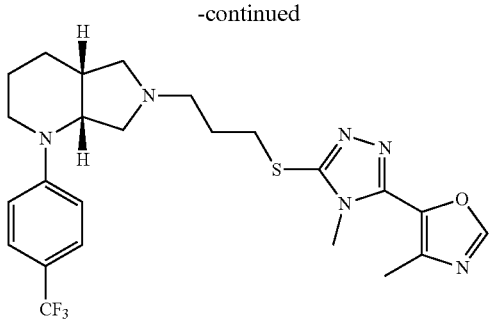

4-methyl-3-(4-methyl-1,3-oxazol-5-yl)-5-[(3-{1-[4-(trifluoromethyl)phenyl]-octahydro-1H-pyrrolo[3,4-b]pyridin-6-yl}propyl)sulfanyl]-4H-1,2,4-triazole (E231, 40 mg) was separated into the single enantiomers by preparative chiral HPLC, obtaining 12 mg of 3-({3-[(4aS,7aS or 4aR,7aR)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole (E232, Enantiomer 1) and 12 mg of 3-({3-[(4aR,7aR or 4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole (E233, Enantiomer 2).

Preparative Chromatography:

| Column | Chiralpak AD-H (25 × 2 cm), 5 μm |
|---|---|
| Mobile phase | n-Hexane/(2-Propanol/Methanol) 30/70% v/v |
| Flow rate (mL/min) | 14 |
| DAD detection | 220 nm |
| Loop | 1000 μL |
| injection | 20 mg (each injection) |

Example 232 Enantiomer 1: ret. time 8.6 min, 100% ee MS (m/z): 507.3 [MH]$^+$.

Example 233 Enantiomer 2: ret. time 11.8 min, 100% ee MS (m/z): 507.3 [MH]$^+$.

Preparation 142: 3-{6-benzyl-octahydro-1H-pyrrolo[3,4-b]pyridin-1-yl}benzonitrile

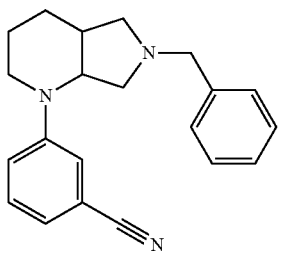 [SMILES: N#Cc1cccc(N2CCCC3CN(Cc4ccccc4)CC32)c1]

To a solution of 6-benzyl-octahydro-1H-pyrrolo[3,4-b]pyridine (100 mg, 0.46 mmol) and 3-bromobenzonitrile (93 mg, 0.508 mmol) in Toluene (1 mL) at RT, BINAP (29 mg, 0.046 mmol), Pd$_2$(dba)$_3$ (13 mg, 0.0138 mmol) and t-BuONa (88 mg, 0.92 mmol) were added and nitrogen was purged for 10 min then the mixture was shaken in a PLS apparatus at 100° C. ON. The reaction mixture was partitioned between water and DCM, organic phase was separated, dried and concentrated under reduced pressure. Crude was purified by FC on SiO$_2$ cartridge (eluting from cHex to EtOAc) affording 54 mg of title compound (p142, y=37%). MS (m/z): 318.3 [MH]$^+$.

Preparation 143: 3-{octahydro-1H-pyrrolo[3,4-b]pyridin-1-yl}benzonitrile

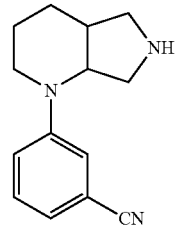 [SMILES: N#Cc1cccc(N2CCCC3CNCC32)c1]

3-{6-benzyl-octahydro-1H-pyrrolo[3,4-b]pyridin-1-yl}benzonitrile (p142, 54 mg, 0.17 mmol) was dissolved in MeOH (5 mL) under N$_2$ and ammonium formate (107 mg, 1.7 mmol) was added followed by Pd/C (6 mg). The resulting mixture was stirred at reflux for 1 h. After cooling it was filtered over a pad of Celite®, the solvent was evaporated and the residue loaded on a SCX cartridge washing with MeOH and eluting with NH$_3$ 1 M in MeOH affording 23 mg of title compound (p143, y=crude) that was used as such in the next step. MS (m/z): 228.2 [MH]$^+$.

Example 234: 3-[6-(3-{[4-methyl-5-(4-methyl-1,3-oxazol-5-yl)-4H-1,2,4-triazol-3-yl]-sulfanyl}propyl)-octahydro-1H-pyrrolo[3,4-b]pyridin-1-yl]benzonitrile (E234)

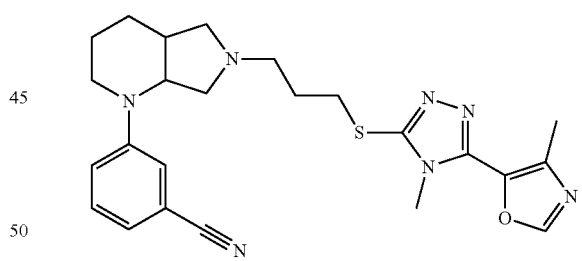

3-{octahydro-1H-pyrrolo[3,4-b]pyridin-1-yl}benzonitrile (p143, 23 mg, 0.1 mmol), 3-[(3-chloropropyl)sulfanyl]-4-methyl-5-(4-methyl-1,3-oxazol-5-yl)-4H-1,2,4-triazole (p3, 16 mg, 0.06 mmol), Na$_2$CO$_3$ (7 mg, 0.06 mmol) and NaI (9 mg, 0.06 mmol) were dissolved in DMF (52 μL) and heated at 60° C. ON. The mixture was diluted with water and DCM, phases were separated and organic one was dried and evaporated. The residue was purified by FC on NH cartridge (eluting from cHex to 50% EtOAc) to afford 22 mg of title compound (E234, y=47%). NMR: $^1$H NMR (CDCl$_3$) δ: 7.96 (s, 1H), 7.33 (br. s., 1H), 7.00-7.21 (m, 3H), 4.24-4.48 (m, 2H), 3.73 (s, 3H), 3.36 (m, 3H), 2.59-3.09 (m, 6H), 2.56 (s, 3H), 2.48 (br. s., 2H), 1.93 (br. s., 3H), 1.83 (br. s., 1H), 1.65 (br. s., 1H). MS (m/z): 464.3 [MH]$^+$.

Example 235: 3-[6-(3-{[4-methyl-5-(4-methyl-1,3-oxazol-5-yl)-4H-1,2,4-triazol-3-yl]sulfanyl}propyl)-octahydro-1H-pyrrolo[3,4-b]pyridin-1-yl]benzonitrile dihydrochloride (E235)

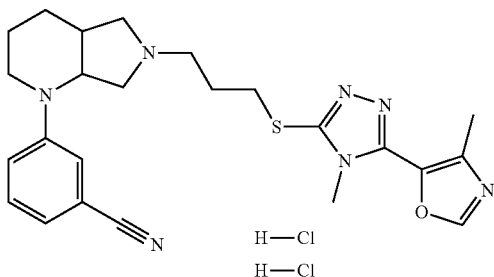

3-[6-(3-{[4-methyl-5-(4-methyl-1,3-oxazol-5-yl)-4H-1,2,4-triazol-3-yl]sulfanyl}propyl)-octahydro-1H-pyrrolo[3,4-b]pyridin-1-yl]benzonitrile (E235, 22 mg) was dissolved in Et₂O/DCM and treated with 2.2 eq of 2N HCl in Et₂O to afford, after evaporation, 22 mg of title compound (E236). MS (m/z): 464.3 [MH]⁺.

Preparation 144: tert-butyl 3-bromo-4-(2-hydroxyethoxy)pyrrolidine-1-carboxylate

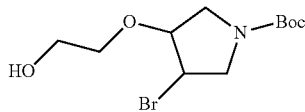

N-Boc-2,5-dihydro-1H-pyrrole (2 g, 11.8 mmol) was dissolved in Ethylene glycol (10 mL). NBS (2.31 g, 13 mmol) was slowly added over 20 minutes at RT in the dark. After ON stirring, the mixture was quenched with water and the crude partitioned between water and EtOAc. The crude was then purified by FC on SiO₂ cartridge (eluting from DCM to 20% EtOAc) obtaining 2.2 g of title compound (p144, y=60%) as colourless oil, which solidified slowly in a white solid. MS (m/z): 310.2[M]⁺.

Preparation 145: tert-butyl 3-bromo-4-{2-[(4-methylbenzenesulfonyl)oxy]-ethoxy}pyrrolidine-1-carboxylate

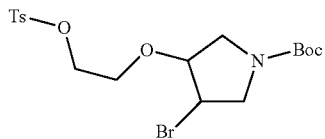 [SMILES: Cc1ccc(S(=O)(=O)OCCOC2CN(C(=O)OC(C)(C)C)CC2Br)cc1]

tert-butyl 3-bromo-4-(2-hydroxyethoxy)pyrrolidine-1-carboxylate (p144, 2.2 g, 7.1 mmol) was dissolved in DCM (30 mL), followed by TEA (1.5 mL, 10.7 mmol) and DMAP (35 mg, cat). A solution of 4-methylbenzene-1-sulfonyl chloride (1.76 g, 9.23 mmol) in DCM (10 mL) was then added dropwise. After ON stirring the reaction was quenched with Sat. NaHCO₃ solution, then phases were separated and the organic one was washed with brine. The organic layer, once dried and evaporated, was purified by FC on SiO₂ cartridge (eluting from DCM to 20% EtOAc) obtaining 3.15 g of title compound (p145, y=crude, 64% purity) that was used in the next step without further purifications. MS (m/z): 464.2[MH]⁺.

Preparation 146: tert-butyl 4-benzyl-octahydropyrrolo[3,4-b]morpholine-6-carboxylate

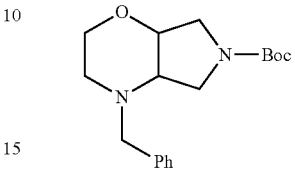

tert-butyl 3-bromo-4-{2-[(4-methylbenzenesulfonyl)oxy]ethoxy}pyrrolidine-1-carboxylate (p145, 3.15 g, 6.8 mmol) was dissolved in Toluene (90 mL) and then Benzylamine (2.3 mL, 21 mmol) was added. The solution was heated at reflux for 24 hrs. The solvent was then removed and the crude was partitioned between water and AcOEt. The organic part was then purified by FC on SiO₂ cartridge (eluting from DCM/EtOAc 9:1 to DCM/EtOAc 8:2), obtaining two batches of the title compound: 308 mg (83% pure) and 584 mg (purity >90%), (p146, total y=35%). MS (m/z): 319.3[MH]⁺.

Preparation 147: tert-butyl octahydropyrrolo[3,4-b]morpholine-6-carboxylate

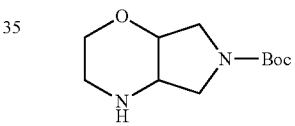

tert-butyl 4-benzyl-octahydropyrrolo[3,4-b]morpholine-6-carboxylate (p146, 0.3 g, 0.91 mmol) was dissolved in EtOH (17 mL) and then Ammonium Formate (574 mg, 9.1 mmol) was added. Pd/C 10% (Cat.) was added and the mixture refluxed for 1 h. The catalyst was then filtered off and the solvent removed. The crude was purified by SCX cartridge eluting with 1N NH₃ in MeOH, obtaining 213 mg of title compound (p147, y=quant). MS (m/z): 229.2[MH]⁺.

Preparation 148: tert-butyl 4-[4-(trifluoromethyl)phenyl]-octahydropyrrolo[3,4-b]morpholine-6-carboxylate

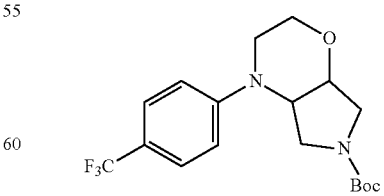

tert-butyl octahydropyrrolo[3,4-b]morpholine-6-carboxylate (p147, 213 mg, 0.93 mmol) was dissolved in Toluene (4.5 mL), followed by t-BuONa (270 mg, 2.8 mmol), Pd₂(dba)₃ (42 mg, 0.046 mmol) and BINAP (29 mg, 0.046 mmol). 4-Bromobenzotrifluoride (130 mg, 0.93 mmol) was added before heating the mixture at 100° C. under microwave irradiation for 1. The volatiles were then removed and the crude partitioned between water and EtOAc, then the organic phase was dried and evaporated and crude material was purified by FC on SiO₂ cartridge (from cHex 85:EtOAc 15 to cHex 70:EtOAc 30) obtaining 340 mg of title compound (p148, y=98%) as yellowish oil. MS (m/z): 373.3 [MH]⁺.

Preparation 149: 4-[4-(trifluoromethyl)phenyl]-octahydropyrrolo[3,4-b]morpholine

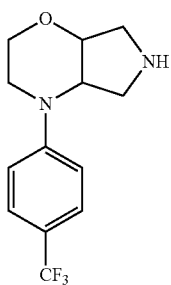

tert-butyl 4-[4-(trifluoromethyl)phenyl]-octahydropyrrolo[3,4-b]morpholine-6-carboxylate (p148, 340 mg; 0.91 mmol) was dissolved in DCM (10 mL) and CF₃COOH (0.5 mL) was added. The mixture was stirred at RT ON, then the volatiles were removed and the crude purified by SCX eluting with 1N NH₃ in MeOH, obtaining 213 mg title compound (p149, y=86%). MS (m/z): 273.2[MH]⁺.

Example 236: 4-methyl-3-(4-methyl-1,3-oxazol-5-yl)-5-[(3-{4-[4-(trifluoromethyl)-phenyl]-octahydropyrrolo[3,4-b]morpholin-6-yl}propyl)sulfanyl]-4H-1,2,4-triazole (E236)

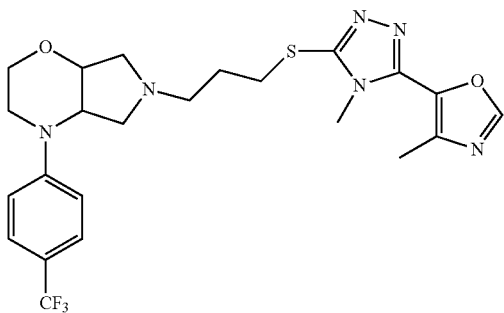 [SMILES: Cc1ncoc1-c1nnc(SCCCN2CC3OCCN(c4ccc(C(F)(F)F)cc4)C3C2)n1C]

4-[4-(trifluoromethyl)phenyl]-octahydropyrrolo[3,4-b]morpholine (p149, 50 mg, 0.184 mmol), 3-[(3-chloropropyl)sulfanyl]-4-methyl-5-(4-methyl-1,3-oxazol-5-yl)-4H-1,2,4-triazole (p3, 55 mg, 0.202 mmol), Na₂CO₃ (24 mg, 0.22 mmol) and NaI (33 mg, 0.22 mmol) were dissolved in DMF (0.2 mL) and heated at 60° C. ON. The mixture was diluted with water and DCM and phases were separated. The organic phase was dried and evaporated. The residue was purified by FC on SiO₂ cartridge (eluting from DCM to 5% of MeOH) to afford 42.5 mg of title compound (E236, y=45%). NMR: ¹H NMR (CDCl₃) δ: 7.95 (s, 1H), 7.45-7.58 (m, 2H), 6.93 (d, 2H), 4.22-4.33 (m, 1H), 4.15-4.21 (m, 1H), 4.02-4.13 (m, 1H), 3.67-3.77 (m, 4H), 3.29-3.42 (m, 4H), 3.14-3.23 (m, 1H), 2.94-3.07 (m, 1H), 2.60-2.87 (m, 4H), 2.56 (s, 3H), 2.03 (br. s., 2H). MS (m/z): 509.3 [MH]⁺.

Example 237 and Example 238: 3-({3-[(4aR,7aS or 4aS,7aR)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole (E237, Enantiomer 1) and 3-({3-[(4aS,7aR or 4aR,7aS)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole (E238, Enantiomer 2)

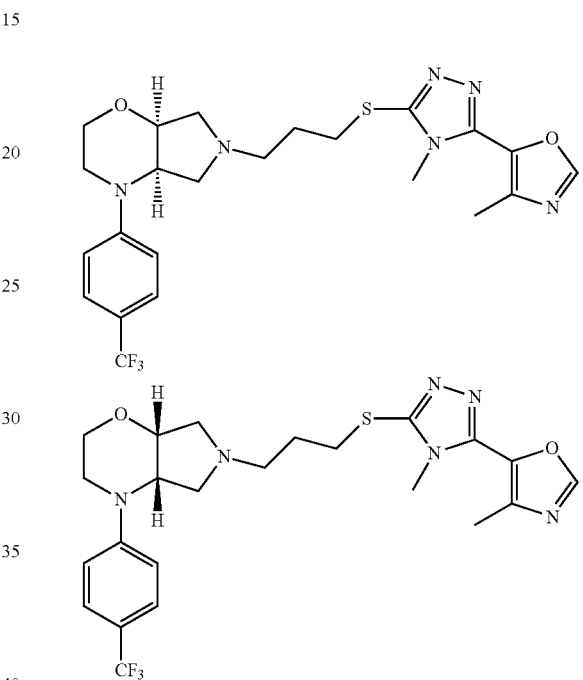

4-methyl-3-(4-methyl-1,3-oxazol-5-yl)-5-[(3-{4-[4-(trifluoromethyl)phenyl]-octahydropyrrolo[3,4-b]morpholin-6-yl}propyl)sulfanyl]-4H-1,2,4-triazole (E236, 40 mg) was separated into the single enantiomers by preparative chiral HPLC, obtaining 16.6 mg of 3-({3-[(4aR,7aS or 4aS,7aR)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole (E237, Enantiomer 1) and 16.5 mg of 3-({3-[(4aS,7aR or 4aR,7aS)-4-[4-(trifluoromethyl)phenyl]-octahydropyrrolo-[3,4-b]morpholin-6-yl]propyl}sulfanyl)-4-methyl-5-(4-methyl-1,3-oxazol-5-yl)-4H-1,2,4-triazole (E238, Enantiomer 2)

Preparative Chromatography:

| | |
|---|---|
| Column | Chiralpak IA (25 × 2 cm), 5 um |
| Mobile phase | n-Hexane/(Ethanol/Methanol/DCM 45/45/10 + 0.1% ipa) 40/60% v/v |
| Flow rate (mL/min) | 18 |
| DAD detection | 220 nm |
| Loop injection | 1100 μL 10 mg (each injection) |

Example 237 Enantiomer 1: ret. time 8.1 min, 100% ee MS (m/z): 509.3 [MH]⁺.

Example 238 Enantiomer 2: ret. time 11 min, 100% ee MS (m/z): 509.3 [MH]⁺.

Example 239: 3-({3-[(4aS,7aR or 4aR,7aS)-4-[4-(trifluoromethyl)phenyl]-octahydropyrrolo-[3,4-b]morpholin-6-yl]propyl}sulfanyl)-4-methyl-5-(4-methyl-1,3-oxazol-5-yl)-4H-1,2,4-triazole dihydrochloride (E239, Enantiomer 2)

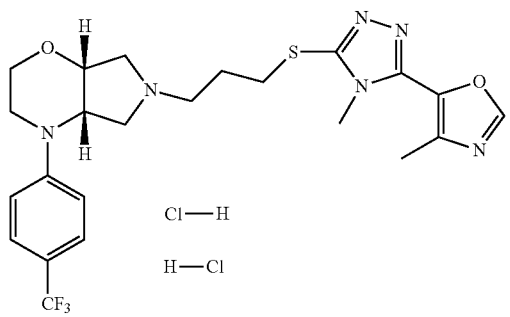

3-({3-[(4aS,7aR or 4aR,7aS)-4-[4-(trifluoromethyl)phenyl]-octahydropyrrolo[3,4-b]morpholin-6-yl]propyl}sulfanyl)-4-methyl-5-(4-methyl-1,3-oxazol-5-yl)-4H-1,2,4-triazole (E238, Enantiomer 2, 16.5 mg) was dissolved in DCM and treated with HCl 2 M in Et$_2$O (2.2 eq). Solvent was eliminated under reduced pressure and the residue triturated with Et$_2$O and dried under vacuum affording 17 mg of title compound (E239, Enantiomer 2). MS (m/z): 509.3 [MH]$^+$.

Preparation 150: tert-butyl 1H-pyrrolo[2,3-c]pyridine-1-carboxylate

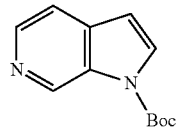 [SMILES: CC(C)(C)OC(=O)n1ccc2ccncc21]

1H-pyrrolo[2,3-c]pyridine (0.3 g, 2.54) was dissolved in DCM (10 mL), followed by TEA (0.71 mL, 5.08 mmol). Di-tert-butyl dicarbonate (830 mg, 3.8 mmol) was added slowly to the mixture, and stirred at RT for 1 h. Water was then added and the mixture was partitioned between water and DCM. The organic layer, once dried, was evaporated and the crude purified by FC on SiO$_2$ cartridge (eluting DCM:EtOAc from 7:3 to 1:1) obtaining 501 mg title compound (p150, y=90%) as brownish oil. MS (m/z): 219.1 [MH]$^+$.

Preparation 151: acetic acid tert-butyl octahydro-1H-pyrrolo[2,3-c]pyridine-1-carboxylate

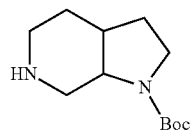

tert-butyl 1H-pyrrolo[2,3-c]pyridine-1-carboxylate (p150, 0.51 g; 2.34 mmol) was dissolved in EtOH (15 mL), followed by Acetic acid (1 mL) and catalytic PtO$_2$. The mixture was hydrogenated at 7 atm for 16 hrs, then the crude was filtered in order to remove the catalyst and the volatiles were evaporated, obtaining 851 mg of title compound (p151). The product was used in the next step without further purification. MS (m/z): 227.2 [MH]$^+$.

Preparation 152: 6-benzyl 1-tert-butyl octahydro-1H-pyrrolo[2,3-c]pyridine-1,6-dicarboxylate

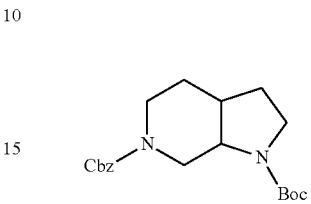

Acetic acid tert-butyl octahydro-1H-pyrrolo[2,3-c]pyridine-1-carboxylate (p151, 850 mg, 2.34 mmol) was dissolved in THF (50 mL), then K$_2$CO$_3$ (1.6 g, 11.7 mmol) was added, followed by Benzyl chloroformate (0.501 mL, 3.51 mmol). The mixture was stirred at RT ON, then the crude was partitioned between water and EtOAc. The organic phase was dried and evaporated, and then the crude was purified by FC on SiO$_2$ cartridge (eluting cHex:EtOAc 9:1) obtaining 670 mg of title compound (p152, y=80%). MS (m/z): 361.3 [MH]$^+$.

Preparation 153: benzyl octahydro-1H-pyrrolo[2,3-c]pyridine-6-carboxylate

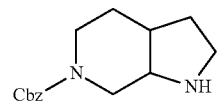 [SMILES: O=C(OCc1ccccc1)N1CCC2CCNC2C1]

6-benzyl 1-tert-butyl octahydro-1H-pyrrolo[2,3-c]pyridine-1,6-dicarboxylate (p152, 300 mg, 0.83 mmol) was dissolved in DCM (10 mL) and treated with CF$_3$COOH (1 mL). The mixture was stirred at RT ON, then the volatiles were removed and the crude purified by SCX eluting with 1 M NH$_3$ in MeOH obtaining 180 mg of title compound (p153, y=84%). NMR: $^1$H NMR (CDCl$_3$) δ: 7.30-7.45 (m, 5H), 5.08-5.22 (m, 2H), 3.77 (br. s., 2H), 3.39-3.51 (m, 1H), 3.00-3.28 (m, 3H), 2.88-3.02 (m, 1H), 2.09-2.23 (m, 1H), 1.87-2.01 (m, 1H), 1.43-1.74 (m, 3H).

Preparation 154: benzyl octahydro-1H-pyrrolo[2,3-c]pyridine-6-carboxylate

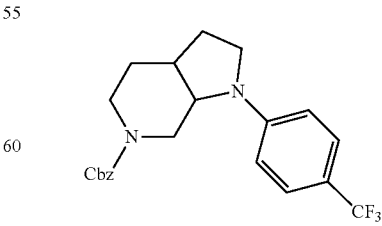

benzyl octahydro-1H-pyrrolo[2,3-c]pyridine-6-carboxylate (p153, 180 mg, 0.7 mmol) was dissolved in Toluene (4.5 mL), then Sodium tert-butoxide (202 mg, 2.1 mmol) was added followed by Pd$_2$(dba)$_3$ (32 mg, 0.035 mmol) and BINAP (22 mg, 0.035 mmol). 4-Bromobenzotrifluoride (158 mg, 0.7 mmol) was added before heating the mixture at 100° C. under microwave radiation for 1 h. The volatiles were then removed and the crude partitioned between water and AcOEt. The organic phase was dried and evaporated and crude material was purified by FC on SiO$_2$ cartridge (eluting cHex:EtOAc 85:15) obtaining 226 mg of title compound (p154, y=80%) as yellowish oil. MS (m/z): 405.3 [MH]$^+$.

Preparation 155: 1-[4-(trifluoromethyl)phenyl]-octahydro-1H-pyrrolo[2,3-c]pyridine

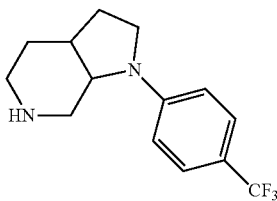 [SMILES: FC(F)(F)c1ccc(N2CCC3CCNCC32)cc1]

benzyl 1-[4-(trifluoromethyl)phenyl]-octahydro-1H-pyrrolo[2,3-c]pyridine-6-carboxylate (p154, 0.226 g, 0.56 mmol) was dissolved in EtOH (10 mL) and then Ammonium Formate (353 mg, 5.6 mmol) was added, followed by Pd/C 10% (Cat.) and the mixture was refluxed for 1 h. The catalyst was then filtered off and the solvent removed. The crude was purified by SCX eluting with 1N NH$_3$ in MeOH, obtaining 140 mg of title compound (p155, y=92%). MS (m/z): 271.2 [MH]$^+$.

Preparation 156: (4-chlorobutyl)sulfanyl]-4-methyl-5-(4-methyl-1,3-oxazol-5-yl)-4H-1,2,4-triazole

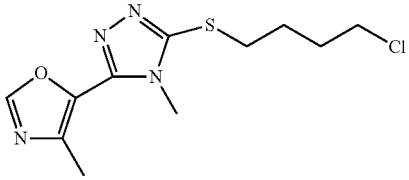 [SMILES: Cc1ncoc1-c1nnc(SCCCCCl)n1C]

To a suspension of 4-methyl-5-(4-methyl-1,3-oxazol-5-yl)-4H-1,2,4-triazole-3-thiol (p2, 300 mg, 1.53 mmol) in a mixture MeOH/Acetone (0.75 mL/1.6 mL) at RT 1-Bromo-4-chlorobutane (230 μL, 1.99 mmol) was added followed by K$_2$CO$_3$ (296 mg, 2.14 mmol) and the mixture was stirred at RT 4 hrs. Then it was partitioned between water and EtOAc and phases were separated. Organic one was washed with brine then dried and concentrated under reduced pressure. Crude material was purified by FC on SiO$_2$ cartridge (eluting from cHex to EtOAc) affording 270 mg of title compound (p156, y=61%). MS (m/z): 287.1 [MH]$^+$.

Example 240: 4-methyl-3-(4-methyl-1,3-oxazol-5-yl)-5-[(4-{1-[4-(trifluoromethyl)phenyl]-octahydro-1H-pyrrolo[2,3-c]pyridin-6-yl}butyl)sulfanyl]-4H-1,2,4-triazole (E240)

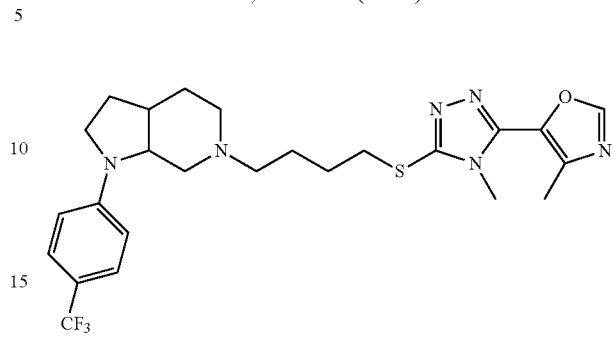

3-[(4-chlorobutyl)sulfanyl]-4-methyl-5-(4-methyl-1,3-oxazol-5-yl)-4H-1,2,4-triazole (p156, 26 mg, 0.09 mmol) was mixed with 1-[4-(trifluoromethyl)phenyl]-octahydro-1H-pyrrolo[2,3-c]pyridine (p155, 20 mg, 0.074 mmol), Na$_2$CO$_3$ (10 mg, 0.1 mmol), NaI (15 mg, 0.1 mmol) and DMF (0.2 mL). The mixture was stirred at 60° C. ON. The solvent was then removed and the crude purified by FC on NH cartridge (cHex/EtOAc from 9:1 to 7:3), obtaining 17 mg of title compound (E240, y=45%). NMR: $^1$H NMR (CDCl$_3$) δ: 7.95 (s, 1H), 7.44 (d, 2H), 6.60 (d, 2H), 4.02 (br. s., 1H), 3.66-3.76 (m, 3H), 3.24-3.48 (m, 4H), 3.10-3.21 (m, 1H), 2.77 (br. s., 1H), 2.55 (s, 3H), 2.34-2.51 (m, 3H), 2.05-2.26 (m, 3H), 1.76-2.01 (m, 6H), 1.26-1.42 (m, 1H). MS (m/z): 521.3 [MH]$^+$.

Example 241: 4-methyl-3-(4-methyl-1,3-oxazol-5-yl)-5-[(3-{1-[4-(trifluoromethyl)phenyl]-octahydro-1H-pyrrolo[2,3-c]pyridin-6-yl}propyl)sulfanyl]-4H-1,2,4-triazole (E241)

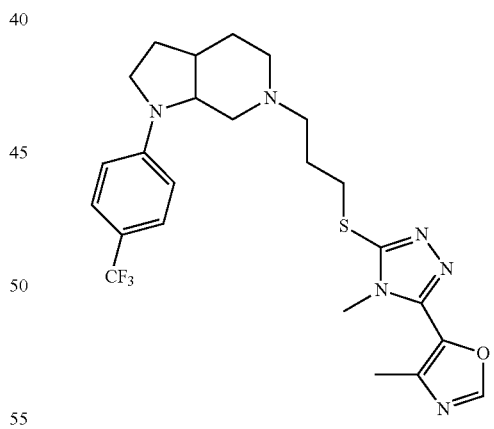

3-[(3-chloropropyl)sulfanyl]-4-methyl-5-(4-methyl-1,3-oxazol-5-yl)-4H-1,2,4-triazole (p3, 61 mg, 0.22 mmol) was mixed with 1-[4-(trifluoromethyl)phenyl]-octahydro-1H-pyrrolo[2,3-c]pyridine (p155, 50 mg, 0.185 mmol), Na$_2$CO$_3$ (28.0 mg, 0.26 mmol), NaI (40 mg, 0.26 mmol) and DMF (0.3 mL). The mixture was stirred at 65° C. ON. The solvent was then removed and the crude purified by FC on NH cartridge (eluting with cHex/EtOAc from 9:1 to 7:3) obtaining 63 mg of title compound (E241, y=57%) as yellowish solid. NMR: $^1$H NMR (CDCl$_3$) δ: 7.94 (s, 1H), 7.44 (d, 2H), 6.54-6.68 (m, 2H), 3.97 (br. s., 1H), 3.64-3.79 (m, 3H), 3.22-3.48 (m, 4H), 3.14 (br. s., 1H), 2.72 (br. s., 1H), 2.33-2.61 (m, 6H), 1.88-2.24 (m, 6H), 1.79 (m, 2H). MS (m/z): 507.3 [MH]+.

Example 242 and Example 243: 3-({3-[(3aR,7aS or 3aS,7aR)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole dihydrochloride (E242, Enantiomer 1) and 3-({3-[(3aS,7aR or 3aR,7aS)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole dihydrochloride (E243, Enantiomer 2)

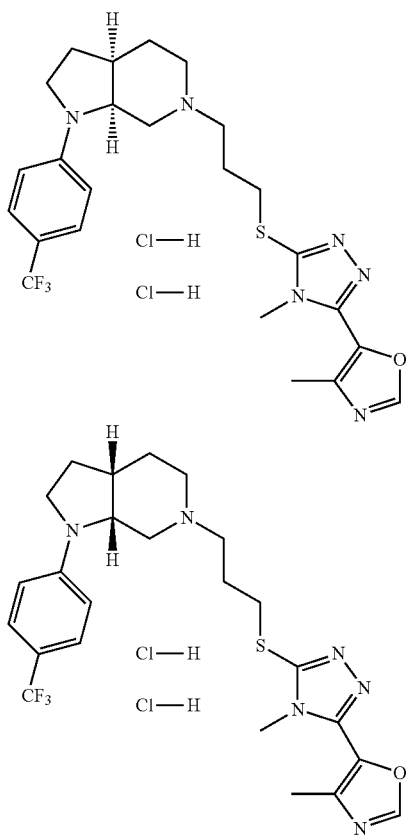

4-methyl-3-(4-methyl-1,3-oxazol-5-yl)-5-[(3-{1-[4-(trifluoromethyl)phenyl]-octahydro-1H-pyrrolo[2,3-c]pyridin-6-yl}propyl)sulfanyl]-4H-1,2,4-triazole (E241, 57 mg) was separated into the single enantiomers by preparative chiral HPLC.

Preparative Chromatography:

| Column | Chiralcel OJ-H (25 × 2 cm), 5 µm |
|---|---|
| Mobile phase | n-Hexane/(Ethanol/Methanol 1/1 + 0.1% ipa) 35/65% v/v |
| Flow rate (mL/min) | 18 |
| DAD detection | 220 nm |
| Loop injection | 2000 µL 28 mg (each injection) | obtaining 21 mg of 3-({3-[(3aR,7aS or 3aS,7aR)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole (E242, Enantiomer 1) and 22 mg of 3-({3-[(3aS,7aR or 3aR,7aS)-1-[4-(trifluoromethyl)phenyl]-octahydro-1H-pyrrolo[2,3-c]pyridin-6-yl]propyl}sulfanyl)-4-methyl-5-(4-methyl-1,3-oxazol-5-yl)-4H-1,2,4-triazole (E243, Enantiomer 2).

Each enantiomer was dissolved in DCM and treated with HCl 1 M in Et2O (2.2 eq). Solvent was eliminated under reduced pressure and the residue was dried under vacuum affording Example 242 (23.7 mg, Enantiomer 1): ret. time 9.4 min, 100% ee MS (m/z): 507.3 [MH]+ & Example 243 (25 mg, Enantiomer 2): ret. time 17.3 min, 100% ee MS (m/z): 507.3 [MH]+.

Preparation 157: tert-butyl octahydro-1H-pyrrolo[2,3-c]pyridine-1-carboxylate

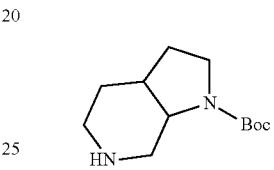

6-benzyl 1-tert-butyl octahydro-1H-pyrrolo[2,3-c]pyridine-1,6-dicarboxylate (p152, 110 mg, 0.31 mmol) was dissolved in EtOH (7 mL), and ammonium formate (195 mg, 3.1 mmol) was added followed by Pd/C (Cat). The mixture was then heated to reflux for 1 h. Then the catalyst was filtered off and the solvent removed to afford 58 mg of title compound (p157, y=crude) that was used in the next step without further purifications. MS (m/z): 227.2 [MH]+.

Preparation 158: tert-butyl 6-[4-(trifluoromethyl)phenyl]-octahydro-1H-pyrrolo[2,3-c]pyridine-1-carboxylate

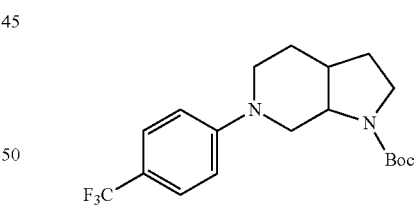

tert-butyl octahydro-1H-pyrrolo[2,3-c]pyridine-1-carboxylate (p157, 58 mg, 0.26 mmol) was dissolved in Toluene (2 mL), and then Sodium tert-butoxide (75 mg, 0.78 mmol) was added followed by Pd2(dba)3 (12 mg, 0.013 mmol) and BINAP (8 mg, 0.013 mmol). 4-Bromobenzotrifluoride (0.04 mL, 0.28 mmol) was added before heating the mixture at 100° C. under microwave radiation for 1 h. The volatiles were then removed and the crude partitioned between water and EtOAc, then the organic phase was dried and evaporated, and crude material was purified by FC on SiO2 cartridge (eluting cHex/EtOAc 80:20) obtaining 60 mg of title compound (p158, y=62%) as yellowish oil. MS (m/z): 371.3 [MH]+.

Preparation 159: 6-[4-(trifluoromethyl)phenyl]-octahydro-1H-pyrrolo[2,3-c]pyridine

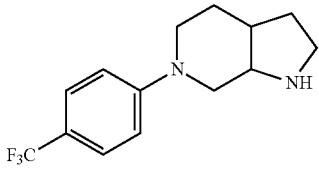 [SMILES: FC(F)(F)c1ccc(N2CCC3CCNC3C2)cc1]

tert-butyl 6-[4-(trifluoromethyl)phenyl]-octahydro-1H-pyrrolo[2,3-c]pyridine-1-carboxylate (p158, 60 mg, 0.16 mmol) was dissolved in DCM (7 mL) and treated with CF$_3$COOH (1 mL). The mixture was stirred at RT ON, then the volatiles were removed and the crude purified by SCX eluting with 1N NH$_3$ in MeOH, obtaining 45 mg of title compound (p159, y=90%). MS (m/z): 271.2 [MH]$^+$.

Example 244: 4-methyl-3-(4-methyl-1,3-oxazol-5-yl)-5-[(3-{6-[4-(trifluoromethyl)phenyl]-octahydro-1H-pyrrolo[2,3-c]pyridin-1-yl}propyl)sulfanyl]-4H-1,2,4-triazole dihydrochloride (E244)

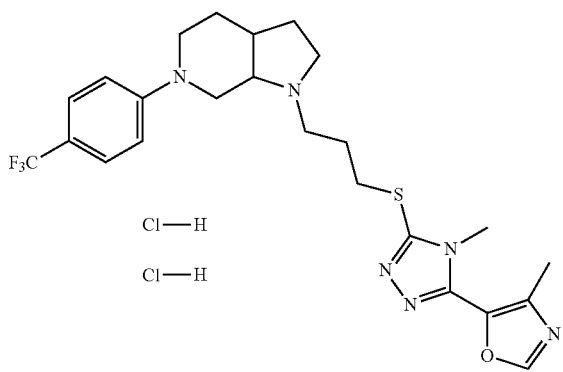

Step A: 3-[(3-chloropropyl)sulfanyl]-4-methyl-5-(4-methyl-1,3-oxazol-5-yl)-4H-1,2,4-triazole (p3, 55 mg; 0.2 mmol), was mixed with 1-[4-(trifluoromethyl)phenyl]-octahydro-1H-pyrrolo[2,3-c]pyridine (p159, 45 mg, 0.17 mmol), Na$_2$CO$_3$ (25.0 mg, 0.24 mmol), NaI (36 mg, 0.24 mmol) and DMF (0.3 mL). The mixture was stirred at 65° C. ON. The solvent was then removed and the crude purified by FC on NH cartridge (eluting cHex/EtOAc from 9:1 to 75:25) obtaining 44 mg of 4-methyl-3-(4-methyl-1,3-oxazol-5-yl)-5-[(3-{6-[4-(trifluoromethyl)phenyl]-octahydro-1H-pyrrolo[2,3-c]pyridin-1-yl}propyl)sulfanyl]-4H-1,2,4-triazole (y=40%) as colourless oil.

Step B: 4-methyl-3-(4-methyl-1,3-oxazol-5-yl)-5-[(3-{6-[4-(trifluoromethyl)phenyl]-octahydro-1H-pyrrolo[2,3-c]pyridin-1-yl}propyl)sulfanyl]-4H-1,2,4-triazole (from Step A, 44 mg) was treated with 1 M HCl in MeOH, obtaining, after evaporation of the solvent, 49 mg of title compound (E244) as light brown solid. NMR: $^1$H NMR (DMSO-d$_6$) δ: 11.27-11.39 (m, 1H), 10.14-10.33 (m, 1H), 8.57 (s, 1H), 7.51 (d, 2H), 7.05 (d, 2H), 3.72-3.87 (m, 3H), 3.69 (s, 3H), 3.55-3.68 (m, 2H), 3.44-3.53 (m, 1H), 3.19-3.33 (m, 3H), 3.03-3.14 (m, 1H), 2.53-2.61 (m, 2H), 2.37 (s, 3H), 2.07-2.29 (m, 3H), 1.87-1.97 (m, 1H), 1.72-1.86 (m, 2H). MS (m/z): 507.3 [MH]$^+$.

Biological Test Methods

[$^3$H]-Spiperone Binding Assay at hD$_3$ and hD$_4$ recombinant receptors CHO cells transiently transfected with human dopamine type 3 or 4 receptors (CHO-hD$_3$ or CHO-hD$_4$, respectively), were re-suspended in 20 mM HEPES, 2 mM EDTA (pH 7.4), homogenised and centrifuged at 40,000 g (20 min, 4° C.). After re-suspension, homogenization and centrifugation as above, the final pellet was re-suspended in 20 mM HEPES, 100 mM NaCl, 10 mM MgCl$_2$, 1 mM EDTA (pH 7.4) and aliquots were kept at −80° C. [$^3$H]-Spiperone Binding experiments were performed in 96 deep-well polypropylene plates in 50 mM Tris/HCl, 120 mM NaCl, 5 mM KCl, 5 mM MgCl$_2$ (pH 7.4). Compounds of invention were serially diluted in DMSO at 100 fold final concentrations in the assay (1% DMSO final in the assay). Displacement was performed in the presence of 0.3 nM [$^3$H]-Spiperone. The reaction was initiated by the addition of membrane suspension (4 µg and 12 µg of protein for CHO-hD$_3$- and CHO-hD$_4$ membranes, respectively) and lasted for 90 or 100 min (for hD$_3$ or hD$_4$ membranes, respectively) at 23° C. in a final volume of 500 µl. Non specific binding (NSB) was determined in the presence of 1 µM Spiperone. The binding reaction was stopped by rapid filtration through GF/B filterplates pre-soaked in 0.5% polyetylenimmine (PEI) using a Packard cell harvester. After washing with ice-cold 0.9% NaCl, the plate was left to dry before the addition of Microscint 20 (50 µl/well, PerkinElmer). Radioactivity was counted with a TopCount (PerkinElmer). Data were analysed by non-linear regression analysis using GraphPad Prism 5.0 (GraphPad Software). Saturation binding experiments were performed similar to the competition binding experiments using a radioligand concentrations ranging from 0.015 to 4.0 nM. Ref: Mackenzie R. G. et al. (1994). *Characterization of the human dopamine D3 receptor expressed in transfected cell lines.* Eur. J. Pharmacol. 266: 79-85.

[$^{125}$I]-7OH-PIPAT Binding Assay at rat native D$_3$ receptor on membranes from rat ventral striatum. Homogenates from frozen rat brain ventral striatum (nucleus accumbens and olfactory tubercles), were prepared as described by Burris et al. (1994). [$^{125}$I]-7OH-PIPAT binding assay at D$_3$ receptors was performed in 50 mM Tris-HCl (pH 7.0), 50 mM NaCl, 100 µM Gpp(NH)p (Guanosine 5'-[β,γ-imido]triphosphate) and 0.02% BSA, i.e. conditions which inhibit the [$^{125}$I]-7-OH-PIPAT binding to D$_2$ and 5HT$_{1A}$ receptors. Compounds of invention were serially diluted in DMSO at 100 fold final concentrations in the assay (1% DMSO final in the assay). Displacement experiments were performed in the presence of 0.2 nM [$^{125}$I]-7OH-PIPAT. The reaction, carried out in a final volume of 200 µl, was initiated by the addition of membrane suspension (about 20 µg/well protein) and lasted 45 min at 37° C. Non specific binding (NSB) was determined in the presence of 1 µM SB277011A. The binding reaction was stopped by rapid filtration through GF/C filterplates pre-soaked in 0.5% polyetylenimmine (PEI) using a Packard cell harvester. After washing with ice-cold 50 mM Tris (pH 7.4) and addition of Microscint 20 (50 µl/well, PerkinElmer), radioactivity was counted with a TopcCount (PerkinElmer). Data were analyzed by non-linear regression analysis using GraphPad Prism 5.0 (GraphPad Software). Ref: Burris. K. D.; Filtz. T. M: Chumpradit. S.; Kung. M. P.; Foulon. C.; Hensler. J. G.; Kung. H. F.; Molinoff P. B. *Characterization of* [125I](R)-*trans*-7-*hydroxy*-2-[N-*propyl*-N-(3'-*iodo*-2'-*propenyl*)*amino*]*tetralin binding to dopamine D3 receptors in rat olfactory tubercle.* J. Pharmacol. Exp. Ther. 1994, 268, 935-942.

[$^3$H]-Spiperone Binding Assay at hD$_2$ recombinant receptor. CHO cells stably expressing human dopamine receptor type 2, long variant (hD$_{2L}$), coupled to Gα16 protein (CHO-Gα16-hD$_{2L}$) were re-suspended in 20 mM HEPES, 2 mM EDTA (pH 7.4), homogenised and centrifuged at 40,000 g (20 min, 4° C.). After re-suspension, homogenization and centrifugation as above, the final pellet was re-suspended in 20 mM HEPES, 100 mM NaCl, 10 mM MgCl$_2$, 1 mM EDTA (pH 7.4) and aliquots were kept at −80° C. [$^3$H]-Spiperone Binding experiments were performed in 96 deep-well polypropylene plates in 50 mM Tris/HCl, 120 mM NaCl, 5 mM KCl, 5 mM MgCl$_2$ (pH 7.4). Compounds of invention were serially diluted in DMSO at 100 fold final concentrations in the assay (1% DMSO final in the assay). Displacement was performed in the presence of 0.08 nM [$^3$H]-Spiperone. The reaction was initiated by the addition of membrane suspension (2 μg of protein for CHO-hD$_2$ membranes) and lasted for 120 min at 23° C. in a final volume of 1000 μl. Non specific binding (NSB) was determined in the presence of 0.1 μM Spiperone. The binding reaction was stopped by rapid filtration through GF/B filterplates pre-soaked in 0.5% polyetylenimmine (PEI) using a Packard cell harvester. After washing with ice-cold 0.9% NaCl, the plate was left to dry before the addition of Microscint 20 (50 μl/well, PerkinElmer). Radioactivity was counted with a TopCount (PerkinElmer). Data were analysed by non-linear regression analysis using GraphPad Prism 5.0 (GraphPad Software) or XLfit Version 5.2.0.0 (Copyright © 2006-2009 ID Business Solutions Ltd). Saturation binding experiments were performed similar to the competition binding experiments using a radioligand concentrations ranging from 0.011 to 3.0 nM. Ref: Durcan M. J. et al. (1995). *Is Clozapine selective for the dopamine D4 receptor? Life Sciences.* 57: 275-283. Petrus J. et al. (2001). *Real-time analysis of dopamine: antagonist interactions at recombinant human D2long receptor upon modulation of its activation state. Brit. J. Pharmacol.* 134, 88±97.

Functional Calcium Assay at hD$_2$ recombinant receptor. CHO cells stably expressing human dopamine receptor type 2, long variant (hD$_{2L}$), coupled to Gα16 protein (CHO-Gα16-hD$_{2L}$) were seeded into black walled clear-base 384-well plates at a density of 8,000 cells per well and grown overnight at 37° C. After washing with the assay buffer (20 mM HEPES, 145 mM NaCl, 5 mM KCl, 5.5 mM glucose, 1 mM MgCl$_2$ and 2 mM CaCl$_2$, pH 7.4) containing 2.5 mM Probenecid, cells were incubated with the cytoplasmic Ca$^{2+}$ probe Fluo-4 AM at 1 μM (final concentration), 37° C. for 60 min. Plates were washed three times as above and placed into a Fluorometric Imaging Plate Reader (FLIPR Tetra, Molecular Devices) to monitor cell fluorescence (ex=470-495 nm, em=515-575 nm) before and after the addition of different concentrations of test compounds. Compounds of invention were dissolved in DMSO and 200-fold diluted with assay buffer plus 0.01% Pluronic F-127. Cells were exposed first to test compounds for 10 min, then to a submaximal concentration of the hD$_2$ receptor agonist dopamine (EC$_{80}$, 50-140 nM). The fluorescence before compound addition (baseline) and before and after addition of agonist challenge was monitored. The peak of Ca$^{2+}$ stimulation (baseline subtracted) was plotted versus the concentration of test compound and the curve fitted using a four-parameter logistic equation (XLfit) to assess the agonist/antagonist potency and maximal response.

The compounds of the invention listed above have pKi values within the range of 7.0-10.5 at the dopamine D3 receptor.

The compounds of the invention listed above have selectivity over D2 preferably greater than 10 fold.

The following Table reports the values of some of the Examples:

| EX | D3 pKi | D2 fpKi | D2 pKi |
| --- | --- | --- | --- |
| 2 | 8.76 | 7.23 | |
| 5 | 8.65 | 6.86 | |
| 6 | 8.54 | 7.27 | |
| 7 | 8.85 | 8.24 | |
| 10 | 9.19 | 8.66 | 7.47 |
| 11 | 8.23 | 6.51 | |
| 12 | 8.38 | 6.73 | |
| 15 | 7.94 | 6.43 | |
| 16 | 8.91 | 6.84 | |
| 17 | 8.69 | 7.04 | |
| 20 | 8.34 | 6.3 | |
| 21 | 8.92 | 7.27 | 7.21 |
| 22 | 8.86 | 6.94 | |
| 23 | 9.06 | 7.34 | |
| 24 | 8.16 | 6.53 | |
| 25 | 8.97 | 8.36 | 7.69 |
| 26 | 7.86 | 6.21 | |
| 27 | 8.58 | | 6.3 |
| 28 | 9.38 | | 7.98 |
| 29 | 8.28 | | 6.34 |
| 30 | 8.53 | 7.20 | 6.79 |
| 34 | 8.51 | 6.34 | |
| 35 | 8.28 | 6.33 | |
| 36 | 7.94 | 6.03 | |
| 39 | 8.16 | 5.81 | |
| 40 | 7.57 | 5.89 | |
| 41 | 8.56 | nt | nt |
| 44 | 9.04 | 6.54 | |
| 45 | 8.27 | 5.88 | |
| 46 | 7.10 | nt | |
| 48 | 7.29 | 5.79 | |
| 49 | 7.06 | <5 | |
| 50 | 7.28 | <5 | |
| 51 | 8.83 | nt | |
| 54 | 8.60 | nt | |
| 55 | 8.35 | 6.7 | |
| 56 | 9.48 | nt | |
| 59 | 9.40 | nt | |
| 60 | 9.39 | 6.55 | |
| 61 | 9.39 | nt | |
| 64 | 9.74 | 7.36 | |
| 65 | 9.08 | 6.41 | |
| 66 | 7.94 | <5 | |
| 69 | 7.93 | 5.83 | |
| 70 | 7.68 | <5 | |
| 71 | 7.47 | nt | |
| 76 | 7.70 | 6.86 | |
| 77 | 7.57 | 5.91 | |
| 78 | 7.58 | 6.33 | |
| 79 | 7.76 | 6.06 | |
| 80 | 8.35 | 6.7 | 7.24 |
| 81 | 8.40 | 6.83 | |
| 84 | 8.51 | 7.05 | |
| 85 | 8.70 | 6.77 | |
| 86 | 7.91 | 6.07 | |
| 87 | 7.29 | 6.24 | |
| 88 | 7.33 | 5.98 | |
| 89 | 8.84 | 6.76 | |
| 92 | 8.39 | 6.81 | |
| 93 | 8.70 | 6.85 | 6.77 |
| 94 | 8.68 | 7.32 | |
| 95 | 8.68 | 6.98 | |
| 96 | 9.07 | 7.94 | 7.46 |
| 97 | 7.95 | 6.72 | |
| 99 | 8.64 | | 6.19 |
| 100 | 8.34 | 6.85 | 6.58 |
| 101 | 7.91 | 6.62 | 6.43 |
| 102 | 8.03 | 6.62 | |
| 105 | 8.00 | 6.11 | 5.97 |
| 106 | 8.39 | 6.53 | 6.54 |
| 107 | 7.50 | 5.77 | |
| 108 | 8.12 | 5.94 | |
| 109 | 8.10 | 6.20 | |

| EX | D3 pKi | D2 fpKi | D2 pKi |
|---|---|---|---|
| 110 | 8.15 | 6.62 | |
| 111 | 8.39 | 6.73 | |
| 112 | 7.78 | 6.16 | |
| 113 | 9.65 | | 7.46 |
| 114 | 9.45 | | 7.02 |
| 115 | 7.96 | | 6.43 |
| 118 | 7.23 | | 5.29 |
| 119 | 8.11 | | 6.59 |
| 120 | 8.52 | | 6.49 |
| 123 | 8.60 | | 6.65 |
| 124 | 7.58 | | 6.18 |
| 125 | 8.48 | | 6.28 |
| 128 | 8.56 | | 6.29 |
| 129 | 8.49 | | 6.37 |
| 130 | 7.62 | | 5.87 |
| 131 | 8.36 | | 6.43 |
| 133 | 8.97 | | 6.22 |
| 134 | 8.88 | 6.95 | |
| 137 | 8.59 | 6.93 | |
| 138 | 8.83 | 6.78 | |
| 139 | 8.83 | 7.41 | |
| 140 | 7.81 | 6.16 | |
| 141 | 8.45 | | 6.14 |
| 144 | 8.15 | | 5.69 |
| 145 | 8.67 | | 6.34 |
| 146 | 8.12 | | 5.82 |
| 147 | 8.01 | | 6.14 |
| 150 | 8.40 | | 6.37 |
| 151 | 7.33 | | 5.85 |
| 152 | 8.52 | | 6.72 |
| 153 | 8.73 | | 6.42 |
| 154 | 8.35 | | 6.00 |
| 155 | 8.25 | | 6.55 |
| 158 | 8.75 | | 6.63 |
| 159 | 7.62 | | 6.17 |
| 160 | 8.75 | | 6.36 |
| 161 | 8.29 | | 6.48 |
| 162 | 8.65 | | 6.81 |
| 163 | 8.59 | | 6.84 |
| 164 | 8.26 | | 6.14 |
| 165 | 8.13 | | 6.19 |
| 166 | 7.81 | | 5.65 |
| 167 | 8.07 | | 6.21 |
| 168 | 8.04 | | 6.21 |
| 171 | 8.16 | | 6.35 |
| 172 | 7.63 | | 5.92 |
| 173 | 7.66 | | 5.64 |
| 174 | 7.87 | | 6.31 |
| 175 | 8.35 | | 6.45 |
| 176 | 8.33 | | 6.69 |
| 177 | 7.84 | | 6.10 |
| 178 | 9.07 | | 7.43 |
| 179 | 8.10 | | 6.43 |
| 182 | 8.21 | | 6.61 |
| 183 | 7.12 | | 6.05 |
| 184 | 8.33 | | 6.00 |
| 185 | 8.45 | | 6.22 |
| 188 | 8.79 | | 6.38 |
| 189 | 7.36 | | 5.70 |
| 190 | 7.73 | | 5.36 |
| 191 | 7.56 | | 5.85 |
| 192 | 8.20 | | 6.25 |
| 193 | 8.19 | | 5.78 |
| 194 | 8.28 | | 6.28 |
| 195 | 9.11 | | 6.41 |
| 196 | 9.23 | | 6.56 |
| 197 | 9.03 | | 5.99 |
| 198 | 9.28 | | 6.72 |
| 199 | 9.29 | | 6.72 |
| 200 | 8.75 | | 6.26 |
| 201 | 8.85 | | 6.14 |
| 202 | 8.42 | | 6.08 |
| 203 | 8.88 | | 6.09 |
| 204 | 8.98 | | 6.09 |
| 205 | 9.19 | | 6.34 |
| 206 | 8.32 | | 5.68 |
| 207 | 8.09 | | 6.39 |
| 208 | 8.12 | | 5.92 |
| 211 | 8.38 | | 6.01 |
| 212 | 7.80 | 6.04 | |
| 213 | 7.64 | nt | |
| 216 | 7.69 | <5 | |
| 217 | 7.09 | | 5.94 |
| 218 | 8.9 | 6.24 | |
| 219 | 8.67 | 6.17 | |
| 221 | 8.96 | 6.16 | |
| 222 | 7.06 | 6.22 | |
| 223 | 7.23 | 6.11 | |
| 226 | 8.43 | 6.82 | |
| 227 | 7.45 | nt | |
| 228 | 7.43 | 5.82 | |
| 229 | 7.74 | 5.92 | |
| 231 | 7.94 | 6.48 | |
| 233 | 8.24 | 7.01 | |
| 235 | 7.95 | 6.16 | |
| 236 | 7.45 | 6.01 | |
| 238 | 7.77 | 6.37 | |
| 240 | 7.13 | 6.46 | |
| 241 | 7.01 | 6.04 | |
| 242 | 7.22 | 6.45 | |
| 244 | 7.39 | nt | |
Embodiment 1
A compound of formula (I) or a pharmaceutically acceptable salt thereof,
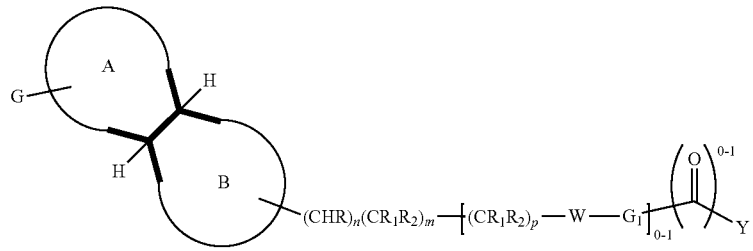

Wherein: is a saturated 4-6 carbocyclic ring, optionally in which one or two carbon atoms is heteroatoms selected among nitrogen and oxygen; and in which the group G is linked to a carbon or nitrogen; such ring may optionally be substituted at the carbon atoms or nitrogen atom by one or more $C_{1-4}$alkyl groups; B is a saturated 4-6 heterocyclic ring in which one or two carbon atoms is heteroatoms selected among Nitrogen or Oxygen and the linking atom is always a Nitrogen atom; such ring may be also substituted at the carbon atoms or, possibly, at the different Nitrogen atom, by one or more $C_{1-4}$alkyl group; G is phenyl, or a 5-6 membered heteroaromatic group, which is optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, halo$C_{1-4}$alkoxy, $SF_5$, —C(=O)$NH_2$, —C(=O)$OR_3$; W is S, $SO_2$, O, $CHR_2$, $NR_3$; n is 0 or 1; m is 1 or 2; p is 1 or 2; z is 0 or 1; R is hydrogen, $C_{1-4}$alkyl; $C_{1-4}$alkoxy; $R_1$ is hydrogen, F, $C_{1-4}$alkyl; hydroxyl, $C_{1-4}$alkoxy; $R_2$ is hydrogen, F, $C_{1-4}$alkyl; hydroxyl, $C_{1-4}$alkoxy; $R_3$ is hydrogen, $C_{1-4}$alkyl; $R_4$ is hydrogen or $C_{1-4}$alkyl; or —C(=O)$C_{1-4}$alkyl; —C(=O)$C_{1-4}$alkoxy$C_{1-4}$alkyl; —C(=O)cyclopropyl; $R_5$ is hydrogen, $C_{1-4}$alkyl; $R_6$ is hydrogen, $C_{1-4}$alkyl; $R_7$ is halogen, $C_{1-4}$alkyl; hydroxyl, $C_{1-4}$alkoxy; $G_1$ is phenyl or a 5-6-membered heteroaromatic group or a 8-11 membered heteroaromatic group; any of which groups is optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, halo$C_{1-4}$alkoxy,
$SF_5$, —C(=O)$NH_2$, —C(=OXO)$_z R_3$; Y is phenyl or a moiety selected from the group consisting of: 5-6 membered heteroaromatic group, a 8-11 membered heteroaromatic group; a saturated mono 3-7 membered carbocyclic group or a 8-11 membered bicyclic carbocyclic group in which one or more atom carbons may be replaced by $N(R_4)_z$, O, S; any of such groups may be optionally substituted by 1, 2 or 3 substituents selected from: halogen, cyano, hydroxyl, $C_{1-4}$alkylamino, $C_{1-4}$alkyl, halo$C_{1-4}$alkyl, $C_{1-4}$alkoxy, halo$C_{1-4}$alkoxy, $C_{1-4}$alkanoyl, —C(=O), —$NHR_4$, —$NR_5R_6$, $SF_5$, —C(=O)(O)$_z R_3$; when $G_1$ is a phenyl group $G_1$ and Y may optionally be fused together to form a benzofused aromatic or heteroaromatic system which might be optionally substituted by one or two substituents selected from: halogen, cyano, hydroxy, amino $C_{1-4}$alkyl, halo$C_{1-4}$alkyl, $C_{1-4}$alkoxy, halo$C_{1-4}$alkoxy, $C_{1-4}$alkanoyl, —C(=O)$NH_2$, —C(=O)$OR_3$, $SF_5$.

Embodiment 2

A compound according to embodiment 1, wherein A and B together have the formula:

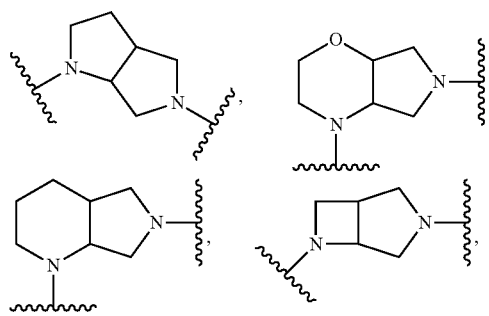

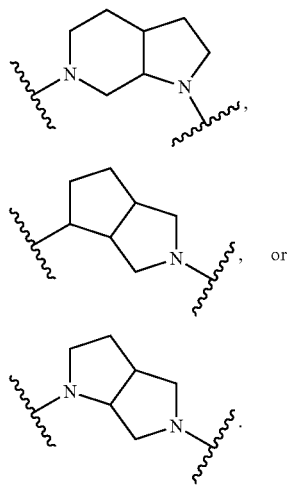

Embodiment 3

A compound of embodiment 1 or embodiment 2, wherein A and B together have the formula:

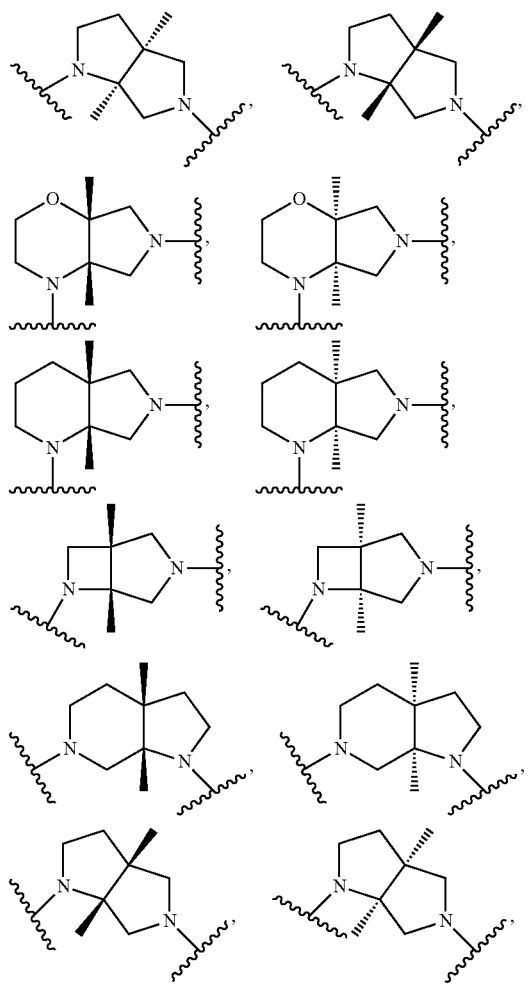

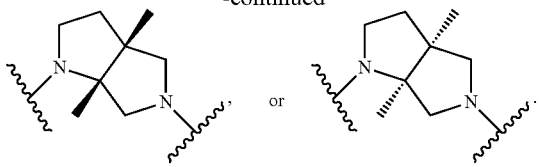

Embodiment 4

A compound according to any one of embodiments 1 to 3, wherein: W is C, O or S; R, $R_1$ and $R_2$ are hydrogen; G is a 6 member heteroaromatic ring or a phenyl optionally substituted by 1, 2 or 3 substituents selected from: halogen, cyano, $C_{1-4}$alkyl, halo$C_{1-4}$alkyl, $C_{1-4}$alkoxy, halo$C_{1-4}$alkoxy; $G_1$ is an optionally substituted 5-6 membered heteroaromatic group; Y is selected from the group consisting of: a saturated mono 3-7 membered carbocyclic group in which 0 or 1 or 2 carbon atoms are replaced by a heteroatom independently selected from O or $NR_3$; or a 5-6 membered heteroaromatic group, optionally substituted by one or two substituents selected from: hydroxyl, $C_{1-4}$alkyl, $(CH_2)_zC(=O)N(R_4R_5)$.

Embodiment 5

A compound according to any one of embodiments 1 to 4, wherein W is S; and $G_1$ is optionally substituted 4-methyl-4H-1,2,4-triazole.

Embodiment 6

A compound according to anyone of embodiments 1-6, selected from: 4-methyl-3-(4-methyl-1,3-oxazol-5-yl)-5-[(3-{1-[4-(trifluoromethyl)phenyl]octahydropyrrolo[3,4-b]pyrrol-5-yl}propyl)sulfanyl]-4H-1,2,4-triazole; 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole, Enantiomer 1; 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole, Enantiomer 2; 3-[5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile; 3-[(3aS,6aS or 3aR,6aR)-5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile, Enantiomer 1; 3-[(3aR,6aR or 3aS,6aS)-5-(3-{[4-methyl-5-(4-methyl-1,3-oxazol-5-yl)-4H-1,2,4-triazol-3-yl]sulfanyl})propyl)-octahydropyrrolo[2,3-c]pyrrol-1-yl]benzonitrile, Enantiomer 2; 4-methyl-3-(4-methyl-1,3-oxazol-5-yl)-5-[(3-{1-phenyl-octahydropyrrolo[2,3-c]pyrrol-5-yl}propyl)-sulfanyl]-4H-1,2,4-triazole; 3-({3-[(3aR,6aR or 3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole, Enantiomer 2; 3-[(3-{1-[2-fluoro-4-(trifluoromethyl)phenyl]-octahydropyrrolo[2,3-c]pyrrol-5-yl}propyl)sulfanyl]-4-methyl-5-(4-methyl-1,3-oxazol-5-yl)-4H-1,2,4-triazole; 3-({3-[(3aS,6aS or 3aR,6aR)-1-[2-fluoro-4-(trifluoromethyl)phenyl]-octahydropyrrolo[2,3-c]pyrrol-5-yl]propyl})sulfanyl)-4-methyl-5-(4-methyl-1,3-oxazol-5-yl)-4H-1,2,4-triazole, Enantiomer 1; 3-({3-[(3aR,6aR or 3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole, Enantiomer 2; 3-({3-[1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole; 3-({3-[(3aS,6aS or 3aR,6aR)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole, Enantiomer 1; 3-({3-[(3aR,6aR or 3aS,6aS)-1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole, Enantiomer 2; 4-methyl-3-(4-methyl-1,3-oxazol-5-yl)-5-[(3-{1-[2-(trifluoromethoxy)phenyl]-octahydropyrrolo[3,4-b]pyrrol-5-yl}propyl)sulfanyl]-4H-1,2,4-triazole; 3-({3-[1-(2,6-difluorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(3,5-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(2,4-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[1-(3-fluorophenyl)-octahydropyrrolo[3,4-b]pyrrol-5-yl]propyl}sulfanyl)-4-methyl-5-(4-methyl-1,3-oxazol-5-yl)-4H-1,2,4-triazole; 3-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole, Enantiomer 1; 3-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-5-(oxan-4-yl)-4H-1,2,4-triazole, Enantiomer 2; 3-({3-[(3aS,6aS or 3aR,6aR)-1-phenyl-octahydropyrrolo[2,3-c]pyrrol-5-yl]propyl}sulfanyl)-4-methyl-5-(oxan-4-yl)-4H-1,2,4-triazole, Enantiomer 1; 3-({3-[1-(4-fluorophenyl)-octahydropyrrolo[3,4-b]pyrrol-5-yl]propyl}sulfanyl)-4-methyl-5-(oxan-4-yl)-4H-1,2,4-triazole; 3-({3-[(3aS,6aS or 3aR,6aR)-1-(4-fluorophenyl)-octahydropyrrolo[3,4-b]pyrrol-5-yl]propyl})sulfanyl)-4-methyl-5-(oxan-4-yl)-4H-1,2,4-triazole, Enantiomer 1; 3-({3-[(3aR,6aR or 3aS,6aS)-1-(4-fluorophenyl)-octahydropyrrolo[3,4-b]pyrrol-5-yl]propyl}sulfanyl)-4-methyl-5-(oxan-4-yl)-4H-1,2,4-triazole, Enantiomer 2; 3-cyclopentyl-4-methyl-5-[(3-{1-[4-(trifluoromethyl)phenyl]-octahydropyrrolo[3,4-b]pyrrol-5-yl}propyl)sulfanyl]-4H-1,2,4-triazole; 3-({3-[(3aS,6aS or 3aR,6aR)-1-[4-(trifluoromethyl)phenyl]-octahydropyrrolo[3,4-b]pyrrol-5-yl]-propyl}sulfanyl)-5-cyclopentyl-4-methyl-4H-1,2,4-triazole, Enantiomer 1; 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclopentyl-4-methyl-4H-1,2,4-triazole, Enantiomer 2; 3-cyclohexyl-4-methyl-5-[(3-{1-[4-(trifluoromethyl)phenyl]-octahydropyrrolo[3,4-b]pyrrol-5-yl}propyl)sulfanyl]-4H-1,2,4-triazol; 3-({3-[(3aS,6aS or 3aR,6aR)-1-[4-(trifluoromethyl)phenyl]-octahydropyrrolo[3,4-b]pyrrol-5-yl]-propyl}sulfanyl)-5-cyclohexyl-4-methyl-4H-1,2,4-triazole, Enantiomer 1; 3-({3-[(3aR,6aR or 3aS,6aS)-1-[4-(trifluoromethyl)phenyl]-octahydropyrrolo[3,4-b]pyrrol-5-yl]propyl}sulfanyl)-5-cyclohexyl-4-methyl-4H-1,2,4-triazole, Enantiomer 2; 3-cyclohexyl-5-({3-[1-(4-fluorophenyl)-octahydropyrrolo[3,4-b]pyrrol-5-yl]propyl}sulfanyl)-4-methyl-4H-1,2,4-triazole; 3-({3-[(3aS,6aS or 3aR,6aR)-1-(4-fluorophenyl)-octahydropyrrolo[3,4-b]pyrrol-5-yl]propyl}sulfanyl)-5-cyclohexyl-4-methyl-4H-1,2,4-triazole, Enantiomer 1; 3-({3-[(3aR,6aR or 3aS,6aS)-1-(4-fluorophenyl)-octahydropyrrolo[3,4-b]pyrrol-5-yl]propyl}sulfanyl)-5-cyclohexyl-4-methyl-4H-1,2,4-triazole, Enantiomer 2; 1-methyl-2-[(3-{1-[4-(trifluoromethyl)phenyl]-octahydropyrrolo-[3,4-b]pyrrol-5-yl}propyl)sulfanyl]-1H-1,3-benzodiazole; 4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}morpholine; 4-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine, Enantiomer 1; 4-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine, Enantiomer 2; 2-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrazine; 2-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine, Enantiomer 1; 2-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine, Enantiomer 2; 3-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile; 2-[5-({3-[1-(4-fluorophenyl)-octahydropyrrolo[3,4-b]pyrrol-5-yl]propyl}sulfanyl)-4-methyl-4H-1,2,4-triazol-3-yl]pyrazine; 2-{4-methyl-5-[(3-{1-[2-(trifluoromethoxy)phenyl]-octahydropyrrolo[3,4-b]pyrrol-5-yl}propyl)sulfanyl]-4H-1,2,4-triazol-3-yl}pyrazine; 2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine; 2-[5-({3-[1-(3-fluorophenyl)-octahydropyrrolo[3,4-b]pyrrol-5-yl]propyl}sulfanyl)-4-methyl-4H-1,2,4-triazol-3-yl]pyrazine; 2-[5-({3-[1-(2,4-difluorophenyl)-octahydropyrrolo[2,3-c]pyrrol-5-yl]propyl})sulfanyl)-4-methyl-4H-1,2,4-triazol-3-yl]pyrazine; 2-[5-({3-[(3aS,6aS or 3aR,6aR)-1-(2,4-difluorophenyl)-octahydropyrrolo[2,3-c]pyrrol-5-yl]propyl}sulfanyl)-4-methyl-4H-1,2,4-triazol-3-yl]pyrazine, Enantiomer 1; 2-[5-({3-[(3aR,6aR or 3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine, Enantiomer 2; 2-[4-methyl-5-({3-[1-(4-methylphenyl)-octahydropyrrolo[3,4-b]pyrrol-5-yl]propyl}sulfanyl)-4H-1,2,4-triazol-3-yl]pyrazine; 2-[5-({3-[1-(3-methoxyphenyl)-octahydropyrrolo[3,4-b]pyrrol-5-yl]propyl}sulfanyl)-4-methyl-4H-1,2,4-triazol-3-yl]pyrazine; 2-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile; 2-[4-methyl-5-({3-[1-(3-methylphenyl)-octahydropyrrolo[3,4-b]pyrrol-5-yl]propyl}sulfanyl)-4H-1,2,4-triazol-3-yl]pyrazine; 2-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}pyrazine; 2-{4-methyl-5-[(3-{1-[3-(trifluoromethoxy)phenyl]-octahydropyrrolo[3,4-b]pyrrol-5-yl}propyl)sulfanyl]-4H-1,2,4-triazol-3-yl}pyrazine; 2-[5-({3-[(3aR,6aR or 3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine, Enantiomer 2; 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyrazine; 2-[5-({3-[(3aS,6aS or 3aR,6aR)-1-[2-(trifluoromethyl)phenyl]-octahydropyrrolo[3,4-b]pyrrol-5-yl]-propyl}sulfanyl)-4-methyl-4H-1,2,4-triazol-3-yl]pyrazine, Enantiomer 1; 2-[5-({3-[1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine; 2-[5-({3-[(3aS,6aS or 3aR,6aR)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine, Enantiomer 1; 2-[5-({3-[(3aR,6aR or 3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine, Enantiomer 2; 2-{5-[(3-{1-[2-fluoro-6-(trifluoromethyl)phenyl]-octahydropyrrolo[3,4-b]pyrrol-5-yl}propyl)sulfanyl]-4-methyl-4H-1,2,4-triazol-3-yl}pyrazine; 2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine; 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrimidine; 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine; 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine; 4-[5-({3-[1-(4-fluorophenyl)-octahydropyrrolo[3,4-b]pyrrol-5-yl]propyl}sulfanyl)-4-methyl-4H-1,2,4-triazol-3-yl]pyrimidine; 3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl})pyridine; 3-[5-({3-[(3aS,6aS or 3aR,6aR)-1-[4-(trifluoromethyl)phenyl]-octahydropyrrolo[3,4-b]pyrrol-5-yl]propyl})sulfanyl)-4-methyl-4H-1,2,4-triazol-3-yl]pyridine trihydrochloride; 3-[5-({3-[(3aR,6aR or 3aS,6aS)-1-[4-(trifluoromethyl)phenyl]-octahydropyrrolo[3,4-b]pyrrol-5-yl]-propyl}sulfanyl)-4-methyl-4H-1,2,4-triazol-3-yl]pyridine; 3-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine; 3-{4-methyl-5-[(3-{1-[2-(trifluoromethyl)phenyl]-octahydropyrrolo[3,4-b]pyrrol-5-yl}propyl)-sulfanyl]-4H-1,2,4-triazol-3 yl}pyridine; 3-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 4-methyl-3-(1-methyl-1H-pyrazol-4-yl)-5-[(3-{1-[4-(trifluoromethyl)phenyl]-octahydropyrrolo[3,4-b]pyrrol-5-yl}propyl)sulfanyl]-4H-1,2,4-triazole; 4-{4-methyl-5-[(3-{1-[4-(trifluoromethyl)phenyl]-octahydropyrrolo[3,4-b]pyrrol-5-yl}propyl)-sulfanyl]-4H-1,2,4-triazol-3-yl}pyridine; 4-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine; 4-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine; 4-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine; 2-{4-methyl-5-[(3-{1-[4-(trifluoromethyl)phenyl]-octahydropyrrolo[3,4-b]pyrrol-5-yl}propyl)-sulfanyl]-4H-1,2,4-triazol-3-yl}pyridine; 2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyridine; 4-methyl-3-(1,3-thiazol-2-yl)-5-[(3-{1-[4-(trifluoromethyl)phenyl]-octahydropyrrolo[3,4-b]pyrrol-5-yl}propyl)sulfanyl]-4H-1,2,4-triazole; 4-methyl-3-(3-methyl-1,2-oxazol-5-yl)-5-[(3-{1-[4-(trifluoromethyl)phenyl]-octahydropyrrolo[3,4-b]pyrrol-5-yl}propyl)sulfanyl]-4H-1,2,4-triazole; 4-methyl-3-(4-methyl-1,3-thiazol-5-yl)-5-[(3-{1-[4-(trifluoromethyl)phenyl]-octahydropyrrolo[3,4-b]pyrrol-5-yl}propyl)sulfanyl]-4H-1,2,4-triazole; 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}-1,2-dihydropyridin-2-one; 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one, Enantiomer 2; 4-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one; 4-[5-({3-[(3aS,6aS or 3aR,6aR)-1-(4-fluorophenyl)-octahydropyrrolo[2,3-c]

pyrrol-5-yl]propyl}-sulfanyl)-4-methyl-4H-1,2,4-triazol-3-yl]-1,2-dihydropyridin-2-one, Enantiomer 1; 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one; 5-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one; 3-({3-[1-(2,6-difluorophenyl)-octahydropyrrolo[3,4-b]pyrrol-5-yl]propyl}sulfanyl)-4-methyl-5-(i-methyl-1H-pyrazol-5-yl)-4H-1,2,4-triazole; 4-methyl-3-(1-methyl-1H-pyrazol-5-yl)-5-[(3-{1-[2-(trifluoromethyl)phenyl]-octahydropyrrolo[3,4-b]pyrrol-5-yl}propyl)sulfanyl]-4H-1,2,4-triazole; 3-({3-[(3aS,6aS or 3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole; 1-methyl-5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one; 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one, Enantiomer 1; 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one, Enantiomer 2; 5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine-2-carboxamide; 5-[5-({3-[(3aS,6aS or 3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide, Enantiomer 1; 5-[5-({3-[(3aR,6aR or 3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide, Enantiomer 2; 5-[5-({3-[1-(4-fluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aS,6aS or 3aR,6aR)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide, Enantiomer 1; 5-[5-({3-[(3aR,6aR or 3aS,6aS)-1-(4-fluorophenyl)-octahydropyrrolo[3,4-b]pyrrol-5-yl]propyl}sulfanyl)-4-methyl-4H-1,2,4-triazol-3-yl]pyridine-2-carboxamide, Enantiomer 2; 5-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide; 5-[5-({3-[(3aS,6aS or 3aR,6aR)-1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide, Enantiomer 1; 5-[5-({3-[(3aR,6aR or 3aS,6aS)-1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide, Enantiomer 2; 5-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyridine-2-carboxamide; 5-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide, Enantiomer 1; 5-[5-({3-[(3aR,6aR or 3aS,6aS)-1-(2,4,6-trifluorophenyl)-octahydropyrrolo[2,3-c]pyrrol-5-yl]propyl}sulfanyl)-4-methyl-4H-1,2,4-triazol-3-yl]pyridine-2-carboxamide, Enantiomer 2; 4-[5-({3-[1-(4-fluorophenyl)-octahydropyrrolo[3,4-b]pyrrol-5-yl]propyl}sulfanyl)-4-methyl-4H-1,2,4-triazol-3-yl]-1-methyl-1,2-dihydropyridin-2-one; 1-methyl-4-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]-1,2-dihydropyridin-2-one; 4-[5-({3-[(3aS,6aS or 3aR,6aR)-1-(2,4,6-trifluorophenyl)-octahydropyrrolo[2,3-c]pyrrol-5-yl]propyl}sulfanyl)-4-methyl-4H-1,2,4-triazol-3-yl]-1-methyl-1,2-dihydropyridin-2-one; 4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol; 4-[5-({3-[(3aS,6aS or 3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol, Enantiomer 1; 4-[5-({3-[(3aR,6aR or 3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol, Enantiomer 2; 4-methyl-3-(4-methyl-1,3-oxazol-5-yl)-5-({3-[(4S or 4R)-4-[4-(trifluoromethyl)phenyl]-octahydrocyclopenta[c]pyrrol-2-yl]propyl}sulfanyl)-4H-1,2,4-triazole, Diasteroisomer 1; 3-({3-[(4aR,7aR or 4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole, Enantiomer 2; or pharmaceutical acceptable salt thereof.

Embodiment 8

A compound of Formula (I), Formula (IA), or Formula (B).

Embodiment 9

A compound of Formula (II), Formula (IIA), or Formula (IIB).

Embodiment 10

A compound of Formula (III), Formula (IIIA), or Formula (IIIB).

Embodiment 11

A compound of Formula (IV), Formula (IVA), or Formula (IVB).

Embodiment 12

A compound of Formula (V), Formula (VA), or Formula (VB).

Embodiment 13

A compound of Formula (VI), Formula (VA), or Formula (VB).

Embodiment 14

A compound of Formula (VII), Formula (VIIA), or Formula (VIIB).

Embodiment 15

A compound of Formula (VIII), Formula (VIIIA), or Formula (VIIIB).

Embodiment 16

A compound of Formula (IX), Formula (IXA), or Formula (IXB).

Embodiment 17

A compound of Formula (X), Formula (XA), or Formula (XB).

Embodiment 18

A compound of any one of embodiments 1 to 17 or a pharmaceutical acceptable salt thereof for use as a medicament.

Embodiment 19

A pharmaceutical composition comprising a compound as embodimented in anyone of embodiments 1 to 17 and a pharmaceutically acceptable carrier.

Embodiment 20

A compound of any one of embodiments 1 to 17 for the use in the treatment of a condition for which modulation of dopamine $D_3$ receptors is beneficial.

Embodiment 21

A compound according to embodiment 20 in which the condition is condition is psychosis or a psychotic condition, or is substance dependency.

Embodiment 22

A compound according to embodiment 20 in which the condition is schizophrenia.

Embodiment 23

A method for treating drug dependency in a patient in need thereof comprising administering to the patient a therapeutically effective amount of a compound of any one of Embodiments 1-17 to treat the drug dependency. In embodiments, the drug dependency is alcohol dependence. In embodiments, the drug dependency is opioid dependence.

Embodiment 24

A method for treating a psychiatric condition in a patient in need thereof comprising administering a therapeutically effective amount of a compound of any one of embodiments 1 to 17 to the patient to treat the psychiatric condition.

Embodiment 25

A method of modulating a dopamine $D_3$ receptor in a patient in need thereof comprising administering a therapeutically effective amount of a compound of any one of embodiments 1 to 17 to the patient to modulate the dopamine $D_3$ receptor.

All publications, including but not limited to patents and patent applications, cited in this specification are herein incorporated by reference as if each individual publication were specifically and individually indicated to be incorporated by reference herein as though fully set forth. It is to be understood that the present invention covers all combinations of particular groups described herein above. The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims described herein.

What is claimed is:

1. A compound of Formula (I-1), Formula (I-2), Formula (I-3), Formula (I-4), Formula (I-5) or Formula (I-6):

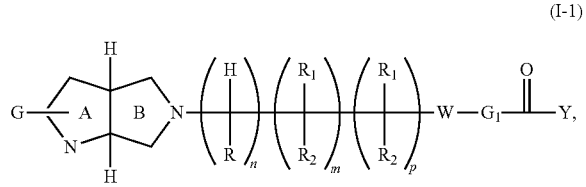

(I-1)

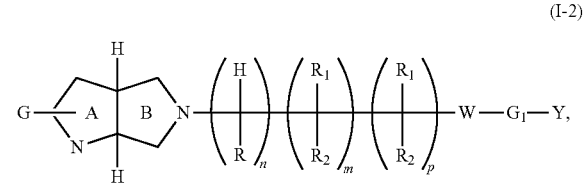

(I-2)

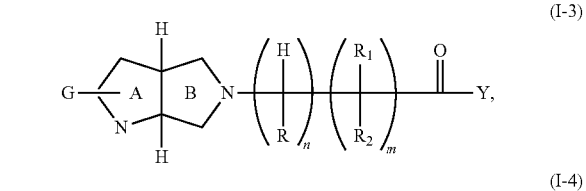

(I-3)

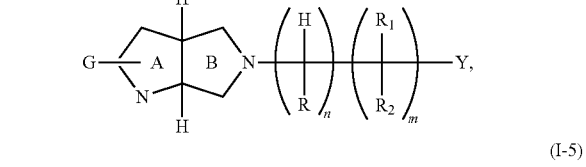

(I-4)

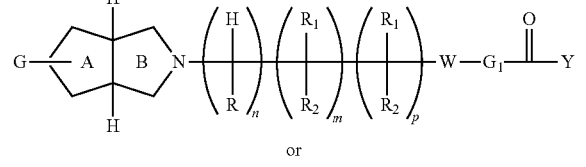

(I-5)

or (I-6)

or a pharmaceutically acceptable salt thereof, wherein:
ring A of the bicyclic ring system is optionally substituted at one or more carbon atoms or the nitrogen atom by one or more $C_{1-4}$ alkyl;
ring B of the bicyclic ring system is optionally substituted at one or more carbon atoms by one or more $C_{1-4}$ alkyl;
G is phenyl or a 5-6 membered heteroaryl, each of which is optionally substituted by one, two, three or four substituents selected from the group consisting of halogen, $SF_5$, CN, OH, $NH_2$, $NHC_{1-4}$ alkyl, $C_{1-4}$ alkyl, $haloC_{1-4}$ alkyl, $C_{1-4}$ alkoxy, $haloC_{1-4}$ alkoxy, $C_{1-4}$ alkanoyl, $C(=O)NH_2$ and $C(=O)OR_3$;
$G_1$ is phenyl, a 5-6 membered heteroaryl or an 8-11 membered heteroaryl, each of which is optionally substituted by one, two, three or four substituents selected from the group consisting of halogen, $SF_5$, CN, OH, $NH_2$, $NHC_{1-4}$ alkyl, $C_{1-4}$ alkyl, $haloC_{1-4}$ alkyl, $C_{1-4}$ alkoxy, $haloC_{1-4}$ alkoxy, $C(=O)NH_2$ and $C(=O)(O)_zR_3$;
R is H, $C_{1-4}$ alkyl or $C_{1-4}$ alkoxy;
each $R_1$ is independently H, F, OH, $C_{1-4}$ alkyl or $C_{1-4}$ alkoxy;
each $R_2$ is independently H, F, OH, $C_{1-4}$ alkyl or $C_{1-4}$ alkoxy;
$R_3$ is H or $C_{1-4}$ alkyl;
$R_4$ is H, $C_{1-4}$ alkyl, $C(=O)C_{1-4}$ alkyl, $C(=O)C_{1-4}$ alkoxy$C_{1-4}$alkyl or $C(=O)$cyclopropyl;
$R_5$ is H or $C_{1-4}$ alkyl;
$R_6$ is H or $C_{1-4}$ alkyl;
W is $-CHR_2-$, $-NR_3-$, $-O-$, $-S-$ or $-S(=O)_2-$;
Y is phenyl or an 8-11 membered heteroaryl, each of which is optionally substituted by one, two or three substituents selected from the group consisting of halogen, $SF_5$, CN, OH, $NR_5R_6$, $NHC_{1-4}$ alkyl, $C_{1-4}$ alkyl, $haloC_{1-4}$ alkyl, $C_{1-4}$ alkoxy, $haloC_{1-4}$ alkoxy, $C_{1-4}$ alkanoyl and $C(=O)(O)_zR_3$; or
Y is a 5-6 membered heteroaryl, which is optionally substituted by one, two or three substituents selected from the group consisting of halogen, =O, $SF_5$, CN, OH, $NR_5R_6$, $NHC_{1-4}$ alkyl, $C_{1-4}$ alkyl, $haloC_{1-4}$ alkyl, $C_{1-4}$ alkoxy, $haloC_{1-4}$ alkoxy, $C_{1-4}$ alkanoyl, $C(=O)NH_2$, $C(=O)(O)_zR_3$ and $(CH_2)_zC(=O)NR_4R_5$, provided that =O can only be a substituent for a carbon atom; or
Y is a monocyclic saturated 3-7 membered carbocyclyl, which is optionally substituted by one, two or three substituents selected from the group consisting of halogen, $SF_5$, CN, OH, $NR_5R_6$, $NHC_{1-4}$ alkyl, $C_{1-4}$ alkyl, $haloC_{1-4}$ alkyl, $C_{1-4}$ alkoxy, $haloC_{1-4}$ alkoxy, $C_{1-4}$ alkanoyl, $C(=O)NH_2$ and $C(=O)(O)_zR_3$, and wherein one or more carbon atoms is optionally replaced by $-N(R_4)_z-$, $-O-$ or $-S-$; or
Y is a bicyclic 8-11 membered carbocyclyl, each of which is optionally substituted by one, two or three substituents selected from the group consisting of halogen, $SF_5$, CN, OH, $NR_5R_6$, $NHC_{1-4}$ alkyl, $C_{1-4}$ alkyl, $haloC_{1-4}$ alkyl, $C_{1-4}$ alkoxy, $haloC_{1-4}$ alkoxy, $C_{1-4}$ alkanoyl, $C(=O)NH_2$ and $C(=O)(O)_zR_3$, and wherein one or more carbon atoms is optionally replaced by $-N(R_4)_z-$, $-O-$ or $-S-$;
m is 1 or 2;
n is 0 or 1;
p is 1 or 2; and
z is 0 or 1.

2. The compound of claim 1, wherein the compound is of Formula (I-2):

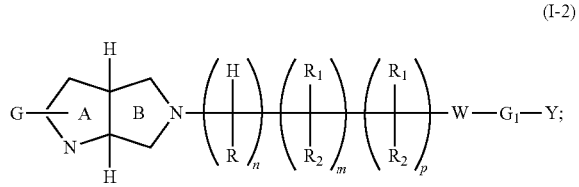

(I-2)

wherein:
G is phenyl or a 6 membered heteroaryl, each of which is optionally substituted by one, two or three substituents selected from the group consisting of halogen, CN, $C_{1-4}$ alkyl, $haloC_{1-4}$ alkyl, $C_{1-4}$ alkoxy and $haloC_{1-4}$ alkoxy;
$G_1$ is an optionally substituted 5-6 membered heteroaryl;
R is H;
each $R_1$ is independently H;
each $R_2$ is independently H;
W is $-CH_2-$, $-O-$ or $-S-$;
Y is a 5-6 membered heteroaryl, which is optionally substituted by one or two substituents selected from the group consisting of OH, $C_{1-4}$ alkyl, $C(=O)NH_2$ and $(CH_2)_zC(=O)NR_4R_5$;
m is 1;
n is 1; and
p is 1.

3. The compound of claim 1, wherein:
$G_1$ is 4-methyl-4H-1,2,4-triazole; and
W is $-S-$.

4. The compound of claim 1, wherein:

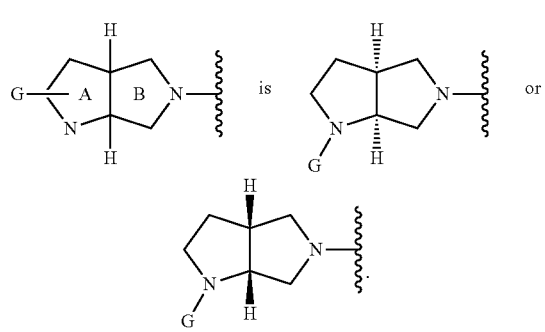

5. The compound of claim 1, wherein:

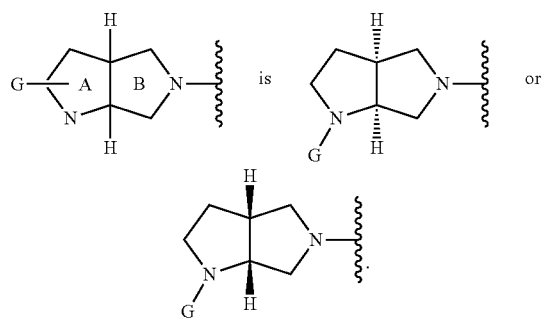

6. The compound of claim 1, wherein:
the compound of Formula (I-1) is:

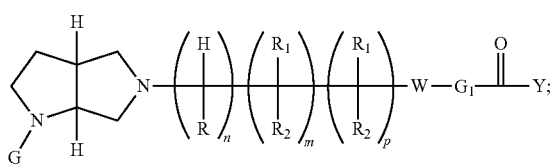

and
the compound of Formula (I-3) is:

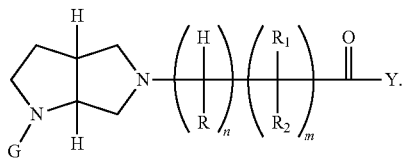

7. The compound of claim 1, wherein:
the compound of Formula (I-2) is:

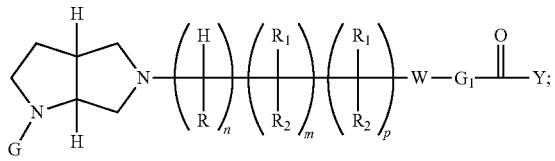

and
the compound of Formula (I-4) is:

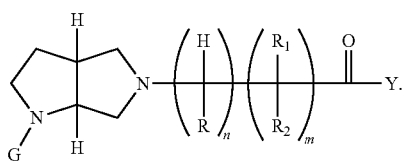

8. The compound of claim 1, wherein:
the compound of Formula (I-2) is:

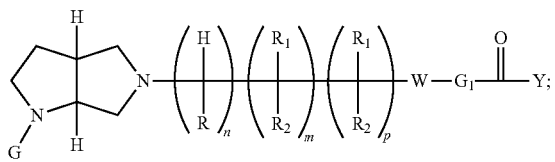

and
the compound of Formula (I-4) is:

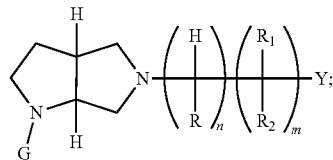

wherein:
G is phenyl or a 5-6 membered heteroaryl, each of which is optionally substituted by one, two, three or four substituents selected from the group consisting of halogen, $SF_5$, CN, OH, $NH_2$, $NHC_{1-4}$ alkyl, $C_{1-4}$ alkyl, $haloC_{1-4}$ alkyl, $C_{1-4}$ alkoxy, $C_{1-4}$ alkanoyl, $C(=O)NH_2$ and $C(=O)OR_3$;

$G_1$ is phenyl, a 5-6 membered heteroaryl or an 8-11 membered heteroaryl, each of which may be optionally substituted by one, two, three or four substituents selected from the group consisting of halogen, $SF_5$, CN, OH, $NH_2$, $NHC_{1-4}$ alkyl, $C_{1-4}$ alkyl, $haloC_{1-4}$ alkyl, $C_{1-4}$ alkoxy, $C(=O)NH_2$ and $C(=O)(O)_zR_3$; and Y is a 5-6 membered heteroaryl, which is optionally substituted by one or two substituents selected from the group consisting of halogen, $SF_5$, CN, OH, $NH_2$, $C_{1-4}$ alkyl, $haloC_{1-4}$ alkyl, $C_{1-4}$ alkoxy, $C_{1-4}$ alkanoyl, $C(=O)NH_2$ and $C(=O)(O)R_3$; or Y is a monocyclic saturated 3-7 membered carbocyclyl, which is optionally substituted by one or two substituents selected from the group consisting of halogen, $SF_5$, CN, OH, $NH_2$, $C_{1-4}$ alkyl, $haloC_{1-4}$ alkyl, $C_{1-4}$ alkoxy, $C_{1-4}$ alkanoyl, $C(=O)NH_2$ and $C(=O)(O)_zR_3$, and wherein one or more carbon atoms is optionally replaced by —$N(R_4)$—, —O— or —S—; or Y is a bicyclic 8-11 membered carbocyclyl, each of which may be optionally substituted by one or two substituents selected from the group consisting of halogen, $SF_5$, CN, OH, $NH_2$, $C_{1-4}$ alkyl, $C_{1-4}$ alkoxy, $C_{1-4}$ alkanoyl, $C(=O)NH_2$ and $C(=O)(O)R_3$, and wherein one or more carbon atoms is optionally replaced by —$N(R_4)$—, —O— or —S—.

9. The compound of claim 1, wherein the compound is:

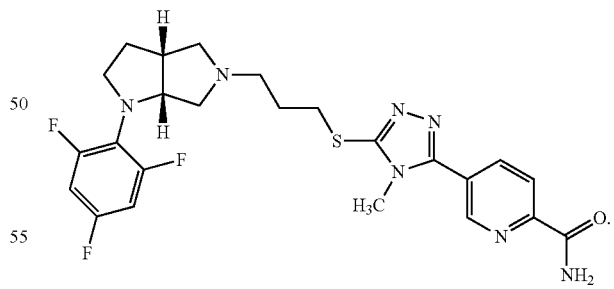

10. The compound of claim 1, wherein the compound is selected from the group consisting of:
4-methyl-3-(4-methyl-1,3-oxazol-5-yl)-5-[(3-{1-[4(trifluoromethyl)phenyl]-octahydropyrrolo[3,4-b]pyrrol-5-yl}propyl)sulfanyl]-4H-1,2,4-triazole;
3-({3-[(3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole;

3-({3-[(3aS,6aS)-1-[4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole;

3-[5-(3-{[4-methyl-5-(4-methyl-1,3-oxazol-5-yl)-4H-1,2,4-triazol-3-yl]sulfanyl}propyl)-octahydropyrrolo[2,3-c]pyrrol-1-yl]benzonitrile;

3-[(3aS,6aS)-5-(3-{[4-methyl-5-(4-methyl-1,3-oxazol-5-yl)-4H-1,2,4-triazol-3-yl]-sulfanyl}propyl)-octahydropyrrolo[2,3-c]pyrrol-1-yl]benzonitrile;

3-[(3aS,6aS)-5-(3-{[4-methyl-5-(4-methyl-1,3-oxazol-5-yl)-4H-1,2,4-triazol-3-yl]-sulfanyl}propyl)-octahydropyrrolo[2,3-c]pyrrol-1-yl]benzonitrile;

4-methyl-3-(4-methyl-1,3-oxazol-5-yl)-5-[(3-{1-phenyl-octahydropyrrolo[2,3-c]pyrrol-5-yl}propyl)sulfanyl]-4H-1,2,4-triazole;

3-({3-[(3aS,6aS)-1-phenyl-octahydropyrrolo[2,3-c]pyrrol-5-yl]propyl}sulfanyl)-4-methyl-5-(4-methyl-1,3-oxazol-5-yl)-4H-1,2,4-triazole;

3-[(3-{1-[2-fluoro-4-(trifluoromethyl)phenyl]-octahydropyrrolo[2,3-c]pyrrol-5-yl]-propyl)sulfanyl]-4-methyl-5-(4-methyl-1,3-oxazol-5-yl)-4H-1,2,4-triazole;

3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole;

3-({3-[(3aS,6aS)-1-[2-fluoro-4-(trifluoromethyl)phenyl]-octahydropyrrolo[2,3-c]pyrrol-5-yl]propyl}sulfanyl)-4-methyl-5-(4-methyl-1,3-oxazol-5-yl)-4H-1,2,4-triazole;

3-({3-[1-(4-fluorophenyl)-octahydropyrrolo[2,3-c]pyrrol-5-yl]propyl}sulfanyl)-4-methyl-5-(4-methyl-1,3-oxazol-5-yl)-4H-1,2,4-triazole;

3-({3-[(3aS,6aS)-1-(4-fluorophenyl)-octahydropyrrolo[2,3-c]pyrrol-5-yl]propyl}-sulfanyl)-4-methyl-5-(4-methyl-1,3-oxazol-5-yl)-4H-1,2,4-triazole;

3-({3-[(3aS,6aS)-1-(4-fluorophenyl)-octahydropyrrolo[2,3-c]pyrrol-5-yl]propyl}-sulfanyl)-4-methyl-5-(4-methyl-1,3-oxazol-5-yl)-4H-1,2,4-triazole;

4-methyl-3-(4-methyl-1,3-oxazol-5-yl)-5-[(3-{1-[2-(trifluoromethoxy)phenyl]-octahydropyrrolo[3,4-b]pyrrol-5-yl}propyl)sulfanyl]-4H-1,2,4-triazole;

3-({3-[1-(2,6-difluorophenyl)-octahydropyrrolo[3,4-b]pyrrol-5-yl]propyl}sulfanyl)-4-methyl-5-(4-methyl-1,3-oxazol-5-yl)-4H-1,2,4-triazole;

3-({3-[1-(3,5-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole;

3-({3-[1-(2,4-dichlorophenyl)-octahydropyrrolo[3,4-b]pyrrol-5-yl]propyl}sulfanyl)-4-methyl-5-(4-methyl-1,3-oxazol-5-yl)-4H-1,2,4-triazole;

3-({3-[1-(3-fluorophenyl)-octahydropyrrolo[3,4-b]pyrrol-5-yl]propyl}sulfanyl)-4-methyl-5-(4-methyl-1,3-oxazol-5-yl)-4H-1,2,4-triazole;

3-({3-[(3aS,6aS)-1-[4-(trifluoromethyl)phenyl]-octahydropyrrolo[2,3-c]pyrrol-5-yl]-propyl}sulfanyl)-4-methyl-5-(oxan-4-yl)-4H-1,2,4-triazole;

3-({3-[(3aS,6aS)-1-[4-(trifluoromethyl)phenyl]-octahydropyrrolo[2,3-c]pyrrol-5-yl]-propyl}sulfanyl)-4-methyl-5-(oxan-4-yl)-4H-1,2,4-triazole;

3-({3-[(3aS,6aS)-1-phenyl-octahydropyrrolo[2,3-c]pyrrol-5-yl]-propyl}sulfanyl)-4-methyl-5-(oxan-4-yl)-4H-1,2,4-triazole;

3-({3-[1-(4-fluorophenyl)-octahydropyrrolo[3,4-b]pyrrol-5-yl]propyl}sulfanyl)-4-methyl-5-(oxan-4-yl)-4H-1,2,4-triazole;

3-({3-[(3aS,6aS)-1-(4-fluorophenyl)-octahydropyrrolo[3,4-b]pyrrol-5-yl]propyl}-sulfanyl)-4-methyl-5-(oxan-4-yl)-4H-1,2,4-triazole;

3-({3-[(3aS,6aS)-1-(4-fluorophenyl)-octahydropyrrolo[3,4-b]pyrrol-5-yl]propyl}-sulfanyl)-4-methyl-5-(oxan-4-yl)-4H-1,2,4-triazole;

3-cyclopentyl-4-methyl-5-[(3-{1-[4-(trifluoromethyl)phenyl]-octahydropyrrolo[3,4-b]pyrrol-5-yl}propyl)sulfanyl]-4H-1,2,4-triazole;

3-({3-[(3aS,6aS)-1-[4-(trifluoromethyl)phenyl]-octahydropyrrolo[3,4-b]pyrrol-5-yl]-propyl}sulfanyl)-5-cyclopentyl-4-methyl-4H-1,2,4-triazole;

3-({3-[(3aS,6aS)-1-[4-(trifluoromethyl)phenyl]-octahydropyrrolo[3,4-b]pyrrol-5-yl]-propyl}sulfanyl)-5-cyclopentyl-4-methyl-4H-1,2,4-triazole;

3-cyclohexyl-4-methyl-5-[(3-{1-[4-(trifluoromethyl)phenyl]-octahydropyrrolo[3,4-b]pyrrol-5-yl}propyl)sulfanyl]-4H-1,2,4-triazol;

3-({3-[(3aS,6aS)-1-[4-(trifluoromethyl)phenyl]-octahydropyrrolo[3,4-b]pyrrol-5-yl]-propyl}sulfanyl)-5-cyclohexyl-4-methyl-4H-1,2,4-triazole;

3-({3-[(3aS,6aS)-1-[4-(trifluoromethyl)phenyl]-octahydropyrrolo[3,4-b]pyrrol-5-yl]-propyl}sulfanyl)-5-cyclohexyl-4-methyl-4H-1,2,4-triazole;

3-cyclohexyl-5-({3-[1-(4-fluorophenyl)-octahydropyrrolo[3,4-b]pyrrol-5-yl]propyl}sulfanyl)-4-methyl-4H-1,2,4-triazole;

3-({3-[(3aS,6aS)-1-(4-fluorophenyl)-octahydropyrrolo[3,4-b]pyrrol-5-yl]propyl}-sulfanyl)-5-cyclohexyl-4-methyl-4H-1,2,4-triazole;

3-({3-[(3aS,6aS)-1-(4-fluorophenyl)-octahydropyrrolo[3,4-b]pyrrol-5-yl]propyl}-sulfanyl)-5-cyclohexyl-4-methyl-4H-1,2,4-triazole;

1-methyl-2-[(3-{1-[4-(trifluoromethyl)phenyl]-octahydropyrrolo[3,4-b]pyrrol-5-yl}propyl)sulfanyl]-1H-1,3-benzodiazole;

4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}morpholine;

4-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine;

4-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]morpholine;

2-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrazine;

2-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine;

2-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrazine;

3-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile;

2-[5-({3-[1-(4-fluorophenyl)-octahydropyrrolo[3,4-b]pyrrol-5-yl]propyl}sulfanyl)-4-methyl-4H-1,2,4-triazol-3-yl]pyrazine;

2-{4-methyl-5-[(3-{1-[2-(trifluoromethoxy)phenyl]-octahydropyrrolo[3,4-b]pyrrol-5-yl}propyl)sulfanyl]-4H-1,2,4-triazol-3-yl}pyrazine;

2-[5-({3-[1-(2,6-difluorophenyl)-octahydropyrrolo[3,4-b]pyrrol-5-yl]propyl}sulfanyl)-4-methyl-4H-1,2,4-triazol-3-yl]pyrazine;

2-[5-({3-[1-(3-fluorophenyl)-octahydropyrrolo[3,4-b]pyrrol-5-yl]propyl}sulfanyl)-4-methyl-4H-1,2,4-triazol-3-yl]pyrazine;

2-[5-({3-[1-(2,4-difluorophenyl)-octahydropyrrolo[2,3-c]pyrrol-5-yl]propyl}sulfanyl)-4-methyl-4H-1,2,4-triazol-3-yl]pyrazine;

2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine;

2-[5-({3-[(3aS,6aS)-1-(2,4-difluorophenyl)-octahydropyrrolo[2,3-c]pyrrol-5-yl]propyl}sulfanyl)-4-methyl-4H-1,2,4-triazol-3-yl]pyrazine;

2-[4-methyl-5-({3-[1-(4-methylphenyl)-octahydropyrrolo[3,4-b]pyrrol-5-yl]propyl}sulfanyl)-4H-1,2,4-triazol-3-yl]pyrazine;

2-[5-({3-[1-(3-methoxyphenyl)-octahydropyrrolo[3,4-b]pyrrol-5-yl]propyl}sulfanyl)-4-methyl-4H-1,2,4-triazol-3-yl]pyrazine;

2-[5-(3-{[4-methyl-5-(pyrazin-2-yl)-4H-1,2,4-triazol-3-yl]sulfanyl}propyl)-octahydropyrrolo[3,4-b]pyrrol-1-yl]benzonitrile;

2-[4-methyl-5-({3-[1-(3-methylphenyl)-octahydropyrrolo[3,4-b]pyrrol-5-yl]propyl}sulfanyl)-4H-1,2,4-triazol-3-yl]pyrazine;

2-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}pyrazine;

2-{4-methyl-5-[(3-{1-[3-(trifluoromethoxy)phenyl]-octahydropyrrolo[3,4-b]pyrrol-5-yl}propyl)sulfanyl]-4H-1,2,4-triazol-3-yl}pyrazine;

2-[5-({3-[(3aS,6aS)-1-[2-(propan-2-yloxy)phenyl]-octahydropyrrolo[3,4-b]pyrrol-5-yl]propyl}sulfanyl)-4-methyl-4H-1,2,4-triazol-3-yl]pyrazine;

2-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}pyrazine;

2-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyrazine;

2-[5-({3-[1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine;

2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine;

2-[5-({3-[(3aS,6aS)-1-(4-fluoro-3-methoxyphenyl)-octahydropyrrolo[3,4-b]pyrrol-5-yl]propyl}sulfanyl)-4-methyl-4H-1,2,4-triazol-3-yl]pyrazine;

2-{5-[(3-{1-[2-fluoro-6-(trifluoromethyl)phenyl]-octahydropyrrolo[3,4-b]pyrrol-5-yl}propyl)sulfanyl]-4-methyl-4H-1,2,4-triazol-3-yl}pyrazine;

2-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyrazine;

4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}pyrimidine;

4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine;

4-[5-({3-[(3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine;

4-[5-({3-[(3aR,6aR)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine;

4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]pyrimidine;

4-[5-({3-[1-(4-fluorophenyl)-octahydropyrrolo[3,4-b]pyrrol-5-yl]propyl}sulfanyl)-4-methyl-4H-1,2,4-triazol-3-yl]pyrimidine;

3-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine;

3-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride;

3-[5-({3-[(3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine trihydrochloride;

3-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine;

3-[5-({3-[(3aR,6aR)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine;

3-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine;

3-{4-methyl-5-[(3-{1-[2-(trifluoromethyl)phenyl]-octahydropyrrolo[3,4-b]pyrrol-5-yl}propyl)sulfanyl]-4H-1,2,4-triazol-3yl}pyridine;

3-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine;

3-[5-({3-[(3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine;

4-methyl-3-(1-methyl-1H-pyrazol-4-yl)-5-[(3-{1-[4-(trifluoromethyl)phenyl]-octahydropyrrolo[3,4-b]pyrrol-5-yl}propyl)sulfanyl]-4H-1,2,4-triazole;

4-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine;

4-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine;

4-{4-methyl-5-[(3-{1-[2-(trifluoromethyl)phenyl]-octahydropyrrolo[3,4-b]pyrrol-5-yl}propyl)sulfanyl]-4H-1,2,4-thiazol-3-yl}pyridine;

4-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine;

4-[5-({3-[(3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]pyridine;

2-{4-methyl-5-[(3-{1-[4-(trifluoromethyl)phenyl]-octahydropyrrolo[3,4-b]pyrrol-5-yl}propyl)sulfanyl]-4H-1,2,4-thiazol-3-yl}pyridine;

2-{4-methyl-5-[(3-{1-[2-(trifluoromethyl)phenyl]-octahydropyrrolo[3,4-b]pyrrol-5-yl}propyl)sulfanyl]-4H-1,2,4-thiazol-3-yl}pyridine;

4-methyl-3-(1,3-thiazol-2-yl)-5-[(3-{1-[4-(trifluoromethyl)phenyl]-octahydropyrrolo[3,4-b]pyrrol-5-yl}propyl)sulfanyl]-4H-1,2,4-triazole;

4-methyl-3-(3-methyl-1,2-oxazol-5-yl)-5-[(3-{1-[4-(trifluoromethyl)phenyl]-octahydropyrrolo[3,4-b]pyrrol-5-yl}propyl)sulfanyl]-4H-1,2,4-triazole;

4-methyl-3-(4-methyl-1,3-thiazol-5-yl)-5-[(3-{1-[4-(trifluoromethyl)phenyl]-octahydropyrrolo[3,4-b]pyrrol-5-yl}propyl)sulfanyl]-4H-1,2,4-triazole;

4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}-1,2-dihydropyridin-2-one;

4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]-1,2-dihydropyridin-2-one;

4-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one;

4-[5-({3-[(3aS,6aS)-1-(4-fluorophenyl)-octahydropyrrolo[2,3-c]pyrrol-5-yl]propyl}-sulfanyl)-4-methyl-4H-1,2,4-triazol-3-yl]-1,2-dihydropyridin-2-one;

5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one;

5-[5-({3-[1-(4-fluorophenyl)-octahydropyrrolo[2,3-c]pyrrol-5-yl]propyl}sulfanyl)-4-methyl-4H-1,2,4-triazol-3-yl]-1,2-dihydropyridin-2-one;

5-{4-methyl-5-[(3-{1-[3-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one;

5-{4-methyl-5-[(3-{1-[2-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one;

5-[5-({3-[(3aS,6aS)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one;

5-[5-({3-[(3aR,6aR)-1-[2-(trifluoromethyl)phenyl]-octahydropyrrolo[3,4-b]pyrrol-5-yl]propyl}sulfanyl)-4-methyl-4H-1,2,4-triazol-3-yl]-1,2-dihydropyridin-2-one;

3-({3-[1-(2,6-difluorophenyl)-octahydropyrrolo[3,4-b]pyrrol-5-yl]propyl}sulfanyl)-4-methyl-5-(1-methyl-1H-pyrazol-5-yl)-4H-1,2,4-triazole;

4-methyl-3-(1-methyl-1H-pyrazol-5-yl)-5-[(3-{1-[2-(trifluoromethyl)phenyl]-octahydropyrrolo[3,4-b]pyrrol-5-yl}propyl)sulfanyl]-4H-1,2,4-triazole;

3-({3-[(3aS,6aS)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole;

3-({3-[(3aR,6aR)-1-[2-(trifluoromethyl)phenyl]-octahydropyrrolo[3,4-b]pyrrol-5-yl]propyl}sulfanyl)-4-methyl-5-(1-methyl-1H-pyrazol-5-yl)-4H-1,2,4-triazole;

1-methyl-5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}-1,2-dihydropyridin-2-one;

5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one;

5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]-1-methyl-1,2-dihydropyridin-2-one;

5-{4-methyl-5-[(3-{1-[4-(trifluoromethyl)phenyl]-octahydropyrrolo[3,4-b]pyrrol-5-yl}propyl)sulfanyl]-4H-1,2,4-triazol-3-yl}pyridine-2-carboxamide;

5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide;

5-[5-({3-[(3aS,6aS)-1-[4-(trifluoromethyl)phenyl]-octahydropyrrolo[3,4-b]pyrrol-5-yl]propyl}sulfanyl)-4-methyl-4H-1,2,4-triazol-3-yl]pyridine-2-carboxamide;

5-[5-({3-[1-(4-fluorophenyl)-octahydropyrrolo[3,4-b]pyrrol-5-yl]propyl}sulfanyl)-4-methyl-4H-1,2,4-triazol-3-yl]pyridine-2-carboxamide;

5-[5-({3-[(3aS,6aS)-1-(4-fluorophenyl)-octahydropyrrolo[3,4-b]pyrrol-5-yl]propyl}-sulfanyl)-4-methyl-4H-1,2,4-triazol-3-yl]pyridine-2-carboxamide;

5-[5-({3-[(3aS,6aS)-1-(4-fluorophenyl)-octahydropyrrolo[3,4-b]pyrrol-5-yl]propyl}-sulfanyl)-4-methyl-4H-1,2,4-triazol-3-yl]pyridine-2-carboxamide;

5-[5-({3-[1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide;

5-[5-({3-[(3aS,6aS)-1-(2,6-difluorophenyl)-octahydropyrrolo[3,4-b]pyrrol-5-yl]propyl}sulfanyl)-4-methyl-4H-1,2,4-triazol-3-yl]pyridine-2-carboxamide;

5-[5-({3-[(3aS,6aS)-1-(2,6-difluorophenyl)-octahydropyrrolo[3,4-b]pyrrol-5 yl]propyl}sulfanyl)-4-methyl-4H-1,2,4-triazol-3-yl]pyridine-2-carboxamide;

5-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]pyridine-2-carboxamide;

5-[5-({3-[(3aS,6aS)-1-(2,4,6-trifluorophenyl)-octahydropyrrolo[2,3-c]pyrrol-5-yl]-propyl}sulfanyl)-4-methyl-4H-1,2,4-triazol-3-yl]pyridine-2-carboxamide;

5-[5-({3-[(3aS,6aS)-1-(2,4,6-trifluorophenyl)-octahydropyrrolo[2,3-c]pyrrol-5-yl]-propyl}sulfanyl)-4-methyl-4H-1,2,4-triazol-3-yl]pyridine-2-carboxamide;

4-[5-({3-[1-(4-fluorophenyl)-octahydropyrrolo[3,4-b]pyrrol-5-yl]propyl}sulfanyl)-4-methyl-4H-1,2,4-triazol-3-yl]-1-methyl-1,2-dihydropyridin-2-one;

1-methyl-4-[4-methyl-5-({3-[1-(2,4,6-trifluorophenyl)-octahydropyrrolo[2,3-c]pyrrol-5-yl]propyl}sulfanyl)-4H-1,2,4-triazol-3-yl]-1,2-dihydropyridin-2-one;

4-[5-({3-[(3aS,6aS)-1-(2,4,6-trifluorophenyl)-octahydropyrrolo[2,3-c]pyrrol-5-yl]-propyl}sulfanyl)-4-methyl-4H-1,2,4-triazol-3-yl]-1-methyl-1,2-dihydropyridin-2-one;

4-[5-({3-[(3aR,6aR)-1-(2,4,6-trifluorophenyl)-octahydropyrrolo[2,3-c]pyrrol-5-yl]-propyl}sulfanyl)-4-methyl-4H-1,2,4-triazol-3-yl]-1-methyl-1,2-dihydropyridin-2-one;

4-{4-methyl-5-[(3-{1-[4-(trifluoromethyl)phenyl]-octahydropyrrolo[2,3-c]pyrrol-5-yl}propyl)sulfanyl]-4H-1,2,4-triazol-3-yl}cyclohexan-1-ol;

4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol;

4-[5-({3-[(3aS,6aS)-1-[4-(trifluoromethyl)phenyl]-octahydropyrrolo[2,3-c]pyrrol-5-yl]propyl}sulfanyl)-4-methyl-4H-1,2,4-triazol-3-yl]cyclohexan-1-ol;

4-methyl-3-(4-methyl-1,3-oxazol-5-yl)-5-({3-[(4S)-4-[4-(trifluoromethyl)phenyl]-octahydrocyclopenta[c]pyrrol-2-yl]propyl}sulfanyl)-4H-1,2,4-triazole; and 3-({3-[(4aS,7aS)-1-[4-(trifluoromethyl)phenyl]-octahydro-1H-pyrrolo[3,4-b]pyridin-6-yl]propyl}sulfanyl)-4-methyl-5-(4-methyl-1,3-oxazol-5-yl)-4H-1,2,4-triazole.

11. The compound of claim 1, wherein the compound is selected from the group consisting of:

285
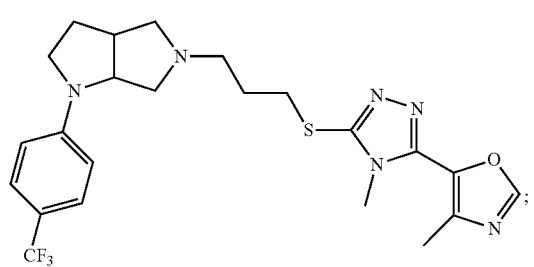
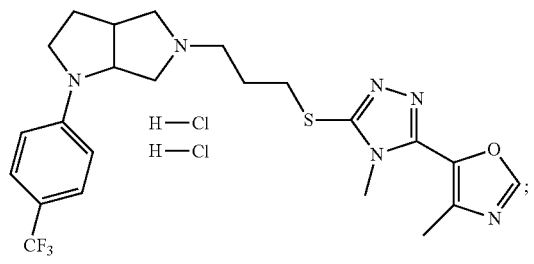
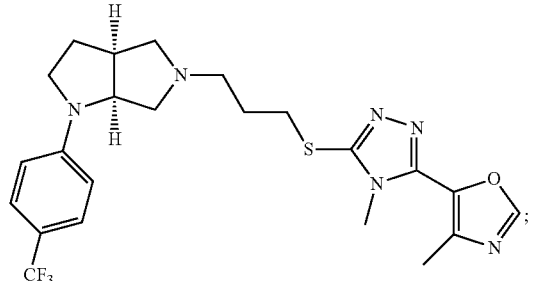
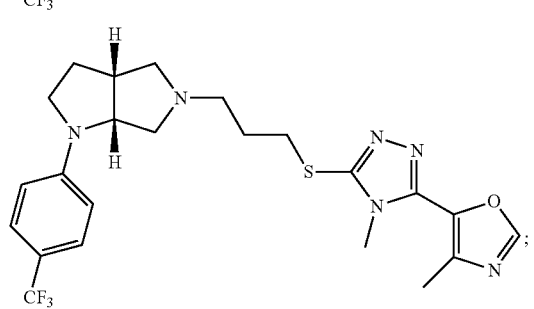
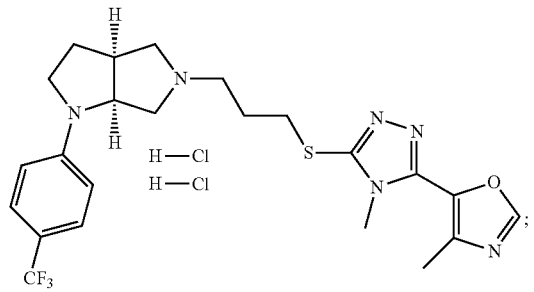
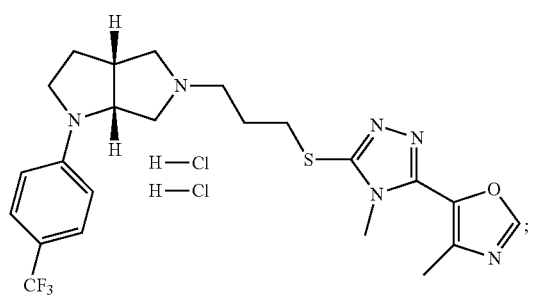
286
-continued
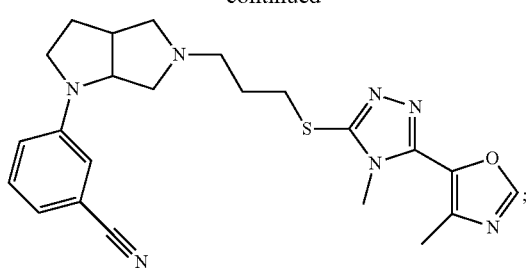
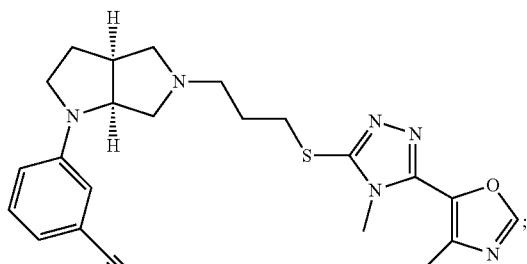
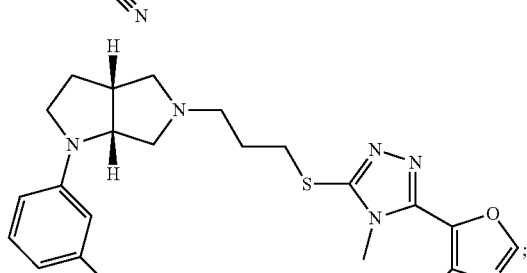
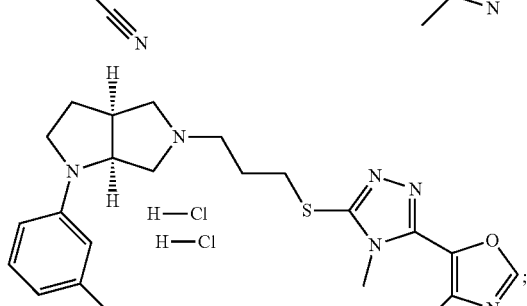
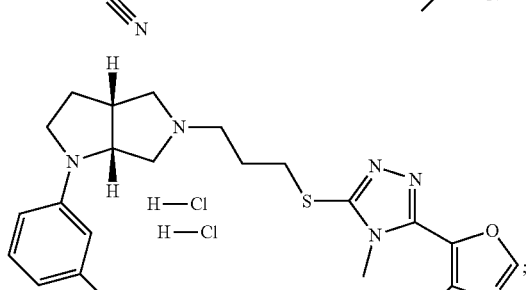
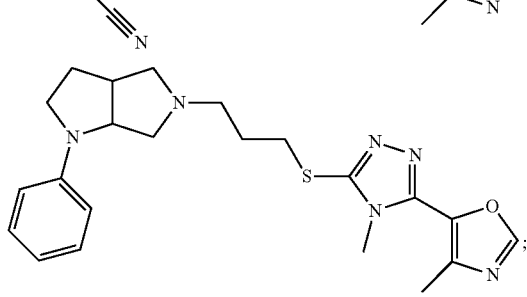

287
-continued
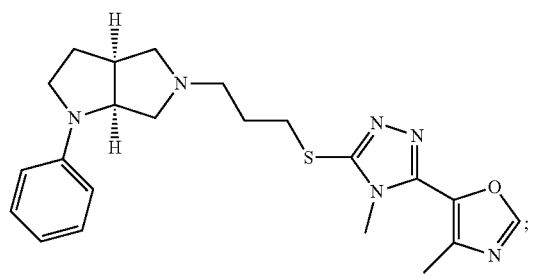
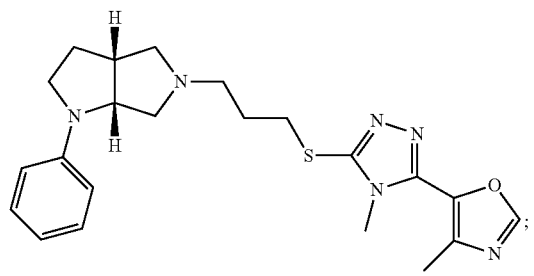
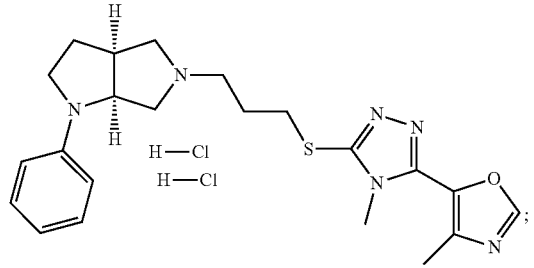
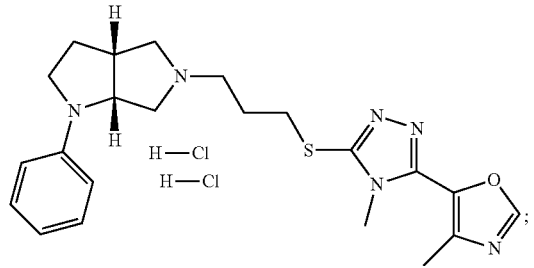
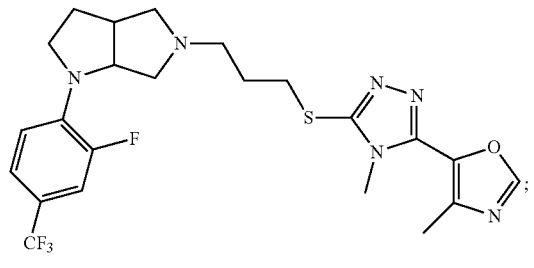
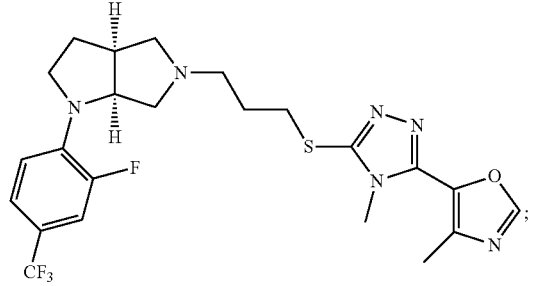
288
-continued
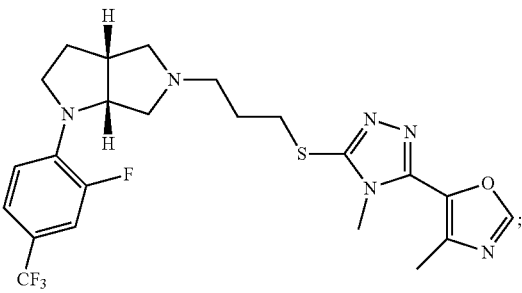
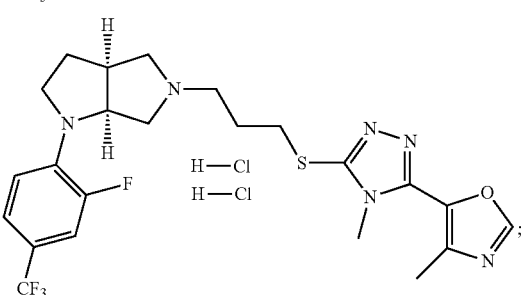
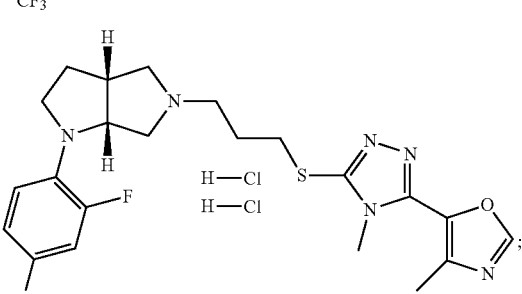
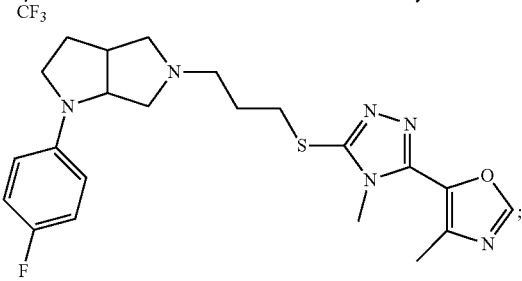
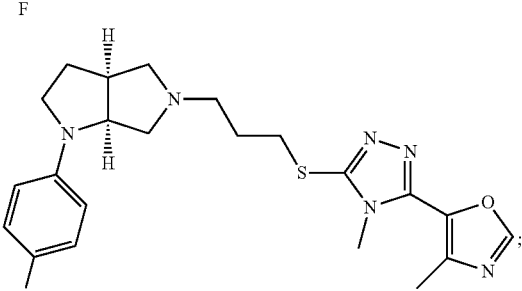
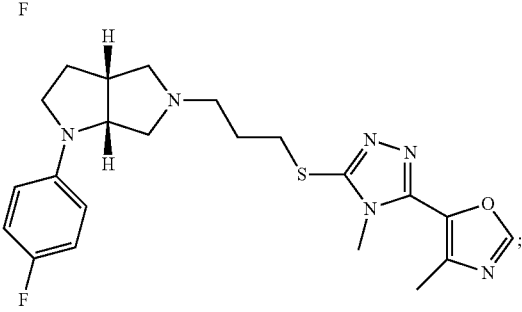

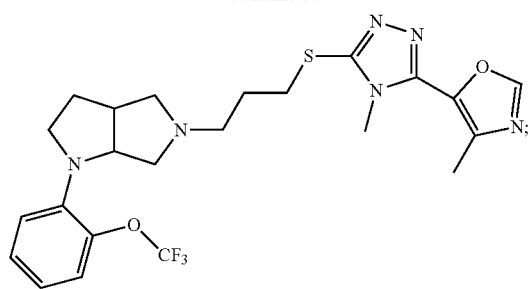
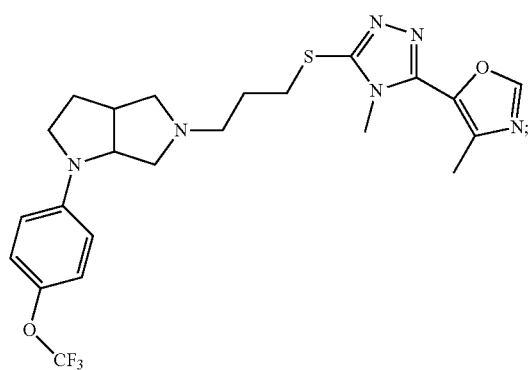
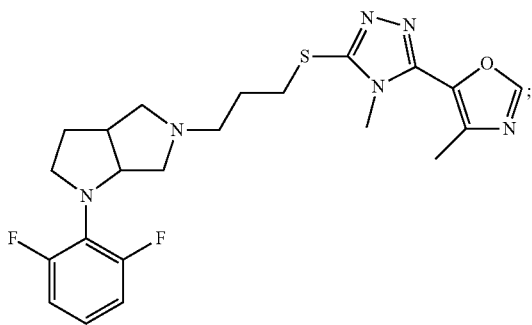
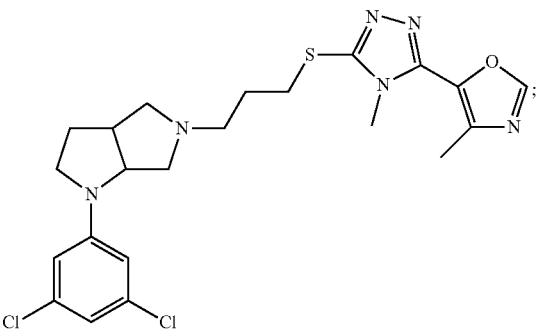
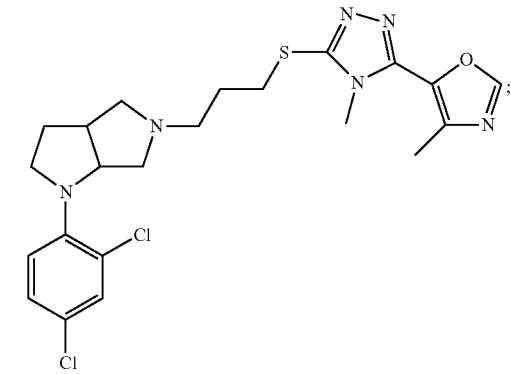
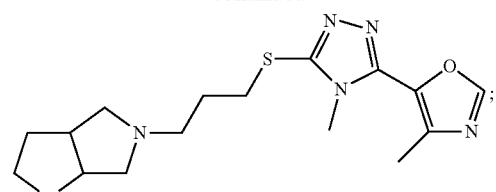
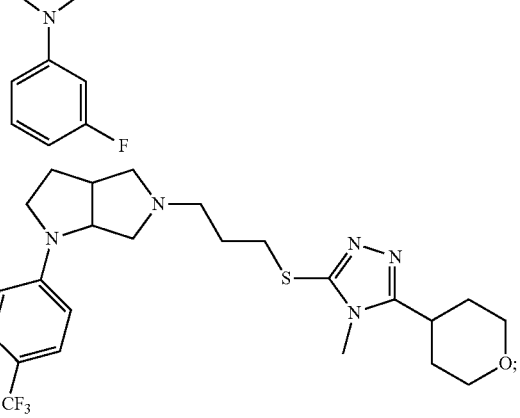
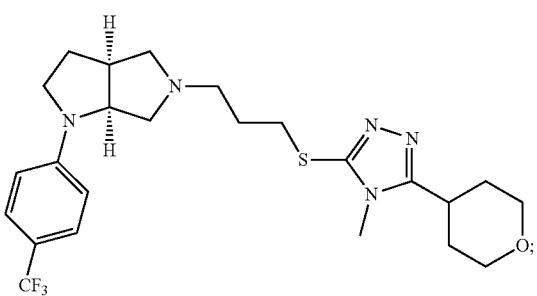
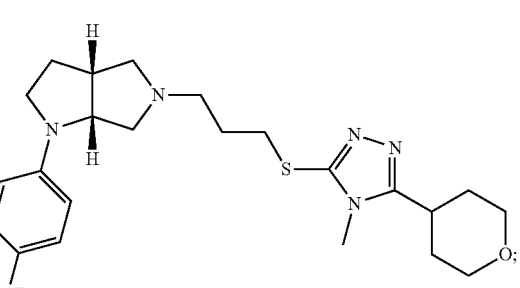
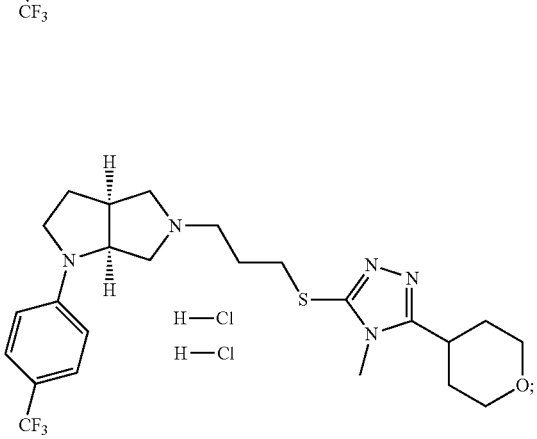

291
-continued
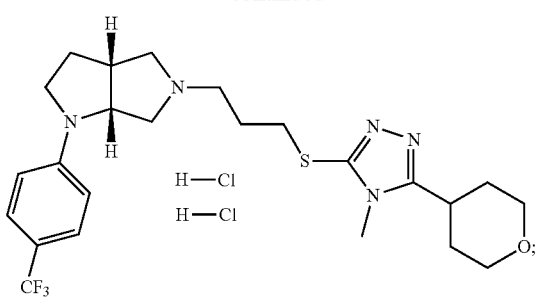
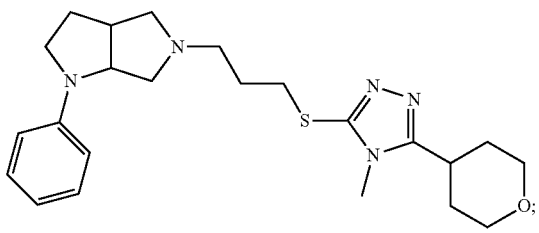
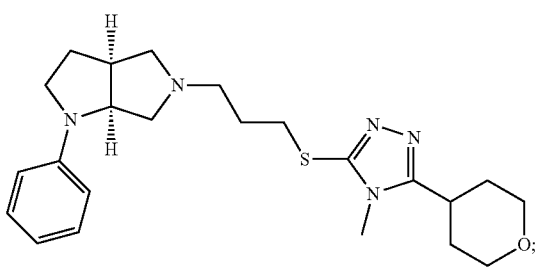
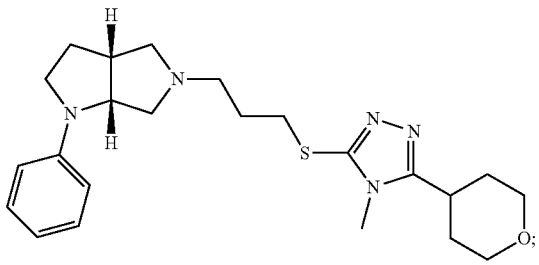
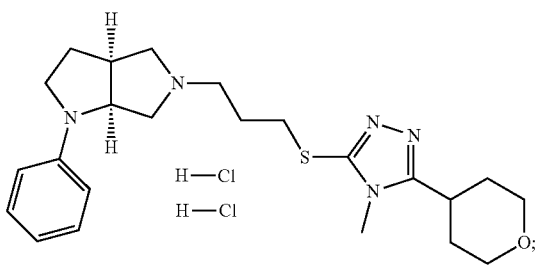
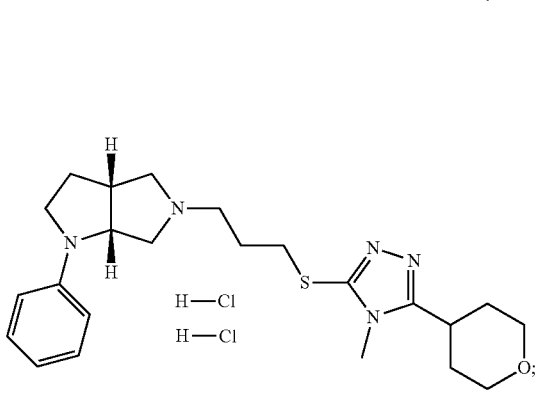
292
-continued
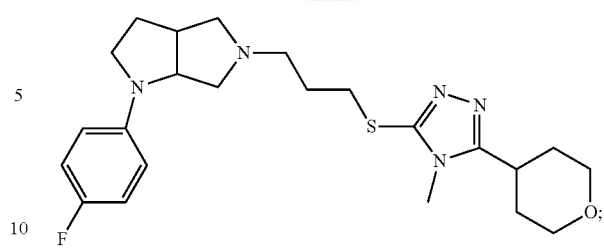
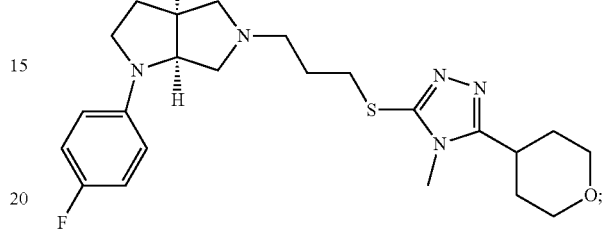
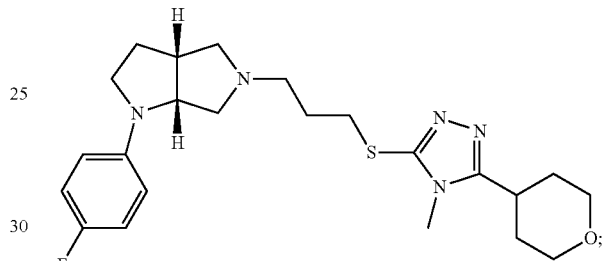
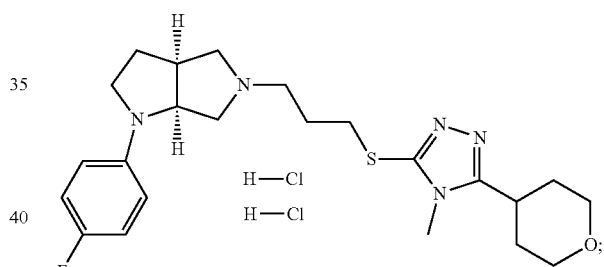
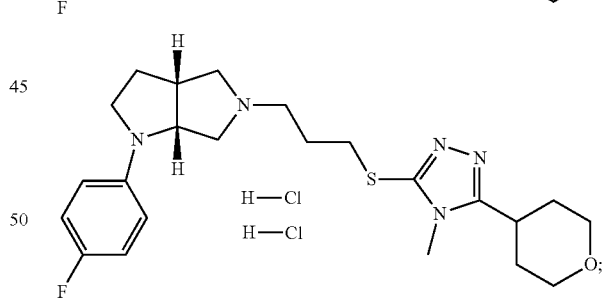
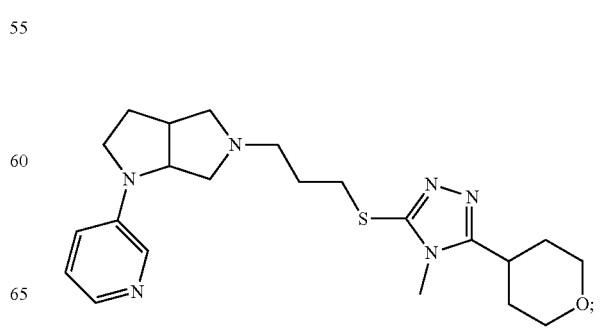

293 294
-continued -continued
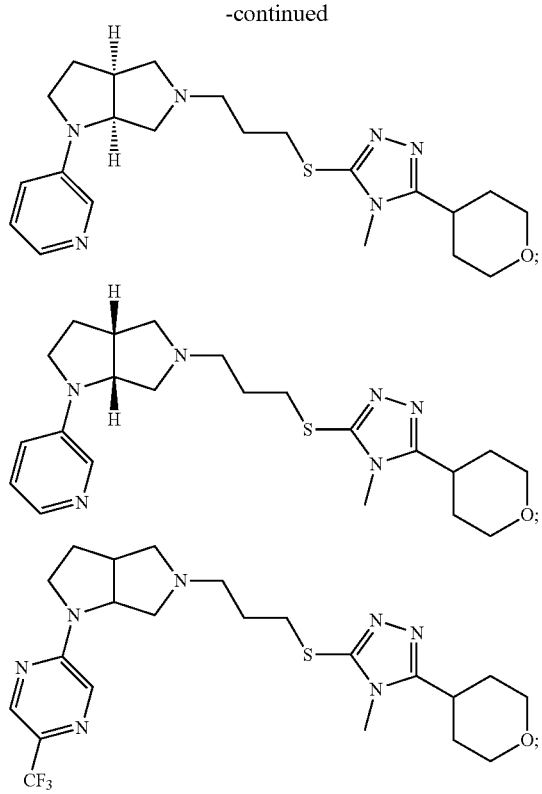
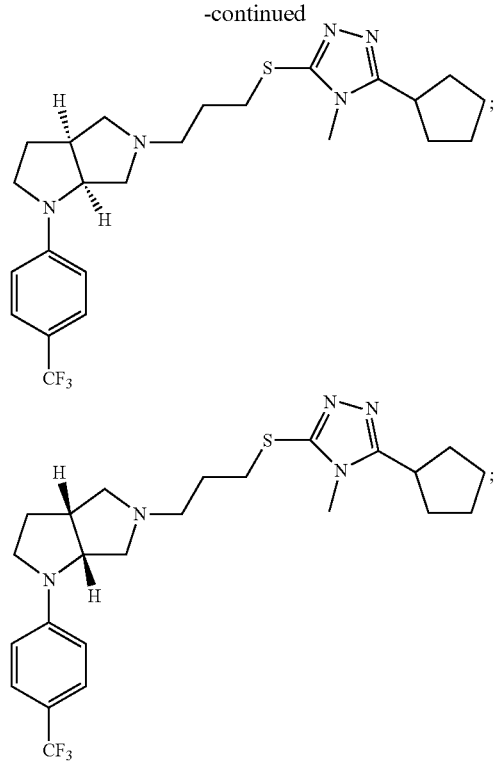
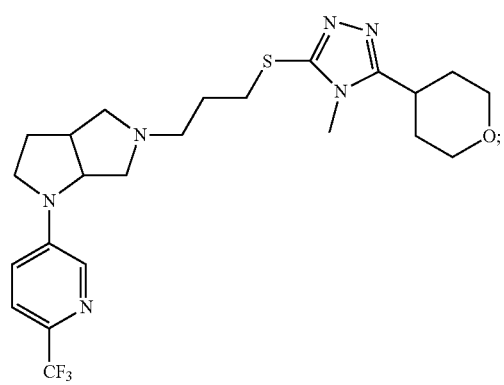
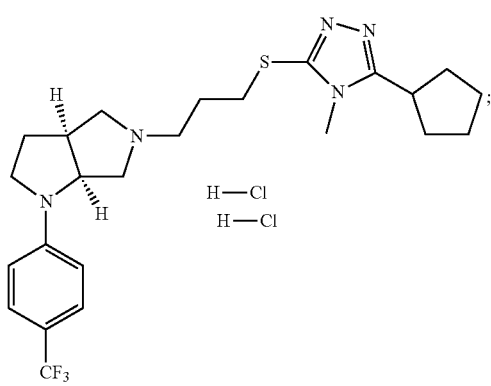
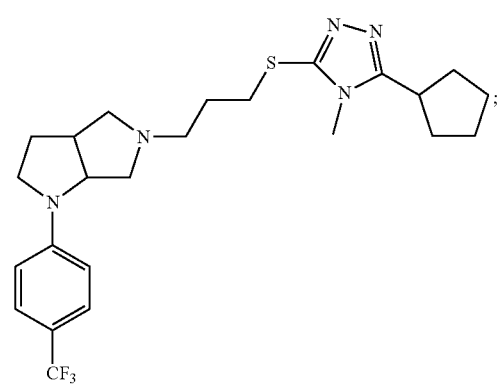
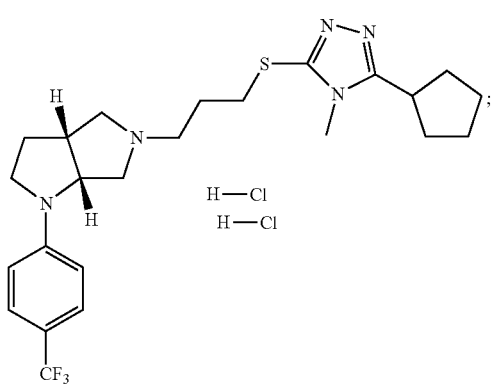

-continued
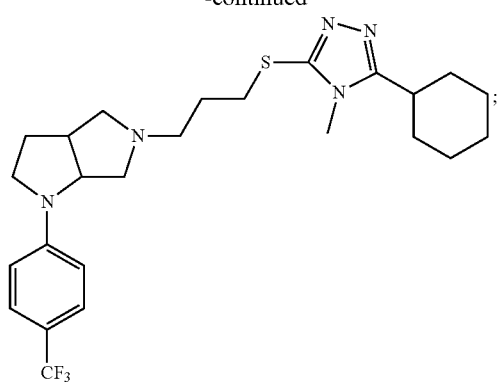
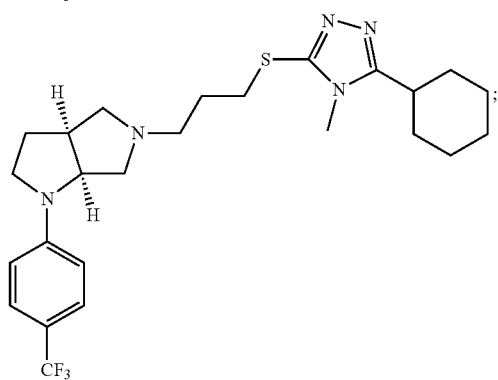
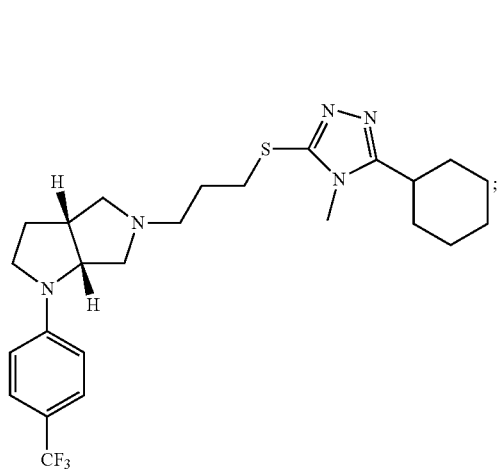
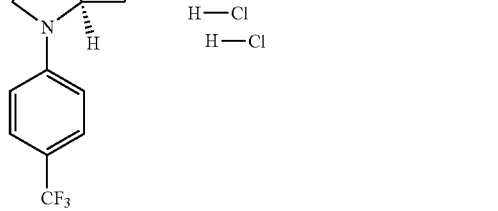
-continued
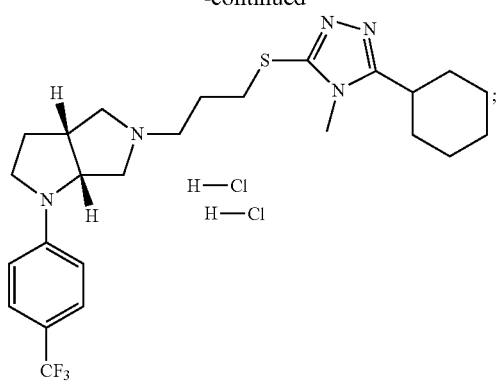
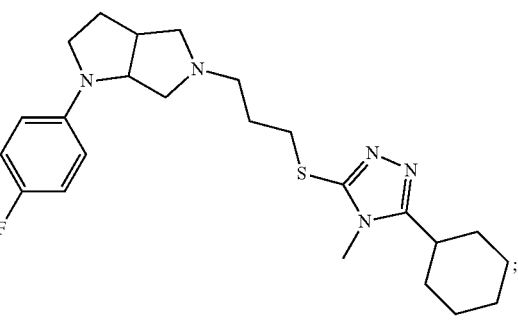
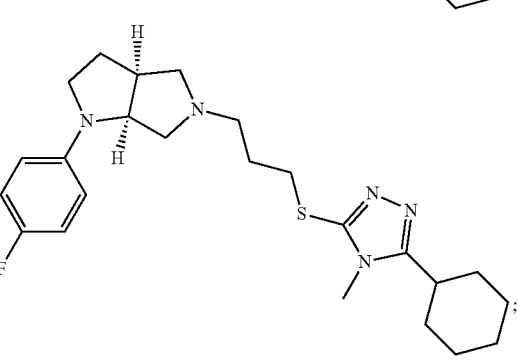
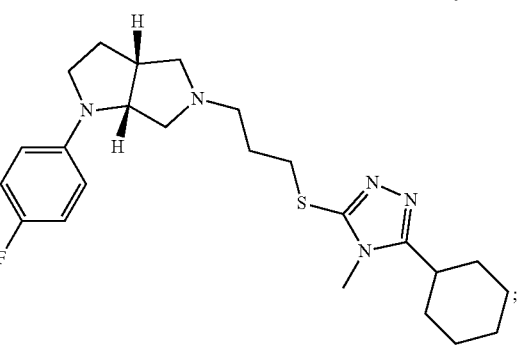
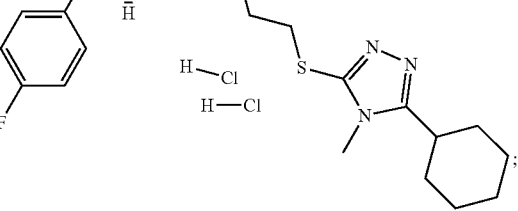

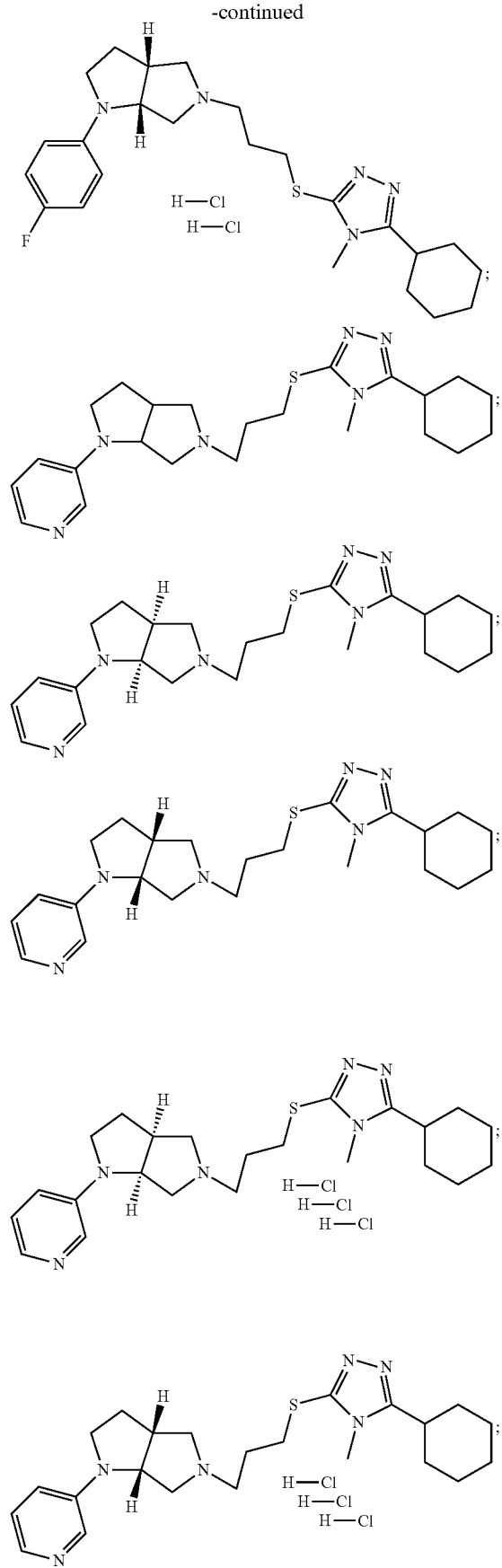
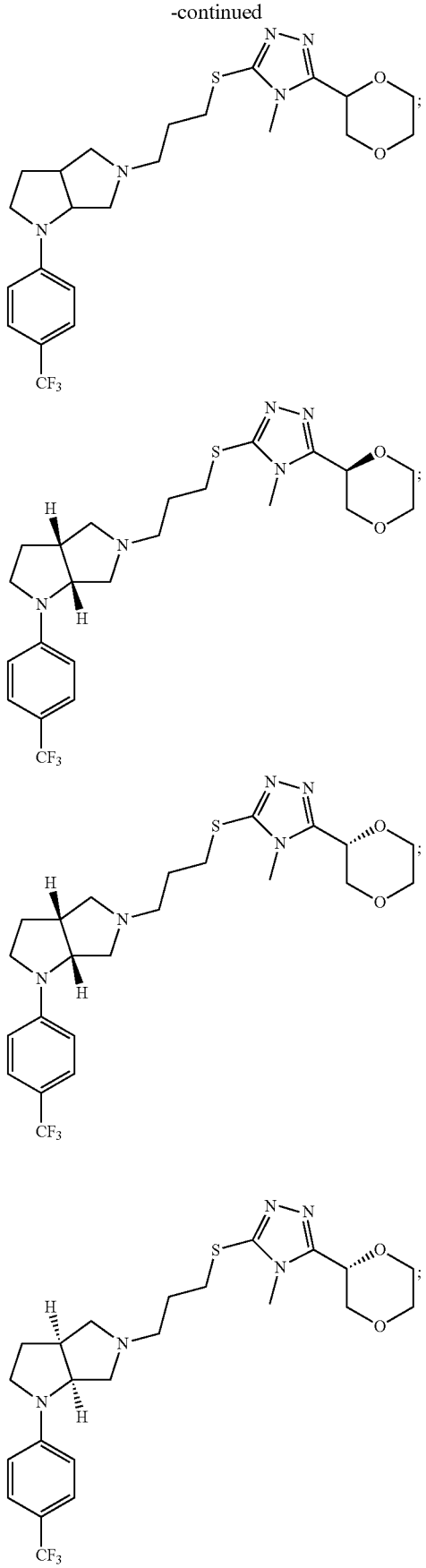

299
-continued
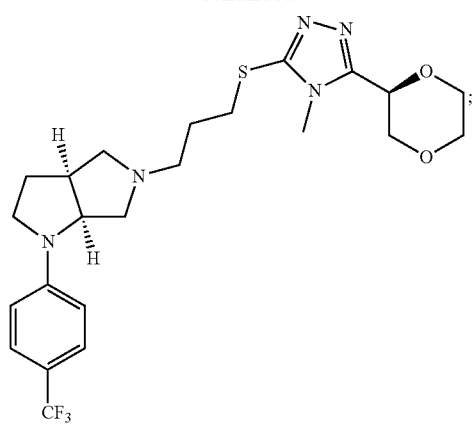
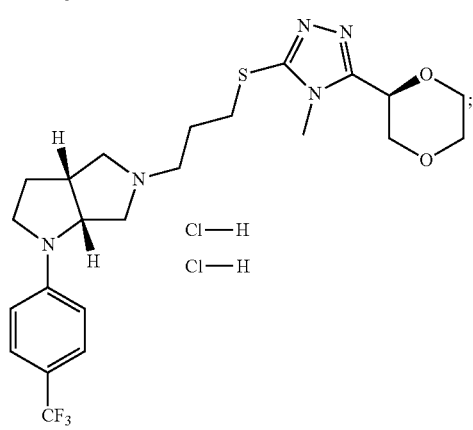
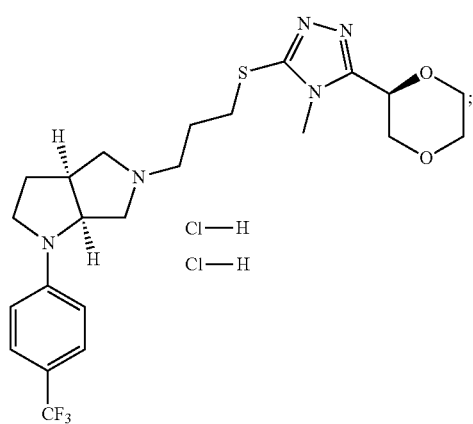
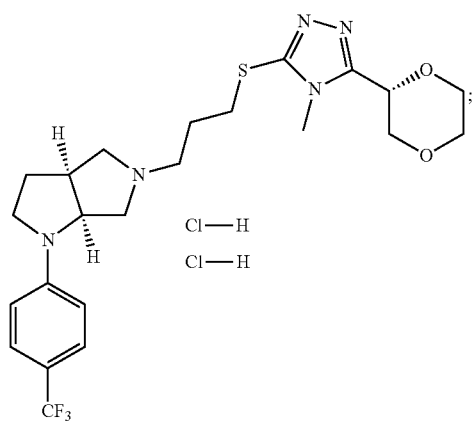
300
-continued
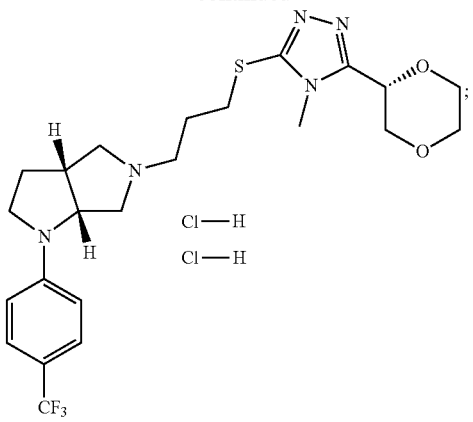
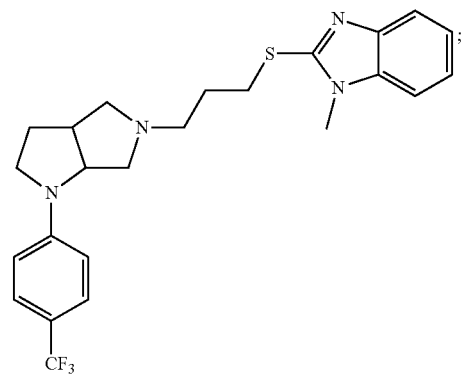
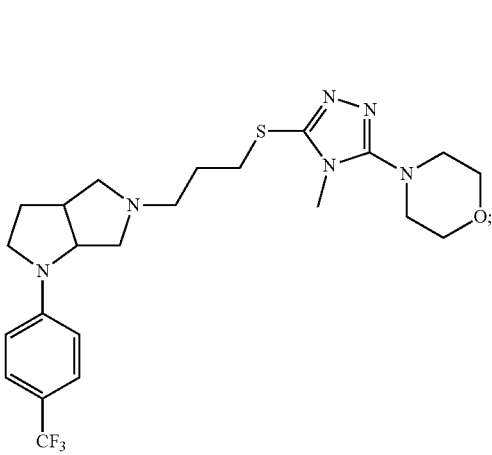
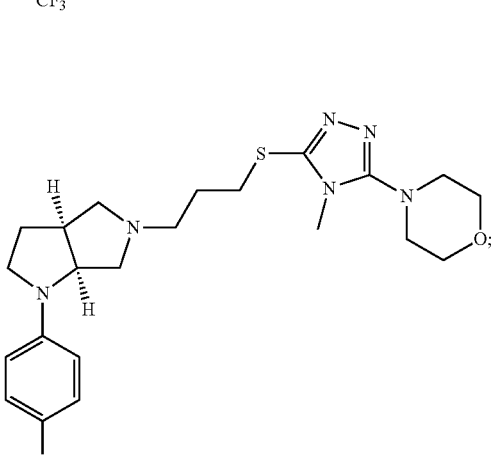

301
-continued
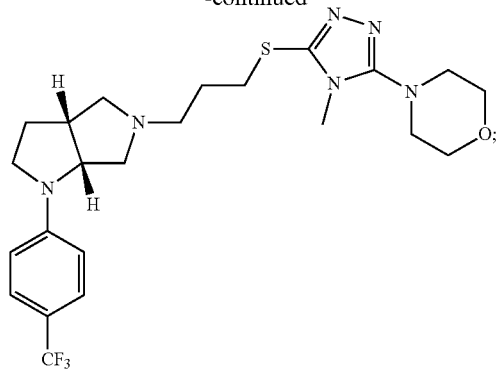
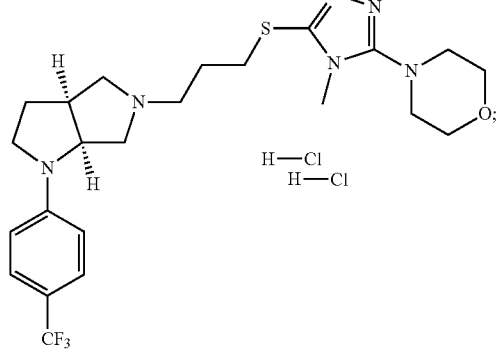
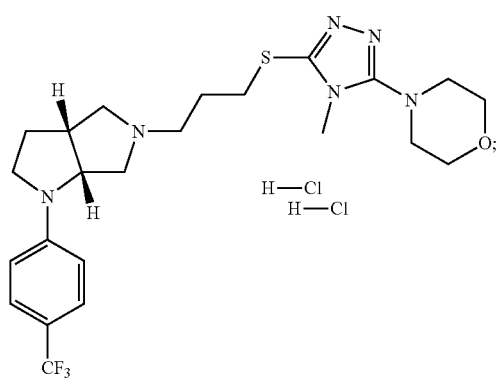
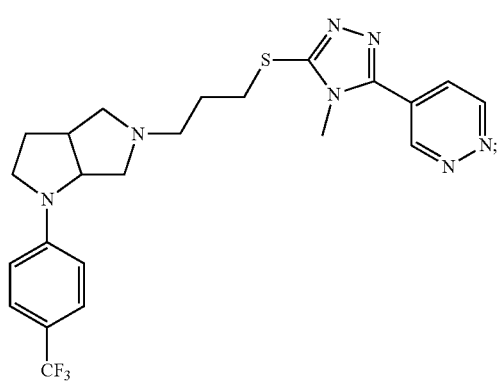
302
-continued
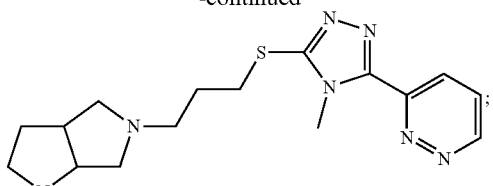
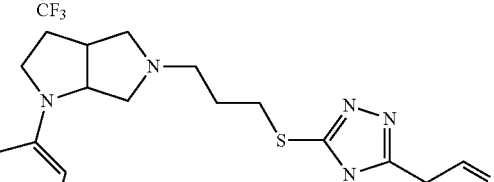
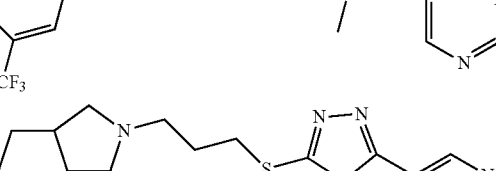
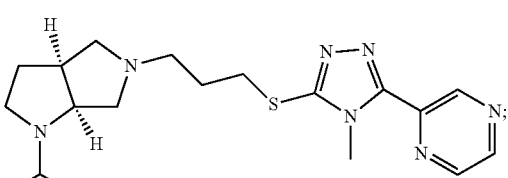
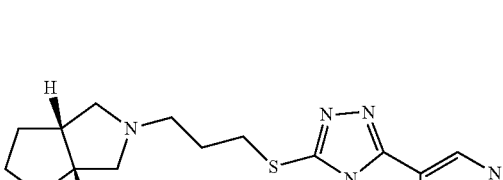

303
-continued
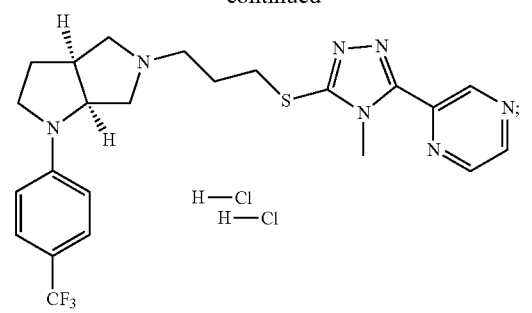
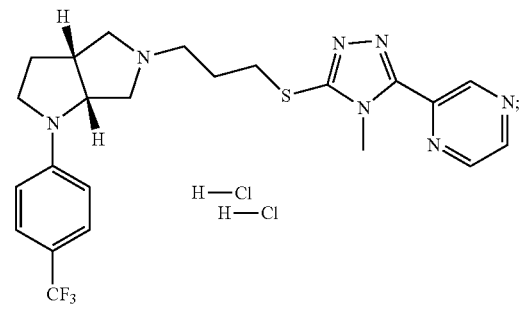
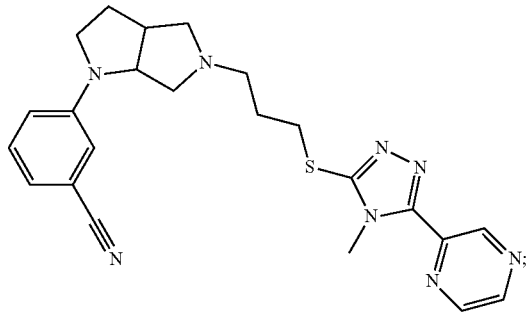
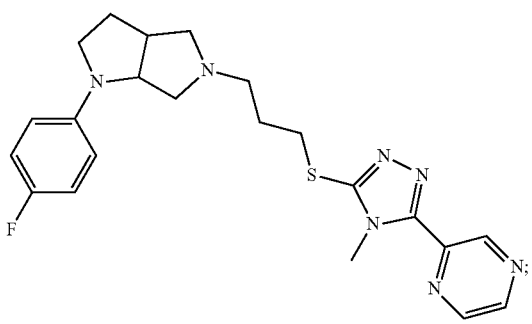
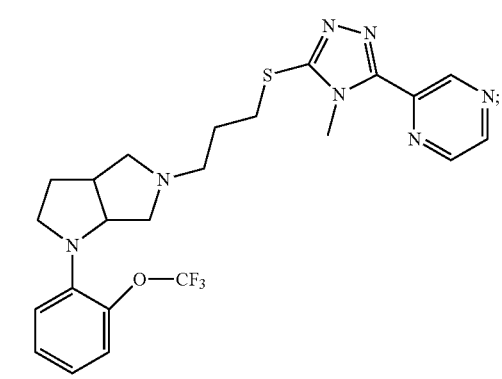
304
-continued
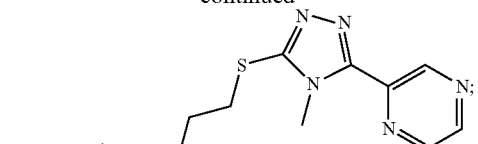
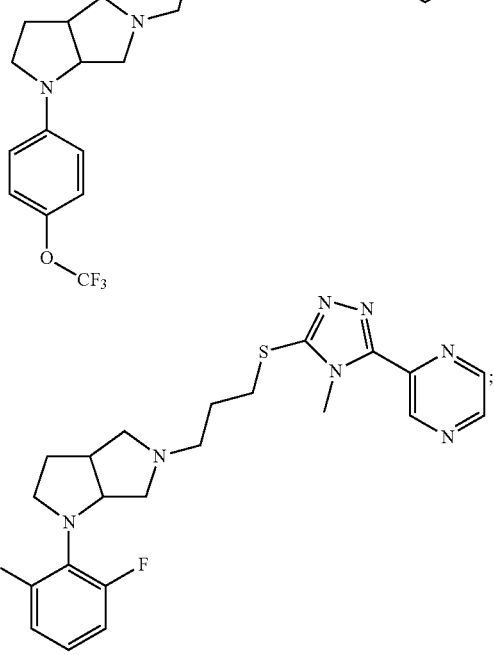
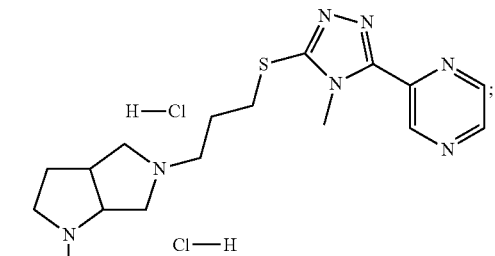
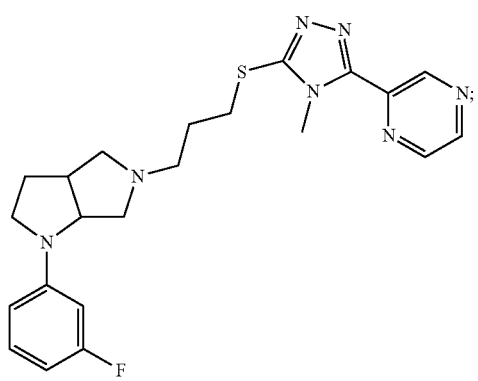

305
-continued
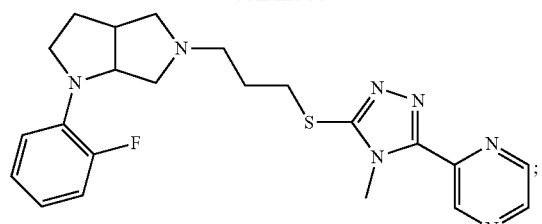
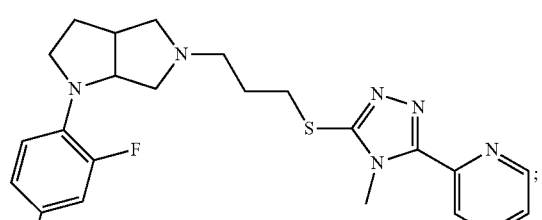
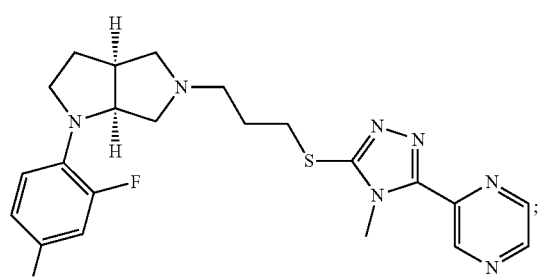
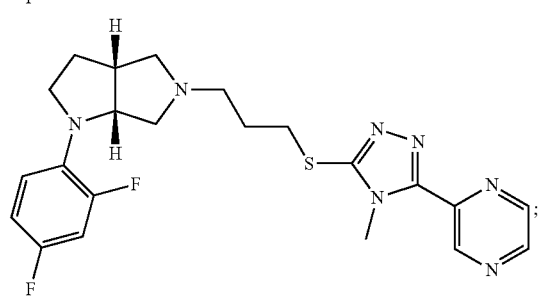
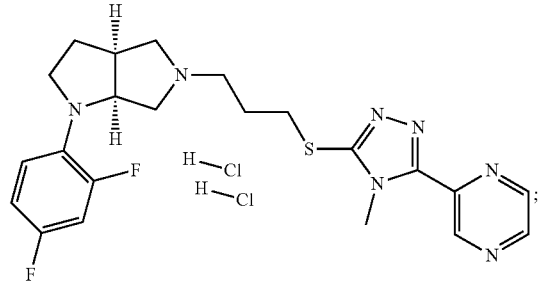
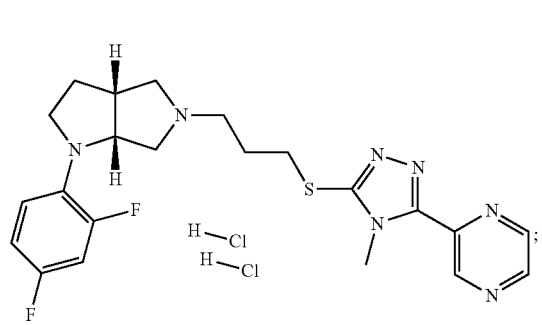
306
-continued
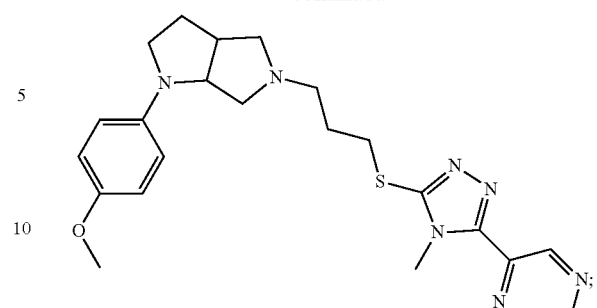
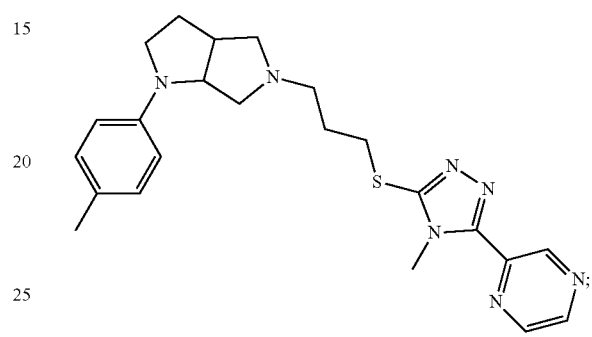
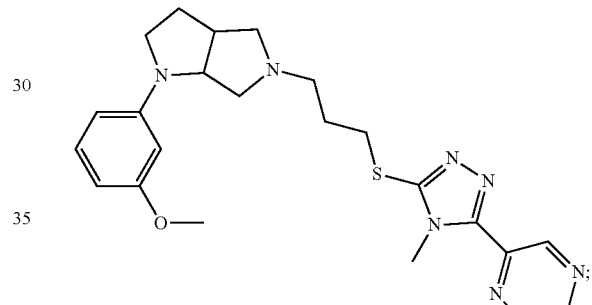
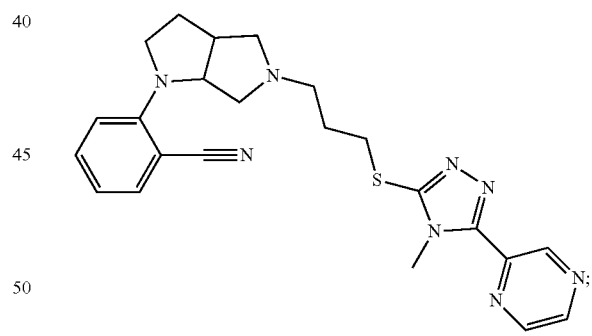
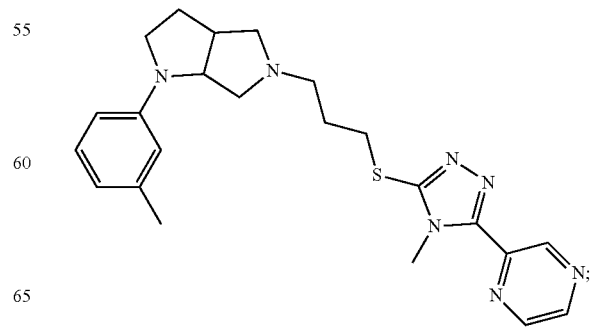

307
-continued
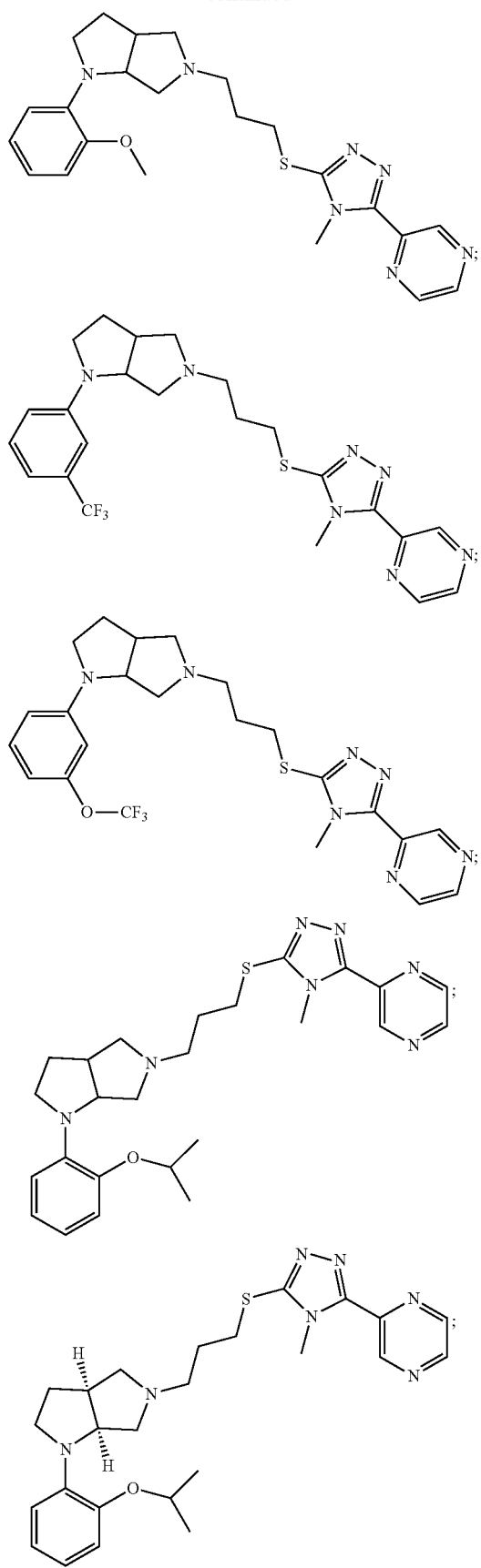
308
-continued
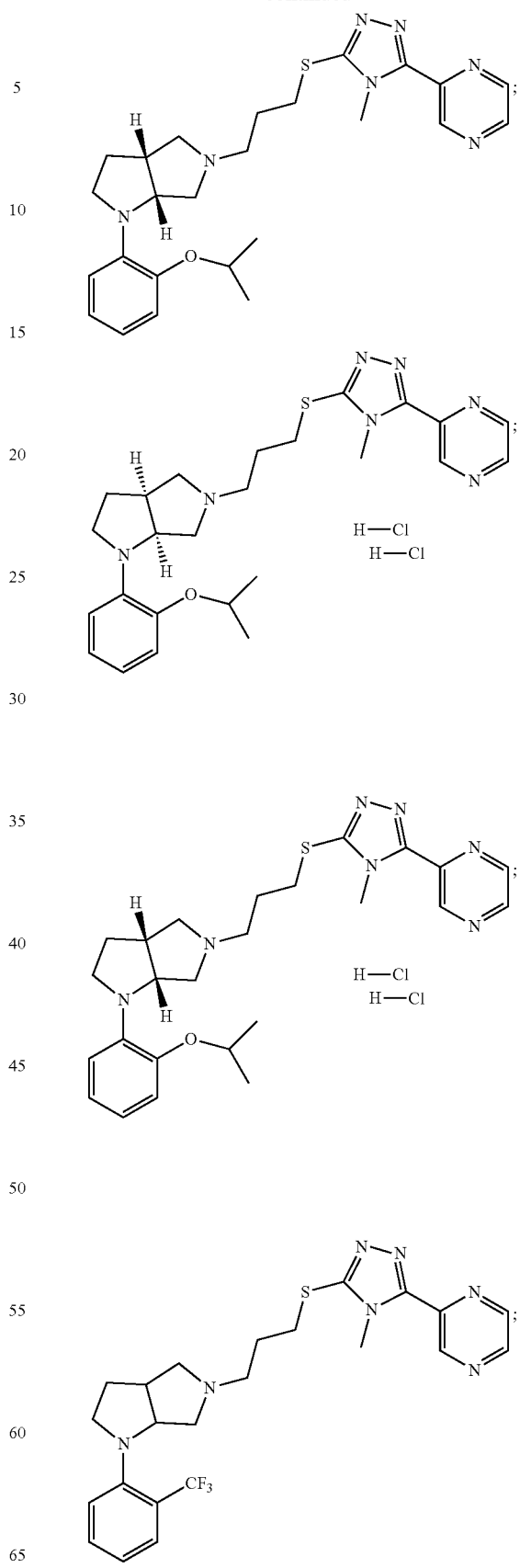

309
-continued
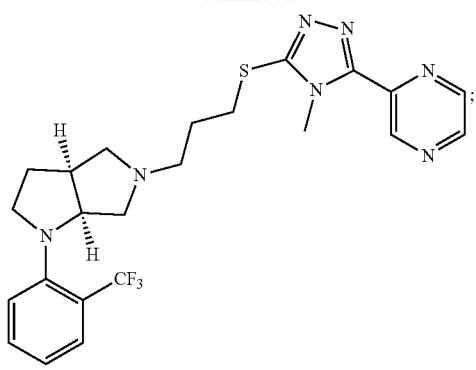
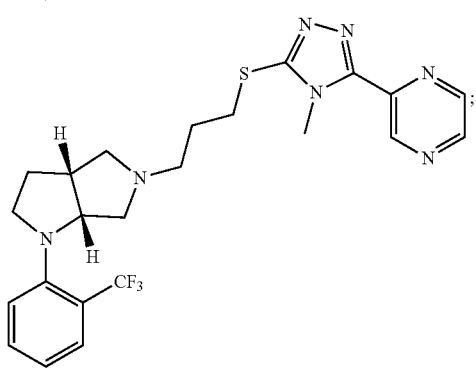
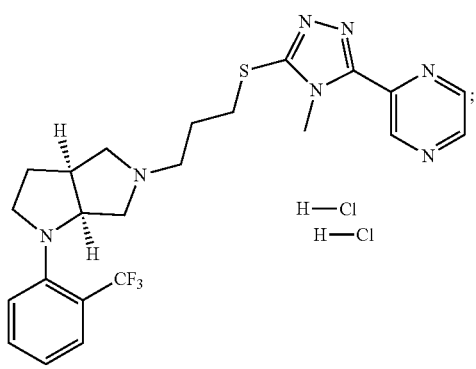
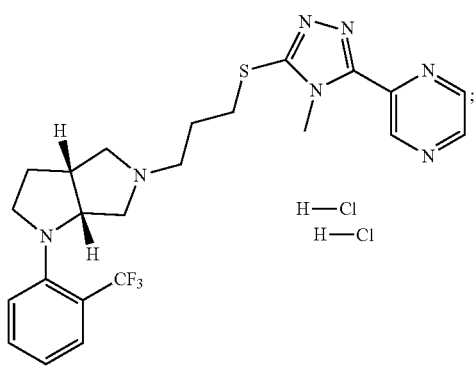
310
-continued
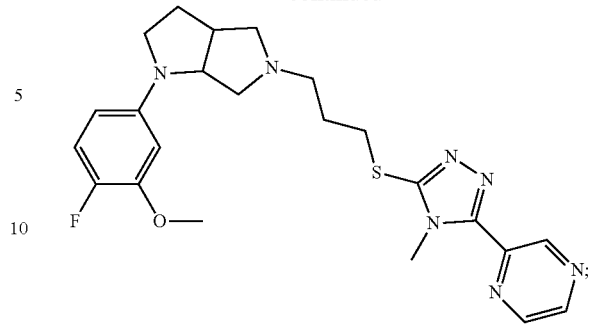
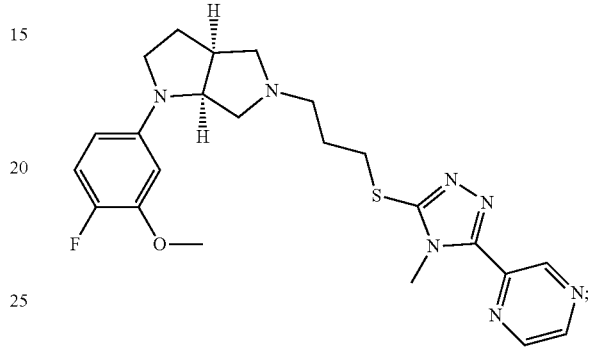
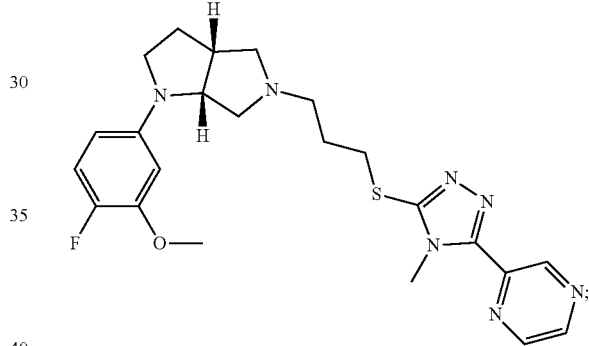
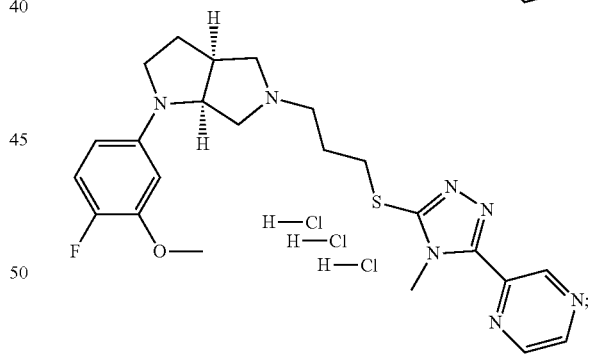
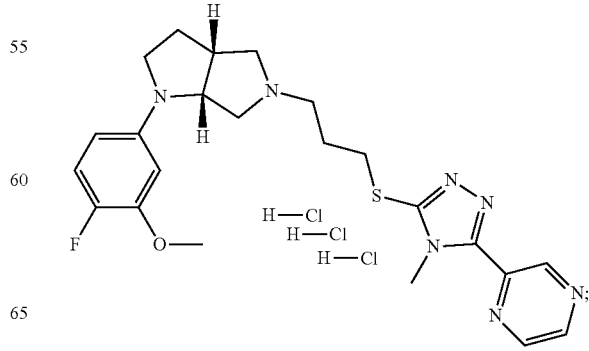

311
-continued
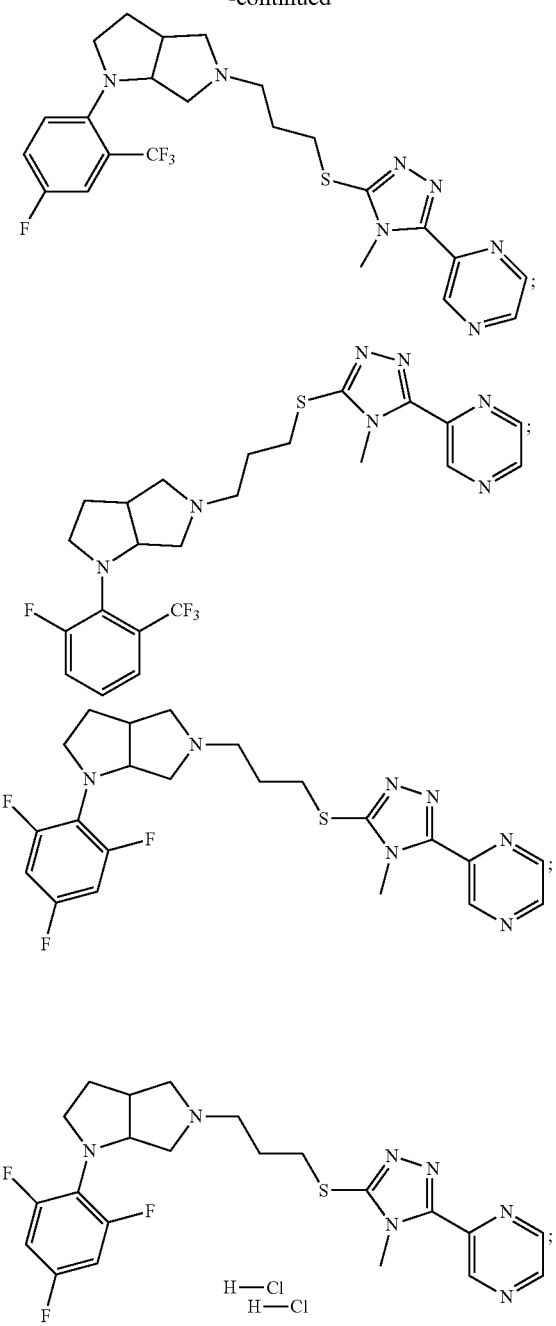
312
-continued
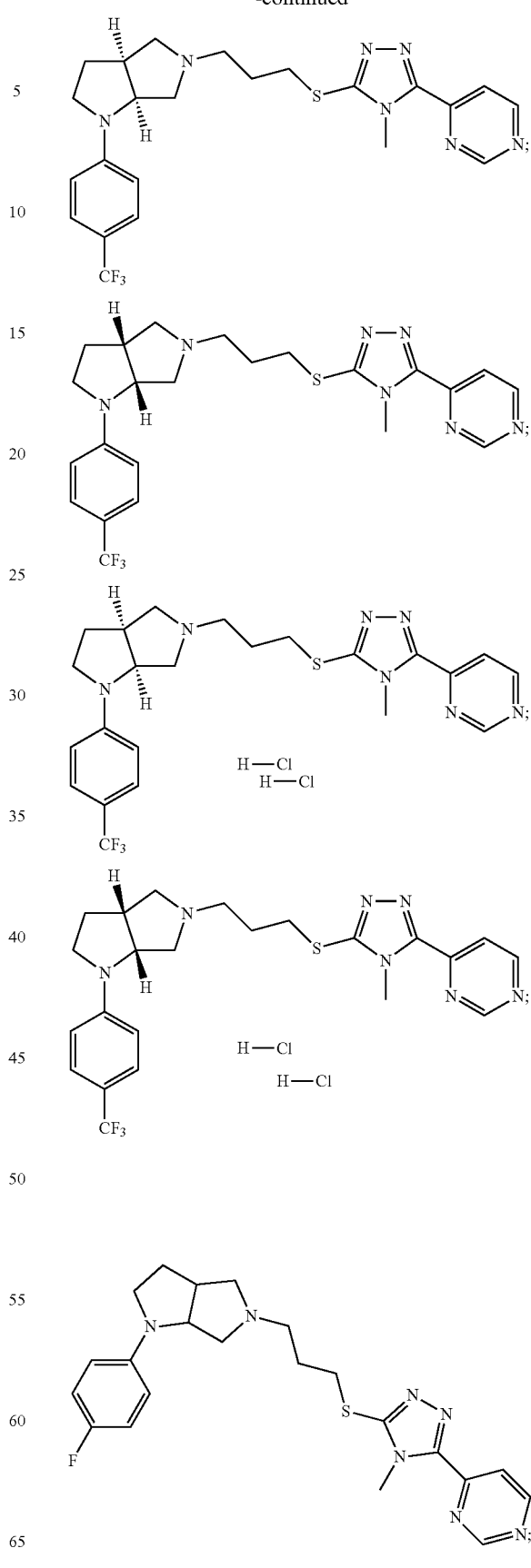

-continued
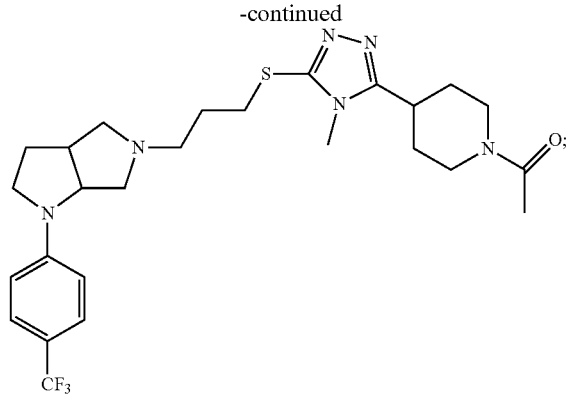
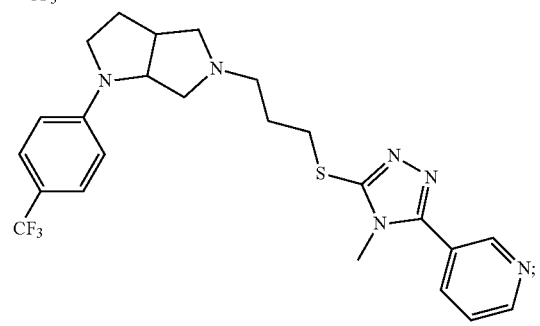
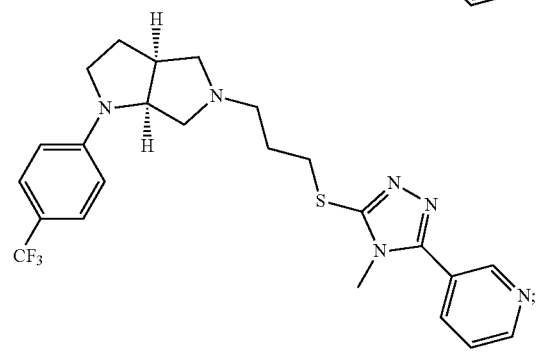
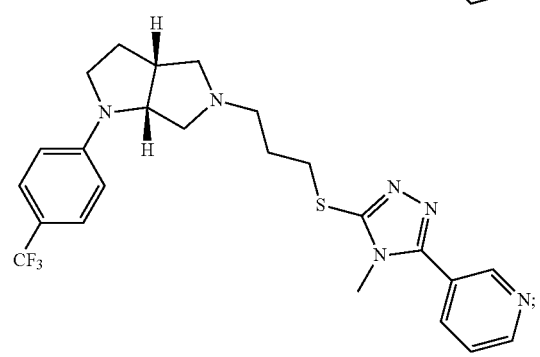
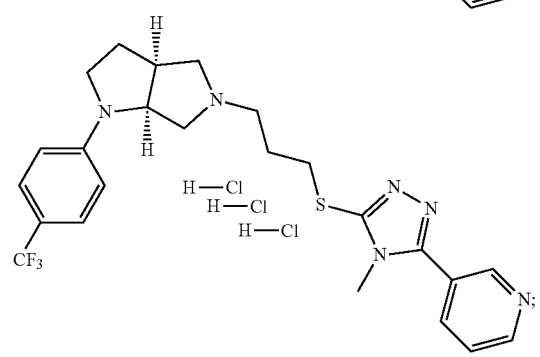
-continued
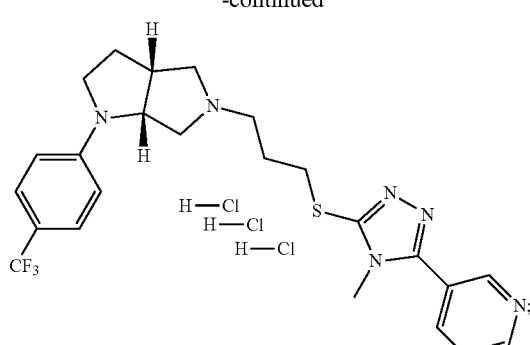
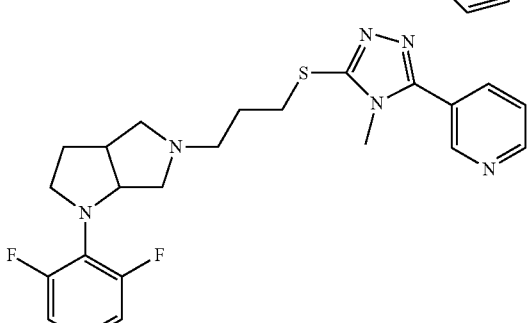
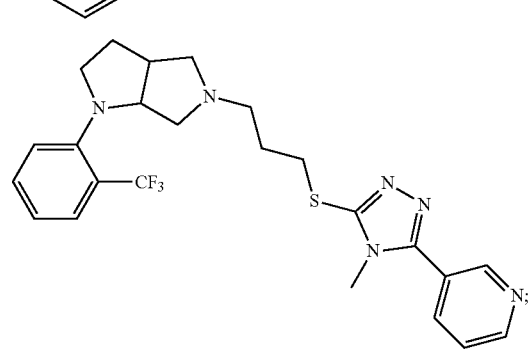
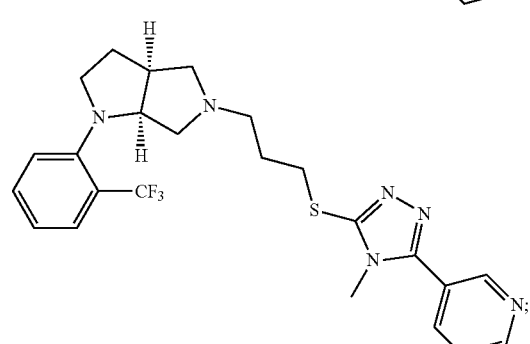
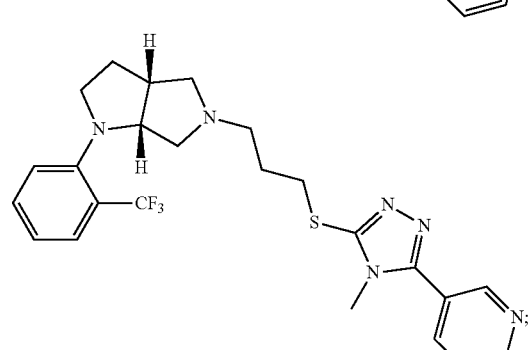

315
-continued
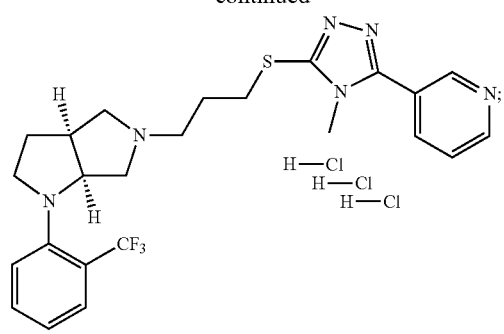
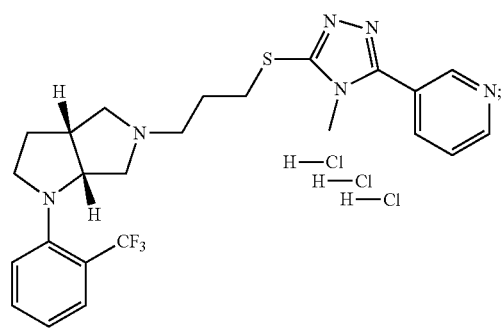
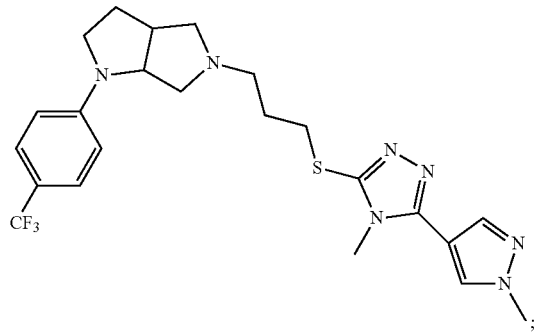
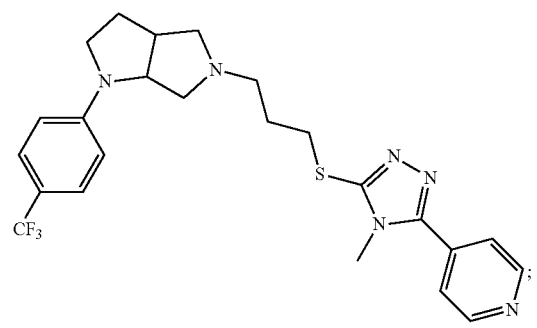
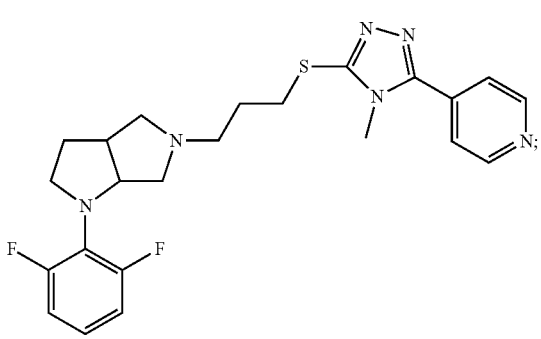
316
-continued
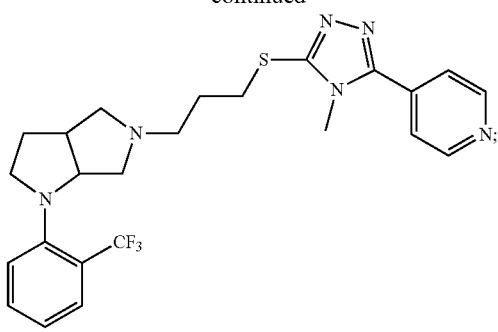
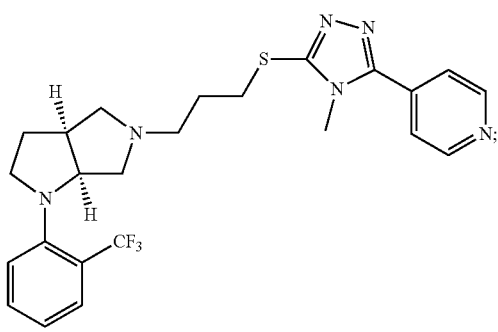
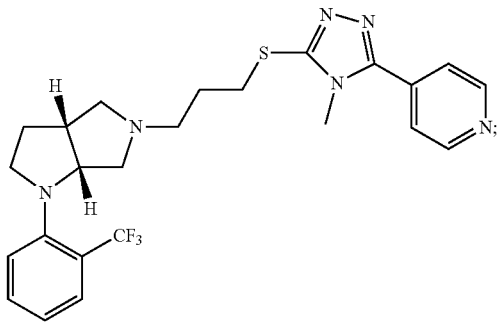
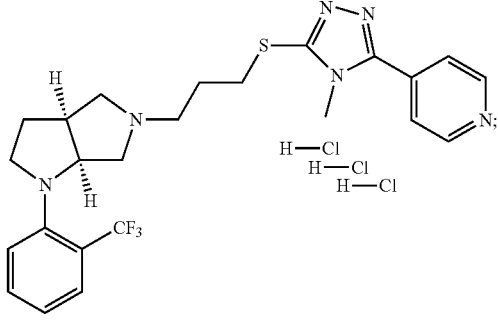
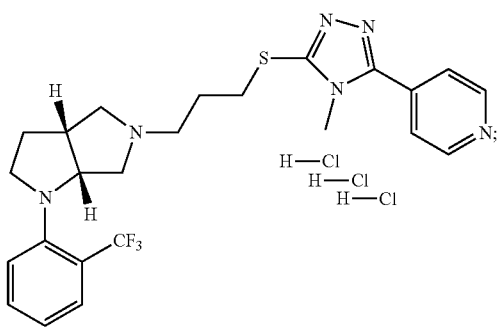

317
-continued
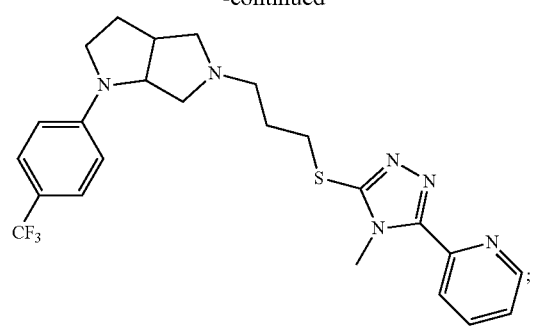
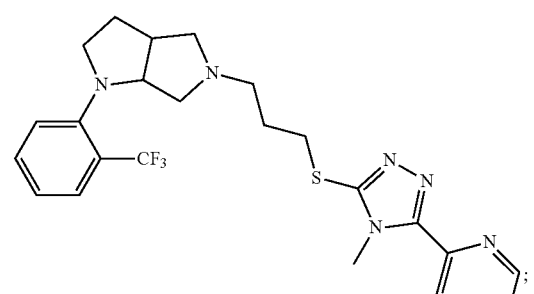
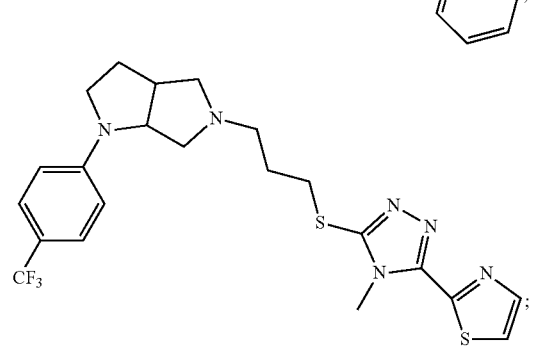
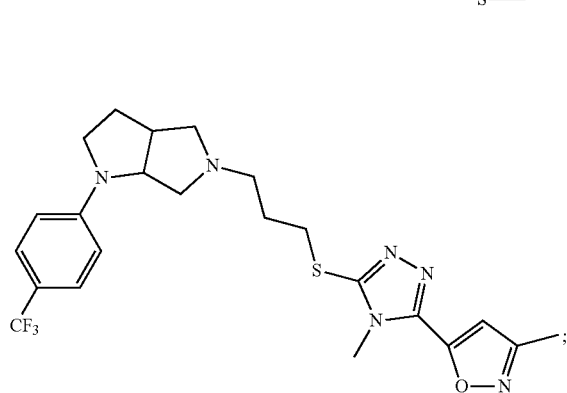
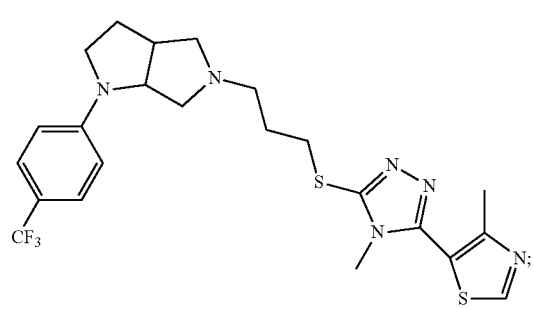
318
-continued
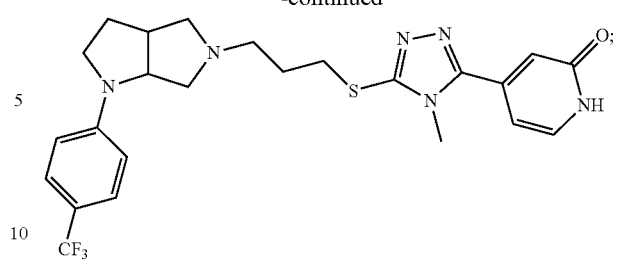
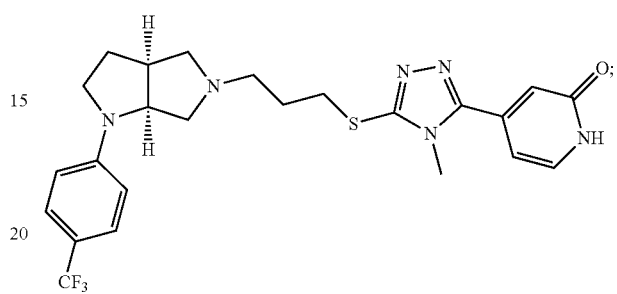
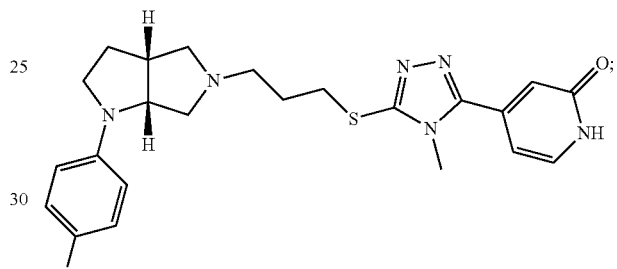
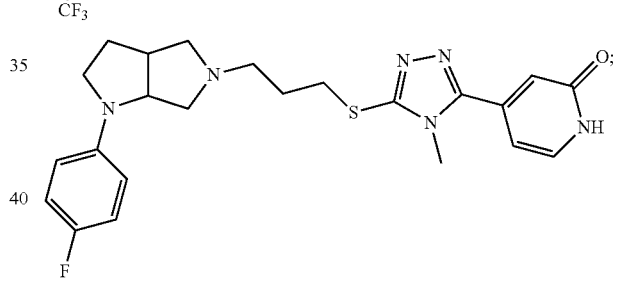
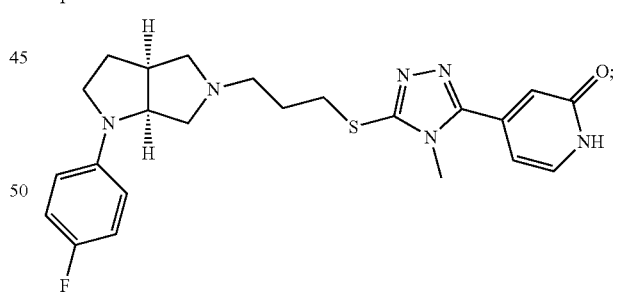
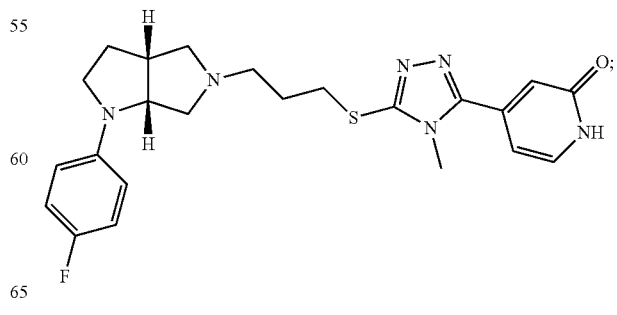

319
-continued
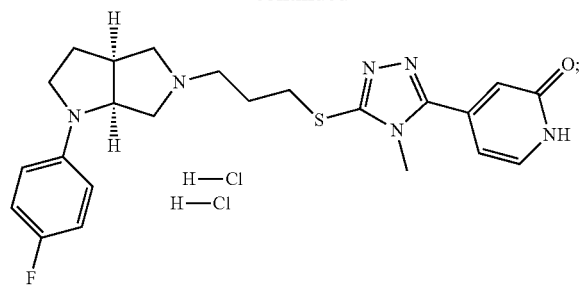
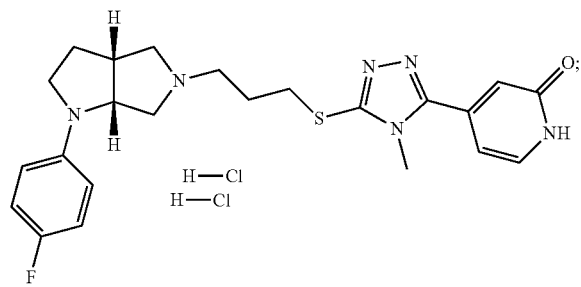
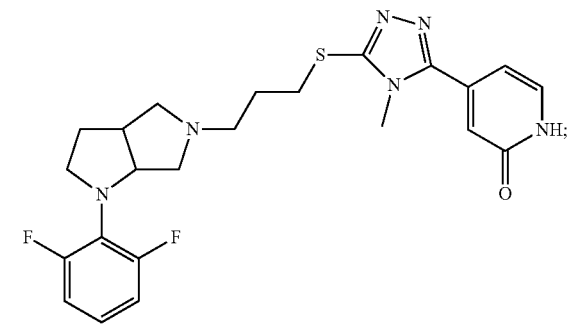
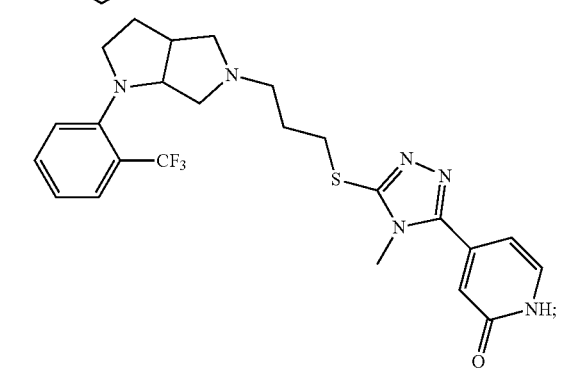
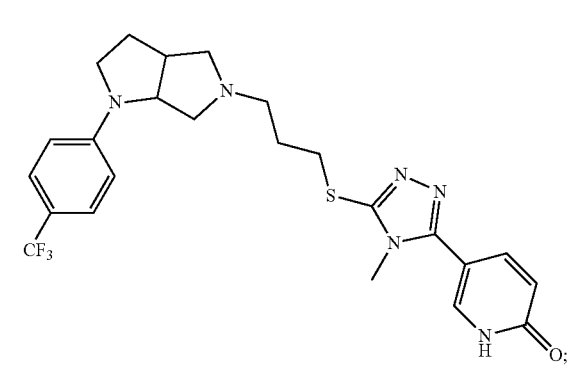
320
-continued
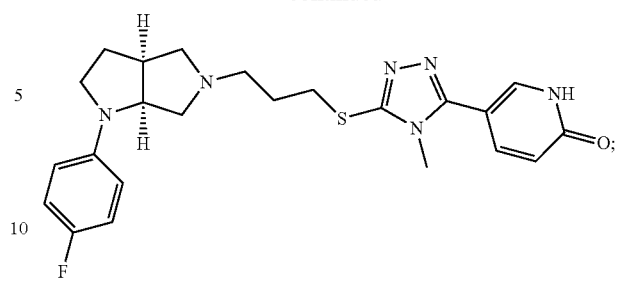
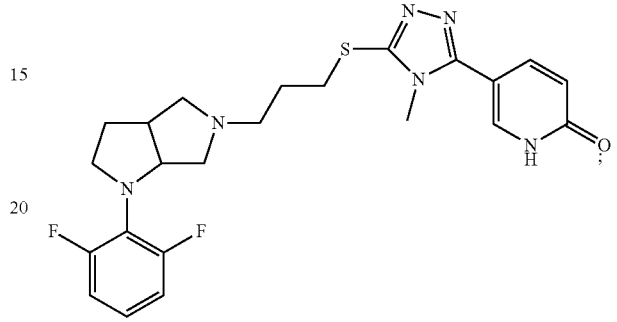
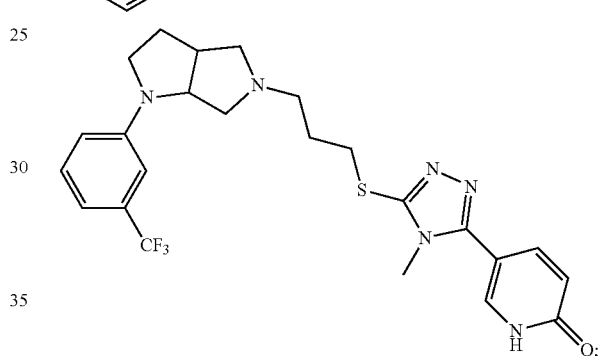
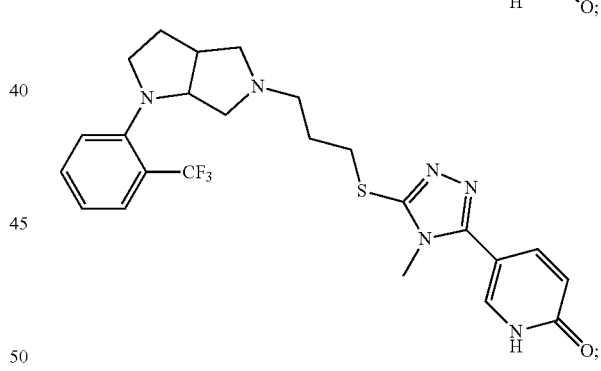
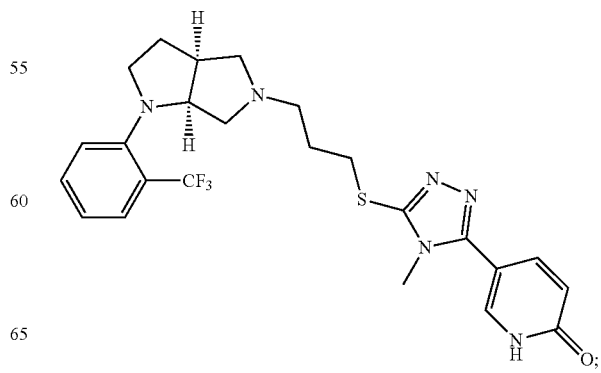

321
-continued
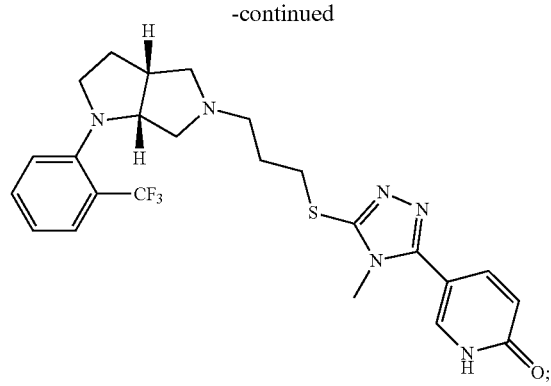
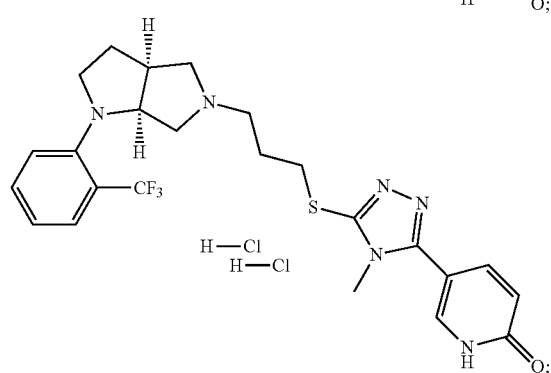
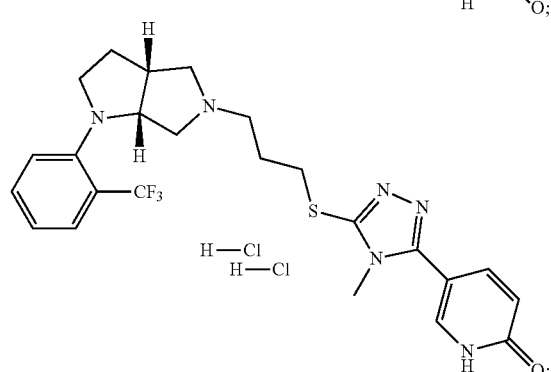
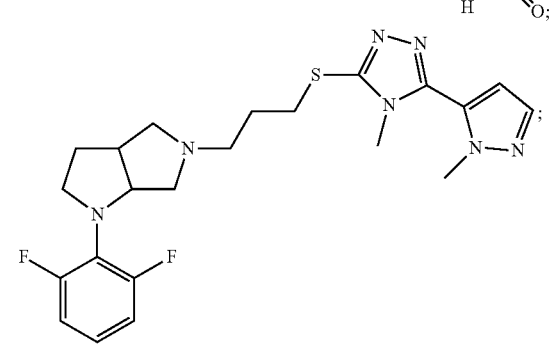
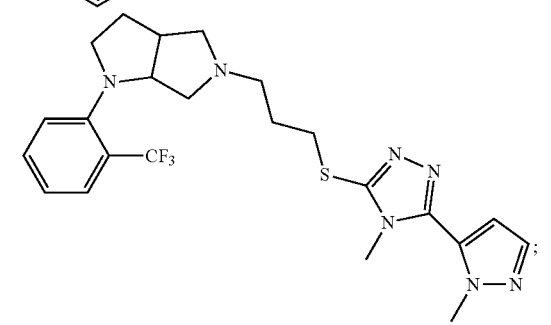
322
-continued
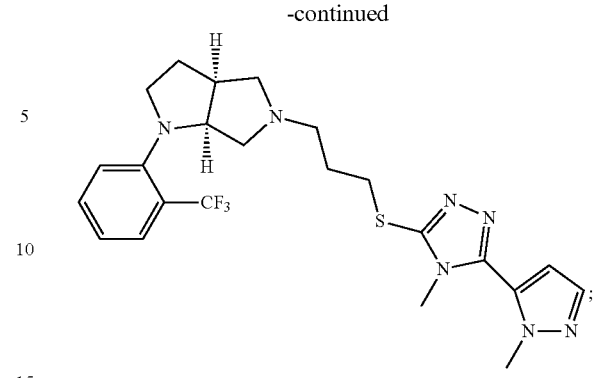
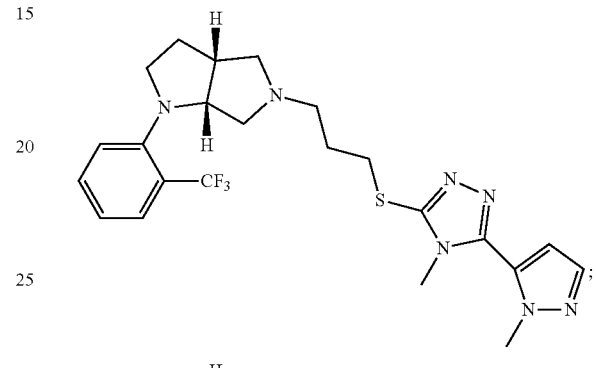
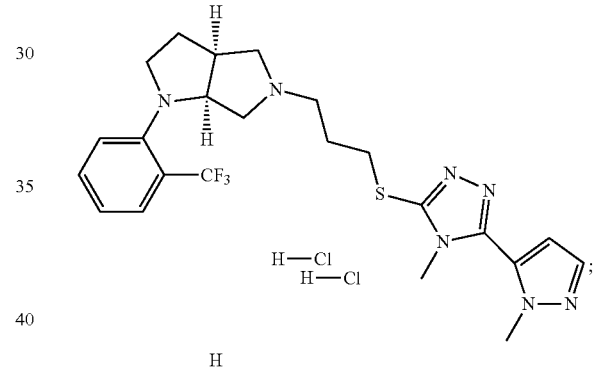
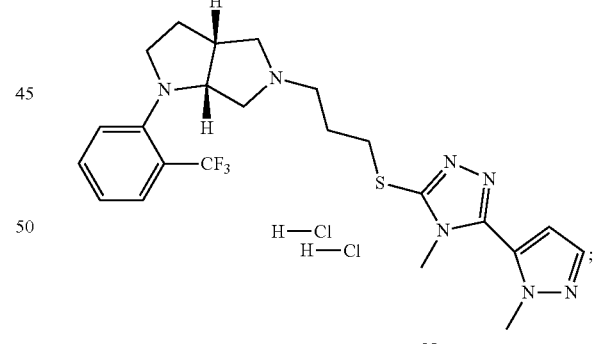
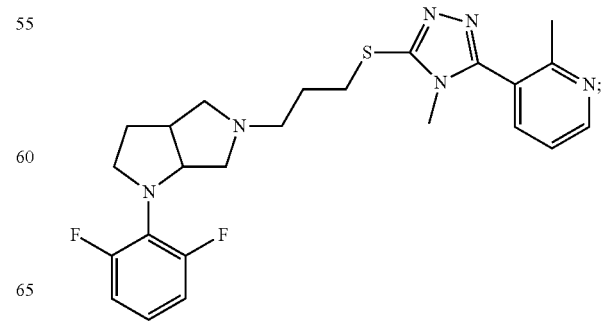

323
-continued
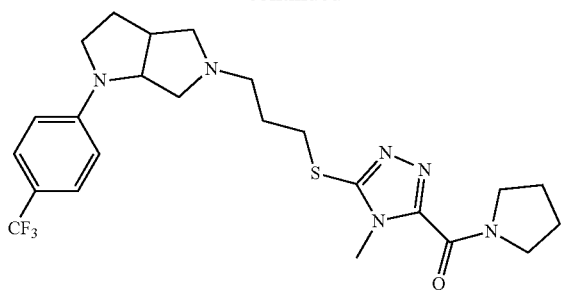
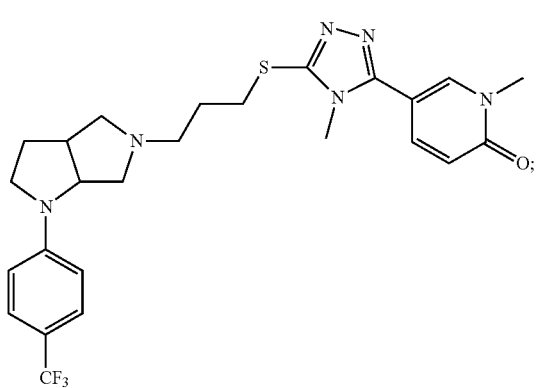
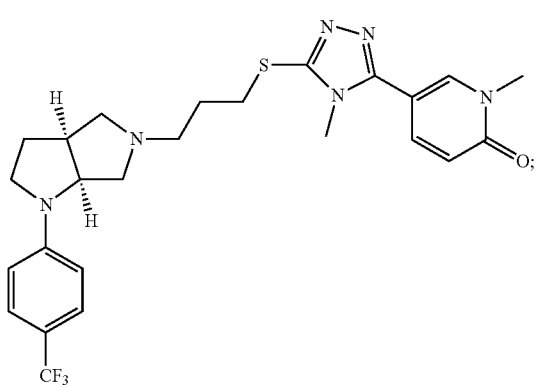
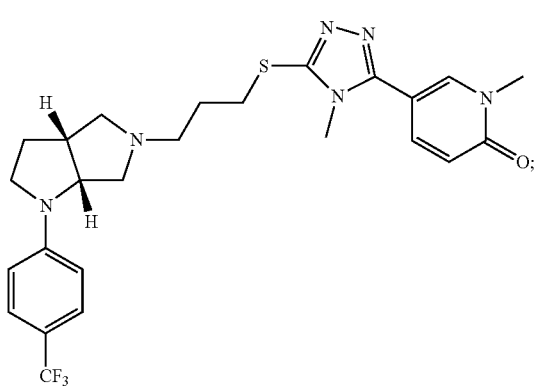
324
-continued
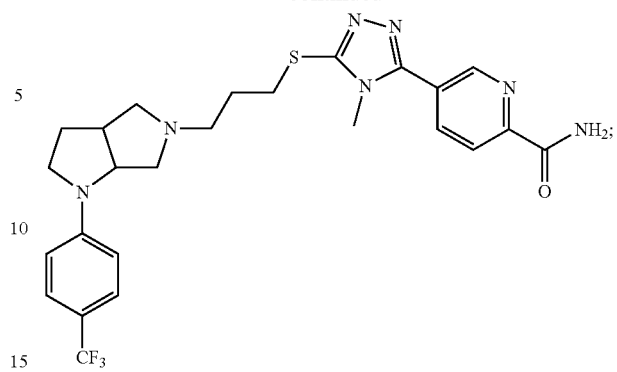
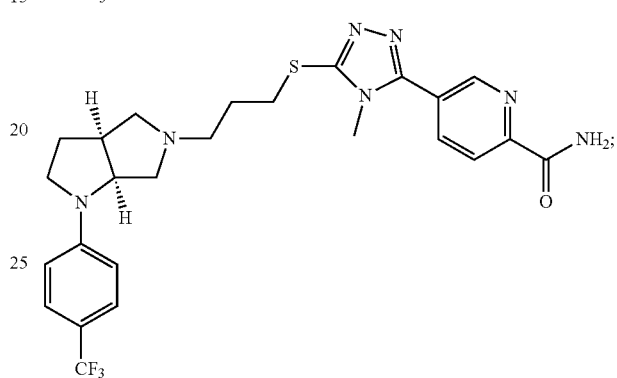
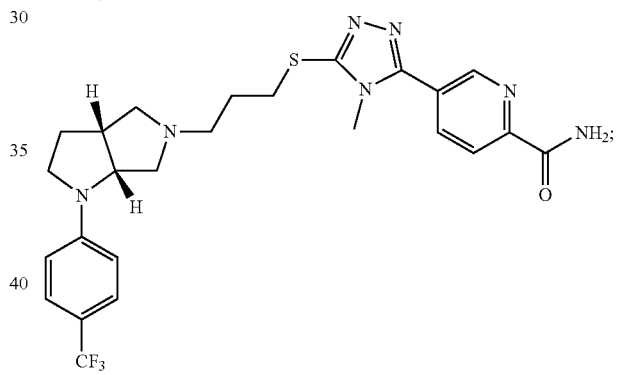
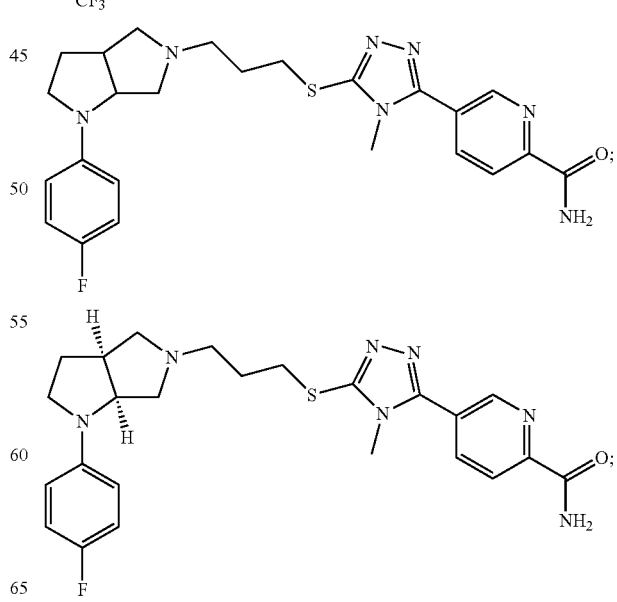

325
-continued
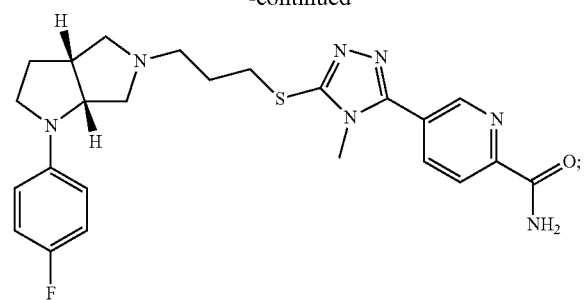
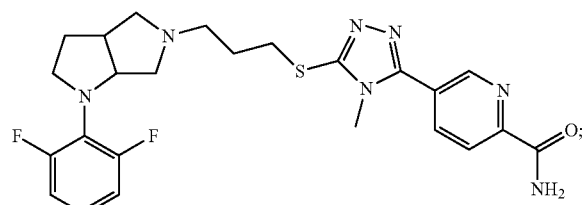
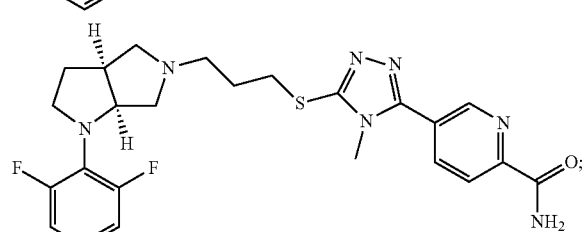
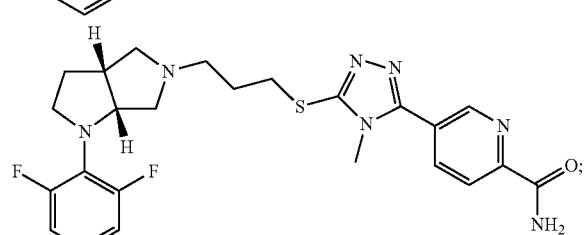
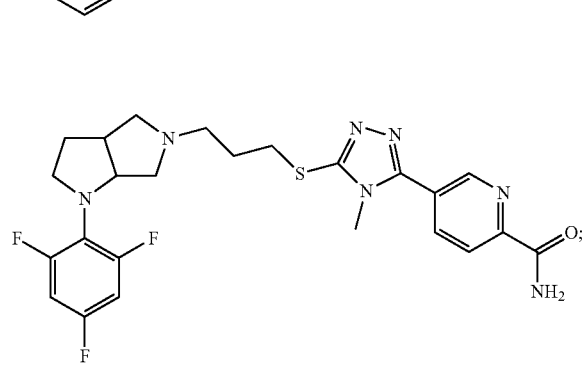
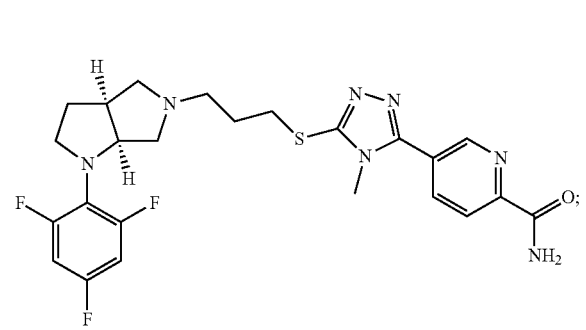
326
-continued
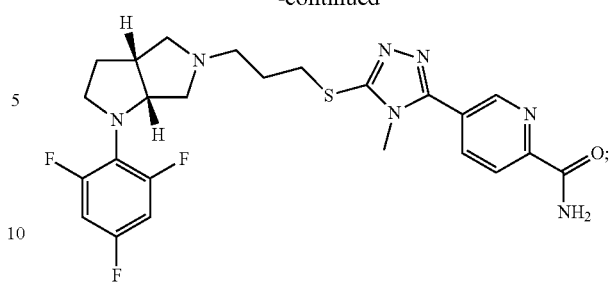
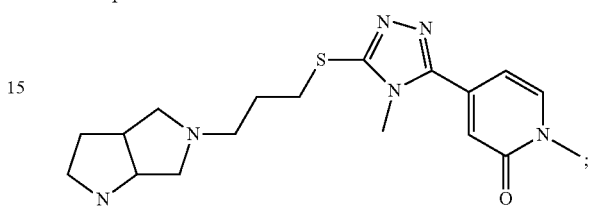
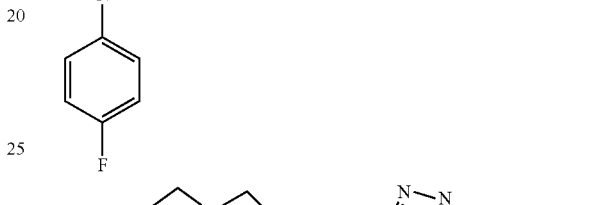
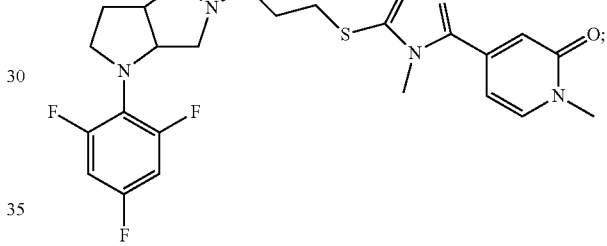
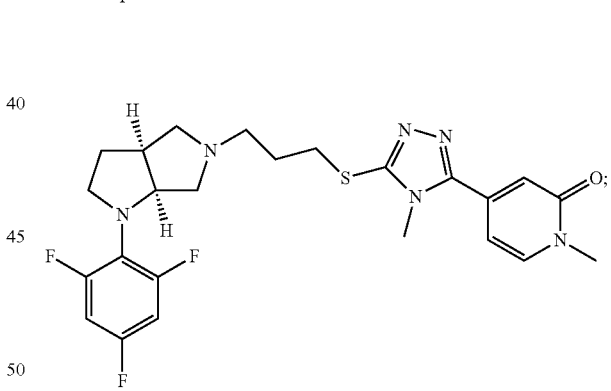
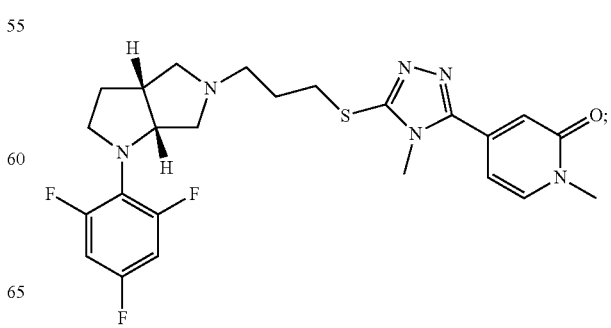

327
-continued
328
-continued
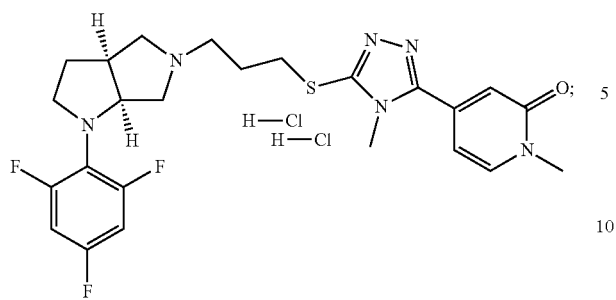
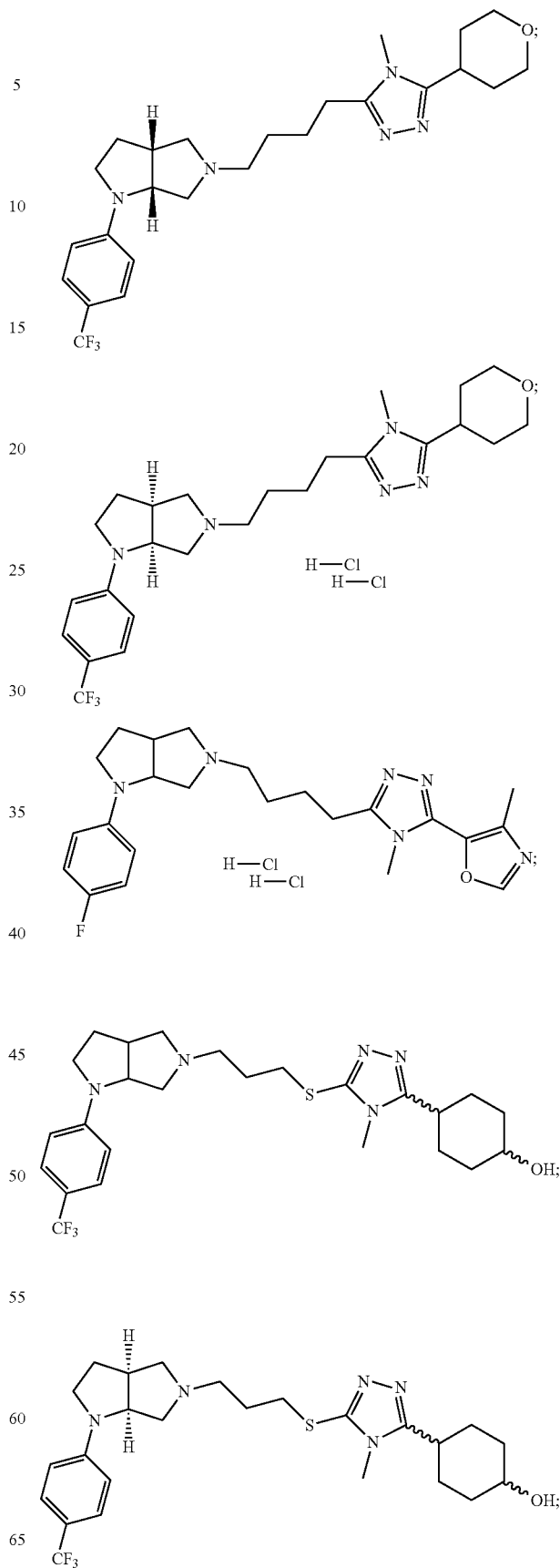

329
-continued

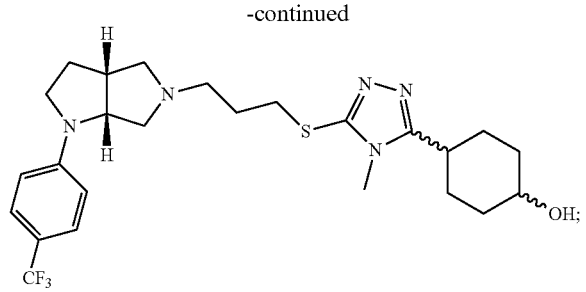

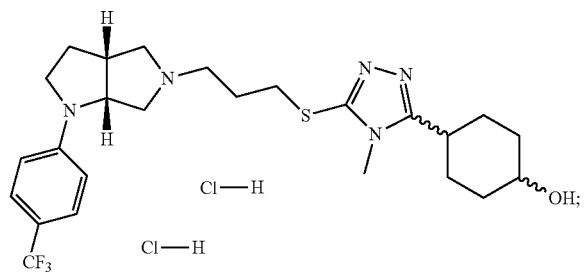

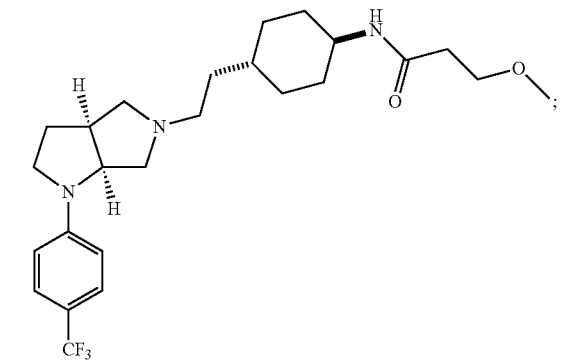

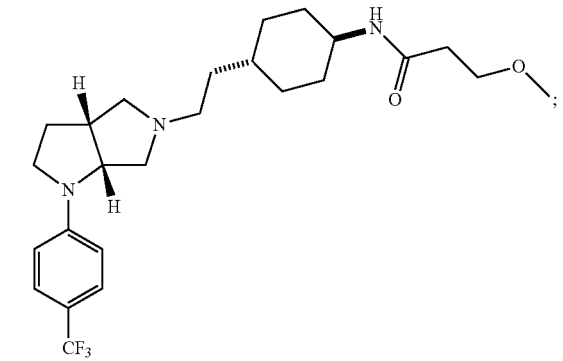

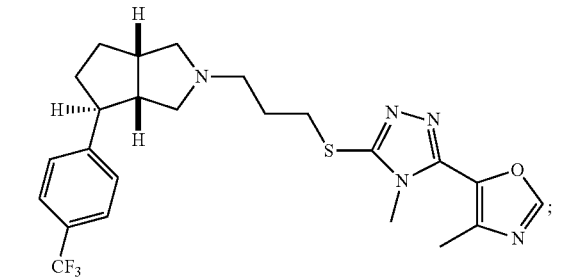

330
-continued

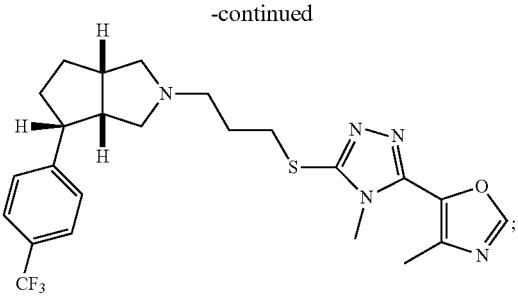

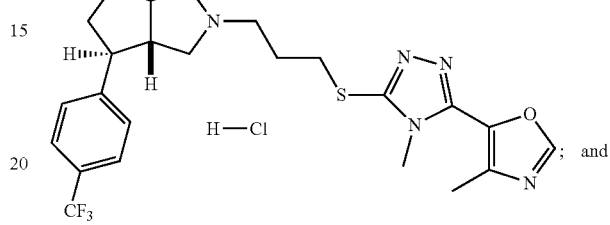

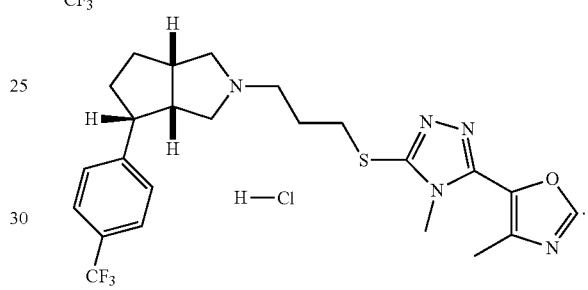

12. A pharmaceutical composition comprising the compound of claim 1 and a pharmaceutically acceptable carrier.

13. A method for modulating a dopamine $D_3$ receptor in a patient, comprising administering to the patient in need thereof a therapeutically effective amount of the compound of claim 3.

14. The method of claim 13, wherein modulating the dopamine $D_3$ receptor is antagonizing the dopamine $D_3$ receptor.

15. The method of claim 13, wherein modulating the dopamine $D_3$ receptor is treating a medical condition that is impacted by the dopamine $D_3$ receptor.

16. The method of claim 15, wherein the medical condition is a psychiatric condition.

17. The method of claim 15, wherein the medical condition is an opioid use disorder.

18. The method of claim 15, wherein the medical condition is a drug dependency.

19. The method of claim 18, wherein the drug dependency is alcohol dependency.

20. The method of claim 18, wherein the drug dependency is opioid dependency.

21. The method of claim 15, wherein the medical condition is an addiction.

22. The method of claim 21, wherein the addiction is gambling.

* * * * *